US011414677B2

(12) United States Patent
Shoulders et al.

(10) Patent No.: US 11,414,677 B2
(45) Date of Patent: Aug. 16, 2022

(54) METHODS AND COMPOSITIONS FOR PERFORMING CONTINUOUS DIRECTED EVOLUTION

(71) Applicant: Massachusetts Institute of Technology, Cambridge, MA (US)

(72) Inventors: Matthew D. Shoulders, Cambridge, MA (US); Chet Berman, Hanover, NH (US); Christopher Lawrence Moore, Cambridge, MA (US); Louis John Papa, Cambridge, MA (US); Samuel Joseph Hendel, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 704 days.

(21) Appl. No.: 16/171,424

(22) Filed: Oct. 26, 2018

(65) Prior Publication Data

US 2019/0153472 A1    May 23, 2019

Related U.S. Application Data

(60) Provisional application No. 62/734,520, filed on Sep. 21, 2018, provisional application No. 62/577,867, filed on Oct. 27, 2017.

(51) Int. Cl.

| | | |
|---|---|---|
| *C12N 15/86* | (2006.01) | |
| *C12N 7/00* | (2006.01) | |
| *C12N 15/10* | (2006.01) | |
| *C12N 15/861* | (2006.01) | |
| *C12N 5/00* | (2006.01) | |
| *C12N 9/12* | (2006.01) | |
| *C12N 9/50* | (2006.01) | |
| *C12N 15/66* | (2006.01) | |

(52) U.S. Cl.
CPC ........... *C12N 15/86* (2013.01); *C12N 5/0018* (2013.01); *C12N 7/00* (2013.01); *C12N 9/1252* (2013.01); *C12N 9/50* (2013.01); *C12N 15/1058* (2013.01); *C12N 15/66* (2013.01); *C12N 15/861* (2013.01); *C12N 2501/999* (2013.01); *C12N 2710/10021* (2013.01); *C12N 2710/10221* (2013.01); *C12N 2710/10321* (2013.01); *C12N 2710/10343* (2013.01); *C12Y 207/07007* (2013.01); *C12Y 304/21014* (2013.01)

(58) Field of Classification Search
None
See application file for complete search history.

(56) References Cited

U.S. PATENT DOCUMENTS 6,291,226 B1    9/2001   Massie et al.

FOREIGN PATENT DOCUMENTS

WO    2012/024351 A2    2/2012

OTHER PUBLICATIONS

Uil et al., Nucleic Acids Research, 2011, 39(5):e30, 14 pages. (Year: 2011).*
Uil et al., Nucleic Acids Research, 2011, 39(5):e30, Supplementary Data, 24 pages. (Year: 2011).*
Elahi et al., Gene Therapy, 2002, 9:1238-1246. (Year: 2002).*
Davis et al., Journal of Virology, Feb. 2010, 84(3):1625-1630. (Year: 2010).*
Berman et al., J. Am. Chem. Soc., Author manuscript, 2019, published in final edited form Dec. 26, 2018, 140(51):18093-18103, 24 pages. (Year: 2019).*
Berman et al., J. Am. Chem. Soc., Author manuscript, 2019, published in final edited form Dec. 26, 2018, 140(51): 18093-18103, Supporting Information, 18 pages. (Year: 2019).*
Alba et al., Gene Therapy, 2005, 12:S18-S27. (Year: 2005).*
Davis et al., Viral mutagenesis as a means for generating novel proteins. J Virol. Feb. 2010;84(3): 1625-30. doi: 10.1128/JVI.01747-09. Epub Nov. 11, 2009. PMID: 19906913; PMCID: PMC2812339.
Elahi et al., Adenovirus-based libraries: efficient generation of recombinant adenoviruses by positive selection with the adenovirus protease. Gene Ther. Sep. 2002;9(18):1238-46. doi: 10.1038/sj.gt.3301793. PMID: 12215891.
Fallaux et al., Characterization of 911: a new helper cell line for the titration and propagation of early region 1-deleted adenoviral vectors. Hum Gene Ther. Jan. 20, 1996;7(2):215-22. doi: 10.1089/hum. 1996.7.2-215. PMID: 8788172.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. PMID: 26258293; PMCID: PMC4589463.
Myers et al., Directed evolution of mutator adenoviruses resistant to antibody neutralization. J Virol. May 2013;87(10):6047-50. doi: 10.1128/JVI.00473-13. Epub Mar. 13, 2013. PMID: 23487468; PMCID: PMC3648140.
Amal et al., Isolation and characterization of packaging cell lines that coexpress the adenovirus E1, DNA polymerase, and preterminal proteins: implications for gene therapy. Gene Ther. 4, 258-263, doi:10.1038/sj.gt.3300378 (1997).
Arnold, Design by directed evolution. Acc. Chem. Res. 1998;31(3):125-131.
Arzumanyan et al., Mutually Orthogonal DNA Replication Systems In Vivo. ACS Synth. Biol. 7, 1722-1729, doi:10.1021/acssynbio. 8b00195 (2018).

(Continued)

*Primary Examiner* — Stacy B Chen
(74) *Attorney, Agent, or Firm* — Wolf, Greenfield & Sacks, P.C.

(57) ABSTRACT

Disclosed herein are methods of performing continuous directed evolution in complex biological systems, including metazoan cells. These methods include the infection of engineered, non-naturally occurring metazoan cells with engineered, non-naturally occurring DNA viruses. The generation of infectious viruses that can infect new cells depends on the evolution of a gene of interest which is driven by an error-prone adenoviral polymerase. Also disclosed herein, are the compositions of engineered, non-naturally occurring metazoan cells and engineered, non-naturally occurring DNA viruses that function as components in the continuous directed evolution methodologies.

20 Claims, 29 Drawing Sheets

Specification includes a Sequence Listing.

(56) References Cited

OTHER PUBLICATIONS

Badran et al. Continuous evolution of Bacillus thuringiensis toxins overcomes insect resistance. Nature 533, 58-63, doi:10.1038/nature17938 (2016).
Banaszynski et al., A rapid, reversible, and tunable method to regulate protein function in living cells using synthetic small molecules. Cell 126, 995-1004, doi: 10.1016/j.cell.2006.07.025 (2006).
Baniecki et al., Regulation of a viral proteinase by a peptide and DNA in one-dimensional space: III. atomic resolution structure of the nascent form of the adenovirus proteinase, J. Biol. Chem., 2013. 288(3):2081-91.
Benihoud et al.,Adenovirus vectors for gene delivery. Curr Opin Biotechnol. Oct. 1999;10(5):440-7. doi: 10.1016/s0958-1669(99)00007-5. PMID: 10508634.
Berman et al., An Adaptable Platform for Directed Evolution in Human Cells. J Am Chem Soc. Dec. 26, 2018; 140(51): 18093-18103. doi: 10.1021/jacs.8b10937. Epub Dec. 14, 2018. PMID: 30427676; PMCID: PMC6467755. Supporting Information.
Bett et al., (1993) Packaging capacity and stability of human adenovirus type 5 vectors, J. Virol., 67, 5911-5921.
Biechele et al., Transcription-based reporters of Wnt/beta-catenin signaling. Cold Spring Harb Protoc. Jun. 2009;2009(6):pdb.prot5223. doi: 10.1101/pdb.prot5223. PMID: 20147181.
Biles et al., (2004) Low-fidelity Pyrococcus furiosus DNA polymerase mutants useful in error-prone PCR, Nucleic Acids Res., 32, e176-e176.
Blainey et al., (2013) Regulation of a Viral Proteinase by a Peptide and DNA in Onedimensional Space: IV. Viral Proteinase Slides Along DNA to Locate and Process Its Substrates, J. Biol. Chem., 288, 2092-2102.
Branon et al., Efficient proximity labeling in living cells and organisms with TurboID. Nat Biotechnol. Sep. 2018;36(8):726-737., doi:10.1038/nbt.4201 (2018).
Bryson et al. Continuous directed evolution of aminoacyl-tRNA synthetases. Nat. Chem. Biol. 13, 1253-1260, doi:10.1038/nchembio.2474 (2017).
Buskirk et al., (2003) In vivo evolution of an RNA-based transcriptional activator, Chem. Biol., 10, 533-540.
Carlson et al., Negative selection and stringency modulation in phage-assisted continuous evolution. Nat. Chem. Biol. 10, 216-222, doi:10.1038/nchembio.1453 (2014).
Chaikind et al., (2016) A programmable Cas9-serine recombinase fusion protein that operates on DNA sequences in mammalian cells, Nucleic Acids Res., 44, 9758-9770.
Collins et al., (2006) Dual selection enhances the signaling specificity of a variant of the quorum-sensing transcriptional activator LuxR, Nat. Biotechnol., 24, 708-712.
Connolly et al., Structure-Based Mutagenesis of Herpes Simplex Virus Glycoprotein D Defines Three Critical Regions at the gD-HveA/HVEM Binding Interface, J. Virol., 2003. 77(14): p. 8127-40.
Cotten et al., (1995) The adenovirus protease is required for virus entry into host cells, Virology, 213, 494-502.
Cuesta et al., (2000) Adenovirus-specific translation by displacement of kinase Mnk1 from cap-initiation complex eIF4F, Embo J., 19, 3465-3474.
Dai et al., (2017) Atomic structures of minor proteins VI and VII in human adenovirus, J. Virol., 91, e00850-00817.
Das et al., Viral Evolution as a Tool to Improve the Tetracycline-regulated Gene Expression System, J. Biol. Chem., 2004. 279(18): p. 18776-82.
Day et al., UV-induced reversion of adenovirus 5ts2 infecting human cells, Photochem. Photobiol., 1981. 34(3):403-06.
De Vega et al., (1998) Mutational analysis of ø29 DNA polymerase residues acting as ssDNA ligands for 3'-5' exonucleolysis, J. Mol. Biol., 279, 807-822.
Dickinson et al., A system for the continuous directed evolution of proteases rapidly reveals drug-resistance mutations. Nat Commun. Oct. 30, 2014;5:5352. doi: 10.1038/ncomms6352. PMID: 25355134; PMCID: PMC4215169.
Dougherty et al., (2009) Directed evolution: new parts and optimized function, Curr. Opin. Biotechnol., 20, 486-491.
Duffy et al., Assessing the contribution of the herpes simplex virus DNA polymerase to spontaneous mutations, BMC Infect. Dis., 2002. 2:7.
Elahi et al., Adenovirus-based libraries: efficient generation of recombinant adenoviruses by positive selection with the adenovirus protease. Gene Ther. 9, 1238-1246, doi:10.1038/sj.gt.3301793 (2002).
Esvelt et al., A system for the continuous directed evolution of biomolecules, Nature, 2011. 472(7344):499-503.
Gai et al., Yeast surface display for protein engineering and characterization. Curr. Opin. Struct. Biol. 17, 467-473, doi:10.1016/j.sbi.2007.08.012 (2007).
Gaj et al., (2013) A comprehensive approach to zinc-finger recombinase customization enables genomic targeting in human cells, Nucleic Acids Res., 41, 3937-3946.
Giger et al., (2013) Evolution of a designed retro-aldolase leads to complete active site remodeling, Nat. Chem. Biol., 9, 494-498.
Gossen et al., Tight control of gene expression in mammalian cells by tetracycline-response promoters, Proc. Natl. Acad. Sci. USA, 1992. 89(12): p. 5547-51.
Graziano et al., (2013) Regulation of a viral proteinase by a peptide and DNA in onedimensional space: II. adenovirus proteinase is activated in an unusual one-dimensional biochemical reaction, J. Biol. Chem., 288, 2068-2080.
Greber et al., The role of the adenovirus protease on virus entry into cells, EMBO J., 1996. 15(8):1766-77.
Grosche et al., Structure-based design and optimization of potent inhibitors of the adenoviral protease, Bioorg. Med. Chem. Lett., 2015. 25(3):438-43.
Hecht et al., Noninducible Tet repressor mutations map from the operator binding motif to the C terminus, J. Bacteriol., 1993. 175(4):1206-10.
Hess et al. Directed evolution using dCas9-targeted somatic hypermutation in mammalian cells. Nat. Methods 13, 1036-1042, doi:10.1038/nmeth.4038 (2016).
Hirai et al., Structure and functions of powerful transactivators: VP16, MyoD and FoxA, Int. J. Dev. Biol., 2010;54, 1589-1596.
Hoeben et al., Adenovirus DNA replication. Cold Spring Harb. Perspect. Biol. 5, a013003, doi:10.1101/cshperspect.a013003 (2013).
Hu et al. Evolved Cas9 variants with broad PAM compatibility and high DNA specificity. Nature 556, 57-63, doi:10.1038/nature26155 (2018).
Italia et al., Expanding the genetic code of mammalian cells, Biochem. Soc. Trans., 2017;45, 555-562.
Iwamoto et al., A general chemical method to regulate protein stability in the mammalian central nervous system, Chem. Biol., 2010. 17(9): p. 981-89.
Kamtekar et al. Insights into strand displacement and processivity from the crystal structure of the protein-primed DNA polymerase of bacteriophage phi29. Mol. Cell 16:609-618, doi: 10.1016/j.molcel.2004.10.019 (2004).
Kaplan et al., Complementation of the temperature-sensitive defect in H5ts125 adenovirus DNA replication in vitro, Proc. Natl. Acad. Sci., 1979;76, 5534-5538.
Kathman et al., A fragment-based method to discover irreversible covalent inhibitors of cysteine proteases, J. Med. Chem., 2014. 57(11):4969-74.
Kim et al., Increasing the genome-targeting scope and precision of base editing with engineered Cas9-cytidine deaminase fusions, Nat. Biotechnol., 2017. 35(4):371-76.
Kim et al. Genome-wide target specificities of CRISPR RNA-guided programmable deaminases. Nat. Biotechnol. 35, 475-480, doi:10.1038/nbt.3852 (2017).
Komor et al., Programmable editing of a target base in genomic DNA without double-stranded DNA cleavage. Nature 2016;533, 420-424, doi:10.1038/nature17946.

(56) References Cited

OTHER PUBLICATIONS

Kovesdi et al., Adenoviral producer cells. Viruses. Aug. 2010;2(8):1681-703. doi: 10.3390/v2081681. Epub Aug. 1, 20106. PMID: 21994701; PMCID: PMC3185730.
Krueger et al., Engineered Tet repressors with recognition specificity for the tetO-4C5G operator variant. Gene 404:93-100, doi: 10.1016/j.gene.2007.09.002 (2007).
Krueger et al., Transactivator mutants with altered effector specificity allow selective regulation of two genes by tetracycline variants, Gene, 2004;331:125-131.
Legrand et al., Fiberless recombinant adenoviruses: virus maturation and infectivity in the absence of fiber, J. Virol., 1999;73, 907-919.
Lichy et al., Separation of the adenovirus terminal protein precursor from its associated DNA polymerase: role of both proteins in the initiation of adenovirus DNA replication, Proc. Natl. Acad. Sci., 1982;79, 5225-5229.
Loew et al., Improved Tet-responsive promoters with minimized background expression. BMC Biotechnol. 10, 81, doi:10.1186/1472-6750-10-81 (2010).
Logan et al., Adenovirus tripartite leader sequence enhances translation of mRNAs late after infection, Proc. Natl. Acad. Sci., 1984;81, 3655-3659.
Lonberg-Holm et al., (1976) Unrelated animal viruses share receptors, Nature, 259, 679-681.
Lucher, L. A. Abortive adenovirus infection and host range determinants. Curr. Top. Microbiol. Immunol. 199 ( Pt 1), 119-152 (1995).
Luo et al., (2007) A protocol for rapid generation of recombinant adenoviruses using the AdEasy system, Nat. Protoc., 2, 1236-1247.
Ma et al. Targeted AID-mediated mutagenesis (TAM) enables efficient genomic diversification in mammalian cells. Nat. Methods 13, 1029-1035, doi:10.1038/nmeth.4027 (2016).
Maier et al., (2010) An N-terminal domain of adenovirus protein VI fragments membranes by inducing positive membrane curvature, Virology, 402, 11-19.
Mangel et al., (1996) Characterization of three components of human adenovirus proteinase activity in vitro, J. Biol. Chem., 271, 536-543.
Meng et al. Convergent transcription at intragenic super-enhancers targets AID-initiated genomic instability. Cell 159, 1538-1548, doi:10.1016/j.cell.2014.11.014 (2014).
Meyerhans et al. Temporal fluctuations in HIV quasispecies in vivo are not reflected by sequential HIV isolations. Cell 58, 901-910, doi: 10.1016/0092-8674(89)90942-2 (1989).
Moncivais et al., (2012) Tetracycline repressor-based mammalian two-hybrid systems, Methods Mol. Biol., 812, 259-273.
Moore et al., A Processive Protein Chimera Introduces Mutations across Defined DNA Regions In Vivo. J. Am. Chem. Soc., doi:10. 1021/jacs.8b04001 (2018).
Muck-Hausl et al., Ad 2.0: a novel recombineering platform for high-throughput generation of tailored adenoviruses, Nucleic Acids Res., 2015. 43(8): e50.
O'Loughlin et al., Diversification and specialization of HIV protease function during in vitro evolution. Mol. Biol. Evol. 23, 764-772, doi:10.1093/molbev/msj098 (2006).
Oualikene et al., (2000) Protease-deleted adenovirus vectors and complementing cell lines: potential applications of single-round replication mutants for vaccination and gene therapy, Hum. Gene Ther., 11, 1341-1353.
Packer et al., Methods for the directed evolution of proteins. Nat. Rev. Genet. 16, 379-394, doi:10.1038/nrg3927 (2015).
Peck et al., Directed evolution of a small-molecule-triggered intein with improved splicing properties in mammalian cells. Chem. Biol. 18, 619-630, doi:10.1016/j.chembiol.2011.02.014 (2011).
Persson et al., (1985) Virus-receptor interaction in the adenovirus system: characterization of the positive cooperative binding of virions on HeLa cells, J. Virol., 54, 92-97.
Phillips et al. Host proteostasis modulates influenza evolution. eLife 6, e28652, doi: 10.7554/eLife.28652 (2017).
Piatkevich et al. A robotic multidimensional directed evolution approach applied to fluorescent voltage reporters. Nat. Chem. Biol. 14, 352-360, doi:10.1038/s41589-018-0004-9 (2018).
Ptashne et al., (1997) Transcriptional activation by recruitment, Nature, 386:569-577.
Radany et al., Increased spontaneous mutation frequency in human cells expressing the page PBS2-encoded inhibitor of uracil-DNA glycosylase, Mutat. Res., 2000. 461(1):41-58.
Ramos et al., (2005) The TetR family of transcriptional repressors, Microbiol. Mol. Biol. Rev., 69, 326-356.
Rice et al., (1985) Isolation and analysis of adenovirus type 5 mutants containing deletions in the gene encoding the DNA-binding protein, J. Virol., 56, 767-778.
Risso-Ballester et al., Genome-wide estimation of the spontaneous mutation rate of human adenovirus 5 by high-fidelity deep sequencing, PLoS Pathog., 2016. 12(11): e1006013.
Romero et al., Exploring protein fitness landscapes by directed evolution. Nat. Rev. Mol. Cell Biol. 10, 866-876, doi:10.1038/nrm2805 (2009).
Russell, Update on adenovirus and its vectors. J. Gen. Virol. 81, 2573-2604, doi: 10.1099/0022-1317-81-11-2573 (2000).
Sanjuan et al., Viral mutation rates. J. Virol. 84, 9733-9748, doi:10. 1128/JVI.00694-10 (2010).
Saribasak et al., Uracil DNA glycosylase disruption blocks Ig gene conversion and induces transition mutations, J. Immunol., 2006. 176(1):365-71.
Shaner et al. Improved monomeric red, orange and yellow fluorescent proteins derived from *Discosoma* sp. red fluorescent protein. Nat. Biotechnol. 22, 1567-1572, doi:10.1038/nbt1037 (2004).
Sharan et al., (2009) Recombineering: a homologous recombination-based method of genetic engineering, Nat. Pro toe., 4, 206-223.
Smith, (2016) Directed evolution of adenoviruses, Methods Mol. Biol., 1382:187-196.
Song et al., (1997) Functional characterization of the Major Late Promoter of mouse adenovirus Type 1, Virology, 235, 109-117.
Suzuki et al., (2015) Preferable sites and orientations of transgene inserted in the adenovirus vector genome: The E3 site may be unfavorable for transgene position, Gene Ther. 22:421-429.
Uil et al., Directed adenovirus evolution using engineered mutator viral polymerase, Nucleic Acids Res., 2011. 39(5): e30.
Uil et al., (2009) A lentiviral vector-based adenovirus fiber-pseudotyping approach for expedited functional assessment of candidate retargeted fibers, J. Gene. Med., 11, 990-1004.
Vidal et al., (1999) Yeast forward and reverse 'n'-hybrid systems, Nucleic Acids Res., 27:919-929.
Von Seggern et al., (1999) A helper-independent adenovirus vector with E1, E3, and fiber deleted: structure and infectivity of fiberless particles, J. Virol., 73, 1601-1608.
Von Seggern et al., (2000) Adenovirus vector pseudotyping in fiber-expressing cell lines: improved transduction of Epstein-Barr virus-transformed B cells, J. Virol., 74, 354-362.
Wang et al., (2006) Evolving proteins in mammalian cells using somatic hypermutation, Nat. Protoc., 1, 1346-1350.
Wang et al., Directed molecular evolution by somatic hypermutation. Protein Eng. Des. Sei. 17, 659-664, doi:10.1093/protein/gzh080 (2004).
Wang et al., Evolution of new nonantibody proteins via iterative somatic hypermutation, Proc. Natl. Acad. Sci. U S A, 2004. 101(48): 16745-49.
Wang et al., Genome-wide somatic hypermutation. PNAS 101, 7352-7356, doi:10.1073/pnas.0402009101 (2004).
Wang et al., Improved seamless mutagenesis by recombineering using ccdB for counterselection. Nucleic Acids Res., 2014. 42(5): e37.
Webster et al., Activation of adenovirus-coded protease and processing of preterminal protein. J. Virol. 68, 7292-7300 (1994).
Wechman et al., Adenovirus with DNA packaging gene mutations increased virus release, Viruses, 2016. 8(12).
Williams et al., Isolation of temperature-sensitive mutants of adenovirus type 5, J. Gen. Virol., 1971. 11(2): p. 95-101.
Yoshikawa et al., AID enzyme-induced hypermutation in an actively transcribed gene in fibroblasts, Science, 2002. 296(5575):2033-36.

(56) References Cited

OTHER PUBLICATIONS

Yueh et al., Translation by ribosome shunting on adenovirus and hsp70 mRNAs facilitated by complementarity to 18S rRNA, Genes Dev., 2000. 14(4):414-21.
Zetsche et al. Cpf1 is a single RNA-guided endonuclease of a class 2 CRISPR-Cas system. Cell 163, 759-771, doi:10.1016/j.cell.2015.09.038 (2015).
Zhao et al., (2014) A new look at adenovirus splicing, Virology, 456-457:329-341.
Zhou et al., (1996) Development of a complementing cell line and a system for construction of adenovirus vectors with E1 and E2a deleted, J. Virol., 70:7030-7038.
PCT/US2018/057683, Feb. 20, 2019, International Search Report and Written Opinion.
PCT/US2018/057683, May 7, 2020, International Preliminary Report on Patentability.
NCBI 87 Complete genomes: Adenoviridae. 2020.
Abbink et al., Construction and evaluation of novel rhesus monkey adenovirus vaccine vectors. J. Virol. 2015, 89 (3), 1512-22.
Baxi et al., Recombinant bovine adenovirus type 3 expressing bovine viral diarrhea virus glycoprotein E2 induces an immune response in cotton rats. Virology. Dec. 5, 2000;278(1):234-43. doi: 10.1006/viro.2000.0661. PMID: 11112498.
Berk, 2013. Adenoviridae, 1704-1731. In: Knipe DM, Howley PM, Cohen JI, Griffin DE, Lamb RA, Martin MA, Racaniello VR, Roizman B (Ed). Fields Virology. 6th ed, vol. 2. Wolters Kluwer/Lippincott Williams & Wilkins, Philadelphia, PA.
Crosby et al., IIIa deleted adenovirus as a single-cycle genome replicating vector. Virology. Aug. 2014;462-463:158-165.
Gustin et al., Encapsidation of viral DNA requires the adenovirus LI 52/55-kilodalton protein. J. Virol. 1998, 72 (10), 7860-70.
Hodges et al., Multiply deleted [E1, polymerase-, and pTP-] adenovirus vector persists despite deletion of the preterminal protein. J Gene Med. Jul.-Aug. 2000;2(4):250-9. doi: 10.1002/1521-2254(200007/08)2:4<250::AID-JGM113>3.0.CO;2-3. PMID: 10953916.
Hodges et al., Adenovirus vectors with the 100K gene deleted and their potential for multiple gene therapy applications. J. Virol. 2001, 75 (13), 5913-20.
Karen et al., Adenovirus core protein VII protects the viral genome from a DNA damage response at early times after infection. J. Virol. 2011, 85 (9), 4135-42.
Liu et al., A thermolabile mutant of adenovirus 5 resulting from a substitution mutation in the protein VIII gene. J Virol. Mar. 1985;53(3):920-5. doi: 10.1128/JVI.53.3.920-925.1985. PMID: 3973969; PMCID: PMC254727.
Matsugo et al., A potential bat adenovirus-based oncolytic virus targeting canine cancers. Sci. Rep. 2021, 11 (1), 16706.
Matsugo et al., Establishment of a simple and efficient reverse genetics system for canine adenoviruses using bacterial artificial chromosomes. Viruses 2020, 12 (7).
Morrison et al., Generation of E3-deleted canine adenoviruses expressing canine parvovirus capsid by homologous recombination in bacteria. Virology. Feb. 1, 2002;293(1):26-30. doi: 10.1006/viro.2001.1262. PMID: 11853396.
Ostapchuk et al., Characterization of Empty adenovirus particles assembled in the absence of afunctional adenovirus IVa2protein. J Virol. Jun. 2011;85(11):5524-31. doi: 10.1128/JVI.02538-10. Epub Mar. 30, 2011. PMID: 21450831; PMCID: PMC3094949.
Papa et al., Genetic engineering by DNA recombineering. Curr. Protoc. Chem. Biol. 2019, 11 (3), e70.
Reddy et al., Development of porcine adenovirus-3 as an expression vector. J Gen Virol. Mar. 1999;80 ( Pt 3):563-570. doi: 10.1099/0022-1317-80-3-563. PMID: 10091994.
Ruzsics et al., Engineering adenovirus genome by bacterial artificial chromosome (BAC) technology. Methods Mol. Biol. 2014, 1089, 143-58.
Shayakhmetov et al., Deletion of penton RGD motifs affects the efficiency of both the internalization and the endosome escape of viral particles containing adenovirus serotype 5 or 35 fiber knobs. J Virol. Jan. 2005;79(2):1053-61. doi: 10.1128/JVI.79.2.1053-1061.2005. Erratum in: J Virol. Apr. 2005;79(7):4553. PMID: 15613334; PMCID: PMC538548.
Wu et al., The adenovirus L4-33K protein regulates both late gene expression patterns and viral DNA packaging. J. Virol. 2013, 87 (12), 6739-47.
Wu et al., The adenovirus L4-22K protein is multifunctional and is an integral component of crucial aspects of infection. J. Virol. 2012, 86 (19), 10474-83.
Youil et al., Hexon gene switch strategy for the generation of chimeric recombinant adenovirus. Hum Gene Ther. Jan. 20, 2002;13(2):311-20. doi: 10.1089/10430340252769824. PMID: 11812286.
Yu et al., A simplified system for generating recombinant E3-deleted canine adenovirus-2. Plasmid. Jan. 2015;77:1-6. doi: 10.1016/j.plasmid.2014.10.005. Epub Oct. 31, 2014. PMID: 25450764.

* cited by examiner

| Substitution (AA or location) | Max Freq. Observed | Fixed? |
|---|---|---|
| E147K | 98% | Yes |
| CMV-Enhancer | 23% | Yes |
| H100Y | 14% | No |
| CMV-Enhancer | 11% | No |
| Pre-gene | 8% | Yes |
| Pre-gene | 7% | No |
| D178E | 4% | No |

GOI selection based on regulation of prot stability

GOI selection based on cellular localization

GOI selection based on stop codon suppression

293A (+ wt AdPol)

METHODS AND COMPOSITIONS FOR PERFORMING CONTINUOUS DIRECTED EVOLUTION

RELATED APPLICATIONS

This application claims priority under 35 USC § 119(e) to U.S. provisional patent application No. 62/734,520, filed Sep. 21, 2018 and U.S. provisional application No. 62/577,867, filed Oct. 27, 2017, the entire contents of which are incorporated herein by reference.

GOVERNMENT SUPPORT

This invention was made with Government support under Grant No. GM119162 awarded by the National Institutes of Health. The Government has certain rights in the invention.

FIELD

Disclosed herein are methods of performing continuous directed evolution in complex biological systems, including metazoan cells. These methods include the infection of engineered, non-naturally occurring metazoan cells with engineered, non-naturally occurring DNA viruses. The generation of infectious viruses that can infect new cells depends on the evolution of a gene of interest which is driven by an error-prone DNA virus DNA polymerase. Also disclosed herein, are the compositions of engineered, non-naturally occurring metazoan cells and engineered, non-naturally occurring DNA viruses that function as components in the continuous directed evolution methodologies.

BACKGROUND

Existing directed evolution platforms typically involve either nonliving or simple biologically systems, such as bacteria or yeast. Generally, performing directed evolution in non-living or simple biological systems is a time-intensive process because these system require discrete steps for mutagenesis, screening/selection, and amplification—requiring a number of weeks for a single round of directed evolution. The principal alternative approach, directed evolution by somatic hypermutation, relies on the tedious screening of positive variants by fluorescence-assisted cell sorting (FACS) and requires at least a week for a single round of directed evolution because of the slow growth rate of eukaryotic cells (Wang et al., Proc. Natl. Acad. Sci. U.S.A. 2004 Nov. 30; 101(48):16745-49). Both the FACS approach to screening and the slow cellular growth rate significantly limit the size of the library that can be effectively screened and amplified using directed evolution by somatic hypermutation.

SUMMARY

Genetic engineers have long aspired to create tailored biomolecules with new or improved functions. However, these aspiration have been limited by the shortcomings of currently available technologies, such as "cheating" mechanisms that can subvert selection. Provided herein are methodologies that overcome these shortcomings and their compositions.

Disclosed herein are compositions of components of directed evolution systems. In one aspect, the compositions of engineered, non-naturally occurring DNA viruses are provided. In some embodiments, the engineered, non-naturally occurring DNA virus comprises a modified genome, wherein the modified genome comprises: (a) an integration of at least one polynucleic acid sequence comprising the sequence of a transcribable gene of interest; (b) a deletion of the sequence encoding for the viral DNA polymerase; and (c) a deletion of at least one sequence encoding for a protein necessary for the production of infectious DNA virus particles.

In some embodiments, the engineered, non-naturally occurring DNA virus is an adenovirus. In some embodiments, the engineered, non-naturally occurring adenovirus is derived from an adenovirus selected from the genera consisting of Adenovirus, Aviadenovirus, Ichtadenovirus, Mastadenovirus, and Siadenovirus. In some embodiments, the engineered, non-naturally occurring adenovirus is derived from a Mastadenovirus adenovirus. In some embodiments, the adenovirus is a human adenovirus selected from the group consisting of HAdV-A, HAdV-B, HAdV-C, HAdV-D, HAdV-E, HAdV-F, and HAdV-G. In some embodiments, the human adenovirus is a HAdV-C adenovirus selected from the group consisting of HAd2 and HAd5.

In some embodiments, the at least one sequence encoding for a protein necessary for the production of infectious DNA virus particles is not the sequence of the adenoviral fiber protein. In some embodiments, the at least one sequence encoding for a protein necessary for the production of infectious DNA virus particles comprises the sequence encoding for the adenoviral protease.

In another aspect, compositions of engineered, non-naturally occurring metazoan cells are provided. In some embodiments, the engineered, non-naturally occurring living metazoan cell comprises a modified genome, wherein the modified genome comprises: (a) an integration of a polynucleic acid sequence comprising the sequence of an error-prone DNA virus DNA polymerase and (b) an integration of at least one polynucleic acid sequence comprising a sequence encoding for an expressible protein, wherein said expressible protein is necessary for the production of infectious DNA virus particles.

In some embodiments, the metazoan cell from which the non-naturally occurring living metazoan cell is derived is susceptible to DNA virus infection in the metazoan cell's native state. In some embodiments, the engineered, non-naturally occurring living metazoan cell is derived from the group consisting of a human, mouse, rat, cat, dog, pig, guinea pig, hamster, sheep, macaque, and chimpanzee cell. In some embodiments, the engineered, non-naturally occurring living metazoan cell is derived from a human cell line. In some embodiments, the human cell line is HEK-293.

In some embodiments, the sequence of the error-prone DNA virus DNA polymerase is the sequence of an error-prone adenoviral DNA polymerase. In some embodiments, the sequence of the error-prone DNA virus DNA polymerase is a non-natural adenoviral polymerase sequence derived from a sequences selected from the group consisting of the HAd2 DNA polymerase sequence and the HAd5 DNA polymerase sequence. In some embodiments, the sequence of the error-prone DNA virus DNA polymerase is a non-natural adenoviral DNA polymerase sequence derived from the HAd5 DNA polymerase sequence. In some embodiments, the non-natural adenoviral DNA polymerase sequence derived from the HAd5 DNA polymerase sequence comprises the HAd5 DNA polymerase sequence with at least one mutation selected from the group consisting of T286I, N417A, F421Y, S506T, V585A, and D827A. In some embodiments, the non-natural adenoviral DNA polymerase sequence derived from the HAd5 DNA polymerase sequence is SEQ ID NO: 27.

In some embodiments, the sequence encoding for a protein necessary for the production of infectious DNA virus particles is not the sequence of the adenoviral fiber protein. In some embodiments, the sequence encoding for a protein necessary for the production of infectious DNA virus particles comprises the sequence of the adenoviral protease.

Also disclosed herein are methods of performing continuous directed evolution in complex biological systems, including metazoan cells. In some embodiments, methods of performing continuous directed evolution of a polynucleic acid sequences that comprises the sequence of at least one gene of interest are provided. In some embodiments, the method comprises infecting engineered, non-naturally occurring living metazoan cells with at least one engineered, non-naturally occurring DNA virus, wherein: (a) the at least one engineered, non-naturally occurring DNA virus comprises a modified genome, wherein the modified genome comprises: an integration of at least one polynucleic acid sequence comprising the sequence of a transcribable gene of interest; a deletion of the sequence encoding for the viral DNA polymerase; and a deletion of at least one sequence encoding for a protein necessary for the production of infectious DNA virus particles; (b) the engineered, non-naturally occurring living metazoan cells comprise modified genomes, wherein each modified genome comprises: an integration of a polynucleic acid sequence comprising the sequence of an error-prone DNA virus DNA polymerase and an integration of at least one polynucleic acid sequence comprising the sequence encoding for the protein necessary for the production of infectious DNA virus particles in (a) under the control of a functionally-coupled promoter, optionally a transcriptionally-coupled promoter; and (c) generating infectious DNA virus particles by the engineered, non-naturally occurring living metazoan cells infected with the at least one engineered, non-naturally occurring DNA virus, wherein the generation of the infectious DNA virus particles is dependent upon the evolution of the at least one polynucleic acid sequence comprising the sequence of the transcribable gene of interest in (a), wherein said evolution is driven by the error-prone DNA virus DNA polymerase encoded by the polynucleic acid sequence of (b). In some embodiments, the method further comprises screening the engineered, non-naturally occurring living metazoan cells for highly infectious DNA virus particles.

In some embodiments, at least one of the at least one polynucleic acid sequences comprising the sequence of a transcribable gene of interest in (a) is a protein coding sequence, wherein expression and translation of the protein coding sequence generates at least one protein product.

In some embodiments, the at least one protein product, when unevolved, induces the expression of the at least one polynucleic acid sequence comprising the sequence encoding for the protein necessary for the production of infectious DNA virus particles in (b), and administering an agent that decreases the capability of the at least one protein product of inducing expression of the protein necessary for the production of infectious DNA virus particles in (b).

In some embodiments, the at least one protein product, when unevolved, inhibits the expression of the at least one polynucleic acid sequence comprising the sequence encoding for the protein necessary for the production of infectious DNA virus particles in (b).

In some embodiments, the at least one protein product, when unevolved, cannot induce the expression of the at least one polynucleic acid sequence comprising the sequence encoding for the protein necessary for the production of infectious DNA virus particles in (b).

In some embodiments, the at least one protein product, when unevolved, regulates the stability of the protein necessary for the production of infectious DNA viruses.

In some embodiments, the at least one protein product, when unevolved, regulates the subcellular trafficking of the protein necessary for the production of infectious DNA viruses.

In some embodiments, the sequence encoding for the protein necessary for the production of infectious DNA virus particles in (b) further comprises the sequence of an inhibitory tag, wherein the sequence of the protein necessary for the production of infectious DNA virus particles and the sequence of the inhibitory tag are coupled, and wherein: (a) translation of the sequence comprising the sequence encoding for the protein necessary for the production of infectious DNA virus particles and the sequence of the inhibitory tag generates a tagged protein and (b) removal of inhibitory tag in (a) is dependent upon the evolution of the at least one polynucleic acid sequence comprising the sequence of the gene of interest.

In some embodiments, the inhibitory tag is selected from the group consisting of a protein degradation tag or a protein sequestration tag. In some embodiments, the inhibitory tag is protein degradation tag, wherein the protein degradation tag is a degron tag. In some embodiments, the gene of interest is a protease.

In some embodiments, at least one of the at least one polynucleic acid sequences comprising the sequence of a transcribable gene of interest in (a) is the sequence of a non-coding RNA. In some embodiments, the sequence encoding for the protein necessary for the production of infectious DNA virus particles in (b) further comprises a premature stop codon in the sequence encoding for the at least one protein necessary for the production of infectious DNA virus particles. In some embodiments, the sequence of the gene of interest comprises the sequence of a tRNA. In some embodiments, the sequence of the gene of interest comprises the sequence of an aminoacyl tRNA synthetase.

In some embodiments, the at least one sequence encoding for a protein necessary for the production of infectious DNA virus particles is not the sequence of the adenoviral fiber protein. In some embodiments, at least one of the at least one sequence encoding for a protein necessary for the production of infectious DNA viral particles comprises the sequence encoding for the adenoviral protease.

In some embodiments, the at least one engineered, non-naturally occurring DNA virus is derived from an adenovirus. In some embodiments, the adenovirus selected from the genera consisting of Adenovirus, Aviadenovirus, Ichtadenovirus, Mastadenovirus, and Siadenovirus. In some embodiments, the adenovirus is derived from a Mastadenovirus adenovirus. In some embodiments, the adenovirus is a human adenovirus selected from the group consisting of HAdV-A, HAdV-B, HAdV-C, HAdV-D, HAdV-E, HAdV-F, and HAdV-G. In some embodiments, the human adenovirus is a HAdV-C adenovirus selected from the group consisting of HAd2 and HAd5.

In some embodiments, the engineered, non-naturally occurring living metazoan cells are derived from the group consisting of a human, mouse, rat, cat, dog, pig, guinea pig, hamster, sheep, macaque, and chimpanzee cells. In some embodiments, the engineered, non-naturally occurring living metazoan cells are derived from a human cell line. In some embodiments, the human cell line is HEK-293.

In some embodiments, the sequence of the error-prone DNA virus DNA polymerase is a non-natural adenoviral polymerase sequence derived from a sequences selected from the group consisting of the HAd2 and HAd5 DNA polymerase sequence. In some embodiments, the sequence of the error-prone DNA virus DNA polymerase is a non-natural adenoviral DNA polymerase sequence derived from the HAd5 DNA polymerase sequence. In some embodiments, the non-natural adenoviral DNA polymerase sequence derived from the HAd5 DNA polymerase sequence comprises the HAd5 DNA polymerase sequence with at least one mutation selected from the group consisting of T286I, N417A, F421Y, S506T, V585A, and D827A. In some embodiments, the non-natural adenoviral DNA polymerase sequence derived from the HAd5 DNA polymerase sequence consisting of SEQ ID NO: 27.

In some embodiments, the error-prone adenoviral DNA polymerase is constitutively expressed in the engineered, non-naturally occurring metazoan cells.

In some embodiments, a small molecule is added to the culture conditions to increase selection stringency, wherein the small molecule decreases the functionality of the protein necessary for the production of infectious DNA viral particles.

In some embodiments, the engineered, non-naturally occurring living metazoan cells are in suspension.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 18A. Prot stability is regulated by a degron. Only stabilization or removal of the degron by the GOI results in functional prot. FIG. 18B. Prot is localized to some subcellular compartment via a localization signal (such as a nuclear ex-port signal). GOI variants that are able to induce prot transport to the nucleus, where it is required for proper function, will result in functional adenovirus. FIG. 18C. A translational couple to evolve aaRS/tRNA pairs. A premature amber stop codon at a permissive site in prot results in termination and a nonfunctional, truncated prot. However, if a functional aaRS/tRNA pair is able to suppress the amber stop codon, prot will be translated in full.

FIG. 19A. Schematic of an engineered adenovirus type-5 vector in which genes for adenoviral polymerase (AdPol) and pro-tease (AdProt) are removed and a gene encoding the biomolecule of interest (BOI) for directed evolution is introduced, as well as a fluorescent protein (FP) for visualization during infection. FIG. 19B. Schematic of engineered human cells constitutively expressing a highly error-prone AdPol (termed EP-Pol) and conditionally ex-pressing AdProt at levels directly dependent on BOI activity. FIG. 19C. Schematic for adenoviral-based directed evolution of BOIs in human cells: (i) The BOI is delivered into the human cell via ade-noviral infection. (ii) EP-Pol introduces mutations into the BOI gene, generating a mutational library. (iii) The desired BOI function is coupled to the expression or activity of AdProt such that (iv) only functional BOI variants result in viral propagation. (v) If the BOI variant is non-functional, AdProt is not expressed or active and the adenovirus encoding that variant is outcompeted.

FIG. 20A. Crystal structure of the +29 DNA polymerase (PDBID 1 XHZ) (Kamtekar S. et al., Mol. Cell 16, 609-618 (2004)), an AdPol homolog, with the locations of homologous mutations used to create EP-Pol indicated (Kamtekar S. et al., Mol. Cell 16, 609-618, doi: 10.1016/j.molcel.2004.10.019 (2004)). FIG. 20B. Either parental HEK293A cells or cells constitutively expressing EP-Pol were infected with a GFP-encoding ΔAdPol-adenovirus (CFP. ΔAdPol.GFP). The virus propagated only on EP-Pol trans-complementing cells. Similar results were obtained for wild-type AdPol (FIG. 24). FIG. 20C. ΔAdPol-adenovirus (AdGLΔPol [Uil T. G. et al., Nucleic Acids Res., 39(5): e30 (2011); Lichy J. H. et al., Proc. Natl. Acad. Sci., 79, 5225-5229 (1982)])) was serially passaged on EP-Pol expressing cells for ten passages, after which a 6.5 kb genomic fragment was amplified from an ~30 clone pool. Illumina sequencing identified mutations throughout the amplified region. For substitution values, see TABLE 4. FIG. 20D. Mutational spectrum of EP-Pol evaluated by next-generation sequencing.

FIG. 21A. Schematic of the competition experiment between adenoviruses that carry the gene for wild-type tetracycline transactivator ($tTA_{wt}$.mCherry) versus viruses that carry inactive tTA ($tTA_{mut}$.GFP). HEK293A cells stably encoding the gene for adenoviral protease (AdProt) under control of the endogenous tTA operator are infected by an initial ratio of 1:100 or 1:1,000 $tTA_{wt}$.mCherry to $tTA_{mut}$.GFP viruses. Viral media was serially passaged onto a new plate of cells for three rounds. The viral populations were then determined via flow cytometry. FIG. 21B. Quantification of flow cytometry data from the competition experiment. The proportion of $tTA_{wt}$.mCherry adenoviruses relative to $tTA_{mut}$.GFP adenoviruses rapidly increased with each passage. The initial ratio of the 1:1,000 sample (labeled N.D.; not detectable) was not experimentally quantifiable owing to the low amount of tTAwt.mCherry adenovirus present, and was therefore derived by dilution of the 1:100 initial ratio. For raw flow cytometry data, see FIG. 26 and FIG. 27. FIG. 21C. AdProt-based selection pressure in combination with administration of a small molecule AdProt inhibitor (structure shown) provides access to an orders of magnitude-wide dynamic range of selection pressure. tTA-inducible AdProt cells were infected with $tTA_{wt}$.mCherry adenovirus, and treated with a combination of doxycycline (dox) and the AdProt inhibitor. The resulting viral supernatant was titered by flow cytometry. The titer of the adenovirus treated with 20 µM AdProt inhibitor and 2 nM dox was too low to be accurately detected (N.D.; not detectable).

FIG. 22A. Serial-passaging schemes for evolving functional tTA variants that gain dox resistance in human cells. Two approaches to selection pressure were used, either with increasing dox concentrations (Trial 1) or a constant, moderate dox concentration (Trial 2). FIG. 22B. tTA-induced GFP expression in the presence of dox after each round of evolution for Trial 1. Phenotyping cells were infected with passaged viral populations and analyzed by flow cytometry. The percentage of infected GFP-positive cells at each passage in the presence of dox was normalized to the percentage of infected GFP-positive cells at each passage in the absence of dox. N.D.=not detectable owing to low viral titer. FIG. 22C. Non-reference allele frequencies for all mutations observed at >1% frequency over the course of the directed evolution experiment for Trial 1 (see FIG. 28 for Trial 2). A schematic of the sequenced amplicon is shown below the x-axis for reference. FIG. 22D. Mutational trajectories of four mutations identified in Trial 1, including two non-coding mutations in the CMV promoter upstream of the tTA gene. FIG. 22E. Mutational trajectories of four abundant mutations identified in Trial 2, including two non-coding mutations in the CMV promoter upstream of the tTA gene. FIG. 22F. Plasmids encoding the tTA variants that fixed in Trials 1 and 2 were transfected, along with the pLVX-TRE3G.eGFP reporter plasmid, into HEK293A cells with or without dox (N=3). Two days later, flow cytometry was performed to examine tTA variant activity in the presence versus the absence of 20 µM dox.

FIG. 30A. Two adenoviral polymerase-expressing single colony HEK293A cell lines were created. One expressed the wild-type adenoviral polymerase (wt-AdPol), the other EP-Pol. Both proteins were tagged with an HA antigen for immunoblot detection. FIGS. 30B-30D. Either parental HEK293A cells (FIG. 30B), cells stably expressing wt-AdPol (FIG. 30C), or EP-Pol (FIG. 30D) were infected with a GFP-encoding ΔAdPol-adenovirus. The virus propagated only on wt AdPol or EP-Pol trans-complementing cells.

FIG. 33A. Adenovirus fiber is a trimeric protein with each subunit consisting of a tail domain, 22-repeat shaft domain, and knob domain. FIG. 33B. Western blot of various fiber-expressing cell lines.

FIG. 37A. Structure of vinyl sulfone protease inhibitor. FIG. 37B. The titer of Ad5.GFP in response to a single round of passaging in the presence of various concentrations of protease inhibitor. FIG. 37C. The titer of tTAwt.mCherry viruses decreased in a dose-dependent manner when grown in the presence of varying concentrations of a vinyl sulfone AdProt inhibitor in both the absence and presence of 2 nM dox.

FIG. 38A. Non-reference allele frequencies for all mutations observed at >1% frequency over the course of the directed evolution experiment for Trial 1. Schematic of the sequenced amplicon is shown below the x-axis for reference. FIG. 38B. Non-reference allele frequencies at >1% frequency over the course of the directed evolution experiment for Trial 2. FIG. 38C. Mutational frequency of the four abundant mutations in Trial 1, including two noncoding mutations in the CMV promoter upstream of the tTA gene. FIG. 38D. Mutational trajectories of four abundant mutations identified in Trial 2, including two non-coding mutations in the CMV promoter upstream of the tTA gene.

FIG. 39A. tTA variants were co-transfected in triplicate with the pLVX.TRE3G.eGFP reporter plasmid into HEK293A cells and dox was added. Two days later, flow cytometry was performed to examine the inducibility of tTA variants in the presence of dox. FIG. 39B. RT-qPCR data showing tTA transcripts driven by CMV promoter mutants. Relative transcription levels are normalized to mCherry transcript levels since mCherry expression was driven by a different promoter on the same plasmid.

FIG. 40A. If these cells are infected with a virus that does not contain an active BOI, the lack of active AdProt means that the virus cannot replicate. FIG. 40B. If the selector cells are infected with a virus that carries an active BOI, active AdProt is produced, allowing the virus to replicate. Viral titers of the two populations are compared by flow cytometry.

FIG. 41A. Recombinase circuit to select for Cre function. Cre recombines the loxP sites to delete the polyA terminator signal, allowing transcription of AdProt downstream. FIG. 41B. tRNA/amino-acyl tRNA synthetase circuit to select for synthetases that can charge amber stop codon tRNAs. Only if the synthetase charges a tRNA with an amber stop anticodon will the premature stop codon in AdProt be suppressed, allowing translation of the full length gene.

FIG. 45A. Experimental setup for the enrichment experiment. $tTA_{wt}$.mCherry.ΔAdPol.adenovirus and $tTA_{mut}$.mCherry.ΔAdPol.adenovirus were mixed at a ratio of 1:10 and used to infect reporter cells. Cells were sorted on both mCherry fluorescence and eGFP fluorescence to sort for infected, induced cells. Following the sort, the resulting adenovirus was amplified, and used to infect reporter cells again to analyze the enrichment of eGFP induction. FIG. 45B. Density plots of the enrichment experiment for $tTA_{mut}$. mCherry. ΔAdPol.adenovirus, $tTA_{wt}$.mCherry. ΔAdPol.adenovirus, the 1:10 mixture before enrichment, and the 1:10 mixture after enrichment, in order from left to right. The level of adenovirus-induced eGFP induction was determined by dividing the number of infected cells expressing eGFP (Q2) by the total number of infected cells.

DETAILED DESCRIPTION

Our limited understanding of the relationship between a gene's primary sequence and a protein's three-dimensional structure/function severely limits our ability to rationally design genes and proteins. Platforms that harness the power of directed evolution offer an alternative strategy. By mimicking nature's processes of mutagenesis, screening/selection, and amplification, scientists have created new biomolecules with a diverse array of functions (Arnold F. H., Acc. Chem. Res. 1998 Feb. 28; 31(3):125-31).

Figure 1:
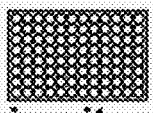
FIG. 1. Advantages/disadvantages of directed evolution platforms for metazoan applications. Many directed evolution systems exist, including in vitro-, bacterial-, and yeast-based systems. In all of these systems, mechanisms exist to mutagenize genes of interest, select for positive variants, and even evolve biomolecules continuously. However, each of these systems lack the environment of the metazoan cell, including the proper post-translational modification networks, appropriate biological machinery (sub-cellular compartments, transcriptional machinery, etc.), and the proper proteostasis networks. Importantly, no robust system to mutagenize and select for biomolecules continuously in human cells has previously been described.

While directed evolution is a powerful methodology, virtually all current directed evolution platforms are limited to mutating and selecting for biomolecule function either in test tubes, bacteria, or yeast (FIG. 1). Most of these systems require discrete steps for mutagenesis, screening/selection, and amplification, which can take weeks in order to do a single round of directed evolution. Moreover, biomolecules created in these simple systems often fail to function when they are transferred to more complex metazoan systems, and some desirable functions are too reliant on metazoan biology for scientists to be able to design valid selection schemes in simpler organisms or in a test tube.

The principal alternative approach—directed evolution by somatic hypermutation—relies on the tedious screening of positive variants by fluorescence-assisted cell sorting (FACS) and requires at least a week for a single round of directed evolution because of the slow growth rate of metazoan cells (Wang et al., Proc. Natl. Acad. Sci. USA 2004 Nov. 30; 101(48):16745-49; Das et al., J. Biol. Chem. 2004 Apr. 30; 279(18):18776-82). Both the FACS approach to screening and the slow cellular growth rate significantly limit the size of the library that can be effectively screened and amplified using directed evolution by somatic hypermutation.

Consequently, there is a great need for a robust, generalizable directed evolution platform in metazoan cells. Indeed, biomedical research and clinical applications generally rely on biomolecules functioning in such systems. While there have been a few attempts at creating platforms for directed evolution in human cells, these systems are either very limited in their utility or suffer from "cheating" mechanisms (e.g., non-specific mutation of the host cell genome that overcomes the selective evolutionary pressure) that can subvert selection (Wang et al., Proc. Natl. Acad. Sci. USA 2004 Nov. 30; 101(48):16745-49; Das et al. J. Biol. Chem. 2004 Apr. 30; 279(18): 18776-82).

Described herein are methods of performing continuous directed evolution that overcome many of the limitations of existing systems. First, these methods facilitate directed evolution in metazoan cells, including human cells. Second, these methods rely on the rapid replication of DNA viruses, such as adenovirus, which enable rapid library amplification and multiple rounds of directed evolution within a week—significantly faster than other approaches for continuous directed evolution and somatic hypermutation approaches. Third, these methods generally facilitate the testing of library sizes several orders of magnitude larger than current screening-based approaches. Indeed, performing the methods described herein on cells in suspension culture allows continuous directed evolution at bioreactor scale. Fourth, these methods are much less prone to cheating selection because they do not involve the mutation of the host cell genome. Finally, the continuous nature of the platform for performing continuous directed evolution enables multiplexing directed evolution experiments with ease.

Taken together, the continuous nature of the system, the selection based evolution approach, and the rapid amplification of the evolving DNA viruses combine to make a highly scalable platform for directed evolution in metazoan cells. By providing a robust, generalizable approach to directed evolution in metazoan cells, this methodology has significant potential for guiding the design of therapeutics, not just directly developing them. For example, the methodologies described herein enable researchers to study how proto-oncogenes evolve on the path to cancer or in response to chemotherapeutics. Such experiments are extremely insightful to design of drugs against oncogene targets (e.g., the directed evolution of monobodies that inhibit oncogenes).

Disclosed herein are compositions of engineered, non-naturally occurring components of a continuous directed evolution system. As used herein, the term "continuous directed evolution system" refers to a platform that facilitates the seamless integration of mutagenesis, screening/selection, and amplification of biomolecules in an uninterrupted cycle. As used herein, the term "engineered, non-naturally occurring" refers to compositions (e.g., molecules, organisms or bioparticles) that do not exist naturally, but that have been modified in a laboratory setting. As such, these compositions arise from human innovation. In some embodiments, the organism or bioparticle (e.g., virus) comprises a modified genome. The term "modified genome," as used herein, refers to a non-natural genome, wherein the natural genome has been altered or edited by a polynucleic acid integration or deletion. As used herein, the term "integration" refers to instances in which extrinsic genetic material is added to a natural genome. As used herein, the term "deletion" refers to instances in which intrinsic genetic material is removed from a natural genome. In some embodiments, a modified genome comprises a replacement or substitution, wherein the replacement or substitution comprises deletion and integration of similar genetic material. Various means of performing genome modification are known to those with skill in the art and include, but are not limited to, recombinant cloning, homologous recombination, and nonhomologous end-joining and may involve the use of engineered nucleases such as zinc finger nucleases, transcription activator like effector nucleases, and/or CRISPR/Cas nucleases.

As used herein, the term "polynucleic acid" refers to a string of nucleotides linked together via phosphodiester bonds. Nucleotides come in a variety of forms which are known to those having skill in the art. The term "polynucleic acid sequence," as used herein, refers to the sequence of nucleotides in a polynucleic acid molecule. In some embodiments, a polynucleic acid is a single-stranded DNA (i.e., ssDNA). In other embodiments, a polynucleic acid is a double-stranded DNA (i.e., dsDNA). In other embodiments, a polynucleic acid is a single-stranded RNA (i.e., ssRNA). In yet other embodiments, a polynucleic acid is a double-stranded RNA (i.e., dsRNA). In still other embodiments, a polynucleic acid is a double-stranded hybrid of a ssDNA and a ssRNA.

In one aspect, compositions of engineered, non-naturally occurring DNA viruses are provided. In some embodiments, the composition of the engineered, non-naturally occurring DNA virus comprises a modified viral genome, wherein the modified viral genome comprises (a) an integration of at least one polynucleic acid sequence comprising the sequence of a transcribable gene of interest, (b) a deletion of the sequence encoding for the viral DNA polymerase, and (c) a deletion of at least one sequence encoding for a protein necessary for the production of infectious DNA virus particles.

The term "DNA virus" refers to a group of viruses whose genetic material is in the form of DNA. A DNA virus may possess a genome that is double-stranded DNA or a genome that is single-stranded DNA. Examples of DNA viruses are known to those having skill in the art, and include but are not limited to viruses of the families Adenoviridae, Ascoviridae, Ampullaviridae, Anelloviridae, Asfarviridae, Baculoviridae, Bidnaviridae, Corticoviridae, Circoviridae, Geminiviridae, Genomoviridae, Herpesviridae, Inoviridae, Iridoviridae, Lipothrixviridae, Microviridae, Nanoviridae, Nimaviridae, Papovaviridae, Phycodnaviridae, Pleolipoviridae, Polydnaviridae, Poxviridae, Parvoviridae, Spiraviridae, and Tectiviridae.

In some embodiments, the engineered, non-naturally occurring DNA virus is an engineered, non-naturally occurring adenovirus. The term "adenovirus," as used herein, refers to a family of non-enveloped icosahedral nucleocapsid viruses that contain a double-stranded DNA genome. Adenoviruses are frequently used to deliver genes into human cells for biological study (Benihoud et al., Curr. Opin. Biotechnol. 1999 October; 10(5)440-47). The adenovirus genome encodes for a DNA polymerase (i.e., an adenoviral DNA polymerase) that is responsible for replicating the genome independent of the host machinery. Importantly, unlike VSV and other retroviruses, adenovirus is a lytic virus, meaning any infected cells are killed at the conclusion of the viral replication cycle. This removes infected cells from culture and significantly reduces the possibility of selection subversion.

In some embodiments, the engineered, non-naturally occurring adenovirus is derived from an adenovirus selected from the genera consisting of Atadenovirus, Aviadenovirus, Ichtadenovirus, Mastadenovirus, and Siadenovirus. In some embodiments, the engineered, non-naturally occurring adenovirus is derived from a Mastadenovirus adenovirus. In some embodiments, the engineered, non-naturally occurring adenovirus is a human adenovirus selected from the group consisting of HAdV-A, HAdV-B, HAdV-C, HAdV-D, HAdV-E, HAdV-F, and HAdV-G. Examples of human adenoviruses within these groups are known to those having skill in the art and include, but are not limited to, HAdV1, HAdV2, HAdV3, HAdV4, HAdV5, HAdV6, HAdV7, HAdV8, HAdV9, HAdV10, HAdV11, HAdV12, HAdV13, HAdV14, HAdV15, HAdV16, HAdV17, HAdV18, HAdV19, HAdV20, HAdV21, HAdV22, HAdV23, HAdV24, HAdV25, HAdV26, HAdV27, HAdV28, HAdV29, HAdV30, HAdV31, HAdV32, HAdV33, HAdV34, HAdV35, HAdV36, HAdV36, HAdV38, HAdV39, HAdV40, HAdV41, HAdV42, HAdV43, HAdV44, HAdV45, HAdV46, HAdV47, HAdV48, HAdV49, HAdV50, HAdV51, HAdV52, HAdV53, HAdV54, HAdV55, HAdV56, and HAdV57. In some embodiments, an engineered, non-naturally occurring adenovirus is derived from an HAdV-C adenovirus selected from the group consisting of HAd2 and HAd5. In some embodiments, the non-naturally occurring adenovirus is derived from HAd2.

The term "protein necessary for the production of infectious DNA virus particles," as used herein, refers to protein, whose absence from a host cell infected with a DNA virus (or absence in its native form), decreases the generation of infectious DNA virus particles by at least 25%, 30%, 40%, 50%, 60%, 70%, 75%, 80%, 90%, 95% or 100% relative to generation of infectious particles in the presence of protein (or presence in its native form). Methods of measuring and comparing viral particle infectivity are known to those with skill in the art, and include, but are not limited to, comparisons of plaque forming units (pfu), multiplicity of infection (moi), and TCID50. Proteins that are necessary for the generation of infectious DNA virus particles are known to those having skill in the art. For example, those of adenovirus include, but are not limited to the adenoviral protease, adenoviral fiber protein, pVI, and E2A. In some embodiments, the at least one sequence encoding for a protein necessary for the production of infectious DNA virus particles is not the sequence of the adenoviral fiber protein. In some embodiments, the at least one sequence encoding for a protein necessary for the production of infectious DNA virus particles comprises the sequence encoding for the adenoviral protease.

The terms, "gene of interest" or "biomolecule of interested" are used interchangeably and refer to any DNA sequence, or polynucleic acid molecule or protein molecule encoded by the DNA sequence, that one seeks to evolve. For example, in some embodiments, the gene of interest (or biomolecule of interest) is the sequence of a programming region (i.e., does not code for an RNA; e.g., a promoter). In other embodiments, the gene of interest (or biomolecule of interest) comprises a DNA sequence that can be transcribed or is "transcribable." As used herein, the terms "transcribed" and "transcription" refer to the process in which a particular segment of DNA is copied into RNA.

In some embodiments, the gene of interest (or biomolecule of interest) comprises the sequence of a non-coding RNA (i.e., does not code for a protein). For example, in some embodiments the sequence of the gene of interest encodes the sequence of an RNA selected form the list consisting of rRNA, tRNA, tmRNA, snRNA, snoRNA, scaRNA, gRNA, RNase P, RNase MRP, antisense RNA, crRNA, lncRNA, miRNA, piRNA, siRNA, and shRNA. Other forms of non-coding RNA are known to those having skill in the art.

In other embodiments, the gene of interest (or biomolecule of interest) encodes the sequence of a mRNA that can be translated. The terms "translation" or "translated" refer to the process in which a particular mRNA is decoded to generate a polypeptide or protein. As used herein, the terms "polypeptide" or protein" refer to a string of amino acids linked together via amide bonds. Amino acids come in a variety of forms which are known to those having skill in the art. The term "amino acid sequence," as used herein, refers to the sequence of amino acids in a protein or a polypeptide.

In another aspect, compositions of engineered, non-naturally occurring metazoan cells are provided. In some embodiments, the engineered, non-naturally occurring metazoan cells comprise a modified genome, wherein the modified genome comprises (a) an integration of a polynucleic acid sequence comprising the sequence of an error-prone DNA virus DNA polymerase, and (b) an integration of at least one polynucleic acid sequence comprising a sequence encoding for an expressible protein, wherein said expressible protein is necessary for the production of infectious DNA virus particles.

The term, "metazoan," as used herein, refers to animals that are multicellular, mitochondrial eukaryotes. In some embodiments, an engineered, non-naturally occurring living metazoan cell is derived from a metazoan cell that is susceptible to DNA virus infection in the metazoan cell's native state. In other embodiments, the metazoan cell has been modified so as to facilitate the infection of the cell by a DNA virus.

In some embodiments, an engineered, non-naturally occurring living metazoan cell is derived from the group consisting of a human, mouse, rat, cat, dog, pig, guinea pig, hamster, sheep, macaque, and chimpanzee cell. In some embodiments, the engineered, non-naturally occurring living metazoan cell is derived from a human cell line. In some embodiments, the human cell line is an E1-transcomplementing cell line. Examples of E1-transcomplementing cell lines are known to those with skill in the art. In some embodiments, the human cell line is HEK-293. In some embodiments, the non-naturally occurring living metazoan cells are in suspension.

As used herein, the term "error-prone DNA virus DNA polymerase" refers to a native virus DNA polymerase has an increased error rate when exposed to certain conditions. For example, the addition of a small molecule may increase the error-rate of a DNA polymerase. Alternatively, the coexpression of an interacting protein may increase the error-rate of a DNA polymerase. The term "error-prone DNA virus DNA polymerase" also refers to an engineered, non-naturally occurring DNA polymerase in which mutations have been introduced into the sequence of the DNA polymerase, wherein said mutations increase the error rate of the DNA polymerase. The term "error-prone" refers to an error rate that is higher than that of the native form of the DNA virus DNA polymerase in its native conditions by at least 25%, 30%, 40%, 50%, 60%, 70%, 75%, 80%, 90%, 95% or 100%. Methods of measuring the error rate of a DNA polymerase are known to those having skill in the art.

In some embodiments, the sequence of an error-prone DNA virus DNA polymerase is the sequence of an error-prone adenoviral DNA polymerase. In some embodiments, the sequence of the error-prone adenoviral polymerase sequence is a non-natural sequence derived from a sequences selected from the group consisting of the HAd2 polymerase sequence and the HAd5 polymerase sequence or a sequence having about 50%, 60%, 70%, 75%, 80%, 85%, 90%, 91%, 92%, 93%, 94%, 95%, 96%, 97%, 98%, or 99% identity to at least a portion of the sequence of the HAd1 polymerase or HAd5 polymerase, wherein the portion of the sequence comprises about 30%, 40%, 50%, 60%, 70%, 75%, 80%, 85%, 90%, 91%, 92%, 93%, 94%, 95%, 96%, 97%, 98%, or 99% of the native HAd1 polymerase or HAd5 polymerase sequence. In some embodiments, the sequence of a DNA viral DNA polymerase is connected to another sequence, wherein expression and translation of the sequences generates a fused protein. In some embodiments, the sequence of the DNA viral DNA polymerase is connected to a sequence that facilitates expression of the DNA polymerase. In some embodiments, the sequence of the DNA viral DNA polymerase is expressed constitutively. In other embodiments, the sequence of the DNA viral DNA polymerase is expressed conditionally.

In some embodiments, the non-natural adenoviral polymerase sequence is derived from the HAd5 polymerase sequence. In some embodiments, the non-natural polymerase sequence derived from the HAd5 polymerase sequence comprises the HAd5 polymerase sequence with at least one mutation selected from the group consisting of T286I, N417A, F421Y, S506T, V585A, and D827A. In some embodiments the HAd5 polymerase sequence is SEQ ID NO: 27.

In some embodiments, the sequence encoding for a protein necessary for the production of infectious DNA virus particles is not the sequence of the adenoviral fiber protein. In some embodiments, the sequence encoding for a protein necessary for the production of infectious DNA virus particles is the sequence of the adenoviral protease or a sequence having about 50%, 60%, 70%, 75%, 80%, 85%, 90%, 91%, 92%, 93%, 94%, 95%, 96%, 97%, 98%, or 99% identity to at least a portion of the sequence of the adenoviral protease, wherein the portion of the sequence comprises about 30%, 40%, 50%, 60%, 70%, 75%, 80%, 85%, 90%, 91%, 92%, 93%, 94%, 95%, 96%, 97%, 98%, or 99% of the native adenoviral protease sequence. In some embodiments, the sequence of the adenoviral protease is connected to another sequence, wherein expression and translation of the sequences generates a fused protein. In some embodiments, the sequence of the adenoviral protease is connected to a sequence that facilitates expression of the adenoviral protease. For example, in some embodiments, the sequence of the adenoviral protease is connected to a tripartite leader sequence.

Other terms describing compositions of engineered, non-naturally occurring metazoan cells (e.g., "protein necessary for adenovirus infection") carry the same meanings as those described above describing compositions of engineered, non-naturally occurring adenoviruses.

In another aspect, compositions of engineered, non-naturally occurring eukaryotic cells are provided, for example producer cells, mutator cells, and selector cells. As used herein, the term "producer cell" refers to a metazoan cell that expresses: (i) a wild-type viral polymerase and (ii) a protein necessary for the production of infectious DNA virus particles. In some embodiments, the producer cell constitutively expresses the wild-type viral polymerase and/or the protein necessary for the production of infectious DNA virus particles. In other embodiments, the producer cell inducibly expresses the wild-type viral polymerase and/or the protein necessary for the production of infectious DNA virus particles. In some embodiments, the wild-type viral polymerase is AdPol. In some embodiments, the protein necessary for the production of infectious DNA virus particles is AdProt. Through trans-complementation, producer cells infected with an engineered, non-naturally occurring DNA virus described herein facilitate production of nascent adenoviruses containing the necessary deletions and the gene encoding the gene of interest/biomolecule of interest.

The term "mutator cell" as used herein, refers to a metazoan cell that expresses: (i) a protein necessary for the production of infectious DNA virus particles and (ii) an error-prone DNA virus DNA polymerase. In some embodiments, the mutator cell constitutively expresses the error-prone polymerase and/or the protein necessary for the production of infectious DNA virus particles. In other embodiments, the mutator cell inducibly expresses the error-prone viral polymerase and/or the protein necessary for the production of infectious DNA virus particles. In some embodiments, the error-prone viral polymerase is EP-Pol. In some embodiments, the protein necessary for the production of infectious DNA virus particles is AdProt. Mutator cells infected with an engineered, non-naturally occurring DNA virus described herein facilitate production of a diverse library prior to imparting selection on an evolving gene of interest/biomolecule of interest.

As used herein, the term "selector cell" refers to a metazoan cell that (i) expresses a protein necessary for the production of infectious DNA virus particles and an error-prone DNA virus DNA polymerase and that (ii) couples expression and/or function of the protein necessary for the production of infectious DNA virus particles with the evolving gene of interest/biomolecule of interest. The cell line construction of selector cells allows one to perform evolution in a near continuous process by simply passaging the virus on the selector cells. In some embodiments, the selector cell constitutively expresses the error-prone polymerase and/or the protein necessary for the production of infectious DNA virus particles. In other embodiments, the selector cell inducibly expresses the error-prone viral polymerase and/or the protein necessary for the production of infectious DNA virus particles. In some embodiments, the error-prone viral polymerase is EP-Pol. In some embodiments, the protein necessary for the production of infectious DNA virus particles is AdProt.

Also disclosed herein are methods of performing continuous directed evolution using the components described above. In some embodiments, a method of performing continuous directed evolution of a polynucleic acid sequence is described, wherein said polynucleic acid sequence comprises the sequence of at least one gene of interest, said method comprising infecting engineered, non-naturally occurring living metazoan cells (i.e., selector cells) with at least one engineered, non-naturally occurring DNA virus, wherein: (a) the at least one engineered, non-naturally occurring DNA virus comprises a modified genome, wherein the modified genome comprises an integration of at least one polynucleic acid sequence comprising the sequence of a transcribable gene of interest, a deletion of the sequence encoding for the viral DNA polymerase, a deletion of at least one sequence encoding for a protein necessary for the production of infectious DNA virus particles; (b) the engineered, non-naturally occurring living metazoan cells (i.e., selector cells) comprise modified genomes, wherein each modified genome comprises an integration of a polynucleic acid sequence comprising a sequence of an error-prone DNA virus DNA polymerase, an integration of at least one polynucleic acid sequence comprising the sequence encoding for the protein necessary for the production of infectious DNA virus particles in (a) under the control of a functionally-coupled promoter, such as a transcriptionally-coupled promoter; and (c) the generation of infectious DNA viruses by the engineered, non-naturally occurring living metazoan cells infected with the at least one engineered, non-naturally occurring DNA virus is dependent upon the evolution of the at least one polynucleic acid sequence comprising the sequence of the transcribable gene of interest in (a), wherein said evolution is driven by the error-prone DNA virus DNA polymerase encoded by the polynucleic acid sequence of (b).

In some embodiments, the method comprises infecting engineered, non-naturally occurring living metazoan cells (i.e., producer cells) with at least one engineered, non-naturally occurring DNA virus, wherein: (a) the at least one engineered, non-naturally occurring DNA virus comprises a modified genome, wherein the modified genome comprises an integration of at least one polynucleic acid sequence comprising the sequence of a transcribable gene of interest, a deletion of the sequence encoding for the viral DNA polymerase, and a deletion of at least one sequence encoding for a protein necessary for the production of infectious DNA virus particles; and (b) the engineered, non-naturally occurring living metazoan cells (i.e., producer cells) comprise modified genomes, wherein each modified genome comprises an integration of a polynucleic acid sequence comprising a sequence of a wild-type DNA virus DNA polymerase and an integration of at least one polynucleic acid sequence comprising the sequence encoding for the protein necessary for the production of infectious DNA virus particles in (a) under the control of a functionally-coupled promoter, such as a transcriptionally-coupled promoter, wherein infection of the non-naturally occurring living metazoan cells (i.e., producer cells) facilitates production of nascent adenoviruses containing the necessary deletions and the gene encoding the gene of interest of interest.

In some embodiments, the method comprises infecting engineered, non-naturally occurring living metazoan cells (i.e., mutator cells) with at least one engineered, non-naturally occurring DNA virus, wherein: (a) the at least one engineered, non-naturally occurring DNA virus comprises a modified genome, wherein the modified genome comprises an integration of at least one polynucleic acid sequence comprising the sequence of a transcribable gene of interest, a deletion of the sequence encoding for the viral DNA polymerase, a deletion of at least one sequence encoding for a protein necessary for the production of infectious DNA virus particles; and (b) the engineered, non-naturally occurring living metazoan cells (i.e., mutator cells) comprise modified genomes, wherein each modified genome comprises an integration of a polynucleic acid sequence comprising a sequence of an error-prone DNA virus DNA polymerase and an integration of at least one polynucleic acid sequence comprising the sequence encoding for the protein necessary for the production of infectious DNA virus particles in (a) under the control of a functionally-coupled promoter, such as a transcriptionally-coupled promoter, wherein said infection facilitates the production of a diverse library prior to imparting selection on an evolving gene of interest.

In some embodiments, the method comprises sequentially infecting producer cells, mutator cells, and selector cells. See, for example, Example 18.

In some embodiments, the sequence encoding for the protein necessary for the production of infectious DNA virus particles in (b) is the same as the sequence encoding for the protein necessary for the production of infectious DNA virus particles in (a). In other embodiments, the sequence encoding for the protein necessary for the production of infectious DNA virus particles in (b) is different from the sequence encoding for the protein necessary for the production of infectious DNA virus particles in (a). For example, the integrated sequence of the protein necessary for the production of infectious DNA particles in the engineered, non-naturally occurring living metazoan cells may comprise the functional sequence of the deleted sequence of the protein necessary for the production of infectious DNA particles in the at least one engineered, non-naturally occurring DNA virus. The term "functional sequence" refers to a minimal sequence of a protein that is required for the protein to carry out its desired function. For example, an engineered, non-naturally occurring DNA virus genome may comprise a deletion of the entire adenoviral protease sequence and an engineered non-natural metazoan cell genome may comprise an integration of the sequence of a functional protease domain of the adenoviral protease sequence (or a fusion protein containing the functional protease domain). Alternatively, an engineered, non-naturally occurring DNA virus genome may comprise a deletion of a segment of a adenoviral protease sequence (rendering the protein produced nonfunctional) and an engineered non-natural metazoan cell genome may comprise an integration the entire sequence of the adenoviral protease. Additional permutations of these examples would be clear to one having skill in the art.

In some embodiments, the method further comprises administering to the metazoan cells an inhibitor of the protein necessary for the production of infectious DNA viral particles so as to expand the dynamic range of selection pressure on the cells. For example, in some embodiments the protein necessary for the production of infectious DNA viral particles is the adenoviral protease and the inhibitor is vinyl sulfone.

In some embodiments, the sequence of the viral DNA polymerase in (a) is the same as the error-prone DNA virus DNA polymerase in (b). In other embodiments, the sequence of the viral DNA polymerase in (a) is different from the error-prone DNA virus DNA polymerase.

In some embodiments, the method further comprises screening the engineered, non-naturally occurring living metazoan cells for highly infectious DNA virus particles. Various methods of screening adenoviruses for highly infectious viral particles are known to those having skill in the art. See e.g., Examples 26-27.

As used herein, the term "infecting" refers to exposing the engineered, non-naturally occurring living metazoan cells to engineered, non-naturally occurring DNA viruses under conditions that allow the cellular uptake of the modified genome of the engineered, non-naturally occurring DNA viruses.

As used herein, "functionally-coupled" refers to a direct or indirect functional interaction of the sequence encoding for the protein necessary for the production of infectious DNA viral particles that allows for expression, under certain conditions, of the protein necessary for the production of infectious DNA viral particles. In some embodiments, the functional coupling facilitates constitutive expression. In other embodiments, the functional coupling facilitates conditional expression. Functional coupling can include transcriptional coupling, protein or polynucleic acid stability coupling, subcellular trafficking coupling, folding coupling, translational coupling, post-translational modification coupling, protein or polynucleic acid degradation coupling, and protein sequestration coupling. Thus, interactions between a polynucleic acid encoding for the protein necessary for the production of infectious DNA viral particles or the protein itself and other molecules that regulate or modulate (increase or decrease) transcription, protein or polynucleic acid stability, subcellular trafficking, folding, translation, post-translational modification, protein or polynucleic acid degradation, and/or protein sequestration can be used in the evolution processes described herein.

As used herein, the term "transcriptionally-coupled" refers to an interaction between the sequence encoding for the protein necessary for the production of infectious DNA viral particles and a promoter sequence, wherein the interaction allows for expression of the protein necessary for the production of infectious DNA viral particles. In some embodiments, the transcriptional coupling facilitates constitutive expression. In other embodiments, the transcriptional coupling facilitates conditional expression.

As used herein, the term "evolution" refers to the introduction of at least one selectable genetic mutation (e.g., insertions, deletions, substitutions, etc.) in the genome of an organism or bioparticle. As used herein, the term "dependent upon" refers to an interaction between the process of evolution and the enzymatic activity of the error-prone DNA polymerase. In this case, the term refers to the introduction of mutations during replication of the genome by the error-prone DNA polymerase (i.e., the continuous evolution system design is such that the DNA sequence encoding for the gene of interest is replicated by the error-prone DNA polymerase).

The term "unevolved," as used herein, refers to state in which the sequence of a gene of interest is unable to perform a desired function (e.g., generate a protein that can induce expression, inhibit expression, cleave a polypeptide a desired location, or cleave a polynucleic acid at a desired location or overcome a translational roadblock). In some embodiments, the unevolved state of the gene of interest is the gene of interest's native sequence (e.g., the native sequence of a protein coding gene). In other embodiments, the unevolved state of the gene of interest is a non-native sequence.

In some embodiments, at least one of the at least one polynucleic acid sequences comprising the sequence of a transcribable gene of interest in is a protein coding sequence, wherein expression and translation of the protein coding sequence generates at least one protein product.

In some embodiments, the at least one protein product, when unevolved, induces the expression of the at least one polynucleic acid sequence comprising the sequence encoding for the protein necessary for the production of infectious DNA virus particles; however, the induction is inhibited by the concomitant administration of an agent that decreases the capability of the at least one protein product of inducing expression of the protein necessary for the production of infectious DNA virus particles. In this way, a protein can be evolved to overcome the inhibitory effect of the agent. For example, at least two protein products, when unevolved, may induce said expression, wherein a protein-protein interaction between the at least two protein products is necessary for the induction of expression; however, the agent decreases the ability the proteins to interact. In another example, the at least one protein, when unevolved, may induce said expression by directly binding to the transcriptionally-coupled promoter; however, the agent decreases the ability of the protein to bind the promoter. Additionally, the at least one protein, when unevolved, may induce said expression by inhibiting the binding of at least one transcriptional inhibitor protein to the transcriptionally-coupled promoter. In such instances, the inhibition of binding may be achieved through a protein-protein interaction between the at least one protein and the at least one transcriptional inhibitor protein or by inhibiting the expression of the at least one transcriptional inhibitor protein (here, the agent may decrease the ability of the proteins to interact or decrease the ability of the transcriptional inhibitor protein to bind the promoter). Additional permutations of these examples would be clear to one having skill in the art. As used herein, the term "an agent that decreases the capability" refers to an agent, whose presence decrease the ability of a protein produced from transcription and translation of the sequence of the gene of interest to induce expression of the sequence encoding for the protein necessary for the production of infectious DNA virus particles by least 25%, 30%, 40%, 50%, 60%, 70%, 75%, 80%, 90%, 95% or 100% relative to the level of expression in the absence of the agent. Methods of measuring expression are known to those having skill in the art.

In other embodiments, the at least one protein product, when unevolved, inhibits the expression of the at least one polynucleic acid sequence comprising the sequence encoding for the protein necessary for the production of infectious DNA virus particles. For example, at least two protein products, when unevolved, may inhibit said expression, wherein a protein-protein interaction between the at least two protein products is necessary for the inhibition of expression and at least one of the at least two protein products directly binds to the transcriptionally-coupled promoter that drives expression of the sequence encoding for the protein necessary for the production of infectious DNA virus particles. In another example, the at least one protein, when unevolved, may inhibit said expression by directly binding to the transcriptionally-coupled promoter. Additionally, the at least one protein, when unevolved, may inhibit said expression by inhibiting the binding of at least one transcriptional activator protein to the transcriptionally-coupled promoter. In such instances, the inhibition of binding may be achieved through a protein-protein interaction between the at least one protein and the at least one transcriptional inhibitor protein or by decreasing the expression of the at least one transcriptional inhibitor protein. Additional permutations of these examples would be clear to one having skill in the art.

In other embodiments, the at least one protein product, when unevolved, cannot induce the expression of the at least one polynucleic acid sequence comprising the sequence encoding for the protein necessary for the production of infectious DNA virus particles; however, the at least one protein product, when evolved, can induce said expression.

For example, the at least one protein product, when unevolved, may not bind to the transcriptionally-coupled promoter of the protein necessary for the production of infectious DNA virus particles. Alternatively, that the at least one protein product, when unevolved, may bind to the transcriptionally-coupled promoter of the protein necessary for the production of infectious DNA virus particles but fail to induce its expression. The phrase "cannot induce the expression," as used herein, refers to a state in which the unevolved gene of interest increases the expression levels of the sequence encoding for the protein necessary for production of infectious DNA virus particles by less than 5%. Additional permutations of these examples would be clear to one having skill in the art.

The term "transcriptional activator protein," as used herein, refers to an agent that induces the expression of a target sequence by binding to the promoter of the target sequence. The term "transcriptional inhibitor protein" as used herein, refers to an agent that inhibits the expression of a target sequence by binding to the promoter of the target sequence.

As used herein, the phrases "induces the expression," "inducing the expression," "inhibits the expression," and "inhibiting the expression" refer to changes in expression levels (increase, increases, decreases, and decreases, respectively) of at least 25%, 30%, 40%, 50%, 60%, 70%, 75%, 80%, 90%, 95% or 100% relative to the expression level in the absence of the indicated factor (e.g., the transcriptional activator protein, the transcriptional inhibitor protein, or the unevolved gene of interest). Methods of measuring expression are known to those having skill in the art.

The term "decreasing the binding," as used herein, refers to a decrease in the binding of the transcriptional activator protein or the transcriptional inhibitor protein to the transcriptionally-coupled promoter by least 25%, 30%, 40%, 50%, 60%, 70%, 75%, 80%, 90%, 95% or 100% relative to the level of binding in the absence of the indicated agent (e.g., a protein produced from the unevolved gene of interest). Methods of measuring promoter binding are known to those having skill in the art.

In some embodiments, the at least one protein product, when unevolved, regulates the stability of the protein necessary for the production of infectious DNA viruses. For example, the at least one protein product may cause the degradation of the protein necessary for the production of infectious DNA viruses via the ubiquitin-proteasome pathway or the lysosomal proteolysis pathway.

In other embodiments, the at least one protein product, when unevolved, regulates the subcellular trafficking of the protein necessary for the production of infectious DNA viruses. For example, in some embodiments, the at least one protein product sequesters the protein necessary for the production of infectious DNA viruses in the nucleus or a subcellular organelle. In still other embodiments, the at least one protein product, when unevolved, does not regulate the subcellular trafficking of the protein necessary for the production of infectious DNA viruses; however, the at least one protein product, when evolved, can regulate said trafficking.

In other embodiments, the at least one protein product, when unevolved, regulates the folding of the protein necessary for the production of the infectious DNA viruses. In other embodiments, the at least one protein product, when evolved, regulates the folding of the protein necessary for the production of the infectious DNA viruses.

In other embodiments, the at least one protein product, when unevolved, regulates a post-translational modification of the protein necessary for the production of the infectious DNA viruses. In other embodiments, the at least one protein product, when evolved, regulates a post-translational modification of the protein necessary for the production of the infectious DNA viruses. Examples of post-translational modifications are known to those having skill in the art.

In other embodiments, the sequence encoding for the protein necessary for the production of infectious DNA virus particles further comprises the sequence of an inhibitory tag, wherein the sequence of the protein necessary for the production of infectious DNA virus particles and the sequence of the inhibitory tag are coupled, and wherein: (a) translation of the sequence comprising the sequence encoding for the protein necessary for the production of infectious DNA virus particles and the sequence of the inhibitory tag generates a tagged protein; and (b) removal of inhibitory tag in (a) is dependent upon the evolution of the at least one polynucleic acid sequence comprising the sequence of the gene of interest.

As used herein, the term "inhibitory tag" refers to an agent that, when coupled to a protein, decreases a desired function of that protein by least 25%, 30%, 40%, 50%, 60%, 70%, 75%, 80%, 90%, 95% or 100% relative to the function in the absence of the inhibitory tag. The term "coupled" as used herein refers to a physical interaction between inhibitory tag and the protein necessary for the production of infectious DNA virus particles. The term "removal" as used herein refers to a decoupling of the inhibitory tag and the protein necessary for the production of infectious DNA virus particles.

In some embodiments, the inhibitory tag is selected from the group consisting of a protein degradation tag or a protein sequestration tag. The term "protein degradation tag" refers to tag that when coupled to the protein necessary for the production of infectious DNA virus particles, stimulates degradation of the protein. Examples of protein degradation tags are known to those having skill in the art. In some embodiments, the protein degradation tag is a degron tag. The term "protein sequestration tag" refers to tag that when coupled to the protein necessary for the production of infectious DNA virus particles, sequesters the protein from the location where its desired function is performed. For example, the protein necessary for the production of infectious DNA virus particles can be sequestered in the nucleus or a subcellular organelle. Examples of protein sequestration tags are known to those having skill in the art.

In some embodiments, the gene of interest is a protease. In some embodiments, the protease, when unevolved, is unable to cleave or remove an inhibitory tag that is coupled to the protein necessary for the production of infectious DNA virus particles. Examples of proteases are known to those of skill in the art.

In other embodiments, at least one of the at least one polynucleic acid sequences comprising the sequence of a transcribable gene of interest is the sequence of a non-coding RNA. In some embodiments, the sequence encoding for the protein necessary for the production of infectious DNA virus particles in (b)(ii) further comprises a premature stop codon in the sequence encoding for the at least one protein necessary for the production of infectious DNA virus particles. In such embodiments, the generation of a functional protein necessary for production of infectious DNA virus particles via translation of mRNA produced by transcription of the at least one polynucleic acid sequence comprising the sequence encoding for the protein necessary for the production of infectious viral particles is dependent upon the evolution of the at least one polynucleic acid sequence comprising the sequence of the gene of interest— that is integrated in the genome of the at least one engineered, non-naturally occurring DNA virus.

In some embodiments, the sequence of the gene of interest comprises the sequence of a tRNA. The term "tRNA," as used herein, refers to a transfer RNA, which is an adaptor molecule that serves as a link between the nucleotide sequence of a mRNA and the amino acid sequence of a protein. The sequences of tRNAs are known to those having skill in the art.

In some embodiments, the sequence of the gene of interest comprises the sequence of an aminoacyl tRNA synthetase. The term "aminoacyl tRNA synthetase," as used herein, refers to an enzyme that attaches the appropriate amino acid to its respective tRNA. The nucleotide and amino acid sequences of aminoacyl tRNA synthetases are known to those having skill in the art.

In some embodiments, a small molecule is added to the culture conditions to increase selection stringency, wherein the small molecule decreases the functionality of the protein necessary for the production of infectious DNA viral particles—that is integrated in the genome of the engineered, non-naturally occurring metazoan cells. As used herein, the term "decreases the functionality" refers to a decrease in a desired function of the protein necessary for the production of infectious DNA viral particles in the presence of a small molecule by least 25%, 30%, 40%, 50%, 60%, 70%, 75%, 80%, 90%, 95% or 100% relative to the function of the protein in the absence of the small molecule.

EXAMPLES

Materials and Methods
Vectors and Cloning:
  Primers:
  Primers used in this study are listed in TABLE 1.
  WT-Pol and EP-Pol vectors:
  Lentiviral vectors containing WT-Pol and EP-Pol were a generous gift of Dr. Robert Hoeben (Leiden University).
  cProt vector:
  A 641 nt fragment containing adenoviral protease (prot) was amplified from the Ad5 genome and ligated into pTRE-Tight (Clontech) using SalI and XbaI. A 223 nt gene block containing the Ad5 tripartite leader sequence (TPL) was amplified with EcoRI and BamHI sites and inserted directly upstream of prot to form pTRE-Tight.TPL.Prot. From this vector, an 852 nt fragment containing TPL.Prot was amplified with NotI and XbaI sites, and inserted into pENTR1A (ThermoFisher). LR clonase II enzyme mixture (ThermoFisher) was used to clone the TPL.Prot fragment into pLenti.CMV.Hygro (w117-1) (ThermoFisher).
  iProt Vector:
  TPL and Prot were amplified separately from pTRE-Tight.TPL.Prot using two sets of primers and reassembled into pTRE-Tight to make a seamless form of TPL.Prot, without an internal restriction enzyme site. TPL-Prot was amplified from pTRE-Tight.TPL.Prot, and assembled with NotI-digested pLVX.Tight.Puro (Takara Biosciences) to form pLVX.Tight.TPL.Prot.Puro.
  Adenoviral Constructs:
  Adenoviral constructs were generated using ccdB recombineering in Escherichia coli, as previously published (Wang et al., Nucleic Acid Res. 2014 Jun. 12; 57(11): 4969-74). Briefly, a selectable/counterselectable cassette that expresses both a kanamycin resistance gene and the ccdB toxin is generated by PCR with primer overhangs that introduce flanking 50 bp homology arms that target the region of interest. The selectable/counterselectable cassette is then inserted into the region of interest by electroporating the PCR product into cells carrying the adenoviral genome in a bacterial artificial chromosome (BAC) and expressing the λ red recombineering machinery. Cells that have inserted the selectable/counterselectable cassette into the adenoviral genome BAC are selected for on LB agar plates containing kanamycin, which kills any cells that have not integrated the selectable/counterselectable cassette, and arabinose, which induces the expression of ccdA to neutralize the ccdB toxin. Next a second cassette containing the desired changes and that has flanking 50 bp homology arms targeting the region of interest is generated by annealing oligos in the case of a deletion or by PCR in the case of an insertion. The second cassette is electroporated into the cells with the selectable/counterselectable cassette inserted into the region of interest and that are expressing the λ red recombineering machinery. Cells that replace the selectable/counterselectable cassette with the second cassette are selected for on LB agar plates containing chloramphenicol, which maintains the adenoviral genome BAC, and lacks arabinose such that ccdB is no longer neutralized and kills any cells that have not replaced the selectable/counterselectable marker. Modifications were confirmed by Sanger sequencing.
Generating Adenovirus from Transfection:
  All adenoviruses were produced by transfecting a linearized vector into their corresponding trans-complementing cells (Δpol adenovirus on WT-Pol cells, Δpol.Δprot adenoviruses on WT-Pol/cProt cells, etc.). 24 µg DNA, 144 µL PEI, 1 mL OptiMEM (Gibco) were combined, incubated at RT for 15 minutes, and then added to a confluent 15 cm plates of cProt cells (~10 million cells). Media was replaced 8 hours after transfection. Media was replaced every two or three days until plaques were observed, which occurred about three weeks after the transfection. Once plaques were observed, cytopathic effect was observed in all cells within five days. The virus was harvested by a freeze-thawing three times and centrifuging at >3,000 rpm for 10 minutes.
Cell Imaging:
  A 6-well plate was seeded with 500,000 cells of iProt cells (EP-Pol and iProt vector). The next day, wells were infected with 10 uL of either TTA.Δpol.Δprot.mCherry or CFP.Δpol.Δprot adenovirus. Five days later, images were taken on an Olympus U-TB190 microscope.
Deep Sequencing of EP-Pol Passages:
  TTA.Δpol.mCherry adenoviruses were passaged on WT-Pol and EP-Pol expressing cells for 10 passages. Viral DNA from all passages 1, 3, 5, and 10 was purified using a Nucleospin Virus Kit (Takara Bio). Samples were prepped for sequencing using the Nextera DNA Library Prep protocol (Illumina), and run on a MiSeq. Substitution scores were determined as previously described (Uil et al., Nucleic Acid Res. 2011 March; 39(5):e30).
qPCR of Protease Expression:
  6-well plates were seeded with 500,000 iProt cells in DMEM with Tet-approved FBS (Takara Bio). The next day, cells were either transfected with TTA or an empty vector. 3 g DNA was transfected after a 15-minute incubation with 18 µL PEI and 250 µL OptiMEM (Gibco). The media was removed after 8 hours and replaced with 2 mL DMEM with Tet-approved FBS.
  Three days post-transfection, the cells were harvested using the RNeasy RNA mini prep kit (Omega Bio-Tek). cDNA was made from the harvested RNA using a reverse-transcription kit (Applied Biosciences), and added to a 384-well plate along with SYBR Green (Kappa) and primers specific to the adenoviral protease gene in technical quadruplicate. The qPCR was run in a LightCycler 480 (Roche), and Cp values were calculated from the resultant amplification curves.

Passaging for TTA Evolution:

Viral Amplification and Diversification:

500 μL of the TTA.Δpol.Δprot adenovirus was amplified on cProt cells that expressed EP-Pol instead of WT-Pol, creating a diverse viral population. After five days, cytopathic effect was observed in all cells. This amplified virus was harvested as described above.

Continuous Evolution Procedure:

Three 15 cm semiconfluent dishes of iProt cells (~5 million cells) were infected with either 250, 500 or 1,000 μL of the amplified virus in the presence of 1 ng/mL of doxycycline. Plates are monitored for plaques every day. If more than one plate shows a plaque on the same day, the plate with the lowest volume of virus added was used for the next round of evolution.

The day after a plaque is observed, three 15 cm semiconfluent dishes of iProt cells are infected in the presence of 1 ng/mL doxycycline. The three dishes are infected with 250, 500 or 1,000 μL of media from the previous round's dish. 2 mL of media are saved in Eppendorf tubes and stored at −80 C for future analysis.

Dox Evolution Sequencing:

DNA was harvested from 200 μL of the media that was saved after each round of evolution using a viral DNA prep kit. The region of DNA encompassing the CMV promoter and the TTA gene was PCR amplified from 1 μL of the harvested DNA. The resulting PCR product was purified and prepared for Illumina sequencing through the Nextera DNA Library Prep protocol (Illumina). Each position within the TTA gene and CMV promoter had at least 1,000 reads.

Figure 17:
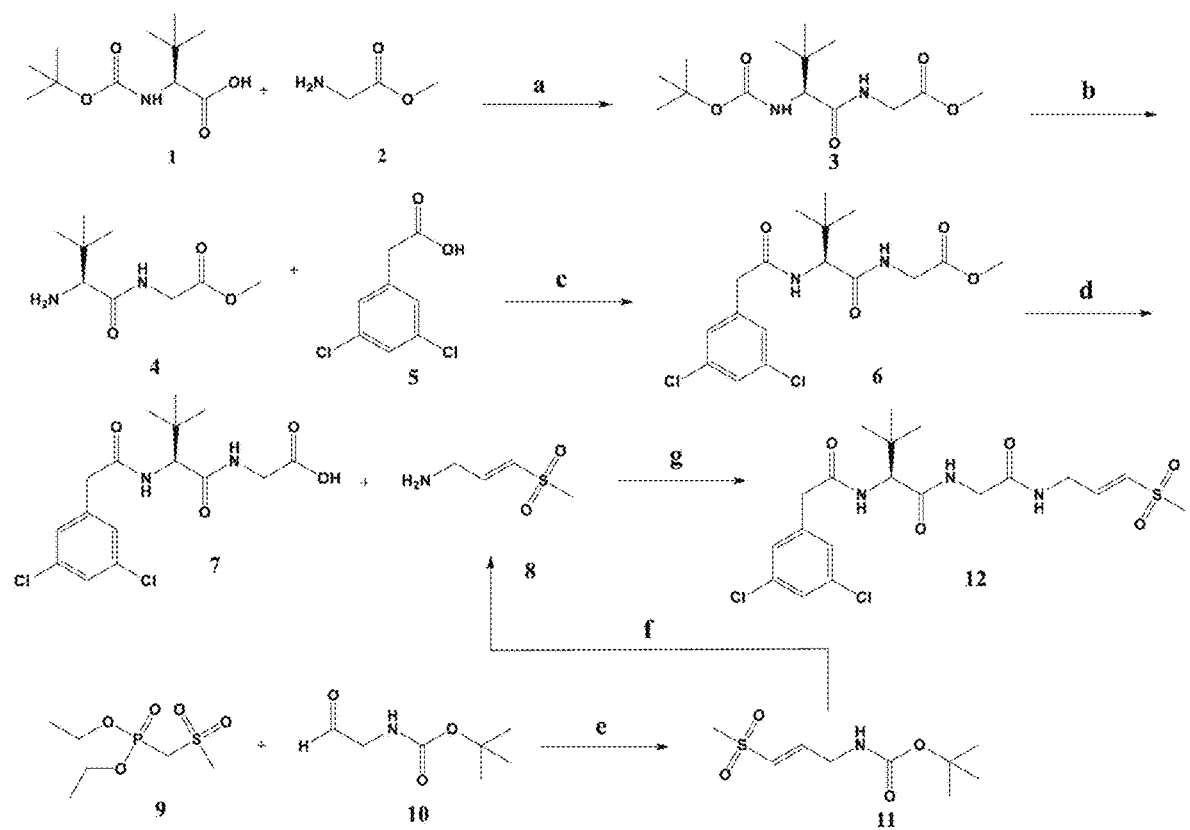
FIG. 17. Synthesis of the adenovirus protease inhibitor. Reagents and conditions: a. HBTU, HOBT, DIPEA, DCM, rt 16 hr 90%; b. 1M HCl in THF, rt, 3.5 hr 97%; c. EDC, DIPEA, DCM, rt 16 hr 34%; d. LiOH 6:1 THF:H20, rt 2 hr 100%; e. NaH, THF, 0° C.→rt 2 hr 21%; f. TFA, rt 2.5 hr 91%; and g. HBTU, HOBT, DIPEA, DCM, rt 16 hr 24%.

Synthesis of the Adenovirus Protease Inhibitor:

The adenovirus protease inhibitor 12 was previously reported and synthesized following a similar route (FIG. 17) (Grosche et al., Bioorg. Med. Chem. Lett. 2015 Feb. 1; 25(3): 438-43). Compound 8 was synthesized using a previously published protocol (FIG. 17) (Kathman et al., J. Med. Chem. 2014 Jun. 12; 57(11): 4969-74).

Adenovirus Selection Using the Adenovirus Protease Inhibitor:

293A cells were seeded at 106 cells/well in a 6-well dish. GFP-expressing adenoviruses were used to infect these cells (MOI=1), and the protease inhibitor was added at various concentrations. Two days later, many of the samples showed signs of full CPE, and the adenoviruses were harvested as previously described. 293As were seeded in a 96-well plate at 40,000 cells/well, and inhibitor treated adenovirus samples were used to infect these wells at various dilutions of supernatant (30 μL, 3 μL, 0.3 μL, or 0.03 μL). Cells were analyzed for GFP fluorescence by flow cytometry on a BD LSR II analyzer, and viral titers were quantified in samples that fell in the linear range of infection (1 virion per cell).

TABLE 1

DNA primers used in this study.

| Primer Name | Primer Sequence | SEQ ID NO: |
|---|---|---|
| SalI.Prot Forward | aaaaaaGGATCCACCATGGGCTCCAGTG | 1 |
| XbaI.Prot Reverse | aaaaaGTCGACttacatgtttttcaagtgacaaaaagaag | 2 |
| EcoRI.TPL Forward | aaaaaaGCGGCCGCactctcttccgcatcg | 3 |
| BamHI.TPL Reverse | aaaaaaTCTAGAttacatgtttttcaagtgacaaaaagaag | 4 |
| NotI.TPL.Prot Forward | aaaaaaGCGGCCGCactctcttccgcatcg | 5 |
| TPL Assembly Forward | atcgcctggagaattcactctcttccgcatcgct | 6 |
| TPL Assembly Reverse | ctcactggagcccattgcgactgtgactggttag | 7 |
| TPL-Prot Forward | tggagaaggatccgcactctcttccgcatcgct | 8 |
| TPL-Prot Reverse | atctagagccggcgcttacatgtttttcaagtgacaaaaagaag | 9 |
| E1 kanccdB Forward | atacaaaactacataagaccccaccttatatattctttcccacccttaagccacgcccaCCCTCATCAGTGCCAACATAGTAAG | 10 |
| E1 kanccdB Reverse | aataagaggaagtgaaatctgaataattttgtgttactcatagcgcgtaataCCGCTCATTAGGCGGGC | 11 |
| E1 CMV Promoter Forward | atacaaaactacataagaccccaccttatatattctttcccacccttaagccacgcccaCAGATATACGCGTTGACATTG | 12 |
| E1 bGH polyA Reverse | aataagaggaagtgaaatctgaataattttgtgttactcatagcgcgtaataGAAGCCATAGAGCCCAC | 13 |
| E4 kanccdB Forward | caaaaaacccacaacttcctcaaatcgtcacttccgttttcccacgttacCCCTCATCAGTGCCAACATAGTAAG | 14 |
| E4 kanccdB Reverse | agtaacttgtatgtgttgggaattgtagttttcttaaaatgggaagtgacCCGCTCATTAGGCGGGC | 15 |

TABLE 1-continued

DNA primers used in this study.

| Primer Name | Primer Sequence | SEQ ID NO: |
|---|---|---|
| E4 SV40 Promoter Forward | caaaaaacccacaacttcctcaaatcgtcacttccgttttcccacgttacTTCTGTGGAAT GTGTGTCAGTTAGGG | 16 |
| E4 SV40 polyA Reverse | agtaacttgtatgtgttgggaattgtagttttcttaaaatgggaagtgacCTCTAGCTAGA GGTCGACGGTATAC | 17 |
| Pol kanccdB Forward | tcccgcgcttcttggaactttacattgtgggccacaacatcaacggccctCCCTCATCAG TGCCAACATAGTAAG | 18 |
| Pol kanccdB Reverse | ggcacctcggaacggttgttaattacctgggcggcgagcacgatctcgtcCCGCTCATT AGGCGGGC | 19 |
| delPol oligo Forward | gcgcggccttccggagcgaggtgtgggtgagcgcaaaggtgtccctgaccatgaccagcatga agggcacgagctgcttcccaaaggcccccatccaag | 20 |
| delPol oligo Reverse | cttggatgggggcctttgggaagcagctcgtgcccttcatgctggtcatggtcagggacacctttg cgctcacccacacctcgctccggaaggccgcgc | 21 |
| Prot kanccdB Forward | ggcaacgccacaacataaagaagcaagcaacatcaacaacagctgccgccCCTCATC AGTGCCAACATAGTAAG | 22 |
| Prot kanccdB Reverse | tacaaataaaagcatttgcctttattgaaagtgtctctagtacattatttCCGCTCATTAGG CGGGC | 23 |
| delProt oligo Forward | ggcaacgccacaacataaagaagcaagcaacatcaacaacagctgccgccaaataatgtacta gagacactttcaataaaggcaaatgcttttatttgta | 24 |
| delProt oligo Reverse | Tacaaataaaagcatttgcctttattgaaagtgtctctagtacattatttggcggcagctgttgttgat gttgcttgcttctttatgttgtggcgttgcc | 25 |

Example 1. General Platform Design

All evolution platforms rely on genetic mutation. In nature, polymerases serve as evolutionary drivers—DNA polymerases during DNA replication and RNA polymerases during RNA transcription. As such, many continuous directed evolution platforms utilize error-prone polymerases.

Some polymerases, such as the RNA polymerases of RNA viruses, have high mutation rates in their native forms. In this regard, an RNA virus, such as VSV, might be an ideal choice for a continuous directed evolution platform. However, methodologies employing an RNA virus would have certain disadvantages. For example, enveloped RNA viruses are significantly less stable than non-enveloped viruses, such as adenovirus. This complicates the storage and manipulation of RNA viral stocks. Moreover, most RNA viruses tend to replicate poorly in cell culture under stringent selection conditions, such as those that are required for successful directed evolution. Finally, retroviral vectors, such as VSV, are budding viruses that leave the host cell intact and prone to continued infection. This increases the possibility that viruses carrying maladaptive GOIs will cheat the system by infecting cells that were previously infected by viruses carrying adaptive GOIs (i.e., selection subversion). Consequently, it becomes very important to ensure that the residence time of the host cells in an infecting culture is as short as possible while still ensuring efficient viral replication.

On the other hand, DNA virus, such as adenoviruses, would seem to be a poor choice for a continuous evolution platform. Unlike RNA viruses, adenoviruses, like most double-stranded DNA viruses, have mutation rates that are too low to create the library sizes necessary for successful directed evolution experiments (Risso-Ballester et al., PLoS Pathog. 2004 Nov. 8; 12(11):e1006013). Thus, in their native forms/culture conditions, adenoviruses would not be amenable to a continuous directed evolution platform. However, in other aspects, an adenovirus platform would have various benefits relative to an RNA virus platform. First, adenovirus is lab friendly. It is frequently used to deliver genes into human cells for biological study (Benihoud et al., Curr. Opin. Biotechnol. 1999 October; 10(5)440-47). It is very robust and safe to work with, and carries its own DNA polymerase that is responsible for replicating the adenoviral genome independent of the host machinery. Importantly, unlike VSV and other retroviruses, adenovirus is a lytic virus, meaning any infected cells are killed at the conclusion of the viral replication cycle. This removes infected cells from culture and significantly reduces the possibility of selection subversion.

Figure 3:
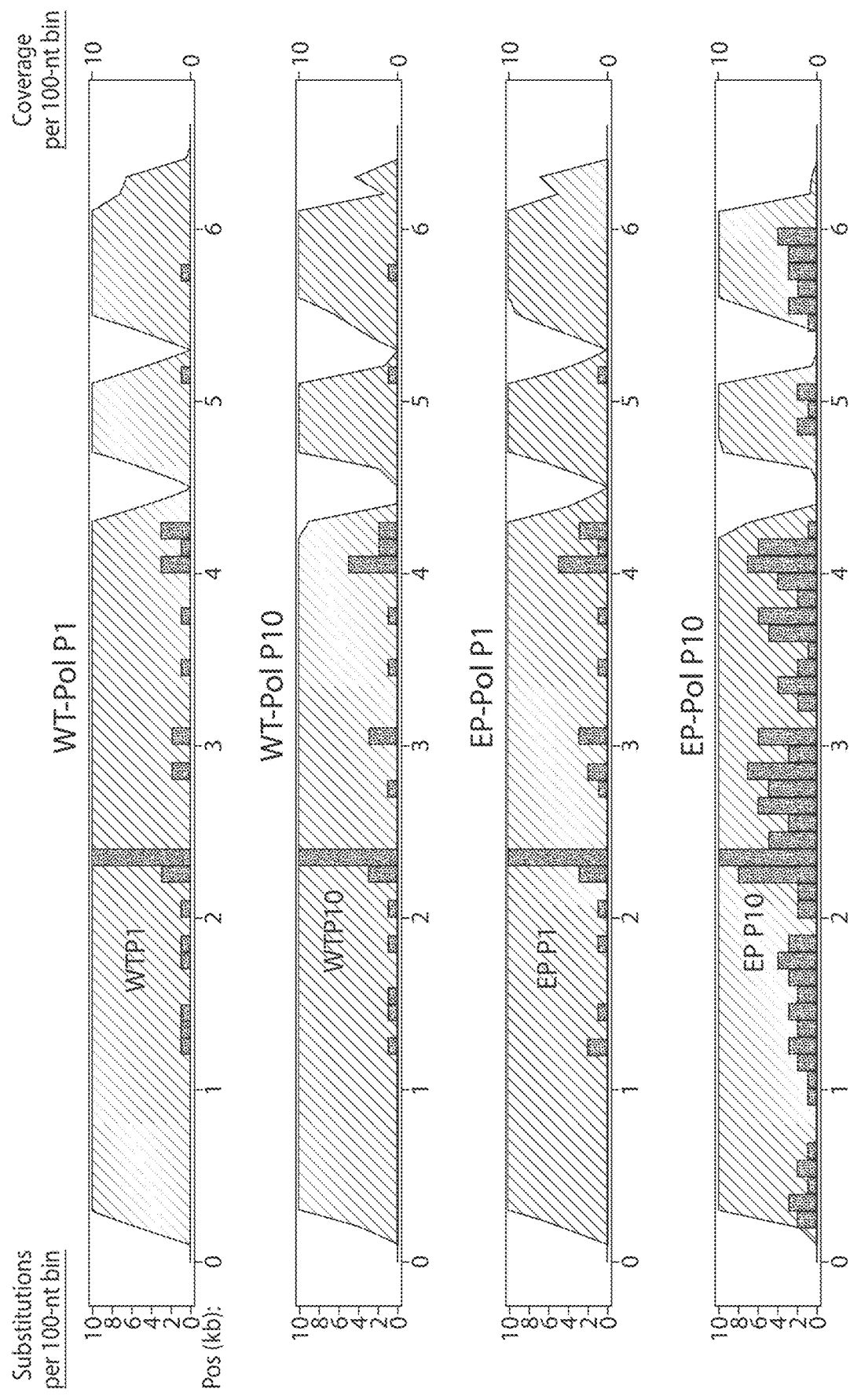
FIG. 3. EP-Pol shows a high rate of mutagenesis compared to wild-type AdPol (WT-Pol). Viruses were passaged ten times on HEK-293A cells expressing either WT-Pol or EP-Pol. Pools of ~50 clones of each virus were then amplified, and a 6.5 kb region of the genome was amplified for next-gen sequencing. The plot shows coverage across the 6.5 kb region in light grey and substitutions per 100-nt bin in dark grey. The data shows that adenovirus passaged on EP-Pol accumulates significantly more mutations across 10 passages than viruses on WT-Pol.
Figure 4:
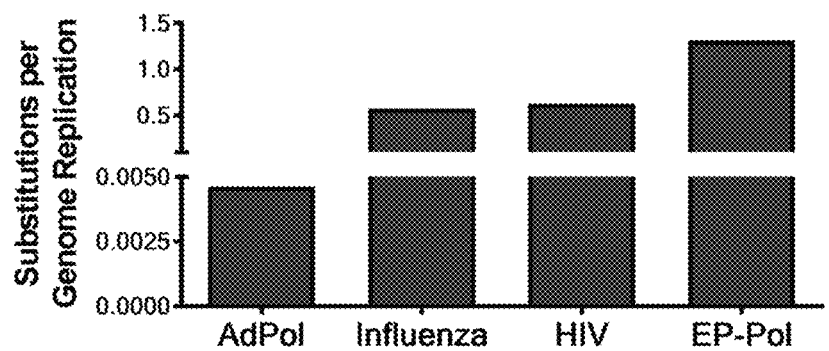
FIG. 4. Comparison of error rates of common human viruses. AdPol has a very low error-rate; far lower than what is necessary for efficient directed evolution. By contrast, EP-Pol, has a significantly higher error rate that is comparable to highly mutagenic RNA viruses such as influenza and HIV.

Here, adenovirus was utilized as a means to deliver and mutate a gene of interest ("GOI") and to select for and amplify positive variants that emerge. These methods rely upon an error-prone version of the adenoviral polymerase, which was designed by combining two previously discovered mutations that exhibit positive epistasis (Uil et al., Nucleic Acid Res. 2011 March; 39(5):e30). The first mutation, F421Y, is in the exonuclease domain of the polymerase and is hypothesized to reduce stabilization of ssDNA, thus reducing proofreading activity. The second mutation, D827A, is in the nucleotide binding site and is hypothesized to reduce geometric selection of the incoming nucleotide. Together, these two mutations comprise an error-prone adenoviral polymerase (termed EP-Pol) that mutates the adenoviral genome at a rate that is several orders of magnitude greater than the wild type adenoviral polymerase (FIGS. 3 and 4). Importantly, EP-Pol is capable of generating gene libraries large enough to perform directed evolution.

Figure 5:
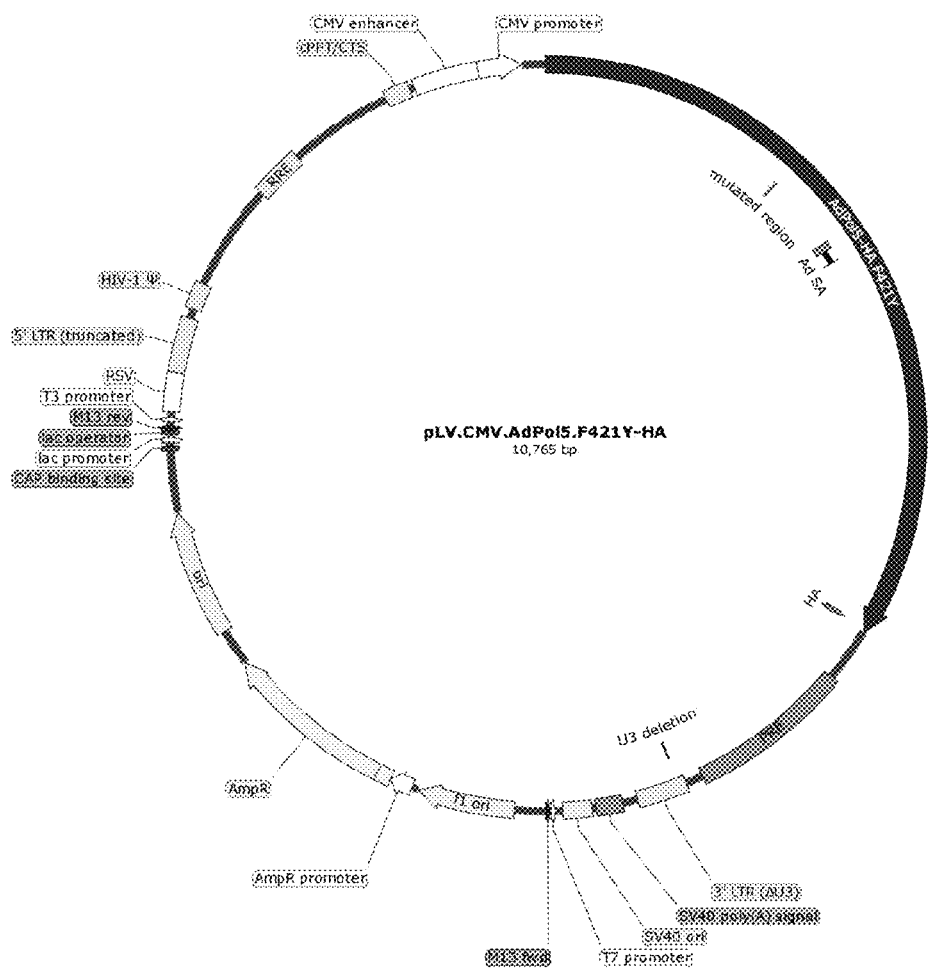
FIG. 5. Vector map of lentivirus constructs for expression of HA-tagged adenovirus polymerase variants. Construct design is the same for both WT-Pol and EP-Pol.
Figure 6:
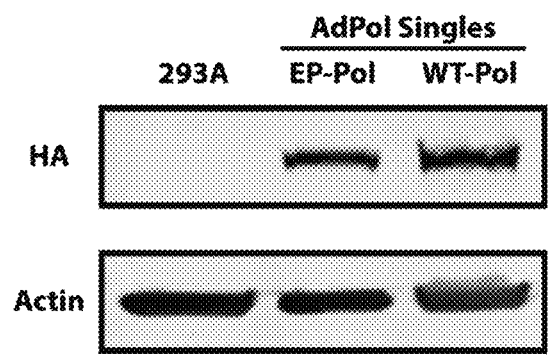
FIG. 6. Western blot of HA-tagged adenovirus polymerase stably expressed in HEK-293A cells. Two separate cell lines, one expressing EP-Pol and one expression the WT-Pol, were created.

To avoid the possibility of EP-Pol mutating its own gene back to a less error-prone version, the adenoviral polymerase gene was deleted from the viral genome and integrated into a human HEK293-derived cell line capable of expressing EP-Pol in trans (FIGS. 1, 5, and 6). In this way, the adenovirus functions as an orthogonal means of replication that allows the gene of interest to be evolved in a metazoan cellular environment, without permitting selection subversion (cheating) that could occur due to mutating the host genome. In order to design the adenoviral vectors necessary to perform directed evolution in metazoan cells, plasmid construction methodologies were optimized. Because of the large size of the adenoviral genome (36000 bp), making the targeted mutations needed to engineer the platform by traditional molecular biology approaches was impossible. Therefore, lambda-red recombination, was used as a strategy to make designer adenoviral mutants (Mück-Hausl M., et al, Nucleic Acid Res. 2015 Apr. 30; 43(8):e50).

Figure 7:
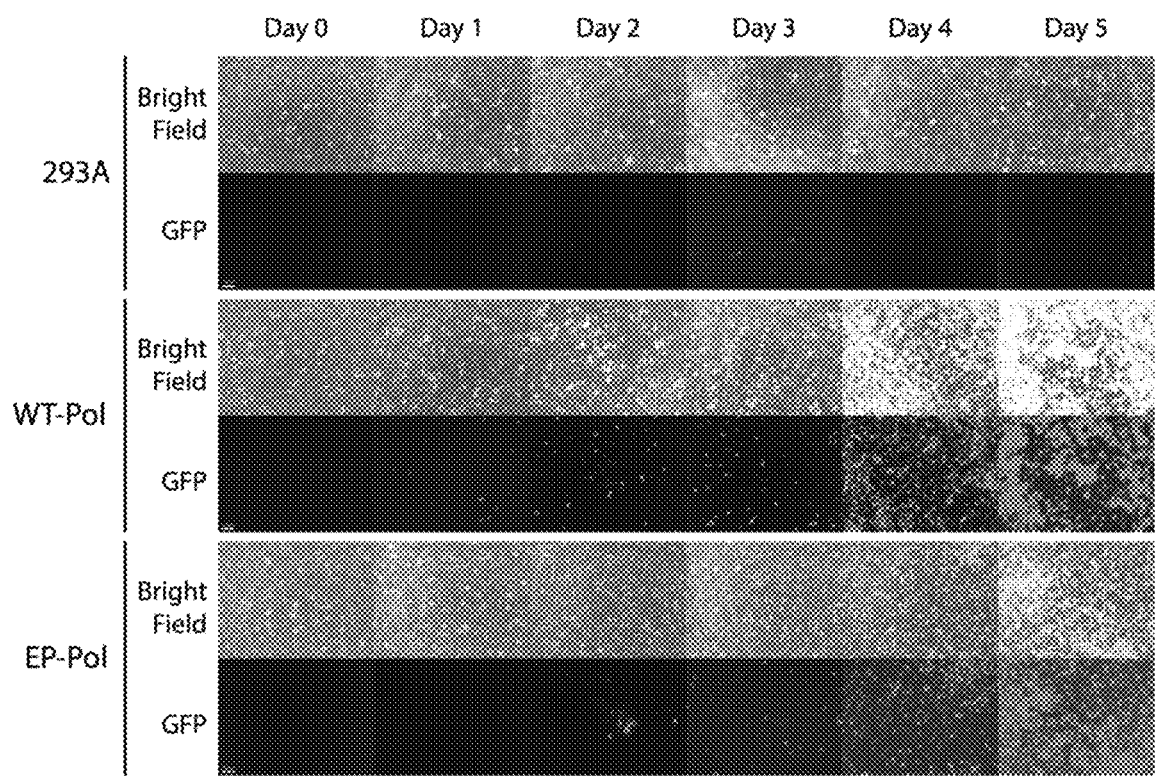
FIG. 7. Trans-complementation of AdPol supports pol-deleted adenoviral replication. AdPol-expressing cell lines were infected at a low MOI with GFP-expressing adenovirus that was deleted for adenovirus polymerase. Infection was monitored by fluorescence over five days. While 293A that did not express adenovirus polymerase showed fluorescence, indicating successful infection, the infection did not spread. Only adenovirus infecting polymerase trans-complemented cell lines (WT-Pol, EP-Pol) were able to spread.

Thus, constructs were created that allowed either the expression of the wild type polymerase (WT-Pol) or EP-Pol in trans in a human HEK293-derived cell line (FIGS. 5 and 6). These cells were then infected with a GFP-expressing version of the Δpol-adenovirus. The Δpol-adenoviruses only grew on cells expressing either WT-Pol or EP-Pol, indicating that Δpol-adenoviruses depend on the adenovirus polymerase being provided in trans (FIG. 7). By setting up this polymerase trans-complementation system, adenovirus can be used as an orthogonal means of replication that allows a gene to be evolved in the metazoan cellular environment, without permitting selection subversion (cheating) that could occur due to mutating the host genome. Fresh hosts are thus constantly replenished during the course of an evolution experiment.

Figure 18A:
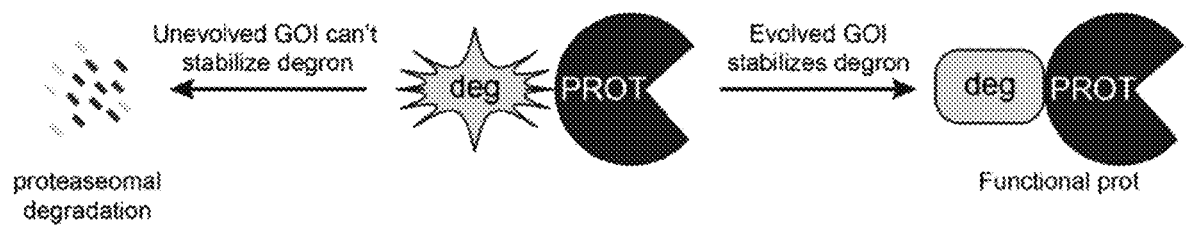
FIGS. 18A-18C. Selected examples of the many possible alternative selection schemes that do not rely on a transcriptional couple.
Figure 18B:
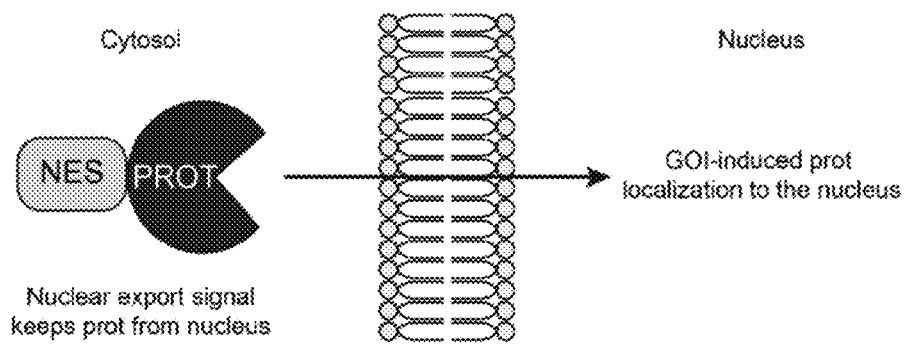
Figure 18C:
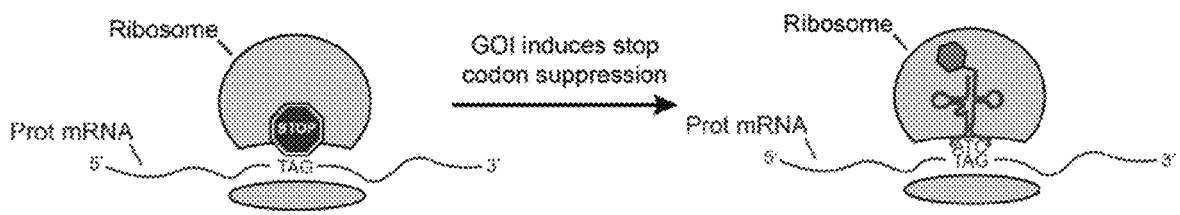

Various selection strategies were tested for directed evolution, including FACS-based screening and antibiotic selection—neither of which yielded positive GOI variants. Instead, selection was accomplished in this system by coupling positive GOI function to expression of a protein necessary for adenovirus infection (FIG. 1). For example, one can evolve a GOI based on coupling transcription of a selectable marker. However, there are many ways beyond a direct transcriptional couple in which one can attain coupled selection in this system. For instance, one can employ a translational couple in the directed evolution of tRNA/amino-acyl tRNA synthetase (aaRS) pairs (Liu and Schultz, Annu. Rev. Biochem., 2010; 79:413-44). This can be accomplished by coupling evolution of the tRNA/aarS pair to suppression of an amber stop codon in the selectable marker (FIG. 18C). One can also evolve specificity of proteases by fusing the selectable marker to a degron that the protease has to chop off (Dickinson et al., Nat. Commun., 2014 Oct. 30; 5:5352) or evolve a selectable marker to overcome a subcellular localization signal (FIGS. 18A and 18B). In this way, the GOI function is coupled to proper function of the selectable marker.

Figure 8:
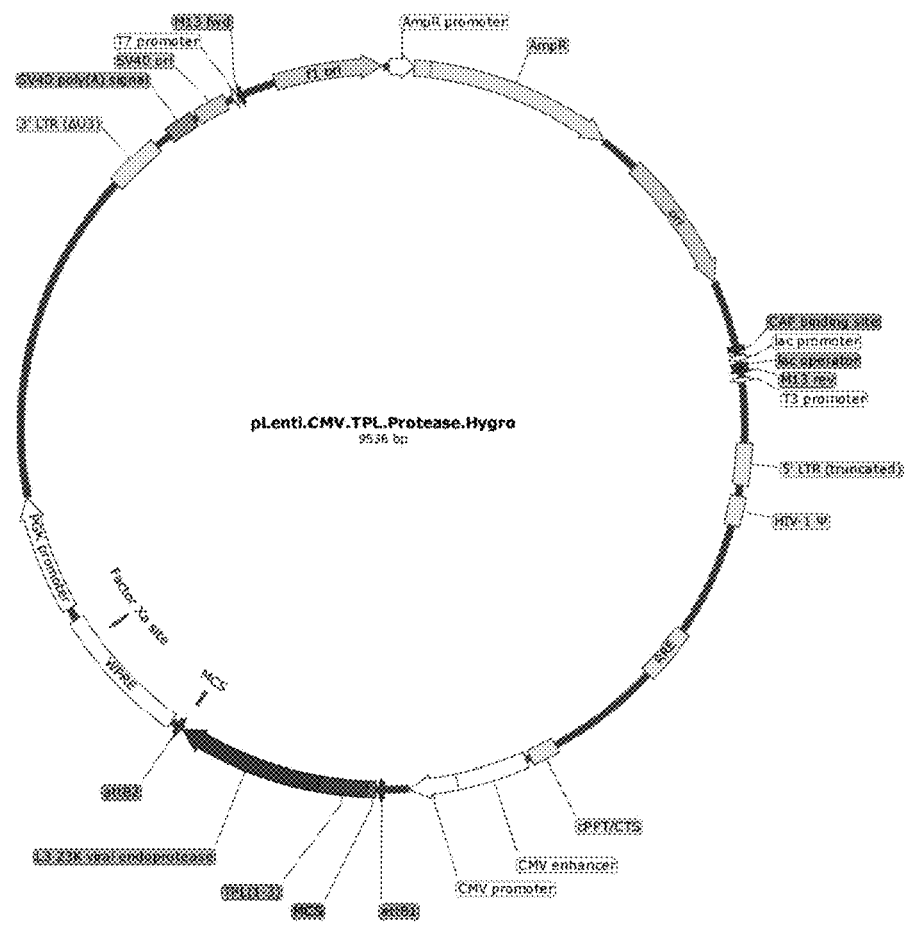
FIG. 8. Vector map of lentiviral construct for constitutive ad-prot expression. This construct has a tripartite leader sequence appended 5' to the start codon of ad-prot. This tripartite leader sequence facilitates robust expression throughout the adenoviral life cycle.
Figure 9:
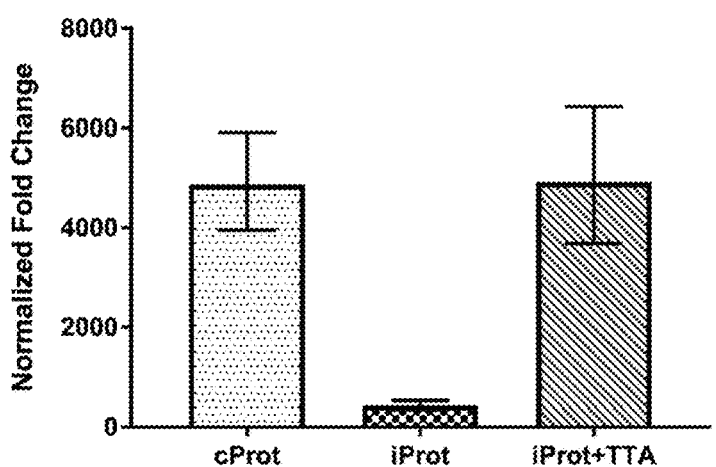
FIG. 9. Validation of adenovirus protease-expressing cell lines. Cell lines stably expressing protease under control of constitutive (cProt) and inducible (iProt) promoters were created. These cell lines were validated by qPCR analysis of protease mRNA expression. The cProt cell line also contains WT-Pol and is used to produce pol-deleted/prot-deleted adenoviruses. The iProt cell line also contains EP-Pol and is used to evolve the tet-transactivator in pol-deleted/prot-deleted adenoviruses. The iProt cell line shows low expression of protease unless the tet-transactivator (TTA) is transfected. All samples were normalized to protease expression in a 293A cell line that does not contain the adenovirus protease gene.

Here, an adenoviral gene that is vital to robust adenoviral infection was used as a selectable maker (Flint, Encyclopedia of Life Sciences, 2001). Numerous adenoviral proteins were tested for their ability to impart selection on an evolving GOI. Most adenoviral proteins that were tested in this system did not work for selection of an evolving GOI in initial efforts (e.g., adenoviral fiber protein, pVI, and E2A) and some did not work for selection of an evolving GOI even after extensive efforts to optimize (i.e., fiber). However, one protein tested, adenoviral protease—important for both viral entry and viral maturation (Greber et al., J. EMBO 1996 Apr. 15; 15(8):1766-77; Baniecki et al., J. Biol. Chem. 2013 Jan. 18; 288(3):2081-91)—functioned well in this system. To demonstrate that adenovirus protease was required for viral infection and can impart selection on an adenovirus, protease was stably expressed in the WT-Pol and EP-Pol cell lines (FIGS. 8 and 9). This construct contains a tripartite leader sequence, which facilitated robust expression throughout the adenoviral life cycle (Yueh and Scnheider, Genes Dev., 2000 Feb. 15; 14(4):414-21). Adenoviral protease was then deleted from the genome of the Δpol-adenoviruses to make ΔpolΔprot-adenoviruses. The replication of the ΔpolΔprot-adenoviruses was then tested on cell lines that express either polymerase and prot, polymerase alone, or neither protein. This demonstrated that only cells that expressed both polymerase and protease in trans can support replication of ΔpolΔprot-adenoviruses.

Figure 2:
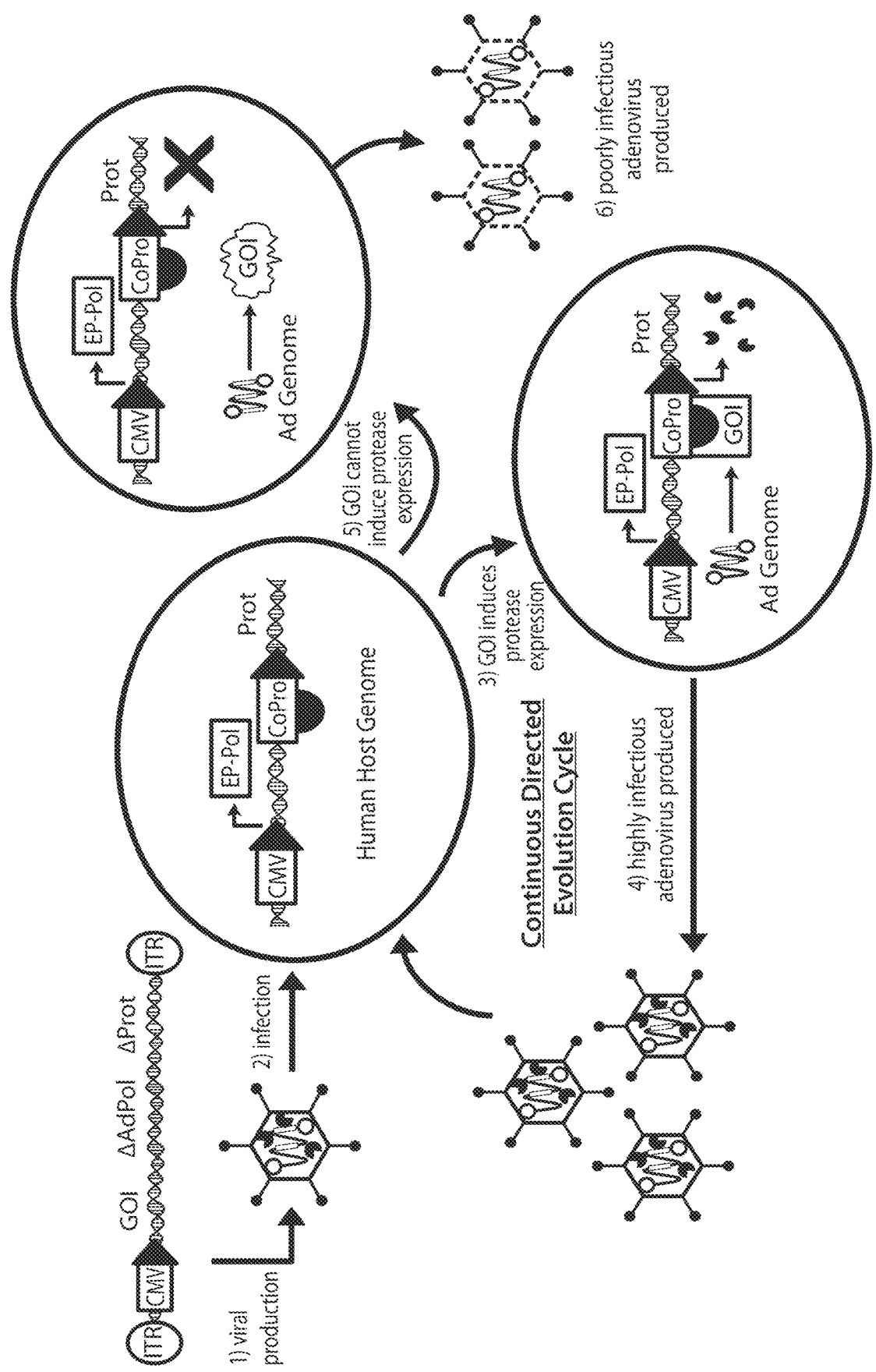
FIG. 2. Continuous directed evolution in human cells by co-opting viral replication. Here a DNA virus is represented by adenovirus: 1) Adenoviruses that contain a gene of interest ("GOI") and are deleted for both adenoviral polymerase (AdPol) and protease (Prot) genes are produced. 2) Metazoan cells that constitutively express an error-prone adenoviral polymerase (EP-pol) and that express adenoviral protease (Prot) under the control of a transcriptionally-coupled promoter (CoPro) are infected with the adenoviruses. 3) If the GOI can induce protease expression, 4) infectious viruses are produced that can infect new cells. 5) If the GOI cannot induce protease expression, 6) poorly infectious adenoviruses are produced. ITR: inverted terminal repeats.

In order to couple expression of the adenoviral protease to the evolving GOI, the gene was placed under control of an inducible promoter in the carefully optimized EP-Pol cell line (FIG. 2). GOI variants that are able to induce expression of trans-complemented adenoviral protease result in infectious virions, carrying the gene for the positive variant. These viruses can then go on to infect new cells in a continuous directed evolution cycle. However, if the GOI is not able to induce expression of trans-complemented adenoviral protease, no infectious virions are produced. These variants are subsequently diluted out during propagation of the viral population.

Through this system, GOI variants that are able to induce expression of trans-complemented adenoviral protease result in infectious virions, carrying the gene for the positive variant. These viruses can then go on to infect new cells in a continuous directed evolution cycle. GOI variants that are unable to induce expression of trans-complemented adenoviral protease, do not produce infectious virions. These variants are subsequently diluted out during propagation of the viral population (FIG. 1).

Example 2. Proof of Principle: Evolution of Tet-Transactivator in Human Cells

To demonstrate the functionality of the continuous directed evolution platform described in Example 1, the tetracycline-dependent transactivator protein (tet-transactivator) was incorporated as a GOI and evolved to be doxycycline independent (Gossen M. and Bujard H., Proc. Natl. Acad. Sci. USA 1992 Jun. 15; 89(12):5547-51). The tet-transactivator protein is a transcription factor that is often used for small molecule regulated expression in mammalian cells. In the absence of doxycycline, it binds to its target promoter, inducing expression of the downstream gene. In the presence of doxycycline, the tet-transactivator does not bind to its target promoter, and the downstream gene is not expressed.

Figure 10:
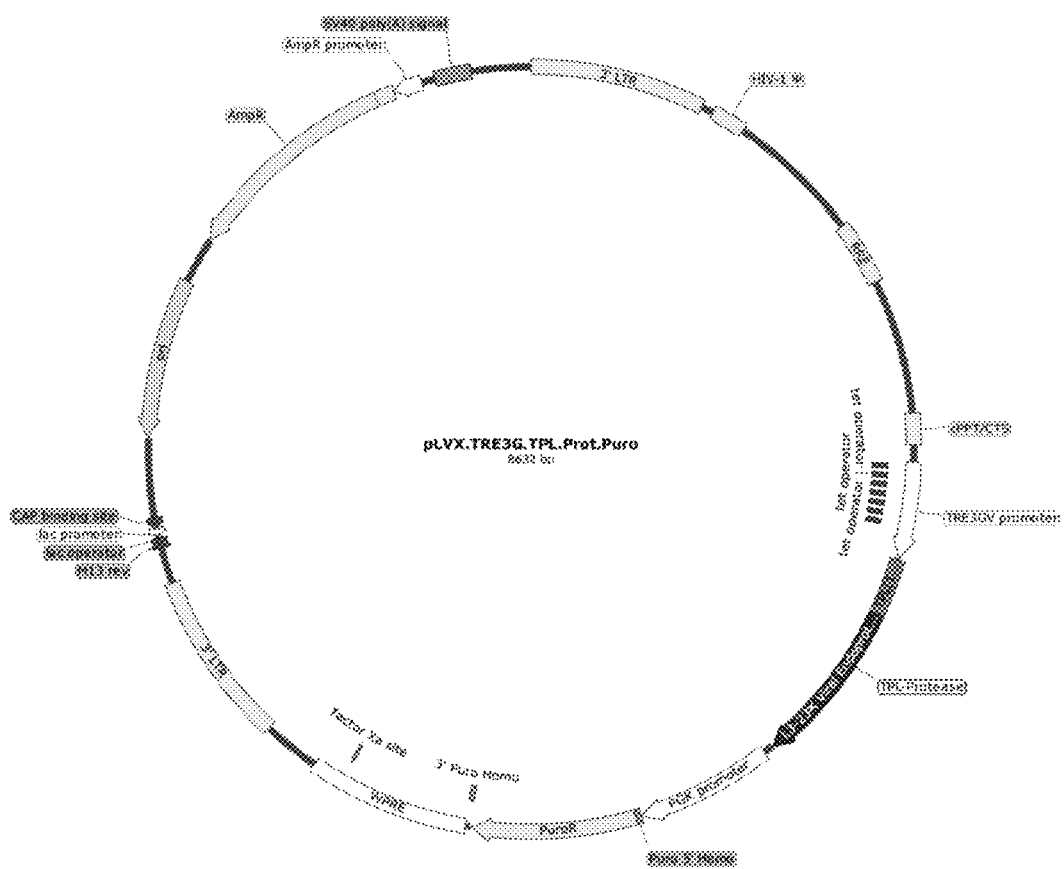
FIG. 10. Vector map of lentiviral construct for TTA-inducible ad-prot expression. This plasmid contains ad-prot under transcriptional control of the TRE3G promoter.
Figure 11:
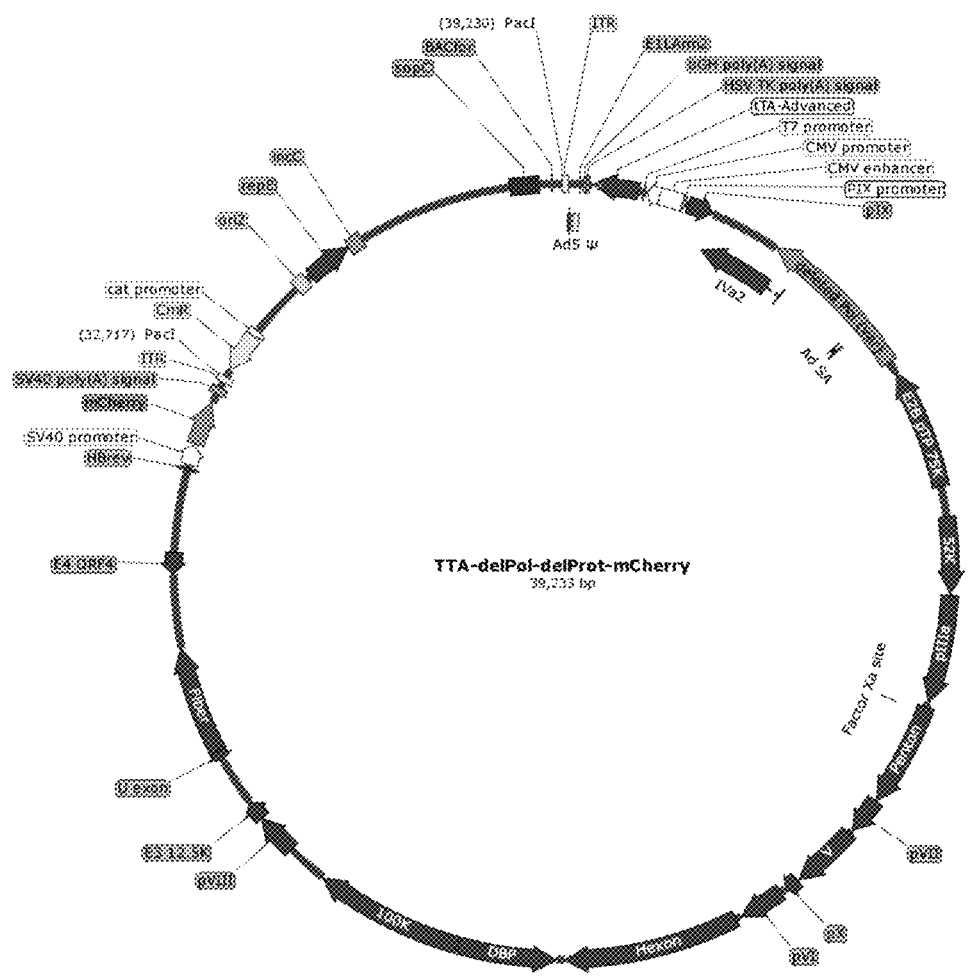
FIG. 11. Vector map of TTA-Δpol-Δprot-adenovirus used in directed evolution experiments. This map outlines the key adenoviral genes, as well as the expression cassettes that were inserted for expression of TTA and mCherry. The adenovirus genome is excised from this plasmid by digestion with PacI prior to transfection to generate adenovirus.
Figures 12, 13:
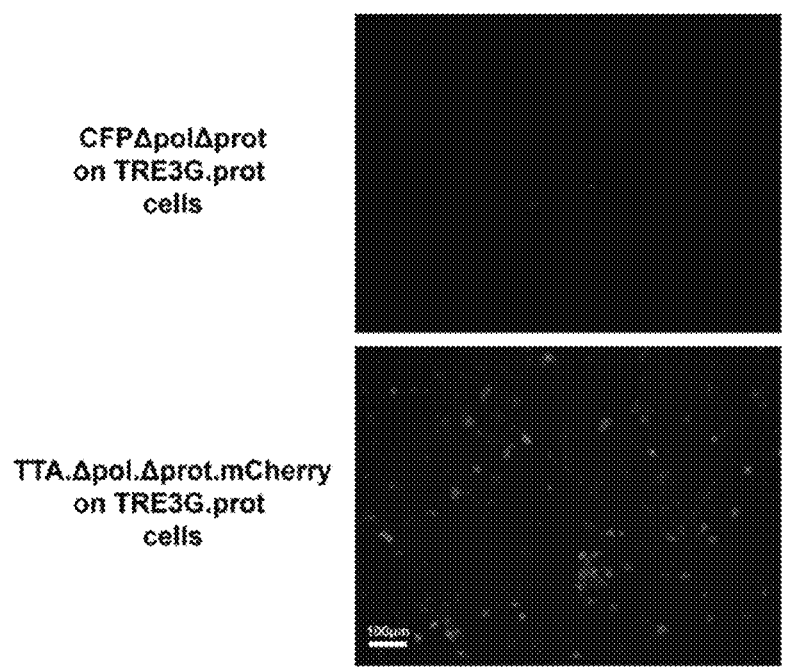
FIG. 12. TRE3G.prot cells are able to impart selective growth on ΔpolΔprot-adenoviruses that contain the tet-transactivator. ΔpolΔprot-adenoviruses that lack the tet-transactivator (CFPΔpolΔprot) were unable to spread on TRE3G.prot cells.
FIG. 13. Top frequency mutations observed at any passage. Mutations were determined to be fixed if they reached a stable level for the duration of passaging.

In order to evolve the tet-transactivator to be doxycycline independent, the adenoviral protease gene was placed under the control of the tet-transactivator promoter (termed TRE3G), in the EP-Pol cell line (FIGS. 9 and 10). The TTA gene was also cloned into the ΔpolΔprot-adenoviruses (FIG. 11). TRE3G prot cells were then infected with ΔpolΔprot- or TTA-ΔpolΔprot-adenoviruses. Only TTA-ΔpolΔprot-adenovirus are able to grow on TRE3G-prot cells (FIG. 12). These results indicate that inducible expression of adenovirus protease is able to select for viruses that express the tet-transactivator.

In order to demonstrate that all the components could work together to evolve GOIs, TTA was evolved to be doxycycline insensitive (Gossen M. and Bujard H., Proc.

Figure 14:
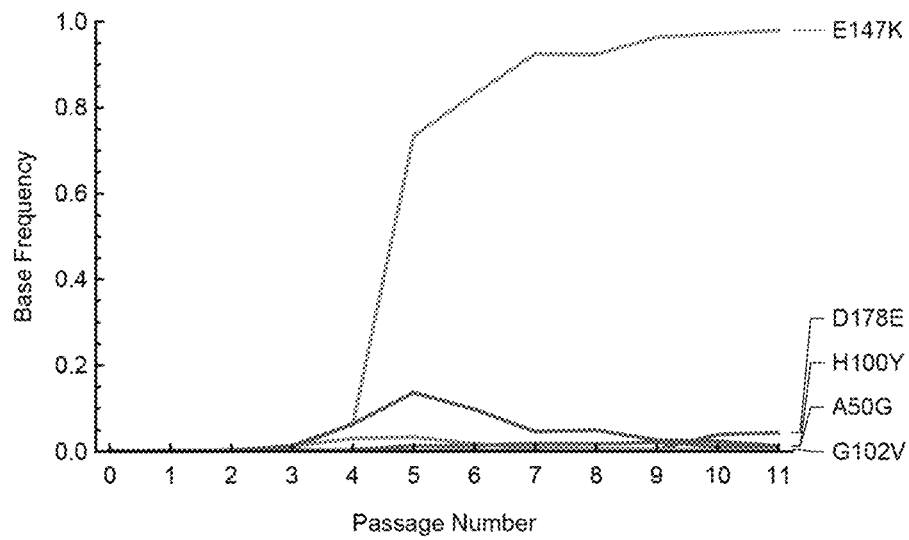
FIG. 14. Directed evolution of doxycycline insensitivity results in accumulation of specific mutants. The tet-transactivator was amplified from different passages of the directed evolution and sequenced in order to determine the relative frequencies of mutants within the population. Previously discovered doxycycline-insensitive mutants were found to accumulate to various levels throughout the course of the directed evolution experiment. At passage 4, several mutations were observed, including E147K, D178E, H100Y, A50G, and G102V. After further passages, the E147K mutation accumulated to almost 100% frequency. Overall, this experiment provides proof-of-principle that continuous directed evolution in human cells using adenovirus is possible.

Natl. Acad. Sci. USA 1992 Jun. 15; 89(12):5547-51). ΔpolΔprot-adenovirus was passaged on the TRE3G-prot cells, in the presence of doxycycline. In theory, only adenoviruses that had an evolved TTA that bound the TRE3G promoter in the presence of doxycycline would be able to induce expression of prot and continue to propagate. Using this system, the tet-transactivator was quickly evolved to be insensitive to doxycycline (in <5 viral passages). Next-generation sequencing identified multiple mutations that were previously known to cause doxycycline insensitivity and multiple novel mutations (FIGS. 13 and 14) (Hect, et al., J. Bacteriol., 1993 February; 175(4): 1206-10). Furthermore, most of these mutations mapped to the doxycycline binding site, providing further evidence for the idea that the TTA specifically evolved to be immune to doxycycline. Interestingly, additional mutations were found in the promoter of the TTA that were also enriched during directed evolution, highlighting the ability of the platform to find solutions that would not be attainable in other systems that rely on non-mammalian promoters or constructs. This experiment shows that the adenovirus-based system can be easily used to evolve biomolecules of interest in metazoan cells.

Example 3: Increasing Selection Stringency

Figure 15:
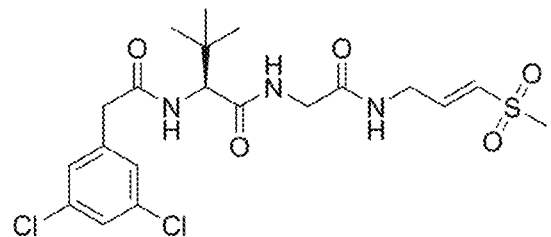
FIG. 15. Structure of adenovirus protease inhibitor used to tune selection stringency.
Figure 16:
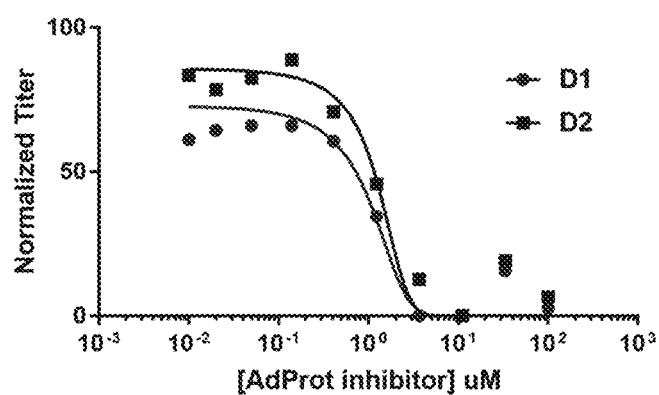
FIG. 16. Inhibition of adenovirus growth with an adenovirus protease inhibitor. HEK-293A cells were infected with GFP-expressing adenovirus (MOI=1) and treated with various concentrations of protease inhibitor. Viruses were harvested after 2 days and used to re-infect HEK-293A at various volumes to determine titer. Fluorescent cells were analyzed by flow cytometry.

Experiment were designed to tune selection stringency. To boost selection stringency of the system, experiments using adenovirus protease inhibitor (originally developed by Novartis) were designed (Grosche et al., Bioorg. Med. Chem. Lett. 2015 Feb. 1; 25(3): 438-43). The compound was synthesized, and its ability to inhibit adenoviral growth was tested (FIG. 15). These experiments demonstrated that the compound was able to reduce adenoviral titers by at least four orders of magnitude, below the limit of detection for the assay (FIG. 16). Thus, using the inhibitor to lower the concentration of active protease in the cell line, can increase the selection stringency on evolving GOIs.

Example 4: Development of Suspension Cell Lines

Experiments were designed to develop a suspension cell line for use in continuous evolution systems. An HEK-293F-derived cell line was designed that contains both EP-Pol and TRE3G.prot. Because HEK-293Fs can be grown to higher densities in larger volumes than HEK-293As, these cells will facilitate the testing of larger libraries of adenoviruses and, thus, increase the efficiency of the directed evolution process. Furthermore, HEK-293Fs are amenable to growth in a bioreactor, which could allow us to establish a "lagoon"-like evolution system (Esvelt et al., Nature 2011 Apr. 28; 472 (7344):499-503).

Example 5: Alternative DNA Viruses

While the continuous evolutions platforms described in Examples 1 and 2 above involve an engineered adenovirus replication system to mediate directed evolution of genes of interest, other engineered DNA viruses would function likewise. For example, herpes simplex virus 2 (HSV-2) was previously shown to have a DNA polymerase with a sufficiently high mutation rate as to be able to skirt drug selections (Duffy et al., BMC Infect. Dis. 2002 May 7; 2:7). Furthermore, various HSV genes have been identified as necessary for the generation of infectious HSV particles, which can potentially be used as selectable markers in a continuous evolution platform. One gene in particular, glycoprotein D, has been previously trans-complemented, and is necessary for HSV infection (Connolly et al., J. Virol. 2003 July; 77(14):8127-40). Thus, one could set up a trans-complementation system using an HSV-2 DNA virus where its native polymerase mutates the GOI, and selection could be based on proper function of glycoprotein D.

Example 6: Mutagenic Variants of DNA Viral DNA Polymerases

Mutagenesis can theoretically be achieved using a mutagenic variant of any DNA viral DNA polymerase. Mutagenic polymerase variants have been reported in both adenovirus (Uil et al., Nucleic Acid Res. 2011 March; 39(5):e30) and herpes simplex virus 2 (Duffy et al., BMC Infect. Dis. 2002 May 7; 2:7) and can conceivably be developed for any viral DNA polymerase.

Alternative mutagenesis methods that can be used with any DNA virus include radiation and chemical mutagens. For example, ultraviolet light (Wechman et al., Viruses. 2016 Dec. 20; 8(12); Day and Ziolkowski, Photochem. Photobiol. 1981 September; 34(3):403-06) and mutagenic chemical agents such as nitrous acid, hydroxylamine or 5-bromo-deoxyuridine (Williams et al., J. Gen. Virol. 1971 May; 11(2):95-101) have been used successfully to mutate adenovirus. Furthermore, the expression of DNA damaging enzymes such as activation-induced cytidine deaminase (Yoshikawa et al., Science. 2002 Jun. 14; 296(5575):2033-06) or Apobec1-dCas9 fusions (Kim et al., Nat. Biotechnol. 2017 April; 35(4):371-76) can allow for global mutagenesis or gRNA-directed site-specific mutagenesis, respectively, for any DNA present in the human cell, including viral DNA.

The use of cell lines that are deficient in DNA repair pathways can also be used in conjunction with the above mutagenesis methods in order to further boost the mutation rate. For example, disruption of uracil DNA glycosylase (a component of the base-excision repair pathway) leads to increased spontaneous mutagenesis (Saribasak et al., J. Immunol. 2006 Jan. 1; 176(1):365-71). Another way to increase the spontaneous mutation rate is to express protein inhibitors of DNA repair pathways, such as Uracil Glycosylase Inhibitor (Ugi) which inhibits the aforementioned uracil DNA glycosylase (Radany et al., Mutat. Res. 2000 Sep. 15; 461(1):41-58).

Example 7. Additional Selection Schemes

Continuous evolution platforms are not limited to embodiments comprising a transcriptional couple. Indeed, the continuous evolution platforms described herein, include, but are not limited to, continuous selection embodiments that comprise coupling to protein translation, enzymatic activity, protein-protein interactions, protein trafficking, and protein modifications. Here, various examples of these embodiments are provided.

Protein Modification:

β-catenin is constitutively ubiquitinated and degraded; however, oncogenic mutations disrupt β-catenin ubiquitination and allow it to travel to the nucleus and induce tumorigenesis. In the context of a continuous evolution platform, the adenoviral protease gene could be placed under the control of a β-catenin-inducible promoter, and an adenovirus carrying the wild-type β-catenin gene (the GOI) could be created (Biechele et al., Cold Spring Harb. Protoc. 2009 June; 2009(6):pdb.prot5223). Only β-catenin variants that are able to skirt ubiquitination and localize in the nucleus will be able to induce transcription of the viral protease, resulting in the production of infectious DNA viral particles. While the ultimate step is a transcriptional couple, this highlights how one can select based on other functions such as localization or proteasomal escape.

Enzymatic Activity:

Dickinson et. al. demonstrated a selection scheme in which one can evolve generalizable (not adenoviral protease) protease activity or specificity in bacteria (Dickinson et al., Nat. Commun., 2014 Oct. 30; 5:5352). In the context of a continuous evolution platform, one could fuse—using a linker that includes a target protease cleavage amino acid sequence—the adenoviral protease gene to a degron that causes the adenoviral protease to be constitutively degraded (Iwamoto et al., Chem. Biol. 2010 Sep. 24; 17(9):981-88). One could then place the protease of interest (GOI) in the adenoviral genome. Only proteases that are able to successfully cleave the degron off of the adenoviral protease would survive and propagate. In this case, selection would be based on functional protease escaping the proteasome.

Protein Translation:

The traditional approach for evolving new amino-acyl-tRNA-synthetases (aaRS) is to place an amber stop codon in a selectable gene and force the organism to incorporate the unnatural amino acid at that position to survive (Liu and Schultz, Annu. Rev. Biochem., 2010; 79:413-44). In the context of a continuous evolution platform, one could place an amber stop codon at a permissive site in the adenoviral protease gene and put the aaRS and a corresponding tRNA in the adenoviral genome (GOIs). Only aaRS that are able to charge tRNAs with unnatural amino acids to be incorporated at the amber stop codon will propagate.

Small-Molecule Inhibition:

Perhaps the simplest directed evolution platform one could undertake is the evolution of antibiotic resistance (e.g. methotrexate). In the context of a continuous evolution platform, one could place the antibiotic resistance marker (e.g. DHFR) in the adenoviral genome and dose the culture with methotrexate. Only variants that are able to induce cellular resistance to methotrexate will allow the virus to propagate.

Example 8. Materials and Methods for Examples 9-12

Cloning Methods:

All PCR reactions for cloning and assembling recombineering targeting cassettes were performed using Q5 High Fidelity DNA Polymerase (New England BioLabs). Restriction cloning was performed using restriction endonucleases and Quick Ligase from New England BioLabs. Adenoviral constructs were engineered using ccdB recombineering, as previously described (Wang H. et al., Nucleic Acids Res. 42, e37 (2014)) and further optimized herein. Primers were obtained from Life Technologies and Sigma-Aldrich (TABLE 5). The TPL Gene block was obtained from Integrated DNA Technologies (TABLE 5). Sequences for all plasmids developed here can be obtained from GenBank using the accession numbers provided in TABLE 6.

TABLE 2

Adenoviruses constructed and used in this study.

| Name | Modifications relative to wild-type Ad5 |
|---|---|
| AdCFP | E1R-CFP ΔE1 ΔE3 |
| CFP.ΔAdPol.GFP | E1R-CFP ΔE1 ΔE3 ΔAdPol E4R-GFP |

TABLE 2-continued

Adenoviruses constructed and used in this study.

| Name | Modifications relative to wild-type Ad5 |
|---|---|
| tTA$_{wt}$.mCherry | E1L-tTA ΔE1 ΔE3 ΔAdProt ΔAdPol E4R-mCherry |
| tTA$_{wt}$.GFP | E1L-tTAaak ΔE1 ΔE3 ΔAdProt ΔAdPol E4R-GFP |
| Cre.Ad | E1L-Cre ΔE1 ΔE3 ΔAdProt ΔAdPol E4R-mCherry |
| LeuRS.Ad | E1L-LeuRS ΔE1 ΔE3 ΔAdProt ΔAdPol E4R-mCherry |
| AdEvolve-DEST | E1L-DEST ΔE1 ΔE3 ΔAdProt ΔAdPol E4R-mCherry |
| ΔAdProtΔAdPol-adenovirus | E1R-CFP ΔE1 ΔE3 ΔAdProt ΔAdPol |
| AdGLΔPol (Uil, T. G. et al., Nucleic Acids Res. 39, e30 (2011)) | E1L-Luciferase-GFP ΔE1 ΔE3 |

Note:
All viruses used in this work were derived from AdCFP except for AdGLΔPol, which was previously reported (Uil, T. G. et al., Nucleic Acids Res. 39, e30 (2011)).

Cell Culture:

Cells were cultured at 37° C. and 5% $CO_2$(g). New cell lines were derived from a parent HEK293A cell line (ATCC) and cultured in Dulbecco's modified Eagle's medium (DMEM; Cellgro) supplemented with 10% fetal bovine serum (FBS; Cellgro), 1% penicillin-streptomycin (Cellgro), and 1% L-glutamine (Cellgro). For assays involving the tetracycline (Tet)-dependent transcriptional activation system (directed evolution of dox insensitivity, promoter activity assays, and reverse genetics), Tet-approved FBS (Takara Bio) was used. The producer and mutator cell lines (TABLE 3) were cultured in 50 μg/mL hygromycin (Thermo Fisher) to stably maintain transgenes, while the selector and phenotyping cell lines (TABLE 3) were cultured in 1 μg/mL puromycin (Corning) for the same purpose.

TABLE 3

Cell lines used in this study.

| Cell line | Polymerase | Transgene cassette |
|---|---|---|
| Producer | AdPol | CMV.AdProt |
| Mutator | EP-Pol | CMV.AdProt |
| Selector | EP-Pol | TRE3G.AdProt |
| Phenotyping | AdPol | TRE3G.eGFP |

Note:
All cell lines were derived from HEK293A cells.

Generation of Cell Lines by Lentiviral Transduction:

In a typical protocol, ~9×10$^6$ HEK293FT cells (Thermo Fisher) were plated on a poly-D-lysine-coated 10 cm plate. The next day, the cells were co-transfected with plasmids from a third-generation lentiviral packaging system (Dull T. et al., J. Virol. 72, 8463-8471 (1998)): 15 μg RRE, 6 μg REV, 3 μg VSVG, and 15 μg transfer vector using 60 μL Lipofectamine 2000 (Thermo Fisher). Cultures were maintained in 5 mL total volume of OPTI-MEM (Gibco) during the transfection. After 8 h, the media was exchanged for fresh DMEM. After 48 h, media was harvested and centrifuged for 5 min at 3,200×g to clear the cell debris. The supernatant was used to transduce HEK293A cells supplemented with 4 μg/mL polybrene (Sigma-Aldrich). After 24 h, the media was exchanged for fresh DMEM. 48 h later, media was exchanged again for DMEM containing appropriate antibiotics to select stable cell lines.

Adenovirus Production:

Adenoviruses were produced by transfecting a PacI (New England BioLabs)-linearized vector into appropriate trans-complementing HEK293A cells (ΔAdPol adenoviruses on wild-type AdPol cells, ΔAdProtΔAdPol adenoviruses on producer cells; see TABLE 3). 24 µg of PacI-linearized adenovirus vectors mixed with 144 µL polyethyleneimine (Sigma-Aldrich) in 1 mL OptiMEM (Gibco) was added to a 15 cm plate of producer cells (TABLE 3; ~3×10$^7$ cells). Media was replaced 8 h post-transfection, and then intermittently replaced every 2-3 days until plaques were observed (typically ~3 weeks). Once plaques were detected, cytopathic effect was observed in all cells within 5 days. Upon complete cytopathic effect, the cells and media were harvested and subjected to three freeze/thaw cycles. The cell debris was removed by centrifugation at 3,200×g for 15 min and the supernatant stored at −80° C.

Mutagenesis Rate Determination:

The mutagenic potential of AdPol variants was evaluated following a previously reported protocol (Uil T. G. et al., Nucleic Acids Res. 39, e30 (2011)). Briefly, a polymerase-deleted Ad5, AdGLΔPol, was subjected to 10 serial passages on cultures of 911 cells (Fallaux F. J. et al., Hum. Gene Ther. 7, 215-222 (1996)) expressing EP-Pol in order to accumulate mutations. After 10 serial passages, 911 cells expressing wild-type AdPol were infected in a 6-well plate at ~50 plaque-forming units/well in order to amplify pools of 50 viral clones for sequencing. Using pools of 50 or fewer clonal viruses ensured that mutations present in only one clone will be present at a frequency above the threshold of detection. From each 50-clone viral pool, a 6.5-kb fragment was amplified and prepared for deep sequencing. Libraries were subjected to 32 cycles of single-read sequencing by an Illumina Genome Analyzer II.

Figure 24:
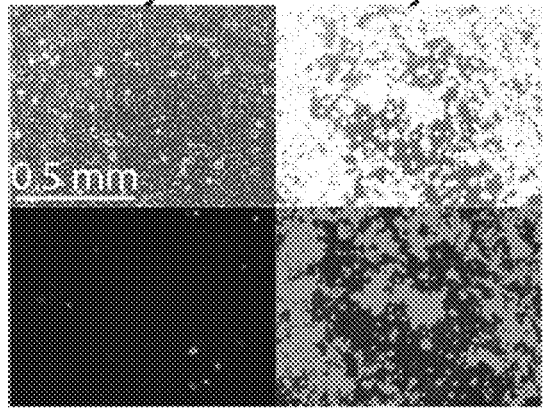
FIG. 24. Transcomplementation of wild-type adenoviral polymerase (AdPol). Parental HEK293A cells stably expressing wt AdPol were infected with a GFP-encoding ΔAdPol-adenovirus (CFP.ΔAdPol.GFP). The virus propagated robustly on these AdPol expressing cells.

AdPol and AdProt Trans-Complementation Assays:

The day before beginning the assay, a 6-well plate was seeded with ~1×10$^6$ of the indicated cells. The next day, individual wells were infected with the indicated adenoviruses at a low MOI (<0.5) in order to permit observation of the presence or absence of a spreading infection. AdPol and EP-Pol trans-complementation (see FIG. 24 for AdPol and FIG. 20B for EP-Pol) was tested by monitoring CFP.ΔAdPol.GFP adenovirus infection on either AdPol- or EP-Pol-expressing HEK293A cells. Pictures were taken with an Olympus U-TB190 microscope. AdProt and AdPol double trans-complementation (see FIG. 25) was tested by monitoring ΔAdProtΔAdPol-adenovirus (TABLE 2) infection on producer cells. Pictures were taken with a Nikon Eclipse TE200 microscope.

Determining Adenoviral Titer by Flow Cytometry:

Adenoviral titers were determined through flow cytometry. Known volumes of AdPol- and AdProt-deleted viral supernatants were added to AdPol-expressing HEK293A cells. 2-3 days post-infection, cells were washed once with media, stained with 0.2 µg/mL DAPI, and then analyzed on a BD LSR II Analyzer for fluorescent protein expression. Infectious titers were determined by measuring the percentage of cells infected by a known volume of virus. To minimize counting cells that were infected by more than one virus and to minimize any background fluorescence, data were only considered if they fell within the linear range, which typically encompassed samples where 1-10% of cells were infected.

Competition Experiments:

A confluent dish of selector cells (TABLE 3; ~15 million cells) was infected with either a 1:100 or 1:1,000 mixture of tTA$_{wt}$:tTA$_{mut}$ adenovirus (MOI~0.25; TABLE 2). Plates were monitored for the appearance of spreading infection, defined by fluorescent "comets" or plaques, every 24 h. One day after the observation of spreading infection, 1 mL of media was transferred to a new semi-confluent dish (~1×10$^7$ cells) of selector cells for the next passage (see TABLE 3), and 2 mL of media was stored at −80° C. for later analysis. To analyze the relative amounts of each virus present after each passage, the relative adenoviral titers was measured by flow cytometry (see above). The ratio of tTA$_{wt}$ and tTA$_{mut}$ viruses was determined by taking the ratio of cells expressing only mCherry and only GFP.

AdProt inhibitor experiments: A confluent 12-well plate of selector cells (TABLE 3) (~4×10$^5$ cells/well) was infected with tTA$_{wt}$.mCherry adenovirus (MOI~5). After 4 h, the cells were washed with PBS (Corning), and the AdProt inhibitor was added at the indicated concentrations (0 µM, 1 µM, 20 µM) in the absence or presence of 2 nM doxycycline (dox; Sigma-Aldrich). After 6 days, media and cells were harvested and subjected to three freeze/thaw cycles, and analyzed by flow cytometry (see above).

TABLE 4

Tabulation of next-generation sequencing results and experimental parameters used to estimate the EP-Pol mutation rate.1

| Estimated number of clones sequenced | Size of the region sequenced and analyzed (bp) | Substitution load per million bp | Substitutions per Ad genome per viral generation |
|---|---|---|---|
| 27.3* | 6020 | 365 | 1.31** |

*Viral pool size was estimated based on intra-experiment titrations during pool preparations
**Assuming a genome size of 36 kb and that 27.3 genomes were sequenced. Each of the 10 passages was defined as a generation.

Continuous Evolution Workflow:

Before initiating directed evolution, 500 µL of a tTA$_{wt}$.mCherry adenovirus was amplified on mutator cells (see TABLE 3) to create a diverse viral population. After 5 days, cytopathic effect was observed in all cells. This amplified virus was harvested with three freeze/thaw cycles. Three 15 cm, semi-confluent dishes of selector cells (TABLE 3) (~1×10$^7$ cells/plate) were infected with either 250, 500, or 1,000 µL of the amplified virus in the presence of dox. Plates were monitored for plaques every day. If more than one plate displayed a plaque on the same day, the plate with the lowest volume of virus added was used for the next round of evolution. The day after a plaque was observed, three 15 cm semi-confluent dishes of selector cells were again infected in the presence of dox. The three dishes were infected with 250, 500, or 1,000 µL of media from the previous round by direct transfer without a freeze/thaw step. 2 mL of media were saved in Eppendorf tubes and stored at −80° C. for future analysis. In Trial 1, the concentration of dox was increased to 200 nM at passage 7 and then to 20 µM in passages 8-12. In Trial 2, the concentration of dox was held constant at 200 nM for all seven passages.

Measuring Promoter Activity of Viral Populations:

To follow changes in promoter activity developing during Trial 1, phenotyping cells (TABLE 3) were plated in a 96-well plate at ~40,000 cells/well. The next day, 30 µL of media from passages 1-12 was used to infect two rows of the 96-well plate. Media was removed 5 h post-infection and replaced with media containing 0 µM or 20 µM dox. The cells were then analyzed by flow cytometry (see above for sample preparation) for simultaneous expression of mCherry, indicating that the cell was infected, and GFP, indicating that the promoter was activated by the tTA protein.

Viral Genome Isolation for Next-Generation Sequencing:

Using a viral DNA isolation kit (NucleoSpin Virus; Macherey-Nagel), DNA was harvested from 200 µL of the media that was saved after each round of evolution. A 1.75 kb region of DNA encompassing the CMV promoter and the tTA gene was PCR-amplified from 1 µL of the harvested DNA for 20 rounds of amplification using 5'-ctacataagacccc-caccttatatattctttcc-3' (SEQ ID NO: 199) and 5'-agcgg-gaaaactgaataagaggaagtgaaatc-3' (SEQ ID NO: 200) forward and reverse primers, respectively. The resulting PCR product was purified and prepared for Illumina sequencing via the Nextera DNA Library Prep protocol (Illumina). 250 bp paired-end sequencing was run on a MiSeq (Illumina). Sequencing reads were aligned to the amplicon sequence, which was derived from the tTA$_{wt}$.mCherry adenovirus sequence using bwa mem 0.7.12-r1039 [RRID: SCR_010910]. Allele pileups were generated using samtools v1.5 mpileup [RRID:SCR_002105] with flags -d 10000000 -excl-flags 2052, and allele counts/frequencies were extracted (Li H. et al., Bioinformatics 25, 2078-2079 (2009); Li H. Bioinformatics 27, 2987-2993 (2011)). Each position within the tTA gene and CMV promoter had at least 1,000-fold coverage.

Reverse Genetics of tTA Variants:

HEK-293A cells were seeded in a 12-well plate at ~4×10$^5$ cells/well. The next day, 0.2 µg of the pBud.tTA.mCherry vector was co-transfected with 1 µg of the pLVX-TRE3G.eGFP vector using 7.2 µL of polyethyleneimine (Polysciences) and 100 µL OPTI-MEM. 8 h post-transfection, media was exchanged and 20 µM dox was added. 48 h post-transfection, cells were analyzed by flow cytometry (see above for sample preparation). Promoter activity was calculated based on the mean fluorescence intensity of GFP fluorescence, backgated for only mCherry-expressing cells.

Wild-Type AdPol and EP-Pol Vectors:

The lentiviral vector encoding HA-tagged wild-type AdPol was previously described (Uil T. G. et al., Nucleic Acids Res. 39, e30 (2011)). Mutations were introduced by site-directed mutagenesis. CMV.AdProt vector: A 641 bp fragment containing adenoviral protease (AdProt) was amplified from the Ad5 genome using the primers BamHI.AdProt Forward and SalI.AdProt Reverse (TABLE 5) and ligated into pTRETight (Clontech) using BamHI and SalI to make the pTRE-Tight.AdProt vector. The Ad5 Tripartite leader sequence (TPL) was amplified from the TPL gene block using the primers TPL.GA.Forward and TPL.GA.Reverse (TABLE 5) and the pTRE-Tight.AdProt vector was amplified using the primers Tight.AdProt.GA.Forward and Tight.AdProt.GA.Reverse (TABLE 5). The TPL and pTRE-Tight.AdProt amplicons were assembled using the HiFi DNA assembly kit (New England Biolabs) to create the pTRE-Tight.TPL.AdProt vector. From this vector, an 852 bp fragment containing TPL.AdProt was amplified using the primers NotI.TPL.AdProt.Forward and XbaI.TPL.AdProt.Reverse (TABLE 5) and inserted into the pENTR1A vector (Thermo Fisher) using NotI and XbaI. The LR clonase II enzyme mixture (Thermo Fisher) was used to recombine the TPL.AdProt fragment from pENTR1A.TPL.AdProt into pLenti.CMV.Hygro (w117-1) (Thermo Fisher).

TABLE 5

Primers used to construct lentiviral and adenoviral plasmids through cloning and recombineering.

| Name | Sequence - 5' to 3' | SEQ ID NO: |
|---|---|---|
| BamHI.AdProt.Forward | aaaaaaggatccaccatgggctccagtgag | 37 |
| SalI.AdProtReverse | aaaaagtcgacttacatgttttcaagtgacaaaaagaag | 38 |
| EcoRI.TPL.Forward | aaaaaagcggccgcactctcttccgcatcg | 39 |
| BamHI.TPL.Reverse | aaaaaatctagattacatgttttcaagtgacaaaaagaag | 40 |
| TPL.GA.Forward | atcgcctggagaattcactctcttccgcatcgct | 41 |
| TPL.GA.Reverse | ctcactggagcccattgcgactgtgactggttag | 42 |
| TPL Gene Block | aaaaaagaattcactctcttccgcatcgctgtctgcgagggccagctgttgggctcgcggttga ggacaaactcttcgcggtctttccagtactcttggatcggaaacccgtcggcctccgaacaggt actccgccgccgagggacctgagcgagtccgcatcgaccggatcggaaaacctctcgaga aaggcgtctaaccagtcacagtcgcaggatccttttt | 43 |
| Tight.AdProt.GA.Forward | atgggctccagtgagcag | 44 |
| Tight.AdProt.GA.Reverse | gaattctccaggcgatctg | 45 |
| NotI.TPL.AdProt.Forward | aaaaaagcggccgcactctcttccgcatcg | 46 |
| XbaI.TPL.AdProt.Reverse | aaaaaatctagattacatgttttcaagtgacaaaaagaag | 47 |
| TPL.AdProt GA.Forward | tggagaaggatccgcactctcttccgcatcgct | 48 |
| TPL.AdProt GA.Reverse | atctagagccggcgcttacatgttttcaagtgacaaaaagaag | 49 |
| NotI.eGFP.Forward | aaaaaaagcggccgccgccaccatggtgag | 50 |
| EcoRI.eGFP.Reverse | aaaaaagaattccggccgctttacttgtac | 51 |
| NotI.mCherry.Forward | aaaaaagcggccgcgcaccatggtgagcaag | 52 |
| Xhoi.mCherry.Reverse | aaaaaactcgagactacttgtacagctcgtccatg | 53 |

TABLE 5-continued

Primers used to construct lentiviral and adenoviral plasmids through cloning and recombineering.

| Name | Sequence - 5' to 3' | SEQ ID NO: |
|---|---|---|
| SalI.TTA.Forward | aaaaaagtcgacatgtctagactggacaagagcaaag | 54 |
| BamHI.TTA.Reverse | aaaaaaggatccttacccggggagcatgtcaagg | 55 |
| NotI.TPL.Forward | aaaaaagcggccgcactctcttccgcatcg | 56 |
| XbaI.AdProt.Reverse | aaaaaatctagattacatgttttcaagtgacaaaaagaag | 57 |
| pENTR1A.AdProt.FLAG.Forward | taatctagacccagctttcttgtacaaagttggcattataag | 58 |
| pENTR1A.AdProt.FLAG.Reverse | agaaagctgggtctagattacttatcgtcgtcatccttgtaatccatgttttcaagtgacaaaaagaagtggcg | 59 |
| LoxP2Term.GA.Forward | agtcgactggatccggtaccgccgcatcaacgagctc | 60 |
| LoxP2Term.GA.Reverse | gagagtgcggccgcgaattcgaggcccagagggtacc | 61 |
| pENT.AdProt.GA.Forward | gaattcgcggccgcac | 62 |
| pENT.AdProt.GA.Reverse | ggtaccggatccagtcgac | 63 |
| L8.STOP.Forward | cagtgagcaggaatagaaagccattgtcaaagatcttggttgtgg | 64 |
| L8.STOP.Reverse | ctttgacaatggctttctattcctgctcactggagcccattg | 65 |
| E1.kanccdB.Forward | atacaaaactacataagaccccaccttatatattctttcccacccttaaccctcatcagtgccaacatagtaag | 66 |
| E1.kanccdB.Reverse | aataagaggaagtgaaatctgaataattttgtgttactcatagcgcgtaaccgctcattaggcgggc | 67 |
| TetR.kanccdB.Forward | tggaactaatcatatgtggcctggagaaacagctaaagtgcgaaagcggcccgctcattaggcgggc | 68 |
| TetR.kanccdB.Reverse | cgcgaacaaatgtggtatggctgattatgatcctctagagataattctagccctcatcagtgccaacatagtaag | 69 |
| E1.CMV.Promoter.Forward | atacaaaactacataagaccccaccttatatattctttcccacccttaagccacgcccacagatatacgcgttgacattg | 70 |
| E1.bGH.polyA.Reverse | aataagaggaagtgaaatctgaataattttgtgttactcatagcgcgtaatagaagccatagagcccac | 70 |
| E4.kanccdB.Forward | caaaaaacccacaacttcctcaaatcgtcacttccgttttcccacgttaccccctcatcagtgccaacatagtaag | 72 |
| E4.kanccdB.Reverse | agtaacttgtatgtgttgggaattgtagttttcttaaaatgggaagtgacccgctcattaggcgggc | 73 |
| E4.SV40.Promoter.Forward | caaaaaacccacaacttcctcaaatcgtcacttccgttttcccacgttacttctgtggaatgtgtgtcagttaggg | 74 |
| E4.SV40.polyA.Reverse | agtaacttgtatgtgttgggaattgtagttttcttaaaatgggaagtgacctctagctagaggtcgacggtatac | 75 |
| Pol.kanccdB Forward | tcccgcgcttcttggaactttacattgtgggccacaacatcaacggccctccctcatcagtgccaacatagtaag | 76 |
| Pol.kanccdB Reverse | ggcacctcggaacggttgttaattacctgggcggcgagcacgatctcgtcccgctcattaggcgggc | 77 |
| delPol.Forward | gcgcggccttccggagcgaggtgtgggtgagcgcaaaggtgtccctgaccatgaccagcatgaagggcacgagctgcttcccaaaggccccccatccaag | 78 |
| delPol.Reverse | cttggatgggggcctttgggaagcagctcgtgcccttcatgctggtcatggtcagggacacctttgcgctcacccacacctcgctccggaaggccgcgc | 79 |
| AdProt.kanccdB.Forward | ggcaacgccacaacataaagaagcaagcaacatcaacaacagctgccgccccctcatcagtgccaacatagtaag | 80 |
| AdProt.kanccdB.Reverse | tacaaataaaagcatngcctttattgaaagtgtctctagtacattatttccgctcattaggcgggc | 81 |

TABLE 5-continued

Primers used to construct lentiviral and adenoviral plasmids through cloning and recombineering.

| Name | Sequence - 5' to 3' | SEQ ID NO: |
|---|---|---|
| delAdProt.Forward | ggcaacgccacaacataaagaagcaagcaacatcaacaacagctgccgccaaataatgtac tagagacactttcaataaaggcaaatgcttttatttgta | 82 |
| delAdProt.Reverse | tacaaataaaagcatttgcctttattgaaagtgtctctagtacattatttggcggcagctgttgttga tgttgcttgcttctttatgttgtggcgttgcc | 83 |

TRE3G.AdProt Vector:

TPL-AdProt was amplified from pTRE-Tight.TPL.AdProt using the primers TPL.AdProt.GA.Forward and TPL.AdProt.GA.Reverse (TABLE 5) and assembled with NotI-digested pLVX.Tight.Puro (Takara Biosciences) using the HiFi DNA assembly kit to form pLVX.Tight.TPL.AdProt.Puro. A fragment containing TPL.AdProt was obtained from pLVX.Tight.TPL.AdProt.Puro by digestion with EcoRI and BamHI and ligated into the pLVX.TRE3G vector (Takara Bio) to create the pLVX.TRE3G.AdProt vector.

Tre3G.Egfp Vector:

A 762 bp fragment containing eGFP was amplified from the eGFP-N3 vector (Takara Bio) using the primers NotI.eGFP.Forward and EcoRI.eGFP.Reverse (TABLE 5) and ligated into the pLVX-TRE3G vector (Takara Bio) using NotI and EcoRI to create the pLVX-TRE3G.eGFP vector.

tTA Variant Vectors:

A 743 bp fragment containing mCherry was amplified from a pcDNA3.1-mCherry template plasmid using the primers NotI.mCherry.Forward and XhoI.mCherry.Reverse (TABLE 5) and inserted into the pBudCE4.1 vector (Thermo Fisher) using NotI and XhoI to create the pBud.mCherry vector. A 771 bp fragment containing tTA was amplified from a tTA.mCherry adenoviral vector using the primers SalI.TTA.Forward and BamHI.TTA.Reverse (TABLE 5) and inserted into the pBud.mCherry vector using BamHI and SalI to create the pBud.tTA.mCherry vector. Site-directed mutagenesis was then performed on pBud.tTA.mCherry using a Quick-Change II XL Site-Directed Mutagenesis Kit (Agilent) to generate the indicated point mutations in tTA (FIG. 22F).

TABLE 6

Plasmid sequence accession numbers.

| Vector Name | GenBank Accession Number | SEQ ID NO: |
|---|---|---|
| Wild-type AdPol vector | MH325099 | 84 |
| EP-Pol vector | MR325100 | 85 |
| pTRE-Tight.TPL.AdProt | MR325101 | 86 |
| CMV.AdProt | MR325102 | 87 |
| pLVX.TRE3G.AdProt | MH325103 | 88 |
| pLVX.TRE3G.eGFP | MH325104 | 89 |
| pBud.tTA.mCherry | MH325105 | 90 |
| R6K-kan-ccdB | MH325106 | 91 |
| pcDNA3.1-mCherry template plasmid | MH325107 | 92 |
| pcDNA3.1-GFP template plasmid | MH325108 | 93 |
| pcDNA3.1-tTA template plasmid | MH325109 | 94 |
| pcDNA3.1-tTA$_{aak}$ template plasmid | MH325110 | 95 |
| pcDNA3.1-KanFDEST template plasmid | MH325111 | 96 |
| AdCFP | MH325112 | 97 |

TABLE 6-continued

Plasmid sequence accession numbers.

| Vector Name | GenBank Accession Number | SEQ ID NO: |
|---|---|---|
| tTA$_{wt}$-mCherry | MH325113 | 98 |
| tTA$_{mut}$-GFP | MH325114 | 99 |
| AdEvolve-DEST | MH325115 | 100 |
| ΔAdProtΔAdPol-adenovirus | MH325116 | 101 |

Adenoviral Constructs:

Adenoviral constructs were engineered using ccdB recombineering, as previously described, 2 in DH10B Escherichia coli carrying the adenovirus type 5 genome in a chloramphenicol-resistant bacterial artificial chromosome (AdBAC). Cells carrying an AdBAC were transformed with the temperature-sensitive psc101l-gbaA recombineering plasmid (Wang H. et al., Nucleic Acids Res. 42, e37 (2014)), plated on LB (Difco) agar (Alfa Aesar) with 10 μg/mL tetracycline (Cal-BioChem) and 10 μg/mL chloramphenicol (Alfa Aesar), and incubated for 24 h at 30° C. Colonies were selected and grown in LB containing 10 μg/mL tetracycline and 10 μg/mL chloramphenicol overnight at 30° C. (18-21 h). Overnight cultures were diluted 25-fold in LB with 10 μg/mL tetracycline and 10 μg/mL chloramphenicol and grown at 30° C. for ~2 h until attaining an OD600 of 0.3-0.4. The ccdA antitoxin and recombineering machinery were then induced by adding L-arabinose (Chem-Impex) and L-rhamnose (Sigma Aldrich) to a final concentration of 2 mg/mL each and then growing the cultures at 37° C. for 40 min to an OD600 of ~0.6. The cultures were then placed on ice, washed twice with ice-cold, sterile ddH2O, resuspended in ~25 μL of ice-cold, sterile ddH2O, and electroporated with ~200 ng of the appropriate kan-ccdB targeting cassette (1.8 kV, 5.8 ms, 0.1 cm cuvette, BioRad Micropulser). The cells were then recovered in super optimal broth with catabolite repression (SOC; Teknova) with 2 mg/mL L-arabinose at 30° C. for 2 h, then plated on LB agar plates with 50 μg/mL kanamycin (Alfa Aesar) and 2 mg/mL L-arabinose and incubated for 24 h at 30° C. Colonies that grew under these conditions had incorporated the kan-ccdB targeting cassette and were picked in triplicate and grown in LB with 50 μg/mL kanamycin and 2 mg/mL L-arabinose at 30° C. for 18-21 h. Note that the colonies were picked in triplicate because multimers of the AdBAC formed at a high rate (~30-50% of colonies) during the first recombineering step. Such multimers cannot be successfully recombineered in the next step. Picking three colonies and recombineering them separately in parallel increases the chances of picking a monomer that can be successfully recombineered. The cultures were then diluted 25-fold in LB with 50 μg/mL kanamycin and 2 mg/mL L-arabinose and grown at 30° C. for ~2 h until they reached an OD$_{600}$ of 0.3-0.4. The recombineering machinery was then induced by adding L-rhamnose to a final concentration of 2 mg/mL and then growing the cultures at 37° C. for 40 min to an OD$_{600}$ of ~0.6. The cultures were then placed on ice, washed twice with ice-cold, sterile ddH$_2$O, resuspended in ~25 µL of ice-cold, sterile ddH2O, and electroporated with ~200 ng of the final targeting cassette intended to replace the kan-ccdB cassette currently integrated in the genome (1.8 kV, 5.8 ms, 0.1 cm cuvette, BioRad Micropulser). The cells were then recovered in SOC with 2 mg/mL L-arabinose at 30° C. for 2 h, and then were washed once with LB to remove the L-arabinose and prevent continued production of the ccdA antitoxin. The cultures were then plated on LB agar plates at various dilutions with 10 µg/mL tetracycline and 10 µg/mL chloramphenicol and incubated for 24 h at 37° C. Without the ccdA antitoxin, the ccdB toxin will kill cells that have not replaced the integrated kan-ccdB cassette with the final targeting cassette. The colonies that grow should, in principle, have the desired final targeting cassette integrated, but were always screened by PCR or sequencing to confirm cassette integration as some colonies may simply inactivate the ccdB toxin.

The following modifications were made using the primers in TABLE 5 to obtain the adenoviruses (TABLE 2) used in this work:

TABLE 7

List of modifications and their means of production.

| Modification | Genotype | KanccdB cassette primers used with R6K-kan-ccdB template plasmid (unless stated otherwise) | Final targeting cassette oligos or primers and template (if applicable) | Purpose of modification |
|---|---|---|---|---|
| AdPol Deletion | ΔAdPol | Pol.kanccdB.Forward and Pol.kanccdB.Reverse | delPol.Forward and delPol.Reverse (annealed oligos) | To prevent evolution of the adenoviral polymerase. The error-prone version was expressed in trans. |
| Insertion of mCherry | E4R-mCherry | E4.kanccdB.Forward and E4.kanccdB.Reverse | E4.SV40.Promoter.Forward and E4.SV40.Reverse were used to amplify from pcDNA3.1-mCherry template plasmid | mCherry was inserted to enable the visualization of infected cells. The E4 position with the rightward facing orientation was previously shown to allow for optimal expression and viral titer (Suzuki M. et al., Gene Ther. 22, 421-429 (2015)). |
| Insertion of eGFP | E4R-eGFP | E4.kanccdB.Forward and E4.kanccdB.Reverse | E4.SV40.Promoter.Forward and E4.SV40.Reverse were used to amplify from pcDNA3.1-eGFP template plasmid | eGFP was inserted to enable the visualization of infected cells. The E4 position with the rightward facing orientation was previously shown to allow for optimal expression and viral titer (Suzuki M. et al., Gene Ther. 22, 421-429 (2015)). |
| AdProt Deletion | ΔAdProt | AdProt.kanccdB.Forward and AdProt.kanccdB.Reverse | delAdProt.Forward and delAdProt.Reverse (annealed oligos) | This essential viral gene was deleted so that viral replication could become dependent on the conditional expression of the adenoviral protease in trans. |
| Insertion of active tTA | E1L-tTA | E1.kanccdB.Forward and E1.kanccdB.Reverse | E1.CMV.Promoter.Forward and E1.bGH.polyA.Reverse used to amplify from pcDNA3.1-tTA template plasmid | tTA was inserted as the evolution target that must evolve to express adenoviral protease from the host genome for efficient viral propagation. The E1 position with the leftward facing orientation was previously shown to allow for optimal expression and viral titer (Suzuki M. et al., Gene Ther. 22, 421-429 (2015)). |
| Insertion of inactive tTA | E1L tTA$_{aak}$ | E1.kanccdB.Forward and E1.kanccdB.Reverse | E1.CMV.Promoter.Forward and E1.bGH.polyA.Reverse used to amplify from pcDNA3.1-tTA$_{aak}$ template plasmid | An inactive version of tTA that recognizes a different tet operator (Krueger M. et al., Gene 404, 93-100 (2007)) was inserted to generate a negative control virus. |

TABLE 7-continued

List of modifications and their means of production.

| Modification | Genotype | KanccdB cassette primers used with R6K-kan-ccdB template plasmid (unless stated otherwise) | Final targeting cassette oligos or primers and template (if applicable) | Purpose of modification |
|---|---|---|---|---|
| Insertion of DEST cassette | E1L-DEST | E1L.KanccdB.Forward and E1.kanccdB.Reverse used to amplify from pcDNA3.1-KanFDEST template plasmid | Not applicable, only the first step is required | Insertion of a DEST cassette into the E1 position with the leftward facing orientation. The DEST cassette has attR sites that allow users to insert genes via Gateway cloning. |
| Replacement of the low copy BAC origin with the high copy pUC origin | Not applicable | N/A, the replacement is a one-step recombineering since the origin switches from chloramphenicol to ampicillin resistant | BAC2pUC.Forward and BAC2pUC.Reverse used to amplify the pUC origin cassette from pAd/CMV/V5-DEST (Thermo Fisher). | Switching to a high copy pUC origin allowed for the preparation of concentrated, purified DNA, which was necessary for transfection and successful adenovirus production. |

Once a clone with all of the desired genetic changes was found and confirmed by Sanger sequencing, the AdBAC single-copy replication origin was replaced with the high copy pUC origin. The cells with the correct clone were grown in LB containing 10 µg/mL tetracycline and 10 µg/mL chloramphenicol overnight at 30° C. (18-21 h). Overnight cultures were diluted 25-fold in LB with 10 µg/mL tetracycline and 10 µg/mL chloramphenicol and grown at 30° C. for ~2 h until attaining an OD600 of 0.3-0.4. The recombineering machinery was then induced by adding L-rhamnose to a final concentration of 2 mg/mL each and then growing the cultures at 37° C. for 40 min to an OD600 of ~0.6. The cultures were then placed on ice, washed twice with ice-cold, sterile ddH2O, resuspended in ~25 µL of ice-cold, sterile ddH2O, and electroporated with ~200 ng of the pUC origin cassette (1.8 kV, 5.8 ms, 0.1 cm cuvette; BioRad Micropulser). The cells were recovered in SOC at 30° C. for 2 h, then plated on LB agar plates with 100 µg/mL ampicillin and incubated for 24 h at 37° C. The resulting amp-resistant colonies should have the pUC origin inserted and were checked by verifying expected restriction digestion patterns. The colonies were grown in 25 mL LB containing 100 µg/mL ampicillin and the DNA was purified using the Zymo-PURE II plasmid midiprep kit (Zymo Research) according to the manufacturer's instructions. The DNA was digested with PacI overnight at 37° C. in order to liberate and linearize the adenoviral genome. The linearized DNA was purified using the E.Z.N.A. cycle pure kit (Omega Biotek) according to the manufacturer's instructions.

Example 9. Mutagenesis

Directed evolution methodologies have transformed our ability to generate biomolecules with improved or novel functionalities (Packer M. S. and Liu D. R., Nat. Rev. Genet. 16, 379-394 (2015); Gai S. A. and Wittrup K. D., Curr. Opin. Struct. Biol. 17, 467-473 (2007); Romero P. A. and Arnold F. H., Nat. Rev. Mol. Cell Biol. 10, 866-876 (2009); Shaner N. C. et al., Nat. Biotechnol. 22, 1567-1572 (2004); Branon T. C. et al., Nat. Biotechnol., doi:10.1038/nbt.4201 (2018); Arzumanyan G. A. et al., ACS Synth. Biol. 7, 1722-1729 (2018)). The vast majority of directed evolution experiments are performed in test tubes, bacteria, or yeast. While these strategies have yielded many successes, they also frequently lead to products that fail to function optimally when later introduced into complex metazoan systems. The evolved functions can be derailed by off-target interactions, poor protein folding or stability, pleiotropic outputs, or other serious problems that arise because the biomolecules were discovered and optimized in overly simplistic environments (Zetsche B. et al., Cell 163, 759-771 (2015); Peck S. H. et al., Chem. Biol. 18, 619-630 (2011); Piatkevich K. D. et al., Nat. Chem. Biol. 14, 352-360 (2018)). This frontier challenge could be most directly addressed by leveraging the human cell itself as the design, engineering, and quality control factory for directed evolution-mediated biomolecule discovery and optimization.

Extant strategies for directed evolution in human cells rely almost entirely on fluorescent screens to identify active biomolecule variants. The most common technique is in vitro plasmid mutagenesis followed by transfection and screening (Banaszynski L. A. et al., Cell 126, 995-1004 (2006)). This approach is slow, labor-intensive, and significantly constrains library sizes. Other methods include in vivo mutagenesis through somatic hypermutation in immune cells followed by fluorescent screening (Wang C. L. et al., Protein Eng. Des. Sel. 17, 659-664 (2004); Wang L. et al., Proc. Natl. Acad. Sci. U.S.A. 101, 16745-16749 (2004)), or the use of robotic cell-picking techniques to more comprehensively screen for desired phenotypes across multiple dimensions (e.g., both extent and localization of a fluorescent signal) (Piatkevich K. D. et al., Nat. Chem. Biol. 14, 352-360 (2018)). These methods, while valuable, are still slow, inefficient, limited to fluorescent readouts for selection, and have limited library sizes (~$10^5$ variants for the most recent robotic platform). Another recent development has been the use of cytidine deaminase fused to Cas9 variants to introduce mutations into endogenous genes in human cells and selecting or screening for desired phenotypes (Ma Y. et al., Nat. Methods 13, 1029-1035 (2016); Hess G. T. et al., Nat. Methods 13, 1036-1042 (2016); Komor A. C. et al., Nature 533, 420-424 (2016)). However, these methods require the design and synthesis of many guide RNAs to tile along regions of interest, which can be labor intensive and may require guide RNAs to be redesigned as mutations accumulate. Moreover, directed evolution achieved via in vivo mutagenesis of the human genome is limited by the slow growth rate of human cells and the high potential for false positives ('cheating') associated with any strategy that relies on cell selection or screening.

A broadly useful human cell-based directed evolution platform requires several critical features: (1) Large mutational libraries expressed in the human cell; (2) Selection schemes providing a broad dynamic range for selection and minimal opportunities for cheating; (3) Capacity to evolve multiple biomolecule functions; (4) Applicability across multiple cell types; and (5) Ideally, a minimal need for experimenter intervention during evolution experiments.

Inspiration for such a platform can be drawn from prior efforts coupling biomolecule function to viral replication using HIV (Das A. T. et al., J. Biol. Chem. 279, 18776-18782 (2004)) or bacteriophage (Esvelt K. M. et al., Nature 472, 499-503 (2011)). However, HIV-based strategies suffer from an inability of the virus to propagate under strong selection pressure or in most cell types, and raise safety concerns surrounding large-scale HIV culture. The M13 bacteriophage used in phage-assisted continuous evolution provides large mutational libraries and enables rapid rounds of selection and mutagenesis for biomolecules carrying out diverse functions, but only permits directed evolution in bacterial cells.

With these parameters and challenges in mind, this study aimed to devise a broadly useful human cell-based directed evolution platform. It was rationalized that adenovirus type-5 would be a practical vector for directed evolution of biomolecules in human cells, owing to its genetic tractability and broadly infectious nature in many human cell types (Lucher L. A., Curr. Top. Microbiol. Immunol. 199 (Pt 1), 119-152 (1995); Amalfitano A. and Chamberlain J. S., Gene Ther. 4, 258-263 (1997)). Conceptually, if the replication of a highly mutagenic adenovirus somehow depended on the activity of a biomolecule of interest (BOI) encoded in the adenoviral genome, then a simple directed evolution scheme for evolving diverse BOI functions in human cells could be feasible.

Figure 19A:
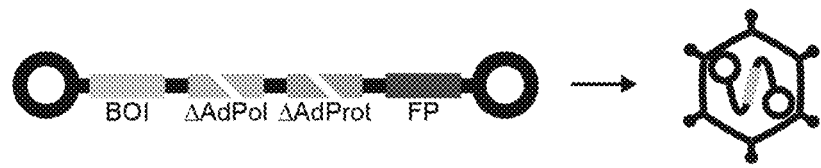
FIGS. 19A-19C. Human cell-based directed evolution platform overview.
Figure 19B:
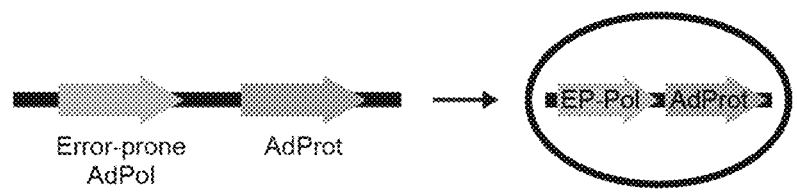
Figure 19C:
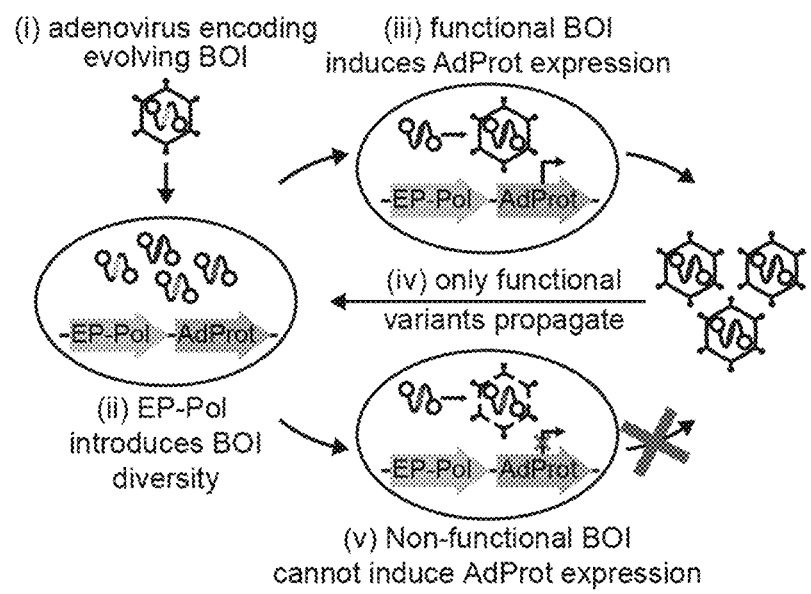

To achieve this concept, the essential adenoviral DNA polymerase (AdPol) and protease (AdProt) genes were first deleted from an adenoviral genome that also encoded the BOI for evolution (FIG. 19A). The resulting partially gutted adenovirus is incapable of replication outside engineered human cells. The missing AdPol was trans-complemented by constitutive expression, within human cells, of a newly engineered and highly mutagenic AdPol variant to enable the generation of large mutational libraries during viral replication. AdProt expression in the human cells was then engineered to depend conditionally upon BOI function (FIG. 19B). Directed evolution experiments in this system rely on simply serially passaging the BOI-encoding adenovirus while mutagenesis and selection continuously occur (FIG. 19C).

Here, the key features of this new platform are presented, including mutagenesis, selection, and enrichment parameters. The platform's utility was demonstrated via proof-of-concept directed evolution experiments in which multiple transcription factor variants were evolved, directly in the human cell environment, that maintained high levels of function while gaining resistance to a small molecule inhibitor. Altogether, this platform holds significant potential to not only enable the development of new research tools, but also to enhance our understanding of metazoan evolutionary biology and our ability to rapidly generate and optimize biomolecular therapeutics.

Adenovirus type-5 relies on its own DNA polymerase, AdPol, for replication of its double-stranded DNA genome (Hoeben R. C. and Uil T. G., Cold Spring Harb. Perspect. Biol. 5 (2013)). The high fidelity AdPol has an estimated mutation rate of $\sim 1.3 \times 10^{-7}$ mutations per base per viral passage, based on high fidelity deep sequencing experiments performed by Sanjtian and co-workers (Risso-Ballester J. et al., PLOS Pathog. 12, e1006013 (2016)). Such a low mutation rate is insufficient to generate the large library sizes necessary for laboratory time-scale directed evolution. This study sought to increase the mutation rate of adenovirus by engineering a highly mutagenic variant of AdPol.

Previous studies identified two amino acid substitutions in AdPol, F421Y and D827A, that separately increase the mutation rate of AdPol, likely through distinct mechanisms (FIG. 21A) (Uil T. G. et al., Nucleic Acids Res. 39, e30 (2011)). In the 429 bacteriophage polymerase (Davis J. N. and van den Pol A. N., J. Virol. 84, 1625-1630 (2010)), an AdPol homolog, the amino acid analogous to F421 occurs in the proofreading exonuclease domain, suggesting that the F421Y AdPol variant may have weakened proofreading capacity. The amino acid analogous to D827 occurs in the fingers domain involved in selection of incoming nucleotides, again suggesting a possible mechanism for the reduced fidelity of D827A AdPol. It was reasoned that combining these two substitutions to create the F421Y/D827ΔAdPol double-mutant, which was termed error-prone AdPol (or EP-Pol), would allow us to further increase the mutation rate while still supporting robust adenovirus propagation.

Figure 20A:
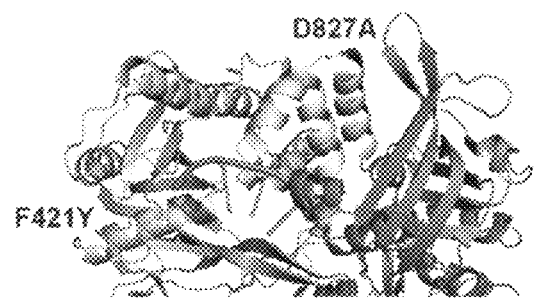
FIGS. 20A-20D.
Figure 20B:
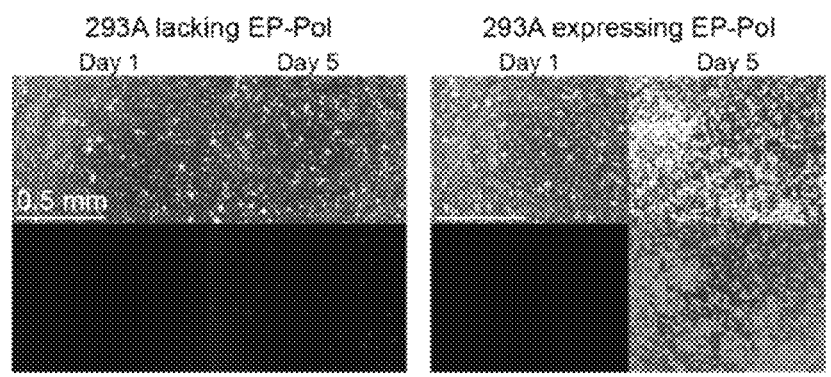

To test this hypothesis, recombineering was used to inactivate the AdPol gene encoded by the adenovirus type-5 genome via an internal deletion (see TABLE 2 for a list of adenoviral constructs employed). Next, HEK293A cells were stably transduced with an HA-tagged version of either wild-type AdPol or EP-Pol (see TABLE 3) for a list of cell lines employed). It was observed that ΔAdPol adenoviruses (CFP.ΔAdPol.GFP where CFP and GFP correspond to cyan and green fluorescent protein, respectively) propagated only on cells that expressed either AdPol (FIG. 24) or EP-Pol in trans (FIG. 20B). Further, it was observed that EP-Pol and wild-type AdPol both supported robust ΔAdPol-adenovirus replication.

Figures 20C, 20D:
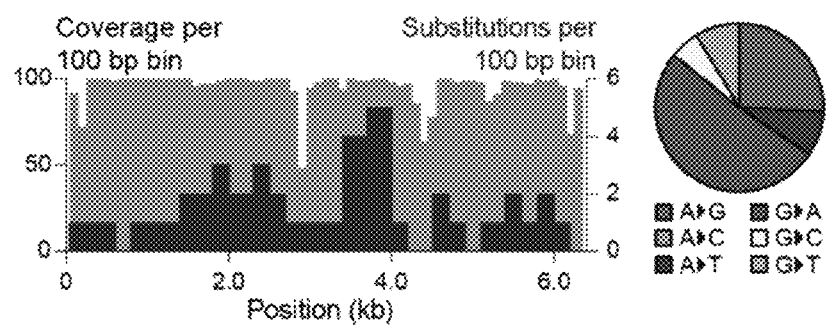

The mutation rate endowed by EP-Pol was next assessed. After passaging ΔAdPol-adenovirus (AdGLΔPol) on EP-Pol trans-complementing human cells for 10 serial passages, a 6.5 kb region of the genome was deep sequenced (FIG. 20C; see also TABLE 4). This sequencing revealed a mutation rate of $3.7 \times 10^5$ mutations per base per passage. As the adenoviral genome is ~35 kb, this mutation rate indicates that EP-Pol introduced ~1.3 mutations into the genome per infected cell per passage. Moreover, EP-Pol displayed a broad mutational spectrum, including both transitions and transversions (FIG. 20D).

The EP-Pol mutation rate measured was ~370-fold greater than the error rate of wild-type AdPol previously evaluated by the same method (Uil T. G. et al., Nucleic Acids Res. 39, e30 (2011)). However, the number of mutations induced by wild-type AdPol was very low, near our limit of detection. Compared to the previously reported mutation rate of wild-type AdPol (Risso-Ballester J. et al., PLOS Pathog. 12, e1006013 (2016)), the mutation rate of EP-Pol was enhanced ~280-fold. Both comparisons indicate that the EP-Pol mutation rate is similar to highly mutagenic RNA viruses that can readily evolve on laboratory timescales (Sanjuan R. et al., Viral mutation rates. J. Virol. 84, 9733-9748 (2010); Davis J. N. and van den Pol A. N., J. Virol. 84, 1625-1630 (2010); Phillips A. M. et al., eLife 6, e28652 (2017)).

The lower limit of the library size was next estimated in a given passage (or 'round') of directed evolution using EP-Pol. A typical round of directed evolution might reasonably involve infecting $3.0 \times 10^8$ human cells at a low MOI. Each round of directed evolution ends once ~75% of cells (~$2.3 \times 10^8$ cells) are infected. Because ~1.3 mutations are introduced per cell per replication, and because there is at least one replication in each round of evolution since the infection occurs at low MOI, it was estimated that there are ~$3.0 \times 10^8$ adenoviral variants after one passage. Assuming a typical 1 kb gene encoding the BOI comprises ~1/30 of the engineered adenoviral genome, there would be ~$1 \times 10^7$ variants of the BOI in the population after one round of evolution. This calculation is a lower limit because it does not account for any genetic diversity at the beginning of each round. Additionally, there is likely to be more than a single replication in each round of evolution, which would further increase library complexity. Regardless, even this conservative estimate indicates that one can generate virtually all single, many double, and some triple mutants in a single round of evolution. Notably, the mutations are continuously introduced instead of requiring in vitro mutagenesis physically separated from selection and propagation steps.

Example 10. Selection

The next objective was to design an appropriate selection scheme capable of coupling BOI activity to adenoviral propagation. After extensive testing of assorted adenoviral genes, a scheme based on deleting the gene for adenoviral protease (AdProt) from the viral genome and then providing AdProt in trans from the human host cell (Elahi S. M. et al., Gene Ther. 9, 1238-1246 (2002)) was developed. AdProt has vital functions in viral uncoating, DNA replication, and viral maturation (Greber U. F., et al., EMBO J. 15, 1766-1777 (1996); Webster A. et al., J. Virol. 68, 7292-7300 (1994)). Importantly, AdProt is a 'late gene' expressed mainly after DNA replication of the adenoviral genome (Webster A. et al., J. Virol. 68, 7292-7300 (1994)). Because AdProt is not required in the early stages of infection, BOI variants can be generated by mutagenesis before selection pressure is applied during a given infection.

Figure 25:
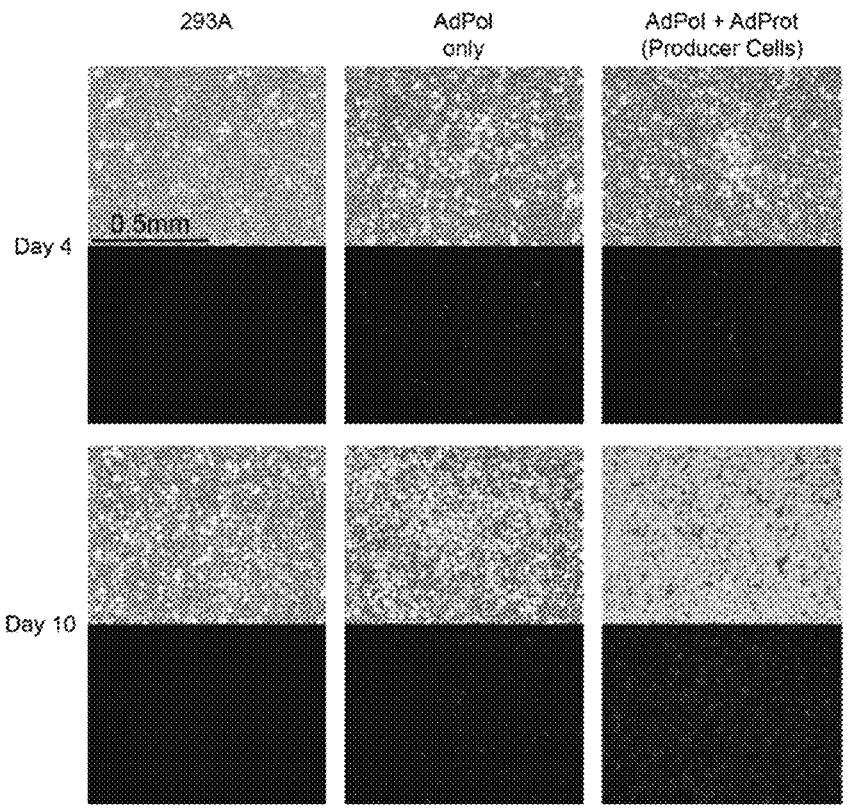
FIG. 25. ΔAdProtΔAdPol-adenovirus was used to infect HEK293A cells, AdPol-expressing cells, or producer cells (TABLE 3) at a low multiplicity of infection (<0.5). The infection was monitored over 10 days. The parental HEK293A cells showed no visible sign of infection, likely because without AdPol expression the copy number of the CFP gene was too low in the cell to easily visualize fluorescence with laboratory microscopes. The AdPol-expressing cells showed a strong CFP signal indicating a robust infection, however the infection did not spread owing to a lack of AdProt. In contrast, the producer cells trans-complementing both AdPol and AdProt were able to support a spreading infection, with every cell in the plate infected by day 10.

Whether AdProt trans-complementation could be achieved was first tested in the context of an adenovirus already requiring AdPol trans-complementation. AdProt was stably expressed in an AdPol-expressing cell line, termed "producer" cells (see TABLE 3). Next, the progress of an adenovirus infection of ΔΔAdProtΔAdPol-adenovirus on AdPol-expressing versus AdPol- and AdProt-expressing cells was monitored. It was observed that only the cell line constitutively expressing both AdProt and AdPol supported robust replication of ΔAdProtΔAdPol-adenovirus (FIG. 25). Thus, host cell expression of AdPol and AdProt can successfully support the replication of an AdPol- and AdProt-deleted adenovirus, permitting both the facile production of ΔAdProtΔAdPol-adenoviruses and providing a potential mechanism to impart selection pressure in a directed evolution experiment.

The capacity of this AdProt-complementation strategy to confer sufficient selection pressure to drive a directed evolution workflow was next evaluated. For this purpose, a competition experiment was performed on a model BOI, the tetracycline (tet)-transactivator (tTA) (Gossen M. and Bujard H., Proc. Natl. Acad. Sci. U.S.A. 89, 5547-5551 (1992); Loew R. et al., BMC Biotechnol. 10, 81 (2010)). Wild-type tTA ($tTA_{wt}$) binds its endogenous operator, with a consensus sequence of 5'-CCTATCAGTGATAGA-3' (SEQ ID NO: 209), to induce downstream gene transcription. A tTA variant ($tTA_{mut}$) that is incapable of binding to the endogenous operators has also been reported (Krueger M. et al., Gene 404, 93-100 (2007)). $tTA_{mut}$ instead possesses enhanced affinity for the mutant 5'-CCcgTCAGTGAcgGA-3' (SEQ ID NO: 210) operator. ΔAdProtΔAdPol-adenoviruses were engineered that expressed either $tTA_{wt}$ and mCherry ($tTA_{wt}$.mCherry) or $tTA_{mut}$ and GFP ($tTA_{mut}$.GFP). AdPol-expressing HEK293A cells were then stably transduced with a lentiviral vector that provided AdProt under control of the endogenous tTA operator (termed "selector" cells, see TABLE 3). In this cell line, $tTA_{wt}$.mCherry adenovirus should be able to strongly induce AdProt and propagate, whereas $tTA_{mut}$.GFP should not induce AdProt and therefore should not form infectious virions. Because these viruses express different fluorescent markers, relative viral populations can be assessed using flow cytometry upon infection of human cells that do not express AdProt in order to prevent propagation and therefore more accurately quantify the resulting viral populations.

Figure 21A:
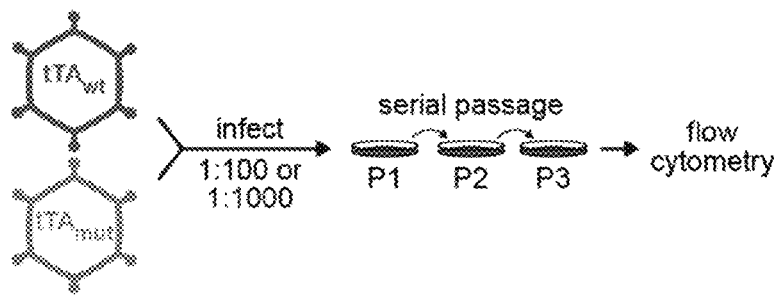
FIGS. 21A-21C.
Figure 21B:
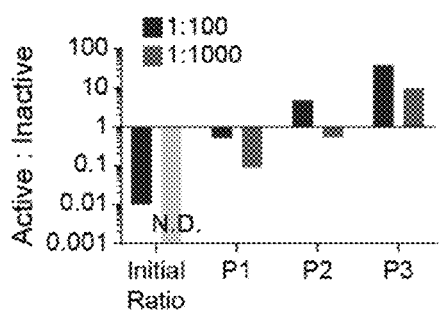

To test the hypothesis that AdProt induction could enable enrichment of active over inactive BOI variants, $tTA_{wt}$.mCherry and $tTA_{mut}$.GFP were co-infected at an MOI of ~0.25 in selector cells (see TABLE 3) at initial ratios of 1:100 or 1:1,000 (FIG. 21A). Three serial passages were then performed on selector cells, and the resulting viral populations were analyzed via infection of AdPol-expressing but AdProt-lacking HEK293A cells followed by flow cytometry. In the initial passage, the $tTA_{wt}$.mCherry adenovirus enriched at least 40-50-fold over the $tTA_{mut}$.GFP adenovirus (FIG. 21B). Furthermore, across three rounds of passaging, the $tTA_{wt}$.mCherry adenoviruses were consistently enriched to >90% of the adenoviral population regardless of the starting ratios. Thus, the AdProt-based selection strategy can rapidly enrich active BOIs that are initially present at low frequency in a viral population.

Figure 21C:
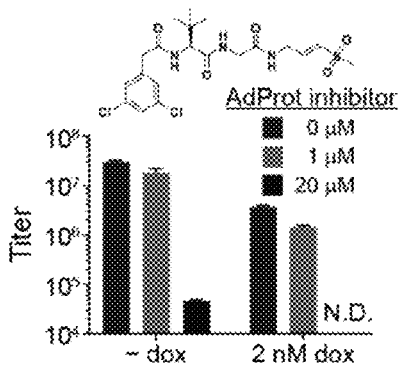

The dynamic range of selection pressure for AdProt was next evaluated. A large dynamic range, meaning that the quantity of AdProt produced scales with viral production, would be beneficial for the incremental evolution of BOI variants with increasing activity. The tTA-based genetic circuit was used to examine the dynamic range of AdProt selection through the application of the tTA allosteric inhibitor, doxycycline (dox). In the presence of dox, tTA is unable to bind its target operator and AdProt expression should be turned off. When $tTA_{wt}$.mCherry-expressing adenovirus was challenged with inhibitory concentrations of dox, an ~10-fold decrease in viral titer was observed (FIG. 21C, blue bars).

While an order of magnitude difference in infectivity provides some dynamic range for selecting improved BOI activity, an improvement to 2-3 orders of magnitude dynamic range would be beneficial. Enzymes like AdProt provide a significant advantage as selection markers in this regard, owing to the potential of small molecule inhibitors administered at defined concentrations to provide an expanded dose-response regime. A small molecule inhibitor could also provide a way to dynamically tune selection pressure from low to high levels as a given directed evolution experiment proceeds. Indeed, when $tTA_{wt}$.mCherry-expressing adenoviruses were challenged with various concentrations of the vinyl sulfone AdProt inhibitor shown in FIG. 21C (Grosche P. et al., Bioorg. Med. Chem. Lett. 25, 438-443 (2015)), it was found that the inhibitor reduced the infectious titer of the tTA$_{wt}$.mCherry virus >600-fold, providing ready access to the desired 2-3 orders magnitude dynamic range. Notably, the AdProt inhibitor even further reduced infectious titer in the presence of dox (FIG. 21C), further increasing the accessible dynamic range for this particular experiment through a combination of regulated AdProt expression and direct AdProt inhibition.

Example 11. Directed Evolution of Functional, Drug-Resistant tTA Variants in Human Cells The feasibility of actually evolving BOI function in human cells using this platform was next tested. For proof-of-concept, experiments were designed to evolve tTA variants that retained transcription-inducing activity but gained resistance to their small molecule inhibitor, dox. Specifically, the tTA$_{wt}$.mCherry virus was serially passaged in the presence of dox in a "selector" cell line (see TABLE 3) that inducibly expressed AdProt under control of the endogenous tTA operator. A low multiplicity of infection (~0.05) was maintained to minimize the probability that viruses encoding distinct tTA variants would co-infect the same cell. Viral supernatant was transferred to fresh cell plates upon the first appearance of spreading infection, with the goal of selecting for viruses that encode functional, but dox-resistant, tTA variants.

Figure 22A:
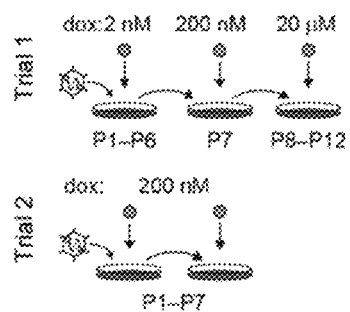
FIGS. 22A-22F.
Figure 22B:
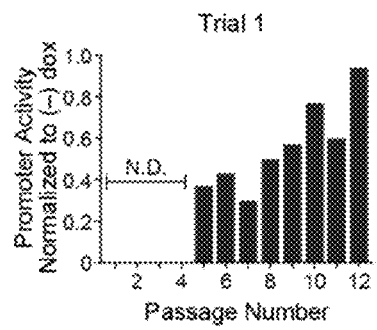

Two evolution experiments were run in parallel (Trials 1 and 2) with different selection pressure strategies (FIG. 22A). In Trial 1, the selection pressure was tuned over time, increasing the dox concentration from 2 nM up to 20 μM. In Trial 2, the selection pressure was kept constant by maintaining the dox concentration at 200 nM. In order to test whether dox-resistant tTA variant enriched in the population, the viral media from each passage in Trial 1 was used to infect a "phenotyping" cell line (see TABLE 3) containing GFP under control of the endogenous tTA operator in the presence of dox. This phenotyping cell line lacked AdProt, allowing the virus to infect the cells and induce GFP expression, but not to proliferate. GFP induction was measured by the viral population harvested after each serial passage in the presence of 20 μM dox in these phenotyping cells using flow cytometry (FIG. 22B). Substantial dox-resistant tTA activity emerged by passage 5, suggesting that dox-resistant variant(s) of tTA may have arisen and enriched in the viral population.

Figure 22C:
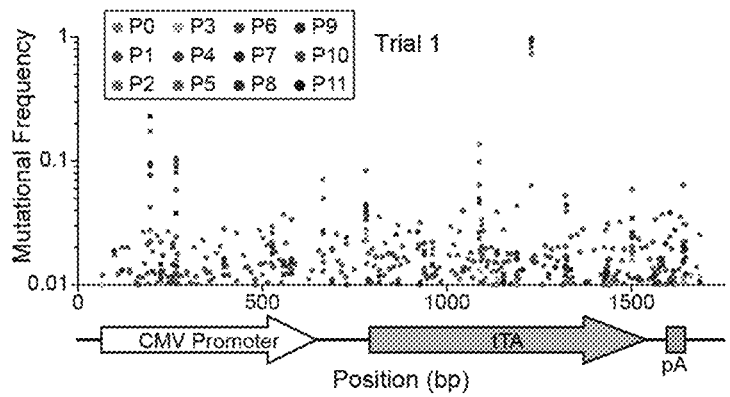
Figure 22D:
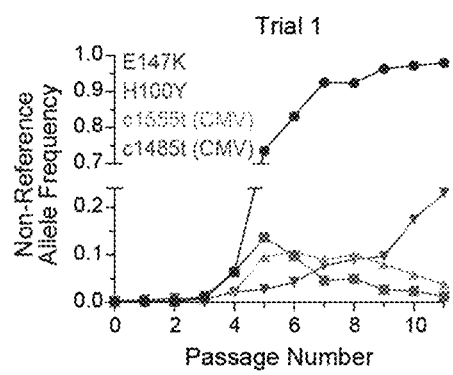
Figure 22E:
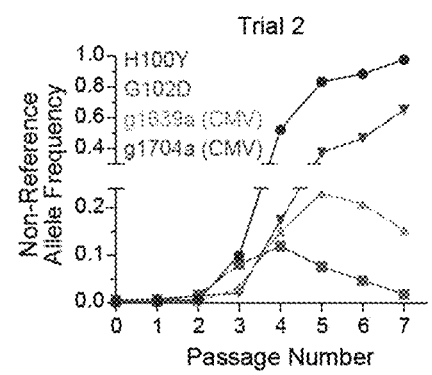
Figure 22F:
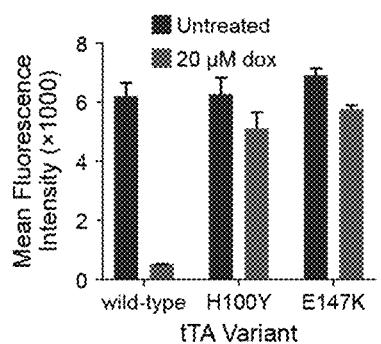
Figure 28:
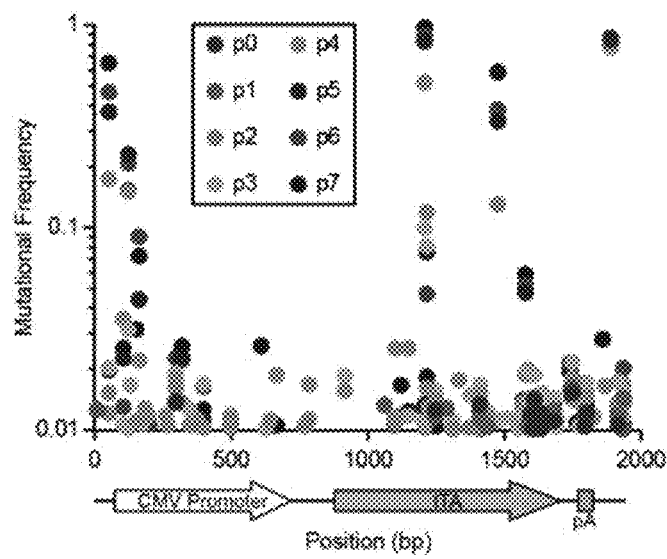
FIG. 28. Non-reference allele frequencies at >1% frequency over the course of the directed evolution experiment for Trial 2.

Whether mutations in the tTA gene contributed to this decreased dox sensitivity was examined. A 1.75-kb region of the adenoviral genome containing the tTA open reading frame was amplified and sequenced from virus harvested at each passage during both Trials. Using this approach, >200 unique mutations were detected that attained ≥1% frequency by passage 4 in Trial 1, even though promoter activity at passage 4 was still undetectable (FIG. 22C). In Trial 2, 43 mutations attained ≥1% by passage 4 (FIG. 28). By passage 5, a single amino acid substitution in tTA attained >70% frequency in the viral population in both trials (E147K in Trial 1 and H100Y in Trial 2), rapidly becoming fully fixed in the population thereafter (FIGS. 22D-22E). Both mutations observed were previously reported to confer dox-resistance in tTA (Hecht B. et al., J. Bacteriol. 175, 1206-1210 (1993)), which was further confirmed through transient co-transfection of a plasmid encoding eGFP under control of the endogenous tTA operator along with wild-type, E147K or H100Y tTA-encoding plasmids into HEK293A cells in the presence or absence of dox (FIG. 22F). Additional mutations that were also previously reported to confer dox-resistance were also observed at >10% frequency early in the directed evolution experiment (H100Y in Trial 1 and G102D in Trial 2).

These results highlight both the different outcomes that can derive from repeated evolution experiments and the capacity of the platform to explore sequence space in human cells. Additionally, these results demonstrate that one can evolve biomolecules using two different selection pressure protocols (gradually increasing pressure or constant, moderately high pressure). In summary, the directed evolution protocol can successfully generate and rapidly enrich functional BOI variants in human cells, merely by serial passaging of a BOI-encoding adenovirus.

Example 12. Discussion

Here reported is the development, characterization, and proof-of-principle application of a highly adaptable platform for directed evolution of diverse BOI functions in human cells. In this platform (FIG. 19C), human cells are infected by a BOI-encoding adenovirus lacking the essential AdProt and AdPol genes. A newly engineered, highly error-prone variant of AdPol, EP-Pol, constitutively expressed by the human cells, replicates the adenoviral genome. The resulting error-prone DNA replication introduces mutations into the BOI gene at a high rate, thereby continuously generating mutant libraries for selection. BOI variants are then expressed during viral infection of the human cell, and continuously tested for activity via a selection couple in which functional BOI variants induce higher levels of AdProt activity stemming from an AdProt gene cassette installed in the human cells. Because AdProt activity is linked to the virus' capacity to propagate, functional BOI variants are continuously enriched in the evolving viral population, whereas non-functional BOI variants result in non-viable virions that cannot propagate.

Application of the platform is straightforward, such that genes encoding a BOI can be integrated into the adenoviral genome using Gateway cloning (Hartley J. L. et al., Genome Res. 10, 1788-1795, doi:DOI 10.1101/gr.143000 (2000)), followed by plasmid transfection into a producer cell line that constitutively expresses both AdPol and AdProt to generate a starter adenovirus population (FIG. 28). Directed evolution then simply involves serial passaging of the adenovirus on user-defined 'selector cells'.

In developing this platform, adenovirus was used rather than a natively mutagenic RNA virus owing to adenovirus' relative safety, broad tropism, ease of manipulation, and capacity to propagate even under strong selection pressure. The adenoviruses used for directed evolution experiments were E1-, E3-, AdPol- and AdProt-deleted. All of these genes are required for adenoviral replication in the wild. Thus, the safety of working with these partially gutted adenoviruses is maximized as they can only replicate in human cells that provide these essential genes in trans, and cannot replicate in unmodified human cells (Uil T. G. et al., Nucleic Acids Res. 39, e30 (2011); Elahi S. M. et al., Gene Ther. 9, 1238-1246 (2002); Russell W. C., J. Gen. Virol. 81, 2573-2604 (2000)). Moreover, the removal of this large portion of the adenoviral genome means that genes as large as ~7 kb can potentially be introduced and evolved in the platform. The broad tropism of adenovirus (Lucher L. A., Curr. Top. Microbiol. Immunol. 199 (Pt 1), 119-152 (1995)) is beneficial because it means that directed evolution experiments can, in principle, be performed in many different human cell types depending on the objective of a particular experiment. Finally, from a genome engineering perspective, the optimized recombineering protocols allow the necessary facile manipulation of the adenoviral genome (Wang H. et al., Nucleic Acids Res. 42, e37 (2014)).

Despite the manifold benefits of the choice to use adenovirus, this choice presented significant challenges because both wild-type and even the previously reported error-prone AdPol variants (Uil T. G. et al., Nucleic Acids Res. 39, e30 (2011)) are relatively high fidelity, and therefore unlikely to enable the creation of mutational libraries at a sufficiently high rate to support continuous directed evolution of novel BOIs. To address this issue, EP-Pol was engineered, a highly mutagenic AdPol variant that pushes the adenoviral mutation rate into the regime of RNA viruses such as HIV and influenza that are well-known to rapidly evolve on laboratory timescales (Phillips A. M. et al., eLife 6, e28652 (2017); Meyerhans A. et al., Cell 58, 901-910 (1989); O'Loughlin T. L. et al., Mol. Biol. Evol. 23, 764-772 (2006)). Trans-complementation of EP-Pol was used via constitutive expression in the host cell to prevent reversion to wild-type AdPol that could occur if one modified an adenovirally encoded AdPol gene, thereby ensuring that mutagenic activity remains at a constant, high level throughout directed evolution experiments.

This mutagenesis approach does introduce mutations into the adenoviral genome outside the gene for the BOI that can potentially be negatively selected and consequently reduce library size. The 6.5 kb genomic region that was sequenced (FIGS. 20A-20D) was chosen because it contained both protein coding regions necessary for adenoviral replication and non-coding regions that should not face severe selection pressure. Comparing these domains across the sequenced region, only a two-fold difference was observed between the mutation rate in the inactivated AdPol gene, which should not be under any selection pressure in the trans-complementing system, and the neighboring pIX, IVa2, and pTP genes, suggesting that such negative selection only impacts the mutation rate at most two-fold.

Because AdPol selectively replicates only adenoviral DNA, EP-Pol can only introduce mutations into the adenoviral genome. This mutagenesis technique thus represents an improvement over other strategies that evolve genes directly in the human genome. In such strategies, off-target mutations can arise through basal or through the enhanced mutagenesis rates, which can subvert selection pressure and generate false positives. Furthermore, even recent mutagenesis methods that target specific genes within the human genome, by using somatic hypermutation (Wang C. L. et al., Protein Eng. Des. Sel. 17, 659-664 (2004); Wang L. et al., Proc. Natl. Acad. Sci. U.S.A. 101, 16745-16749 (2004)) or Cas9-fusion proteins (Ma Y. et al., Nat. Methods 13, 1029-1035 (2016); Hess G. T. et al., Nat. Methods 13, 1036-1042 (2016); Komor A. C. et al., Nature 533, 420-424 (2016)), still display significant off-target genetic modification (Meng F. L. et al., Cell 159, 1538-1548 (2014); Kim D. et al., Nat. Biotechnol. 35, 475-480 (2017); Wang C. L. et al., PNAS 101, 7352-7356 (2004)). Especially given the large size of the human genome, many pathways to cheating selection may be available. The use of an orthogonal replication system means that the human host cells are discarded and replaced with each passage, preventing mutation accumulation in the human cell that could potentially cheat selection pressure. This advantage, combined with the much more rapid growth of adenovirus relative to human cells allowing a larger number of directed evolution rounds in a given time period, highlights the ability of the platform to quickly scan mutational space with minimal risk of selection subversion.

It was found that AdProt can serve as a robust selectable marker for adenovirus-mediated directed evolution in human cells. As an enzyme with catalytic activity, one might not expect AdProt to exhibit a dynamic range of selection. However, it was observed that AdProt was able to modulate viral titers ~10-fold in response to protease levels. Importantly, it was discovered that a small molecule inhibitor of protease could be easily used to further enhance this dynamic range to several orders of magnitude. It is noteworthy that the AdProt inhibitor may also be employed to actively fine-tune selection stringency over the course of a directed evolution experiment, simply by modulating the compound's concentration in cell culture media.

AdProt-based selection was used to evolve transcriptionally active variants of tTA that gained dox-resistance. Across two replicates of the experiment, two different tTA variants ultimately fixed in the population, both of which were indeed dox-resistant. A large number of lower frequency mutations were also observed at various passages above the 1% threshold for detection. The observation of these variants suggests that the platform is effectively screening sequence space for a selective advantage, particularly as the vast majority of mutations are unlikely to ever attain a frequency of 1% in the evolving viral population.

While this proof-of-concept experiment specifically highlights how AdProt-based selection could be used to evolve transcription factors, the platform should be readily generalizable to evolve a variety of other biological functions. Indeed, examples of the necessary selection couples already exist for an assortment of protein classes, including TALENs (Hubbard B. P. et al., Nat. Methods. 12, 939-942 (2015)), proteases (Dickinson B. C. et al., Nat. Commun. 5, 5352 (2014)), protein-protein interactions (Badran A. H. et al., Nature 533, 58-63 (2016)), RNA polymerases (Esvelt K. M. et al., Nature 472, 499-503 (2011); Carlson J. C. et al., Nat. Chem. Biol. 10, 216-222 (2014)), amino-acyl tRNA synthetases (Bryson D. I. et al., Nat. Chem. Biol. 13, 1253-1260 (2017)), Cas9 (Hu J. H. et al., Nature 556, 57-63 (2018)), and beyond.

Looking forward, there are a number of improvements that would further enhance this platform's practicability and applicability. The current system relies on serial passaging of adenovirus on adherent cells. Transitioning to suspension cells would enable variant libraries several orders of magnitude larger than one can currently explore. The integration of emerging targeted mutagenesis techniques, such as MutaT7 (Moore C. L. et al., J. Am. Chem. Soc., doi: 10.1021/jacs.8b04001 (2018)), could further focus mutations only to the BOI gene and also increase mutation library size. Additionally, the present system is only capable of positive selection. Implementation of a negative selection strategy would enable the platform to evolve biomolecules that are more selective and specific for a given activity. Phage-assisted continuous evolution in bacteria can afford larger library sizes with more tunable mutation rates, in addition to dynamic selections that occur on the order of hours, not days (Esvelt K. M. et al., Nature 472, 499-503 (2011)). Critically, while adenovirus-mediated directed evolution explores mutational space more slowly than phage-assisted continuous evolution, it makes possible similar experiments in the metazoan cell environment for the first time.

The platform offers several advantages relative to extant strategies for human cell-based directed evolution that rely on time-intensive screens and extensive in vitro manipulations. The use of adenovirus allows researchers to continuously mutate, select, and amplify genes of interest by simply transferring viral supernatant from one cell plate to the next. Owing to this simple viral passaging protocol, library sizes are restricted only by a researcher's tissue culture capacity. Cheating is minimized because mutations are specifically directed to the viral genome. Safety is maximized because the adenoviruses used lack multiple genes required for replication in the wild. Moreover, the user-defined nature of the selector cell and the broad tropism of adenovirus type 5 enable directed evolution to be performed in a diverse array of human cell types.

By making it possible for researchers to evolve diverse BOI functions in the same environment in which the BOIs are intended to function, this human cell-based directed evolution platform holds significant potential to enable researchers to rapidly evolve a wide variety of biomolecules in human cells. Thus, this method should impact not just the development of new tools for research, but also the understanding of metazoan evolutionary biology and the ability to rapidly generate effective biomolecular therapeutics.

Example 13. Materials and Methods for Examples 14-16

Vectors and Cloning
Materials:

All enzymes were obtained from New England BioLabs unless stated otherwise. All primers were obtained from either ThermoFisher or Sigma Aldrich. Gene blocks were obtained from Integrated DNA Technologies. All primers are listed in TABLE 11. AdGLΔPol was constructed as previously described (Uil T. G. et al., Nucleic Acids Res., 39(5): e30 (2011)).

Adenoviral Cloning:

Adenoviral constructs were engineered using ccdB recombineering, as previously described (Wang H. et al., Nucleic Acids Res. 42, e37 (2014)), in DH10B E. coli carrying the Adenovirus type 5 genome in a chloramphenicol-resistant bacterial artificial chromosome (AdBAC). Cells carrying an AdBAC were transformed with the temperature-sensitive psc101-gbaA recombineering plasmid (Wang H. et al., Nucleic Acids Res. 42, e37 (2014)), plated on LB (Difco) agar (Alfa Aesar) with 10 µg/mL tetracycline (CalBioChem) and 10 µg/mL chloramphenicol (Alfa Aesar), and incubated for 24 h at 30° C. Colonies were selected and grown in LB containing 10 µg/mL tetracycline and 10 µg/mL chloramphenicol overnight at 30° C. (18-21 h). Overnight cultures were diluted 25-fold in LB with 10 µg/mL tetracycline and 10 µg/mL chloramphenicol and grown at 30° C. for ~2 h until attaining an $OD_{600}$ of 0.3-0.4. The ccdA antitoxin and recombineering machinery were then induced by adding L-arabinose (Chem-Impex) and L-rhamnose (Sigma Aldrich) to a final concentration of 2 mg/mL each and then growing the cultures at 37° C. for 40 min to an $OD_{600}$ of ~0.6. The cultures were then placed on ice, washed twice with ice-cold, sterile ddH2O, resuspended in ~25 µL of ice-cold, sterile ddH2O, and electroporated with ~200 ng of the appropriate kan-ccdB targeting cassette (1.8 kV, 5.8 ms, 0.1 cm cuvette, BioRad Micropulser). The cells were then recovered in super optimal broth with catabolite repression (SOC; Teknova) with 2 mg/mL L-arabinose at 30° C. for 2 h, then plated on LB agar plates with 50 µg/mL kanamycin (Alfa Aesar) and 2 mg/mL L-arabinose and incubated for 24 h at 30° C. Colonies that grew under these conditions had incorporated the kan-ccdB targeting cassette and were picked in triplicate and grown in LB with 50 µg/mL kanamycin and 2 mg/mL L-arabinose at 30° C. for 18-21 h. (Note: The colonies were picked in triplicate because multimers of the AdBAC formed at a high rate (~30-50% of colonies) during the first recombineering step. These multimers are unable to be successfully recombineered in the next step. Picking three colonies and recombineering them separately in parallel increases the chances of picking a monomer that can be successfully recombineered.) The cultures were then diluted 25-fold in LB with 50 µg/mL kanamycin and 2 mg/mL L-arabinose and grown at 30° C. for ~2 h until they reached an $OD_{600}$ of 0.3-0.4. The recombineering machinery was then induced by adding L-rhamnose to a final concentration of 2 mg/mL and then growing the cultures at 37° C. for 40 min to an $OD_{600}$ of ~0.6. The cultures were then placed on ice, washed twice with ice-cold, sterile ddH2O, resuspended in ~25 µL of ice-cold, sterile ddH$_2$O, and electroporated with ~200 ng of the final targeting cassette intended to replace the kan-ccdB cassette currently integrated in the genome (1.8 kV, 5.8 ms, 0.1 cm cuvette, BioRad Micropulser). The cells were then recovered in SOC with 2 mg/mL L-arabinose at 30° C. for 2 h, and then were washed once with LB to remove the L-arabinose and prevent continued production of the ccdA antitoxin. The cultures were then plated on LB agar plates at various dilutions with 10 µg/mL tetracycline and 10 µg/mL chloramphenicol and incubated for 24 h at 37° C. Without the ccdA antitoxin, the ccdB toxin will kill cells that have not replaced the integrated kan-ccdB cassette with the final targeting cassette. The colonies that grow should have the final targeting cassette integrated, but were screened by PCR or sequencing to confirm cassette integration as some colonies may simply inactivate the ccdB toxin.

Once a clone with all of the desired genetic changes was found and confirmed by Sanger sequencing, the AdBAC single-copy replication origin was replaced with the high copy pUC origin. The cells with the correct clone were grown in LB containing 10 µg/mL tetracycline and 10 µg/mL chloramphenicol overnight at 30° C. (18-21 h). Overnight cultures were diluted 25-fold in LB with 10 µg/mL tetracycline and 10 µg/mL chloramphenicol and grown at 30° C. for ~2 h until attaining an $OD_{600}$ of 0.3-0.4. The recombineering machinery was then induced by adding L-rhamnose to a final concentration of 2 mg/mL each and then growing the cultures at 37° C. for 40 min to an $OD_{600}$ of ~0.6. The cultures were then placed on ice, washed twice with ice-cold, sterile ddH$_2$O, resuspended in ~25 µL of ice-cold, sterile ddH2O, and electroporated with ~200 ng of the pUC origin cassette (1.8 kV, 5.8 ms, 0.1 cm cuvette, BioRad Micropulser). The cells were then recovered in SOC at 30° C. for 2 h, then plated on LB agar plates with 100 µg/mL ampicillin and incubated for 24 h at 37° C. The resulting ampicillin-resistant colonies should have the pUC origin inserted and were checked by verifying expected restriction digestion patterns. The colonies were grown in 25 mL LB containing 100 µg/mL ampicillin and the DNA was purified using the ZymoPURE II plasmid midiprep kit (Zymo Research) according to the manufacturer's instructions. The DNA was digested with PacI overnight at 37° C. in order to liberate and linearize the adenoviral genome. The linearized DNA was purified using the E.Z.N.A. cycle pure kit (Omega Bio-tek) according to the manufacturer's instructions.

All adenoviruses were generated from a parent Ad5.CFP vector derived from pAd/CMV/V5-DEST (ThermoFisher).

The following modifications in TABLE 10 were made using primers in TABLE 11 to obtain the adenoviruses in TABLE 8.

Wild-Type AdPol and EP-Pol Vectors:

The lentiviral vector encoding HA-tagged wild-type AdPol was previously described (Uil T. G. et al., Nucleic Acids Res., 39(5): e30 (2011)). Mutations were introduced by site-directed mutagenesis. These vectors were used to make all cell lines described in this study (TABLE 9).

E2A Expression Vector:

The pcDNA3-derived vector containing the E2A gene was digested with KpnI and XhoI and inserted into pENTR1A to form pENTR1A.E2A. The E2A gene was then recombined into pLenti. CMV.Hygro.DEST (w117-1) (Addgene) using LR Clonase II Enzyme Mix (ThermoFisher) to form pLenti.CMV.E2A (Campeau E. et al., PLoS One, 4, e6529 (2009)).

pVI Expression Vector:

A 781 bp fragment containing the pVI gene was amplified from the HAd5 genome using primers pVI.BamHI F and pVI.SalI R (TABLE 11) and inserted into pTRE-Tight (Takara Bio) using BamHI and SalI to form pTRE-Tight.pVI. A 236 bp fragment containing the Ad5 Tripartite leader sequence (TPL) was amplified from the TPL gene block using primers TPL.pVI GA F and TPL.pVI GA R (TABLE 11), and the 3293 bp pTRE-Tight.pVI was amplified using primers TRE.pVI GA F and TRE.pVI GA R (TABLE 8). These fragments were assembled using NEB HiFi Master Mix to form pTRE-Tight.TPL.pVI. pTRE-Tight.TPL.pVI was digested using NotI and XbaI and inserted into pENTR1A to form pENTR1A.TPLpVI. The TPL.pVI gene was then recombined into pLenti.CMV.Hygro.DEST (w117-1) using LR Clonase II Enzyme Master Mix to form pLenti.CMV. TPL.pVI.

Fiber Expression Vector:

A 1773 bp fragment containing the fiber gene was amplified from the Had5 genome using primers Fiber.BamHI F and Fiber. SalI R (TABLE 11) and inserted into pTRE-Tight using BamHI and SalI to form pTRE-Tight.Fiber. A 234 bp fragment containing the TPL was amplified from the TPL gene block using primers TPL.Fiber GA F and TPL.Fiber GA R (TABLE 11), and the 4497 bp pTRE-Tight.Fiber was amplified using primers TRE.Fiber GA F and TRE.Fiber GA R (TABLE 11). These fragments were assembled using NEB HiFI Master Mix to form pTRE-Tight.TPL.Fiber. A 1983 bp fragment containing TPL.Fiber was amplified using primers NotI.TPL F and XbaI.Fiber R (TABLE 11) and inserted into pENTR1A using NotI and XbaI to form pENTR1A.TPL.Fiber. The TPL.Fiber gene was then recombined into pLenti.CMV.Hygro.Dest (w117-1) using LR Clonase II Enzyme Master Mix to form pLenti.CMV.TPL.Fiber.

Protease Expression Vector:

A 641 bp fragment containing adenoviral protease (prot) was amplified from the Ad5 genome using primers BamHI.AdProt F and SalI.AdProt R (TABLE 11) and ligated into pTRE-Tight using BamHI and SalI to make the pTRE-Tight.AdProt vector. The TPL was amplified from the TPL gene block using primers TPL. GA F and TPL.AdProt GA R (TABLE 11), and the pTRE-Tight.AdProt vector was amplified using primers TRE.AdProt GA F and TRE.AdProt GA R (TABLE 11). These fragments were assembled using the NEB HiFi assembly kit to create the pTRE-Tight.TPL.AdProt vector. From this vector, an 852 bp fragment containing TPL.AdProt was amplified using primers NotI.TPL F and XbaI.AdProt.R (TABLE 11) and inserted into the pENTR1A vector using NotI and XbaI. The TPL.AdProt gene was then recombined into pLenti.CMV.Hygro (w117-1) using LR clonase II Enzyme Master Mix to form pLenti.CMV.TPL.AdProt.

Cell Culture and Lentivirus Transduction

Cell Culture:

All cells were cultured at 37° C. and 5% $CO_2$. All cell lines were derived from a parent HEK293A cell line (ATCC) and cultured in Dulbecco's modified Eagle's medium (DMEM; Cellgro) supplemented with 10% fetal bovine serum (FBS; Cellgro), 1% penicillin-streptomycin (Cellgro), and 1% L-glutamine (Cellgro). Cell lines that express the selection genes (E2A, pVI, fiber, or AdProt) were cultured in 50 µg/mL hygromycin (Thermo Fisher) to stably maintain transgenes.

Generation of Cell Lines by Lentiviral Transduction:

In a typical protocol, ~9×10$^6$ 293FT cells were plated on a poly-D-lysine-coated 10 cm dish. The next day, the cells were co-transfected with plasmids from the previously described third-generation packaging system (Dull T. et al., J. Virol. 72, 8463-8471 (1998)): 15 µg RRE, 6 µg REV, 3 g VSVG, and 15 µg transfer vector using 60 µL Lipofectamine 2000 (Thermo Fisher). Cultures were maintained in 5 mL total volume of OPTI-MEM (Gibco) throughout the transfection. After 8 h, the media was exchanged for fresh DMEM. After 48 h, media was harvested and centrifuged for 5 min at 162×g to clear the cell debris. The supernatant was used to transduce HEK293A cells supplemented with 4 µg/mL polybrene (Sigma). After 24 h, the media was exchanged for fresh DMEM. After 48 h, media was exchanged again for DMEM containing 50 µg/mL hygromycin to select stable cell lines (as indicated above).

Determination of the Mutagenic Potential of EP-Pol:

The mutagenic potential of EP-Pol was evaluated following a previously reported protocol (Uil T. G. et al., Nucleic Acids Res., 39(5): e30 (2011)). Briefly, a polymerase-deleted Ad5, AdGLΔAdPol, was subjected to 10 serial passages on cultures of 911 cells expressing EP-Pol in order to accumulate mutations. After 10 serial passages, 911 cells expressing wild-type AdPol were infected in a 6-well plate at ~50 plaque-forming units/well in order to amplify pools of 50 viral clones for sequencing. Using pools of 50 or fewer clonal viruses ensures that mutations present in only one clone will be present at a frequency above the threshold of detection. From each 50-clone viral pool, a 6.5 kb fragment was amplified and prepared for deep sequencing. Libraries were subjected to 32 cycles of single-read sequencing by an Illumina Genome Analyzer II (GA-II).

Immunoblotting:

50 µg of protein lysate was separated on a 10% SDS-PAGE polyacrylamide gel and transferred to a nitrocellulose membrane. EP-Pol and actin protein levels were detected using an a-HA (Santa Cruz; sc-7392) or α-actin antibody (Sigma; A1978) as indicated. Fiber was detected using an α-fiber antibody (Thermo Fisher; 4D2). pVI was detected using an α-pVI monoclonal antibody obtained as a generous gift from Dr. Harald Wodrich (Université Bordeaux) (Martinez R. et al., J. Virol., 89, 2121-2135 (2015)).

RT-qPCR:

cDNA was made from 1 µg of purified RNA using the High Capacity cDNA Reverse Transcription Kit (Applied Biosystems). qPCR was run for E2A (primers: E2AL and E2AR), AdProt (primers: AdProt L and AdProt R), and RPLP2 (primers RPLP2 L and RPLP2 F) (TABLE 11) on a LightCycler 480 II (Roche) to confirm expression.

Generating Adenovirus from Transfection:

All adenoviruses were produced by transfecting a PacI-linearized vector into appropriate trans-complementing HEK293A cells. Briefly, 24 µg of PacI-digested adenovirus vectors transfected with 144 μL PEI, 1 mL OptiMEM (Gibco) into a 15 cm plate of the corresponding cell line (10 million cells). Media was replaced 8 h after transfection. Media was then intermittently replaced every 2-3 days until plaques were observed (typically ~3 weeks). Once plaques were observed, CPE was observed in all cells within 5 d. Upon complete CPE, the cells and media were harvested, and then frozen at −80° C. for at least 30 min and then thawed at 37° C. for 15 min for three total freeze/thaw cycles. The cell debris was removed by centrifugation at >1,462×g for 15 min and the supernatant was moved to a new Eppendorf tube and stored at −80° C. until use.

Trans-Complementation Assays:

The day before beginning the assay, a 6-well plate was seeded with ~$10^6$ of the indicated cells. The next day, individual wells were infected with the indicated adenoviruses at a low multiplicity of infection (<0.5) in order to enable observation of the presence or absence of a spreading infection. The AdPol trans-complementation assay (FIGS. 30A-30D) was monitored using an Olympus U-TB190 microscope and the CFP.ΔAdPol.GFP adenovirus. The AdProt/AdPol double trans-complementation assay (FIG. 25) was monitored using a Nikon Eclipse TE200 microscope and the ΔAdProtΔAdPol-adenovirus.

TABLE 10

Modifications to adenoviral vectors.

| Modification | Genotype | KanccdB cassette primers used with R6K-kan-ccdB template plasmid (unless stated otherwise) | Final targeting cassette oligos or primers and template (if applicable) | Purpose of modification |
|---|---|---|---|---|
| AdPol deletion | ΔAdPol | delAdPol ccdb F and delAdPol ccdb R | delAdPol F and delAdPol R | To prevent evolution of the adenoviral polymerase. The error-prone version was expressed in trans |
| E2A1 deletion | ΔE2A1 | E2A1 ccdb F and E2A1 ccdb R | E2A1 F and E2A1 R | Deletion to make selectable marker |
| E2A2 deletion | ΔE2A2 | E2A2 ccdb F and E2A2 ccdb | E2A2 F and E2A2 R | Deletion to make selectable marker |
| Fiber deletion | ΔFib | delFib ccdb F and delFib ccdb R | delFib F and delFib R | Deletion to make selectable marker |
| AdProt deletion | Δprot | delAdProt ccdb F and delAdProt ccdb R | delAdProt F and delAdProt R | Deletion to make selectable marker |
| Insertion of eGFP | E4R-eGFP | E4 ccdb F and E4 ccdb R | E4 SV40 F and E4 SV40 R | Visualization and maintenance of genome size |
| Replacement of the low copy BAC origin with the high copy pUC origin | N/A | N/A, the replacement is a one-step recombineering since the origin switches from chloramphenicol to ampicillin resistant | BAC2pUC F and BAC2pUC R used to amplify the pUC origin from pAd/CMV/V5-DEST | High copy origin to allow for the preparation of concentrated, purified DNA for transfection and adenoviral production |

TABLE 11

Primers used in this study.

| Name | Sequence - 5' to 3' | SEQ ID NO: |
|---|---|---|
| delAdPol ccdb F | TCCCGCGCTTCTTGGAACTTTACATTGTGGGCCACAACATCAACGGCCCTCCCTCATCAGTGCCAACATAGTAAG | 102 |
| delAdPol ccdb R | GGCACCTCGGAACGGTTGTTAATTACCTGGGCGGCGAGCACGATCTCGTCCCGCTCATTAGGCGGGC | 103 |
| delAdPol F | GCGCGGCCTTCCGGAGCGAGGTGTGGGTGAGCGCAAAGGTGTCCCTGACCATGACCAGCATGAAGGGCACGAGCTGCTTCCCAAAGGCCCCCATCCAAG | 104 |
| delAdPol R | CTTGGATGGGGGCCTTTGGGAAGCAGCTCGTGCCCTTCATGCTGGTCATGGTCAGGGACACCTTTGCGCTCACCCACACCTCGCTCCGGAAGGCCGCGC | 105 |
| E2A1 ccdb F | ACCATTTGTAGCGCCACATCTTCTCTTTCTTCCTCGCTGTCCACGATTACCCCTCATCAGTGCCAACATAGTAAG | 106 |
| E2A1 ccdb R | AGAGGAGCAGCGCGAAACCACCCCCGAGCGCGGACGCGGTGCGGCGCGACCCGCTCATTAGGCGGGC | 107 |
| E2A1 F | ACCATTTGTAGCGCCACATCTTCTCTTTCTTCCTCGCTGTCCACGATTACGTCGCGCCGCACCGCGTCCGCGCTCGGGGGTGGTTTCGCGCTGCTCCTCT | 108 |

TABLE 11-continued

Primers used in this study.

| Name | Sequence - 5' to 3' | SEQ ID NO: |
|---|---|---|
| E2A1 R | AGAGGAGCAGCGCGAAACCACCCCCGAGCGCGGACGCGGTGCGGCGCGACGTAATCGTGGACAGCGAGGAAGAAAGAGAAGATGTGGCGCTACAAATGGT | 109 |
| E2A2 ccdb F | CTCCACAGGCTGCGCACCATCACCAACGCGTTTAGCAGGTCGGGCGCCGACCCTCATCAGTGCCAACATAGTAAG | 110 |
| E2A2 ccdb R | CCCCAACCATGGAGGACGTGTCGTCCCCGTCCCCGTCGCCGCCGCCTCCCCCGCTCATTAGGCGGGC | 111 |
| E2A2 F | CTCCACAGGCTGCGCACCATCACCAACGCGTTTAGCAGGTCGGGCGCCGAGGGAGGCGGCGGCGACGGGGACGGGGACGACACGTCCTCCATGGTTGGGG | 112 |
| E2A2 R | CCCCAACCATGGAGGACGTGTCGTCCCCGTCCCCGTCGCCGCCGCCTCCCTCGGCGCCCGACCTGCTAAACGCGTTGGTGATGGTGCGCAGCCTGTGGAG | 113 |
| delpVI ccdb F | TAAAAAGTCTGGACTCTCACGCTCGCTTGGTCCTGTAACTATTTTGTAGACCCTCATCAGTGCCAACATAGTAAG | 114 |
| delpVI ccdb R | TCTGGCGGCGACATGGACGCATACATGACACACACACGACACGTTAGCTACCGCTCATTAGGCGGGC | 115 |
| delpVI F | ATAAAAAGTCTGGACTCTCACGCTCGCTTGGTCCTGTAACTATTTTGTAGATAGCTAACGTGTCGTATGTGTGTCATGTATGCGTCCATGTCGCCGCCAG | 116 |
| delpVI R | TCTGGCGGCGACATGGACGCATACATGACACACACACGACACGTTAGCTATCTACAAAATAGTTACAGGACCAAGCGAGCGTGAGAGTCCAGACTTTTTA | 117 |
| delFib ccdb F | TTTCCTCCTGTTCCTGTCCATCCGCACCCACTATCTTCATGTTGTTGCAGCCCTCATCAGTGCCAACATAGTAAG | 118 |
| delFib ccdb R | TGGCAAATATTTCATTAATGTAGTTGTGGCCAGACCAGTCCCATGAAAATCCGCTCATTAGGCGGGC | 119 |
| delFib F | TTTCCTCCTGTTCCTGTCCATCCGCACCCACTATCTTCATGTTGTTGCAGATTTTCATGGGACTGGTCTGGCCACAACTACATTAATGAAATATTTGCCA | 120 |
| delFib R | TGGCAAATATTTCATTAATGTAGTTGTGGCCAGACCAGTCCCATGAAAATCTGCAACAACATGAAGATAGTGGGTGCGGATGGACAGGAACAGGAGGAAA | 121 |
| delAdProt ccdb F | GGCAACGCCACAACATAAAGAAGCAAGCAACATCAACAACAGCTGCCGCCCCCTCATCAGTGCCAACATAGTAAG | 122 |
| delAdProt ccdb R | TACAAATAAAAGCATTTGCCTTTATTGAAAGTGTCTCTAGTACATTATTTCCGCTCATTAGGCGGGC | 123 |
| delAdProt F | GGCAACGCCACAACATAAAGAAGCAAGCAACATCAACAACAGCTGCCGCCAAATAATGTACTAGAGACACTTTCAATAAAGGCAAATGCTTTTATTTGTA | 124 |
| delAdProt R | TACAAATAAAAGCATTTGCCTTTATTGAAAGTGTCTCTAGTACATTATTTGGCGGCAGCTGTTGTTGATGTTGCTTGCTTCTTTATGTTGTGGCGTTGCC | 125 |
| E4 ccdb F | CAAAAAACCCACAACTTCCTCAAATCGTCACTTCCGTTTTCCCACGTTACCCCTCATCAGTGCCAACATAGTAAG | 126 |
| E4 ccdb R | AGTAACTTGTATGTGTTGGGAATTGTAGTTTTCTTAAAATGGGAAGTGACCCGCTCATTAGGCGGGC | 127 |
| E4 SV40 F | CAAAAAACCCACAACTTCCTCAAATCGTCACTTCCGTTTTCCCACGTTACTTCTGTGGAATGTGTGTCAGTTAGGG | 128 |
| E4 SV40 R | AGTAACTTGTATGTGTTGGGAATTGTAGTTTTCTTAAAATGGGAAGTGACCTCTAGCTAGAGGTCGACGGTATAC | 129 |
| BAC2pUC F | CCCGGGAATTCGGATCTGC | 130 |
| BAC2pUC R | CCGGGAATTCGGATCCTTGAAGAC | 131 |

TABLE 11-continued

Primers used in this study.

| Name | Sequence - 5' to 3' | SEQ ID NO: |
|---|---|---|
| pVI.BamHI F | AAAAAAGGATCCACCATGGAAGACATCAACTTTGCGTC | 132 |
| pVI.SalI R | AAAAAAGTCGACTCAGAAGCATCGTCGGC | 133 |
| TPL.pVI GA F | ATCGCCTGGAGAATTCACTCTCTTCCGCATCGCT | 134 |
| TPL.pVI GA R | AAAGTTGATGTCTTCCATTGCGACTGTGACTGGTTAG | 135 |
| TRE.pVI GA F | ATGGAAGACATCAACTTTGC | 136 |
| TRE.pVI GA R | GAATTCTCCAGGCGATCTG | 137 |
| Fiber.BamHI F | AAAAAAGGATCCACCATGAAGCGCGC | 138 |
| Fiber.SalI R | AAAAAAGTCGACTTATTCTTGGGCAATGTATGAAAAAGTG | 139 |
| TPL. GA F | ATCGCCTGGAGAATTCACTCTCTTCCGCATCGCT | 140 |
| TPL.Fiber GA R | GTCTTGCGCGCTTCATTGCGACTGTGACTGGTTAG | 141 |
| TRE.Fiber GA F | ATGAAGCGCGCAAGACCG | 142 |
| TRE.Fiber GA R | GAATTCTCCAGGCGATCTGAC | 143 |
| NotI.TPL F | AAAAAAGCGGCCGCACTCTCTTCCGCATCG | 144 |
| XbaI.Fiber R | AAAAAATCTAGATTATTCTTGGGCAATGTATGAAAAAGTG | 145 |
| BamHI.AdProt F | AAAAAAGGATCCACCATGGGCTCCAGTGAG | 146 |
| SalI.AdProt R | AAAAAGTCGACTTACATGTTTTTCAAGTGACAAAAAGAAG | 147 |
| TPL.AdProt GA R | ATCTAGAGCCGGCGCTTACATGTTTTTCAAGTGACAAAAAGAAG | 148 |
| TRE.AdProt GA F | ATGGGCTCCAGTGAGCAG | 149 |
| TRE.AdProt GA R | GAATTCTCCAGGCGATCTG | 150 |
| XbaI.Prot R | AAAAAATCTAGATTACATGTTTTTCAAGTGACAAAAAGAAG | 151 |
| E2A L | AGACCTGGCTGAACGAGGAG | 152 |
| E2A R | TGGGCTCGTGATGCTTGTAG | 153 |
| AdProt L | GGGTACCCAACTCCATGCTC | 154 |
| AdProt R | AAGTGGCGCTCCTAATCTGC | 155 |
| RPLP2 F | CCATTCAGCTCACTGATAACCTTG | 156 |
| RPLP2 R | CGTCGCCTCCTACCTGCT | 157 |

Example 14. Mutagenesis System and Adenoviral DNA Polymerase Trans-Complementation Directed evolution methodologies have transformed our ability to generate biomolecules with improved or novel functionalities (Packer M. S. and Liu D. R., Nat. Rev. Genet. 16, 379-394 (2015); Gai S. A. and Wittrup K. D., Curr. Opin. Struct. Biol. 17, 467-473 (2007); Romero P. A. and Arnold F. H., Nat. Rev. Mol. Cell Biol. 10 (2009); Shaner N. C. et al., Nat. Biotechnol. 22, 1567-1572 (2004); Branon, T. C. et al., Nat. Biotechnol. (2018); Arzumanyan G. A., et al. ACS Synth. Biol. 7, 1722-1729 (2018)). The majority of directed evolution experiments are performed in test tubes, bacteria, or yeast. While these strategies can be successful, they frequently lead to products that fail to function optimally when later introduced into complex metazoan systems. The evolved functions can be derailed by such problems as off-target interactions, poor protein folding or stability, pleiotropic outputs, mistrafficking, chemical modification, or other serious problems that arise because the biomolecules were discovered and optimized in overly simplistic environments (Zetsche B. et al., Cell 163, 759-771 (2015); Peck S. H. et al., Chem. Biol. 18, 619-630 (2011); Piatkevich K. D. et al., Nat. Chem. Biol. 14, 352-360 (2018)). This challenge could be most directly addressed by leveraging the human cell itself as the design, engineering, and quality control factory for directed evolution-mediated biomolecule discovery and optimization.

Extant strategies for directed evolution in human cells rely almost entirely on fluorescent screens to identify active biomolecule variants. The most common technique is in vitro plasmid mutagenesis followed by transfection and screening (Banaszynski L. A. et al., Cell 126, 995-1004 (2006)). This approach is slow, labor-intensive, and significantly constrains library sizes. Other methods include in vivo mutagenesis through somatic hypermutation in immune cells followed by fluorescent screening, or the use of robotic cell-picking techniques to more comprehensively screen for desired phenotypes across multiple dimensions (e.g., both intensity and localization of a fluorescent signal) (Piatkevich K. D. et al., Nat. Chem. Biol. 14, 352-360, doi:10.1038/s41589-018-0004-9 (2018); Wang C. L. et al., Protein Eng. Des. Sel. 17, 659-664 (2004); Wang L. et al., Proc. Natl. Acad. Sci. USA, 2004. 101(48): p. 16745-49 (2004)). These methods, while valuable, are still slow, inefficient, limited to fluorescent readouts for selection, and have limited library sizes (~$10^5$ variants for the most recent robotic platform) (Piatkevich K. D. et al., Nat. Chem. Biol. 14, 352-360, doi:10.1038/s41589-018-0004-9 (2018)). Another development has been the use of cytidine deaminase fused to Cas9 variants to introduce mutations into endogenous genes in human cells, followed by selecting or screening for desired phenotypes (Ma Y et al., Nat. Methods 13, 1029-1035, doi:10.1038/nmeth.4027 (2016); Hess G. T. et al., Nat. Methods 13, 1036-1042, doi:10.1038/nmeth.4038 (2016); Komor A. C. et al., Nature 533, 420-424 (2016)). However, this approach requires the design and synthesis of many guide RNAs to tile along regions of interest, which requires guide RNAs to be redesigned as mutations accumulate. Moreover, directed evolution achieved via in vivo mutagenesis of the human genome is limited by the slow growth rate of human cells and the high potential for false positives ("cheating") associated with any strategy that relies on cell selection or screening in a background of overexpression of DNA-damaging enzymes.

A broadly useful human cell-based directed evolution platform requires several critical features: (1) large mutational libraries expressed in the human cell; (2) selection schemes providing a broad dynamic range for selection and minimal opportunities for cheating; (3) capacity to evolve multiple biomolecule functions; (4) applicability across multiple cell types; and (5) ideally, a minimal need for experimenter intervention during evolution experiments.

Prior efforts have coupled biomolecule function to viral replication using HIV or bacteriophage (Das A. T. et al., J. Biol. Chem. 279(18): p. 18776-82 (2004); Esvelt K. M. et al., Nature. 472(7344): p. 499-503 (2011)). However, HIV-based strategies suffer from an inability of the virus to propagate under strong selection pressure or in most cell types, and also raise safety concerns surrounding large-scale HIV culture. The M13 bacteriophage used in phage-assisted continuous evolution provides large mutational libraries and enables rapid rounds of continuous mutagenesis and selection for biomolecules carrying out diverse functions, but only permits directed evolution in bacterial cells.

With these parameters and challenges in mind, this study was directed at devising a broadly useful, human cell-based directed evolution platform. It was hypothesized that adenovirus type-5 would be a practical vector for directed evolution of biomolecules in human cells, owing to its genetic tractability and broadly infectious nature in many human cell types (Lucher L. A. Curr. Top. Microbiol. Immunol. 199 (Pt 1), 119-152 (1995); Amalfitano A. and Chamberlain J. S., Gene Ther. 4, 258-263 (1997)). Conceptually, if the replication of a highly mutagenic adenovirus somehow depended on the activity of a biomolecule of interest (BOI) encoded in the adenoviral genome, then a simple directed evolution scheme for evolving diverse BOI functions in human cells could be feasible.

To achieve this concept, the essential adenoviral DNA polymerase (AdPol) and protease (AdProt) genes were deleted from an adenoviral genome that also encoded the BOI for evolution (FIG. 19A). The resulting partially gutted adenovirus is incapable of replication outside engineered human cells. The missing AdPol was trans-complemented by constitutive expression, within human cells, of a newly engineered and highly mutagenic AdPol variant to enable the generation of large mutational libraries during viral replication. AdProt expression in the human cells was then engineered to depend conditionally upon BOI function (FIG. 19B). Directed evolution experiments in this system, at least in theory, then relies on simply serially passaging the BOI-encoding adenovirus while mutagenesis and selection continuously occur (FIG. 19C).

Here, the approach to overcoming the above challenges is described. Described herein is a mutagenesis platform that harnesses adenovirus' own replication system to generate diverse mutational libraries for directed evolution. This platform was engineered to minimize the likelihood of selection subversion due to host cell mutagenesis or fluctuations in the mutation rate. Numerous genes were tested for trans-complementation in order to establish a viable selection platform. It was ultimately found that the adenovirus protease gene (AdProt) could be used as a selectable marker for evolving BOIs. Together, the establishment and validation of both the mutagenesis platform and selection platform comprise the main components necessary for adenovirus-mediated directed evolution in human cells.

First, an adenoviral replication system was devised that would be highly error-prone to more efficiently generate mutational libraries for directed evolution. Adenovirus is a double-stranded, non-enveloped DNA virus that relies on its own DNA polymerase (AdPol) for genome replication (Hoeben R. C. and Uil T. G., Cold Spring Harb. Perspect. Biol. 5, a013003 (2013)). The high fidelity wild-type AdPol is, however, incapable of supporting a laboratory-timescale directed evolution experiment. Previous studies identified two amino acid substitutions in adenoviral polymerase, F421Y and D827A, that can individually lower the fidelity of AdPol while still enabling efficient replication (Uil T. G. et al., Nucleic Acids Res., 2011. 39(5): e30). Based on the crystal structure of the homologous Φ29 phage DNA polymerase, the F421Y and D827A mutations likely affect distinct aspects of polymerase fidelity (FIG. 20A) (Kamtekar S. et al., Mol. Cell 16, 609-618 (2004)). In Φ29 DNA polymerase, the homologous residue to F421, F65, is in the proofreading domain, forms van der waals contacts with multiple bases in the ssDNA and likely stabilizes the strand for exonuclease activity (de Vega M. et al., J. Mol. Biol., 279, 807-822 (1998)). Mutating F65 to tyrosine (F65Y) in tl29 DNA polymerase was shown to reduce exonuclease activity by over 10-fold, and doubled the rate of base misincorporation. While Φ29 DNA polymerase does not have a homologous residue to D827, in Pfu DNA polymerase, the homologous residue to D827, D473, is in the fingers domain. D473 forms an extensive hydrogen bonding network with multiple adjacent residues (Biles B. D. and Connolly B. A., Nucleic Acids Res., 32, e176-e176 (2004)). Mutagenesis of D473 likely makes the fingers domain more flexible, reducing the geometric selection on the incoming nucleotide in the enzyme binding pocket. It was hypothesized that combining these two mutations to create the F421Y/D827A double-mutant, which we termed error-prone AdPol (or EP-Pol), would allow us to further increase the mutation rate while still supporting robust adenovirus propagation.

One concern with using the F421Y/D827ΔAdPol double mutant (error-prone adenoviral polymerase; EP-Pol), is that random mutations may arise in the AdPol gene itself (Smith J. G., Methods Mol. Biol., 1382, 187-196 (2016)). There may even be selection pressure for EP-Pol to mutate its own gene to increase its fidelity. To avoid this possibility, a trans-complementation system was established, whereby the wild-type AdPol is inactivated from the adenoviral genome by excision of 571 nucleotides, and EP-Pol is expressed in the human cell. Trans-complementation of EP-Pol potentially affords the opportunity to manipulate the mutation rate in the system by altering the AdPol variant used without having to further engineer the adenoviral genome during a directed evolution experiment.

The first step in creating an AdPol trans-complementation system was to delete AdPol from the adenoviral genome. Owing to the large size of the adenoviral genome, a recombination-based cloning approach was used to make seamless deletions and insertions in the adenoviral genome. This approach, termed AdEasy, was previously used to engineer AdPol-deleted adenoviral genomes for trans-complementation studies (Uil T. G. et al., Nucleic Acids Res., 39(5): e30 (2011); Luo J. et al., A protocol for rapid generation of recombinant adenoviruses using the AdEasy system, Nat. Protoc., 2, 1236-1247 (2007)). AdEasy requires large, 500 bp homology arms to recombine a nucleotide region of interest in an engineered *Escherichia coli* cell line termed BJ5183 cells. Attempted at designing the recombination cassette for AdPol deletion via overlap extension PCR were unsuccessful even after extensive efforts and optimization.

Therefore an alternative recombination-based cloning approach was used, termed lambda-red recombineering, which requires much shorted 30-50 bp homology arms (Sharan S. K. et al., Nat. Protoc., 4, 206-223 (2009); Landy A., Annu. Rev. Biochem., 58, 913-949 (1989)). Lambda-red recombineering requires a counterselectable marker to select for seamless recombinations. Our prior work utilized a galK counterselection scheme in concert with a DH10B-derived *E. coli* cell line that was auxotrophic for galactose (Warming S. et al., Nucleic Acids Res., 33, e36 (2005)). However, it was found the auxotrophic positive selection to be too slow and too weak for reliably selecting positive recombinants. Both positive and negative selection steps require growth for three days for colonies to appear. Also, while we were able to recombine using the galK counterselectable marker, we frequently found that after the negative selection step, the parent sequence would reappear, indicating that the first recombination step was too weak to reliably select for galK-only constructs.

Figure 29:
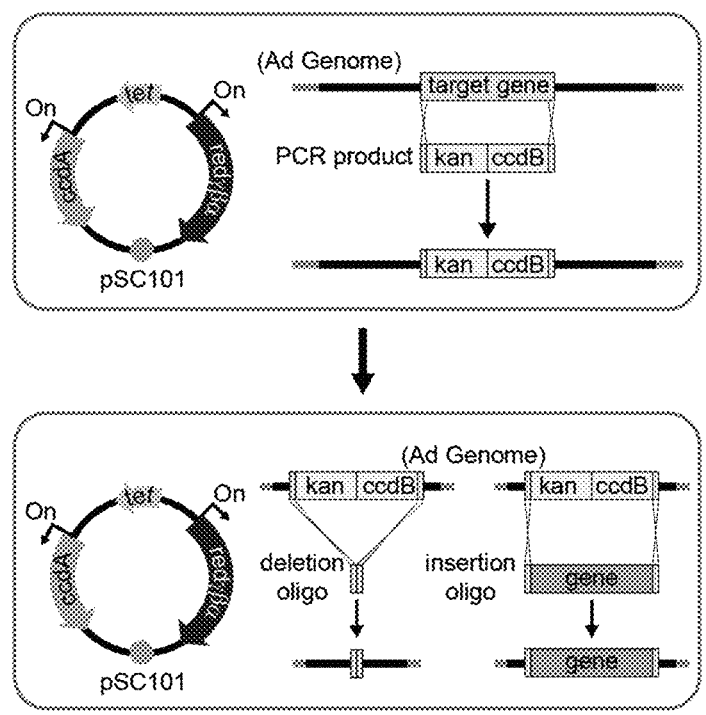
FIG. 29. Recombineering counter selection scheme to make a targeted, seamless deletion in the adenoviral genome. (i) The ccdA antitoxin and recombineering machinery are induced from the pSC101 plasmid in DH10B cells containing the adenoviral genome in the form of a bacterial artificial chromosome (BAC). (ii) A PCR product containing the ccdB-Kan counterselection marker flanked by short homology arms is electroporated into the DH10B cells and recombined into the site of deletion. Positive recombinants are selected on Kan. (iii) Only the recombineering machinery is induced from the pSC101 plasmid, in order to select against the ccdB toxin. (iv) For deletions, a short deletion oligo containing the relevant homology arms is electroporated into the DH10B cells. For insertions, a gene insertion flanked by the relevant homology arms is electroporated into the DH10B cells. Positive recombinants are selected on Chlor to select for the Ad Genome BAC.

We next transitioned to an alternative counterselection scheme that relies on the ccdB/ccdA toxin/antitoxin system (FIG. 29) (Wang H. et al., Nucleic Acids Res. 42, e37 (2014)). In this approach, the pSC101-gbaA plasmid that encodes for the ccdA antitoxin and recombineering machinery (induced by L-arabinose and L-rhamnose respectively) is introduced into a DH10B cell line along with a bacterial artificial chromosome (BAC) encoding the adenoviral genome. A kanamycin (kan)-ccdB selection/counterselection marker is then targeted to the desired locus in the adenoviral genome using 30-50 bp homology arms that are introduced by PCR primer overhangs. Induction of the recombineering machinery incorporates the marker into the adenoviral genome using the homology arms and resulting in the induction of ccdA to prevent the ccdB toxin from killing the cell. The cells are then plated on kan to positively select for recombinants carrying the kan-ccdB marker. In the next step, the targeting cassette is produced with homology arms that flank the kan-ccdB marker. Genes of interest can be placed between homology arms of the targeting cassette to insert genes into the adenoviral genome, or the homology arms can be directly fused together to produce a deletion in the adenoviral genome. The kan-ccdB marker is replaced by the targeting cassette upon induction of the recombineering machinery. Counterselection against the kan-ccdB marker is performed by not inducing the ccdA antitoxin, such that only cells that successfully replace the kan-ccdB marker with the targeting cassette will survive.

It was found that the optimized recombineering approach outlined above facilitated consistent seamless deletions, insertions, and mutations at any location in the adenoviral genome. Recombineering was first used to make a 571 nt deletion in Ad5.CFP (see TABLE 8 for adenovirus constructs used in this study) that inactivates the AdPol gene without affecting any known splice sites within the AdPol coding sequence (Uil T. G. et al., Nucleic Acids Res., 39(5): e30 (2011)). eGFP was also inserted into the E4 region with rightward facing orientation (E4R) to maintain the proper genome size to allow for efficient viral production, and to serve as an additional fluorophore for visualization of infection (Bett A. J. et al., J. Virol., 67, 5911-5921 (1993)). Placing transgenes in the E4R region was shown to allow for optimal transgene expression and viral titer (Suzuki M. et al., Gene Ther. 22, 421-429 (2015)).

Figure 30A:
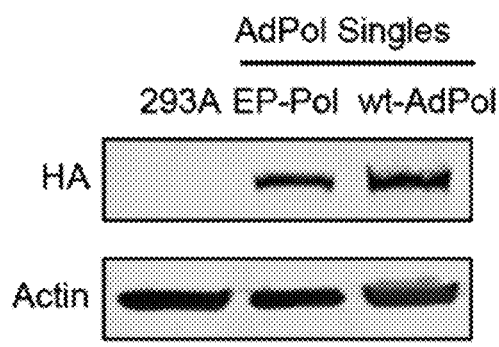
FIGS. 30A-30D. Trans-complementation of adenoviral polymerase.

The next component required for the EP-Pol trans-complementation system was an EP-Pol-expressing human cell line. HEK293A cells were stably transduced with hemagglutinin-epitope (HA)-tagged wild-type AdPol or HA-tagged EP-Pol to support ΔAdPol-adenovirus replication, and single colonies were isolated (for a list of cell lines used in this study, see TABLE 9). Expression of AdPol was analyzed via Western blot detection of the HA-tagged construct (FIG. 30A). Two single colonies were found that expressed either wild-type AdPol or EP-Pol, and further experiments were performed with these cells.

TABLE 8

Adenoviruses constructed and used in this study.

| Name | Modifications relative to wild-type Ad5 |
|---|---|
| Ad5.CFP | E1R-CFP ΔE1 ΔE3 |
| CFP.ΔAdPol.GFP | E1R-CFP ΔE1 ΔE3 ΔAdPol E4R-eGFP |
| AdGLΔPol (Uil, T. G. et al., Nucleic Acids Res. 39, e30 (2011)) | E1L-Luciferase-GFP ΔE1 ΔE3 |
| CFP. ΔAdPol. ΔE2A1.GFP | E1LR-CFP ΔE1 ΔE3 ΔAdPol ΔE2A1 E4R-eGFP |
| CFP. ΔAdPol. ΔE2A2.GFP | E1LR-CFP ΔE1 ΔE3 ΔAdPol ΔE2A2 E4R-eGFP |
| CFP. ΔAdPol. ΔpVI.GFP | E1LR-CFP ΔE1 ΔE3 ΔAdPol ΔpVI E4R-eGFP |
| CFP. ΔAdPol. ΔFS2.GFP | E1LR-CFP ΔE1 ΔE3 ΔAdPol ΔFS2 E4R-eGFP |
| CFP. ΔAdPol. ΔAdProt | E1LR-CFP ΔE1 ΔE3 ΔAdPol ΔAdProt E4R-eGFP |

Note:
All viruses used in this work were derived from AdCFP except for AdGLΔPol, which was previously reported (Uil, T. G. et al., Nucleic Acids Res. 39, e30 (2011)). Ad5.CFP GenBank Accession Number: MH325112 (SEQ ID NO: 97).

TABLE 9

Cell lines used in this study.

| Cell line | Polymerase | Transgene cassette |
|---|---|---|
| wt-AdPol | wt-AdPol | None |
| EP-Pol | EP-Pol | None |
| E2A | wt-AdPol | CMV.E2A |
| PVI | wt-AdPol | CMV.pVI |
| 633 | none | CMV.Fiber |
| Fiber | wt-AdPol | CMV.Fiber |
| Short Fiber | wt-AdPol | CMV.Short Fiber |
| AdProt | wt-AdPol | CMV.AdProt |

Note:
All cell lines were derived from HEK293A cells except the 633 cell line, which was A549-derived.

Figure 30B:
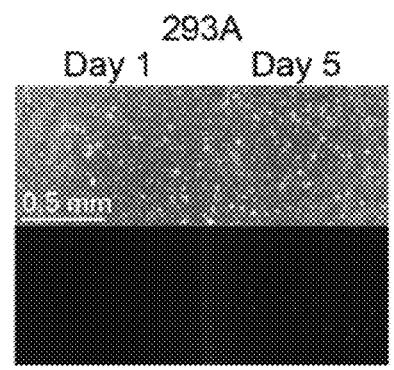
Figure 30C:
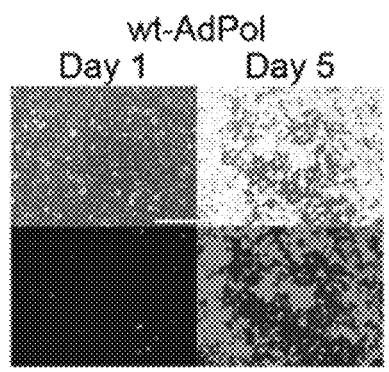
Figure 30D:
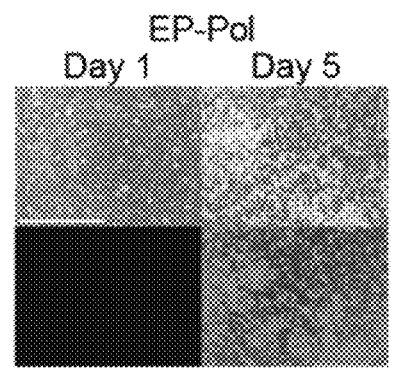

With single-colony cell lines expressing wild-type AdPol or EP-Pol in hand, the dependence of ΔAdPol adenovirus replication on cellular AdPol expression was assessed. HEK293A cells that either did or did not express the HA-tagged AdPol variants were infected with GFP-expressing ΔAdPol adenoviruses and monitored the infection. These infections were performed at a low multiplicity of infection (MOI<<1) to ensure that one could effectively monitor the infection as it spread. After one day of infection, robust GFP expression was observed in the wild-type AdPol and EP-Pol expressing cell lines, but only moderate GFP expression in the HEK293A cell line (FIG. 30B-30D). The difference in GFP expression between AdPol-expressing cell lines and the HEK293A cells is likely a result of AdPol-mediated replication of the adenoviral genome-expressed eGFP gene. As AdPol replicates the genome, the eGFP gene is replicated and the gene copy number increases, resulting in increased eGFP transcription and protein expression. The cells were monitored over time to assess whether the infection spread. After 5 days, eGFP was expressed throughout the plate and largescale cytopathic effect (CPE) was observed only in the AdPol-expressing cell lines. As eGFP is only expressed in cells infected by the eGFP.ΔPol.adenovirus, this result indicates that ΔAdPol adenoviruses propagated only on human cells that trans-complement AdPol with wild-type AdPol or EP-Pol. Moreover, EP-Pol and wild-type AdPol were similarly capable of supporting robust ΔAdPol-adenovirus replication.

The mutation rate of EP-Pol was next assessed by passaging ΔAdPol-adenovirus on EP-Pol trans-complementing human cells for multiple generations. Subsequent next-generation sequencing of a 6.5 kb region of the adenoviral genome in a small pool of passaged clones revealed a mutation rate of approximately $3.7 \times 10^{-5}$ per base per cell infection cycle, which is >280-fold higher than the estimated spontaneous mutation rate of wild-type AdPol (FIG. 20C, TABLE 4) (Risso-Ballester J. et al., PLoS Pathogy. 12(11): e1006013 (2016)). This increase in mutation rate endows EP-Pol with a mutagenic capacity similar to highly mutagenic RNA viruses that can readily evolve on lab timescales (Risso-Ballester J. et al., PLoS Pathogy. 12(11): e1006013 (2016); Sanjuin R. et al., J. Virol. 84, 9733-9748 (2010); Phillips A. M. et al., eLife 6, e28652 (2017)). Moreover, EP-Pol displays a broad mutational spectrum, including both transitions and transversions (FIG. 20D).

Based on these results, the lower limit of the library size was estimated in a given passage (or 'round') of directed evolution using EP-Pol. A typical round of directed evolution might reasonably involve infecting $3.0 \times 10^8$ human cells at a low MOI. Each round of directed evolution concludes once ~75% of cells (~$2.3 \times 10^8$ cells) are infected. Because ~1.3 mutations are introduced per cell per replication, and because there is at least one replication in each round of evolution since the infection occurs at low MOI, it was estimated that there are ~$3.0 \times 10^8$ adenoviral variants after one passage. Assuming a typical 1 kb gene encoding the BOI comprises ~1/30 of the engineered adenoviral genome, there would be ~$1 \times 10^7$ variants of the BOI in the population after one round of evolution. This calculation is a lower limit because it does not account for any genetic diversity at the beginning of each round. Additionally, there is likely to be more than a single replication in each round of evolution, which would further increase library complexity. Regardless, even this conservative estimate indicates that one can generate virtually all single, many double, and some triple mutants in a typical BOI gene single round of evolution.

This mutagenesis system has a number of advantages over current standard directed evolution systems. Trans-complemented EP-Pol allows continual introduction of mutations into the evolving BOI instead of requiring in vitro mutagenesis physically separated from selection and propagation steps. Mutagenesis is accomplished by simply passaging the evolving adenovirus on cells that express EP-Pol. Furthermore, because EP-Pol is specific for the adenoviral genome, the possibility of selection subversion owing to random mutagenesis of the human genome is significantly reduced compared to global mutagenesis methods (Badran A. H. and Liu D. R., Nat. Commun., 6, 8425 (2015)). Additionally, the human cell dies as a result of infection and is discarded as part of the serial passaging protocol, further reducing the possibility of selection subversion as a result of mutations in the human cell. Overall, this trans-complementation-based EP-Pol mutagenesis system should provide a robust approach to in vivo library generation, that reliably mutates BOIs while minimizing researcher intervention.

Example 15. Development of Trans-Complementation Systems for Putative Selection Schemes The next objective was to design an appropriate selection circuit capable of coupling BOI activity to adenoviral propagation. The selection gene employed to create the circuit requires a number of characteristics: 1) the gene must be essential for viral replication to ensure efficient enrichment of positive BOI variants; 2) the gene must be amenable to trans-complementation to allow for creation of the genetic circuit; 3) the gene cannot be susceptible to "cheating" in which the BOI finds alternative paths to allow for viral replication; 4) the gene should have a high dynamic range so that greater expression of the selection gene results in greater amplification of the evolving BOI; and 5) ideally the gene would function after viral genome replication to allow for mutagenic library generation prior to selection (Flint S. J., Adenoviruses, Encyclopedia of Life Sciences (2001)). With these desired characteristics in mind, the possibility of using four different genes encoding Early gene 2A (E2A), precursor protein VI (pVI), Fiber, and AdProt as selectable markers was explored for adenovirus-mediated directed evolution.

E2A:

The adenoviral E2A gene encodes for a single-stranded DNA binding protein that has distinct functions in both early gene transcription and DNA replication (Stillman B. W., In Genetic Engineering: Principles and Methods (Setlow, J. K., and Hollaender, A., Eds.), pp 1-27, Springer US, Boston, Mass. (1985)). E2A functions as a vital processivity factor for adenoviral DNA replication: both unwinding the double-stranded genome, and stabilizing the resulting single-stranded DNA (Flint S. J., Adenoviruses, Encyclopedia of Life Sciences (2001)). The vital functions of E2A in both transcription and DNA replication suggest that it would allow for sufficient selection pressure and potentially have a high dynamic range. On the other hand, E2A is expressed early in adenoviral infection, prior to DNA replication, which could hamper the generation of a mutagenic library prior to selection.

Importantly, E2A has been previously trans-complemented, indicating that one should be able to engineer a genetic circuit to allow for genetic selection. Two different deletion constructs were pursued to test trans-complementation of E2A (TABLE 8). The first construct, results in deletion of a 242 bp segment of E2A spanning from nt 67-nt 308. This deletion results in a frameshift mutation that prematurely terminates translation (Rice S. A. and Klessig D. F., J. Virol., 56, 767-778 (1985)). The second construct was created by deletion of 1176 bp from nt 119-nt 1294 in the E2A gene (Zhou H. et al., J. Virol., 70, 7030-7038 (1996)). This deletion also results in a frameshift, but also removes most of the coding sequence of E2A. Both deletions were made by recombineering in the previously developed ΔAdPol adenoviral constructs described above.

Figure 31:
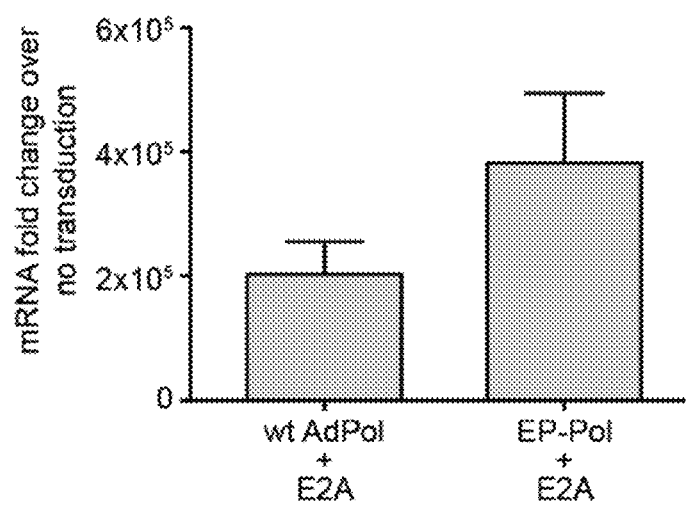
FIG. 31. mRNA expression of E2A in AdPol-expressing cells.

To generate cell lines capable of trans-complementing the E2A deletion, the E2A gene was cloned into a lentiviral vector and used this construct to stably transduce the wild-type AdPol-expressing cell line (TABLE 9). Since there are no antibodies available against E2A, the resulting expression was analyzed at the transcript level by qPCR (FIG. 31). Based on the qPCR data, the E2A transcript was only detectable in the E2A-expressing cell lines.

Simultaneous trans-complementation was next tested of ΔAdPolΔE2A-adenoviruses by transfecting linearized genomes into the Pol/E2A expressing cell line. Unfortunately, despite extensive optimization and efforts we were unable to generate ΔAdPolΔE2A-adenoviruses by transfection. Successfully trans-complementation of E2A may require better analysis of protein expression. Since there are no currently available commercial antibodies against E2A, this may require either epitope tagging of the E2A protein, or generation of specific antibodies.

pVI:

pVI is a late adenoviral gene that plays many diverse roles in the adenovirus life cycle. Following viral endocytosis, the N-terminal amphipathic helix of pVI mediates endosomal escape by inducing positive membrane curvature in a pH-dependent process (Maier O. et al., Virology, 402, 11-19 (2010)). During viral capsid maturation, a C-terminal cleavage peptide of pVI interacts with the viral endoprotease (AdProt) to facilitate cleavage of viral precursor proteins from the interior of the capsid (Blainey P. C. et al., J. Biol. Chem., 288, 2092-2102 (2013)). Finally, the mature protein VI is a minor cement protein in the interior of the capsid, and binds the exterior of the capsid to interior proteins (Dai X. et al., J. Virol., 91 (2017)).

Consistent with the important and diverse roles of pVI during many viral processes, pVI is required for adenoviral infection. The structural role of pVI indicates that pVI may have a high dynamic range as a selection marker. In contrast to enzymes, structural proteins generally exhibit greater dynamic range of selection since the number of resulting structures (in the case of pVI, the number of mature virions) are directly proportional to the amount of the structural protein present (Esvelt K. M. et al., Nature. 472(7344): p. 499-503 (2011)). Therefore, lower pVI expression should result in fewer mature viral capsids, and greater pVI expression should support greater production of mature adenoviral capsids. pVI is also expressed after viral DNA replication, allowing generation of a mutagenic library prior to selection. However, to our knowledge, pVI has not been previously trans-complemented, and it has been suggested that in vitro expression of pVI is toxic to cells (private correspondence with Dr. Jason Smith, University of Washington). Nevertheless, a pVI trans-complementation strategy was pursued similar to those we pursued for AdPol and E2A.

The entire pVI coding sequence was first deleted from a ΔAdPol-adenovirus by recombineering (TABLE 8). A stable cell line was generated next that expressed pVI (TABLE 9). Ectopic expression of pVI required additional engineering to incorporate a necessary leader sequence termed the tripartite leader, or TPL. Late adenoviral genes such as pVI require the TPL to allow for high expression throughout the adenoviral infection (Logan J. and Shenk T., Proc. Natl. Acad. Sci., 81, 3655-3659 (1984)). During late adenoviral infection, adenovirus inhibits cap-dependent translation by inhibiting formation of the proper translation initiation complex, eIF4F (Cuesta R. et al., Embo J., 19, 3465-3474 (2000)). The TPL allows late adenoviral genes to subvert cap-dependent translation by interacting directly with ribosomal RNA through a process termed ribosomal shunting (Yueh A. and Schneider R. J., Genes Dev. 14(4): p. 414-21 (2000)).

Figure 32:
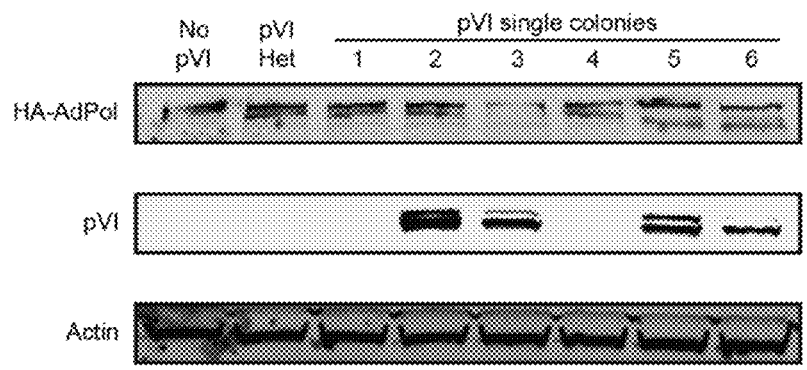
FIG. 32. pVI single colony expression analyzed by Western blot.

Wild-type AdPol expressing cells were stably transduced with lentivirus containing TPL-fused pVI and isolated single colonies. Both AdPol and pVI expression were analyzed by Western blot (FIG. 32). It was found that the pVI heterostable cell lines (pVI Het) expressed pVI at levels too low to detect by Western blot. However, some single colonies expressed pVI to a much greater degree, although expression level varied from clone to clone. Most single colonies also expressed two separate protein bands. The biological significance of this banding pattern is unclear, but it could be a result of either proteolytic digestion or alternative splicing.

Two separate single colonies were tested for their ability to trans-complement ΔpVIΔAdPol-adenovirus: colony number two owing to high pVI expression, and colony number six owing to the single pVI band observed. Colonies number two and six were transfected with linearized ΔpVIΔAdPol-adenovirus to generate ΔpVIΔAdPol virions. However, like E2A, we were unable to generate any adenovirus from either transfection. It is likely that there are other regulatory factors such as vital alternative splice sites that may contribute to pVI activity (Zhao H. et al., Virology, 456-457, 329-341 (2014)).

Figure 33A:
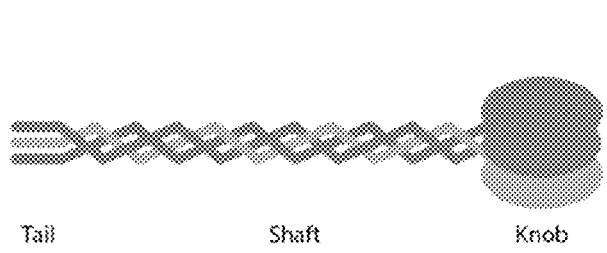
FIGS. 33A-33B. Fiber domain architecture and cell line expression.

Fiber:

The adenovirus fiber protein is a 62 kDa trimeric protein located at each of the twelve vertices on the icosahedral adenoviral capsid (Flint S. J., Adenoviruses, Encyclopedia of Life Sciences (2001)). Fiber mediates host cell recognition through its interaction with the coxsackie virus and adenovirus receptor (CAR) on the surface of target cells (Lonberg-Holm K. et al., Nature, 259, 679-681 (1976)). Fiber consists of three primary domains: a tail that associates other structural proteins within the adenoviral capsid, a series of twenty-two shaft repeats, and a knob domain that interacts with cell receptors (FIG. 33A). The replication of adenoviruses deleted and then trans-complemented for fiber has been extensively studied (Von Seggern D. J. et al., J. Virol., 73, 1601-1608 (1999); Uil T. G. et al., J. Gene. Med., 11, 990-1004 (2009)). Adenoviruses deleted for fiber are 10,000-fold less infectious than fiber-containing adenoviruses, indicating a potentially high dynamic range for selection (Legrand V. et al., J. Virol., 73, 907-919 (1999)). Furthermore, fiber binds cooperatively to multivalent receptors, indicating that fiber may exhibit a high dynamic range as a selection marker (Persson R. et al., J. Virol., 54, 92-97 (1985)). Finally, like pVI, fiber is expressed late in adenoviral infection allowing for mutagenic replication prior to selection.

Trans-complementation of fiber in the system required extensive engineering of both the adenoviral genome and cell line. Following previous studies involving fiber deletion, all but the last 85 nucleotides were deleted of the fiber coding sequence by recombineering to make a ΔAdPolΔfiber-adenoviral genome (TABLE 8) (Uil T. G. et al., J. Gene. Med., 11, 990-1004 (2009)). To generate an AdPol/fiber expressing cell line, an A549-derived cell line was obtained that highly expresses fiber, termed '633' (TABLE 9). The 633 cell line was transduced with lentiviral vectors containing AdPol, however, a high-expressing clonal cell line was not obtained (Von Seggern D. J. et al., J. Virol., 74, 354-362 (2000)).

We next attempted to generate high-expressing fiber cell lines from the previously established AdPol expressing cell lines. The wild-type AdPol expressing cells were stably transduced with TPL-fused fiber lentivirus and analyzed expression by Western blot (TABLE 9). However, it was found that fiber expression in a 293A-derived cell line was significantly lower than fiber expression in either an adenoviral infection, or in the 633 cell line (FIG. 33A, lane 2, lane 4).

Figure 33B:
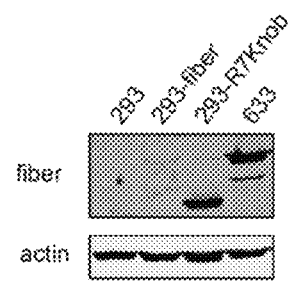

Previous studies report that shortening fiber by reducing the number of shaft repeats from 22 to 7 significantly increases ectopic expression of the protein (Uil T. G. et al., J. Gene. Med., 11, 990-1004 (2009)). A cell line expressing the shortened fiber construct was generated and it was found that fiber expression was significantly increased (FIG. 33B, lane 3 R7Knob) (TABLE 9).

We therefore attempted simultaneous trans-complementation of both fiber and AdPol by transfecting ΔAdPolΔfiber-adenovirus into the AdPol/short fiber-expressing cell line. After about 2 weeks, the formation of 'comets' of fluorescent cells was seen, indicating that the virus had been successfully produced from a progenitor cell, and reabsorbed into neighboring cells (data not shown). Unfortunately, these comets failed to increase in size, and uninfected cells grew back around the comets, indicating that the infection failed to effectively spread. Considering we observed initial formation of comets that failed to spread further, it is possible that the isolated cell line has developed heterogeneity in fiber expression, so that most of the cells in the culture cannot support propagation ΔAdPolΔfiber-adenovirus. Extensive testing and rescreening of fiber-expressing single colony cell lines may result in a homogenous cell line that is capable of supporting infection of ΔAdPolΔfiber-adenovirus.

Adenoviral Protease:

The final adenoviral gene examined for its utility as a selectable marker was the adenoviral protease (AdProt). AdProt is a 23 kDa cysteine protease that plays an important role in both viral entry, and viral maturation (Mangel W. F. et al., J. Biol. Chem., 271, 536-543 (1996); Cotten M. and Weber J. M., Virology, 213, 494-502 (1995)). Upon initial assembly of the adenoviral pro-capsid, AdProt cleaves viral precursor proteins in order to generate the mature, stable capsid (Blainey P. C. et al., J. Biol. Chem., 288, 2092-2102 (2013)). Like fiber and pVI, AdProt is produced late in adenoviral infection, after DNA replication. The vital functions of AdProt also suggest that it is completely necessary for viral growth. Furthermore, despite concerns regarding AdProt toxicity, AdProt had been previously trans-complemented by one group, suggesting that one could likely engineer it to serve as a selectable marker (Oualikene W. et al., Hum. Gene Ther., 11, 1341-1353 (2000)). We were concerned that as an enzyme, AdProt may not afford a large dynamic range of selection, as enzyme turnover may allow enough activity to generate mature virions. However, we were encouraged by the fact that AdProt is highly constrained in the interior of the viral capsid, indicating that adenovirus may require multiple molecules of AdProt per capsid to effectively cleave all of its substrates (Graziano V., J. Biol. Chem., 288, 2068-2080 (2013)).

Figure 34:
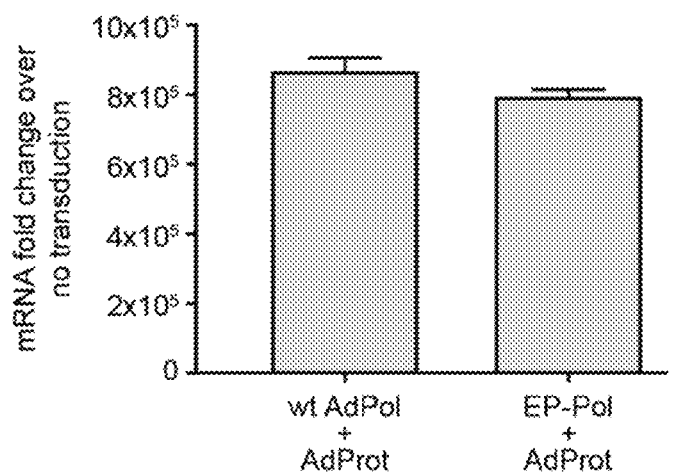
FIG. 34. mRNA expression of AProt in AdPol-expressing cells.

The AdProt gene was first deleted from a ΔAdPol-adenovirus by recombineering (TABLE 8). We next generated a TPL-AdProt/AdPol-expressing clonal cell line by lentiviral transduction of the AdPol-expressing cell line (TABLE 9). Since there is no antibody available against AdProt, we analyzed expression by qPCR (FIG. 34). We found that we were only able to detect AdProt mRNA expression in the AdProt-expressing cell line. To test double-trans-complementation of AdPol and AdProt, we transfected linearized CFP-ΔAdProt-ΔAdPol-adenoviral genomes into the AdProt/AdPol expressing cell line. After two weeks, we began to see fluorescent comets form indicating a successful initial viral production. After three weeks, most of the cells exhibited CPE, and all were fluorescing blue, suggesting that the infection had progressed effectively throughout the entire plate.

For AdProt to act as a selectable marker in adenovirus-mediated directed evolution, ΔAdProt-ΔAdPol adenovirus would need to be dependent on AdProt expression and function to propagate. To test the necessity of AdProt for adenoviral production, AdProt/AdPol cells, AdPol cells, and normal HEK-293A cells were infected with the newly generated CFPΔAdProtΔAdPol adenovirus at a low MOI (<<1) and monitored the infection (FIG. 25). The HEK-293A cells exhibited only modest CFP fluorescence, possibly due to a low adenoviral genome copy number. The AdPol cells exhibited robust CFP fluorescence, likely because AdPol was present to increase the copy number of the adenoviral genome, and thus the CFP gene. While the CFPΔAdProtΔAdPol adenovirus was able to infect the AdPol cells, the virus failed to propagate. Only the AdProt/AdPol cells were able to support a spreading infection of ΔAdProtΔAdPol adenovirus, demonstrating the absolute necessity of AdProt expression to adenoviral replication.

Example 16. Discussion

Here, efforts to generate the necessary components of an adenovirus-mediated, human cell-based directed evolution platform have been described. A mutagenesis system was created based on a designed error-prone adenoviral polymerase capable of generating genetic libraries on the scale necessary for robust directed evolution. A selection system was derived based on the adenoviral protease gene that enables continuous selection by simply passaging the adenovirus from one plate to the next. Together, the mutagenesis and selection systems comprise the basic components necessary to do adenovirus-mediated directed evolution in human cells.

In developing this platform, adenovirus was chosen rather than a natively mutagenic RNA virus owing to adenovirus' relative safety, broad tropism, ease of manipulation, and capacity to propagate even under strong selection pressure. The adenoviruses used for directed evolution experiments were E1-, E3-, AdPol- and AdProt-deleted. All of these genes are required for adenoviral replication in the wild. Thus, the safety of working with these partially gutted adenoviruses is maximized as they can only replicate in human cells that provide these essential genes in trans, and cannot replicate in unmodified human cells (Uil T. G. et al., Nucleic Acids Res., 39(5): e30 (2011); Russell W. C. J. Gen. Virol. 81, 2573-2604 (2000); Elahi S. M. et al., Gene Ther. 9, 1238-1246 (2002)). Moreover, the removal of this large portion of the adenoviral genome means that genes as large as ~7 kb can potentially be introduced and evolved in the platform. The broad tropism of adenovirus is beneficial because it means that directed evolution experiments can, in principle, be performed in many different human cell types depending on the objective of a particular experiment (Lucher L. A. Curr. Top. Microbiol. Immunol. 199 (Pt 1), 119-152 (1995)). Finally, from a genome engineering perspective, the optimized recombineering protocols allow the necessary facile manipulation of the adenoviral genome (Wang H. et al., Nucleic Acids Res. 42, e37 (2014)).

Despite the manifold benefits of the choice to use adenovirus, this study faced a significant challenge because both wild-type and even the previously reported error-prone AdPol variants have relatively high fidelity, and were therefore unlikely to enable the creation of mutational libraries at a sufficiently high rate to support continuous directed evolution of novel BOIs (Uil T. G. et al., Nucleic Acids Res., 39(5): e30 (2011)). To address this issue, EP-Pol was engineered, a highly mutagenic AdPol variant that pushes the adenoviral mutation rate into the regime of RNA viruses such as HIV and influenza that are well-known to rapidly evolve on laboratory timescales (Phillips A. M. et al., eLife 6, e28652 (2017); Meyerhans A. et al., Cell 58, 901-910 (1989); O'Loughlin T. L. et al., Mol. Biol. Evol. 23, 764-772 (2006)). Trans-complementation of EP-Pol was used via constitutive expression in the host cell to prevent reversion to wild-type AdPol that could occur if we modified an adenovirally encoded AdPol gene, thereby ensuring that mutagenic activity remains at a constant, high level throughout directed evolution experiments.

The mutagenesis system combines the effect of two distinct mutations in the adenoviral polymerase to cooperatively increase the mutation rate by over 280-fold. This system should allow the generation of a new mutation during each viral replication cycle, and conservatively support library sizes of $10^7$-$10^9$ members. As expected, EP-Pol causes far more transitions than transversions. Interestingly, no A→C transversions were observed, despite the fact that a minor population of A→C transversions were observed in the F421Y single mutant (Uil T. G. et al., Nucleic Acids Res., 39(5): e30 (2011)). It is possible that the sample size was too small to detect if A→C transversions occur at a low level with EP-Pol. Alternatively, the cooperative effects of the F421Y/D827A double mutant could have shifted the mutational biases so that the A→C transversion is no longer possible.

This mutagenesis approach does introduce mutations into the adenoviral genome outside the gene for the BOI. Such mutations can potentially be negatively selected and consequently reduce library size. The 6.5 kb genomic region we sequenced (FIGS. 20C-20D) was chosen because it contained both protein coding regions necessary for adenoviral replication and non-coding regions that should not face significant selection pressure. Comparing these domains across the sequenced region, only a two-fold difference between the mutation rate in the inactivated AdPol gene was observed, which should not be under any selection pressure in the trans-complementing system, and the neighboring pIX, IVa2, and pTP genes, suggesting that such negative selection only impacts the mutation rate at most two-fold.

Because AdPol selectively replicates only adenoviral DNA, EP-Pol can only introduce mutations into the adenoviral genome. This mutagenesis technique thus represents an improvement over other strategies that evolve genes directly in the human genome. In such strategies, off-target mutations can arise through basal or through the enhanced mutagenesis rates, which can subvert selection pressure and generate false positives. Furthermore, even recent mutagenesis methods that target specific genes within the human genome, by using somatic hypermutation (Wang C. L. et al., Protein Eng. Des. Sel. 17, 659-664 (2004)) or Cas9-fusion proteins (Wang L. et al., Proc. Natl. Acad. Sci. USA. 101(48): p. 16745-49 (2004); Ma Y. et al., Nat. Methods 13, 1029-1035, doi:10.1038/nmeth.4027 (2016); Hess G. T. et al., Nat. Methods 13, 1036-1042, doi:10.1038/nmeth.4038 (2016); Komor A. C. et al., Nature 533, 420-424 (2016)), still display significant off-target genetic modification (Meng F. L. et al., Cell 159, 1538-1548 (2014); Kim D. et al., Nat. Biotechnol. 35, 475-480 (2017); Wang C. L. et al., PNAS 101, 7352-7356 (2004)). Especially given the large size of the human genome, many pathways to cheating selection may be available. The use of an orthogonal replication system means that the human host cells are discarded and replaced with each passage, preventing mutation accumulation in the human cell that could potentially cheat selection pressure. This advantage, combined with the much more rapid growth of adenovirus relative to human cells allowing a larger number of directed evolution rounds in a given time period, highlights the ability of the platform to quickly scan mutational space with minimal risk of selection subversion.

While the mutagenesis system is capable of supporting laboratory-based directed evolution, some improvements can be made to both characterization of the mutation rate and the mutagenesis approach overall. Because the deep sequencing approach only sequences a very small subset of the viral population (a few dozen clones), the reported mutation rate only follows a specific viral lineage, and fails to elucidate the diversity of mutations generated in the whole viral population. We were only able to sample a few clones because it was necessary to obtain mutational signals above the ~1% error threshold of deep sequencing approaches (Howison M. et al., bioRxiv (2018)). New strategies to sample preparation and data analysis introduce redundancy into the deep sequencing pipeline to make more accurate base calls (Schmitt M. W. et al., Proc. Natl. Acad. Sci., 109, 14508-14513 (2012)). This so-called "duplex sequencing" approach has been used to more accurately assess the mutation rate of wild-type AdPol, and could be used for the same purposes on EP-Pol to better characterize the mutational diversity (Risso-Ballester J. et al., PLoS Pathog. 12(11): e1006013 (2016)).

Alternatively, experimental approaches that assess the rate of reversion of non-permissive mutations have been employed to assess the mutation rate of higher organisms and pathogens alike (Sanjuin R. et al., J. Virol. 84, 9733-9748 (2010); Luria S. E. and DelbrUck M., Genetics, 28, 491-511 (1943)). In fluctuation analysis, a selection for a known mutation is used as a proxy to assess the mutation rate. Because the method is based on the number of specific mutants relative to the number of non-mutants, one can reasonably assess the population diversity based off the likelihood of the single permissive mutation arising. This experiment is repeated several times to assess the distribution of permissive mutations and more accurately determine the overall mutation rate over multiple viral generations. One drawback of this approach in analyzing a mutagenic polymerase is that it fails to account for nucleotide biases that may favor certain mutations over others. To perform fluctuation analysis on EP-Pol, we could take advantage of known temperature sensitive viral mutants to assess the titer in both the absence and presence of temperature-dependent selection (Kaplan L. M. et al., Proc. Natl. Acad. Sci., 76, 5534-5538 (1979); Day R. S. and Ziolowski C. H. J., Photochem. Photobiol., 34(3): p. 403-06 (1981)).

The ability of four different adenoviral genes were also assessed to serve as selectable markers in a directed evolution system. Of the four genes tested, only AdProt was successful in a double-trans-complementation scheme with AdPol. Fortunately, AdProt was also completely selectable: ΔAdProt-ΔAdPol adenoviruses failed to grow on cells that did not express AdProt.

We encountered significant difficulties in trans-complementing various other adenoviral genes for genetic selection. Two of the genes we failed to trans-complement, E2A and fiber, have been previously trans-complemented by others (Zhou H. et al., J. Virol., 70, 7030-7038 (1996); Uil T. G. et al., J. Gene. Med., 11, 990-1004 (2009)). Trans-complementation of adenoviral genes is inherently disruptive to the adenoviral replication cycle, which is tightly regulated during normal infection (Flint S. J., Adenoviruses, Encyclopedia of Life Sciences (2001)). It was found that expressing the adenoviral polymerase in trans already reduces the infectious titer ~10-fold (data not shown) likely due to dysregulation of expression. Simultaneously expressing E2A, which is also involved in DNA replication, in trans may be too much for the virus to overcome.

For fiber, previous labs have found that strong in trans expression is necessary for robust adenoviral infection (Von Seggern D. J. et al., J. Virol., 73, 1601-1608 (1999); Uil T. G. et al., J. Gene. Med., 11, 990-1004 (2009)). While we were able to achieve higher fiber expression using a short fiber construct, we were still unable to support a strong adenoviral infection. We did observe an initial infection event, indicated by the appearance of a "comet" of highly fluorescent cells in close proximity. These comets are indicative of successful viral production and subsequent reabsorption in neighboring cells. However, the virus failed to spread beyond this initial infection event. Given how close this fiber cell line was to successful trans-complementation of fiber, it is possible that one could screen for higher-expressing fiber clones and achieve the expression necessary to support infection. Alternatively, designing closer mimetics of the canonical adenoviral expression, such as driving transcript expression via the adenovirus major late promoter, could create a more viable trans-complementation system for late genes such as fiber and/or pVI (Song B. and Young C. S. H., Virology, 235, 109-117 (1997)).

While AdProt is able to act as a selectable marker for adenoviral replication, it is possible that there are better selection genes available. HAd5 encodes at least 36 individual proteins (GenBank: AC_000008.1), of which only a fraction have been trans-complemented. Based on the desired characteristics of a selectable marker, other adenoviral structural proteins such as hexon, penton, IIIA, VII, and VIII, may be useful (Russell W. C., J. Gen. Virol. 81, 2573-2604 (2000)).

Example 17. Materials and Methods for Examples 18-24

Vectors and Cloning:
Materials:
All enzymes were obtained from New England BioLabs unless stated otherwise. All primers were obtained from either ThermoFisher or Sigma Aldrich. Gene blocks were obtained from Integrated DNA Technologies. All primers are listed in TABLE 14. LV-Cre pLKO. 1 was a gift from Elaine Fuchs (Addgene plasmid #25997) (Beronja S. et al., Nat. Med., 16, 821-827 (2010)) and was used as a template to recombineer Cre recombinase into the adenoviral genome, and pANAP was a gift from Peter Schultz (Addgene plasmid #48696) (Chatterjee A. et al., J. Am. Chem. Soc., 135, 12540-12543 (2013)).

Adenoviral Cloning:
All adenoviruses were generated from a parent Ad5.CFP vector derived from pAd/CMV/V5-DEST (ThermoFisher). Adenoviral constructs were engineered using ccdB recombineering, as previously described (Wang H. et al., Nucleic Acids Res. 42, e37 (2014)), in DH10B $Escherichia\ coli$ carrying the Adenovirus type 5 genome in a chloramphenicol-resistant bacterial artificial chromosome (AdBAC). Cells carrying an AdBAC were transformed with the temperature-sensitive psc101-gbaA recombineering plasmid (Wang H. et al., Nucleic Acids Res. 42, e37 (2014)), plated on LB (Difco) agar (Alfa Aesar) with 10 µg/mL tetracycline (CalBioChem) and 10 µg/mL chloramphenicol (Alfa Aesar), and incubated for 24 h at 30° C. Colonies were selected and grown in LB containing 10 µg/mL tetracycline and 10 µg/mL chloramphenicol overnight at 30° C. (18-21 h). Overnight cultures were diluted 25-fold in LB with 10 µg/mL tetracycline and 10 µg/mL chloramphenicol and grown at 30° C. for ~2 h until attaining an $OD_{600}$ of 0.3-0.4. The ccdA antitoxin and recombineering machinery were then induced by adding L-arabinose (Chem-Impex) and L-rhamnose (Sigma Aldrich) to a final concentration of 2 mg/mL each and then growing the cultures at 37° C. for 40 min to an $OD_{600}$ of ~0.6. The cultures were then placed on ice, washed twice with ice-cold, sterile ddH2O, resuspended in ~25 µL of ice-cold, sterile $ddH_2O$, and electroporated with ~200 ng of the appropriate kan-ccdB targeting cassette (1.8 kV, 5.8 ms, 0.1 cm cuvette, BioRad Micropulser). The cells were then recovered in super optimal broth with catabolite repression (SOC; Teknova) with 2 mg/mL L-arabinose at 30° C. for 2 h, then plated on LB agar plates with 50 µg/mL kanamycin (Alfa Aesar) and 2 mg/mL L-arabinose and incubated for 24 h at 30° C. Colonies that grew under these conditions had incorporated the kan-ccdB targeting cassette and were picked in triplicate and grown in LB with 50 µg/mL kanamycin and 2 mg/mL L-arabinose at 30° C. for 18-21 h. (Note: The colonies were picked in triplicate because multimers of the AdBAC formed at a high rate (~30-50% of colonies) during the first recombineering step. These multimers are unable to be successfully recombineered in the next step. Picking three colonies and recombineering them separately in parallel increases the chances of picking a monomer that can be successfully recombineered.) The cultures were then diluted 25-fold in LB with 50 µg/mL kanamycin and 2 mg/mL L-arabinose and grown at 30° C. for ~2 h until they reached an $OD_{600}$ of 0.3-0.4. The recombineering machinery was then induced by adding L-rhamnose to a final concentration of 2 mg/mL and then growing the cultures at 37° C. for 40 min to an $OD_{600}$ of ~0.6. The cultures were then placed on ice, washed twice with ice-cold, sterile $ddH_2O$, resuspended in ~25 µL of ice-cold, sterile $ddH_2O$, and electroporated with ~200 ng of the final targeting cassette intended to replace the kan-ccdB cassette currently integrated in the genome (1.8 kV, 5.8 ms, 0.1 cm cuvette, BioRad Micropulser). The cells were then recovered in SOC with 2 mg/mL L-arabinose at 30° C. for 2 h, and then were washed once with LB to remove the L-arabinose and prevent continued production of the ccdA antitoxin. The cultures were then plated on LB agar plates at various dilutions with 10 µg/mL tetracycline and 10 µg/mL chloramphenicol and incubated for 24 h at 37° C. Without the ccdA antitoxin, the ccdB toxin will kill cells that have not replaced the integrated kan-ccdB cassette with the final targeting cassette. The colonies that grow should have the final targeting cassette integrated, but were screened by PCR or sequencing to confirm cassette integration as some colonies may simply inactivate the ccdB toxin.

Once a clone with all of the desired genetic changes was found and confirmed by Sanger sequencing, the AdBAC single-copy replication origin was replaced with the high copy pUC origin. The cells with the correct clone were grown in LB containing 10 µg/mL tetracycline and 10 µg/mL chloramphenicol overnight at 30° C. (18-21 h). Overnight cultures were diluted 25-fold in LB with 10 µg/mL tetracycline and 10 µg/mL chloramphenicol and grown at 30° C. for ~2 h until attaining an $OD_{600}$ of 0.3-0.4. The recombineering machinery was then induced by adding L-rhamnose to a final concentration of 2 mg/mL each and then growing the cultures at 37° C. for 40 min to an $OD_{600}$ of ~0.6. The cultures were then placed on ice, washed twice with ice-cold, sterile ddH2O, resuspended in ~25 µL of ice-cold, sterile ddH2O, and electroporated with ~200 ng of the pUC origin cassette (1.8 kV, 5.8 ms, 0.1 cm cuvette, BioRad Micropulser). The cells were then recovered in SOC at 30° C. for 2 h, then plated on LB agar plates with 100 µg/mL ampicillin and incubated for 24 h at 37° C. The resulting ampicillin-resistant colonies should have the pUC origin inserted and were checked by verifying expected restriction digestion patterns. The colonies were grown in 25 mL LB containing 100 µg/mL ampicillin and the DNA was purified using the ZymoPURE II plasmid midiprep kit (Zymo Research) according to the manufacturer's instructions. The DNA was digested with PacI overnight at 37° C. in order to liberate and linearize the adenoviral genome. The linearized DNA was purified using the E.Z.N.A. cycle pure kit (Omega Bio-tek) according to the manufacturer's instructions.

The following modifications in TABLE 15 were made using primers in TABLE 14 to obtain the adenoviruses used in this work (TABLE 12).

TRE3G.AdProt Expression Vector:

A 641 bp fragment containing adenoviral protease (AdProt) was amplified from the Ad5 genome using the primers BamHI.AdProt F and SalI.AdProt R (TABLE 14) and ligated into pTRE-Tight (Clontech) using BamHI and SalI to make the pTRE-Tight.AdProt vector. The Ad5 Tripartite leader sequence (TPL) was amplified from the TPL gene block (TABLE 14) using the primers TPL.GA F and TPL.AdProt GA R (TABLE 14) and the pTRE-Tight.AdProt vector was amplified using the primers TRE.AdProt GA F and TRE.AdProt GA R (TABLE 14). The TPL and pTRE-Tight.AdProt amplicons were assembled using the HiFi DNA assembly kit (New England Biolabs) to create the pTRE-Tight.TPL.AdProt vector. TPL-prot was amplified from pTRE-Tight.TPL.AdProt using the primers TPL.AdProt GA F and TPL.AdProt GA R (TABLE 14) and assembled with NotI-digested pLVX.Tight.Puro (Takara Biosciences) using the HiFi DNA assembly kit to form pLVX.Tight.TPL.AdProt.Puro. A fragment containing TPL.AdProt was obtained from pLVX.Tight.TPL.AdProt.Puro by digestion with EcoRI and BamHI and ligated into the pLVX.TRE3G vector (Takara Bio) to create the pLVX.TRE3G.AdProt vector.

Figure 39A:
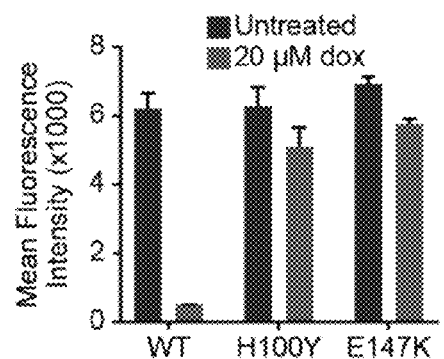
FIGS. 39A-39B. Reverse genetics to validate observed dox-resistant and CMV promoter mutants.
Figure 39B:
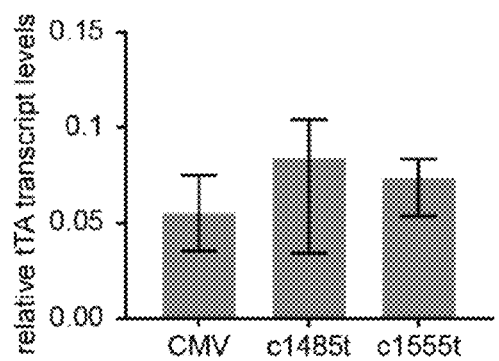

Tre3G.Egfp Vector:

A 762 bp fragment containing eGFP was amplified from the eGFP-N3 vector (Takara Bio) using the primers NotI.eGFP F and EcoRI.eGFP R (TABLE 14) and ligated into the pLVX-TRE3G vector (Takara Bio) using NotI and EcoRI to create the pLVX-TRE3G.eGFP vector.

tTA variant vectors:

A 743 bp fragment containing mCherry was amplified from a pcDNA3.1-mCherry template plasmid using the primers NotI.mCherry F and XhoI.mCherry R (TABLE 14) and inserted into the pBudCE4.1 vector (Thermo Fisher) using NotI and XhoI to create the pBud.mCherry vector. A 771 bp fragment containing tTA was amplified from a tTA.mCherry adenoviral vector using the primers SalI.TTA F and BamHI.TTA R (TABLE 14) and inserted into the pBud.mCherry vector using BamHI and SalI to create the pBud.tTA.mCherry vector. Site-directed mutagenesis was then performed on pBud.tTA.mCherry using a QuickChange II XL Site-Directed Mutagenesis Kit (Agilent) to generate the indicated point mutations in tTA, and CMV (FIGS. 39A-39B).

AdProt.Flag Vector:

From the pTRE-Tight.TPL.AdProt vector, an 852 bp fragment containing TPL.AdProt was amplified using primers NotI.TPL F and XbaI.AdProt.R (TABLE 14) and inserted into the pENTR1A vector using NotI and XbaI to form pENTR1A.TPL.AdProt. A FLAG epitope tag was inserted into pENTR1A.TPL.AdProt using primers pENTR1A.AdProt.FLAG F and pENTR1A.AdProt.FLAG R (TABLE 14) and using the QuickChange II XL Site-Directed Mutagenesis Kit to form pENTR1A.TPL.AdProt.FLAG.

This vector was then recombined with pcDNA-DEST40 using LR Clonase II Enzyme Master Mix to form pcDNA.TPL.AdProt.FLAG.

(LoxP)$_2$Term.AProt Vector:

A vector containing an SV40-polyA terminator flanked by two loxP sites was purchased from GeneArt (ThermoFisher). From this vector, a 370 bp fragment containing the floxed SV40-terminator signal was amplified using primers LoxP2Term GA F and LoxP2Term GA R (TABLE 14). The pENTR1A.TPL.AdProt.FLAG vector was linearized using pENT.AdProt GA F and pENT.AdProt GA R (TABLE 14). The two amplicons were assembled to form pENTR1A. (LoxP)$_2$Term.TPL.AdProt.FLAG using the NEB HiFi DNA assembly kit. This vector was then recombined with pcDNA-DEST40 using LR Clonase II Enzyme Master Mix to form pcDNA.(LoxP)2Term.TPL.AdProt.FLAG.

AdProt(STOP) Vector:

pENTR1A.TPL.AdProt.FLAG was mutagenized using primers L8.STOP F and L8.Stop R (TABLE 14) to form pENTR1A.TPL.AdProt(STOP).FLAG using the QuickChange II XL Site-Directed Mutagenesis Kit. This vector was then recombined with pcDNA-DEST40 using LR Clonase II Enzyme Master Mix to form pcDNA. TPL.AdProt (STOP). FLAG.

pLeu-tRNA.LeuRS Vector: A 2607 bp Fragment Containing LeuRS, the E. coli Leucyl-tRNA synthetase, was amplified from DH10B E. coli genomic DNA using the primers HindIII.LeuRS.F and XhoI.LeuRS.R (TABLE 14) and inserted into pANAP (Chatterjee A. et al., J. Am. Chem. Soc., 135, 12540-12543 (2013)) using HindIII and XhoI to create the pLeu-tRNA.LeuRS vector.

pLeu-tRNA.GFP(STOP) Vector:

Site-directed mutagenesis was performed on the pcDNA3.1-CMV.GFP plasmid using a QuickChange II XL Site-Directed Mutagenesis Kit (Agilent) and the primers Tyr40TAG.Forward and Tyr40TAG.Reverse (TABLE 14) to introduce a premature stop codon at position 40 in eGFP. Then a 750 bp fragment containing eGFP(STOP) was amplified from the site-directed mutagenesis product using the primers HindIII.eGFP.Forward and XhoI.eGFP.Reverse (TABLE 14) and inserted into pANAP (Chatterjee A. et al., J. Am. Chem. Soc., 135, 12540-12543 (2013)) using HindIII and XhoI to create the pLeu-tRNA.GFP(STOP) vector.

Cell Culture and Lentivirus Transduction:

Cell Culture:

All cells were cultured at 37° C. and 5% $CO_2$. All cell lines were derived from a parent HEK293A cell line (ATCC) and cultured in Dulbecco's modified Eagle's medium (DMEM; Cellgro) supplemented with 10% fetal bovine serum (FBS; Cellgro), 1% penicillin-streptomycin (Cellgro), and 1% L-glutamine (Cellgro). Cell lines that constitutively express AdProt were cultured in 50 µg/mL Hygromycin B (Thermo Fisher), and cell lines that inducibly express AdProt or GFP were cultured in 1 µg/mL puromycin (Corning) to stably maintain transgenes. The producer cell line that expressed AdProt from both constitutive and inducible promoters was cultured in both hygromycin and puromycin.

Generation of Cell Lines by Lentiviral Transduction:

In a typical protocol, ~9×10$^6$ 293FT cells were plated on a poly-D-lysine-coated 10 cm dish. The next day, the cells were co-transfected with plasmids from the previously described third-generation packaging system (Wang H. et al., Nucleic Acids Res. 42, e37 (2014)): 15 µg RRE, 6 µg REV, 3 µg VSVG, and 15 µg transfer vector using 60 µL Lipofectamine 2000 (Thermo Fisher). Cultures were maintained in 5 mL total volume of OPTI-MEM (Gibco) throughout the transfection. After 8 h, the media was exchanged for fresh DMEM. After 48 h, media was harvested and centrifuged for 5 min at 162×g to clear the cell debris. The supernatant was used to transduce HEK293A cells supplemented with 4 µg/mL polybrene (Sigma). After 24 h, the media was exchanged for fresh DMEM. After 48 h, media was exchanged again for DMEM containing 50 µg/mL hygromycin to select stable cell lines (as indicated above).

RT-qPCR:

cDNA was made from 1 µg of purified RNA using the High Capacity cDNA Reverse Transcription Kit (Applied Biosystems). qPCR was run for AdProt (primers: AdProt L and AdProt R) and housekeeping gene RPLP2 (primers: RPLP2 F and RPLP2 R) (TABLE 14) on a LightCycler 480 II (Roche) to confirm expression.

Generating Adenovirus from Transfection:

All adenoviruses were produced by transfecting a PacI-linearized vector into appropriate trans-complementing HEK293A cells. Briefly, 24 µg of PacI-digested adenovirus vectors transfected with 144 µL PEI, 1 mL OptiMEM (Gibco) into a 15 cm plate of the corresponding cell line (10 million cells). Media was replaced 8 h after transfection. Media was then intermittently replaced every 2-3 days until plaques were observed (typically ~3 weeks). Once plaques were observed, cytopathic effect (CPE) was observed in all cells within 5 d. Upon complete CPE, the cells and media were harvested, and then frozen at −80° C. for at least 30 min and then thawed at 37° C. for 15 min for three total freeze/thaw cycles. The cell debris was removed by centrifugation at >1,462×g for 15 min and the supernatant was moved to a new Eppendorf tube and stored at −80° C. until use.

Determining Adenoviral Titer by Flow Cytometry:

Adenoviral titers were determined through flow cytometry. Known volumes of AdPol- and AdProt-deleted viral supernatants were added to AdPol-expressing HEK293A cells. 2-3 days post-infection, cells were washed once with media, stained with 0.2 µg/mL DAPI, and then analyzed on a BD LSR II Analyzer for fluorescent protein expression. Infectious titers were determined by measuring the percentage of cells infected by a known volume of virus. To minimize counting cells that were infected by more than one virus and to minimize any background fluorescence, data were only considered if they fell within the linear range, which typically encompassed samples where 1-10% of cells were infected.

Competition Experiments:

A confluent dish of TRE3G.AdProt cells (~15 million cells) (TABLE 13) was infected with either a 1:100 or 1:1000 mixture of $tTA_{wt}$:$tTA_{mut}$ adenovirus (multiplicity of infection~0.25) (TABLE 12). Plates were monitored for the appearance of spreading infection (defined by fluorescent "comets" or plaques) every 24 h. One day after the observation of spreading infection, 1 mL of media was immediately transferred to a fresh, semiconfluent dish (~5 million cells) of selector cells, and 2 mL of media was stored at −80° C. for later analysis. After three passages, viral populations from each passage were analyzed by flow cytometry.

Doxycycline Dose Response:

A semi-confluent dish of TRE3G.AdProt cells (~160,000 cells) (TABLE 13) was infected with $tTA_{wt}$. mCherry adenovirus (multiplicity of infection ~2.5) (TABLE 12). After 3 h, the cells were washed twice, and fresh tet-approved media (Takara Bio) supplemented with various concentrations of dox was added. 5 days later, the virus lysates were harvested and viral titers were analyzed by flow cytometry.

AdProt Inhibitor Experiments:

The AdProt inhibitor was synthesized as described (Grosche P. et al., Bioorg. Med. Chem. Lett., 25(3):p. 438-43 (2015)).

To test the ability of the AdProt inhibitor to inhibit adenoviral replication, a confluent 6-well plate of HEK293A cells (~10$^6$ cells) was infected with Ad5.GFP (MOI~1) (TABLE 12), and various concentrations of the AdProt inhibitor were added. After 48 h, viral supernatants were harvested and titered by flow cytometry, as described above.

To test the combined effects of the AdProt inhibitor in the context of the tTA genetic circuit, a confluent 12-well plate of TRE3G.AdProt cells (~400,00 cells) (TABLE 13) was infected with $tTA_{wt}$.mCherry adenovirus (multiplicity of infection~5) (TABLE 12). After 4 h, the cells were washed, and the adenoviral protease inhibitor was added at the indicated concentrations (0 µM, 1 µM, 20 µM) in the absence or presence of 2 nM dox. After 6 d, media and cells were harvested with three freeze/thaw cycles as described above. Harvested viral samples were titered by flow cytometry.

Continuous Evolution Workflow:

Before initiating directed evolution, 500 µL of the $tTA_{wt}$.mCherry adenovirus (TABLE 12) was amplified on a 10 cm semi-confluent dish of mutator cells (TABLE 13), creating a diverse viral population. After 5 days, cytopathic effect was observed in all cells. This amplified virus was harvested with three freeze/thaw cycles as described above. Three 15 cm, semi-confluent dishes of TRE3G.AdProt cells (~5 million cells) were infected with either 250, 500, or 1,000 µL of the amplified virus in the presence of dox. Plates were monitored for plaques every day. If more than one plate displayed a plaque on the same day, the plate with the lowest volume of virus added was used for the next round of evolution. The day after a plaque was observed, three 15 cm semi-confluent dishes of TRE3G.AdProt cells were again infected in the presence of 1 ng/mL dox. The three dishes were infected with 250, 500, or 1,000 µL of viral supernatant from the previous round's dish. 2 mL of media were saved in Eppendorf tubes and stored at −80° C. for future analysis. In Trial 1, the concentration of dox was 2 nM for passages 1-6. At passage 7, the concentration of dox was increased to 200 nM. For passages 8-12, the concentration of dox was further increased to 20 μM. In Trial 2, the concentration of dox was held constant at 200 nM.

Analyzing Promoter Activity in Passaged Viral Supernatant:

TRE3G.GFP cells (TABLE 13) were plated in a 96-well plate at ~40,000 cells/well. The next day, 30 μL of passages 1-12 was used to infect two rows of the 96-well plate. Media was exchanged with or without 20 μM dox 5 h post-infection. 72 h post-infection, the cells were washed once with media, and stained with 0.2 μg/mL DAPI (Thermo Fisher). Cells were trypsinized and analyzed on a BD LSR II analyzer.

tTA Evolution Sequencing:

Using a viral DNA isolation kit (NucleoSpin Virus, Macherey-Nagel), DNA was harvested from 200 μL of the media that was saved after each round of evolution. A 1.75 kb region of DNA encompassing the CMV promoter and the tTA gene was PCR-amplified from 1 μL of the harvested DNA for 20 rounds of amplification using primers sequencing F and sequencing R (TABLE 14). The resulting PCR product was purified and prepared for Illumina sequencing via the Nextera DNA Library Prep protocol (Illumina). 250 base pair paired-end sequencing was run on a MiSeq (Illumina). Sequencing reads were aligned to the amplicon sequence, which was derived from the $tTA_{wt}$.mCherry adenovirus sequence, using bwa mem 0.7.12-r1039 [RRID: SCR 010910]. Allele pileups were generated using samtools v 0.1.5 mpileup [RRID:SCR_002105] with flags -d 10000000 -excl-flags 2052, and allele counts/frequencies were extracted (Li H. et al., Bioinformatics, 25, 2078-2079 (2009); Li H., Bioinformatics, 27, 2987-2993 (2011)). Each position within the tTA gene and CMV promoter had at least 1,000-fold coverage.

Reverse Genetics of tTA Variants:

HEK-293A cells were seeded in a 12-well plate (~400,000 cells/well). The next day, 0.2 μg of the pBud.tTA.mCherry vector was co-transfected with 1 μg of the pLVX-TRE3G.eGFP vector using 7.2 μL of polyethyleneimine (Polysciences) and 100 μL OPTI-MEM. 8 h post-transfection, media was exchanged and dox was added at 20 μM. 48 h post-transfection, samples were stained with 0.2 μg/mL DAPI, and analyzed on a BD LSR II analyzer.

Reverse Genetics of CMV Variants by RT-qPCR:

1 μg of pBud.tTA.mCherry was used to transfect HEK-293A cells seeded in a 12-well plate (~400,000 cells/well) in triplicate. cDNA preparation and RT-qPCR were run as described for tTA (primers: tTA F and tTA R), and mCherry (primers: mCherry F and mCherry R) (TABLE 14) to assess the relative transcript levels of tTA driven by CMV promoter mutants.

Selection Circuit Experiments:

HEK-293A cells expressing wild-type AdPol were plated in a 12-well plate (350,000 cells/well). The next day, each 1 μg circuit ((LoxP)$_2$Term.Prot, AdProt(STOP), or AdProt-.FLAG as a positive control was transfected into six wells of a 12-well with 6 μL PEI in 100 μL OPTI-MEM. For the AdProt(STOP) circuit, 0.5 mg was co-transfected with pLeu-tRNA.GFP(STOP). Media was changed 4 h post-transfection. The next day, transfected wells were infected with either the relevant BOI virus, or $TTA_{wt}$.mCherry as a negative control at MOI=5. Cells were washed 3× with media 3 h post-infection. The infections were harvested four days later, and titered following the protocol below.

TABLE 12

Adenoviruses constructed and used in this study.

| Name | Modifications relative to wild-type Ad5 |
|---|---|
| Ad5.CFP | E1R-CFP ΔE1 ΔE3 |
| CFP.ΔAdPol.GFP | E1R-CFP ΔE1 ΔE3 ΔAdPol E4R-GFP |
| $tTA_{wt}$.mCherry | E1L-tTA ΔE1 ΔE3 ΔAdProt ΔAdPol E4R-mCherry |
| $tTA_{mut}$.GFP | E1L-tTAaak ΔE1 ΔE3 ΔAdProt ΔAdPol E4R-GFP |
| Cre.Ad | E1L-Cre ΔE1 ΔE3 ΔAdProt ΔAdPol E4R-mCherry |
| LeuRS.Ad | E1L-LeuRS ΔE1 ΔE3 ΔAdProt ΔAdPol E4R-mCherry |
| AdEvolve-DEST | E1L-DEST ΔE1 ΔE3 ΔAdProt ΔAdPol E4R-mCherry |
| ΔAdProtΔAdPol-adenovirus | E1R-CFP ΔE1 ΔE3 ΔAdProt ΔAdPol |

Note:
All viruses used in this work were derived from Ad5.CFP (Genbank accession number: MH325112; SEQ ID NO: 97) except for Ad5.GFP.

TABLE 13

Cell lines used in this study.

| Cell line | Polymerase | Transgene cassette |
|---|---|---|
| Producer | Wild-type AdPol | CMV.AdProt/TRE3G.AdProt |
| Mutator | EP-Pol | CMV.AdProt |
| Selector | EP-Pol | TRE3G.AdProt |
| Phenotyping | AdPol | TRE3G.eGFP |

Note:
All cell lines were derived from HEK293A cells except the 633 cell line, which was A549-derived.

TABLE 14

Primers employed. The following primers were used to construct expression, adenoviral, and lentiviral plasmids, and to run qPCR experiments.

| Name | Sequence - 5' to 3' | SEQ ID NO: |
|---|---|---|
| delAdPol ccdb F | TCCCGCGCTTCTTGGAACTTTACATTGTGGGCCACAACATCAACGGCCCTCCCTCATCAGTGCCAACATAGTAAG | 102 |
| delPol ccdb R | GGCACCTCGGAACGGTTGTTAATTACCTGGGCGGCGAGCACGATCTCGTCCCGCTCATTAGGCGGGC | 158 |
| delPol F | GCGCGGCCTTCCGGAGCGAGGTGTGGGTGAGCGCAAAGGTGTCCCTGACCATGACCAGCATGAAGGGCACGAGCTGCTTCCCAAAGGCCCCCATCCAAG | 159 |

TABLE 14-continued

Primers employed. The following primers were used to construct expression, adenoviral, and lentiviral plasmids, and to run qPCR experiments.

| Name | Sequence - 5' to 3' | SEQ ID NO: |
| --- | --- | --- |
| delPol R | CTTGGATGGGGGCCTTTGGGAAGCAGCTCGTGCCCTTCATGCTGGTCATGGTCAGGGACACCTTTGCGCTCACCCACACCTCGCTCCGGAAGGCCGCGC | 160 |
| delAdProt F | GGCAACGCCACAACATAAAGAAGCAAGCAACATCAACAACAGCTGCCGCCAAATAATGTACTAGAGACACTTTCAATAAAG-GCAAATGCTTTTATTTGTA | 124 |
| delAdProt R | TACAAATAAAAGCATTTGCCTTTATTGAAAGTGTCTCTAGTACATTATTTGGCGGCAGCTGTTGTTGATGTTGCTTGCTTCTTTATGTTGTGGCGTTGCC | 125 |
| E1.ccdb F | ATACAAAACTACATAAGACCCCCACCTTATATATTCTTTCCCACCCTTAACCCTCATCAGTGCCAACATAGTAAG | 161 |
| E1.ccdb R | AATAAGAGGAAGTGAAATCTGAATAATTTTGTGTTACTCATAGCGCGTAACCGCTCATTAGGCGGGC | 162 |
| E1.CMV F | ATACAAAACTACATAAGACCCCCACCTTATATATTCTTTCCCACCCTTAAGCCACGCCCACAGATATACGCGTTGACATTG | 163 |
| E1.BGHR R | AATAAGAGGAAGTGAAATCTGAATAATTTTGTGTTACTCATAGCGCGTAATAGAAGCCATAGAGCCCAC | 164 |
| E4.ccdb F | CAAAAAACCCACAACTTCCTCAAATCGTCACTTCCGTTTTCCCACGTTACCCCTCATCAGTGCCAACATAGTAAG | 165 |
| E4.ccdb R | AGTAACTTGTATGTGTTGGGAATTGTAGTTTTCTTAAAATGGGAAGTGACCCGCTCATTAGGCGGGC | 166 |
| E4.SV40P F | CAAAAAACCCACAACTTCCTCAAATCGTCACTTCCGTTTTCCCACGTTACTTCTGTGGAATGTGTGTCAGTTAGGG | 167 |
| E4.SV40pA R | AGTAACTTGTATGTGTTGGGAATTGTAGTTTTCTTAAAATGGGAAGTGACCTCTAGCTAGAGGTCGACGGTATAC | 168 |
| Cre.ccdB F | TGGAACTAATCATATGTGGCCTGGAGAAACAGCTAAAGTGCGAAAGCGGCCCGCTCATTAGGCGGGC | 169 |
| Cre.ccdB R | CGCGAACAAATGTGGTATGGCTGATTATGATCCTCTAGAGATAATTCTAGCCCTCATCAGTGCCAACATAGTAAG | 170 |
| Cre F | TGGCTAGCGTTTAAACTTAAGCTTGGTACCCCTCCGCGGGGATCCTCTAGGCCACCATGCCCAAGAAGAAGAGGAAG | 171 |
| Cre R | CGCGAACAAATGTGGTATGGCTGATTATGATCCTCTAGAGATAATTCTAGCTAATCGCCATCTTCCAGCAGG | 172 |
| BAC2pUC F | CCCGGGAATTCGGATCTGC | 130 |
| BAC2pUC R | CCGGGAATTCGGATCCTTGAAGAC | 131 |
| BamHI.AdProt F | AAAAAAGGATCCACCATGGGCTCCAGTGAG | 146 |
| SalI.AdProt R | AAAAAGTCGACTTACATGTTTTTCAAGTGACAAAAAGAAG | 147 |
| TPL Gene Block | AAAAAAGAATTCACTCTCTTCCGCATCGCTGTCTGCGAGGGCCAGCTGTTGGGCTCGCGGTTGAGGACAAACTCTTCGCGGTCTTTCCAGTACTCTTGGATCGGAAACCCGTCGGCCTCCGAACAGGTACTCCGCCGCCGAGGGACCTGAGCGAGTCCGCATCGACCGGATCGGAAAACCTCTCGAGAAAGGCGTCTAACCAGTCACAGTCGCAGGATCCTTTTTT | 43 |
| TPL. GA F | ATCGCCTGGAGAATTCACTCTCTTCCGCATCGCT | 140 |
| TPL.AdProt GA R | ATCTAGAGCCGGCGCTTACATGTTTTTCAAGTGACAAAAAGAAG | 148 |
| TRE.AdProt GA F | ATGGGCTCCAGTGAGCAG | 149 |
| TRE.AdProt GA R | GAATTCTCCAGGCGATCTG | 150 |

TABLE 14-continued

Primers employed. The following primers were used to construct expression, adenoviral, and lentiviral plasmids, and to run qPCR experiments.

| Name | Sequence - 5' to 3' | SEQ ID NO: |
| --- | --- | --- |
| TPL.AdProt GA F | TGGAGAAGGATCCGCACTCTCTTCCGCATCGCT | 173 |
| NotI.eGFP F | AAAAAAAGCGGCCGCCGCCACCATGGTGAG | 174 |
| EcoRI.eGFP R | AAAAAAGAATTCCGGCCGCTTTACTTGTAC | 175 |
| NotI.mCherry F | AAAAAAGCGGCCGCGCACCATGGTGAGCAAG | 176 |
| XhoI.mCherry R | AAAAAACTCGAGACTACTTGTACAGCTCGTCCATG | 177 |
| SalI.TTA F | AAAAAAGTCGACATGTCTAGACTGGACAAGAGCAAAG | 178 |
| BamHI.TTA R | AAAAAAGGATCCTTACCCGGGGAGCATGTCAAGG | 179 |
| NotI.TPL F | AAAAAAGCGGCCGCACTCTCTTCCGCATCG | 144 |
| XbaI.AdProt R | AAAAAATCTAGATTACATGTTTTTCAAGTGACAAAAAGAAG | 180 |
| pENTR1A.Ad Prot FLAG F | TAATCTAGACCCAGCTTTCTTGTACAAAGTTGGCATTATAAG | 181 |
| pENTR1A.Ad Prot FLAG R | AGAAAGCTGGGTCTAGATTACTTATCGTCGTCATCCTTGTAATCCATGTT TTTCAAGTGACAAAAAGAAGTGGCG | 182 |
| LoxP2Term GA F | AGTCGACTGGATCCGGTACCGCCGCATCAACGAGCTC | 183 |
| LoxP2Term GA R | GAGAGTGCGGCCGCGAATTCGAGGCCCAGAGGGTACC | 184 |
| pENT.AdProt GA F | GAATTCGCGGCCGCAC | 185 |
| pENT.AdProt GA R | GGTACCGGATCCAGTCGAC | 186 |
| L8.STOP F | CAGTGAGCAGGAATAGAAAGCCATTGTCAAAGATCTTGGTTGTGG | 187 |
| L8.STOP R | CTTTGACAATGGCTTTCTATTCCTGCTCACTGGAGCCCATTG | 188 |
| HindIII.LeuRS F | AAAAAAAAGCTTATGCAAGAGCAATACCGCCC | 189 |
| XhoI.LeuRS R | AAAAAACTCGAGTTAGCCAACGACCAGATTGAGGAG | 190 |
| Tyr40TAG F | AGGGCGATGCCACCTAGGGCAAGCTG | 191 |
| Tyr40TAG R | CAGCTTGCCCTAGGTGGCATCGCCCT | 192 |
| HindIII.eGFP F | AAAAAAAAGCTTGCCACCATGGTGAGCAAGG | 193 |
| XhoI.eGFP R | AAAAAACTCGAGTTACTTGTACAGCTCGTCCATGCC | 194 |
| AdProt L | GGGTACCCAACTCCATGCTC | 155 |
| AdProt R | AAGTGGCGCTCCTAATCTGC | 156 |
| tTA F | CTGGAGAACGCACTGTACGC | 195 |
| tTA R | GAAGTGGGGGCATAGAATCG | 196 |
| mCherry F | TCAAGCAGAGGCTGAAGCTG | 197 |
| mCherry R | TCGTTGTGGGAGGTGATGTC | 198 |
| RPLP2 F | CCATTCAGCTCACTGATAACCTTG | 157 |

TABLE 14-continued

Primers employed. The following primers were used to construct expression, adenoviral, and lentiviral plasmids, and to run qPCR experiments.

| Name | Sequence - 5' to 3' | SEQ ID NO: |
|---|---|---|
| RPLP2 R | CGTCGCCTCCTACCTGCT | 158 |
| Sequencing F | CTACATAAGACCCCCACCTTATATATTCTTTCC | 199 |
| Sequencing R | AGCGGGAAAACTGAATAAGAGGAAGTGAAATC | 200 |

TABLE 15

Modifications made to generate adenoviruses used in this study.

| Modification | Genotype | KanccdB cassette primers used with R6K-kan-ccdB template plasmid (unless stated otherwise) | Final targeting cassette oligos or primers and template (if applicable) | Purpose of modification |
|---|---|---|---|---|
| AdPol deletion | ΔAdPol | delPol ccdb F and delPol ccdb R | delPol F and delPol R | To prevent evolution of the adenoviral polymerase. The error-prone version was expressed in trans |
| AdProt deletion | ΔAdProt | delAdProt ccdb F and delAdProt ccdb R | delAdProt F and delAdProt R | Deletion to make selectable marker |
| tTA insertion | tTA | E1.ccdb F and E1.ccdb R | E1.CMV F and E1 BGHR | Insertion for directed evolution |
| Cre insertion | Cre | Cre.ccdB F and Cre.ccdB R | Cre F and Cre R | Insertion for genetic selection circuits |
| LeuRS insertion | LeuRS | E1.ccdb F and E1.ccdb R | E1.CMV.Promoter.Forward and E1.bGH.polyA.Reverse used to amplify from pLeu-tRNA.LeuRS | Insertion for genetic selection circuits |
| mCheriy insertion | mCherry | E4.ccdb F and E4.ccdb R | E4.SV40P F and E4.SV40pA R | Insertion for visualization of viral infection |
| GFP insertion | GFP | E4.ccdb F and E4.ccdb R | E4.SV40P F and E4.SV40pA R | Insertion for visualization of viral infection |
| Replacement of the low copy BAC origin with the high copy pUC origin | N/A | N/A, the replacement is a one-step recombineering since the origin switches from chloramphenicol to ampicillin resistant | BAC2pUC F and BAC2pUC R used to amplify the pUC origin from pAd/CMV/V5-DEST | High copy origin to allow for the preparation of concentrated, purified DNA for transfection and adenoviral production |

Example 18. Improving Production of ΔAdProtAΔPol.Adenoviruses

Researchers frequently turn to directed evolution to engineer biomolecules with novel or improved functions (Romero P. A. and Arnold F. H., Nat. Rev. Mol. Cell Biol. 10 (2009); Packer M. S. and Liu D. R., Nat. Rev. Genet. 16, 379-394 (2015); Shaner N. C. et al., Nat. Biotechnol. 22, 1567-1572 (2004); Gai S. A. and Wittrup K. D., Curr. Opin. Struct. Biol. 17, 467-473 (2007)). The integrated processes of mutagenesis, selection, and amplification of biomolecules of interest (BOIs) with tailored functions is most typically accomplished in the test tube, in bacteria, or in yeast (Giger L. et al., Nat. Chem. Biol., 9, 494-498 (2013); Branon, T. C. et al., Nat. Biotechnol. (2018)). While these methods are well-suited to evolve particular phenotypes, they often fail to produce biological activities that reliably function in the complex human cellular environment (Zetsche B. et al., Cell 163, 759-771 (2015); Peck S. H. et al., Chem. Biol. 18, 619-630 (2011)). Biological processes that are unique to human cells (e.g. exclusive signal transduction pathways, distinctive post-translational modifications, altered cellular trafficking) often negatively affect the outcome of BOI activities that were evolved in simpler systems, and shuttled into human systems. While there are a few methods for directed evolution directly in the human cellular environment, these approaches either require in vitro library generation, or rely on cellular somatic hypermutation followed by complicated and labor-intensive screening processes that have a high potential for false positives (Banaszynski L. A. et al., Cell 126, 995-1004 (2006); Wang L. and Tsien R. Y, Nat. Protoc., 1, 1346-1350 (2006); Wang L. et al., Proc. Natl. Acad. Sci. USA. 101(48): p. 16745-49 (2004); Hess G. T. et al., Nat. Methods 13, 1036-1042 (2016); Piatkevich K. D. et al., Nat. Chem. Biol. 14, 352-360 (2018)). New approaches are needed for directed evolution in human cells that minimize both the laborious nature of mutagenesis and screening, and the potential for false positives.

Towards this end, a new system for continuous directed evolution was created, based on the replication cycle of the human pathogen, adenovirus. In this approach, the replication of a highly mutagenic adenovirus was coupled to the activity of an evolving BOI encoded in the adenoviral genome. This approach relies on a trans-complementation system in which the adenoviral protease (AdProt) gene is deleted from the adenoviral genome, and its expression and/or function is coupled to BOI activity. The BOI is mutated through a similar trans-complementation system in which the adenoviral polymerase (AdPol) is deleted from the adenoviral genome, and an error-prone polymerase (EP-Pol) expressed via the human cellular host generates mutations during viral replication (Uil T. G. et al., Nucleic Acids Res., 39(5): e30 (2011)).

Figure 23:
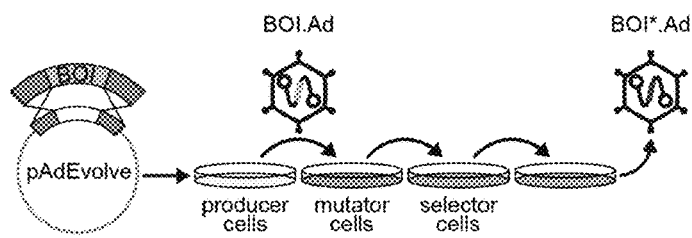
FIG. 23. The gene encoding a biomolecule of interest (BOI) is first inserted into pAdEvolve. "Producer" cells (see cell lines listed in TABLE 3) are used to generate ΔAdProtΔAdPol-adenoviruses carrying the BOI gene. If desired, the BOI gene can be mutated prior to selection by first passaging the adenovirus on a "mutator" cell line constitutively expressing EP-Pol. A "selector" cell line tailored to the activity of interest is generated by the researcher, followed by serial passaging of viral supernatants on the selector cells. Directed evolution is accomplished through serial passaging of viral supernatants on selector cells to evolve the BOI (BOI*).

A four-component system was envisioned for the adenovirus-mediated directed evolution process that includes an engineered adenoviral construct and three cell lines (FIG. 23). The engineered adenoviral genome, termed pAdEvolve contains the necessary deletions for both AdPol and AdProt to support mutagenesis and selection respectively (for a list of adenoviral constructs used in this study, see TABLE 12). All the researcher needs to do is recombine the gene encoding the target BOI into the plasmid at a region defined for robust expression (Suzuki M. et al., Gene Ther. 22, 421-429 (2015)). The linearized AdEvolve genome is transfected into a "producer" cell line that constitutively expresses both wild-type AdPol (wt-AdPol) and AdProt to generate nascent adenoviruses containing the necessary deletions, and the gene encoding the BOI (for a list of cell lines used in this study, see TABLE 13). Adenoviruses are then passaged on a "mutator" cell line prior to selection. Previous studies support the concept of generating a diverse library prior to imparting selection on an evolving BOI (Esvelt K. M. et al., Nature. 472(7344): p. 499-503 (2011)). The mutator cell line accomplishes this by constitutively expressing both the mutagenic EP-Pol and the AdProt selection gene. Finally, viruses are serially passaged on a user-generated "selector" cell line. This cell line couples expression and/or function of AdProt to the desired function of the evolving BOI. The selector cell line also expresses EP-Pol to simultaneously mutate the BOI throughout the selection process. The cell line construction allows the researcher to evolve BOIs in a near continuous process by simply passaging the AdEvolve virus on the selector cells.

The directed evolution protocol was then tested using a simple, highly evolvable model BOI. Transcription factors exhibit a high degree of evolvability as their target function can trivially be coupled to expression of a selectable marker (Dougherty M. J. and Arnold F. H., Curr. Opin. Biotechnol., 20, 486-491 (2009)). One class of transcription factors has a two-domain architecture: a DNA binding domain (DBD) that binds to a target operator in close proximity to the open reading frame (ORF), and a transcriptional activation domain (TAD) that recruits the transcriptional machinery such as RNA Pol II to the site of transcription (Ptashne M. and Gann A., Nature, 386, 569-577 (1997)). Frequently, these transcription factors also have a domain that binds a ligand to regulate gene expression in response to environmental conditions. Each of these components can be altered to affect function. The DBD can be evolved to recognize an altered promoter sequence, the TAD can be evolved for improved activity, and the regulatory region can be evolved to respond to other ligands (Hubbard B. P. et al., Nat. Methods. 12, 939-942 (2015); Buskirk A. R. et al., Chem. Biol., 10, 533-540 (2003); Collins C. H. et al., Nat. Biotechnol., 24, 708-712 (2006)). Furthermore, the domain architecture can be split into its individual components and used to evolve protein-protein interactions (PPIs) via N-hybrid systems (Vidal M. and Legrain P., Nucleic Acids Res., 27, 919-929 (1999)).

Based on these parameters, experiments were designed to evolve an engineered transcription factor that is frequently used for inducible gene expression in mammalian cells, termed the tetracycline-dependent transcriptional activator (tTA) (Gossen M. and Bujard H., Proc. Natl. Acad. Sci. USA 89(12): p. 5547-51 (1992)). tTA is a fusion between two proteins: the bacterial tet repressor (tetR), and 3 copies of the VP16 transactivation domain (VP48). TetR acts as a homodimer, binding to a palindromic operator repeat sequence within TRE, and binding doxycycline (dox) within its regulatory core at the homodimer interface (Ramos J. L. et al., Microbiol. Mol. Biol. Rev., 69, 326-356 (2005)). VP16 consists of a 12-amino acid minimal transcriptional activation domain derived from the herpes simplex virus transcription factor by the same name (Hirai H. et al., Int. J. Dev. Biol., 54, 1589-1596 (2010)). In the absence of its small molecule regulator, (dox, tTA binds to its target operator, the tet-responsive element (TRE) to induce transcription of downstream genes. However, in the presence of dox, tTA is unable to bind to TRE, and gene expression is turned off. In this manner, researchers can use tTA and dox to inducibly regulate the level of gene expression in mammalian cells.

tTA was chosen as a BOI for pilot directed evolution studies owing to its reliability as an inducible transcription system, the absence of homologs in eukaryotic systems, and the strong literature precedent for evolvability. As a bacterial promoter system that evolved as an antibiotic resistance mechanism, integration of the tTA system in human cells should reduce pleiotropic effects that could have unintended effects on selection. The tTA system has been employed numerous times to evolve or report on a multitude of activities included altered DNA binding specificity, resistance to dox, altered small molecule specificity, and PPIs via two-hybrid assays (Krueger M. et al., Gene 404, 93-100 (2007); Hecht B. et al., 1993. 175(4): p. 1206-10 (1993); Krueger C. et al., Gene, 331, 125-131 (2004); Moncivais K. and Zhang Z. J., Methods Mol. Biol., 812, 259-273 (2012)). tTA has even been evolved by viral replication in mammalian cells, although this was only done to improve the overall activity in the context of HIV replication (Das A. T. et al., J. Biol. Chem. 279(18): p. 18776-82 (2004)). These diverse directed evolution experiments gave us confidence that tTA could serve as a highly evolvable model protein in our adenovirus-mediated directed evolution system.

Here, the development of a transcriptional circuit that allows adenovirus to replicate dependent on tTA-induced expression of AdProt is outlined. The selectability of this circuit was characterized through viral competition experiments, which demonstrated that one can evolve genes using adenovirus by evolving dox resistance in tTA. Finally, the selection scheme was extended beyond transcriptional activation, demonstrating that the system can be used to evolve BOIs with a diverse array of functions.

Improved production of ΔAdProtAΔPol.adenoviruses was first sought by further modifying the previously designed constitutive AdPol/AdProt producer cells (see above for construction and characterization of this cell line). Previous studies suggested that ectopic AdProt expression can enhance the cytopathic effect, and possibly reduce viral titers (Massie B. and Oualikene W., U.S. Pat. No. 6,291, 226B1 (2001)). Researchers have shown that using a tTA-inducible system to limit AdProt expression only to periods of viral production can mitigate the toxic effects of AdProt.

While no toxicity associated with the CMV promoter-driven AdProt-expressing cell line was observed, it was surmised that one could further improve viral production by adding tTA-inducible AdProt expression to constitutive AdProt expression. AdProt/AdPol expression cells were stably transduced with lentivirus containing an inducible AdProt cassette (TRE3G.AdProt) to make a new cell line termed AdProt-constitutive/inducible, henceforth called "producer cells" (TABLE 13). Interestingly, in the absence of tTA, there is a drop in AdProt expression, while in the presence of tTA, AdProt levels increase (FIG. 35) (Loew R. et al., BMC Biotechnol. 10, 81 (2010)). Furthermore, the producer cells were able to reliably produce and propagate ΔAdProtΔAdPol adenoviruses.

Example 19. Preparation of Components for Directed Evolution of tTA

There are two primary components necessary for directed evolution of the tet-transactivator protein: a tTA-carrying adenovirus, and a cell line that induces AdProt under control of a tet-responsive promoter. A tTA expression cassette was recombineered into the E1L region of the ΔAdProtΔAdPol adenoviral genome (TABLE 12) (Suzuki M. et al., Gene Ther. 22, 421-429 (2015)).

Figure 35:
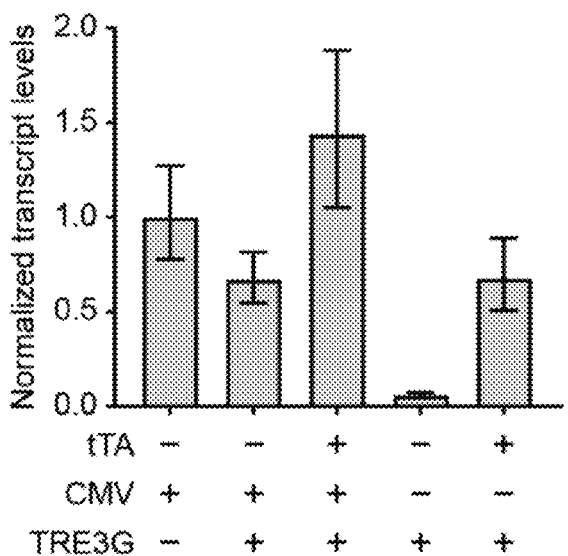
FIG. 35. qPCR data of AdaProt-expressing cell lines. Cell lines are labeled by the promoter driving AdProt expression (either CMV for constitutive expression or TRE3G for inducible expression). Inducible samples were also transiently transfected with a tTA-expressing vector to test the inducibility of the cell line. All samples were normalized to the CMV.AdProt cell line.

Next, experiments were designed to generate a "selector" cell line that could selectively enrich for tTA-active adenoviruses. An EP-Pol expressing cell line was stably transduced with TRE3G.AdProt lentivirus. Subsequently, these cell lines were transiently transfected with plasmids expressing tTA. It was found through RT-qPCR that tTA induced >10-fold higher expression of AdProt compared to untransfected control samples. (FIG. 35). This experiment also showed that AdProt was expressed even in the absence of tTA, although the protein levels could not be evaluated owing to the lack of an antibody against AdProt.

Example 20. Enrichment of Active BOI Variants in a tTA Transcriptional Circuit To examine whether the TRE3G.AdProt cell line could be used to enrich for viruses containing positive variants from a large pool of negative variants, a competition experiment was performed using the tTA system. Wild-type tTA ($tTA_{wt}$), binds its wild-type target operator, with a consensus sequence of CCTATCAGTGATAGA (SEQ ID NO: 209), to induce target gene transcription. A tetR variant that is incapable of binding to wild-type operators has been reported, instead possessing an enhanced affinity for the mutant CCcgTCAGTGAcgGA operator (SEQ ID NO: 210) (Krueger M. et al., Gene 404, 93-100 (2007)). Because tTA is simply a fusion between tetR and a VP48 trans-activation domain, it was hypothesized that a tTA variant based off the mutant tetR (termed $tTA_{mut}$) would exhibit the same altered DNA binding specificity. ΔAdProtΔAdPol-adenoviruses were engineered that expressed either $tTA_{wt}$ and mCherry ($tTA_{wt}$.mCherry) or $tTA_{mut}$ and GFP ($tTA_{mut}$.GFP) using different fluorescent markers to observe populations of viruses in infected cells by flow cytometry (FIG. 21A, TABLE 12).

Figure 26:
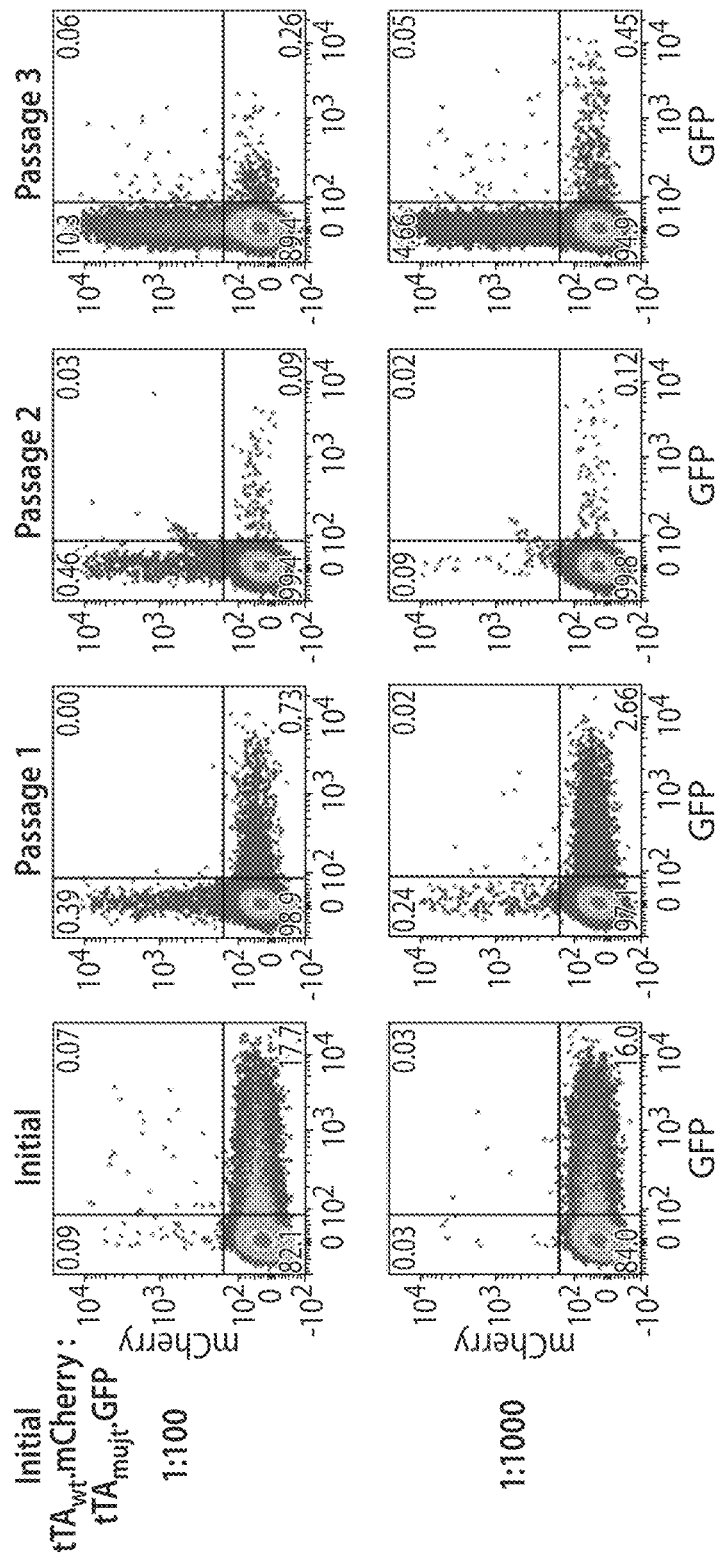
FIG. 26. Flow cytometry data showing infection with mixed samples of tTA$_{wt}$.mCherry adenoviruses and tTA$_{mut}$.GFP adenoviruses (TABLE 2) over three serial passages. Density plots show cells infected with tTA$_{wt}$.mCherry adenoviruses (Q1), tTA$_{mut}$.GFP adenoviruses (Q4), or both (Q3). Quantifications of each quadrant as a percentage of the total population are shown.
Figure 27:
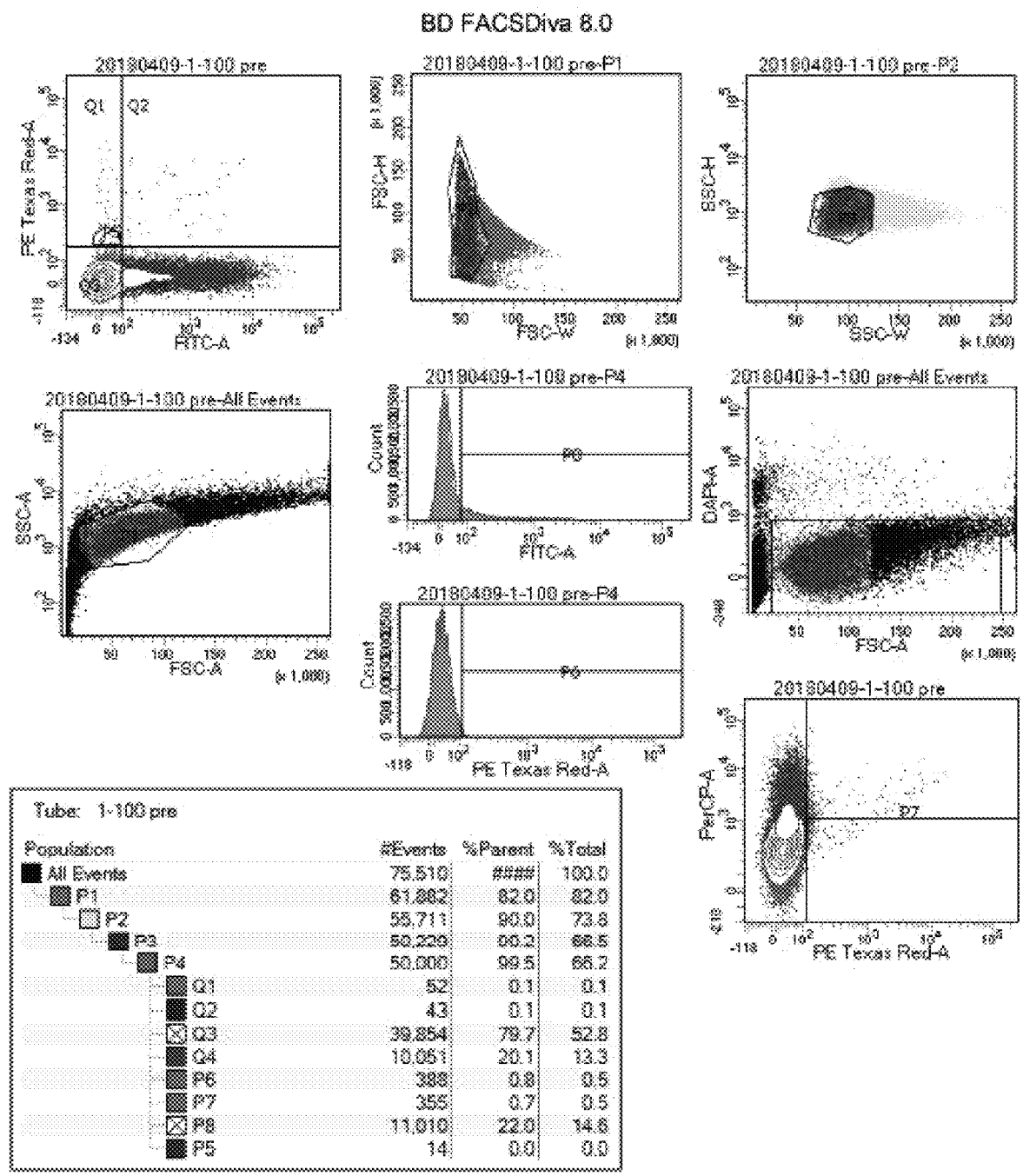
FIG. 27. Example raw flow cytometry data. Gates P1-P3 were used to eliminate cell debris and cell aggregates. Gate P4 was used to remove dead cells by only gating for DAPI-negative cells. Gates Q1-Q4 were used to gate for GFP-positive and mCherry-positive cells. This specific data set was used to calculate the initial ratio of tTA$_{wt}$.mCherry virus to tTA$_{mut}$.GFP virus in the competition experiment (FIG. 20A and FIG. 26).

To test the hypothesis that AdProt induction could enable enrichment of active over inactive BOI variants, $tTA_{wt}$.mCherry and $tTA_{mut}$.GFP at an MOI of ~0.25 were co-infected in selector cells (TABLE 13) at initial ratios of 1:100 or 1:1,000 (FIG. 21A). Three serial passages were then performed on selector cells, and the resulting viral populations were analyzed via infection of AdPol-expressing but AdProt-lacking HEK293A cells followed by flow cytometry (FIG. 26). In the initial passage, the $tTA_{wt}$.mCherry adenovirus enriched at least 40-50-fold over the $tTA_{mut}$.GFP adenovirus (FIG. 21B). Furthermore, across three rounds of passaging, the $tTA_{wt}$.mCherry adenoviruses were consistently enriched to >90% of the adenoviral population regardless of the starting ratios. Thus, the AdProt-based selection strategy can rapidly enrich active BOIs that are initially present at low frequency in a viral population.

Figure 36:
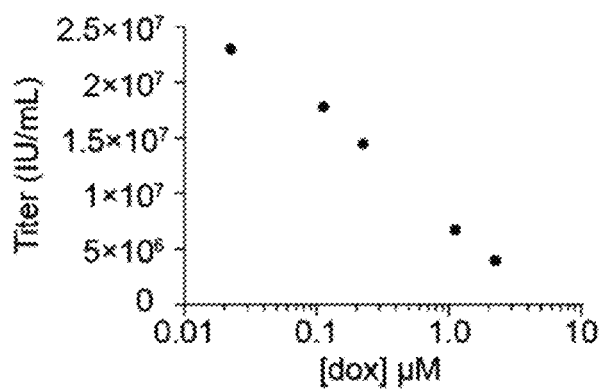
FIG. 36. Dose response of tTA-mCherry titer when treated with doxycycline. TTA$_{wt}$.mCherry adenovirus displayed a linear reduction in infectivity in response to dox treatment in TRE3G.AdProt cells. Titer is given in "infectious units per mL" (IU/mL), which is defined as the number of viruses per mL that are able to elicit a fluorescent signal in cells when analyzed by flow cytometry.

Example 21. Expanding the Dynamic Range of Selection Using a Selective Adenoviral Protease Inhibitor The dynamic range of selection pressure was next evaluated for AdProt. A large dynamic range, meaning that the quantity of AdProt produced scales with viral production, would be beneficial for the incremental evolution of BOI variants with increasing activity. The tTA-based genetic circuit was used to examine the dynamic range of AdProt selection through the application of the tTA allosteric inhibitor, dox. In the presence of dox, tTA is unable to bind its target operator and AdProt expression should be turned off. A synchronous infection was performed with tTA-ΔAdProtΔAdPol adenovirus on TRE3G.AdProt cells, and dox was added at various concentrations. The viral titers were then analyzed by flow cytometry analysis of mCherry, which was expressed from the viral genome (FIG. 36). It was found that dox was able to modulate adenoviral titers by ~10-fold in the context of a synchronous infection. It was also found that the linear range of dox spanned two orders of magnitude, indicating that one could potentially tune selection pressure relative to the observed viral infectivity by simply adding more dox.

Figure 37A:
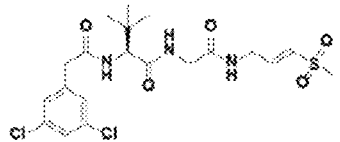
FIGS. 37A-37C. Adenovirus protease inhibitor.
Figure 37B:
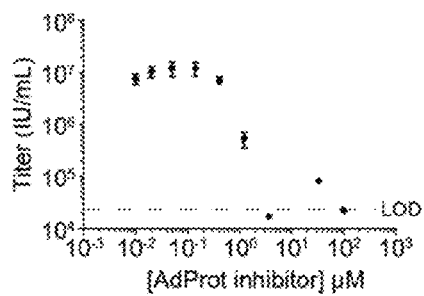

While an order of magnitude difference in infectivity provides some dynamic range for selecting improved BOI activity, an improvement of 2-3 orders of magnitude dynamic range would be beneficial. Enzymes like AdProt provide a significant advantage as selection markers in this regard, owing to the potential of small molecule inhibitors administered at defined concentrations to provide an expanded dose-response regime. A small molecule inhibitor could also provide a way to dynamically tune selection pressure from low to high levels throughout a directed evolution experiment. We synthesized a previously reported vinyl sulfone inhibitor that was shown to be selective for AdProt in vitro when compared to a panel of human cathepsins (FIG. 37A) (Grosche P. et al., Bioorg. Med. Chem. Lett., 25(3):p. 438-43 (2015)). The ability of the vinyl sulfone inhibitor to inhibit adenoviral replication was next assessed. A synchronous infection on HEK293 cells was performed with an adenovirus that contained both AdPol and AdProt, and the infections were treated with various concentrations of the inhibitor (TABLE 12). The resulting viral lysate was harvested, and the virus was titered by flow cytometry (FIG. 37B). It was found that the vinyl sulfone compound drastically reduced adenoviral replication, and inhibitory concentrations were in agreement with values previously reported in the literature (EC50=5-14 μM). Furthermore, the range of inhibitory concentrations spanned almost two orders of magnitude, indicating that we could potentially tune the concentration of the inhibitor to match the desired strength of selection.

Figure 37C:
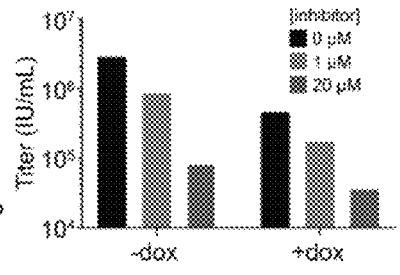

The ability of the vinyl sulfone inhibitor to inhibit adenoviral replication was next tested in the context of the tTA transcriptional circuit. Indeed, when $tTA_{wt}$.mCherry-expressing adenoviruses were challenged with various concentrations of the vinyl sulfone AdProt inhibitor, it was found that the inhibitor reduced the infectious titer of the $tTA_{wt}$.mCherry virus >600-fold, providing ready access to the desired 2-3 orders magnitude dynamic range. Notably, the AdProt inhibitor even further reduced infectious titer in the presence of dox, further increasing the accessible dynamic range for this particular experiment through a combination of regulated AdProt expression and direct AdProt inhibition (FIG. 37C).

Example 22. Proof-of Concept Directed Evolution of Functional tTA Variants that Acquire Doxycycline Resistance To demonstrate the viability of this approach to evolve biomolecules in human cells, a simple directed evolution experiment was designed that both demonstrated the various components of the system. We specifically aimed to evolve tTA variants that retain transcription-inducing activity but gain resistance to their small molecule inhibitor, dox. Previously, noninducible variants of TetR were screened by saturation mutagenesis, and 93 different mutants were characterized, indicating a high likelihood of finding at least one dox-resistant variant if our selection was sufficiently strong (Hecht B. et al., 1993. 175(4): p. 1206-10 (1993)).

Prior to selection, the $tTA_{wt}$.mCherry virus was first passaged on "mutator" cells that constitutively expressed both EP-Pol and AdProt in order to generate an initial pool of diversity in the viral population (TABLE 13). To evolve dox resistance in tTA, the $tTA_{wt}$.mCherry virus was then serially passaged in the presence of dox in the "selector" cell line that constitutively expressed EP-Pol and AdProt was inducibly expressed under control of the tTA target operator (FIG. 22A). A low initial MOI (~0.05) was maintained during the directed evolution experiment to minimize the probability that viruses encoding distinctive tTA mutants co-infect the same cell. Viral supernatant was transferred to fresh cell plates upon the first appearance of spreading infection to select for viruses that encode the dox-resistant tTA variants.

Two evolution experiments were run in parallel (Trials 1 and 2) with different selection pressure strategies (FIG. 22A). In Trial 1, the selection pressure was tuned over time, increasing the dox concentration from 2 nM up to 20 µM. In Trial 2, selection pressure was kept constant by maintaining the dox concentration at 200 nM. To test whether dox-resistant tTA variants were enriched in the population, the viral media from each passage in Trial 1 was used to infect a "phenotyping" cell line containing GFP under control of the endogenous tTA operator (TABLE 13). The phenotyping cell line lacked AdProt, allowing the virus to infect the cells and induce GFP expression, but not to proliferate. GFP induction was measured by the viral population harvested after each serial passage in the presence of 20 µM dox in these cells using flow cytometry (FIG. 22B). Dox-resistant tTA activity emerged at passage 5, suggesting that dox-resistant variant(s) of tTA may have arisen and enriched in the viral population.

Figure 38A:
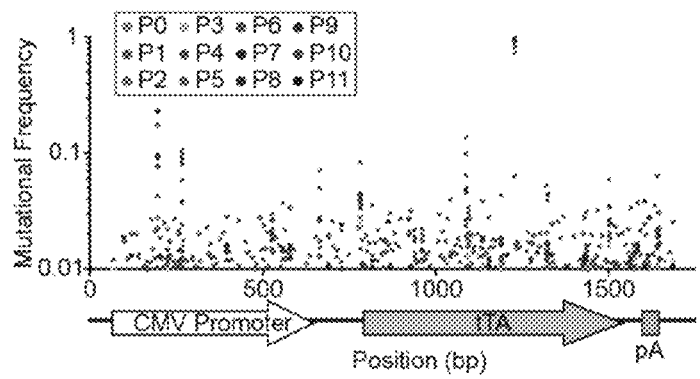
FIGS. 38A-38D. Deep sequencing of evolved viral populations.

Whether mutations in the tTA gene contributed to this decreased dox sensitivity was next examined. We amplified and sequenced a 1.75-kb region of the adenoviral genome containing the tTA open reading frame from virus harvested at each passage during both trials. Using this approach, >200 unique mutations were detected that attained ≥1% frequency by passage 4 in Trial 1, even though promoter activity at passage 4 was still undetectable (FIG. 38A). In Trial 2, 43 mutations attained ≥1% by passage 4 (FIG. 38C). By passage 5, a single amino acid substitution in tTA attained >70% frequency in the viral population in both trials (E147K in Trial 1 and H100Y in Trial 2). Both of these mutations became fully fixed in the population within 1-3 passages (FIGS. 38C-38D). Both mutations were previously reported to confer dox-resistance in tTA, which we further confirmed through transient co-transfection of a plasmid encoding eGFP under control of the endogenous tTA operator along with wild-type E147K, or H100Y tTA-encoding plasmids into HEK293A cells in the presence or absence of dox (FIGS. 39A-39B) (Hecht B. et al., 1993. 175(4): p. 1206-10 (1993)). Additional mutations that were previously reported to confer dox-resistance were also observed at >10% frequency at early passages in the directed evolution experiment (H100Y in Trial 1 and G102D in Trial 2).

Figure 38B:
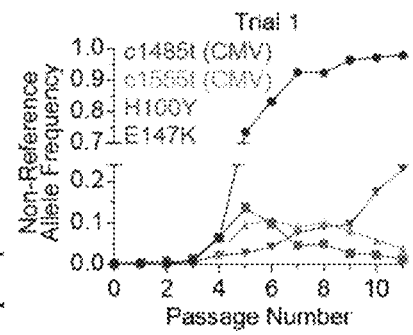
Figure 38C:
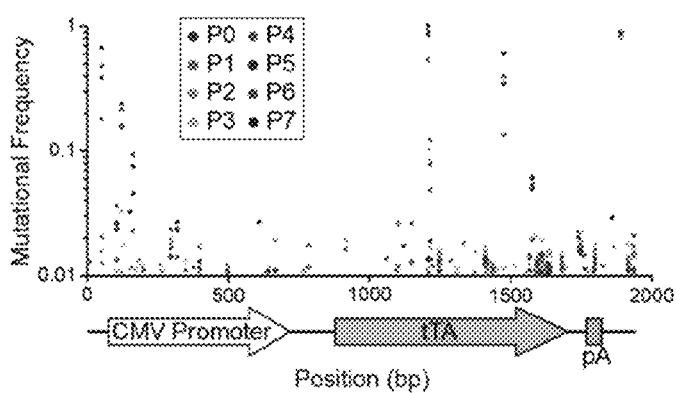
Figure 38D:
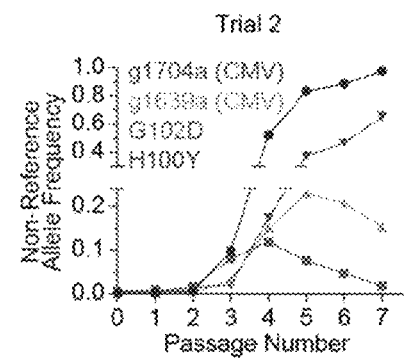

While Trial 1 appears to have significantly more mutations above 1% than Trial 2, most of these mutations occur in passage 4 (FIGS. 38A-38B). In Trial 1, while over 200 mutations were observed above 1% in passage 4, only 12 mutations were seen above 1% in passage 3, and only 21 mutations were seen above 1% in passage 5. These findings suggest that the observed increase may have been an experimental artifact resulting from PCR conditions during sample preparation.

Interestingly, Trial 2 appeared to enrich positive variants slightly faster than Trial 1. In Trial 2, the most prominent mutation, H100Y, reached 9% frequency by passage 3, while the most prominent mutation in Trial 1, E147K, did not begin to increase significantly until passage 4, where it reached 6% frequency (FIGS. 38C-38D). Between passages 3 and 4, both Trial 1 and Trial 2 were under constant selection pressure, suggesting that the higher concentration of dox in Trial 2 resulted in faster enrichment of dox resistant activity.

Enrichment of mutations were also observed in the CMV promoter region in both trials. We hypothesized that these mutations may have caused greater expression of tTA to induce higher concentrations of AdProt. c1485t and c1555t mutations were tested via reverse-transcription quantitative PCR (RT-qPCR) of tTA driven by CMV promoters carrying these mutations (FIGS. 39A-39B). However, we found no significant difference in CMV promoter activity.

Example 23. Generalizable Testing of Selection Circuits

Figure 40A:
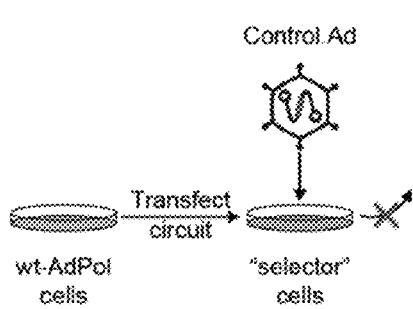
FIGS. 40A-40B. Generalized experiment to test diverse genetic selection circuits. A genetic circuit that places the AdProt gene under control of some BOI function is transfected into wild-type AdPol cells to form model "selector" cells.
Figure 40B:
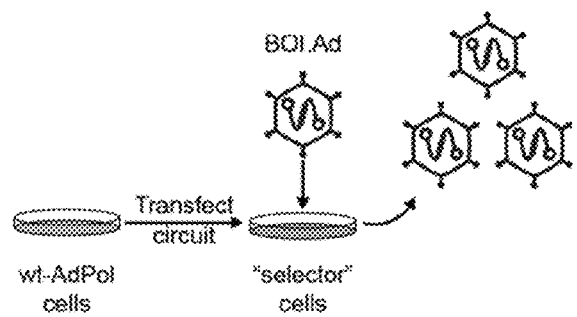

Through directed evolution of tTA, we were able to demonstrate how a selection circuit can be used to evolve a transcription factor in human cells. In the interest of extending the utility of the platform beyond directed evolution of transcription factors, we sought to demonstrate how alternative selection circuits could be used to evolve different types of functions. To evaluate these new circuits, a rapid functional test was created to analyze selection in a given circuit (FIGS. 40A-40B). In these experiments, AdProt is placed under control of a given BOI function and is transiently transfected into wild-type AdPol expressing cells to generate a model "selector" cell line. The next day, this selector cell line is infected with viruses that either carry a model BOI that can induce prot expression or activity, or a control virus that lacks the model BOI. After a few days, the adenoviruses are harvested, and the titers of the BOI-positive and BOI-negative viruses are compared. Two different types of selection circuits were used for model BOI activities: recombinase and amino-acyl-tRNA synthetase.

Recombinase Circuit:

Recombinases are frequently used to predictably modify plasmids and genomes through site-specific DNA recombination (Meinke G. et al., Chem. Rev., 116, 12785-12820 (2016)). They are highly desirable as directed evolution targets owing to their potential utility in genome editing (Gaj T. et al., Proc. Natl. Acad. Sci., 108, 498-503 (2011)). Cre recombinase is a tyrosine-type site-specific recombinase that recombines DNA at loxP recognition sites and is pervasively used in both molecular biology and genome editing (Sharan S. K. et al., Nat. Protoc., 4, 206-223 (2009); Parkitna J. R. et al., Methods Mol. Biol., 530, 325-342 (2009)). We chose to use Cre as a model BOI for a recombinase-based selection circuit.

Figure 41A:
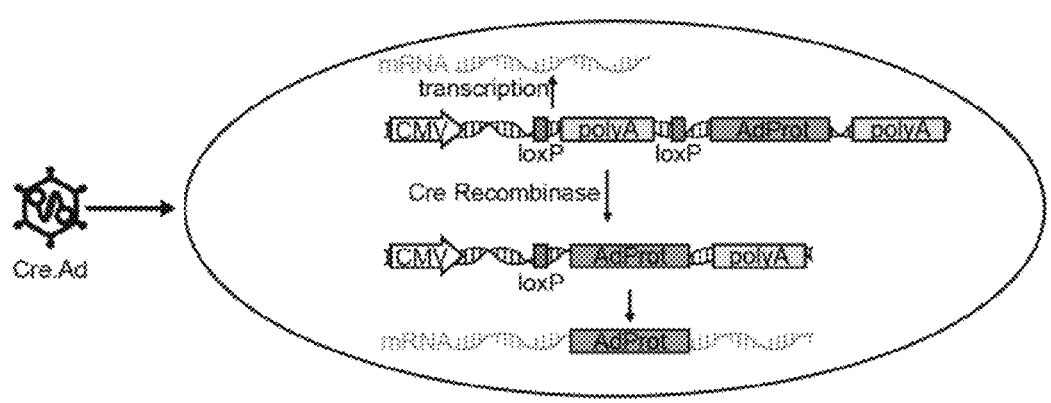
FIGS. 41A-41B. Genetic selection circuits to evolve diverse functions.

Previous recombinase reporter circuits have been designed for other proteins (Esvelt K. M. et al., Nature. 472(7344): p. 499-503 (2011); Chaikind B. et al., Nucleic Acids Res., 44, 9758-9770 (2016)). In the selection circuit described herein, an SV40 polyA terminator signal is placed upstream of the AdProt gene, flanked by two loxP sites (FIG. 41A). If Cre is not present, transcription will be terminated at the SV40 poly A signal. However, if a Cre.ΔAdProtΔAdPol.adenovirus infects a cell line containing this circuit, Cre will recombine the two loxP sites, effectively deleting the SV40 polyA terminator, and allowing transcription of the downstream AdProt gene. In this way, the recombinase circuit should be selective for adenoviruses that carry an active Cre variant.

Amino Acyl tRNA Synthetase Circuit:

amino-acyl tRNA synthetases (aaRS) are a highly sought after directed evolution target as they enable genetic code expansion (Liu C. C. and Schultz P. G., Annu. Rev. Biochem. 79: p. 413-44 (2010)). Owing to the requirement that tRNA/aaRS encoding for unnatural amino acids (UAAs) be completely orthogonal to all endogenous tRNA/aaRS pairs, they are typically shuttled from one organism to be evolved and used in a second organism. This requirement is even more drastic for genetic code expansion in mammalian cells as there is currently no robust way to evolve tRNA/aaRS pairs in human cells. To generate tRNA/aaRS pairs that function in mammalian cells, the tRNA/aaRS pair must be endogenous to one organism, evolved in a second organism, then shuttled to the third organism, mammalian cells. Thus, a target tRNA/aaRS pair must be orthogonal to the endogenous pairs in two distinct organisms, while still functioning to charge the tRNA specifically with the UAA. As a result, only a few UAAs have been used in human cells, and they are all used with just a few tRNA/aaRS pairs that are promiscuous for several UAAs (Italia J. S. et al., Biochem. Soc. Trans., 45, 555-562 (2017)). A reliable method for evolving tRNA/aaRS pairs in human cells would enable researchers to greatly expand the repertoire of UAAs that can be translated in mammalian systems.

Figure 41B:
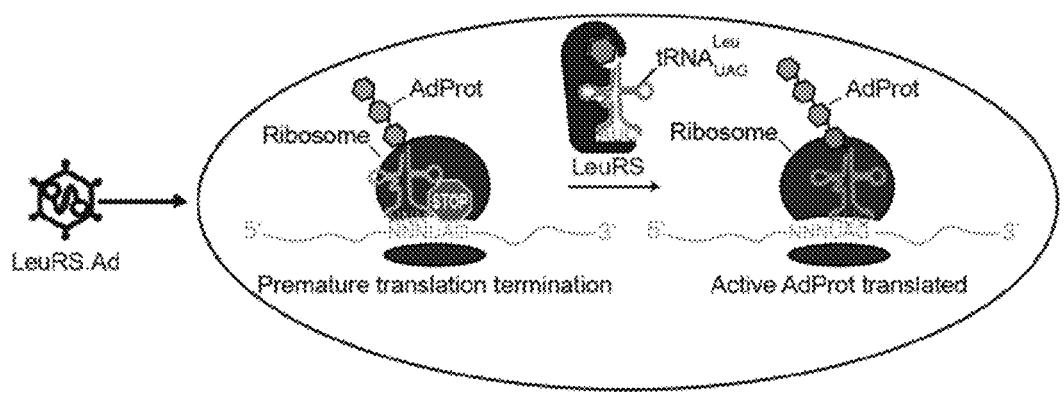

A Leucine tRNA/amino-acyl tRNA synthetase pair (tRNA$^{Leu}$/LeuRS) that charged a tRNA that recognized the amber stop codon with leucine was chosen for analysis. By using a canonical amino acid for our circuit, we did not need to supplement the cells with a UAA. Typically, directed evolution of tRNA/aaRS pairs involves placement of a premature amber stop codon in a selectable marker. Only synthetases that can charge an amber stop anticodon tRNA with the unnatural amino acid will be able to suppress the amber stop codon and translate the full selection marker. In order to set up a similar system, the AdProt gene was mutated to introduce an amber stop codon at leucine 8 (termed AdProt-STOP) (FIG. 41B). If cells transfected with AdProt-STOP and the amber stop antocodon tRNA were infected with an adenovirus encoding LeuRS, the tRNA would be charged with leucine and incorporated into the AdProt sequence in place of the amber stop codon, and full length AdProt would be expressed. If LeuRS is not present, the AdProt sequence would be prematurely terminated at position 8, and the adenovirus would be unable to propagate.

Figure 42:
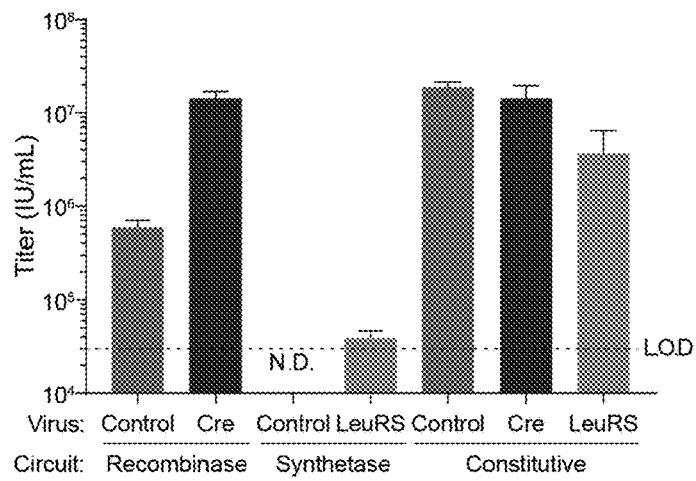
FIG. 42. Testing diverse selection circuits. Cells were transfected with either the recombinase circuit, amino-acyl tRNA synthetase circuit with the relevant tRNAs, or a constitutive AdProt positive control plasmid. Transfected cells were then infected with ΔAdProt.adenovirus carrying the either relevant gene (Cre for the recombinase circuit, LeuRS for the synthetase circuit), or a control gene (tTA). The infections were allowed to progress for four days before they were harvested and titered by flow cytometry. Titers are given in infectious units per milliliter. N.D.=not detected, and indicates that the titer of the control virus fell below the limit of detection (L.O.D.) and therefore could not be accurately assessed.

Both the recombinase and synthetase circuits were transfected, and their ability to support the replication of AdProt-deleted adenoviruses that expressed the relevant biomolecule and adenoviruses that expressed an irrelevant biomolecule was tested (FIG. 42). It was found that the Cre.Ad replicated over 20-fold better than a control adenovirus on the recombinase circuit. On the amino-acyl tRNA synthetase circuit, the control adenovirus was unable to replicate at all, while the LeuRS.Ad was able to replicate efficiently. The control adenovirus, Cre.Ad, and LeuRS.Ad all replicated robustly on a control circuit that constitutively expressed protease. Altogether, these data indicate that both recombinase and amino-acyl tRNA synthetase circuits could select for adenoviruses carrying the relevant genes by coupling gene function to AdProt activity.

Example 24. Discussion

Here, directed evolution was performed on the tet-transactivator to gain resistance to its small molecule regulator, dox, while retaining transcriptional activation activity. A transcriptional circuit was generated that coupled adenoviral replication to tTA-induced expression of prot. Enrichment of tTA activity was characterized in this circuit by performing competition experiments with adenoviruses that lacked tTA or carried inactive tTA variants. Dox resistance was then evolved by passaging a tTA.ΔAdPol.Δprot adenovirus on selector cells in the presence of dox. Two previously reported dox resistant mutants were identified that we validated by reverse genetics. It was also demonstrated how one can use a small molecule inhibitor to tune the selection stringency of AdProt, and how different selection circuits could be used to drive the directed evolution of diverse functions.

As described herein, AdProt can serve as a robust selectable marker for adenovirus-mediated directed evolution in human cells. As an enzyme with catalytic activity, one might not expect AdProt to exhibit a dynamic range of selection. However, as shown herein, AdProt was able to modulate viral titers ~10-fold in response to protease levels. Importantly, a small molecule inhibitor of protease described herein could be easily used to further enhance this dynamic range to several orders of magnitude. It is noteworthy that the AdProt inhibitor may also be employed to actively fine-tune selection stringency over the course of a directed evolution experiment, simply by modulating the compound's concentration in cell culture media. Indeed, the vinyl sulfone inhibitor was able to reduce adenoviral infectivity in the context of the tTA transcriptional circuit by treating with and without dox. However, if the inhibitor increased the selection pressure on the inactive variant relative to the active variant, we would expect the tTA-adenoviruses passaged in the presence of dox to exhibit a greater reduction in titer relative to the tTA-adenoviruses passaged without dox. While there was a significant difference in the titers between the +dox and -dox samples, the degree of reduction upon treatment with the inhibitor did not change. It is unclear from this assay if the inhibitor would modulate the selection stringency of different variants in the same infection. Performing the competition experiments in the presence of the protease inhibitor could be more enlightening. Nevertheless, using this specific inhibitor should enable one to tune selection stringency, and improve the dynamic range of the AdProt selection circuit.

In our directed evolution experiments, multiple mutations were observed in the promoter regions upstream of the tTA coding sequence. While neither CMV mutation in Trial 1 appeared to affect tTA expression, it is possible these mutations have other effects that assist in viral replication. The c1555t mutation in particular enriches towards the last few passages of Trial 1. This mutation destroys an SP1 transcription factor binding site towards the beginning of the CMV promoter (Meier J. L. and Stinski M. F., Intervirology, 39, 331-342 (1996)). Since SP1 binding sites are bi-directional, it is possible that the promoter is driving greater expression of the adenoviral pIX gene. The pIX promoter is positioned only 15 bp from the 5'-end of the CMV promoter, and only 144 bp from c1555. It is possible that strong pIX expression from the CMV promoter is maladaptive for adenovirus, and there would be a selective advantage to reducing expression. In support of this theory, in Trial 2 enrichment was also seen of the g1704a mutation, which destroys an SP1 binding site in the pIX promoter itself (Babiss L. E. and Vales L. D., J. Virol., 65, 598-605 (1991)). Elucidating the role of these mutations in pIX expression could help us better understand how transgene positioning in the adenoviral genome influences adenoviral replication.

In theory, one can efficiently screen genetic libraries consisting of $10^8$ members using a combination of EP-Pol-mediated mutagenesis and AdProt-mediated selection. To increase the library sizes one can screen, one can simply scale-up infections. By running the directed evolution experiments in more plates, one can increase our library sizes at least 10-fold. While one can likely run directed evolution in even larger cultures, the limitations associated with researcher-run tissue culture capacity become greater. The current system relies on serial passaging of adenovirus on adherent cells. Transitioning to suspension cells would enable variant libraries several orders of magnitude larger than one can currently explore. The integration of emerging targeted mutagenesis techniques, such as Muta-T7, could further focus mutations only to the BOI gene and also increase mutation library size (Moore C. L. et al., J. Am. Chem. Soc. (2018)).

Larger library sizes require greater enrichment during selection to efficiently pull out positive variants. The viral competition experiment described herein demonstrated that one can enrich positive variants roughly 50-fold. However, in the three passages tested, enrichment of $tTA_{wt}$-mCherry adenovirus decreased from 50 to 10 between passages one and two. While it is expected that positive variants will not enrich as well as the population frequency asymptotically approaches 1, it is unclear how enrichment would change at even lower initial ratios. The competition experiment was run at ratios of 1:100 and 1:1000, far higher than what one would expect for a positive variant that emerges in an initial library. These ratios enabled us to accurately quantify enrichment via flow cytometry, however this approach is limited for assessing enrichment of ultra-low frequency variants.

The next-generation sequencing performed on the evolved viral populations provides a valuable supplement to the phenotypic enrichment analysis performed via the competition experiments. Analyzing allele frequencies across the serial passaging experiment allows one to explore how individual variants were enriched from one passage to the next. Unfortunately, the error rate of next generation sequencing is roughly 0.24% per base, which does not allow one to analyze allele frequencies much deeper than the phenotypic enrichment analysis (Pfeiffer F. et al., Sci. Rep., 8, 10950 (2018)). Nevertheless, one can still analyze enrichment of individual alleles and how they fluctuate throughout the directed evolution experiment. A 5-12-fold enrichment of the E147K variants and H100Y variants were seen during the most dramatic amplifications, a more modest rate than what was seen in the competition experiments. The fact that greater enrichment was seen in a competition experiment between adenoviruses containing distinct tTA variants that bind to different promoters suggests that the DNA binding selection may be more stringent than the dox-based selection. This hypothesis is supported by the fact that dox-resistant mutations in Trial 2, the more stringent selection, enriched more quickly than dox-resistant mutations in Trial 1.

Finally, it was demonstrated how one can use AdProt-based selection to evolve other functions such as recombinase activity or amino-acyl-tRNA synthetase activity. Both of these activities are highly sought after for both research and therapeutic purposes, and the ability to evolve these functions in human cells is desirable (Italia J. S. et al., Biochem. Soc. Trans., 45, 555-562 (2017); Gaj T. et al., Nucleic Acids Res., 41, 3937-3946 (2013)). To perform directed evolution to generate recombinases with truly altered specificity, or tRNA/aaRS pairs that can specifically incorporate unnatural amino acids, a robust negative selection approach is required to select against nonspecific activities (Liu C. C. and Schultz P. G., Annu. Rev. Biochem. 79: p. 413-44 (2010); Carlson J. C. et al., Nat. Chem. Biol. 10, 216-222 (2014)). As shown herein, an adenoviruses carrying a functional recombinase or aaRS replicates better on AdProt-based selection circuits than adenoviruses carrying irrelevant BOIs. Furthermore, these experiments demonstrate the utility of using a rapid transfection experiment to test new selection schemes. This experimental setup obviates the need for cell line generation, and should enable researchers to quickly test their selection circuit for feasibility prior to cell line development and serial passaging. Selection couples for an assortment of protein classes including TALENs, proteases, protein-protein interactions, RNA polymerases, Cas9 and beyond could all be tested using this approach (Esvelt K. M. et al., Nature. 472(7344): p. 499-503 (2011); Hubbard B. P. et al., Nat. Methods. 12, 939-942 (2015); Dickinson B. C. et al., Nat. Commun. 5: p. 5352 (2014); Hu J. H. et al., Nature 556, 57-63 (2018)).

The platform described herein offers several advantages relative to extant strategies for human cell-based directed evolution that rely on time-intensive screens and extensive in vitro manipulations. The use of adenovirus allows researchers to continuously mutate, select, and amplify genes of interest by simply transferring viral supernatant from one cell plate to the next. Due to this simple viral passaging protocol, library sizes are restricted only by a researcher's tissue culture capacity. Cheating is minimized because mutations are specifically directed to the viral genome. Safety is maximized because the adenoviruses used lack multiple genes required for replication in the wild. Moreover, the user-defined nature of the selector cell and the broad tropism of adenovirus type 5 enable directed evolution to be performed in a diverse array of human cell types.

By making it possible for researchers to evolve diverse BOI functions in the same environment in which the BOIs are intended to function, this human cell-based directed evolution platform holds significant potential to enable researchers to rapidly evolve a wide variety of biomolecules in human cells. Thus, this method should impact the development of new tools for research, our ability to rapidly generate effective biomolecular therapeutics, and our understanding of metazoan evolutionary biology.

Example 25. Materials and Methods for Examples 26-27

Vectors and Cloning:

Materials:

All enzymes were obtained from New England BioLabs unless stated otherwise. All primers were obtained from either ThermoFisher or Sigma Aldrich. All primers are listed in TABLE 18. eCFP-expression vector and RFP.ΔAdPol.adenovirus vector were generated in-house and sequences are available upon request.

Adenoviral Cloning:

All adenoviruses were generated from a parent Ad5.CFP vector derived from pAd/CMV/V5-DEST (ThermoFisher). Adenoviral constructs were engineered using ccdB recombineering, as previously described (Wang H. et al., Nucleic Acids Res. 42, e37 (2014)), in DH10B *Escherichia coli* carrying the Adenovirus type 5 genome in a chloramphenicol-resistant bacterial artificial chromosome (AdBAC). Cells carrying an AdBAC were transformed with the temperature-sensitive psc101-gbaA recombineering plasmid (Wang H. et al., Nucleic Acids Res. 42, e37 (2014)), plated on LB (Difco) agar (Alfa Aesar) with 10 μg/mL tetracycline (CalBioChem) and 10 μg/mL chloramphenicol (Alfa Aesar), and incubated for 24 h at 30° C. Colonies were selected and grown in LB containing 10 μg/mL tetracycline and 10 μg/mL chloramphenicol overnight at 30° C. (18-21 h). Overnight cultures were diluted 25-fold in LB with 10 μg/mL tetracycline and 10 μg/mL chloramphenicol and grown at 30° C. for ~2 h until attaining an $OD_{600}$ of 0.3-0.4. The ccdA antitoxin and recombineering machinery were then induced by adding L-arabinose (Chem-Impex) and L-rhamnose (Sigma Aldrich) to a final concentration of 2 mg/mL each and then growing the cultures at 37° C. for 40 min to an $OD_{600}$ of ~0.6. The cultures were then placed on ice, washed twice with ice-cold, sterile $ddH_2O$, resuspended in ~25 μL of ice-cold, sterile $ddH_2O$, and electroporated with ~200 ng of the appropriate kan-ccdB targeting cassette (1.8 kV, 5.8 ms, 0.1 cm cuvette, BioRad Micropulser). The cells were then recovered in super optimal broth with catabolite repression (SOC; Teknova) with 2 mg/mL L-arabinose at 30° C. for 2 h, then plated on LB agar plates with 50 μg/mL kanamycin (Alfa Aesar) and 2 mg/mL L-arabinose and incubated for 24 h at 30° C. Colonies that grew under these conditions had incorporated the kan-ccdB targeting cassette and were picked in triplicate and grown in LB with 50 μg/mL kanamycin and 2 mg/mL L-arabinose at 30° C. for 18-21 h. (Note: The colonies were picked in triplicate because multimers of the AdBAC formed at a high rate (~30-50% of colonies) during the first recombineering step. These multimers are unable to be successfully recombineered in the next step. Picking three colonies and recombineering them separately in parallel increases the chances of picking a monomer that can be successfully recombineered.) The cultures were then diluted 25-fold in LB with 50 μg/mL kanamycin and 2 mg/mL L-arabinose and grown at 30° C. for ~2 h until they reached an $OD_{600}$ of 0.3-0.4. The recombineering machinery was then induced by adding L-rhamnose to a final concentration of 2 mg/mL and then growing the cultures at 37° C. for 40 min to an $OD_{600}$ of ~0.6. The cultures were then placed on ice, washed twice with ice-cold, sterile $ddH_2O$, resuspended in ~25 μL of ice-cold, sterile $ddH_2O$, and electroporated with ~200 ng of the final targeting cassette intended to replace the kan-ccdB cassette currently integrated in the genome (1.8 kV, 5.8 ms, 0.1 cm cuvette, BioRad Micropulser). The cells were then recovered in SOC with 2 mg/mL L-arabinose at 30° C. for 2 h, and then were washed once with LB to remove the L-arabinose and prevent continued production of the ccdA antitoxin. The cultures were then plated on LB agar plates at various dilutions with 10 μg/mL tetracycline and 10 g/mL chloramphenicol and incubated for 24 h at 37° C. Without the ccdA antitoxin, the ccdB toxin will kill cells that have not replaced the integrated kan-ccdB cassette with the final targeting cassette. The colonies that grow should have the final targeting cassette integrated, but were screened by PCR or sequencing to confirm cassette integration as some colonies may simply inactivate the ccdB toxin.

Once a clone with all of the desired genetic changes was found and confirmed by Sanger sequencing, the AdBAC single-copy replication origin was replaced with the high copy pUC origin. The cells with the correct clone were grown in LB containing 10 μg/mL tetracycline and 10 μg/mL chloramphenicol overnight at 30° C. (18-21 h). Overnight cultures were diluted 25-fold in LB with 10 μg/mL tetracycline and 10 μg/mL chloramphenicol and grown at 30° C. for ~2 h until attaining an $OD_{600}$ of 0.3-0.4. The recombineering machinery was then induced by adding L-rhamnose to a final concentration of 2 mg/mL each and then growing the cultures at 37° C. for 40 min to an $OD_{600}$ of ~0.6. The cultures were then placed on ice, washed twice with ice-cold, sterile $ddH_2O$, resuspended in ~25 μL of ice-cold, sterile ddH2O, and electroporated with ~200 ng of the pUC origin cassette (1.8 kV, 5.8 ms, 0.1 cm cuvette, BioRad Micropulser). The cells were then placed on SOC at 30° C. for 2 h, then plated on LB agar plates with 100 μg/mL ampicillin and incubated for 24 h at 37° C. The resulting ampicillin-resistant colonies should have the pUC origin inserted and were checked by verifying expected restriction digestion patterns. The colonies were grown in 25 mL LB containing 100 μg/mL ampicillin and the DNA was purified using the ZymoPURE II plasmid midiprep kit (Zymo Research) according to the manufacturer's instructions. The DNA was digested with PacI overnight at 37° C. in order to liberate and linearize the adenoviral genome. The linearized DNA was purified using the E.Z.N.A. cycle pure kit (Omega Bio-tek) according to the manufacturer's instructions.

The following modifications in TABLE 19 were made using primers in TABLE 18 to obtain the adenoviruses used in this work (TABLE 16).

Ptre3G.Egfp Vector:

A 762 bp fragment containing eGFP was amplified from the eGFP-N3 vector (Takara Bio) using the primers NotI.eGFP F and EcoRI.eGFP R (TABLE 18) and ligated into the pLVX-TRE3G vector (Takara Bio) using NotI and EcoRI to create the pLVX-TRE3G.eGFP vector.

Ptre3G.Puror Vector:

The pLVX-TRE3G vector was linearized using primers LVX F and LXV R (TABLE 18), and a 439 bp fragment containing blastR was amplified from pLenti6/V5-DEST (Thermo Fisher) using primers LVX.blast F and LVX.blast R (TABLE 18). The two amplicons were assembled to form pLVX.TRE3G.blast using the HiFi DNA assembly kit (New England Biolabs). A 629 bp fragment containing puroR was amplified from pLVX.TRE3G using primers NotI.puro F and EcoRI.puro R (TABLE 18) and was ligated into pLVX.TRE3G.blast using NotI and EcoRI to form pLVX.TRE3G.puroR.

Ptre3G.Blastr Vector:

A 428 bp fragment containing blastR was amplified from pLenti6/V5-DEST (Thermo Fisher) using primers NotI.blast F and EcoRI.blast R (TABLE 18) and ligated into pLVX-TRE3G to form TRE3G.blastR.

Cell Culture and Lentivirus Transduction:

Cell Culture:

All cells were cultured at 37° C. and 5% $CO_2$. All cell lines were derived from a parent HEK293A cell line (ATCC) that constitutively expressed either wild-type or error-prone AdPol (see chapter 2) and cultured in Dulbecco's modified Eagle's medium (DMEM; Cellgro) supplemented with 10% fetal bovine serum (FBS; Cellgro), 1% penicillin-streptomycin (Cellgro), and 1% L-glutamine (Cellgro). eGFP reporter cells and TRE3G.blastR cells were cultured in 1 µg/mL puromycin (Corning), and TRE3G.puroR cells were cultured in 5 µg/mL blasticidin (Thermo Fisher) to stably maintain transgenes (TABLE 17).

Generation of Cell Lines by Lentiviral Transduction:

In a typical protocol, ~9×10$^6$ 293FT cells were plated on a poly-D-lysine-coated 10 cm dish. The next day, the cells were co-transfected with plasmids from the previously described third-generation packaging system (Dull T. et al., J. Virol. 72, 8463-8471 (1998)): 15 µg RRE, 6 µg REV, 3 µg VSVG, and 15 µg transfer vector using 60 µL Lipofectamine 2000 (Thermo Fisher). Cultures were maintained in 5 mL total volume of OPTI-MEM (Gibco) throughout the transfection. After 8 h, the media was exchanged for fresh DMEM. After 48 h, media was harvested and centrifuged for 5 min at 162×g to clear the cell debris. The supernatant was used to transduce HEK293A cells supplemented with 4 µg/mL polybrene (Sigma). After 24 h, the media was exchanged for fresh DMEM. After 48 h, media was exchanged again for DMEM containing either 1 µg/mL puromycin or 5 µg/mL blasticidin to select stable cell lines (as indicated above).

Generating Adenovirus from Transfection:

All adenoviruses were produced by transfecting a PacI-linearized vector into appropriate trans-complementing HEK293A cells. Briefly, 24 µg of PacI-digested adenovirus vectors transfected with 144 µL PEI, 1 mL OptiMEM (Gibco) into a 15 cm plate of the corresponding cell line (10 million cells). Media was replaced 8 h after transfection. Media was then intermittently replaced every 2-3 days until plaques were observed (typically ~3 weeks). Once plaques were observed, cytopathic effect (CPE) was observed in all cells within 5 d. Upon complete CPE, the cells and media were harvested, and then frozen at −80° C. for at least 30 min and then thawed at 37° C. for 15 min for three total freeze/thaw cycles. The cell debris was removed by centrifugation at >1,462×g for 15 min and the supernatant was moved to a new Eppendorf tube and stored at −80° C. until use.

Determining Adenoviral Titer by Flow Cytometry:

Adenoviral titers were determined through flow cytometry. Known volumes of AdPol-deleted viral supernatants were added to wild-type AdPol cells (TABLE 17). The next day, cells were washed once with media, stained with 0.2 µg/mL DAPI, and then analyzed on a BD LSR II Analyzer for fluorescent protein expression. Infectious titers were determined by measuring the percentage of cells infected by a known volume of virus. To minimize counting cells that were infected by more than one virus and to minimize any background fluorescence, data were only considered if they fell within the linear range, which typically encompassed samples where 1-10% of cells were infected.

Testing the eGFP Reporter Cell Line by Transient Transfection of tTA:

1.5 µg each of a Tet-On Advanced vector (Takara Bio), and eCFP vector were co-transfected with 6 µL PEI into a 6-well plate seeded with eGFP reporter cells (~10$^6$ cells per well) (TABLE 17). Two days later, cells were harvested in 600 µL media and analyzed on a BD LSR Fortessa HTS Analyzer for fluorescent protein expression. Cells were excited using a 405 nm and 488 nm laser. Cells were back-gated for CFP expression at 450/50 nm emission to ensure that only transfected cells were analyzed. eGFP inducibility was quantified at 515/20 nm emission at based on the number of eGFP+ cells.

Enrichment of Active BOI Variants Via FACS:

A 1:10 mixture of tTA$_{wt}$.mCherry.ΔAdPol.adenovirus: tTA$_{mut}$.mCherry.ΔAdPol.adenovirus (TABLE 16) was used to infect reporter cells (TABLE 17) seeded in a 6-well plate (~10$^6$ cells per well) at an overall MOI=1. Two days later, cells were stained with 0.2 µg/mL DAPI, harvested in 600 µL media, and sorted on a BD FACS Aria. Cells were excited using a 405 nm, 488 nm, and 561 nm laser. 16,481 cells were harvested based on a stringent gate for both mCherry fluorescence (emission at 610/20 nm), and eGFP fluorescence (emission at 530/30). Cells were harvested in media, and plated on top of wild-type AdPol-expressing cells to allow the adenovirus to amplify from the sorted cells. 8 days later, viral supernatants were harvested and titered as described above, and used to infect reporter cells seeded in a 6-well plate (~10$^6$ cells per well) at an overall MOI=1. The next day, cells were stained with 0.2 µg/mL DAPI, harvested in 600 µL media, and analyzed on a BD FACS Aria using the same parameters.

Resazurin Assay:

A 96-well plate was seeded with HEK293A cells (~15,000) and treated with either puromycin HCl (Corning), Hygromycin B (Thermo Fisher), Blasticidin S HCl (Thermo Fisher), or G418 (Enzo). Two days later, 10 µL of 0.1 mg/mL resazurin (MilliporeSigma) was added and incubated for 1.5 h. Media was transferred to a fresh 96-well plate and fluorescence was analyzed on a Bio-Tek Synergy H1 Hybrid Microplate Reader.

Time Course of Antibiotic Inhibition of Adenoviral Replication:

RFP.ΔAdPol.adenovirus (TABLE 16) was used to infect a 24-well plate of wild-type AdPol cells (150,000 cells/well) (TABLE 17) at MOI=1, and either blasticidin or puromycin was added at various time points following the infection. Viral supernatants were harvested ~48 h post-infection, and titered by flow cytometry as described above.

tTA-Induced Resistance to Antibiotic Inhibition of Adenoviral Replication:

Either RFP.ΔAdPol.adenovirus, or tTA.mCherry.ΔAdPol.adenovirus (TABLE 16) was used to infect a 24-well plate of either wild-type AdPol cells, TRE3G.puroR cells, or TRE3G.blastR cells (150,000 cells/well) (TABLE 17) at MOI=1, and either puromycin or blasticidin was added 10 h post-infection. Viral supernatants were harvested ~48 h post-infection, and titered by flow cytometry as described above.

Enrichment of tTA-Expressing Adenovirus:

A 1:10 mixture of tTA.mCherry.ΔAdPol.adenovirus and CFP.GFP.ΔAdPol.adenovirus (TABLE 16) was used to infect a 24-well plate of TRE3G.blastR cells (150,000 cells/well) (TABLE 17) at MOI=0.7, and blasticidin was added 10 h post-infection. Viral supernatants were harvested ~48 h post-infection, and titered by flow cytometry as described above.

TABLE 16

Adenoviruses constructed and used in this study.

| Name | Modifications relative to wild-type Ad5 |
|---|---|
| tTA$_{wt}$.mCherry.ΔAdPol | E1L-tTA ΔE1 ΔE3 ΔAdProt ΔAdPol E4R-mCherry |
| tTA$_{mut}$.mCherry.ΔAdPol | E1L-tTA$_{aak}$ ΔE1 ΔE3 ΔAdProt ΔAdPol E4R-GFP |
| RFP.ΔAdPol | *E1L-RFP1.2 ΔE1 ΔE3 ΔAdProt ΔAdPol |
| CFP.GFP.ΔAdPol | E1R-CFP ΔE1 ΔE3 ΔAdPol E4R-GFP |

*RFP1.2 was described previously (Wang L. et al., Proc. Natl. Acad. Sci. U S A. 101(48): p. 16745-49 (2004)).

Note:
All viruses used in this work were derived from Ad5.CFP (Genbank accession number: MH325112: SEQ ID NO: 97).

TABLE 17

Cell lines used in this study.

| Cell line | Polymerase | Transgene cassette |
|---|---|---|
| Wild-type AdPol | wt-AdPol | None |
| Reporter | EP-Pol | TRE3G.eGFP |
| TRE3G.puroR | wt-AdPol | TRE3G.puroR |
| TRE3G.blastR | wt-AdPol | TRE3G.puroR |

Note:
All cell lines were derived from HEK293A.

TABLE 18

Primers used in this study.

| Name | Sequence - 5' to 3' | SEQ ID NO: |
|---|---|---|
| delAdPol ccdb F | TCCCGCGCTTCTTGGAACTTTACATTGTGGGCCACAACATCAAC GGCCCTCCCTCATCAGTGCCAACATAGTAAG | 102 |
| delPol ccdb R | GGCACCTCGGAACGGTTGTTAATTACCTGGGCGGCGAGCACGA TCTCGTCCCGCTCATTAGGCGGGC | 158 |
| delPol F | GCGCGGCCTTCCGGAGCGAGGTGTGGGTGAGCGCAAAGGTGTC CCTGACCATGACCAGCATGAAGGGCACGAGCTGCTTCCCAAAG GCCCCCATCCAAG | 159 |
| delPol R | CTTGGATGGGGGCCTTTGGGAAGCAGCTCGTGCCCTTCATGCT GGTCATGGTCAGGGACACCTTTGCGCTCACCCACACCTCGCTCC GGAAGGCCGCGC | 160 |
| E1.ccdb F | ATACAAAACTACATAAGACCCCCACCTTATATATTCTTTCCCAC CCTTAACCCTCATCAGTGCCAACATAGTAAG | 161 |
| E1.ccdb R | AATAAGAGGAAGTGAAATCTGAATAATTTTGTGTTACTCATAG CGCGTAACCGCTCATTAGGCGGGC | 162 |
| E1.CMV F | ATACAAAACTACATAAGACCCCCACCTTATATATTCTTTCCCAC CCTTAAGCCACGCCCACAGATATACGCGTTGACATTG | 163 |
| E1.BGHR R | AATAAGAGGAAGTGAAATCTGAATAATTTTGTGTTACTCATAG CGCGTAATAGAAGCCATAGAGCCCAC | 164 |
| E4.ccdb F | CAAAAAACCCACAACTTCCTCAAATCGTCACTTCCGTTTTCCCA CGTTACCCCTCATCAGTGCCAACATAGTAAG | 165 |
| E4.ccdb R | AGTAACTTGTATGTGTTGGGAATTGTAGTTTTCTTAAAATGGGA AGTGACCCGCTCATTAGGCGGGC | 166 |
| E4.SV40P F | CAAAAAACCCACAACTTCCTCAAATCGTCACTTCCGTTTTCCCA CGTTACTTCTGTGGAATGTGTGTCAGTTAGGG | 167 |
| E4.SV40pA R | AGTAACTTGTATGTGTTGGGAATTGTAGTTTTCTTAAAATGGGA AGTGACCTCTAGCTAGAGGTCGACGGTATAC | 168 |
| BAC2pUC F | CCCGGGAATTCGGATCTGC | 130 |
| BAC2pUC R | CCGGGAATTCGGATCCTTGAAGAC | 131 |
| NotI.eGFP F | AAAAAAGCGGCCGCCGCCACCATGGTGAG | 174 |
| EcoRI.eGFP R | AAAAAGAATTCCGGCCGCTTTACTTGTAC | 175 |
| LVX F | CGGGGCGCGTCTGGAAC | 201 |
| LVX R | GGTAAGCTTGGGCTGCAGG | 202 |
| LVX.blast F | ACCTGCAGCCCAAGCTTACCATGGCCAAGCCTTTG | 203 |
| LVX blast R | ATTGTTCCAGACGCGCCCCGTTAGCCCTCCCACACATAACCAG AG | 204 |
| NotI.puro F | AAAAAAGCGGCCGCACCATGACCGAGTACAAGCCCACG | 205 |

TABLE 18-continued

Primers used in this study.

| Name | Sequence - 5' to 3' | SEQ ID NO: |
|---|---|---|
| EcoRI.puro R | AAAAAAGAATTCTCAGGCACCGGGCTTGC | 206 |
| NotI.blast F | AAAAAAGCGGCCGCACCATGGCCAAGCCTTTG | 207 |
| EcoRI.blast R | AAAAAAGAATTCTTAGCCCTCCCACACATAACCAG | 208 |

TABLE 19

Modifications made to generate adenoviruses used in this study.

| Modification | Genotype | KanccdB cassette primers used with R6K-kan-ccdB template plasmid (unless stated otherwise) | Final targeting cassette oligos or primers and template (if applicable) | Purpose of modification |
|---|---|---|---|---|
| AdPol deletion | ΔAdPol | delPol ccdb F and delPol ccdb R | delPol F and delPol R | To prevent evolution of the adenoviral polymerase. The error-prone version was expressed in trans |
| tTA insertion | tTA | E1.ccdb F and E1.ccdb R | E1.CMV F and E1 BGHR | Insertion as model BOI |
| mCherry insertion | mCherry | E4.ccdb F and E4.ccdb R | E4.SV40P F and E4.SV40pA R | Insertion for visualization of viral infection |
| eGFP insertion | eGFP | E4.ccdb F and E4.ccdb R | E4.SV40P F and E4.SV40pA R | Insertion for visualization of viral infection |
| Replacement of the low copy BAC origin with the high copy pUC origin | N/A | N/A, the replacement is a one-step recombineering since the origin switches from chloramphenicol to ampicillin resistant | BAC2pUC F and BAC2pUC R used to amplify the pUC origin from pAd/CMV/V5-DEST | High copy origin to allow for the preparation of concentrated, purified DNA for transfection and adenoviral production |

Figure 43:
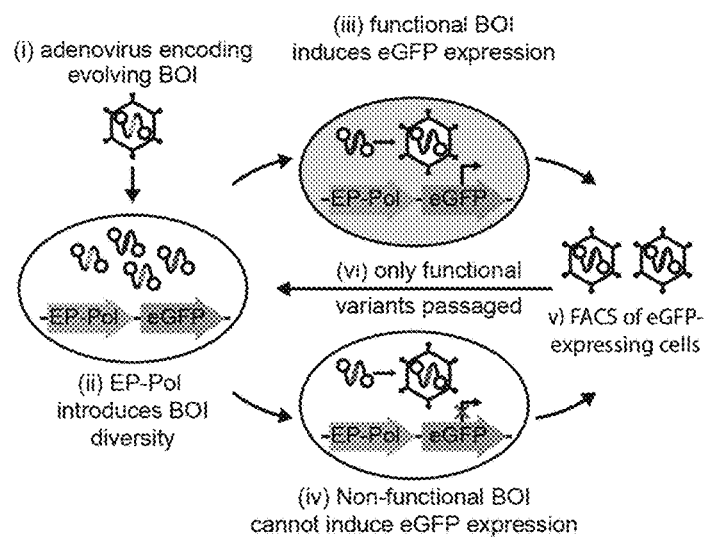
FIG. 43. Screening positive BOI variants using an eGFP reporter gene. (i) An adenovirus encoding an evolving BOI that is deleted for the adenoviral polymerase (AdPol) infects an engineered reporter cell line. (ii) Ectopically-expressed EP-Pol generates a mutational library of BOI variants. (iii) Functional BOI variants can induce eGFP expression, while (iv) nonfunctional variants cannot. (v) FACS is performed to sort cells expressing eGFP, and thus containing functional BOI variants. (vi) The functional variants are passaged for amplification and the next round of sorting.

Example 26. FACS-Based Screening of Positive BOI Variants for Adenovirus-Mediated Directed Evolution A fluorescence-activated cell sorting-(FACS)-based screening approach was developed for adenovirus-mediated directed evolution based on BOI-coupled expression of an eGFP reporter gene (FIG. 43). ΔAdPol.adenoviruses carrying both the gene encoding the BOI and an mCherry gene as a fluorescent reporter of infection (see TABLE 16 for adenoviruses used in this study) are used to infect cells that express EP-Pol to generate mutational libraries, and express functional eGFP under control of the desired BOI function, termed reporter cells (see TABLE 17 for cell lines used in this study). Adenoviruses that carry functional BOI variants will induce expression of eGFP. Reporter cells are sorted based on both mCherry fluorescence to detect infected cells, and eGFP fluorescence to detect BOI-induced expression of eGFP via FACS. Sorted cells are subsequently added to a plate of cells that express EP-Pol to amplify the adenovirus population before the next round of screening while simultaneously generating mutational diversity in the BOI.

Figure 44:
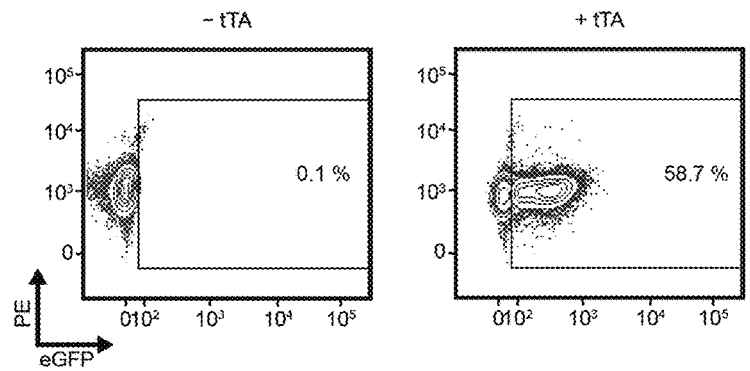
FIG. 44. tTA-induced eGFP expression in the reporter cell line. Reporter cells were co-transfected with tTA-expressing and eCFP-expressing plasmids and transfected cells were analyzed for eGFP expression by flow cytometry. PE fluorescence is shown on the y-axis to assess autofluorescence.

The eGFP screening approach was tested using tTA as a model BOI (Gossen M. and Bujard H., Proc. Natl. Acad. Sci. USA 89(12): p. 5547-51 (1992)). To generate a suitable reporter cell line for tTA activity, an HEK293A cell line that already expressed EP-Pol was stably transduced with lentivirus expressing eGFP under transcriptional control of a tTA-inducible promoter (full operon, termed TRE3G.eGFP), and isolated single colonies (TABLE 17) (Loew R. et al., BMC Biotechnol. 10, 81 (2010)). This reporter cell line was co-transfected with a plasmid that expressed tTA, and a plasmid that expressed CFP as a transfection control, and analyzed eGFP fluorescence by flow cytometry (FIG. 44). In the absence of tTA, less than 1% of reporter cells were positive for eGFP expression. However, in the presence of tTA, over 58% of cells expressed eGFP, indicating that this cell line could report on tTA activity via eGFP fluorescence.

Figure 45A:
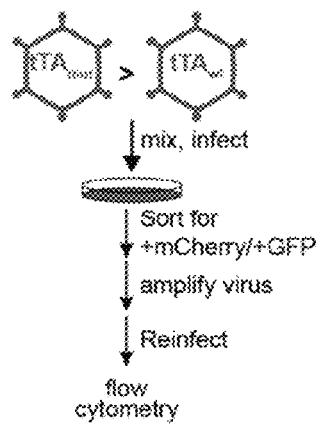
FIGS. 45A-45B. Enrichment of adenoviruses encoding positive BOI variants using FACS.
Figure 45B:
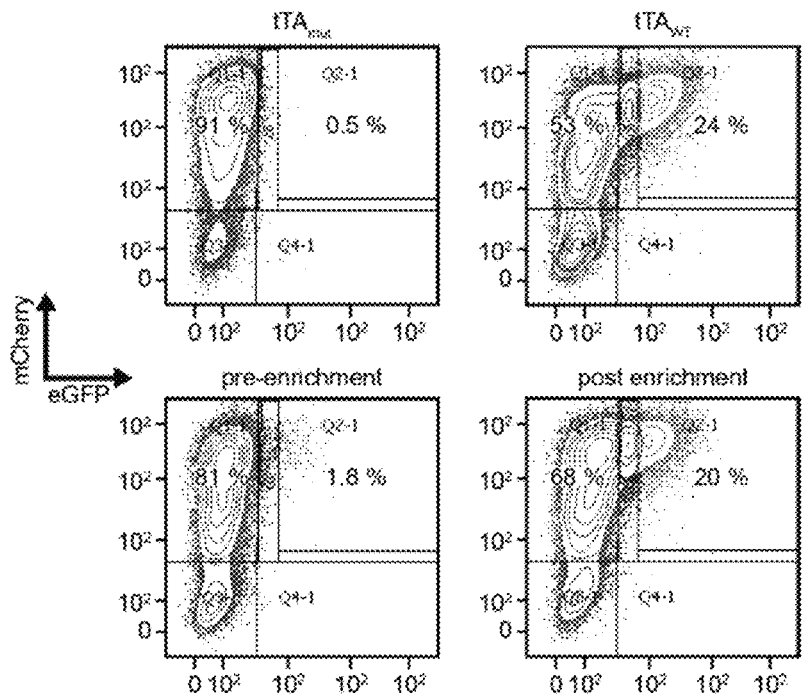
Figure 46A:
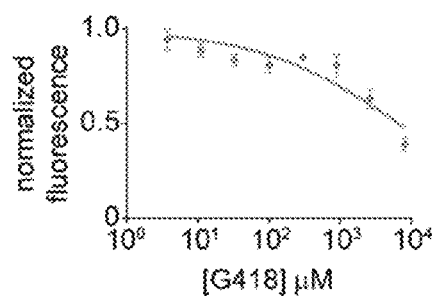
FIGS. 46A-46D. Resazurin assay to assess acute toxicity of common tissue culture antibiotics. HEK293A cells were treated for two days with either G418 (FIG. 46A), puromycin (FIG. 46B), blasticidin (FIG. 46C), or hygromycin (FIG. 46D), and cell viability was analyzed by resazurin fluorescence.
Figure 46B:
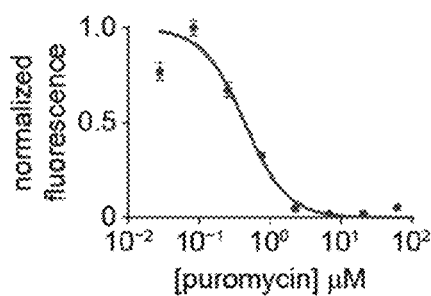
Figure 46C:
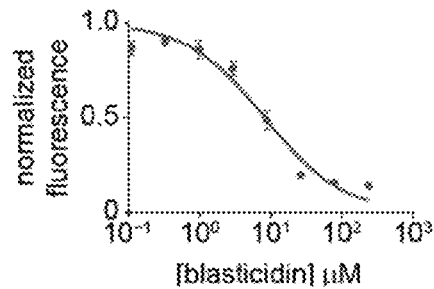
Figure 46D:
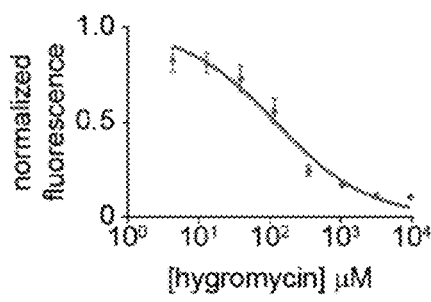

Whether this cell line could be used to enrich for adenoviruses carrying positive tTA variants was next tested. Wild-type tTA (tTA$_{wt}$), binds its wild-type target operator, with a consensus sequence of CCTATCAGTGATAGA (SEQ ID NO: 209), to induce target gene transcription. A tetR variant that is incapable of binding to wild-type operators has been reported, instead possessing an enhanced affinity for the mutant CCcgTCAGTGAcgGA (SEQ ID NO: 210) operator (Krueger M. et al., Gene 404, 93-100 (2007)). Because tTA is simply a fusion between tetR and a VP48 trans-activation domain, it was hypothesized that a tTA variant based off the mutant tetR (termed tTA$_{mut}$) would exhibit the same altered DNA binding specificity.

mCherry.ΔAdPol-adenoviruses were engineered that expressed either tTA$_{wt}$ or tTA$_{mut}$, and the reporter cells were infected at an MOI of 1 to maintain a large library size, and a ratio of 1:10 tTA$_{wt}$.ΔAdPol.adenovirus: tTA$_{mut}$.ΔAdPol.adenovirus (FIGS. 45A-45B, TABLE 16).

Only cells that exhibited the most intense mCherry signal and eGFP fluorescence signal were sorted to ensure we sorted only cells that were infected by tTA$_{wt}$.ΔAdPol.adenovirus. Sorted cells were plated on a pre-plated culture of cells expressing wild-type AdPol to amplify the ΔAdPol.adenovirus population from the sorted cells. The ability of the resulting adenovirus population to induce eGFP fluorescence was analyzed by re-infecting the reporter cells and analyzing mCherry and eGFP fluorescence by flow cytometry. It was found that the percentage of infected cells that were positive for eGFP increased to 23% from 2% in the initial sort, a 10-fold increase in adenovirus-mediated eGFP activity. While we were unable to determine the relative amount of tTA$_{wt}$.ΔAdPol.adenovirus to tTA$_{mut}$.ΔAdPol.adenovirus because both adenoviruses had the same fluorescent marker, it is clear from the 10-fold increase in eGFP fluorescence that we were able to successfully enrich for tTA$_{wt}$.ΔAdPol.adenoviruses using eGFP as a fluorescent reporter.

Example 27. Antibiotic Selection of Positive BOI Variants for Adenovirus-Mediated Directed Evolution Experiments were designed to create an antibiotic selection-based platform for adenovirus-mediated directed evolution of BOIs. For an antibiotic selection to be successfully employed as a means of selecting for positive BOI variants in adenovirus-mediated directed evolution, the timing of antibiotic treatment and the swiftness with which translation is inhibited is key. The infection must progress sufficiently so that the BOI is expressed and able to induce expression of the antibiotic resistance marker before translation is inhibited. However, the antibiotic must halt the infection before the nascent adenovirus is produced. Therefore, there must be a window of time between induction of antibiotic resistance and viral production for selection to be successful. The antibiotic also must be acutely toxic, so that the culture can be treated after the antibiotic resistance marker has had a chance to be translated, and yet the antibiotic can still act before the nascent adenoviruses is produced. Ideally, the antibiotic would also have a large dynamic range of selection so that adenoviral replication can be both minimally inhibited at early passages when the BOI exhibits only moderate fitness, and maximally inhibited at later passages when the BOI exhibits greater fitness.

To test the acute toxicity of various antibiotics, a resazurin assay was conducted on four common antibiotics used in mammalian tissue culture: hygromycin B, puromycin, blasticidin, and G418 (FIGS. 46A-46D). HEK293A cells were treated with various concentrations of each antibiotic for two days, and the resazurin fluorescence signal was analyzed. While puromycin, hygromycin B, and blasticidin were completely toxic over the two-day treatment, G418 was only mildly toxic at the highest concentrations. Puromycin exhibited the smallest dynamic range of selection with inhibition of less than two orders of magnitude, while blasticidin and hygromycin both exhibited over two orders of magnitude dynamic range of inhibitory concentrations.

Figure 47A:
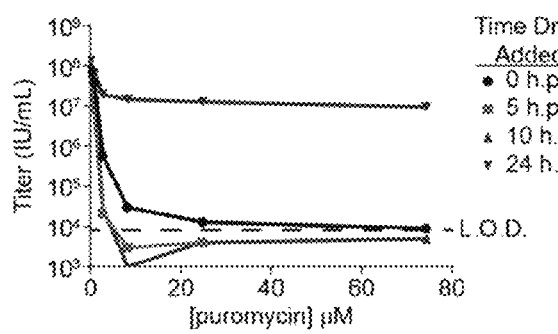
FIGS. 47A-47B. Time-course of antibiotic-mediated inhibition of adenoviral infection. HEK293A cells expressing wild-type AdPol were infected with RFP.ΔAdPol.adenovirus and treated with either a) puromycin, or b) blasticidin at various time points post-infection (h.p.i.=hours post-infection). After 2 days, the infections were harvested and titered by flow cytometry. Titers are given in infectious units per milliliter (IU/mL), defined as the volume of adenoviral supernatant required to induce fluorescence in a cell as analyzed by flow cytometry. Dashed line represents the limit of detection (L.O.D) of the assay. Titers below this limit are inaccurate due to the percentage of infected cells being below the 1% error threshold of flow cytometry.
Figure 47B:
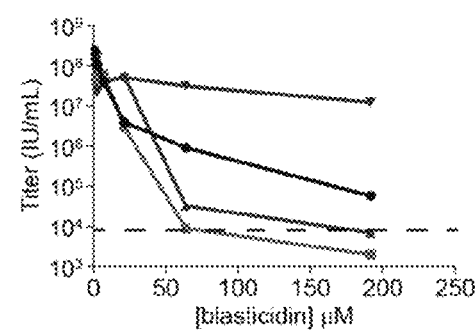

The timing of antibiotic selection on adenoviral replication was next tested. Wild-type AdPol-expressing cells were infected with RFPΔAdPol.adenovirus at MOI=1 and treated with various concentrations of puromycin or blasticidin either 5 h, 10 h, or 24 h post-infection (FIGS. 47A-47B, TABLE 16). Two days post-infection, the adenovirus was harvested, and adenoviral titers were analyzed by flow cytometry. It was found that both puromycin and blasticidin were able to reduce adenoviral infection at least 10,000-fold if the cultures were treated up to 10 h post-infection. Neither puromycin nor blasticidin were able to inhibit adenoviral replication when treatment was initiated 24 h post-infection. The time period between 10 h and 24 h post-infection represents the latest time period that we can treat cells following adenoviral infection and still attain strong inhibition of adenoviral replication. In order to positively select for positive BOIs using antibiotic selection, the antibiotic resistance marker must be expressed and functional within the 10-24 h window.

Figure 48A:
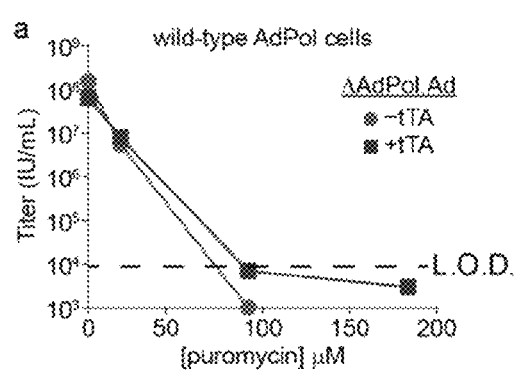
FIGS. 48A-48D. tTA-induced resistance to antibiotic mediated inhibition of adenoviral infection. Either wild-type AdPol cells, TRE3G.puroR cells, or TRE3G.blastR cells were infected with ΔAdPol.adenovirus encoding either tTA (+tTA) or RFP (−tTA). Ten hours post-infection, wild-type AdPol cells were treated with either puromycin (FIG. 48A) or (FIG. 48B) blasticidin, TRE3G.puroR cells were treated with puromycin (FIG. 48C), and TRE3G.blastR cells were treated with blasticidin (FIG. 48D). After 2, days, the infections were harvested and titered by flow cytometry. Titers are given in infectious units per milliliter (IU/mL), defined as the volume of adenoviral supernatant required to induce fluorescence in a cell as analyzed by flow cytometry. Dashed line represents the limit of detection (L.O.D) of the assay. Titers below this limit are inaccurate owing to the percentage of infected cells being below the 1% error threshold of flow cytometry.
Figure 48B:
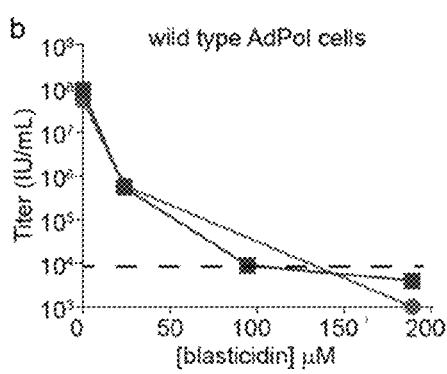
Figure 48C:
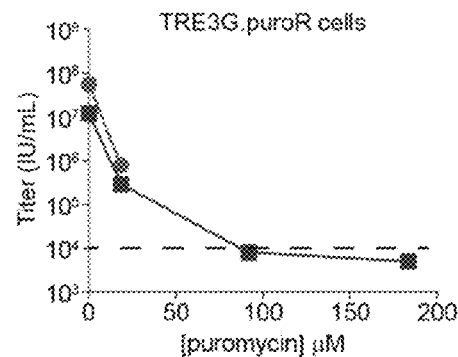
Figure 48D:
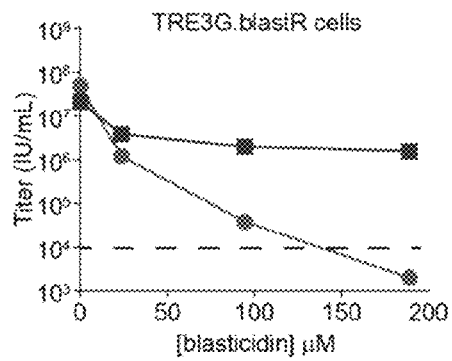

To test whether induced antibiotic resistance can allow adenovirus to escape acute antibiotic inhibition, new cell lines were constructed that express an antibiotic resistance marker under control of tTA. Wild-type AdPol expressing cells were stably transduced with lentivirus expressing either blasticidin-S-deaminase (blastR) or puromycin N-acetyl-transferase (puroR) under control of the TRE3G promoter (termed TRE3G.blastR and TRE3G.puroR respectively) (TABLE 17). TRE3G.blastR, TRE3G.puroR, and wild type AdPol cell lines were infected with ΔAdPol.adenovirus that either expressed tTA, or red fluorescent protein (RFP), and treated with either blasticidin (for iBlastR) or puromycin (for iPuroR) 10 h post-infection (FIGS. 48A-48D). As expected, both puromycin and blasticidin treatment inhibited both RFP-expressing and tTA-expressing ΔAdPol.adenovirus replication in the wild-type AdPol cell line, as no resistance marker could be expressed (FIGS. 48A-48B). It was also found that puromycin was equally toxic to both tTA-expressing and RFP-expressing ΔAdPol.adenovirus in the TRE3G.puroR cell line, indicating that either the cell line did not properly integrate the TRE3G.puroR cassette, or that puroR failed to rescue the adenovirus before puromycin inhibited translation (FIG. 48C). Interestingly, it was found that tTA.ΔAdPol.adenovirus was completely resistant to blasticidin treatment in the TRE3G.blastR cell line, while RFPA.AdPol.adenovirus was still inhibited (FIG. 48D). This result indicates that the combination of tTA and TRE3G.blastR was able to rescue blasticidin-mediated inhibition of adenovirus. Furthermore, this result indicated that adenovirus encoding an active BOI could be rescued from antibiotic selection, while adenovirus encoding an inactive BOI would be inhibited.

Figure 49:
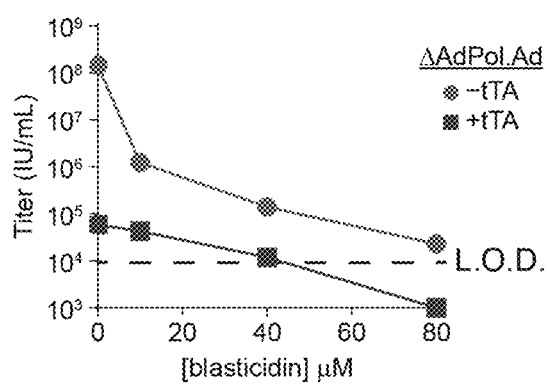
FIG. 49. Enrichment of adenoviruses encoding positive BOI variants by antibiotic selection. TRE3G.blastR cells were infected with a 1:10 mixture of ΔAdPol.adenovirus encoding either tTA (+tTA) or CFP (−tTA) and treated with blasticidin 10 h post-infection. Two days post-infection, adenoviruses were harvested and titered by flow cytometry. Titers are given in infectious units per milliliter (IU/mL), defined as the volume of adenoviral supernatant required to induce fluorescence in a cell as analyzed by flow cytometry. Dashed line represents the limit of detection (L.O.D) of the assay. Titers below this limit are inaccurate due to the percentage of infected cells being below the 1% error threshold of flow cytometry.

Whether inducible blasticidin resistance could enrich for adenovirus containing an active BOI over an adenovirus carrying an inactive BOI was next tested. The TRE3G.blastR cell line was simultaneously transfected with two ΔAdPol.adenoviruses (FIG. 49, TABLE 16, TABLE 17). The first adenovirus encoded for tTA and mCherry while the second adenovirus encoded for only CFP. The two different fluorophores allow us to assess the relative populations of the two adenoviruses by flow cytometry on infected cells. The two adenoviruses were mixed at a ratio of 1:10 tTA.mCherry.ΔAdPol.adenovirus: CFP.ΔAdPol.adenovirus and were treated with blasticidin 10 h post-infection. Four days later, the infections were harvested, and the relative populations of the tTA.mCherry.ΔAdPol.adenovirus and CFP.ΔAdPol.adenovirus were analyzed by flow cytometry. Interestingly, the CFP.ΔAdPol.adenovirus was over 1000-fold higher titer than the tTA.mCherry.ΔAdPol.adenovirus in the absence of blasticidin. When 20 µM blasticidin was added, the CFP.ΔAdPol.adenovirus titer dropped over 100-fold, while the tTA.mCherry.ΔAdPol.adenovirus titer remained steady. While the tTA.mCherry.ΔAdPol.adenovirus did not increase in titer during the experiment, it still enriched due to the drop in CFP.ΔAdPol.adenovirus titer. This experiment clearly demonstrates that one can use antibiotic selection to enrich for adenoviruses encoding positive BOI variants.

Sequences:

WT-Pol-HA: HA tag is underlined (SEQ ID NO: 26)

```
atggccttggctcaagctcaccgggcccgtcgtcttcacgcagaggcgccagattcaggagatcaaccgccgcgtcgtcgcgttcgc
cagcaacctacgcgcgcagcaccagctcctgcccgcgcgcggcgccgacgtgcccctgcccctctcccggcgggtccggagcc
cccctacctccggggggctcgcccgcgtcaccgcttttagatgcatcatccaaggacacccccgcggcccaccgcccgccgcgcgg
taccgtagtcgcgccgcggggatgcggcctcttgcaagccatcgacgccgccaccaaccagccctggaaattaggtatcacctgg
atctagcccgcgccctgacccgtctatgcgaggtaaacctgcaggagctcccgcctgacctgacgccgcgggagctccagaccatg
gacagctcccatctgcgcgatgttgtcatcaagctccgaccgccgcgcggacatctggactttgggctcgcgcggcgtggtggtc
cgatccaccgtaactcccctcgagcagccagacggtcaaggacaagcagccgaagtagaagaccaccagccaaacccgccaggc
gagggctcaaattcccactctgcttccttgtgcgcggtcgtcaggtcaacctcgtgcaggatgtacagcccgtgcaccgctgccagta
ctgcgcacgttttacaaaagccagcacgagtgttcggcccgtcgcagggacttctactttcaccacatcaatagccactcctccaattg
gtggcgggagatccagttcttcccgatcggctcgcatcctcgcaccgagcgtctctttgtcacctacgatgtagagacctatacttggat
ggggcctttgggaagcagctcgtgcccttcatgctggtcatgaagttcggcggagatgagcctctagtgactgccgcgcgagacct
agccgcgaaccttggatgggaccgctgggaacaagaccgcttaccttctactgcatcacccagaaaaaatggccataggtcgcca
gtttaggaccttcgcgaccacctgcaaatgctaatggcccgtgacctgtggagctcattcgtcgcttccaaccctcatcttgcagactgg
gccctttcagagcacgggctcagctcccctgaagagctcacctacgaggaacttaaaaaattgccttccatcaagggcatcccgcgctt
cttggaactttacattgtgggccacaacattaatgggtttgacgagatcgtgctcgccgcccaggtaattaacaaccgttccgaggtgcc
gggacccttccgcatcacacgcaactttatgcctcgcgcgggaaagatactcttcaacgatgtccacttcgccctgccaaatccgcgtt
ccaaaaagcgcacggactttttgctctgggagcagggcggatgcgacgacactgacttcaaataccagtacctcaaagtcatggtcag
ggacacctttgcgctcacccacacctcgctccggaaggccgcgcaggcatacgcgctacccgtagaaaagggatgctgcgcctacc
aggccgtcaaccagttctacatgctaggctcttaccgttcggaggccgacgggtttccgatccaagagtactggaaagaccgcgaag
agtttgtcctcaaccgcgagctgtggaaaaaaaagggacaggataagtatgacatcatcaaggaaaccctggactactgcgccctag
acgtgcaggtcaccgccgagctggtcaacaagctgcgcgactcctacgcctccttcgtgcgtgacgcggtaggtctcacagacgcca
gcttcaacgtcttccagcgtccaaccatatcatccaactcacatgccatcttcaggcagatagtcttccgagcagagcagcccgcccgt
agcaacctcggtcccgacctcctcgctccctcgcacgaactatacgattacgtgcgcgccagcatccgcggtggaagatgctacccta
catatcttggaatactcagagagcccctctacgtttacgacatttgcggcatgtacgcctccgcgctcacccacccccatgccatgggtc
ccccactcaacccatacgagcgcgcgcttgccgcccgcgcatggcagcaggcgctagacttgcaaggatgcaagatagactacttc
gacgcgcgcctgctgcccggggtctttaccgtggacgcagaccccccggacgagacgcagctagaccccctaccgccattctgctc
gcgcaagggcggccgcctctgctggaccaacgagcgcctacgcggagaggtagccaccagcgttgaccttgtcaccctgcacaac
cgcggttggcgcgtgcacctggtgcccgacgagcgcaccaccgtctttcccgaatggcggtgcgttgcgcgcgaatacgtgcagct
aaacatcgcggccaaggagcgcgccgatcgcgacaaaaaccaaaccctgcgctccatcgccaagttgctgtccaacgccctctacg
ggtcgtttgccaccaagcttgacaacaaaaagattgtcttttctgaccagatggatgcggccaccctcaaaggcatccgcgggcca
ggtgaatatcaaatcctcctcgttttttggaaactgacaatcttagcgcagaagtcatgcccgcttttcagagggagtactcaccccaaca
gctggccctcgcagacagcgatgcggaagagagtgaggacgaacgcgcccccaccccctttataccccccttcaggaacaccc
ggtcacgtggcctacacctacaaaccaatcaccttccttgatgccgaagagggcgacatgtgtcttcacaccctggagcgagtggacc
ccctagtggacaacgaccgctaccctcccacttagcctccttcgtgctggcctggacgcgagcctttgtctcagagtggtccgagtttc
tatacgaggaggaccgcggaacaccgctcgaggacaggcctctcaagtctgtatacggggacacggacagccttttcgtcaccgag
cgtggacaccggctcatggaaaccagaggtaagaaacgcatcaaaaagcatgggggaaacctggttttttgaccccgaacggccaga
gctcacctggctcgtggaatgcgagaccgtctgcggggcctgcggcgcggatgcctactcccgggaatcggtatttctcgcgcccaa
```

-continued gctctacgccctcaaaagtctgcactgcccctcgtgcggcgcctcctccaagggcaagctgcgcgccaagggccacgccgcggag gggctggactatgacaccatggtcaaatgctacctggccgacgcgcagggcgaagaccggcagcgcttcagcaccagcaggacca gcctcaagcgcaccctggccagcgcgcagcccggagcgcaccccttcaccgtgacccagactacgctgacgaggaccctgcgcc cgtggaaagacatgaccctggcccgtctggacgagcaccgactactgccgtacagcgaaagccgccccaacccgcgaaacgagg agatatgctggatcgagatgccg<u>tacccatacgatgttccggattacgct</u>tag EP-Pol-HA: Mutated codons and HA tag are underlined[10]
(SEQ ID NO: 27)

atggccttggctcaagctcaccgggccgtcgtcttcacgcagaggcgccagattcaggagatcaaccgccgcgtcgtcgcgttcgc cagcaacctacgcgcgcagcaccagctcctgcccgcgcgcggcgccgacgtgcccctgcccccctctcccggcgggtccggagcc cccctacctccgggggctcgcccgcgtcaccgcttttagatgcatcatccaaggacaccccgcggcccaccgcccgccgcgcgg taccgtagtcgcgccgcggggatgcggcctcttgcaagccatcgacgccgccaccaaccagccccctggaaattaggtatcacctgg atctagcccgcgccctgacccgtctatgcgaggtaaacctgcaggagctcccgcctgacctgacgccgcgggagctccagaccatg gacagctcccatctgcgcgatgttgtcatcaagctccgaccgccgcgcggacatctggactttgggctcgcgcggcgtggtggtc cgatccaccgtaactcccctcgagcagccagacggtcaaggacaagcagccgaagtagaagaccaccagccaaaccgccaggc gaggggctcaaattcccactctgcttccttgtgcgcggtcgtcaggtcaacctcgtgcaggatgtacagcccgtgcaccgctgccagta ctgcgcacgttttacaaaagccagcacgagtgttcggcccgtcgcagggacttctactttcaccacatcaatagccactcctccaattg gtggcgggagatccagttcttcccgatcggctcgcatcctcgcaccgagcgtctctttgtcacctacgatgtagagacctatacttggat ggggcctttgggaagcagctcgtgcccttcatgctggtcatgaagttcggcggagatgagcctctagtgactgccgcgcgagacct agccgcgaaccttggatgggaccgctgggaacaagacccgcttaccttctactgcatcacccagaaaaaaatggccataggtcgcca gtttaggacctttcgcgaccacctgcaaatgctaatggcccgtgacctgtggagctcattcgtcgcttccaaccctcatcttgcagactgg gccctttcagagcacgggctcagctcccctgaagagctcacctacgaggaacttaaaaaattgccttccatcaagggcatcccgcgctt cttggaactttacattgtgggccacaacattaatggg<u>tac</u>gacgagatcgtgctcgccgcccaggtaattaacaaccgttccgaggtgc cgggaccccttccgcatcacacgcaactttatgcctcgcgcgggaaagatactcttcaacgatgtcacttcgccctgccaaatccgcgt tccaaaaagcgcacggacttttgctctgggagcagggcggatgcgacgacactgacttcaaataccagtacctcaaagtcatggtca gggacacctttgcgctcacccacacctcgctccggaaggccgcgcaggcatacgcgctaccgctagaaaagggatgctgcgcctac caggccgtcaaccagttctacatgctaggctcttaccgttcggaggccgacgggtttccgatccaagagtactggaaagaccgcgaa gagtttgtcctcaaccgcgagctgtggaaaaaaaagggacaggataagtatgacatcatcaaggaaaccctggactactgcgcccta gacgtgcaggtcaccgccgagctggtcaacaagctgcgcgactcctacgcctccttcgtgcgtgacgcggtaggtctcacagacgcc agcttcaacgtcttccagcgtccaaccatatcatccaactcacatgccatcttcaggcagatagtcttccgagcagagcagcccgcccg tagcaacctcggtcccgacctcctcgctccctcgcacgaactatacgattacgtgcgcgccagcatccgcggtggaagatgctaccct acatatcttggaatactcagagagcccctctacgttacgacatttgccggcatgtacgcctccgcgctcacccacccatgccatggggt cccccactcaacccatacgagcgcgcgcttgccgcccgcgcatggcagcaggcgctagacttgcaaggatgcaagatagactactt cgacgcgcgcctgctgcccggggtctttaccgtggacgcagaccccccggacgagacgcagctagaccccctaccgccattctgct cgcgcaagggcggccgcctctgctggaccaacgagcgcctacgcggagaggtagccaccagcgttgaccttgtcaccctgcacaa ccgcggttggcgcgtgcacctggtgcccgacgagcgcaccaccgtctttcccgaatggcggtgcgttgcgcgcgaatacgtgcagc taaacatcgcggccaaggagcgcgccgatc<u>gct</u>aagaaccaaaccctgcgctccatcgccaagttgctgtccaacgccctctacg ggtcgtttgccaccaagcttgacaacaaaaagattgtcttttctgaccagatggatgcggccaccctcaaaggcatcaccgcgggcca ggtgaatatcaaatcctcctcgttttggaaactgacaatcttagcgcagaagtcatgcccgcttttcagagggagtactcaccccaaca gctggccctcgcagacagcgatgcggaagagagtgaggacgaacgcgccccaccccttttatagcccccttcaggaacaccc ggtcacgtggcctacacctacaaaccaatcaccttccttgatgccgaagagggcgacatgtgtcttcacaccctggagcgagtggacc -continued ccctagtggacaacgaccgctacccctcccacttagcctccttcgtgctggcctggacgcgagcctttgtctcagagtggtccgagtttc tatacgaggaggaccgcggaacaccgctcgaggacaggcctctcaagtctgtatacggggacacggacagccttttcgtcaccgag cgtggacaccggctcatggaaaccagaggtaagaaacgcatcaaaaagcatgggggaaacctggttttttgaccccgaacggccaga gctcacctggctcgtggaatgcgagaccgtctgcggggcctgcggcgcggatgcctactcccgcgaatcggtatttctcgcgcccaa gctctacgccctcaaaagtctgcactgcccctcgtgcggcgcctcctccaagggcaagctgcgcgccaagggccacgccgcggag gggctggactatgacaccatggtcaaatgctacctggccgacgcgcagggcgaagaccggcagcgcttcagcaccagcaggacca gcctcaagcgcaccctggccagcgcgcagcccggagcgcacccctcaccgtgacccagactacgctgacgaggaccctgcgcc cgtggaaagacatgaccctggcccgtctggacgagcaccgactactgccgtacagcgaaagccgccccaacccgcgaaacgagg agatatgctggatcgagatgccgtaccca<u>tacgatgttccggattacgct</u>tag TPL.Prot: Tripartite leader is underlined (SEQ ID NO: 28)

<u>actctcttccgcatcgctgtctgcgagggccagctgttgggctcgcggttgaggacaaactcttcgcggtctttccagtactcttggatcg</u>

<u>gaaaccgtcggcctccgaacaggtactccgccgcgagggacctgagcgagtccgcatcgaccggatcggaaaacctctcgaga</u>

<u>aaggcgtctaaccagtcacagtcgc</u>aatgggctccagtgagcaggaactgaaagccattgtcaaagatcttggttgtgggccatatttt tgggcacctatgacaagcgctttccaggctttgtttctccacacaagctcgcctgcgccatagtcaatacggccggtcgcgagactggg ggcgtacactggatggcctttgcctggaacccgcactcaaaaacatgctacctctttgagccattggcttttctgaccagcgactcaag caggtttaccagtttgagtacgagtcactcctgcgccgtagcgccattgcttcttccccgaccgctgtataacgctggaaaagtccacc caaagcgtacagggggcccaactcggccgcctgtggactattctgctgcatgtttctccacgcctttgccaactggcccaaactcccat ggatcacaaccccaccatgaaccttattaccggggtacccaactccatgctcaacagtccccaggtacagcccaccctgcgtcgcaac caggaacagctctacagcttcctggagcgccactcgccctacttccgcagccacagtgcgcagattaggagcgccacttcttttttgtca cttgaaaaacatgtaa Full Vectors:
R6K-KCS Selectable/Counterselectable Cassette Template Plasmid (ccdB Recombineering Selection) (SEQ ID NO: 29):
This vector was used as a template for generating the counterselectable marker for recombineering by PCR.

CCTCCCACACATAACCAGGAGGTCAGATTatgcagtttaaggtttacacctataaaagagagagccgttatc gtctgtttgtggatgtacagagtgatattattgacacgcccgggcgacggatggtgatcccctggccagtgcacgtctgctgtcagata aagtctcccgtgaactttacccggtggtgcatatcggggatgaaagctggcgcatgatgaccaccgatatggccagtgtgccggtctc cgttatcggggaagaagtggctgatctcagccaccgcgaaaatgacatcaaaaacgccattaacctgatgttctggggaatataaccc agAAGCTTagcaaaagctaaaaccaggagctatttaatggcaacagttaaccagctggtacgcaaaccacgtgctcgcaaagtt gcgaaaagcaacgtgcctgcgctggaagcatgcccgcaaaaacgtggcgtatgtactcgtgtatatactaccactcctaaaaaaccga actccgcgctgcgtaaagtatgccgtgttcgtctgactaacggtttcgaagtgacttcctacatcggtggtgaaggtcacaacctgcagg agcactccgtgatcctgatccgtggcggtcgtgttaaagaccccggggtgttcgttaccacaccgtacgtggtgcgcttgactgctccg gcgttaaagaccgtaagcaggctcgttccaagtatggcgtgaagcgtcctaaggcttaatggttcgcccgcctaatgagcgggcttttt ttGAATTCTTTTTTAATTCgatctgaagatcagcagttcaacctgttgatagtacgtactaagctctcatgtttcacgtacta agctctcatgtttaacgtactaagctctcatgtttaacgaactaaaccctcatggctaacgtactaagctctcatggctaacgtactaagctc tcatgtttcacgtactaagctctcatgtttgaacaataaaattaatataaatcagcaacttaaatagcctctaaggttttaagttttataagaaa aaaagaatatataaggcttttaaagcttttaaggtttaacggttgtggacaacaagccagggatgtaacgcactgagaagcccttagag -continued cctctcaaagcaattttgagtgacacaggaacacttaacggctgacatgGGATCCccctcatcagtgccaacatagtaagcCA GTATACACTCCGCTAGCgcggccgcCTCGAGTTTCGACCTGCAGCCTGTTGACAATTA

ATCATCGGCATAGTATATCGGCATAGTATAATACGACAAGGTGAGGAACTAAAC

CATGGGATCGGCCATTGAACAAGATGGATTGCACGCAGGTTCTCCGGCCGCTTGG

GTGGAGAGGCTATTCGGCTATGACTGGGCACAACAGACAATCGGCTGCTCTGAT

GCCGCCGTGTTCCGGCTGTCAGCGCAGGGGCGCCCGGTTCTTTTTGTCAAGACCG

ACCTGTCCGGTGCCCTGAATGAACTGCAGGACGAGGCAGCGCGGCTATCGTGGC

TGGCCACGACGGGCGTTCCTTGCGCAGCTGTGCTCGACGTTGTCACTGAAGCGGG

AAGGGACTGGCTGCTATTGGGCGAAGTGCCGGGGCAGGATCTCCTGTCATCTCAC

CTTGCTCCTGCCGAGAAAGTATCCATCATGGCTGATGCAATGCGGCGGCTGCATA

CGCTTGATCCGGCTACCTGCCCATTCGACCACCAAGCGAAACATCGCATCGAGCG

AGCACGTACTCGGATGGAAGCCGGTCTTGTCGATCAGGATGATCTGGACGAAGA

GCATCAGGGGCTCGCGCCAGCCGAACTGTTCGCCAGGCTCAAGGCGCGCATGCC

CGACGGCGATGATCTCGTCGTGACCCATGGCGATGCCTGCTTGCCGAATATCATG

GTGGAAAATGGCCGCTTTTCTGGATTCATCGACTGTGGCCGGCTGGGTGTGGCGG

ACCGCTATCAGGACATAGCGTTGGCTACCCGTGATATTGCTGAAGAGCTTGGCGG

CGAATGGGCTGACCGCTTCCTCGTGCTTTACGGTATCGCCGCTCCCGATTCGCAG

CGCATCGCCTTCTATCGCCTTCTTGACGAGTTCTTCTGAGGGGATCAATTCTCTAG

AGCTCGCTGATCAGCCTCGACtgtaccGTTAGC pcDNA3.1 TTA Template Plasmid (SEQ ID NO: 30):
This plasmid served as a template for various tet-transactivator construct designs in order to recombineer them into the adenoviral vectors.

GACGGATCGGGAGATCTCCCGATCCCCTATGGTGCACTCTCAGTACAATCTGCTC

TGATGCCGCATAGTTAAGCCAGTATCTGCTCCCTGCTTGTGTGTTGGAGGTCGCT

GAGTAGTGCGCGAGCAAAATTTAAGCTACAACAAGGCAAGGCTTGACCGACAAT

TGCATGAAGAATCTGCTTAGGGTTAGGCGTTTTGCGCTGCTTCGCGATGTACGGG

CCAGATATACGCGTTGACATTGATTATTGACTAGTTATTAATAGTAATCAATTAC

GGGGTCATTAGTTCATAGCCCATATATGGAGTTCCGCGTTACATAACTTACGGTA

AATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGA

GTATTTACGGTAAACTGCCCACTTGGCAGTACATCAAGTGTATCATATGCCAAGT

ACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCT

ATTACCATGGTGATGCGGTTTTGGCAGTACATCAATGGGCGTGGATAGCGGTTTG

ACTCACGGGGATTTCCAAGTCTCCACCCCATTGACGTCAATGGGAGTTTGTTTTG

GCACCAAAATCAACGGGACTTTCCAAAATGTCGTAACAACTCCGCCCCATTGACG

CAAATGGGCGGTAGGCGTGTACGGTGGGAGGTCTATATAAGCAGAGCTCTCTGG

CTAACTAGAGAACCCACTGCTTACTGGCTTATCGAAATTAATACGACTCACTATA

GGGAGACCCAAGCTGGCTAGCGTTTAAACTTAAGCTTGGTACcCCTCCGCGGGGA

TCCTCTAGTCAGCTGACGCGTCCTATGTCTAGACTGGACAAGAGCAAAGTCATAA

```
ACTCTGCTCTGGAATTACTCAATGAAGTCGGTATCGAAGGCCTGACGACAAGGA

AACTCGCTCAAAAGCTGGGAGTTGAGCAGCCTACCCTGTACTGGCACGTGAAGA

ACAAGCGGGCCCTGCTCGATGCCCTGGCAATCGAGATGCTGGACAGGCATCATA

CCCACTTCTGCCCCCTGGAAGGCGAGTCATGGCAAGACTTTCTGCGGAACAACGC

CAAGTCATTCCGCTGTGCTCTCCTCTCACATCGCGACGGGGCTAAAGTGCATCTC

GGCACCCGCCCAACAGAGAAACAGTACGAAACCCTGGAAAATCAGCTCGCGTTC

CTGTGTCAGCAAGGCTTCTCCCTGGAGAACGCACTGTACGCTCTGTCCGCCGTGG

GCCACTTTACACTGGGCTGCGTATTGGAGGATCAGGAGCATCAAGTAGCAAAAG

AGGAAAGAGAGACACCTACCACCGATTCTATGCCCCACTTCTGAGACAAGCAA

TTGAGCTGTTCGACCATCAGGGAGCCGAACCTGCCTTCCTTTTCGGCCTGGAACT

AATCATATGTGGCCTGGAGAAACAGCTAAAGTGCGAAAGCGGCGGGCCGGCCGA

CGCCCTTGACGATTTTGACTTAGACATGCTCCCAGCCGATGCCCTTGACGACTTT

GACCTTGATATGCTGCCTGCTGACGCTCTTGACGATTTGGACCTTGACATGCTCCC

CGGGTAACTAGAATTATCTCTAGAGGATCATAATCAGCCATACCACATTTGTTCgc ggccgcCGGCAATAAAAAGACAGAATAAAACGCACGGGTGTTGGGTCGTTTGTTCG

AATTCTAGCAGGCATGCTGGGGATGCGGTGGGCTCTATGGCTTCTGAGGCGGAA

AGAACCAGCTGGGGCTCTAGGGGGTATCCCCACGCGCCCTGTAGCGGCGCATTA

AGCGCGGCGGGTGTGGTGGTTACGCGCAGCGTGACCGCTACACTTGCCAGCGCC

CTAGCGCCCGCTCCTTTCGCTTTCTTCCCTTCCTTTCTCGCCACGTTCGCCGGCTTT

CCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTG

GACTCTTGTTCCAAACTGGAACAACACTCAACCCTATCTCGGTCTATTCTTTTGAT

TTATAAGGGATTTTGCCGATTTCGGCCTATTGGTTAAAAAATGAGCTGATTTAAC

AAAAATTTAACGCGAATTAATTCTGTGGAATGTGTGTCAGTTAGGGTGTGGAAAG

TCCCCAGGCTCCCCAGCAGGCAGAAGTATGCAAAGCATGCATCTCAATTAGTCA

GCAACCAGGTGTGGAAAGTCCCCAGGCTCCCCAGCAGGCAGAAGTATGCAAAGC

ATGCATCTCAATTAGTCAGCAACCATAGTCCCGCCCCTAACTCCGCCCATCCCGC

CCCTAACTCCGCCCAGTTCCGCCCATTCTCCGCCCCATGGCTGACTAATTTTTTTT

ATTTATGCAGAGGCCGAGGCCGCCTCTGCCTCTGAGCTATTCCAGAAGTAGTGAG

GAGGCTTTTTTGGAGGCCTAGGCTTTTGCAAACCTCCGCGGGGATCCTCTAGTCA

GCTGACGCGTCCTATGTCTAGACTGGACAAGAGCAAAGTCATAAACTCTGCTCTG

GAATTACTCAATGAAGTCGGTATCGAAGGCCTGACGACAAGGAAACTCGCTCAA

AAGCTGGGAGTTGAGCAGCCTACCCTGTACTGGCACGTGAAGAACAAGCGGGCC

CTGCTCGATGCCCTGGCAATCGAGATGCTGGACAGGCATCATACCCACTTCTGCC

CCCTGGAAGGCGAGTCATGGCAAGACTTTCTGCGGAACAACGCCAAGTCATTCC

GCTGTGCTCTCCTCTCACATCGCGACGGGGCTAAAGTGCATCTCGGCACCCGCCC

AACAGAGAAACAGTACGAAACCCTGGAAAATCAGCTCGCGTTCCTGTGTCAGCA

AGGCTTCTCCCTGGAGAACGCACTGTACGCTCTGTCCGCCGTGGGCCACTTTACA

CTGGGCTGCGTATTGGAGGATCAGGAGCATCAAGTAGCAAAAGAGGAAAGAGA
```

-continued
```
GACACCTACCACCGATTCTATGCCCCCACTTCTGAGACAAGCAATTGAGCTGTTC
GACCATCAGGGAGCCGAACCTGCCTTCCTTTTCGGCCTGGAACTAATCATATGTG
GCCTGGAGAAACAGCTAAAGTGCGAAAGCGGCGGGCCGGCCGACGCCCTTGACG
ATTTTGACTTAGACATGCTCCCAGCCGATGCCCTTGACGACTTTGACCTTGATATG
CTGCCTGCTGACGCTCTTGACGATTTGGACCTTGACATGCTCCCCGGGTAACTAG
AATTATCTCTAGAGGATCATAATCAGCCATACCACATTTGTTCGAAATGACCGAC
CAAGCGACGCCCAACCTGCCATCACGAGATTTCGATTCCACCGCCGCCTTCTATG
AAAGGTTGGGCTTCGGAATCGTTTTCCGGGACGCCGGCTGGATGATCCTCCAGCG
CGGGGATCTCATGCTGGAGTTCTTCGCCCACCCCAACTTGTTTATTGCAGCTTATA
ATGGTTACAAATAAAGCAATAGCATCACAAATTTCACAAATAAAGCATTTTTTTC
ACTGCATTCTAGTTGTGGTTTGTCCAAACTCATCAATGTATCTTATCATGTCTGTA
TACCGTCGACCTCTAGCTAGAGCTTGGCGTAATCATGGTCATAGCTGTTTCCTGT
GTGAAATTGTTATCCGCTCACAATTCCACACAACATACGAGCCGGAAGCATAAA
GTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCG
GCCAACGCGCGGGGAGAGGCGGTTTGCGTATTGGGCGCTCTTCCGCTTCCTCGCT
CACTGACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGT
CAGAGGTGGCGAAACCCGACAGGACTATAAAGATACCAGGCGTTTCCCCCTGGA
AGCTCCCTCGTGCGCTCTCCTGTTCCGACCCTGCCGCTTACCGGATACCTGTCCGC
CTTTCTCCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCCGTTCA
GCCCGACCGCTGCGCCTTATCCGGTAACTATCGTCTTGAGTCCAACCCGGTAAGA
CACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTA
GAAGAACAGTATTTGGTATCTGCGCTCTGCTGAAGCCAGTTACCTTCGGAAAAAG
AGTTGGTAGCTCTTGATCCGGCAAACAAACCACCGCTGGTAGCGGTTTTTTTGTT
TGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGG
TCATGAGATTATCAAAAAGGATCTTCACCTAGATCCTTTTAAATTAAAAATGAAG
TTTTAAATCAATCTAAAGTATATATGAGTAAACTTGGTCTGACAGTTACCAATGC
TTAATCAGTGAGGCACCTATCTCAGCGATCTGTCTATTTCGTTCATCCATAGTTGC
CTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAA
TAAACCAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATCGTTGT
```

CAGAAGTAAGTTGGCCGCAGTGTTATCACTCATGGTTATGGCAGCACTGCATAAT

TCTCTTACTGTCATGCCATCCGTAAGATGCTTTTCTGTGACTGGTGAGTACTCAAC

CAAGTCATTCTGAGAATAGTGTATGCGGCGACCGAGTTGCTCTTGCCCGGCGTCA

ATACGGGATAATACCGCGCCACATAGCAGAACTTTAAAAGTGCTCATCATTGGA

AAACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAGC

GTTTCTGGGTGAGCAAAAACAGGAAGGCAAAATGCCGCAAAAAAGGGAATAAG

GGCGACACGGAAATGTTGAATACTCATACTCTTCCTTTTTCAATATTATTGAAGC

ATTTATCAGGGTTATTGTCTCATGAGCGGATACATATTTGAATGTATTTAGAAAA

ATAAACAAATAGGGGTTCCGCGCACATTTCCCCGAAAAGTGCCACCTGACGTC pcDNA3.1 mCherry Template Plasmid (SEQ ID NO: 31):
This vector served as a template to amplify various mCherry construct designs for recombineering into the adenoviral constructs.

GACGGATCGGGAGATCTCCCGATCCCCTATGGTGCACTCTCAGTACAATCTGCTC

TGATGCCGCATAGTTAAGCCAGTATCTGCTCCCTGCTTGTGTGTTGGAGGTCGCT

GAGTAGTGCGCGAGCAAAATTTAAGCTACAACAAGGCAAGGCTTGACCGACAAT

TGCATGAAGAATCTGCTTAGGGTTAGGCGTTTTGCGCTGCTTCGCGATGTACGGG

CCAGATATACGCGTTGACATTGATTATTGACTAGTTATTAATAGTAATCAATTAC

GGGGTCATTAGTTCATAGCCCATATATGGAGTTCCGCGTTACATAACTTACGGTA

AATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGA

GTATTTACGGTAAACTGCCCACTTGGCAGTACATCAAGTGTATCATATGCCAAGT

ACGCCCCCTATTGACGTCAATGACGGTAAATGGCCCGCCTGGCATTATGCCCAGT

ACATGACCTTATGGGACTTTCCTACTTGGCAGTACATCTACGTATTAGTCATCGCT

ATTACCATGGTGATGCGGTTTTGGCAGTACATCAATGGGCGTGGATAGCGGTTTG

ACTCACGGGGATTTCCAAGTCTCCACCCCATTGACGTCAATGGGAGTTTGTTTTG

GCACCAAAATCAACGGGACTTTCCAAAATGTCGTAACAACTCCGCCCCATTGACG

CAAATGGGCGGTAGGCGTGTACGGTGGGAGGTCTATATAAGCAGAGCTCTCTGG

CTAACTAGAGAACCCACTGCTTACTGGCTTATCGAAATTAATACGACTCACTATA

GGGAGACCCAAGCTGGCTAGCGTTTAAACTTAAGCTTGGTACCgcaccatggtgagcaagg gcgaggaggataacatggccatcatcaaggagttcatgcgcttcaaggtgcacatggagggctccgtgaacggccacgagttcgag atcgagggcgagggcgaggccgcccctacgagggcacccagaccgccaagctgaaggtgaccaaggggtggcccccctgccctt cgcctgggacatcctgtcccctcagttcatgtacggctccaaggcctacgtgaagcaccccgccgacatccccgactacttgaagctg tccttccccgagggcttcaagtgggagcgcgtgatgaacttcgaggacggcggcgtggtgaccgtgacccaggactcctccctgca ggacggcgagttcatctacaaggtgaagctgcgcggcaccaacttccccctccgacggccccgtaatgcagaagaagaccatgggct gggaggcctcctccgagcggatgtaccccgaggacggcgccctgaagggcgagatcaagcagaggctgaagctgaaggacggc ggccactacgacgctgaggtcaagaccacctacaaggccaagaagcccgtgcagctgcccggcgcctacaacgtcaacatcaagtt ggacatcacctcccacaacgaggactacaccatcgtggaacagtacgaacgcgccgagggccgccactccaccggcggCATG

GACGAGCTGTACAAGTAGGCGGCCGCATCGATAAGCTTGTCGACGATATCTCTA

-continued

```
GAGGGCCCGTTTAAACCCGCTGATCAGCCTCGACTGTGCCTTCTAGTTGCCAGCC

ATCTGTTGTTTGCCCCTCCCCCGTGCCTTCCTTGACCCTGGAAGGTGCCACTCCCA

CTGTCCTTTCCTAATAAAATGAGGAAATTGCATCGCATTGTCTGAGTAGGTGTCA

TTCTATTCTGGGGGGTGGGGTGGGGCAGGACAGCAAGGGGGAGGATTGGGAAGA

CAATAGCAGGCATGCTGGGGATGCGGTGGGCTCTATGGCTTCTGAGGCGGAAAG

AACCAGCTGGGGCTCTAGGGGGTATCCCCACGCGCCCTGTAGCGGCGCATTAAG

CGCGGCGGGTGTGGTGGTTACGCGCAGCGTGACCGCTACACTTGCCAGCGCCCTA

GCGCCCGCTCCTTTCGCTTTCTTCCCTTCCTTTCTCGCCACGTTCGCCGGCTTTCCC

CGTCAAGCTCTAAATCGGGGGCTCCCTTTAGGGTTCCGATTTAGTGCTTTACGGC

ACCTCGACCCCAAAAAACTTGATTAGGGTGATGGTTCACGTAGTGGGCCATCGCC

CTGATAGACGGTTTTTCGCCCTTTGACGTTGGAGTCCACGTTCTTTAATAGTGGAC

TCTTGTTCCAAACTGGAACAACACTCAACCCTATCTCGGTCTATTCTTTTGATTTA

TAAGGGATTTTGCCGATTTCGGCCTATTGGTTAAAAAATGAGCTGATTTAACAAA

AATTTAACGCGAATTAATTCTGTGGAATGTGTGTCAGTTAGGGTGTGGAAAGTCC

CCAGGCTCCCCAGCAGGCAGAAGTATGCAAAGCATGCATCTCAATTAGTCAGCA

ACCAGGTGTGGAAAGTCCCCAGGCTCCCCAGCAGGCAGAAGTATGCAAAGCATG

CATCTCAATTAGTCAGCAACCATAGTCCCGCCCCTAACTCCGCCCATCCCGCCCC

TAACTCCGCCCAGTTCCGCCCATTCTCCGCCCCATGGCTGACTAATTTTTTTATT

TATGCAGAGGCCGAGGCCGCCTCTGCCTCTGAGCTATTCCAGAAGTAGTGAGGA

GGCTTTTTGGAGGCCTAGGCTTTTGCAAACCTCCGCGGGATCCgcaccatggtgagcaa gggcgaggaggataacatggccatcatcaaggagttcatgcgcttcaaggtgcacatggagggctccgtgaacggccacgagttcg agatcgagggcgagggcgagggccgcccctacgagggcacccagaccgccaagctgaaggtgaccaagggtggccccctgccc ttcgcctgggacatcctgtcccctcagttcatgtacggctccaaggcctacgtgaagcaccccgccgacatccccgactacttgaagct gtccttccccgagggcttcaagtgggagcgcgtgatgaacttcgaggacggcggcgtggtgaccgtgacccaggactcctccctgc aggacggcgagttcatctacaaggtgaagctgcgcggcaccaacttcccctccgacggccccgtaatgcagaagaagaccatgggc tgggaggcctcctccgagcggatgtaccccgaggacggcgccctgaagggcgagatcaagcagaggctgaagctgaaggacgg cggccactacgacgctgaggtcaagaccacctacaaggccaagaagcccgtgcagctgcccggcgcctacaacgtcaacatcaag ttggacatcacctcccacaacgaggactacaccatcgtggaacagtacgaacgcgccgagggcgccgccactccaccggcggCAT

GGACGAGCTGTACAAGTAGTTCGAAATGACCGACCAAGCGACGCCCAACCTGCC

ATCACGAGATTTCGATTCCACCGCCGCCTTCTATGAAAGGTTGGGCTTCGGAATC

GTTTTCCGGGACGCCGGCTGGATGATCCTCCAGCGCGGGGATCTCATGCTGGAGT

TCTTCGCCCACCCCAACTTGTTTATTGCAGCTTATAATGGTTACAAATAAAGCAA

TAGCATCACAAATTTCACAAATAAAGCATTTTTTTCACTGCATTCTAGTTGTGGTT

TGTCCAAACTCATCAATGTATCTTATCATGTCTGTATACCGTCGACCTCTAGCTAG

AGCTTGGCGTAATCATGGTCATAGCTGTTTCCTGTGTGAAATTGTTATCCGCTCAC

AATTCCACACAACATACGAGCCGGAAGCATAAAGTGTAAAGCCTGGGGTGCCTA

ATGAGTGAGCTAACTCACATTAATTGCGTTGCGCTCACTGCCCGCTTTCCAGTCG

GGAAACCTGTCGTGCCAGCTGCATTAATGAATCGGCCAACGCGCGGGGAGAGGC

GGTTTGCGTATTGGGCGCTCTTCCGCTTCCTCGCTCACTGACTCGCTGCGCTCGGT

CGTTCGGCTGCGGCGAGCGGTATCAGCTCACTCAAAGGCGGTAATACGGTTATCC

ACAGAATCAGGGGATAACGCAGGAAAGAACATGTGAGCAAAAGGCCAGCAAAA
```

-continued

```
GGCCAGGAACCGTAAAAAGGCCGCGTTGCTGGCGTTTTTCCATAGGCTCCGCCCC

CCTGACGAGCATCACAAAAATCGACGCTCAAGTCAGAGGTGGCGAAACCCGACA

GGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCGTTCGCTC

CAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAG

CAGCCACTGGTAACAGGATTAGCAGAGCGAGGTATGTAGGCGGTGCTACAGAGT

TCTTGAAGTGGTGGCCTAACTACGGCTACACTAGAAGAACAGTATTTGGTATCTG

CGCTCTGCTGAAGCCAGTTACCTTCGGAAAAGAGTTGGTAGCTCTTGATCCGGC

AAACAAACCACCGCTGGTAGCGGTTTTTTTGTTTGCAAGCAGCAGATTACGCGCA

GAAAAAAAGGATCTCAAGAAGATCCTTTGATCTTTTCTACGGGGTCTGACGCTCA

GTGGAACGAAAACTCACGTTAAGGGATTTTGGTCATGAGATTATCAAAAAGGAT

CTTCACCTAGATCCTTTTAAATTAAAAATGAAGTTTTAAATCAATCTAAAGTATA

TATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATA

ACTACGATACGGGAGGGCTTACCATCTGGCCCCAGTGCTGCAATGATACCGCGA

GACCCACGCTCACCGGCTCCAGATTTATCAGCAATAAACCAGCCAGCCGGAAGG

GCCGAGCGCAGAAGTGGTCCTGCAACTTTATCCGCCTCCATCCAGTCTATTAATT

GTTGCCGGGAAGCTAGAGTAAGTAGTTCGCCAGTTAATAGTTTGCGCAACGTTGT

TGCCATTGCTACAGGCATCGTGGTGTCACGCTCGTCGTTTGGTATGGCTTCATTCA

GCTCCGGTTCCCAACGATCAAGGCGAGTTACATGATCCCCCATGTTGTGCAAAAA

AGCGGTTAGCTCCTTCGGTCCTCCGATCGTTGTCAGAAGTAAGTTGGCCGCAGTG

TTATCACTCATGGTTATGGCAGCACTGCATAATTCTCTTACTGTCATGCCATCCGT

AAGATGCTTTTCTGTGACTGGTGAGTACTCAACCAAGTCATTCTGAGAATAGTGT

ATGCGGCGACCGAGTTGCTCTTGCCCGGCGTCAATACGGGATAATACCGCGCCAC

ATAGCAGAACTTTAAAAGTGCTCATCATTGGAAAACGTTCTTCGGGGCGAAAACT

CTCAAGGATCTTACCGCTGTTGAGATCCAGTTCGATGTAACCCACTCGTGCACCC

AACTGATCTTCAGCATCTTTTACTTTCACCAGCGTTTCTGGGTGAGCAAAAACAG

GAAGGCAAAATGCCGCAAAAAAGGGAATAAGGGCGACACGGAAATGTTGAATA

CTCATACTCTTCCTTTTTCAATATTATTGAAGCATTTATCAGGGTTATTGTCTCAT

GAGCGGATACATATTTGAATGTATTTAGAAAAATAAACAAATAGGGGTTCCGCG

CACATTTCCCCGAAAAGTGCCACCTGACGTC
```

55

Adenovirus Polymerase Expression Construct:
Lentiviral construct allowing for constitutive expression of the HA-tagged adenovirus polymerase. The two sites that were mutated to create EP-Pol are underlined. pLV.CM-V.AdPol-HA (WT-Pol vector) (SEQ ID NO: 32):

```
AATTCATGGCCTTGGCTCAAGCTCACCGGGCCCGTCGTCTTCACGCAGAGGCGCC

AGATTCAGGAGATCAACCGCCGCGTCGTCGCGTTCGCCAGCAACCTACGCGCGC

AGCACCAGCTCCTGCCCGCGCGCGGCGCCGACGTGCCCCTGCCCCCTCTCCCGGC
```

-continued

```
GGGTCCGGAGCCCCCCTACCTCCGGGGGCTCGCCCGCGTCACCGCTTTTAGATG
CATCATCCAAGGACACCCCGCGGCCCACCGCCCGCCGCGCGGTACCGTAGTCG
CGCCGCGGGATGCGGCCTCTTGCAAGCCATCGACGCCGCCACCAACCAGCCCC
TGGAAATTAGGTATCACCTGGATCTAGCCCGCGCCCTGACCCGTCTATGCGAGGT
AAACCTGCAGGAGCTCCCGCCTGACCTGACGCCGCGGGAGCTCCAGACCATGGA
CAGCTCCCATCTGCGCGATGTTGTCATCAAGCTCCGACCGCCGCGCGCGGACATC
TGGACTTTGGGCTCGCGCGGCGTGGTGGTCCGATCCACCGTAACTCCCCTCGAGC
AGCCAGACGGTCAAGGACAAGCAGCCGAAGTAGAAGACCACCAGCCAAACCCG
CCAGGCGAGGGGCTCAAATTCCCACTCTGCTTCCTTGTGCGCGGTCGTCAGGTCA
ACCTCGTGCAGGATGTACAGCCCGTGCACCGCTGCCAGTACTGCGCACGTTTTTA
CAAAAGCCAGCACGAGTGTTCGGCCCGTCGCAGGGACTTCTACTTTCACCACATC
AATAGCCACTCCTCCAATTGGTGGCGGGAGATCCAGTTCTTCCCGATCGGCTCGC
ATCCTCGCACCGAGCGTCTCTTTGTCACCTACGATGTAGAGACCTATACTTGGAT
GGGGGCCTTTGGGAAGCAGCTCGTGCCCTTCATGCTGGTCATGAAGTTCGGCGGA
GATGAGCCTCTAGTGACTGCCGCGCGAGACCTAGCCGCGAACCTTGGATGGGAC
CGCTGGGAACAAGACCCGCTTACCTTCTACTGCATCACCCCAGAAAAAATGGCC
ATAGGTCGCCAGTTTAGGACCTTTCGCGACCACCTGCAAATGCTAATGGCCCGTG
ACCTGTGGAGCTCATTCGTCGCTTCCAACCCTCATCTTGCAGACTGGGCCCTTTCA
GAGCACGGGCTCAGCTCCCTGAAGAGCTCACCTACGAGGAACTTAAAAAATTG
CCTTCCATCAAGGGCATCCCGCGCTTCTTGGAACTTTACATTGTGGGCCACAACA
TTAATGGGTTTGACGAGATCGTGCTCGCCGCCCAGGTAATTAACAACCGTTCCGA
GGTGCCGGGACCCTTCCGCATCACACGCAACTTTATGCCTCGCGCGGGAAAGATA
CTCTTCAACGATGTCACCTTCGCCCTGCCAAATCCGCGTTCCAAAAAGCGCACGG
ACTTTTTGCTCTGGGAGCAGGGCGGATGCGACGACACTGACTTCAAATACCAGTA
CCTCAAAGTCATGGTCAGGGACACCTTTGCGCTCACCCACACCTCGCTCCGGAAG
GCCGCGCAGGCATACGCGCTACCCGTAGAAAAGGGATGCTGCGCCTACCAGGCC
GTCAACCAGTTCTACATGCTAGGCTCTTACCGTTCGGAGGCCGACGGGTTTCCGA
TCCAAGAGTACTGGAAAGACCGCGAAGAGTTTGTCCTCAACCGCGAGCTGTGGA
AAAAAAGGGACAGGATAAGTATGACATCATCAAGGAAACCCTGGACTACTGCG
CCCTAGACGTGCAGGTCACCGCCGAGCTGGTCAACAAGCTGCGCGACTCCTACG
CCTCCTTCGTGCGTGACGCGGTAGGTCTCACAGACGCCAGCTTCAACGTCTTCCA
GCGTCCAACCATATCATCCAACTCACATGCCATCTTCAGGCAGATAGTCTTCCGA
GCAGAGCAGCCCGCCCGTAGCAACCTCGGTCCCGACCTCCTCGCTCCCTCGCACG
AACTATACGATTACGTGCGCGCCAGCATCCGCGGTGGAAGATGCTACCCTACATA
TCTTGGAATACTCAGAGAGCCCCTCTACGTTTACGACATTTGCGGCATGTACGCC
TCCGCGCTCACCCACCCCATGCCATGGGGTCCCCACTCAACCCATACGAGCGCG
CGCTTGCCGCCCGCGCATGGCAGCAGGCGCTAGACTTGCAAGGATGCAAGATAG
ACTACTTCGACGCGCGCCTGCTGCCCGGGGTCTTTACCGTGGACGCAGACCCCCC
GGACGAGACGCAGCTAGACCCCCTACCGCCATTCTGCTCGCGCAAGGGCGGCCG
CCTCTGCTGGACCAACGAGCGCCTACGCGGAGAGGTAGCCACCAGCGTTGACCT
```

-continued

```
TGTCACCCTGCACAACCGCGGTTGGCGCGTGCACCTGGTGCCCGACGAGCGCACC
ACCGTCTTTCCCGAATGGCGGTGCGTTGCGCGCGAATACGTGCAGCTAAACATCG
CGGCCAAGGAGCGCGCCGATCGCGACAAAAACCAAACCCTGCGCTCCATCGCCA
AGTTGCTGTCCAACGCCCTCTACGGGTCGTTTGCCACCAAGCTTGACAACAAAAA
GATTGTCTTTTCTGACCAGATGGATGCGGCCACCCTCAAAGGCATCACCGCGGGC
CAGGTGAATATCAAATCCTCCTCGTTTTTGGAAACTGACAATCTTAGCGCAGAAG
TCATGCCCGCTTTTCAGAGGGAGTACTCACCCCAACAGCTGGCCCTCGCAGACAG
CGATGCGGAAGAGAGTGAGGACGAACGCGCCCCCACCCCCTTTTATAGCCCCCC
TTCAGGAACACCCGGTCACGTGGCCTACACCTACAAACCAATCACCTTCCTTGAT
GCCGAAGAGGGCGACATGTGTCTTCACACCCTGGAGCGAGTGGACCCCCTAGTG
GACAACGACCGCTACCCCTCCCACTTAGCCTCCTTCGTGCTGGCCTGGACGCGAG
CCTTTGTCTCAGAGTGGTCCGAGTTTCTATACGAGGAGGACCGCGGAACACCGCT
CGAGGACAGGCCTCTCAAGTCTGTATACGGGGACACGGACAGCCTTTTCGTCACC
GAGCGTGGACACCGGCTCATGGAAACCAGAGGTAAGAAACGCATCAAAAAGCA
TGGGGGAAACCTGGTTTTTGACCCCGAACGGCCAGAGCTCACCTGGCTCGTGGA
ATGCGAGACCGTCTGCGGGGCCTGCGGCGCGGATGCCTACTCCCCGGAATCGGT
ATTTCTCGCGCCCAAGCTCTACGCCCTCAAAAGTCTGCACTGCCCCTCGTGCGGC
GCCTCCTCCAAGGGCAAGCTGCGCGCCAAGGGCCACGCCGCGGAGGGGCTGGAC
TATGACACCATGGTCAAATGCTACCTGGCCGACGCGCAGGGCGAAGACCGGCAG
CGCTTCAGCACCAGCAGGACCAGCCTCAAGCGCACCCTGGCCAGCGCGCAGCCC
GGAGCGCACCCCTTCACCGTGACCCAGACTACGCTGACGAGGACCCTGCGCCCG
TGGAAAGACATGACCCTGGCCCGTCTGGACGAGCACCGACTACTGCCGTACAGC
GAAAGCCGCCCCAACCCGCGAAACGAGGAGATATGCTGGATCGAGATGCCGTAC
CCATACGATGTTCCGGATTACGCTTAGAGCACGTGACTACATTTAAACCCTAACA
AAACAAAGAGATGGGGTTACTCTCTAAATTTTATGGGTTATGTCATTGGATGTTA
TGGGTCCTTGCCACAAGAACACATCATACAAAAAATCAAAGAATGTTTTAGAAA
ACTTCCTATTAACAGGCCTATTGATTGGAAAGTATGTCAACGAATTGTGGGTCTT
TTGGGTTTTGCTGCCCCTTTTACACAATGTGGTTATCCTGCGTTGATGCCTTTGTA
TGCATGTATTCAATCTAAGCAGGCTTTCACTTTCTCGCCAACTTACAAGGCCTTTC
TGTGTAAACAATACCTGAACCTTTACCCCGTTGCCCGGCAACGGCCACCTCTGTG
CCAAGTGTTTGCTGACGCAACCCCCACTGGCTGGGGCTTGGTCATGGGCCATCAG
CGCATGCGTGGAACCTTTTCGGCTCCTCTGCCGATCCATACTGCGGAACTCCTAG
CCGCTTGTTTTGCTCGCAGCAGGTCTGGAGCAAACATTATCGGGACTGATAACTC
TGTTGTCCTATCCCGCAAATATACATCGTTTCCATGGCTGCTAGGCTGTGCTGCCA
ACTGGATCCTGCGCGGGACGTCCTTTGTTTACGTCCCGTCGGCGCTGAATCCTGC
GGACGACCCTTCTCGGGGTCGCTTGGGACTCTCTCGTCCCCTTCTCCGTCTGCCGT
TCCGACCGACCACGGGGCGCACCTCTCTTTACGCGGACTCCCCGTCTGTGCCTTC
TCATCTGCCGGACCGTGTGCACTTCGCTTCACCTCTGCACGTCGCATGGAGACCA
CCGTGAACGCCCACCAAATATTGCCCAAGGTCTTACATAAGAGGACTCTTGGACT
CTCAGCAATGTCAACGACCGACCTTGAGGCATACTTCAAAGACTGTTTGTTTAAA
GACTGGGAGGAGTTGGGGGAGGAGATTAGGTTAAAGGTCTTTGTACTAGGAGGC
```

-continued

```
TGTAGGCATAAATTGGTCTGCGCACCAGCACCATGTATCACTAGAGCGGGGTACC

TTTAAGACCAATGACTTACAAGGCAGCTGTAGATCTTAGCCACTTTTTAAAAGAA

AAGGGGGGACTTGGAAGGGCTAATTCACTCCCAACGAAGACAAGATCTGCTTTT

TGCTTGTACTGGGTCTCTCTGGTTAGACCAGATCTGAGCCTGGGAGCTCTCTGGC

TAACTAGGGAACCCACTGCTTAAGCCTCAATAAAGCTTGCCTTGAGTGCTTCAAG

TAGTGTGTGCCCGTCTGTTGTGTGACTCTGGTAACTAGAGATCCCTCAGACCCTTT

TAGTCAGTGTGGAAAATCTCTAGCAGTAGTAGTTCATGTCATCTTATTATTCANG

TATTTATAACTTGCAAAGAAATGAATATCAGAGAGTGAGAGGAACTTGTTTATTG

CAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATC

ATGTCTGGCTCTAGCTATCCCGCCCCTAACTCCGCCCAGTTCCGCCCATTCTCCGC

CCCATGGCTGACTAATTTTTTTATTTATGCAGAGGCCGAGGCCGCCTCGGCCTCT

GAGCTATTCCAGAAGTAGTGAGGAGGCTTTTTGGAGGCCTAGGCTTTTGCGTCG

AGACGTACCCAATTCGCCCTATAGTGAGTCGTATTACGCGCGCTCACTGGCCGTC

GTTTTACAACGTCGTGACTGGGAAAACCCTGGCGTTACCCAACTTAATCGCCTTG

CAGCACATCCCCCTTTCGCCAGCTGGCGTAATAGCGAAGAGGCCCGCACCGATC

GCCCTTCCCAACAGTTGCGCAGCCTGAATGGCGAATGGCGCGACGCGCCCTGTA

GCGGCGCATTAAGCGCGGCGGGTGTGGTGGTTACGCGCAGCGTGACCGCTACAC

TTGCCAGCGCCCTAGCGCCCGCTCCTTTCGCTTTCTTCCCTTCCTTTCTCGCCACGT

TCGCCGGCTTTCCCCGTCAAGCTCTAAATCGGGGGCTCCCTTTAGGGTTCCGATTT

AGTGCTTTACGGCACCTCGACCCCAAAAAACTTGATTAGGGTGATGGTTCACGTA

GTGGGCCATCGCCCTGATAGACGGTTTTTCGCCCTTTGACGTTGGAGTCCACGTT

CTTTAATAGTGGACTCTTGTTCCAAACTGGAACAACACTCAACCCTATCTCGGTC

TATTCTTTTGATTTATAAGGGATTTTGCCGATTTCGGCCTATTGGTTAAAAAATGA

GCTGATTTAACAAAAATTTAACGCGAATTTTAACAAAATATTAACGTTTACAATT

TCCCAGGTGGCACTTTTCGGGGAAATGTGCGCGGAACCCCTATTTGTTTATTTTTC

TAAATACATTCAAATATGTATCCGCTCATGAGACAATAACCCTGATAAATGCTTC

AATAATATTGAAAAAGGAAGAGTATGAGTATTCAACATTTCCGTGTCGCCCTTAT

TCCCTTTTTTGCGGCATTTTGCCTTCCTGTTTTTGCTCACCCAGAAACGCTGGTGA

AAGTAAAAGATGCTGAAGATCAGTTGGGTGCACGAGTGGGTTACATCGAACTGG

ATCTCAACAGCGGTAAGATCCTTGAGAGTTTTCGCCCCGAAGAACGTTTTCCAAT

GATGAGCACTTTTAAAGTTCTGCTATGTGGCGCGGTATTATCCCGTATTGACGCC

GGGCAAGAGCAACTCGGTCGCCGCATACACTATTCTCAGAATGACTTGGTTGAGT

ACTCACCAGTCACAGAAAAGCATCTTACGGATGGCATGACAGTAAGAGAATTAT

GCAGTGCTGCCATAACCATGAGTGATAACACTGCGGCCAACTTACTTCTGACAAC

GATCGGAGGACCGAAGGAGCTAACCGCTTTTTTGCACAACATGGGGGATCATGT

AACTCGCCTTGATCGTTGGGAACCGGAGCTGAATGAAGCCATACCAAACGACGA

GCGTGACACCACGATGCCTGTAGCAATGGCAACAACGTTGCGCAAACTATTAAC

TGGCGAACTACTTACTCTAGCTTCCCGGCAACAATTAATAGACTGGATGGAGGCG

GATAAAGTTGCAGGACCACTTCTGCGCTCGGCCCTTCCGGCTGGCTGGTTTATTG
```

-continued

```
CTGATAAATCTGGAGCCGGTGAGCGTGGGTCTCGCGGTATCATTGCAGCACTGGG

GCCAGATGGTAAGCCCTCCCGTATCGTAGTTATCTACACGACGGGGAGTCAGGC

AACTATGGATGAACGAAATAGACAGATCGCTGAGATAGGTGCCTCACTGATTAA

GCATTGGTAACTGTCAGACCAAGTTTACTCATATATACTTTAGATTGATTTAAAA

CTTCATTTTTAATTTAAAAGGATCTAGGTGAAGATCCTTTTTGATAATCTCATGAC

CAAAATCCCTTAACGTGAGTTTTCGTTCCACTGAGCGTCAGACCCCGTAGAAAAG

ATCAAAGGATCTTCTTGAGATCCTTTTTTTCTGCGCGTAATCTGCTGCTTGCAAAC

AAAAAAACCACCGCTACCAGCGGTGGTTTGTTTGCCGGATCAAGAGCTACCAAC

TCTTTTTCCGAAGGTAACTGGCTTCAGCAGAGCGCAGATACCAAATACTGTCCTT

CTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTG

TCTTACCGGGTTGGACTCAAGACGATAGTTACCGGATAAGGCGCAGCGGTCGGG

CTGAACGGGGGGTTCGTGCACACAGCCCAGCTTGGAGCGAACGACCTACACCGA

ACTGAGATACCTACAGCGTGAGCTATGAGAAAGCGCCACGCTTCCCGAAGGGAG

AAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCA

CCTCTGACTTGAGCGTCGATTTTTGTGATGCTCGTCAGGGGGCGGAGCCTATGG

AAAAACGCCAGCAACGCGGCCTTTTTACGGTTCCTGGCCTTTTGCTGGCCTTTTGC

TCACATGTTCTTTCCTGCGTTATCCCCTGATTCTGTGGATAACCGTATTACCGCCT

TTGAGTGAGCTGATACCGCTCGCCGCAGCCGAACGACCGAGCGCAGCGAGTCAG

TGAGCGAGGAAGCGGAAGAGCGCCCAATACGCAAACCGCCTCTCCCCGCGCGTT

GGCCGATTCATTAATGCAGCTGGCACGACAGGTTTCCCGACTGGAAAGCGGGCA

GTGAGCGCAACGCAATTAATGTGAGTTAGCTCACTCATTAGGCACCCCAGGCTTT

ACACTTTATGCTTCCGGCTCGTATGTTGTGTGGAATTGTGAGCGGATAACAATTT

CACACAGGAAACAGCTATGACCATGATTACGCCAAGCGCGCAATTAACCCTCAC

TAAAGGGAACAAAAGCTGGAGCTGCAAGCTTAATGTAGTCTTATGCAATACTCTT

GTAGTCTTGCAACATGGTAACGATGAGTTAGCAACATGCCTTACAAGGAGAGAA

AAAGCACCGTGCATGCCGATTGGTGGAAGTAAGGTGGTACGATCGTGCCTTATTA

GGAAGGCAACAGACGGGTCTGACATGGATTGGACGAACCACTGAATTGGAGGCG

TGGCCTGGGCGGGACTGGGGAGTGGCGAGCCCTCAGATCCTGCATATAAGCAGC

TGCTTTTTGCCTGTACTGGGTCTCTCTGGTTAGACCAGATCTGAGCCTGGGAGCTC

TCTGGCTAACTAGGGAACCCACTGCTTAAGCCTCAATAAAGCTTGCCTTGAGTGC

TTCAAGTAGTGTGTGCCCGTCTGTTGTGTGACTCTGGTAACTAGAGATCCCTCAG

ACCCTTTTAGTCAGTGTGGAAAATCTCTAGCAGTGGCGCCCGAACAGGGACCTGA

AAGCGAAAGGGAAACCAGAGCTCTCTCGACGCAGGACTCGGCTTGCTGAAGCGC

GCACGGCAAGAGGCGAGGGGCGGCGACTGGTGAGTACGCCAAAAATTTTGACTA

GCGGAGGCTAGAAGGAGAGAGATGGGTGCGAGAGCGTCAGTATTAAGCGGGGG

AGAATTAGATCGCGATGGGAAAAAATTCGGTTAAGGCCAGGGGGAAAGAAAAA

ATATAAATTAAAACATATAGTATGGGCAAGCAGGGAGCTAGAACGATTCGCAGT

TAATCCTGGCCTGTTAGAAACATCAGAAGGCTGTAGACAAATACTGGGACAGCT

ACAACCATCCCTTCAGACAGGATCAGAAGAACTTAGATCATTATATAATACAGTA
```

-continued

```
GCAACCCTCTATTGTGTGCATCAAAGGATAGAGATAAAAGACACCAAGGAAGCT

TTAGACAAGATAGAGGAAGAGCAAAACAAAAGTAAGACCACCGCACAGCAAGC

GGCCGCTGATCTTCAGACCTGGAGGAGGAGATATGAGGGACAATTGGAGAAGTG

AATTATATAAATATAAAGTAGTAAAAATTGAACCATTAGGAGTAGCACCCACCA

AGGCAAAGAGAAGAGTGGTGCAGAGAGAAAAAAGAGCAGTGGGAATAGGAGCT

TTGTTCCTTGGGTTCTTGGGAGCAGCAGGAAGCACTATGGGCGCAGCCTCAATGA

CGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGG

CATCAAGCAGCTCCAGGCAAGAATCCTGGCTGTGGAAAGATACCTAAAGGATCA

ACAGCTCCTGGGGATTTGGGGTTGCTCTGGAAAACTCATTTGCACCACTGCTGTG

CCTTGGAATGCTAGTTGGAGTAATAAATCTCTGGAACAGATTGGAATCACACGAC

CTGGATGGAGTGGGACAGAGAAATTAACAATTACACAAGCTTAATACACTC CTT

AATTGAAGAATCGCAAAACCAGCAAGAAAAGAATGAACAAGAATTATTGGAATT

AGATAAATGGGCAAGTTTGTGGAATTGGTTTAACATAACAAATTGGCTGTGGTAT

ATAAAATTATTCATAATGATAGTAGGAGGCTTGGTAGGTTTAAGAATAGTTTTTG

CTGTACTTTCTATAGTGAATAGAGTTAGGCAGGGATATTCACCATTATCGTTTCA

GACCCACCTCCCAACCCCGAGGGGACCCGACAGGCCCGAAGGAATAGAAGAAG

AAGGTGGAGAGAGAGACAGAGACAGATCCATTCGATTAGTGAACGGATCTCGAC

GGTATCGGTTTTAAAAGAAAAGGGGGGATTGGGGGGTACAGTGCAGGGGAAAG

AATAGTAGACATAATAGCAACAGACATACAAACTAAAGAATTACAAAAACAAAT

TACAAAAATTCAAAATTTTATCGATAAGCTTGGGAGTTCCGCGTTACATAACTTA

CGGTAAATGGCCCGCCTGGCTGACCGCCCAACGACCCCCGCCCATTGACGTCAAT

AATGACGTATGTTCCCATAGTAACGCCAATAGGGACTTTCCATTGACGTCAATGG

GTGGAGTATTTACGGTAAACTGCCCACTTGGCAGTACATCAAGTGTATCATATGC

CAAGTACGCCCCCTATTGACGGTCAATGACGGTAAATGGCCCGCCTGGCATTATG

CCCAGTACATGACCTTATGGGACTTTCCTACTTGGCAGTACATCTACGTATTAGTC

ATCGCTATTACCATGGTGATGCGGTTTTGGCAGTACATCAATGGGCGTGGATAGC

GGTTTGACTCACGGGGATTTCCAAGTCTCCACCCCATTGACGTCAATGGGAGTTT

GTTTTGGCACCAAAATCAACGGGACTTTCCAAAATGTCGTAACAACTCCGCCCCA

TTGACGCAAATGGGCGGTAGGCGTGTACGGTGGGAGGTCTATATAAGCAGAGCT

CGTTTAGTGAACCGTCAGATCGCCTGGAGACGCCATCCACGCTGTTTTGACCTCC

ATAGAAGACACCGACKTCTAGCTAGAGGATCCCCCGGGCTGCAGG
```

Ad-Prot Constitutive Expression Construct.

Lentivirus construct for constitutive expression of Ad-prot. The tripartite leader sequence and ad-prot sequence are lowercase. pLenti.CMV.TPL.Protease.Hygro (cProt vector) (SEQ ID NO: 33):

```
CAGGTGGCACTTTTCGGGGAAATGTGCGCGGAACCCCTATTTGTTTATTT

TTCTAAATACATTCAAATATGTATCCGCTCATGAGACAATAACCCTGATA

AATGCTTCAATAATATTGAAAAAGGAAGAGTATGAGTATTCAACATTTCC
```

-continued
```
GTGTCGCCCTTATTCCCTTTTTTGCGGCATTTTGCCTTCCTGTTTTTGCT

CACCCAGAAACGCTGGTGAAAGTAAAAGATGCTGAAGATCAGTTGGGTGC

ACGAGTGGGTTACATCGAACTGGATCTCAACAGCGGTAAGATCCTTGAGA

GTTTTCGCCCCGAAGAACGTTTTCCAATGATGAGCACTTTTAAAGTTCTG

CTATGTGGCGCGGTATTATCCCGTATTGACGCCGGGCAAGAGCAACTCGG

TCGCCGCATACACTATTCTCAGAATGACTTGGTTGAGTACTCACCAGTCA

CAGAAAAGCATCTTACGGATGGCATGACAGTAAGAGAATTATGCAGTGCT
```

-continued

```
GCCATAACCATGAGTGATAACACTGCGGCCAACTTACTTCTGACAACGAT
CGGAGGACCGAAGGAGCTAACCGCTTTTTTGCACAACATGGGGGATCATG
TAACTCGCCTTGATCGTTGGGAACCGGAGCTGAATGAAGCCATACCAAAC
GACGAGCGTGACACCACGATGCCTGTAGCAATGGCAACAACGTTGCGCAA
ACTATTAACTGGCGAACTACTTACTCTAGCTTCCCGGCAACAATTAATAG
ACTGGATGGAGGCGGATAAAGTTGCAGGACCACTTCTGCGCTCGGCCCTT
CCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCG
TAGTTATCTACACGACGGGGAGTCAGGCAACTATGGATGAACGAAATAGA
CAGATCGCTGAGATAGGTGCCTCACTGATTAAGCATTGGTAACTGTCAGA
CCAAGTTTACTCATATATACTTTAGATTGATTTAAAACTTCATTTTTAAT
TTAAAAGGATCTAGGTGAAGATCCTTTTTGATAATCTCATGACCAAAATC
CCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGC
AAACAAAAAAACCACCGCTACCAGCGGTGGTTTGTTTGCCGGATCAAGAG
CTACCAACTCTTTTTCCGAAGGTAACTGGCTTCAGCAGAGCGCAGATACC
AAATACTGTCCTTCTAGTGTAGCCGTAGTTAGGCCACCACTTCAAGAACT
CTGTAGCACCGCCTACATACCTCGCTCTGCTAATCCTGTTACCAGTGGCT
GCTGCCAGTGGCGATAAGTCGTGTCTTACCGGGTTGGACTCAAGACGATA
GTTACCGGATAAGGCGCAGCGGTCGGGCTGAACGGGGGGTTCGTGCACAC
AGCCCAGCTTGGAGCGAACGACCTACACCGAACTGAGATACCTACAGCGT
GAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGA
CTTGAGCGTCGATTTTTGTGATGCTCGTCAGGGGGCGGAGCCTATGGAA
AAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGT
ATTACCGCCTTTGAGTGAGCTGATACCGCTCGCCGCAGCCGAACGACCGA
GCGCAGCGAGTCAGTGAGCGAGGAAGCGGAAGAGCGCCCAATACGCAAAC
CGCCTCTCCCCGCGCGTTGGCCGATTCATTAATGCAGCTGGCACGACAGG
TTTCCCGACTGGAAAGCGGGCAGTGAGCGCAACGCAATTAATGTGAGTTA
GCTCACTCATTAGGCACCCCAGGCTTTACACTTTATGCTTCCGGCTCGTA
TGTTGTGTGGAATTGTGAGCGGATAACAATTTCACACAGGAAACAGCTAT
GACCATGATTACGCCAAGCGCGCAATTAACCCTCACTAAAGGGAACAAAA
GCTGGAGCTGCAAGCTTAATGTAGTCTTATGCAATACTCTTGTAGTCTTG
CAACATGGTAACGATGAGTTAGCAACATGCCTTACAAGGAGAAAAAGC
ACCGTGCATGCCGATTGGTGGAAGTAAGGTGGTACGATCGTGCCTTATTA
GGAAGGCAACAGACGGGTCTGACATGGATTGGACGAACCACTGAATTGCC
GCATTGCAGAGATATTGTATTTAAGTGCCTAGCTCGATACAATAAACGGG
TCTCTCTGGTTAGACCAGATCTGAGCCTGGGAGCTCTCTGGCTAACTAGG
```

-continued

```
GAACCCACTGCTTAAGCCTCAATAAAGCTTGCCTTGAGTGCTTCAAGTAG
TGTGTGCCCGTCTGTTGTGTGACTCTGGTAACTAGAGATCCCTCAGACCC
TTTTAGTCAGTGTGGAAAATCTCTAGCAGTGGCGCCCGAACAGGGACCTG
AAAGCGAAAGGGAAACCAGAGCTCTCTCGACGCAGGACTCGGCTTGCTGA
AGCGCGCACGGCAAGAGGCGAGGGGCGGCGACTGGTGAGTACGCCAAAAA
TTTTGACTAGCGGAGGCTAGAAGGAGAGAGATGGGTGCGAGAGCGTCAGT
ATTAAGCGGGGAGAATTAGATCGCGATGGGAAAAAATTCGGTTAAGGCC
AGGGGGAAAGAAAAAATATAAATTAAAACATATAGTATGGGCAAGCAGGG
AGCTAGAACGATTCGCAGTTAATCCTGGCCTGTTAGAAACATCAGAAGGC
TGTAGACAAATACTGGGACAGCTACAACCATCCCTTCAGACAGGATCAGA
AGAACTTAGATCATTATATAATACAGTAGCAACCCTCTATTGTGTGCATC
AAAGGATAGAGATAAAAGACACCAAGGAAGCTTTAGACAAGATAGAGGAA
GAGCAAAACAAAAGTAAGACCACCGCACAGCAAGCGGCCGCTGATCTTCA
GACCTGGAGGAGGAGATATGAGGGACAATTGGAGAAGTGAATTATATAAA
TATAAAGTAGTAAAAATTGAACCATTAGGAGTAGCACCCACCAAGGCAAA
GAGAAGAGTGGTGCAGAGAGAAAAAAGAGCAGTGGGAATAGGAGCTTTGT
TCCTTGGGTTCTTGGGAGCAGCAGGAAGCACTATGGGCGCAGCCTCAATG
ACGCTGACGGTACAGGCCAGACAATTATTGTCTGGTATAGTGCAGCAGCA
GAACAATTTGCTGAGGGCTATTGAGGCGCAACAGCATCTGTTGCAACTCA
CAGTCTGGGGCATCAAGCAGCTCCAGGCAAGAATCCTGGCTGTGGAAAGA
TACCTAAAGGATCAACAGCTCCTGGGGATTTGGGGTTGCTCTGGAAAACT
CATTTGCACCACTGCTGTGCCTTGGAATGCTAGTTGGAGTAATAAATCTC
TGGAACAGATTGGAATCACACGACCTGGATGGAGTGGGACAGAGAAATTA
ACAATTACACAAGCTTAATACACTCCTTAATTGAAGAATCGCAAAACCAG
CAAGAAAAGAATGAACAAGAATTATTGGAATTAGATAAATGGGCAAGTTT
GTGGAATTGGTTTAACATAACAAATTGGCTGTGGTATATAAAATTATTCA
TAATGATAGTAGGAGGCTTGGTAGGTTTAAGAATAGTTTTTGCTGTACTT
TCTATAGTGAATAGAGTTAGGCAGGGATATTCACCATTATCGTTTCAGAC
CCACCTCCCAACCCCGAGGGGACCCGACAGGCCCGAAGGAATAGAAGAAG
AAGGTGGAGAGAGAGACAGAGACAGATCCATTCGATTAGTGAACGGATCT
CGACGGTTAACTTTTAAAAGAAAAGGGGGGATTGGGGGGTACAGTGCAGG
GGAAAGAATAGTAGACATAATAGCAACAGACATACAAACTAAAGAATTAC
AAAAACAAATTACAAAAATTCAAAATTTTATCGATAAGCTTGGGAGTTCC
GCGTTACATAACTTACGGTAAATGGCCCGCCTGGCTGACCGCCCAACGAC
CCCCGCCCATTGACGTCAATAATGACGTATGTTCCCATAGTAACGCCAAT
AGGGACTTTCCATTGACGTCAATGGGTGGAGTATTTACGGTAAACTGCCC
ACTTGGCAGTACATCAAGTGTATCATATGCCAAGTACGCCCCCTATTGAC
GTCAATGACGGTAAATGGCCCGCCTGGCATTATGCCCAGTACATGACCTT
ATGGGACTTTCCTACTTGGCAGTACATCTACGTATTAGTCATCGCTATTA
CCATGGTGATGCGGTTTTGGCAGTACATCAATGGGCGTGGATAGCGGTTT
GACTCACGGGGATTTCCAAGTCTCCACCCCATTGACGTCAATGGGAGTTT
```

GTTTTGGCACCAAAATCAACGGGACTTTCCAAAATGTCGTAACAACTCCG

CCCCATTGACGCAAATGGGCGGTAGGCGTGTACGGTGGGAGGTCTATATA

AGCAGAGCTCGTTTAGTGAACCGTCAGATCGCCTGGAGACGCCATCCACG

CTGTTTTGACCTCCATAGAAGACACCGACTCTAGTCCAGTGTGGTGGAAT

TCTGCAGATATCAACAAGTTTGTACAAAAAAGCAGGCTTTAAAGGAACCA

ATTCAGTCGACTGGATCCGGTACCGAATTCGCGGCCGCactctcttccgc atcgctgtctgcgagggccagctgtttgggctcgcggttgaggacaaactc ttcgcggtctttccagtactcttggatcggaaacccgtcggcctccgaac aggtactccgccgccagggacctgagcgagtccgcatcgaccggatcgg aaaacctctcgagaaaggcgtctaaccagtcacagtcgcaatgggctcca gtgagcaggaactgaaagccattgtcaaagatcttggttgtgggccatat ttttgggcacctatgacaagcgctttccaggctttgtttctccacacaa gctcgcctgcgccatagtcaatacggccggtcgcgagactgggggcgtac actggatggcctttgcctggaacccgcactcaaaaacatgctacctcttt gagccctttggcttttctgaccagcgactcaagcaggtttaccagtttga gtacgagtcactcctgcgccgtagcgccattgcttcttccccgaccgct gtataacgctggaaaagtccacccaaagcgtacaggggcccaactcggcc gcctgtggactattctgctgcatgtttctccacgcctttgccaactggcc ccaaactcccatggatcacaaccccaccatgaaccttattaccggggtac ccaactccatgctcaacagtcccaggtacagccaccctgcgtcgcaac caggaacagctctacagcttcctggagcgccactcgccctacttccgcag ccacagtgcgcagattaggagcgccacttcttttttgtcacttgaaaaaca tgtaaTCTAGACCCAGCTTTCTTGTACAAAGTGGTTGATATCCAGCACAG

TGGCGGCCGCTCGACAATCAACCTCTGGATTACAAAATTTGTGAAAGATT

GACTGGTATTCTTAACTATGTTGCTCCTTTTACGCTATGTGGATACGCTG

CTTTAATGCCTTTGTATCATGCTATTGCTTCCCGTATGGCTTTCATTTTC

TCCTCCTTGTATAAATCCTGGTTGCTGTCTCTTTATGAGGAGTTGTGGCC

CGTTGTCAGGCAACGTGGCGTGGTGTGCACTGTGTTTGCTGACGCAACCC

CCACTGGTTGGGGCATTGCCACCACCTGTCAGCTCCTTTCCGGGACTTTC

GCTTTCCCCCTCCCTATTGCCACGGCGGAACTCATCGCCGCCTGCCTTGC

CCGCTGCTGGACAGGGGCTCGGCTGTTGGGCACTGACAATTCCGTGGTGT

TGTCGGGGAAGCTGACGTCCTTTCCATGGCTGCTCGCCTGTGTTGCCACC

TGGATTCTGCGCGGGACGTCCTTCTGCTACGTCCCTTCGGCCCTCAATCC

AGCGGACCTTCCTTCCCGCGGCCTGCTGCCGGCTCTGCGGCCTCTTCCGC

GTCTTCGCCTTCGCCCTCAGACGAGTCGGATCTCCCTTTGGGCCGCCTCC

CCGCCTGGAATTCTGCAGATATCCGGACTAGTGATCTCTCGAGGTTAACG

AATTCTACCGGGTAGGGGAGGCGCTTTTCCCAAGGCAGTCTGGAGCATGC

GCTTTAGCAGCCCCGCTGGGCACTTGGCGCTACACAAGTGGCCTCTGGCC

TCGCACACATTCCACATCCACCGGTAGGCGCCAACCGGCTCCGTTCTTTG

GTGGCCCCTTCGCGCCACCTTCTACTCCTCCCCTAGTCAGGAAGTTCCCC

CCCGCCCCGCAGCTCGCGTCGTGCAGGACGTGACAAATGGAAGTAGCACG

TCTCACTAGTCTCGTGCAGATGGACAGCACCGCTGAGCAATGGAAGCGGG

TAGGCCTTTGGGGCAGCGGCCAATAGCAGCTTTGCTCCTTCGCTTTCTGG

GCTCAGAGGCTGGGAAGGGGTGGGTCCGGGGCGGGCTCAGGGGCGGGCT

CAGGGGCGGGGCGGGCGCCCGAAGGTCCTCCGGAGGCCCGGCATTCTGCA

CGCTTCAAAAGCGCACGTCTGCCGCGCTGTTCTCCTCTTCCTCATCTCCG

GGCCTTTCGACCTGCATCCCGCCACCATGAAAAAGCCTGAACTCACCGCG

ACGTCTGTCGAGAAGTTTCTGATCGAAAAGTTCGACAGCGTCTCCGACCT

GATGCAGCTCTCGGAGGGCGAAGAATCTCGTGCTTTCAGCTTCGATGTAG

GAGGGCGTGGATATGTCCTGCGGGTAAATAGCTGCGCCGATGGTTTCTAC

AAAGATCGTTATGTTTATCGGCACTTTGCATCGGCCGCGCTCCCGATTCC

GGAAGTGCTTGACATTGGGGAATTCAGCGAGAGCCTGACCTATTGCATCT

CCCGCCGTGCACAGGGTGTCACGTTGCAAGACCTGCCTGAAACCGAACTG

CCCGCTGTTCTGCAGCCGGTCGCGGAGGCCATGGATGCGATCGCTGCGGC

CGATCTTAGCCAGACGAGCGGGTTCGGCCCATTCGGACCGCAAGGAATCG

GTCAATACACTACATGGCGTGATTTCATATGCGCGATTGCTGATCCCCAT

GTGTATCACTGGCAAACTGTGATGGACGACACCGTCAGTGCGTCCGTCGC

GCAGGCTCTCGATGAGCTGATGCTTTGGGCCGAGGACTGCCCCGAAGTCC

GGCACCTCGTGCACGCGGATTTCGGCTCCAACAATGTCCTGACGGACAAT

GGCCGCATAACAGCGGTCATTGACTGGAGCGAGGCGATGTTCGGGGATTC

CCAATACGAGGTCGCCAACATCTTCTTCTGGAGGCCGTGGTTGGCTTGTA

TGGAGCAGCAGACGCGCTACTTCGAGCGGAGGCATCCGGAGCTTGCAGGA

TCGCCGCGGCTCCGGGCGTATATGCTCCGCATTGGTCTTGACCAACTCT

ATCAGAGCTTGGTTGACGGCAATTTCGATGATGCAGCTTGGGCGCAGGGT

CGATGCGACGCAATCGTCCGATCCGGAGCCGGGACTGTCGGGCGTACACA

AATCGCCCGCAGAAGCGCGGCCGTCTGGACCGATGGCTGTGTAGAAGTAC

TCGCCGATAGTGGAAACCGACGCCCCAGCACTCGTCCGAGGGCAAAGGAA

TAGAGTAGATGCCGACCGAACAAGAGCTGATTTCGAGAACGCCTCAGCCA

GCAACTCGCGCGAGCCTAGCAAGGCAAATGCGAGAGAACGGCCTTACGCT

TGGTGGCACAGTTCTCGTCCACAGTTCGCTAAGCTCGCTCGGCTGGGTCG

CGGGAGGGCCGGTCGCAGTGATTCAGGCCCTTCTGGATTGTGTTGGTCCC

CAGGGCACGATTGTCATGCCCACGCACTCGGGTGATCTGACTGATCCCGC

AGATTGGAGATCGCCGCCCGTGCCTGCCGATTGGGTGCAGATCCGTCGAG

GGCCCGGTACCTTTAAGACCAATGACTTACAAGGCAGCTGTAGATCTTAG

CCACTTTTAAAAGAAAGGGGGGACTGGAAGGGCTAGCTCACTCCCAAC

GAAGACAAGATCTGCTTTTTGCTTGTACTGGGTCTCTCTGGTTAGACCAG

ATCTGAGCCTGGGAGCTCTCTGGCTGCCTAGGGAACCCACTGCTTAAGCC

TCAATAAAGCTTGCCTTGAGTGCTTCAAGTAGTGTGTGCCCGTCTGTTGT

GTGACTCTGGTAACTAGAGATCCCTCAGACCCTTTTAGTCAGTGTGGAAA

ATCTCTAGCAGTAGTAGTTCATGTCATCTTATTATTCAGTATTTATAACT

TGCAAAGAAATGAATATCAGAGAGTGAGAGGAACTTGTTTATTGCAGCTT

-continued

ATAATGGTTACAAATAAAGCAATAGCATCACAAATTTCACAAATAAAGCA

TTTTTTTCACTGCATTCTAGTTGTGGTTTGTCCAAACTCATCAATGTATC

TTATCATGTCTGGCTCTAGCTATCCCGCCCCTAACTCCGCCCAGTTCCGC

CCATTCTCCGCCCCATGGCTGACTAATTTTTTTTATTTATGCAGAGGCCG

AGGCCGCCTCGGCCTCTGAGCTATTCCAGAAGTAGTGAGGAGGCTTTTTT

GGAGGCCTAGGCTTTTGCGTCGAGACGTACCCAATTCGCCCTATAGTGAG

TCGTATTACGCGCGCTCACTGGCCGTCGTTTTACAACGTCGTGACTGGGA

AAACCCTGGCGTTACCCAACTTAATCGCCTTGCAGCACATCCCCCTTTCG

CCAGCTGGCGTAATAGCGAAGAGGCCCGCACCGATCGCCCTTCCCAACAG

TTGCGCAGCCTGAATGGCGAATGGCGCGACGCGCCCTGTAGCGGCGCATT

AAGCGCGGCGGGTGTGGTGGTTACGCGCAGCGTGACCGCTACACTTGCCA

GCGCCCTAGCGCCCGCTCCTTTCGCTTTCTTCCCTTCCTTTCTCGCCACG

TTCGCCGGCTTTCCCCGTCAAGCTCTAAATCGGGGGCTCCCTTTAGGGTT

CCGATTTAGTGCTTTACGGCACCTCGACCCCAAAAAACTTGATTAGGGTG

ATGGTTCACGTAGTGGGCCATCGCCCTGATAGACGGTTTTTCGCCCTTTG

ACGTTGGAGTCCACGTTCTTTAATAGTGGACTCTTGTTCCAAACTGGAAC

AACACTCAACCCTATCTCGGTCTATTCTTTTGATTTATAAGGGATTTTGC

CGATTTCGGCCTATTGGTTAAAAAATGAGCTGATTTAACAAAAATTTAAC

GCGAATTTTAACAAAATATTAACGTTTACAATTTCC

Ad-Prot Inducible Expression Construct:

Lentivirus construct for inducible expression of ad-prot. Ad-prot was placed under control of the TRE3G promoter. The tripartite leader sequence and ad-prot sequence are lowercase. pLVX.TRE3G.TPL.AVP.Puro (iProt vector) (SEQ ID NO: 34):

TGGAAGGGCTAATTCACTCCCAAAGAAGACAAGATATCCTTGATCTGTGG

ATCTACCACACACAAGGCTACTTCCCTGATTAGCAGAACTACACACCAGG

GCCAGGGGTCAGATATCCACTGACCTTTGGATGGTGCTACAAGCTAGTAC

CAGTTGAGCCAGATAAGGTAGAAGAGGCCAATAAAGGAGAGAACACCAGC

TTGTTACACCCTGTGAGCCTGCATGGGATGGATGACCCGGAGAGAGAAGT

GTTAGAGTGGAGGTTTGACAGCCGCCTAGCATTTCATCACGTGGCCCGAG

AGCTGCATCCGGAGTACTTCAAGAACTGCTGATATCGAGCTTGCTACAAG

GGACTTTCCGCTGGGGACTTTCCAGGGAGGCGTGGCCTGGGCGGGACTGG

GGAGTGGCGAGCCCTCAGATCCTGCATATAAGCAGCTGCTTTTTGCCTGT

ACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTC

AAGTAGTGTGTGCCCGTCTGTTGTGTGACTCTGGTAACTAGAGATCCCTC

AGACCCTTTTAGTCAGTGTGGAAAATCTCTAGCAGTGGCGCCCGAACAGG

GACTTGAAAGCGAAAGGGAAACCAGAGGAGCTCTCTCGACGCAGGACTCG

GCTTGCTGAAGCGCGCACGGCAAGAGGCGAGGGGCGGCGACTGGTGAGTA

CGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCG

GTTAAGGCCAGGGGGAAAGAAAAAATATAAATTAAAACATATAGTATGGG

CAAGCAGGGAGCTAGAACGATTCGCAGTTAATCCTGGCCTGTTAGAAACA

TCAGAAGGCTGTAGACAAATACTGGGACAGCTACAACCATCCCTTCAGAC

AGGATCAGAAGAACTTAGATCATTATATAATACAGTAGCAACCCTCTATT

GTGTGCATCAAAGGATAGAGATAAAAGACACCAAGGAAGCTTTAGACAAG

ATAGAGGAAGAGCAAAACAAAAGTAAGACCACCGCACAGCAAGCGGCCGG

CCGCTGATCTTCAGACCTGGAGGAGGAGATATGAGGGACAATTGGAGAAG

TGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGA

ATAGGAGCTTTGTTCCTTGGGTTCTTGGGAGCAGCAGGAAGCACTATGGG

CGCAGCGTCAATGACGCTGACGGTACAGGCCAGACAATTATTGTCTGGTA

TAGTGCAGCAGCAGAACAATTTGCTGAGGGCTATTGAGGCGCAACAGCAT

CTGTTGCAACTCACAGTCTGGGGCATCAAGCAGCTCCAGGCAAGAATCCT

GGCTGTGGAAAGATACCTAAAGGATCAACAGCTCCTGGGGATTTGGGGTT

GCTCTGGAAAACTCATTTGCACCACTGCTGTGCCTTGGAATGCTAGTTGG

AGTAATAAATCTCTGGAACAGATTTGGAATCACACGACCTGGATGGAGTG

GGACAGAGAAATTAACAATTACACAAGCTTAATACACTCCTTAATTGAAG

AATCGCAAAACCAGCAAGAAAAGAATGAACAAGAATTATTGGAATTAGAT

AAATGGGCAAGTTTGTGGAATTGGTTTAACATAACAAATTGGCTGTGGTA

TATAAAATTATTCATAATGATAGTAGGAGGCTTGGTAGGTTTAAGAATAG

TTTTTGCTGTACTTTCTATAGTGAATAGAGTTAGGCAGGGATATTCACCA

TTATCGTTTCAGACCCACCTCCCAACCCCGAGGGGACCCGACAGGCCCGA

AGGAATAGAAGAAGAAGGTGGAGAGAGAGACAGAGACAGATCCATTCGAT

TAGTGAACGGATCTCGACGGTATCGCCTTTAAAAGAAAAGGGGGGATTGG

GGGGTACAGTGCAGGGGAAAGAATAGTAGACATAATAGCAACAGACATAC

AAACTAAAGAACTACAAAAACAAATTACAAAAATTCAAAATTTTCGGGTT

TATTACAGGGACAGCAGAGATCCAGTTTATCGATGAGGCCCTTTCGTCTT

CACTCGAGTTTACTCCCTATCAGTGATAGAGAACGTATGAAGAGTTTACT

CCCTATCAGTGATAGAGAACGTATGCAGACTTTACTCCCTATCAGTGATA

GAGAACGTATAAGGAGTTTACTCCCTATCAGTGATAGAGAACGTATGACC

AGTTTACTCCCTATCAGTGATAGAGAACGTATCTACAGTTTACTCCCTAT

CAGTGATAGAGAACGTATATCCAGTTTACTCCCTATCAGTGATAGAGAAC

GTATGTCGAGGTAGGCGTGTACGGTGGGCGCCTATAAAAGCAGAGCTCGT

TTAGTGAACCGTCAGATCGCCTGGAGCAATTCCACAACACTTTTGTCTTA

TACTTGGATCCGCactctcttccgcatcgctgtctgcgagggccagctgt tgggctcgcggttgaggacaaactcttcgcggtattccagtactcttgga tcggaaacccgtcggcctccgaacaggtactccgccgccgagggacctga gcgagtccgcatcgaccggatcggaaaacctctcgagaaaggcgtctaac cagtcacagtcgcaatgggctccagtgagcaggaactgaaagccattgtc aaagatcttggttgtgggccatatttttttgggcacctatgacaagcgctt -continued

```
tccaggctttgtttctccacacaagctcgcctgcgccatagtcaatacgg
ccggtcgcgagactgggggcgtacactggatggcctttgcctggaacccg
cactcaaaaacatgctacctctttgagccctttggcttttctgaccagcg
actcaagcaggtttaccagtttgagtacgagtcactcctgcgccgtagcg
ccattgcttcttccccgaccgctgtataacgctggaaaagtccacccaa
agcgtacaggggcccaactcggccgcctgtggactattctgctgcatgtt
tctccacgcctttgccaactggccccaaactcccatggatcacaacccca
ccatgaaccttattaccggggtacccaactccatgctcaacagtccccag
gtacagcccaccctgcgtcgcaaccaggaacagctctacagcttcctgga
gcgccactcgccctacttccgcagccacagtgcgcagattaggagcgcca
cttcttttgtcacttgaaaaacatgtaaGCGCCGGCTCTAGATCGCGAA
CGCGTGAATTCTACCGGGTAGGGGAGGCGCTTTTCCCAAGGCAGTCTGGA
GCATGCGCTTTAGCAGCCCCGCTGGGCACTTGGCGCTACACAAGTGGCCT
CTGGCCTCGCACACATTCCACATCCACCGGTAGGCGCCAACCGGCTCCGT
TCTTTGGTGGCCCCTTCGCGCCACCTTCTACTCCTCCCCTAGTCAGGAAG
TTCCCCCCCGCCCCGCAGCTCGCGTCGTCAGGACGTGACAAATGGAAGT
AGCACGTCTCACTAGTCTCGTGCAGATGGACAGCACCGCTGAGCAATGGA
AGCGGGTAGGCCTTTGGGGCAGCGGCCAATAGCAGCTTTGCTCCTTCGCT
TTCTGGGCTCAGAGGCTGGGAAGGGGTGGGTCCGGGGCGGGCTCAGGGG
CGGGCTCAGGGGCGGGCGGGCGCCCGAAGGTCCTCCGGAGGCCCGGCAT
TCTGCACGCTTCAAAAGCGCACGTCTGCCGCGCTGTTCTCCTCTTCCTCA
TCTCCGGGCCTTTCGACCTGCAGCCCAAGCTTACCATGACCGAGTACAAG
CCCACGGTGCGCCTCGCCACCCGCGACGACGTCCCCAGGGCCGTACGCAC
CCTCGCCGCCGCGTTCGCCGACTACCCCGCCACGCGCCACACCGTCGATC
CGGACCGCCACATCGAGCGGGTCACCGAGCTGCAAGAACTCTTCCTCACG
CGCGTCGGGCTCGACATCGGCAAGGTGTGGGTCGCGGACGACGGCGCCGC
GGTGGCGGTCTGGACCACGCCGGAGAGCGTCGAAGCGGGGCGGTGTTCG
CCGAGATCGGCCCGCGCATGGCCGAGTTGAGCGGTTCCCGGCTGGCCGCG
CAGCAACAGATGGAAGGCCTCCTGGCGCCGCACCGGCCCAAGGAGCCCGC
GTGGTTCCTGGCCACCGTCGGCGTCTCGCCCGACCACCAGGGCAAGGGTC
TGGGCAGCGCCGTCGTGCTCCCCGAGTGGAGGCGGCCGAGCGCGCCGGG
GTGCCCGCCTTCCTGGAGACCTCCGCGCCCCGCAACCTCCCCTTCTACGA
GCGGCTCGGCTTCACCGTCACCGCCGACGTCGAGGTGCCCGAAGGACCGC
GCACCTGGTGCATGACCCGCAAGCCCGGTGCCTGACGGGGCGCGTCTGGA
ACAATCAACCTCTGGATTACAAAATTTGTGAAAGATTGACTGGTATTCTT
AACTATGTTGCTCCTTTTACGCTATGTGGATACGCTGCTTTAATGCCTTT
GTATCATGCTATTGCTTCCCGTATGGCTTTCATTTTCTCCTCCTTGTATA
AATCCTGGTTGCTGTCTCTTTATGAGGAGTTGTGGCCCGTTGTCAGGCAA
CGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCC
```

```
CTATTGCCACGGCGGAACTCATCGCCGCCTGCCTTGCCCGCTGCTGGACA
GGGGCTCGGCTGTTGGGCACTGACAATTCCGTGGTGTTGTCGGGGAAGCT
GACGTCCTTTCCATGGCTGCTCGCCTGTGTTGCCACCTGGATTCTGCGCG
GGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCG
CCCTCAGACGAGTCGGATCTCCCTTTGGGCCGCCTCCCCGCCTGGAATTA
ATTCTGCAGTCGAGACCTAGAAAAACATGGAGCAATCACAAGTAGCAATA
CAGCAGCTACCAATGCTGATTGTGCCTGGCTAGAAGCACAAGAGGAGGAG
GAGGTGGGTTTTTCCAGTCACACCTCAGGTACCTTTAAGACCAATGACTT
ACAAGGCAGCTGTAGATCTTAGCCACTTTTTAAAAGAAAAGAGGGGACTG
GAAGGGCTAATTCACTCCCAACGAAGACAAGATATCCTTGATCTGTGGAT
CTACCACACAAGGCTACTTCCCTGATTAGCAGAACTACACACCAGGGC
CAGGGGTCAGATATCCACTGACCTTTGGATGGTGCTACAAGCTAGTACCA
GTTGAGCCAGATAAGGTAGAAGAGGCCAATAAAGGAGAGAACACCAGCTT
GTTACACCCTGTGAGCCTGCATGGGATGGATGACCCGGAGAGAGAAGTGT
TAGAGTGGAGGTTTGACAGCCGCCTAGCATTTCATCACGTGGCCCGAGAG
CTGCATCCGGAGTACTTCAAGAACTGCTGATATCGAGCTTGCTACAAGGG
ACTTTCCGCTGGGGACTTTCCAGGGAGGCGTGGCCTGGGCGGGACTGGGG
AGTGGCGAGCCCTCAGATCCTGCATATAAGCAGCTGCTTTTTGCCTGTAC
TGGGTCTCTCTGGTTAGACCAGATCTGAGCCTGGGAGCTCTCTGGCTAAC
TAGGGAACCCACTGCTTAAGCCTCAATAAAGCTTGCCTTGAGTGCTTCAA
GTAGTGTGTGCCCGTCTGTTGTGTGACTCTGGTAACTAGAGATCCCTCAG
ACCCTTTTAGTCAGTGTGGAAAATCTCTAGCAGTAGTAGTTCATGTCATC
TTATTATTCAGTATTTATAACTTGCAAAGAAATGAATATCAGAGAGTGAG
AGGCCTTGACATTGCTAGCGTTTTACCGTCGACCTCTAGCTAGAGCTTGG
CGTAATCATGGTCATAGCTGTTTCCTGTGTGAAATTGTTATCCGCTCACA
ATTCCACACAACATACGAGCCGGAAGCATAAAGTGTAAAGCCTGGGGTGC
CTAATGAGTGAGCTAACTCACATTAATTGCGTTGCGCTCACTGCCCGCTT
TCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACT
CAAAGGCGGTAATACGGTTATCCACAGAATCAGGGGATAACGCAGGAAAG
AACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAA
ATCGACGCTCAAGTCAGAGGTGGCGAAACCCGACAGGACTATAAAGATAC
CAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGC
TTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGC
CTTATCCGGTAACTATCGTCTTGAGTCCAACCCGGTAAGACACGACTTAT
CGCCACTGGCAGCAGCCACTGGTAACAGGATTAGCAGAGCGAGGTATGTA
```

-continued

GGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAA

AAAGAGTTGGTAGCTCTTGATCCGGCAAACAAACCACCGCTGGTAGCGGT

TTTTTTGTTTGCAAGCAGCAGATTACGCGCAGAAAAAAAGGATCTCAAGA

AGATCCTTTGATCTTTTCTACGGGGTCTGACGCTCAGTGGAACGAAAACT

CACGTTAAGGGATTTTGGTCATGAGATTATCAAAAAGGATCTTCACCTAG

ATCCTTTTAAATTAAAAATGAAGTTTTAAATCAATCTAAAGTATATATGA

GTAAACTTGGTCTGACAGTTACCAATGCTTAATCAGTGAGGCACCTATCT

CAGCGATCTGTCTATTTCGTTCATCCATAGTTGCCTGACTCCCCGTCGTG

TAGATAACTACGATACGGGAGGGCTTACCATCTGGCCCCAGTGCTGCAAT

GATACCGCGAGACCCACGCTCACCGGCTCCAGATTTATCAGCAATAAACC

AGCCAGCCGGAAGGGCCGAGCGCAGAAGTGGTCCTGCAACTTTATCCGCC

TCCATCCAGTCTATTAATTGTTGCCGGGAAGCTAGAGTAAGTAGTTCGCC

AGTTAATAGTTTGCGCAACGTTGTTGCCATTGCTACAGGCATCGTGGTGT

CACGCTCGTCGTTTGGTATGGCTTCATTCAGCTCCGGTTCCCAACGATCA

AGGCGAGTTACATGATCCCCCATGTTGTGCAAAAAAGCGGTTAGCTCCTT

CGGTCCTCCGATCGTTGTCAGAAGTAAGTTGGCCGCAGTGTTATCACTCA

TGGTTATGGCAGCACTGCATAATTCTCTTACTGTCATGCCATCCGTAAGA

TGCTTTTCGTAAGTTGGCCGCAGTGTTATCACTCATGGTTATGGCAGCAC

-continued

TGCATAATTCTCTTACTGTCATGCCATCCGTAAGATGCTTTTCTGTGACT

GGTGAGTACTCAACCAAGTCATTCTGAGAATAGTGTATGCGGCGACCGAG

TTGCTCTTGCCCGGCGTCAATACGGGATAATACCGCGCCACATAGCAGAA

CTTTAAAAGTGCTCATCATTGGAAAACGTTCTTCGGGGCGAAAACTCTCA

AGGATCTTACCGCTGTTGAGATCCAGTTCGATGTAACCCACTCGTGCACC

CAACTGATCTTCAGCATCTTTTACTTTCACCAGCGTTTCTGGGTGAGCAA

AAACAGGAAGGCAAAATGCCGCAAAAAAGGGAATAAGGGCGACACGGAAA

TGTTGAATACTCATACTCTTCCTTTTTCAATATTATTGAAGCATTTATCA

GGGTTATTGTCTCATGAGCGGATACATATTTGAATGTATTTAGAAAAATA

AACAAATAGGGGTTCCGCGCACATTTCCCCGAAAAGTGCCACCTGACGTC

GACGGATCGGGAGATCAACTTGTTTATTGCAGCTTATAATGGTTACAAAT

AAAGCAATAGCATCACAAATTTCACAAATAAAGCATTTTTTTCACTGCAT

TCTAGTTGTGGTTTGTCCAAACTCATCAATGTATCTTATCATGTCTGGAT

CAACTGGATAACTCAAGCTAACCAAAATCATCCCAAACTTCCCACCCCAT

ACCCTATTACCACTGCCAATTACCTAGTGGTTTCATTTACTCTAAACCTG

TGATTCCTCTGAATTATTTTCATTTTAAAGAAATTGTATTTGTTAAATAT

GTACTACAAACTTAGTAGTTTTTAAAGAAATTGTATTTGTTAAATATGTA

CTACAAACTTAGTAGT

CFP.ΔPol.ΔProt Adenovirus (SEQ ID NO: 35):

This vector served as a control in the protease selection experiments.

CATCATCAATAATATACCTTATTTTGGATTGAAGCCAATATGATAATGAGGGGGT

GGAGTTTGTGACGTGGCGCGGGGCGTGGGAACGGGGCGGGTGACGTAGTAGTGT

GGCGGAAGTGTGATGTTGCAAGTGTGGCGGAACACATGTAAGCGACGGATGTGG

CAAAAGTGACGTTTTTGGTGTGCGCCGGTGTACACAGGAAGTGACAATTTTCGCG

CGGTTTTAGGCGGATGTTGTAGTAAATTTGGGCGTAACCGAGTAAGATTTGGCCA

TTTTCGCGGGAAAACTGAATAAGAGGAAGTGAAATCTGAATAATTTTGTGTTACT

CATAGCGCGTAATATTTGTCTAGGGCCGCGGGGACTTTGACCGTTTACGTGGAGA

CTCGCCCAGGTGTTTTTCTCAGGTGTTTTCCGCGTTCCGGGTCAAAGTTGGCGTTT

TATTATTATAGTCAGTCGAAGCTTGGATCCGGTACCTCTAGAATTCTCGAGCGGC

CGCTAGCGACATCGGATCTCCCGATCCCCTATGGTGCACTCTCAGTACAATCTGC

TCTGATGCCGCATAGTTAAGCCAGTATCTGCTCCCTGCTTGTGTGTTGGAGGTCG

CTGAGTAGTGCGCGAGCAAAATTTAAGCTACAACAAGGCAAGGCTTGACCGACA

ATTGCATGAAGAATCTGCTTAGGGTTAGGCGTTTTGCGCTGCTTCGCGATGTACG

GGCCAGATATACGCGTTGACATTGATTATTGACTAGTTATTAATAGTAATCAATT

ACGGGGTCATTAGTTCATAGCCCATATATGGAGTTCCGCGTTACATAACTTACGG

TAAATGGCCCGCCTGGCTGACCGCCCAACGACCCCCGCCCATTGACGTCAATAAT

GACGTATGTTCCCATAGTAACGCCAATAGGGACTTTCCATTGACGTCAATGGGTG

GACTATTTACGGTAAACTGCCCACTTGGCAGTACATCAAGTGTATCATATGCCAA

GTACGCCCCCTATTGACGTCAATGACGGTAAATGGCCCGCCTGGCATTATGCCCA

```
GTACATGACCTTATGGGACTTTCCTACTTGGCAGTACATCTACGTATTAGTCATCG

CTATTACCATGGTGATGCGGTTTTGGCAGTACATCAATGGGCGTGGATAGCGGTT

TGACTCACGGGGATTTCCAAGTCTCCACCCCATTGACGTCAATGGGAGTTTGTTT

TGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCT

GGCTAACTAGAGAACCCACTGCTTACTGGCTTATCGAAATTAATACGACTCACTA

TAGGGAGACCCAAGCTGGCTAGTTAAGCTATCAACAAGTTTGTACAAAAAAGCA

GGCTTTAAAGGAACCAATTCAGTCGACTGGATCCGGTACCACCatgTTCCTGAACT

GCTGCCCAGGTTGCTGTATGGAGCCTGAATTCACCATGgtgagcaagggCGAGGAGCT

GTTCACCGGGGTGGTGCCCATCCTGGTCGAGCTGGACGGCGACGTAAACGGCCA

CAAGTTCAGCGTGTCCGGCGAGGGCGAGGGCGATGCCACCTACGGCAAGCTGAC

CCTGAAGTTCATCTGCACCACCGGCAAGCTGCCCGTGCCCTGGCCCACCCTCGTG

ACCACCCTGACCTGGGGCGTGCAGTGCTTCGCCCGCTACCCCGACCACATGAAGC

AGCACGACTTCTTCAAGTCCGCCATGCCCGAAGGCTACGTCCAGGAGCGCACCAT

CTTCTTCAAGGACGACGGCAACTACAAGACCCGCGCCGAGGTGAAGTTCGAGGG

CGACACCCTGGTGAACCGCATCGAGCTGAAGGGCATCGACTTCAAGGAGGACGG

CAACATCCTGGGGCACAAGCTGGAGTACAACGCCATCAGCGACAACGTCTATAT

CACCGCCGACAAGCAGAAGAACGGCATCAAGGCCAACTTCAAGATCCGCCACAA

CATCGAGGACGGCAGCGTGCAGCTCGCCGACCACTACCAGCAGAACACCCCCAT

CGGCGACGGCCCCGTGCTGCTGCCCGACAACCACTACCTGAGCACCCAGTCCAA

GCTGAGCAAAGACCCCAACGAGAAGCGCGATCACATGGTCCTGCTGGAGTTCGT

GACCGCCGCCGGGATCACTCTCGgcatggacgagctgtacaagGTCGACtatccgtacgacgtaccagac tacgcaTAACCGCGGCCGCACTCGAGATATCTAGACCCAGCTTTCTTGTACAAAGTG

GTTGATCTAGAGGGCCCGCGGTTCGAAGGTAAGCCTATCCCTAACCCTCTCCTCG

GTCTCGATTCTACGCGTACCGGTTAGTAATGAGTTTAAACGGGGGAGGCTAACTG

AAACACGGAAGGAGACAATACCGGAAGGAACCCGCGCTATGACGGCAATAAAA

AGACAGAATAAAACGCACGGGTGTTGGGTCGTTTGTTCATAAACGCGGGGTTCG

GTCCCAGGGCTGGCACTCTGTCGATACCCCACCGAGACCCCATTGGGGCCAATAC

GCCCGCGTTTCTTCCTTTTCCCCACCCCACCCCCCAAGTTCGGGTGAAGGCCCAG

GGCTCGCAGCCAACGTCGGGGCGGCAGGCCCTGCCATAGCAGATCCGATTCGAC

AGATCACTGAAATGTGTGGGCGTGGCTTAAGGGTGGGAAAGAATATATAAGGTG

GGGGTCTTATGTAGTTTTGTATCTGTTTTGCAGCAGCCGCCGCCGCCATGAGCAC

CAACTCGTTTGATGGAAGCATTGTGAGCTCATATTTGACAACGCGCATGCCCCCA

TGGGCCGGGGTGCGTCAGAATGTGATGGGCTCCAGCATTGATGGTCGCCCCGTCC

TGCCCGCAAACTCTACTACCTTGACCTACGAGACCGTGTCTGGAACGCCGTTGGA

GACTGCAGCCTCCGCCGCCGCTTCAGCCGCTGCAGCCACCGCCCGCGGGATTGTG

ACTGACTTTGCTTTCCTGAGCCCGCTTGCAAGCAGTGCAGCTTCCCGTTCATCCGC

CCGCGATGACAAGTTGACGGCTCTTTTGGCACAATTGGATTCTTTGACCCGGGAA

CTTAATGTCGTTTCTCAGCAGCTGTTGGATCTGCGCCAGCAGGTTTCTGCCCTGAA

GGCTTCCTCCCCTCCCAATGCGGTTTAAAACATAAATAAAAAACCAGACTCTGTT

TGGATTTGGATCAAGCAAGTGTCTTGCTGTCTTTATTTAGGGGTTTTGCGCGCGCG
```

```
GTAGGCCCGGGACCAGCGGTCTCGGTCGTTGAGGGTCCTGTGTATTTTTTCCAGG

ACGTGGTAAAGGTGACTCTGGATGTTCAGATACATGGGCATAAGCCCGTCTCTGG

GGTGGAGGTAGCACCACTGCAGAGCTTCATGCTGCGGGGTGGTGTTGTAGATGA

TCCAGTCGTAGCAGGAGCGCTGGGCGTGGTGCCTAAAAATGTCTTTCAGTAGCAA

GCTGATTGCCAGGGGCAGGCCCTTGGTGTAAGTGTTTACAAAGCGGTTAAGCTGG

GATGGGTGCATACGTGGGGATATGAGATGCATCTTGGACTGTATTTTTAGGTTGG

CTATGTTCCCAGCCATATCCCTCCGGGGATTCATGTTGTGCAGAACCACCAGCAC

AGTGTATCCGGTGCACTTGGGAAATTTGTCATGTAGCTTAGAAGGAAATGCGTGG

AAGAACTTGGAGACGCCCTTGTGACCTCCAAGATTTTCCATGCATTCGTCCATAA

TGATGGCAATGGGCCCACGGGCGGCGGCCTGGGCGAAGATATTTCTGGGATCAC

TAACGTCATAGTTGTGTTCCAGGATGAGATCGTCATAGGCCATTTTTACAAAGCG

CGGGCGGAGGGTGCCAGACTGCGGTATAATGGTTCCATCCGGCCCAGGGGCGTA

GTTACCCTCACAGATTTGCATTTCCCACGCTTTGAGTTCAGATGGGGGGATCATG

TCTACCTGCGGGGCGATGAAGAAAACGGTTTCCGGGGTAGGGGAGATCAGCTGG

GAAGAAAGCAGGTTCCTGAGCAGCTGCGACTTACCGCAGCCGGTGGGCCCGTAA

ATCACACCTATTACCGGcTGCAACTGGTAGTTAAGAGAGCTGCAGCTGCCGTCAT

CCCTGAGCAGGGGGGCCACTTCGTTAAGCATGTCCCTGACTCGCATGTTTTCCCT

GACCAAATCCGCCAGAAGGCGCTCGCCGCCCAGCGATAGCAGTTCTTGCAAGGA

AGCAAAGTTTTTCAACGGTTTGAGACCGTCCGCCGTAGGCATGCTTTTGAGCGTT

TGACCAAGCAGTTCCAGGCGGTCCCACAGCTCGGTCACCTGCTCTACGGCATCTC

GATCCAGCATATCTCCTCGTTTCGCGGGTTGGGGCGGCTTTCGCTGTACGGCAGT

AGTCGGTGCTCGTCCAGACGGGCCAGGGTCATGTCTTTCCACGGGCGCAGGGTCC

TCGTCAGCGTAGTCTGGGTCACGGTGAAGGGGTGCGCTCCGGGCTGCGCGCTGG

CCAGGGTGCGCTTGAGGCTGGTCCTGCTGGTGCTGAAGCGCTGCCGGTCTTCGCC

CTGCGCGTCGGCCAGGTAGCATTTGACCATGGTGTCATAGTCCAGCCCCTCCGCG

GCGTGGCCCTTGGCGCGCAGCTTGCCCTTGGAGGAGGCGCCGCACGAGGGGCAG

TGCAGACTTTTGAGGGCGTAGAGCTTGGGCGCGAGAAATACCGATTCCGGGGAG

TAGGCATCCGCGCCGCAGGCCCCGCAGACGGTCTCGCATTCCACGAGCCAGGTG

AGCTCTGGCCGTTCGGGGTCAAAAACCAGGTTTCCCCCATGCTTTTTGATGCGTTT

CTTACCTCTGGTTTCCATGAGCCGGTGTCCACGCTCGGTGACGAAAAGGCTGTCC

GTGTCCCCGTATACAGACTTGAGAGGCCTGTCCTCGAGCGGTGTTCCGCGGTCCT

CCTCGTATAGAAACTCGGACCACTCTGAGACAAAGGCTCGCGTCCAGGCCAGCA

CGAAGGAGGCTAAGTGGGAGGGGTAGCGGTCGTTGTCCACTAGGGGTCCACTC

GCTCCAGGGTGTGAAGACACATGTCGCCCTCTTCGGCATCAAGGAAGGTGATTG

GTTTGTAGGTGTAGGCCACGTGACCGGGTGTTCCTGAAGGGGGGCTATAAAAGG

GGGTGGGGCGCGTTCGTCCTCACTCTCTTCCGCATCGCTGTCTGCGAGGGCCAG

CTGTTGGGGTGAGTACTCCCTCTGAAAAGCGGGCATGACTTCTGCGCTAAGATTG

TCAGTTTCCAAAAACGAGGAGGATTTGATATTCACCTGGCCCGCGGTGATGCCTT

TGAGGGTGGCCGCATCCATCTGGTCAGAAAAGACAATCTTTTTGTTGTCAAGCTT

GGTGGCAAACGACCCGTAGAGGGCGTTGGACAGCAACTTGGCGATGGAGCGCAG
```

-continued

```
GGTTTGGTTTTTGTCGCGATCGGCGCGCTCCTTGGCCGCGATGTTTAGCTGCACGT
ATTCGCGCGCAACGCACCGCCATTCGGGAAAGACGGTGGTGCGCTCGTCGGGCA
CCAGGTGCACGCGCCAACCGCGGTTGTGCAGGGTGACAAGGTCAACGCTGGTGG
CTACCTCTCCGCGTAGGCGCTCGTTGGTCCAGCAGAGGCGGCCGCCCTTGCGCGA
GCAGAATGGCGGTAGGGGGTCTAGCTGCGTCTCGTCCGGGGGTCTGCGTCCAC
GGTAAAGACCCCGGGCAGCAGGCGCGCGTCGAAGTAGTCTATCTTGCATCCTTGC
AAGTCTAGCGCCTGCTGCCATGCGCGGGCGGCAAGCGCGCGCTCGTATGGGTTG
AGTGGGGGACCCCATGGCATGGGTGGGTGAGCGCGGAGGCGTACATGCCGCAA
ATGTCGTAAACGTAGAGGGGCTCTCTGAGTATTCCAAGATATGTAGGGTAGCATC
TTCCACCGCGGATGCTGGCGCGCACGTAATCGTATAGTTCGTGCGAGGGAGCGA
GGAGGTCGGGACCGAGGTTGCTACGGGCGGGCTGCTCTGCTCGGAAGACTATCT
GCCTGAAGATGGCATGTGAGTTGGATGATATGGTTGGACGCTGGAAGACGTTGA
AGCTGGCGTCTGTGAGACCTACCGCGTCACGCACGAAGGAGGCGTAGGAGTCGC
GCAGCTTGTTGACCAGCTCGGCGGTGACCTGCACGTCTAGGGCGCAGTAGTCCAG
GGTTTCCTTGATGATGTCATACTTATCCTGTCCCTTTTTTTTCCACAGCTCGCGGTT
GAGGACAAACTCTTCGCGGTCTTTCCAGTACTCTTGGATCGGAAACCCGTCGGCC
TCCGAACGGTAAGAGCCTAGCATGTAGAACTGGTTGACGGCCTGGTAGGCGCAG
CATCCCTTTTCTACGGGTAGCGCGTATGCCTGCGCGGCCTTCCGGAGCGAGGTGT
GGGTGAGCGCAAAGGTGTCCCTGACCATGACCAGCATGAAGGGCACGAGCTGCT
TCCCAAAGGCCCCCATCCAAGTATAGGTCTCTACATCGTAGGTGACAAAGAGAC
GCTCGGTGCGAGGATGCGAGCCGATCGGGAAGAACTGGATCTCCCGCCACCAAT
TGGAGGAGTGGCTATTGATGTGGTGAAAGTAGAAGTCCCTGCGACGGGCCGAAC
ACTCGTGCTGGCTTTTGTAAAAACGTGCGCAGTACTGGCAGCGGTGCACGGGCTG
TACATCCTGCACGAGGTTGACCTGACGACCGCGCACAAGGAAGCAGAGTGGGAA
TTTGAGCCCCTCGCCTGGCGGGTTTGGCTGGTGGTCTTCTACTTCGGCTGCTTGTC
CTTGACCGTCTGGCTGCTCGAGGGGAGTTACGGTGGATCGGACCACCACGCCGC
GCGAGCCCAAAGTCCAGATGTCCGCGCGCGGCGGTCGGAGCTTGATGACAACAT
CGCGCAGATGGGAGCTGTCCATGGTCTGGAGCTCCCGCGGCGTCAGGTCAGGCG
GGAGCTCCTGCAGGTTTACCTCGCATAGACGGGTCAGGGCGCGGGCTAGATCCA
GGTGATACCTAATTTCCAGGGGCTGGTTGGTGGCGGCGTCGATGGCTTGCAAGAG
GCCGCATCCCCGCGGCGCGACTACGGTACCGCGCGGCGGGCGGTGGGCCGCGGG
GGTGTCCTTGGATGATGCATCTAAAAGCGGTGACGCGGGCGAGCCCCCGGAGGT
AGGGGGGCTCCGGACCCGCCGGGAGAGGGGGCAGGGGCACGTCGGCGCCGCG
CGCGGGCAGGAGCTGGTGCTGCGCGCGTAGGTTGCTGGCGAACGCGACGACGCG
GCGGTTGATCTCCTGAATCTGGCGCCTCTGCGTGAAGACGACGGGCCCGGTGAGC
TTGAaCCTGAAAGAGAGTTCGACAGAATCAATTTCGGTGTCGTTGACGGCGGCCT
GGCGCAAAATCTCCTGCACGTCTCCTGAGTTGTCTTGATAGGCGATCTCGGCCAT
GAACTGCTCGATCTCTTCCTCCTGGAGATCTCCGCGTCCGGCTCGCTCCACGGTG
GCGGCGAGGTCGTTGGAAATGCGGGCCATGAGCTGCGAGAAGGC' GTTGAGGCCT
CCCTCGTTCCAGACGCGGCTGTAGACCACGCCCCCTTCGGCATCGCGGGCGCGCA
TGACCACCTGCGCGAGATTGAGCTCCACGTGCCGGGCGAAGACGGCGTAGTTTC
```

```
GCAGGCGCTGAAAGAGGTAGTTGAGGGTGGTGGCGGTGTGTTCTGCCACGAAGA

AGTACATAACCCAGCGTCGCAACGTGGATTCGTTGATATCCCCCAAGGCCTCAAG

GCGCTCCATGGCCTCGTAGAAGTCCACGGCGAAGTTGAAAAACTGGGAGTTGCG

CGCCGACACGGTTAACTCCTCCTCCAGAAGACGGATGAGCTCGGCGACAGTGTC

GCGCACCTCGCGCTCAAAGGCTACAGGGGCCTCTTCTTCTTCTTCAATCTCCTCTT

CCATAAGGGCCTCCCCTTCTTCTTCTTCTGGCGGCGGTGGGGAGGGGGACACG

GCGGCGACGACGGCGCACCGGGAGGCGGTCGACAAAGCGCTCGATCATCTCCCC

GCGGCGACGGCGCATGGTCTCGGTGACGGCGCGGCCGTTCTCGCGGGGGCGCAG

TTGGAAGACGCCGCCCGTCATGTCCCGGTTATGGGTTGGCGGGGGGCTGCCATGC

GGCAGGGATACGGCGCTAACGATGCATCTCAACAATTGTTGTGTAGGTACTCCGC

CGCCGAGGGACCTGAGCGAGTCCGCATCGACCGGATCGGAAAACCTCTCGAGAA

AGGCGTCTAACCAGTCACAGTCGCAAGGTAGGCTGAGCACCGTGGCGGGCGGCA

GCGGGCGGCGGTCGGGGTTGTTTCTGGCGGAGGTGCTGCTGATGATGTAATTAAA

GTAGGCGGTCTTGAGACGGCGGATGGTCGACAGAAGCACCATGTCCTTGGGTCC

GGCCTGCTGAATGCGCAGGCGGTCGGCCATGCCCCAGGCTTCGTTTTGACATCGG

CGCAGGTCTTTGTAGTAGTCTTGCATGAGCCTTTCTACCGGCACTTCTTCTTCTCC

TTCCTCTTGTCCTGCATCTCTTGCATCTATCGCTGCGGCGGCGGCGGAGTTTGGCC

GTAGGTGGCGCCCTCTTCCTCCCATGCGTGTGACCCCGAAGCCCCTCATCGGCTG

AAGCAGGGCTAGGTCGGCGACAACGCGCTCGGCTAATATGGCCTGCTGCACCTG

CGTGAGGGTAGACTGGAAGTCATCCATGTCCACAAAGCGGTGGTATGCGCCCGT

GTTGATGGTGTAAGTGCAGTTGGCCATAACGGACCAGTTAACGGTCTGGTGACCC

GGCTGCGAGAGCTCGGTGTACCTGAGACGCGAGTAAGCCCTCGAGTCAAATACG

TAGTCGTTGCAAGTCCGCACCAGGTACTGGTATCCCACCAAAAAGTGCGGCGGC

GGCTGGCGGTAGAGGGGCCAGCGTAGGGTGGCCGGGGCTCCGGGGGCGAGATCT

TCCAACATAAGGCGATGATATCCGTAGATGTACCTGGACATCCAGGTGATGCCG

GCGGCGGTGGTGGAGGCGCGCGGAAAGTCGCGGACGCGGTTCCAGATGTTGCGC

AGCGGCAAAAAGTGCTCCATGGTCGGGACGCTCTGGCCGGTCAGGCGCGCGCAA

TCGTTGACGCTCTAGACCGTGCAAAAGGAGAGCCTGTAAGCGGGCACTCTTCCGT

GGTCTGGTGGATAAATTCGCAAGGGTATCATGGCGGACGACCGGGGTTCGAGCC

CCGTATCCGGCCGTCCGCCGTGATCCATGCGGTTACCGCCCGCGTGTCGAACCCA

GGTGTGCGACGTCAGACAACGGGGGAGTGCTCCTTTTGGCTTCCTTCCAGGCGCG

GCGGCTGCTGCGCTAGCTTTTTTGGCCACTGGCCGCGCGCAGCGTAAGCGGTTAG

GCTGGAAAGCGAAAGCATTAAGTGGCTCGCTCCCTGTAGCCGGAGGGTTATTTTC

CAAGGGTTGAGTCGCGGGACCCCCGGTTCGAGTCTCGGACCGGCCGGACTGCGG

CGAACGGGGTTTGCCTCCCCGTCATGCAAGACCCCGCTTGCAAATTCCTCCGGA

AACAGGGACGAGCCCCTTTTTTGCTTTTCCCAGATGCATCCGGTGCTGCGGCAGA

TGCGCCCCCTCCTCAGCAGCGGCAAGAGCAAGAGCAGCGGCAGACATGCAGGG

CACCCTCCCCTCCTCCTACCGCGTCAGGAGGGGCGACATCCGCGGTTGACGCGGC

AGCAGATGGTGATTACGAACCCCCGCGGCGCCGGGCCCGGCACTACCTGGACTT

GGAGGAGGGCGAGGGCCTGGCGCGGCTAGGAGCGCCCTCTCCTGAGCGGcACCC
```

-continued

```
AAGGGTGCAGCTGAAGCGTGATACGCGTGAGGCGTACGTGCCGCGGCAGAACCT

GTTTCGCGACCGCGAGGGAGAGGAGCCCGAGGAGATGCGGGATCGAAAGTTCCA

CGCAGGGCGCGAGCTGCGGCATGGCCTGAATCGCGAGCGGTTGCTGCGCGAGGA

GGACTTTGAGCCCGACGCGCGAACCGGGATTAGTCCCGCGCGCGCACACGTGGC

GGCCGCCGACCTGGTAACCGCATACGAGCAGACGGTGAACCAGGAGATTAACTT

TCAAAAAAGCTTTAACAACCACGTGCGTACGCTTGTGGCGCGCGAGGAGGTGGC

TATAGGACTGATGCATCTGTGGGACTTTGTAAGCGCGCTGGAGCAAAACCCAAA

TAGCAAGCCGCTCATGGCGCAGCTGTTCCTTATAGTGCAGCACAGCAGGGACAA

CGAGGCATTCAGGGATGCGCTGCTAAACATAGTAGAGCCCGAGGGCCGCTGGCT

GCTCGATTTGATAAACATCCTGCAGAGCATAGTGGTGCAGGAGCGCAGCTTGAG

CCTGGCTGACAAGGTGGCCGCCATCAACTATTCCATGCTTAGCCTGGGCAAGTTT

TACGCCCGCAAGATATACCATACCCCTTACGTTCCCATAGACAAGGAGGTAAAG

ATCGAGGGGTTCTACATGCGCATGGCGCTGAAGGTGCTTACCTTGAGCGACGACC

TGGGCGTTTATCGCAACGAGCGCATCCACAAGGCCGTGAGCGTGAGCCGGCGGC

GCGAGCTCAGCGACCGCGAGCTGATGCACAGCCTGCAAAGGGCCCTGGCTGGCA

CGGGCAGCGGCGATAGAGAGGCCGAGTCCTACTTTGACGCGGGCGCTGACCTGC

GCTGGGCCCCAAGCCGACGCGCCCTGGAGGCAGCTGGGGCCGGACCTGGGCTGG

CGGTGGCACCCGCGCGCGCTGGCAACGTCGGCGGCGTGGAGGAATATGACGAGG

ACGATGAGTACGAGCCAGAGGACGGCGAGTACTAAGCGGTGATGTTTCTGATCA

GATGATGCAAGACGCAACGGACCCGGCGGTGCGGGCGGCGCTGCAGAGCCAGCC

GTCCGGCCTTAACTCCACGGACGACTGGCGCCAGGTCATGGACCGCATCATGTCG

CTGACTGCGCGCAATCCTGACGCGTTCCGGCAGCAGCCGCAGGCCAACCGGCTCT

CCGCAATTCTGGAAGCGGTGGTCCCGGCGCGCGCAAACCCCACGCACGAGAAGG

TGCTGGCGATCGTAAACGCGCTGGCCGAAAACAGGGCCATCCGGCCCGACGAGG

CCGGCCTGGTCTACGACGCGCTGCTTCAGCGCGTGGCTCGTTACAACAGCGGCAA

CGTGCAGACCAACCTGGACCGGCTGGTGGGGGATGTGCGCGAGGCCGTGGCGCA

GCGTGAGCGCGCGCAGCAGCAGGGCAACCTGGGCTCCATGGTTGCACTAAACGC

CTTCCTGAGTACACAGCCCGCCAACGTGCCGCGGGGACAGGAGGACTACACCAA

CTTTGTGAGCGCACTGCGGCTAATGGTGACTGAGACACCGCAAAGTGAGGTGTA

CCAGTCTGGGCCAGACTATTTTTTCCAGACCAGTAGACAAGGCCTGCAGACCGTA

AACCTGAGCCAGGCTTTCAAAAACTTGCAGGGGCTGTGGGGGGTGCGGGCTCCC

ACAGGCGACCGCGCGACCGTGTCTAGCTTGCTGACGCCCAACTCGCGCCTGTTGC

TGCTGCTAATAGCGCCCTTCACGGACAGTGGCAGCGTGTCCCGGGACACATACCT

AGGTCACTTGCTGACACTGTACCGCGAGGCCATAGGTCAGGCGCATGTGGACGA

GCATACTTTCCAGGAGATTACAAGTGTCAGCCGCGCGCTGGGGCAGGAGGACAC

GGGCAGCCTGGAGGCAACCCTAAACTACCTGCTGACCAACCGGCGGCAGAAGAT

CCCCTCGTTGCACAGTTTAAACAGCGAGGAGGAGCGCATTTTGCGCTACGTGCAG

CAGAGCGTGAGCCTTAACCTGATGCGCGACGGGGTAACGCCCAGCGTGGCGCTG

GACATGACCGCGCGCAACATGGAACCGGGCATGTATGCCTCAAACCGGCCGTTT

ATCAACCGCCTAATGGACTACTTGCATCGCGCGGCCGCCGTGAACCCCGAGTATT

TCACCAATGCCATCTTGAACCCGCACTGGCTACCGCCCCCTGGTTTCTACACCGG
```

-continued

```
GGGATTCGAGGTGCCCGAGGGTAACGATGGATTCCTCTGGGACGACATAGACGA
CAGCGTGTTTTCCCCGCAACCGCAGACCCTGCTAGAGTTGCAACAGCGCGAGCA
GGCAGAGGCGGCGCTGCGAAAGGAAAGCTTCCGCAGGCCAAGCAGCTTGTCCGA
TCTAGGCGCTGCGGCCCCGCGGTCAGATGCTAGTAGCCCATTTCCAAGCTTGATA
GGGTCTCTTACCAGCACTCGCACCACCCGCCCGCGCCTGCTGGGCGAGGAGGAG
TACCTAAACAACTCGCTGCTGCAGCCGCAGCGCGAAAAAAACCTGCCTCCGGCA
TTTCCCAACAACGGGATAGAGAGCCTAGTGGACAAGATGAGTAGATGGAAGACG
TACGCGCAGGAGCACAGGGACGTGCCAGGCCCGCGCCCGCCCACCCGTCGTCAA
AGGCACGACCGTCAGCGGGGTCTGGTGTGGGAGGACGATGACTCGGCAGACGAC
AGCAGCGTCCTGGATTTGGGAGGGAGTGGCAACCCGTTTGCGCACCTTCGCCCCA
GGCTGGGGAGAATGTTTTAAAAAAAAAAAAaGCATGATGCAAAATAAAAAACTC
ACCAAGGCCATGGCACCGAGCGTTGGTTTTCTTGTATTCCCCTTAGTATGCGGCG
CGCGGCGATGTATGAGGAAGGTCCTCCTCCCTCCTACGAGAGTGTGGTGAGCGC
GGCGCCAGTGGCGGCGGCGCTGGGTTCTCCCTTCGATGCTCCCCTGGACCCGCCG
TTTGTGCCTCCGCGGTACCTGCGGCCTACCGGGGGGAGAAACAGCATCCGTTACT
CTGAGTTGGCACCCCTATTCGACACCACCCGTGTGTACCTGGTGGACAACAAGTC
AACGGATGTGGCATCCCTGAACTACCAGAACGACCACAGCAACTTTCTGACCAC
GGTCATTCAAAACAATGACTACAGCCCGGGGGAGGCAAGCACACAGACCATCAA
TCTTGACGACCGGTCGCACTGGGGCGGCGACCTGAAAACCATCCTGCATACCAA
CATGCCAAATGTGAACGAGTTCATGTTTACCAATAAGTTTAAGGCGCGGGTGATG
GTGTCGCGCTTGCCTACTAAGGACAATCAGGTGGAGCTGAAATACGAGTGGGTG
GAGTTCACGCTGCCCGAGGGCAACTACTCCGAGACCATGACCATAGACCTTATG
AACAACGCGATCGTGGAGCACTACTTGAAAGTGGGCAGACAGAACGGGGTTCTG
GAAAGCGACATCGGGGTAAAGTTTGACACCCGCAACTTCAGACTGGGGTTTGAC
CCCGTCACTGGTCTTGTCATGCCTGGGGTATATACAAACGAAGCCTTCCATCCAG
ACATCATTTTGCTGCCAGGATGCGGGGTGGACTTCACCCACAGCCGCCTGAGCAA
CTTGTTGGGCATCCGCAAGCGGCAACCCTTCCAGGAGGGCTTTAGGATCACCTAC
GATGATCTGGAGGGTGGTAACATTCCCGCACTGTTGGATGTGGACGCCTACCAGG
CGAGCTTGAAAGATGACACCGAACAGGGCGGGGTGGCGCAGGCGGCAGCAAC
AGCAGTGGCAGCGGCGCGGAAGAGAACTCCAACGCGGCAGCCGCGGCAATGCA
GCCGGTGGAGGACATGAACGATCATGCCATTCGCGGCGACACCTTTGCCACACG
GGCTGAGGAGAAGCGCGCTGAGGCCGAAGCAGCGGCCGAAGCTGCCGCCCCCGC
TGCGCAACCCGAGGTCGAGAAGCCTCAGAAGAAACCGGTGATCAAACCCCTGAC
AGAGGACAGCAAGAAACGCAGTTACAACCTAATAAGCAATGACAGCACCTTCAC
CCAGTACCGCAGCTGGTACCTTGCATACAACTACGGCGACCCTCAGACCGGAATC
CGCTCATGGACCCTGCTTTGCACTCCTGACGTAACCTGCGGCTCGGAGCAGGTCT
ACTGGTCGTTGCCAGACATGATGCAAGACCCCGTGACCTTCCGCTCCACGCGCCA
GATCAGCAACTTTCCGGTGGTGGGCGCCGAGCTGTTGCCCGTGCACTCCAAGAGC
TTCTACAACGACCAGGCCGTCTACTCCCAACTCATCCGCCAGTTTACCTCTCTGAC
CCACGTGTTCAATCGCTTTCCCGAGAACCAGATTTTGGCGCGCCCGCCAGCCCCC
```

-continued

```
ACCATCACCACCGTCAGTGAAAACGTTCCTGCTCTCACAGATCACGGGACGCTAC
CGCTGCGCAACAGCATCGGAGGAGTCCAGCGAGTGACCATTACTGACGCCAGAC
GCCGCACCTGCCCCTACGTTTACAAGGCCCTGGGCATAGTCTCGCCGCGCGTCCT
ATCGAGCCGCACTTTTTGAGCAAGCATGTCCATCCTTATATCGCCCAGCAATAAC
ACAGGCTGGGGCCTGCGCTTCCCAAGCAAGATGTTTGGCGGGGCCAAGAAGCGC
TCCGACCAACACCCAGTGCGCGTGCGCGGGCACTACCGCGCGCCCTGGGGCGCG
CACAAACGCGGCCGCACTGGGCGCACCACCGTCGATGACGCCATCGACGCGGTG
GTGGAGGAGGCGCGCAACTACACGCCCACGCCGCCACCAGTGTCCACAGTGGAC
GCGGCCATTCAGACCGTGGTGCGCGGAGCCCGGCGCTATGCTAAAATGAAGAGA
CGGCGGAGGCGCGTAGCACGTCGCCACCGCCGCCGACCCGGCACTGCCGCCCAA
CGCGCGGCGGCGGCCCTGCTTAACCGCGCACGTCGCACCGGCCGACGGGCGGCC
ATGCGGGCCGCTCGAAGGCTGGCCGCGGGTATTGTCACTGTGCCCCCCAGGTCCA
GGCGACGAGCGGCCGCCGCAGCAGCCGCGCCATTAGTGCTATGACTCAGGGTC
GCAGGGGCAACGTGTATTGGGTGCGCGACTCGGTTAGCGGCCTGCGCGTGCCCG
TGCGCACCCGCCCCCCGCGCAACTAGATTGCAAGAAAAAACTACTTAGACTCGT
ACTGTTGTATGTATCCAGCGGCGGCGGCGCGCAACGAAGCTATGTCCAAGCGCA
AAATCAAAGAAGAGATGCTCCAGGTCATCGCGCCGGAGATCTATGGCCCCCCGA
AGAAGGAAGAGCAGGATTACAAGCCCCGAAAGCTAAAGCGGGTCAAAAAGAAA
AAGAAAGATGATGATGATGAACTTGACGACGAGGTGGAACTGCTGCACGCTACC
GCGCCCAGGCGACGGGTACAGTGGAAAGGTCGACGCGTAAAACGTGTTTTGCGA
CCCGGCACCACCGTAGTCTTTACGCCCGGTGAGCGCTCCACCCGCACCTACAAGC
GCGTGTATGATGAGGTGTACGGCGACGAGGACCTGCTTGAGCAGGCCAACGAGC
GCCTCGGGGAGTTTGCCTACGAAAGCGGCATAAGGACATGCTGGCGTTGCCGC
TGGACGAGGGCAACCCAACACCTAGCCTAAAGCCCGTAACACTGCAGCAGGTGC
TGCCCGCGCTTGCACCGTCCGAAGAAAAGCGCGGCCTAAAGCGCGAGTCTGGTG
ACTTGGCACCCACCGTGCAGCTGATGGTACCCAAGCGCCAGCGACTGGAAGATG
TCTTGGAAAAAATGACCGTGGAACCTGGGCTGGAGCCCGAGGTCCGCGTGCGGC
CAATCAAGCAGGTGGCGCCGGGACTGGGCGTGCAGACCGTGGACGTTCAGATAC
CCACTACCAGTAGCACCAGTATTGCCACCGCCACAGAGGGCATGGAGACACAAA
CGTCCCCGGTTGCCTCAGCGGTGGCGGATGCCGCGGTGCAGGCGGTCGCTGCGG
CCGCGTCCAAGACCTCTACGGAGGTGCAAACGGACCCGTGGATGTTTCGCGTTTC
AGCCCCCCGGCGCCCGCGCcGTTCGAGGAAGTACGGCGCCGCCAGCGCGCTACTG
CCCGAATATGCCCTACATCCTTCCATTGCGCCTACCCCCGGCTATCGTGGCTACA
CCTACCGCCCCAGAAGACGAGCAACTACCCGACGCCGAACCACCACTGGAACCC
GCCGCCGCCGTCGCCGTCGCCAGCCCGTGCTGGCCCCGATTTCCGTGCGCAGGGT
GGCTCGCGAAGGAGGCAGGACCCTGGTGCTGCCAACAGCGCGCTACCACCCCAG
CATCGTTTAAAAGCCGGTCTTTGTGGTTCTTGCAGATATGGCCCTCACCTGCCGCC
TCCGTTTCCCGGTGCCGGGATTCCGAGGAAGAATGCACCGTAGGAGGGGCATGG
CCGGCCACGGCCTGACGGGCGGCATGCGTCGTGCGCACCACCGGCGGCGGCGCG
CGTCGCACCGTCGCATGCGCGGCGGTATCCTGCCCCTCCTTATTCCACTGATCGC
CGCGGCGATTGGCGCCGTGCCCGGAATTGCATCCGTGGCCTTGCAGGCGCAGAG
```

-continued

```
ACACTGATTAAAAACAAGTTGCATGTGGAAAAATCAAAATAAAAAGTCTGGACT
CTCACGCTCGCTTGGTCCTGTAACTATTTTGTAGAATGGAAGACATCAACTTTGC
GTCTCTGGCCCCGCGACACGGCTCGCGCCCGTTCATGGGAAACTGGCAAGATATC
GGCACCAGCAATATGAGCGGTGGCGCCTTCAGCTGGGGCTCGCTGTGGAGCGGC
ATTAAAAATTTCGGTTCCACCGTTAAGAACTATGGCAGCAAGGCCTGGAACAGC
AGCACAGGCCAGATGCTGAGGGATAAGTTGAAAGAGCAAAATTTCCAACAAAAG
GTGGTAGATGGCCTGGCCTCTGGCATTAGCGGGGTGGTGGACCTGGCCAACCAG
GCAGTGCAAAATAAGATTAACAGTAAGCTTGATCCCCGCCCTCCCGTAGAGGAG
CCTCCACCGGCCGTGGAGACAGTGTCTCCAGAGGGGCGTGGCGAAAAGCGTCCG
CGCCCCGACAGGGAAGAAACTCTGGTGACGCAAATAGACGAGCCTCCCTCGTAC
GAGGAGGCACTAAAGCAAGGCCTGCCCACCACCCGTCCCATCGCGCCCATGGCT
ACCGGAGTGCTGGGCCAGCACACACCCGTAACGCTGGACCTGCCTCCCCCCGCC
GACACCCAGCAGAAACCTGTGCTGCCAGGCCCGACCGCCGTTGTTGTAACCCGTC
CTAGCCGCGCGTCCCTGCGCCGCGCCGCCAGCGGTCCGCGATCGTTGCGGCCCGT
AGCCAGTGGCAACTGGCAAAGCACACTGAACAGCATCGTGGGTCTGGGGGTGCA
ATCCCTGAAGCGCCGACGATGCTTCTGATAGCTAACGTGTCGTATGTGTGTCATG
TATGCGTCCATGTCGCCGCCAGAGGAGCTGCTGAGCCGCCGCGCGCCCGCTTTCC
AAGATGGCTACCCCTTCGATGATGCCGCAGTGGTCTTACATGCACATCTCGGGCC
AGGACGCCTCGGAGTACCTGAGCCCCGGGCTGGTGCAGTTTGCCCGCGCCACCG
AGACGTACTTCAGCCTGAATAACAAGTTTAGAAACCCCACGGTGGCGCCTACGC
ACGACGTGACCACAGACCGGTCCCAGCGTTTGACGCTGCGGTTCATCCCTGTGGA
CCGTGAGGATACTGCGTACTCGTACAAGGCGCGGTTCACCCTAGCTGTGGGTGAT
AACCGTGTGCTGGACATGGCTTCCACGTACTTTGACATCCGCGGCGTGCTGGACA
GGGGCCCTACTTTTAAGCCCTACTCTGGCACTGCCTACAACGCCCTGGCTCCCAA
GGGTGCCCCAAATCCTTGCGAATGGGATGAAGCTGCTACTGCTCTTGAAATAAAC
CTAGAAGAAGAGGACGATGACAACGAAGACGAAGTAGACGAGCAAGCTGAGCA
GCAAAAAACTCACGTATTTGGGCAGGCGCCTTATTCTGGTATAAATATTACAAAG
GAGGGTATTCAAATAGGTGTCGAAGGTCAAACACCTAAATATGCCGATAAAACA
TTTCAACCTGAACCTCAAATAGGAGAATCTCAGTGGTACGAAACaGAAATTAATC
ATGCAGCTGGGAGAGTCCTaAAAAAGACTACCCCAATGAAACCATGTTACGGTTC
ATATGCAAAACCCACAAATGAAATGGAGGGCAAGGCATTCTTGTAAAGCAACA
AAATGGAAAGCTAGAAAGTCAAGTGGAAATGCAATTTTTCTCAACTACTGAGGCa
gCCGCAGGCAATGGTGATAACTTGACTCCTAAAGTGGTATTGTACAGTGAAGATG
TAGATATAGAAACCCCAGACACTCATATTTCTTACATGCCCACTATTAAGGAAGG
TAACTCACGAGAACTAATGGGCCAACAATCTATGCCCAACAGGCCTAATTACATT
GCTTTTAGGGACAATTTTATTGGTCTAATGTATTACAACAGCACGGGTAATATGG
GTGTTCTGGCGGGCCAAGCATCGCAGTTGAATGCTGTTGTAGATTTGCAAGACAG
AAACACAGAGCTTTCATACCAGCTTTTGCTTGATTCCATTGGTGATAGAACCAGG
TACTTTTCTATGTGGAATCAGGCTGTTGACAGCTATGATCCAGATGTTAGAATTA
TTGAAAATCATGGAACTGAAGATGAACTTCCAAATTACTGCTTTCCACTGGGAGG
```

-continued

```
TGTGATTAATACAGAGACTCTTACCAAGGTAAAACCTAAAACAGGTCAGGAAAA

TGGATGGGAAAAAGATGCTACAGAATTTTCAGATAAAAATGAAATAAGAGTTGG

AAATAATTTTGCCATGGAAATCAATCTAAATGCCAACCTGTGGAGAAATTTCCTG

TACTCCAACATAGCGCTGTATTTGCCCGACAAGCTAAAGTACAGTCCTTCCAACG

TAAAAATTTCTGATAACCCAAACACCTACGACTACATGAACAAGCGAGTGGTGG

CTCCCGGGcTAGTGGACTGCTACATTAACCTTGGAGCACGCTGGTCCCTTGACTAT

ATGGACAACGTCAACCCATTTAACCACCACCGCAATGCTGGCCTGCGCTACCGCT

CAATGTTGCTGGGCAATGGTCGCTATGTGCCCTTCCACATCCAGGTGCCTCAGAA

GTTCTTTGCCATTAAAAACCTCCTTCTCCTGCCGGGCTCATACACCTACGAGTGG

AACTTCAGGAAGGATGTTAACATGGTTCTGCAGAGCTCCCTAGGAAATGACCTA

AGGGTTGACGGAGCCAGCATTAAGTTTGATAGCATTTGCCTTTACGCCACCTTCT

TCCCCATGGCCCACAACACCGCCTCCACGCTTGAGGCCATGCTTAGAAACGACAC

CAACGACCAGTCCTTTAACGACTATCTCTCCGCCGCCAACATGCTCTACCCTATA

CCCGCCAACGCTACCAACGTGCCCATATCCATCCCCTCCCGCAACTGGGCGGCTT

TCCGCGGCTGGGCCTTCACGCGCCTTAAGACTAAGGAAACCCCATCACTGGGCTC

GGGCTACGACCCTTATTACACCTACTCTGGCTCTATACCCTACCTAGATGGAACC

TTTTACCTCAACCACACCTTTAAGAAGGTGGCCATTACCTTTGACTCTTCTGTCAG

CTGGCCTGGCAATGACCGCCTGCTTACCCCCAACGAGTTTGAAATTAAGCGCTCA

GTTGACGGGGAGGGTTACAACGTTGCCCAGTGTAACATGACCAAAGACTGGTTC

CTGGTACAAATGCTAGCTAACTAtAACATTGGCTACCAGGGCTTCTATATCCCAG

AGAGCTACAAGGACCGCATGTACTCCTTCTTTAGAAACTTCCAGCCCATGAGCCG

TCAGGTGGTGGATGATACTAAATACAAGGACTACCAACAGGTGGGCATCCTACA

CCAACACAACAACTCTGGATTTGTTGGCTACCTTGCCCCCACCATGCGCGAAGGA

CAGGCCTACCCTGCTAACTTCCCCTATCCGCTTATAGGCAAGACCGCAGTTGACA

GCATTACCCAGAAAAAGTTTCTTTGCGATCGCACCCTTTGGCGCATCCCATTCTCC

AGTAACTTTATGTCCATGGGCGCACTCACAGACCTGGGCCAAAACCTTCTCTACG

CCAACTCCGCCCACGCGCTAGACATGACTTTTGAGGTGGATCCCATGGACGAGCC

CACCCTTCTTTATGTTTTGTTTGAAGTCTTTGACGTGGTCCGTGTGCACCAGCCGC

ACCGCGGCGTCATCGAAACCGTGTACCTGCGCACGCCCTTCTCGGCCGGCAACGC

CACAACATAAAGAAGCAAGCAACATCAACAACAGCTGCCGCCAAATAATGTACT

AGAGACACTTTCAATAAAGGCAAATGCTTTTATTTGTACACTCTCGGGTGATTAT

TTACCCCCACCCTTGCCGTCTGCGCCGTTTAAAAATCAAAGGGGTTCTGCCGCGC

ATCGCTATGCGCCACTGGCAGGGACACGTTGCGATACTGGTGTTTAGTGCTCCAC

TTAAACTCAGGCACAACCATCCGCGGCAGCTCGGTGAAGTTTTCACTCCACAGGC

TGCGCACCATCACCAACGCGTTTAGCAGGTCGGGCGCCGATATCTTGAAGTCGCA

GTTGGGGCCTCCGCCCTGCGCGCGCGAGTTGCGATACACAGGGTTGCAGCACTG

GAACACTATCAGCGCCGGGTGGTGCACGCTGGCCAGCACGCTCTTGTCGGAGAT

CAGATCCGCGTCCAGGTCCTCCGCGTTGCTCAGGGCGAACGGAGTCAACTTTGGT

AGCTGCCTTCCCAAAAAGGGCGCGTGCCCAGGCTTTGAGTTGCACTCGCACCGTA

GTGGCATCAAAAGGTGACCGTGCCCGGTCTGGGCGTTAGGATACAGCGCCTGCA

TAAAAGCCTTGATCTGCTTAAAAGCCACCTGAGCCTTTGCGCCTTCAGAGAAGAA
```

-continued

```
CATGCCGCAAGACTTGCCGGAAAACTGATTGGCCGGACAGGCCGCGTCGTGCAC

GCAGCACCTTGCGTCGGTGTTGGAGATCTGCACCACATTTCGGCCCCACCGGTTC

TTCACGATCTTGGCCTTGCTAGACTGCTCCTTCAGCGCGCGCTGCCCGTTTTCGCT

CGTCACATCCATTTCAATCACGTGCTCCTTATTTATCATAATGCTTCCGTGTAGAC

ACTTAAGCTCGCCTTCGATCTCAGCGCAGCGGTGCAGCCACAACGCGCAGCCCGT

GGGCTCGTGATGCTTGTAGGTCACCTCTGCAAACGACTGCAGGTACGCCTGCAGG

AATCGCCCATCATCGTCACAAAGGTCTTGTTGCTGGTGAAGGTCAGCTGCAACC

CGCGGTGCTCCTCGTTCAGCCAGGTCTTGCATACGGCCGCCAGAGCTTCCACTTG

GTCAGGCAGTAGTTTGAAGTTCGCCTTTAGATCGTTATCCACGTGGTACTTGTCC

ATCAGCGCGCGCAGCCTCCATGCCCTTCTCCCACGCAGACACGATCGGCACAC

TCAGCGGGTTCATCACCGTAATTTCACTTTCCGCTTCGCTGGGCTCTTCCTCTTCC

TCTTGCGTCCGCATACCACGCGCCACTGGGTCGTCTTCATTCAGCCGCCGCACTG

TGCGCTTACCTCCTTTGCCATGCTTGATTAGCACCGGTGGGTTGCTGAAACCCAC

CATTTGTAGCGCCACATCTTCTCTTTCTTCCTCGCTGTCCACGATTACCTCTGGTG

ATGGCGGGCGCTCGGGCTTGGGAGAAGGGCGCTTCTTTTTCTTCTTGGGCGCAAT

GGCCAAATCCGCCGCCGAGGTCGATGGCCGCGGGCTGGGTGTGCGCGGCACCAG

CGCGTCTTGTGATGAGTCTTCCTCGTCCTCGGACTCGATACGCCGCCTCATCCGCT

TTTTTGGGGGCGCCCGGGGAGGCGGCGGCGACGGGGACGGGGACGACACGTCCT

CCATGGTTGGGGGACGTCGCGCCGCACCGCGTCCGCGCTCGGGGGTGGTTTCGCG

CTGCTCCTCTTCCCGACTGGCCATTTCCTTCTCCTATAGGCAGAAAAAGATCATG

GAGTCAGTCGAGAAGAAGGACAGCCTAACCGCCCCCTCTGAGTTCGCCACCACC

GCCTCCACCGATGCCGCCAACGCGCCTACCACCTTCCCCGTCGAGGCACCCCCGC

TTGAGGAGGAGGAAGTGATTATCGAGCAGGACCCAGGTTTTGTAAGCGAAGACG

ACGAGGACCGCTCAGTACCAACAGAGGATAAAAAGCAAGACCAGGACAACGCA

GAGGCAAACGAGGAACAAGTCGGGCGGGGGACGAAAGGCATGGCGACTACCT

AGATGTGGGAGACGACGTGCTGTTGAAGCATCTGCAGCGCCAGTGCGCCATTAT

CTGCGACGCGTTGCAAGAGCGCAGCGATGTGCCCCTCGCCATAGCGGATGTCAG

CCTTGCCTACGAACGCCACCTATTCTCACCGCGCGTACCCCCCAAACGCCAAGAA

AACGGCACATGCGAGCCCAACCCGCGCCTCAACTTCTACCCCGTATTTGCCGTGC

CAGAGGTGCTTGCCACCTATCACATCTTTTTCCAAAACTGCAAGATACCCCTATC

CTGCCGTGCCAACCGCAGCCGAGCGGACAAGCAGCTGGCCTTGCGGCAGGGCGC

TGTCATACCTGATATCGCCTCGCTCAACGAAGTGCCAAAAATCTTTGAGGGTCTT

GGACGCGACGAGAAGCGCGCGGCAAACGCTCTGCAACAGGAAAACAGCGAAAA

TGAAAGTCACTCTGGAGTGTTGGTGGAACTCGAGGGTGACAACGCGCGCCTAGC

CGTACTAAAACGCAGCATCGAGGTCACCCACTTTGCCTACCCGGCACTTAACCTA

CCCCCCAAGGTCATGAGCACAGTCATGAGTGAGCTGATCGTGCGCCGTGCGCAG

CCCCTGGAGAGGGATGCAAATTTGCAAGAACAAACAGAGGAGGGCCTACCCGCA

GTTGGCGACGAGCAGCTAGCGCGCTGGCTTCAAACGCGCGAGCCTGCCGACTTG

GAGGAGCGACGCAAACTAATGATGGCCGCAGTGCTCGTTACCGTGGAGCTTGAG

TGCATGCAGCGGTTCTTTGCTGACCCGGAGATGCAGCGCAAGCTAGAGGAAACA
```

```
TTGCACTACACCTTTCGACAGGGCTACGTACGCCAGGCCTGCAAGATCTCCAACG

TGGAGCTCTGCAACCTGGTCTCCTACCTTGGAATTTTGCACGAAAACCGCCTTGG

GCAAAACGTGCTTCATTCCACGCTCAAGGGCGAGGCGCGCCGCGACTACGTCCG

CGACTGCGTTTACTTATTTCTATGCTACACCTGGCAGACGGCCATGGGCGTTTGG

CAGCAGTGCTTGGAGGAGTGCAACCTCAAGGAGCTGCAGAAACTGCTAAAGCAA

AACTTGAAGGACCTATGGACGGCCTTCAACGAGCGCTCCGTGGCCGCGCACCTG

GCGGACATCATTTTCCCCGAACGCCTGCTTAAAACCCTGCAACAGGGTCTGCCAG

ACTTCACCAGTCAAAGCATGTTGCAGAACTTTAGGAACTTTATCCTAGAGCGCTC

AGGAATCTTGCCCGCCACCTGCTGTGCACTTCCTAGCGACTTTGTGCCCATTAAG

TACCGCGAATGCCCTCCGCCGCTTTGGGGCCACTGCTACCTTCTGCAGCTAGCCA

ACTACCTTGCCTACCACTCTGACATAATGGAAGACGTGAGCGGTGACGGTCTACT

GGAGTGTCACTGTCGCTGCAACCTATGCACCCCGCACCGCTCCCTGGTTTGCAAT

TCGCAGCTGCTTAACGAAAGTCAAATTATCGGTACCTTTGAGCTGCAGGGTCCCT

CGCCTGACGAAAAGTCCGCGGCTCCGGGGTTGAAACTCACTCCGGGGCTGTGGA

CGTCGGCTTACCTTCGCAAATTTGTACCTGAGGACTACCACGCCCACGAGATTAG

GTTCTACGAAGACCAATCCCGCCCGCCtAATGCGGAGCTTACCGCCTGCGTCATT

ACCCAGGGCCACATTCTTGGCCAATTGCAAGCCATCAACAAAGCCCGCCAAGAG

TTTCTGCTACGAAAGGGACGGGGGGTTTACTTGGACCCCCAGTCCGGCGAGGAG

CTCAACCCAATCCCCCCGCCGCCGCAGCCCTATCAGCAGCAGCCGCGGGCCCTTG

CTTCCCAGGATGGCACCCAAAAAGAAGCTGCAGCTGCCGCCGCCACCCACGGAC

GAGGAGGAATACTGGGACAGTCAGGCAGAGGAGGTTTTGGACGAGGAGGAGGA

GGACATGATGGAAGACTGGGAGAGCCTAGACGAGGAAGCTTCCGAGGTCGAAG

AGGTGTCAGACGAAACACCGTCACCCTCGGTCGCATTCCCCTCGCCGGCGCCCCA

GAAATCGGCAACCGGTTCCAGCATGGCTACAACCTCCGCTCCTCAGGCGCCGCCG

GCACTGCCCGTTCGCCGACCCAACCGTAGATGGGACACCACTGGAACCAGGGCC

GGTAAGTCCAAGCAGCCGCCGCCGTTAGCCCAAGAGCAACAACAGCGCCAAGGC

TACCGCTCATGGCGCGGGCACAAGAACGCCATAGTTGCTTGCTTGCAAGACTGTG

GGGGCAACATCTCCTTCGCCCGCCGCTTTCTTCTCTACCATCACGGCGTGGCCTTC

CCCCGTAACATCCTGCATTACTACCGTCATCTCTACAGCCCATACTGCACCGGCG

GCAGCGGCAGCAACAGCAGCGGCCACACAGAAGCAAAGGCGACCGGATAGCAA

GACTCTGACAAAGCCCAAGAAATCCACAGCGGCGGCAGCAGCAGGAGGAGGAG

CGCTGCGTCTGGCGCCCAACGAACCCGTATCGACCCGCGAGCTTAGAAACAGGA

TTTTTCCCACTCTGTATGCTATATTTCAACAGAGCAGGGGCCAAGAACAAGAGCT

GAAAATAAAAAACAGGTCTCTGCGATCCCTCACCCGCAGCTGCCTGTATCACAA

AAGCGAAGATCAGCTTCGGCGCACGCTGGAAGACGCGGAGGCTCTCTTCAGTAA

ATACTGCGCGCTGACTCTTAAGGACTAGTTTCGCGCCCTTTCTCAAATTTAAGCG

CGAAAACTACGTCATCTCCAGCGGCCACACCCGGCGCCAGCACCTGTtGTCAGCG

CCATTATGAGCAAGGAAATTCCCACGCCCTACATGTGGAGTTACCAGCCACAAAT

GGGACTTGCGGCTGGAGCTGCCCAAGACTACTCAACCCGAATAAACTACATGAG

CGCGGGACCCCACATGATATCCCGGGTCAACGGAATaCGCGCCCACCGAAACCG

AATTCTCcTGGAACAGGCGGCTATTACCACCACACCTCGTAATAACCTTAATCCC
```

```
CGTAGTTGGCCCGCTGCCCTGGTGTACCAGGAAAGTCCCGCTCCCACCACTGTGG

TACTTCCCAGAGACGCCCAGGCCGAAGTTCAGATGACTAACTCAGGGGCGCAGC

TTGCGGGCGGCTTTCGTCACAGGGTGCGGTCGCCCGGGCAGGGTATAACTCACCT

GACAATCAGAGGGCGAGGTATTCAGCTCAACGACGAGTCGGTGAGCTCCTCGCT

TGGTCTCCGTCCGGACGGGACATTTCAGATCGGCGGCGCCGGCCGctCTTCATTCA

CGCCTCGTCAGGCAATCCTAACTCTGCAGACCTCGTCCTCTGAGCCGCGCTCTGG

AGGCATTGGAACTCTGCAATTTATTGAGGAGTTTGTGCCATCGGTCTACTTTAAC

CCCTTCTCGGGACCTCCCGGCCACTATCCGGATCAATTTATTCCTAACTTTGACGC

GGTAAAGGACTCGGCGGACGGCTACGACTGAATGTTAAGTGGAGAGGCAGAGCA

ACTGCGCCTGAAACACCTGGTCCACTGTCGCCGCCACAAGTGCTTTGCCCGCGAC

TCCGGTGAGTTTTGCTACTTTGAATTGCCCGAGGATCATATCGAGGGCCCGGCGC

ACGGCGTCCGGCTTACCGCCCAGGGAGAGCTTGCCCGTAGCCTGATTCGGGAGTT

TACCCAGCGCCCCTGCTAGTTGAGCGGGACAGGGGACCCTGTGTTCTCACTGTG

ATTTGCAACTGTCCTAACCcTGGATTACATCAAGATCTTTGTTGCCATCTCTGTGC

TGAGTATAATAAATACAGAAATTAAAATATACTGGGGCTCCTATCGCCATCCTGT

AAACGCCACCGTCTTCACCCGCCCAAGCAAACCAAGGCGAACCTTACCTGGTACT

TTTAACATCTCTCCCTCTGTGATTTACAACAGTTTCAACCCAGACGGAGTGAGTCT

ACGAGAGAACCTCTCCGAGCTCAGCTACTCCATCAGAAAAAACACCACCCTCCTT

ACCTGCCGGGAACGTACGAGTGCGTCACCGGCCGCTGCACCACACCTACCGCCT

GACCGTAAACCAGACTTTTTCCGGACAGACCTCAATAACTCTGTTTACCAGAACA

GGAGGTGAGCTTAGAAAACCCTTAGGGTATTAGGCCAAAGGCGCAGCTACTGTG

GGGTTTATGAACAATTCAAGCAACTCTACGGGCTATTCTAATTCAGGTTTCTCTA

GAAATGGACGGAATTATTACAGAGCAGCGCCTGCTAGAAAGACGCAGGGCAGCG

GCCGAGCAACAGCGCATGAATCAAGAGCTCCAAGACATGGTTAACTTGCACCAG

TGCAAAAGGGGTATCTTTTGTCTGGTAAAGCAGGCCAAAGTCACCTACGACAGT

AATACCACCGGACACCGCCTTAGCTACAAGTTGCCAACCAAGCGTCAGAAATTG

GTGGTCATGGTGGGAGAAAAGCCCATTACCATAACTCAGCACTCGGTAGAAACC

GAAGGCTGCATTCACTCACCTTGTCAAGGACCTGAGGATCTCTGCACCCTTATTA

AGACCCTGTGCGGTCTCAAAGATCTTATTCCCTTTAACTAATAAAAAAAAATAAT

AAAGCATCACTTACTTAAAATCAGTTAGCAAATTTCTGTCCAGTTTATTCAGCAG

CACCTCCTTGCCCTCCTCCCAGCTCTGGTATTGCAGCTTCCTCCTGGCTGCAAACT

TTCTCCACAATCTAAATGGAATGTCAGTTTCCTCCTGTTCCTGTCCATCCGCACCC

ACTATCTTCATGTTGTTGCAGATGAAGCGCGCAAGACCGTCTGAAGATACCTTCA

ACCCCGTGTATCCATATGACACGGAAACCGGTCCTCCAACTGTGCCTTTTCTTACT

CCTCCCTTTGTATCCCCCAATGGGTTTCAAGAGAGTCCCCCTGGGGTACTCTCTTT

GCGCCTATCCGAACCTCTAGTTACCTCCAATGGCATGCTTGCGCTCAAAATGGGC

AACGGCCTCTCTCTGGACGAGGCCGGCAACCTTACCTCCCAAAATGTAACCACTG

TGAGCCCACCTCTCAAAAAAACCAAGTCAAACATAAACCTGGAAATATCTGCAC

CCCTCACAGTTACCTCAGAAGCCCTAACTGTGGCTGCCGCCGCACCTCTAATGGT

CGCGGGCAACACACTCACCATGCAATCACAGGCCCCGCTAACCGTGCACGACTC
```

-continued

CAAACTTAGCATTGCCACCCAAGGACCCCTCACAGTGTCAGAAGGAAAGCTAGC

CCTGCAAACATCAGGCCCCCTCACCACCACCGATAGCAGTACCCTTACTATCACT

GCCTCACCCCCTCTAACTACTGCCACTGGTAGCTTGGGCATTGACTTGAAAGAGC

CCATTTATACACAAAATGGAAAACTAGGACTAAAGTACGGGGCTCCTTTGCATGT

AACAGACGACCTAAACACTTTGACCGTAGCAACTGGTCCAGGTGTGACTATTAAT

AATACTTCCTTGCAAACTAAAGTTACTGGAGCCTTGGGTTTTGATTCACAAGGCA

ATATGCAACTTAATGTAGCAGGAGGACTAAGGATTGATTCTCAAAACAGACGCC

TTATACTTGATGTTAGTTATCCGTTTGATGCTCAAAACCAACTAAATCTAAGACT

AGGACAGGGCCCTCTTTTTATAAACTCAGCCCACAACTTGGATATTAACTACAAC

AAAGGCCTTTACTTGTTTACAGCTTCAAACAATTCCAAAAAGCTTGAGGTTAACC

TAAGCACTGCCAAGGGGTTGATGTTTGACGCTACAGCCATAGCCATTAATGCAGG

AGATGGGCTTGAATTTGGTTCACCTAATGCACCAAACACAAATCCCCTCAAAACA

AAAATTGGCCATGGCCTAGAATTTGATTCAAACAAGGCTATGGTTCCTAAACTAG

GAACTGGCCTTAGTTTTGACAGCACAGGTGCCATTACAGTAGGAAACAAAAATA

ATGATAAGCTAACTTTGTGGACCACACCAGCTCCATCTCCTAACTGTAGACTAAA

TGCAGAGAAAGATGCTAAACTCACTTTGGTCTTAACAAAATGTGGCAGTCAAAT

ACTTGCTACAGTTTCAGTTTTGGCTGTTAAAGGCAGTTTGGCTCCAATATCTGGA

ACAGTTCAAAGTGCTCATCTTATTATAAGATTTGACGAAAATGGAGTGCTACTAA

ACAATTCCTTCCTGGACCCAGAATATTGGAACTTTAGAAATGGAGATCTTACTGA

AGGCACAGCCTATACAAACGCTGTTGGATTTATGCCTAACCTATCAGCTTATCCA

AAATCTCACGGTAAAACTGCCAAAAGTAACATTGTCAGTCAAGTTTACTTAAACG

GAGACAAAACTAAACCTGTAACACTAACCATTACACTAAACGGTACACAGGAAA

CAGGAGACACAACTCCAAGTGCATACTCTATGTCATTTTCATGGGACTGGTCTGG

CCACAACTACATTAATGAAATATTTGCCACATCCTCTTACACTTTTTCATACATTG

CCCAAGAATAAAGAATCGTTTGTGTTATGTTTCAACGTGTTTATTTTTCAATTGCA

GAAAATTTCGAATCATTTTTCATTCAGTAGTATAGCCCCACCACCACATAGCTTA

TACAGATCACCGTACCTTAATCAAACTCACAGAACCCTAGTATTCAACCTGCCAC

CTCCCTCCCAACACACAGAGTACACAGTCCTTTCTCCCCGGCTGGCCTTAAAAAG

CATCATATCATGGGTAACAGACATATTCTTAGGTGTTATATTCCACACGGTTTCCT

GTCGAGCCAAACGCTCATCAGTGATATTAATAAACTCCCCGGGCAGCTCACTTAA

GTTCATGTCGCTGTCCAGCTGCTGAGCCACAGGCTGCTGTCCAACTTGCGGTTGC

TTAACGGGCGGCGAAGGAGAAGTCCACGCCTACATGGGGGTAGAGTCATAATCG

TGCATCAGGATAGGGCGGTGGTGCTGCAGCAGCGCGCGAATAAACTGCTGCCGC

CGCCGCTCCGTCCTGCAGGAATACAACATGGCAGTGGTCTCCTCAGCGATGATTC

GCACCGCCCGCAGCATAAGGCGCCTTGTCCTCCGGGCACAGCAGCGCACCCTGA

TCTCACTTAAATCAGCACAGTAACTGCAGCACAGCACCACAATATTGTTCAAAAT

CCCACAGTGCAAGGCGCTGTATCCAAAGCTCATGGCGGGGACCACAGAACCCAC

GTGGCCATCATACCACAAGCGCAGGTAGATTAAGTGGCGACCCCTCATAAACAC

GCTGGACATAAACATTACCTCTTTTGGCATGTTGTAATTCACCACCTCCCGGTACC

ATATAAACCTCTGATTAAACATGGCGCCATCCACCACCATCCTAAACCAGCTGGC

CAAAACCTGCCCGCCGGCTATACACTGCAGGGAACCGGGACTGGAACAATGACA

```
GTGGAGAGCCCAGGACTCGTAACCATGGATCATCATGCTCGTCATGATATCAATG

TTGGCACAACACAGGCACACGTGCATACACTTCCTCAGGATTACAAGCTCCTCCC

GCGTTAGAACCATATCCCAGGGAACAACCCATTCCTGAATCAGCGTAAATCCCAC

ACTGCAGGGAAGACCTCGCACGTAACTCACGTTGTGCATTGTCAAAGTGTTACAT

TCGGGCAGCAGCGGATGATCCTCCAGTATGGTAGCGCGGGTTTCTGTCTCAAAAG

GAGGTAGACGATCCCTACTGTACGGAGTGCGCCGAGACAACCGAGATCGTGTTG

GTCGTAGTGTCATGCCAAATGGAACGCCGGACGTAGTCATATTTCCTGAAGCAAA

ACCAGGTGCGGGCGTGACAAACAGATCTGCGTCTCCGGTCTCGCCGCTTAGATCG

CTCTGTGTAGTAGTTGTAGTATATCCACTCTCTCAAAGCATCCAGGCGCCCCCTG

GCTTCGGGTTCTATGTAAACTCCTTCATGCGCCGCTGCCCTGATAACATCCACCA

CCGCAGAATAAGCCACACCCAGCCAACCTACACATTCGTTCTGCGAGTCACACAC

GGGAGGAGCGGGAAGAGCTGGAAGAACCATGTTTTTTTTTTATTCCAAAAGATT

ATCCAAAACCTCAAAATGAAGATCTATTAAGTGAACGCGCTCCCCTCCGGTGGCG

TGGTCAAACTCTACAGCCAAAGAACAGATAATGGCATTTGTAAGATGTTGCACA

ATGGCTTCCAAAAGGCAAACGGCCCTCACGTCCAAGTGGACGTAAAGGCTAAAC

CCTTCAGGGTGAATCTCCTCTATAAACATTCCAGCACCTTCAACCATGCCCAAAT

AATTCTCATCTCGCCACCTTCTCAATATATCTCTAAGCAAATCCCGAATATTAAGT

CCGGCCATTGTAAAAATCTGCTCCAGAGCGCCCTCCACCTTCAGCCTCAAGCAGC

GAATCATGATTGCAAAAATTCAGGTTCCTCACAGACCTGTATAAGATTCAAAAGC

GGAACATTAACAAAAATACCGCGATCCCGTAGGTCCCTTCGCAGGGCCAGCTGA

ACATAATCGTGCAGGTCTGCACGGACCAGCGCGGCCACTTCCCCGCCAGGAACCa

TGACAAAAGAACCCACACTGATTATGACACGCATACTCGGAGCTATGCTAACCA

GCGTAGCCCCGATGTAAGCTTGTTGCATGGGCGGCGATATAAAATGCAAGGTGC

TGCTCAAAAAATCAGGCAAAGCCTCGCGCAAAAAAGAAAGCACATCGTAGTCAT

GCTCATGCAGATAAAGGCAGGTAAGCTCCGGAACCACCACAGAAAAAGACACCA

TTTTTCTCTCAAACATGTCTGCGGGTTTCTGCATAAACACAAAATAAAATAACAA

AAAAACATTTAAACATTAGAAGCCTGTCTTACAACAGGAAAAACAACCCTTATA

AGCATAAGACGGACTACGGCCATGCCGGCGTGACCGTAAAAAAACTGGTCACCG

TGATTAAAAAGCACCACCGACAGCTCCTCGGTCATGTCCGGAGTCATAATGTAAG

ACTCGGTAAACACATCAGGTTGATTCACATCGGTCAGTGCTAAAAAGCGACCGA

AATAGCCCGGGGAATACATACCCGCAGGCGTAGAGACAACATTACAGCCCCCA

TAGGAGGTATAACAAAATTAATAGGAGAGAAAAACACATAAACACCTGAAAAA

CCCTCCTGCCTAGGCAAAATAGCACCCTCCCGCTCCAGAACAACATACAGCGCTT

CCACAGCGGCAGCCATAACAGTCAGCCTTACCAGTAAAAAAGAAAACCTATTAA

AAAAACACCACTCGACACGGCACCAGCTCAATCAGTCACAGTGTAAAAAAGGGC

CAAGTGCAGAGCGAGTATATATAGGACTAAAAAATGACGTAACGGTTAAAGTCC

ACAAAAAACACCCAGAAAACCGCACGCGAACCTACGCCCAGAAACGAAAGCCA

AAAAACCCACAACTTCCTCAAATCGTCACTTCCGTTTTCCCACGTTACGTCACTTC

CCATTTTAAGAAAACTACAATTCCCAACACATACAAGTTACTCCGCCCTAAAACC

TACGTCACCCGCCCCGTTCCCACGCCCCGCGCCACGTCACAAACTCCACCCCCTC
```

ATTATCATATTGGCTTCAATCCAAAATAAGGTATATTATTGATGATGTTAATTAAT

TTAAATCCGCATGCGATATCGAGCTCTCCCGGGAATTCGGATCTGCGACGCGAGG

CTGGATGGCCTTCCCCATTATGATTCTTCTCGcgtttaagggcaccaataactgccttaaaaaaattacgc cccgccctgccactcatcgcagtactgttgtaattcattaagcattctgccgacatggaagccatcacaaacggcatgatgaacctgaat cgccagcggcatcagcaccttgtcgccttgcgtataatatttgcccatggtgaaaacggggcgaagaagttgtccatattggccacgt ttaaatcaaaactggtgaaactcacccagggattggctgagacgaaaaacatattctcaataaacccttagggaaataggccaggtttt caccgtaacacgccacatcttgcgaatatatgtgtagaaactgccggaaatcgtcgtggtattcactccagagcgatgaaaacgtttcag tttgctcatggaaaacggtgtaacaagggtgaacactatcccatatcaccagctcaccgtctttcattgccatacggaattccggatgag cattcatcaggcgggcaagaatgtgaataaaggccggataaaacttgtgcttattttttctttacggtctttaaaaaggccgtaatatccagc tgaacggtctggttataggtacattgagcaactgactgaaatgcctcaaaatgttctttacgatgccattgggatatatcaacggtggtata tccagtgatattactccatatagcttccttagctcctgaaaatctcgataactcaaaaaatacgcccggtagtgatcttatttcattatggtg aaagttggaacctcttacgtgccgatcaacgtctcattttcgccaaaagttggcccagggcttcccggtatcaacagggacaccaggat ttatttattctgcgaagtgatcttccgtcacaggtatttattcgcgataagctcatggagcggcgtaaccgtcgcacaggaaggacagag aaagcgcggatctgggaagtgacggacagaacggtcaggacctggattggggaggcggttgccgccgctgctgctgacggtgtga cgttctctgttccggtcacaccacatacgttccgccattcctatgcgatgcacatgctgtatgccggtataccgctgaaagtctgcaaag cctgatgggacataagtccatcagttcaacggaagtctacacgaaggttttttgcgctggatgtggctgcccggcaccgggtgcagtttg cgatgccggagtctgatgcggttgcgatgctgaaacaattatcctgagaataaatgccttggcctttatatggaaatgtggaactgagtg gatatgctgtttttgtctgttaaacagagaagctggctgttatccactgagaagcgaacgaaacagtcgggaaaatctcccattatcgtag agatccgcattattaatctcaggagcctgtgtagcgtttataggaagtagtgttctgtcatgatgcctgcaagcggtaacgaaaacgattt gaatatgccttcaggaacaatagaaatcttcgtgcggtgttacgttgaagtggagcggattatgtcagcaatggacagaacaacctaat gaacacagaaccatgatgtggtctgtccttttacagccagtagtgctcgccgcagtcgagcgacagggcgaagccctcgagtgagcg aggaagcaccagggaacagcacttatatattctgcttacacacgatgcctgaaaaaacttcccttggggttatccacttatccacgggga tatttttataattatttttttttatagtttttagatcttcttttttagagcgccttgtaggcctttatccatgctggttctagagaaggtgttgtgacaaa ttgccctacagtgtgacaaatcaccctcaaatgacagtcctgtctgtgacaaattgcccttaaccctgtgacaaattgccctcagaagaa gctgatttcacaaagttatccctgcttattgactctatttatttagtgtgacaatctaaaaacttgtcacacttcacatggatctgtcatggcg gaaacagcggttatcaatcacaagaaacgtaaaaatagcccgcgaatcgtccagtcaaacgacctcactgaggcggcatatagtctct cccgggatcaaaaacgtatgctgtatctgttcgttgaccagatcagaaaatctgatggcaccctacaggaacatgacggtatctgcgag atccatgttgctaaatatgctgaaatattcggattgacctctgcggaagccagtaaggatatacggcaggcattgaagagtttcgcgggg aaggaagtggttttttatcgccctgaagaggatgccggcgatgaaaaaggctatgaatcttttccttggtttatcaaacgtgcgcacagtc catccagagggctttacagtgtacatatcaacccatatctcattcccttctttatcgggttacagaaccggtttacgcagtttcggcttagtg aaacaaaagaaatcaccaatccgtatgccatgcgtttatacgaatccctgtgtcagtatcgtaagccggatggctcaggcatcgtctctct gaaaatcgactggatcatagagcgttaccagctgcctcaaagttaccagcgtatgcctgacttccgccgccgcttcctgcaggtctgtgt taatgagatcaacagcagaactccaatgcgcctctcatacattgagaaaagaaaggccgccagacgactcatatcgtattttccttccg cgatatcacttccatgacgacaggatagtctgagggtatctgtcacagatttgagggtggttcgtcacatttgttctgacctactgagggt aatttgtcacagttttgctgtttccttcagcctgcatggattactcatacttttgaactgtaattttaaggaagccaaatttgagggcagtttg tcacagttgatccttctctttcccttcgtcatgtgacctgatatcggggtagttcgtcatcattgatgagggttgattatcacagtttatta ctctgaattggctatccgcgtgtgtacctctacctggagttttccacggtggatatttcttcttgcgctgagcgtaagagctatctgacag aacagttcttctttgcttcctcgccagttcgctcgctatgctcggttacacggctgcggcgagcgctagtgataataagtgactgaggtat gtgctcttcttatctccttttgtagtgttgctcttatttttaaacaactagcggttttttgatgactttgcgattttgttgttgctttgcagtaaattgca agatttaataaaaaacgcaaagcaatgattaaaggatgttcagaatgaaactcatggaaacacttaaccagtgcataaacgctggtcat gaaatgacgaaggctatcgccattgcacagtttaatgatgacagcccggaagcgaggaaaataacccggcgctggagaataggtga -continued agcagcggatttagttggggtttcttctcaggctatcagagatgccgagaaagcagggcgactaccgcacccggatatggaaattcga ggacgggttgagcaacgtgttggttatacaattgaacaaattaatcatatgcgtgatgtgtttggtacgcgattgcgacgtgctgaagac gtataccaccggtgatcggggttgctgcccataaaggtggcgtttacaaaacctcagtttctgttcatcttgctcaggatctggctctgaa ggggctacgtgttttgctcgtggaaggtaacgaccccagggaacagcctcaatgtatcacggatgggtaccagatcttcatattcatg cagaagacactctcctgcctttctatcttggggaaaaggacgatgtcacttatgcaataaagcccacttgctggccggggcttgacattat tccttcctgtctggctctgcaccgtattgaaactgagttaatgggcaaatttgatgaaggtaaactgcccaccgatccacacctgatgctc cgactggccattgaaactgttgctcatgactatgatgtcatagttattgacagcgcgcctaacctgggtatcggcacgattaatgtcgtat gtgctgctgatgtgctgattgttcccacgcctgctgagttgtttgactacacctccgcactgcagttttttcgatatgcttcgtgatctgctcaa gaacgttgatcttaaagggttcgagcctgatgtacgtattttgcttaccaaatacagcaatagtaatggctctcagtccccgtggatggag gagcaaattcgggatgcctggggaagcatggttctaaaaaatgttgtacgtgaaacggatgaagttggtaaaggtcagatccggatga gaactgattgaacaggccattgatcaacgctcttcaactggtgcctggagaaatgctctttctatttgggaacctgtctgcaatgaaatttt cgatcgtctgattaaaccacgctgggagattagataatgaagcgtgcgcctgttattccaaaacatacgctcaatactcaaccggttgaa gatacttcgttatcgacaccagctgcccgatggtggattcgttaattgcgcgcgtaggagtaatggctcgcggtaatgccattactttgc ctgtatgtggtcgggatgtgaagtttactcttgaagtgctccggggtgatagtgttgagaagacctctcgggtatggtcaggtaatgaac gtgaccaggagctgcttactgaggacgcactggatgatctcatcccttcttttctactgactggtcaacagacaccggcgttcggtcgaa gagtatctggtgtcatagaaattgccgatgggagtcgccgtcgtaaagctgctgcacttaccgaaagtgattatcgtgttctggttggcg agctggatgatgagcagatggctgcattatccagattgggtaacgattatcgcccaacaagtgcttatgaacgtggtcagcgttatgcaa gccgattgcagaatgaatttgctggaaatatttctgcgctggctgatgcggaaaatatttcacgtaagattattaccccgctgtatcaacacc gccaaattgcctaaatcagttgttgctcattactcaccccggtgaactatctgcccggtcaggtgatgcacttcaaaaagcctttacagat aaagaggaattacttaagcagcaggcatctaaccttcatgagcagaaaaagctggggtgatatttgaagctgaagaagttatcactctt ttaacttctgtgcttaaaacgtcatctgcatcaagaactagtttaagctcacgacatcagtttgctcctggagcgacagtattgtataaggg cgataaaatggtgcttaacctggacaggtctcgtgttccaactgagtgtatagagaaaattgaggccattcttaaggaacttgaaaagcc agcaccctgatgcgaccacgttttagtctacgtttatctgtctttacttaatgtcctttgttacaggccagaaagcataactggcctgaatatt ctctctgggcccactgttccacttgtatcgtcggtctgataatcagactgggaccacggtcccactcgtatcgtcggtctgattattagtct gggaccacggtcccactcgtatcgtcggtctgattattagtctgggaccacggtcccactcgtatcgtcggtctgataatcagactggga ccacggtcccactcgtatcgtcggtctgattattagtctgggaccatggtcccactcgtatcgtcggtctgattattagtctgggaccacg gtcccactcgtatcgtcggtctgattattagtctggaaccacggtcccactcgtatcgtcggtctgattattagtctgggaccacggtccca ctcgtatcgtcggtctgattattagtctgggaccacgatcccactcgtgttgtcggtctgattatcggtctgggaccacggtcccacttgta ttgtcgatcagactatcagcgtgagactacgattccatcaatgcctgtcaagggcaagtattgacatgtcgtcgtaacctgtagaacgga gtaacctcggtgtgcggttgtatgcctgctgtggattgctgctgtgtcctgcttatccacaacattttgcgcacggttatgtggacaaaata cctggttacccaggccgtgccggcacgttaaccgggCACATTTCCCCGAAAAGTGCCACCTGACGTCT

AAGAAACCATTATTATCATGACATTAACCTATAAAAATAGGCGTATCACGAGGC

CCTTTCGTCTTCAAGaattgGATCCGAATTCCCGGGAGAGCTCGATATCGCATGCGG

ATTTAAATTAATTAA

TTA.ΔPol.ΔProt.mCherry Adenovirus Vector Sequence (SEQ ID NO: 36):
This was the virus was used in the protease selection experiments and directed evolution of dox insensitivity in the tet-transactivator.

CATCATCAATAATATACCTTATTTTGGATTGAAGCCAATATGATAATGAGGGGGT

GGAGTTTGTGACGTGGCGCGGGGCGTGGGAACGGGGCGGGTGACGTAGTAGTGT

```
GGCGGAAGTGTGATGTTGCAAGTGTGGCGGAACACATGTAAGCGACGGATGTGG

CAAAAGTGACGTTTTTGGTGTGCGCCGGTGTACACAGGAAGTGACAATTTTCGCG

CGGTTTTAGGCGGATGTTGTAGTAAATTTGGGCGTAACCGAGTAAGATTTGGCCA

TTTTCGCGGGAAAACTGAataagaggaagtgaaatctgaataattttgtgttactcatagcgcgtaatagAAGCCA

TAGAGCCCACCGCATCCCCAGCATGCCTGCTAGAATTCGAACAAACGACCCAAC

ACCCGTGCGTTTTATTCTGTCTTTTTATTGCCGgcggccgcGAACAAATGTGGTATGG

CTGATTATGATCCTCTAGAGATAATTCTAGTTACCCGGGGAGCATGTCAAGGTCC

AAATCGTCAAGAGCGTCAGCAGGCAGCATATCAAGGTCAAAGTCGTCAAGGGCA

TCGGCTGGGAGCATGTCTAAGTCAAAATCGTCAAGGGCGTCGGCCGGCCCGCCG

CTTTCGCACTTTAGCTGTTTCTCCAGGCCACATATGATTAGTTCCAGGCCGAAAA

GGAAGGCAGGTTCGGCTCCCTGATGGTCGAACAGCTCAATTGCTTGTCTCAGAAG

TGGGGGCATAGAATCGGTGGTAGGTGTCTCTCTTTCCTCTTTTGCTACTTGATGCT

CCTGATCCTCCAATACGCAGCCCAGTGTAAAGTGGCCCACGGCGGACAGAGCGT

ACAGTGCGTTCTCCAGGGAGAAGCCTTGCTGACACAGGAACGCGAGCTGATTTTC

CAGGGTTTCGTACTGTTTCTCTGTTGGGCGGGTGCCGAGATGCACTTTAGCCCCG

TCGCGATGTGAGAGGAGAGCACAGCGGAATGACTTGGCGTTGTTCCGCAGAAAG

TCTTGCCATGACTCGCCTTCCAGGGGGCAGAAGTGGGTATGATGCCTGTCCAGCA

TCTCGATTGCCAGGGCATCGAGCAGGGCCCGCTTGTTCTTCACGTGCCAGTACAG

GGTAGGCTGCTCAACTCCCAGCTTTTGAGCGAGTTTCCTTGTCGTCAGGCCTTCG

ATACCGACTTCATTGAGTAATTCCAGAGCAGAGTTTATGACTTTGCTCTTGTCCA

GTCTAGACATAGGACGCGTCAGCTGACTAGAGGATCCCCGCGGAGGgGTACCAA

GCTTAAGTTTAAACGCTAGCCAGCTTGGGTCTCCCTATAGTGAGTCGTATTAATTT

CGATAAGCCAGTAAGCAGTGGGTTCTCTAGTTAGCCAGAGAGCTCTGCTTATATA

GACCTCCCACCGTACACGCCTACCGCCCATTTGCGTCAATGGGGCGGAGTTGTTA

CGACATTTTGGAAAGTCCCGTTGATTTTGGTGCCAAAACAAACTCCCATTGACGT

CAATGGGGTGGAGACTTGGAAATCCCCGTGAGTCAAACCGCTATCCACGCCCATT

GATGTACTGCCAAAACCGCATCACCATGGTAATAGCGATGACTAATACGTAGAT

GTACTGCCAAGTAGGAAAGTCCCATAAGGTCATGTACTGGGCATAATGCCAGGC

GGGCCATTTACCGTCATTGACGTCAATAGGGGGCGTACTTGGCATATGATACACT

TGATGTACTGCCAAGTGGGCAGTTTACCGTAAATACTCCACCCATTGACGTCAAT

GGAAAGTCCCTATTGGCGTTACTATGGGAACATACGTCATTATTGACGTCAATGG

GCGGGGGTCGTTGGGCGGTCAGCCAGGCGGGCCATTTACCGTAAGTTATGTAAC

GCGGAACTCCATATATGGGCTATGAACTAATGACCCCGTAATTGATTACTATTAA

TAACTAGTCAATAATCAATGTCAACGCGTATATCTGtgggcgtggcttaagggtgggaaagaatat ataaggigggggtcttatgtagattgtatCTGTTTTGCAGCAGCCGCCGCCGCCATGAGCACCAACT

CGTTTGATGGAAGCATTGTGAGCTCATATTTGACAACGCGCATGCCCCCATGGGC

CGGGGTGCGTCAGAATGTGATGGGCTCCAGCATTGATGGTCGCCCCGTCCTGCCC

GCAAACTCTACTACCTTGACCTACGAGACCGTGTCTGGAACGCCGTTGGAGACTG

CAGCCTCCGCCGCCGCTTCAGCCGCTGCAGCCACCGCCCGCGGGATTGTGACTGA

CTTTGCTTTCCTGAGCCCGCTTGCAAGCAGTGCAGCTTCCCGTTCATCCGCCCGCG
```

```
ATGACAAGTTGACGGCTCTTTTGGCACAATTGGATTCTTTGACCCGGGAACTTAA

TGTCGTTTCTCAGCAGCTGTTGGATCTGCGCCAGCAGGTTTCTGCCCTGAAGGCTT

CCTCCCCTCCCAATGCGGTTTAAAACATAAATAAAAAACCAGACTCTGTTTGGAT

TTGGATCAAGCAAGTGTCTTGCTGTCTTTATTTAGGGGTTTTGCGCGCGCGGTAG

GCCCGGGACCAGCGGTCTCGGTCGTTGAGGGTCCTGTGTATTTTTTCCAGGACGT

GGTAAAGGTGACTCTGGATGTTCAGATACATGGGCATAAGCCCGTCTCTGGGGTG

GAGGTAGCACCACTGCAGAGCTTCATGCTGCGGGGTGGTGTTGTAGATGATCCA

GTCGTAGCAGGAGCGCTGGGCGTGGTGCCTAAAAATGTCTTTCAGTAGCAAGCT

GATTGCCAGGGGCAGGCCCTTGGTGTAAGTGTTTACAAAGCGGTTAAGCTGGGA

TGGGTGCATACGTGGGGATATGAGATGCATCTTGGACTGTATTTTTAGGTTGGCT

ATGTTCCCAGCCATATCCCTCCGGGGATTCATGTTGTGCAGAACCACCAGCACAG

TGTATCCGGTGCACTTGGGAAATTTGTCATGTAGCTTAGAAGGAAATGCGTGGAA

GAACTTGGAGACGCCCTTGTGACCTCCAAGATTTTCCATGCATTCGTCCATAATG

ATGGCAATGGGCCCACGGGCGGCGGCCTGGGCGAAGATATTTCTGGGATCACTA

ACGTCATAGTTGTGTTCCAGGATGAGATCGTCATAGGCCATTTTTACAAAGCGCG

GGCGGAGGGTGCCAGACTGCGGTATAATGGTTCCATCCGGCCCAGGGGCGTAGT

TACCCTCACAGATTTGCATTTCCCACGCTTTGAGTTCAGATGGGGGATCATGTC

TACCTGCGGGGCGATGAAGAAAACGGTTTCCGGGGTAGGGGAGATCAGCTGGGA

AGAAAGCAGGTTCCTGAGCAGCTGCGACTTACCGCAGCCGGTGGGCCCGTAAAT

CACACCTATTACCGGcTGCAACTGGTAGTTAAGAGAGCTGCAGCTGCCGTCATCC

CTGAGCAGGGGGCCACTTCGTTAAGCATGTCCCTGACTCGCATGTTTTCCCTGA

CCAAATCCGCCAGAAGGCGCTCGCCGCCCAGCGATAGCAGTTCTTGCAAGGAAG

CAAAGTTTTTCAACGGTTTGAGACCGTCCGCCGTAGGCATGCTTTTGAGCGTTTG

ACCAAGCAGTTCCAGGCGGTCCCACAGCTCGGTCACCTGCTCTACGGCATCTCGA

TCCAGCATATCTCCTCGTTTCGCGGGTTGGGGCGGCTTTCGCTGTACGGCAGTAG

TCGGTGCTCGTCCAGACGGGCCAGGGTCATGTCTTTCCACGGGCGCAGGGTCCTC

GTCAGCGTAGTCTGGGTCACGGTGAAGGGGTGCGCTCCGGGCTGCGCGCTGGCC

AGGGTGCGCTTGAGGCTGGTCCTGCTGGTGCTGAAGCGCTGCCGGTCTTCGCCCT

GCGCGTCGGCCAGGTAGCATTTGACCATGGTGTCATAGTCCAGCCCCTCCGCGGC

GTGGCCCTTGGCGCGCAGCTTGCCCTTGGAGGAGGCGCCGCACGAGGGGCAGTG

CAGACTTTTGAGGGCGTAGAGCTTGGGCGCGAGAAATACCGATTCCGGGGAGTA

GGCATCCGCGCCGCAGGCCCCGCAGACGGTCTCGCATTCCACGAGCCAGGTGAG

CTCTGGCCGTTCGGGGTCAAAAACCAGGTTTCCCCCATGCTTTTTGATGCGTTTCT

TACCTCTGGTTTCCATGAGCCGGTGTCCACGCTCGGTGACGAAAAGGCTGTCCGT

GTCCCCGTATACAGACTTGAGAGGCCTGTCCTCGAGCGGTGTTCCGCGGTCCTCC

TCGTATAGAAACTCGGACCACTCTGAGACAAAGGCTCGCGTCCAGGCCAGCACG

AAGGAGGCTAAGTGGGAGGGGTAGCGGTCGTTGTCCACTAGGGGTCCACTCGC

TCCAGGGTGTGAAGACACATGTCGCCCTCTTCGGCATCAAGGAAGGTGATTGGTT

TGTAGGTGTAGGCCACGTGACCGGGTGTTCCTGAAGGGGGGCTATAAAAGGGGG

TGGGGGCGCGTTCGTCCTCACTCTCTTCCGCATCGCTGTCTGCGAGGGCCAGCTG

TTGGGGTGAGTACTCCCTCTGAAAAGCGGGCATGACTTCTGCGCTAAGATTGTCA
```

```
GTTTCCAAAAACGAGGAGGATTTGATATTCACCTGGCCCGCGGTGATGCCTTTGA

GGGTGGCCGCATCCATCTGGTCAGAAAAGACAATCTTTTTGTTGTCAAGCTTGGT

GGCAAACGACCCGTAGAGGGCGTTGGACAGCAACTTGGCGATGGAGCGCAGGGT

TTGGTTTTTGTCGCGATCGGCGCGCTCCTTGGCCGCGATGTTTAGCTGCACGTATT

CGCGCGCAACGCACCGCCATTCGGGAAAGACGGTGGTGCGCTCGTCGGGCACCA

GGTGCACGCGCCAACCGCGGTTGTGCAGGGTGACAAGGTCAACGCTGGTGGCTA

CCTCTCCGCGTAGGCGCTCGTTGGTCCAGCAGAGGCGGCCGCCCTTGCGCGAGCA

GAATGGCGGTAGGGGGTCTAGCTGCGTCTCGTCCGGGGGTCTGCGTCCACGGT

AAAGACCCCGGGCAGCAGGCGCGCGTCGAAGTAGTCTATCTTGCATCCTTGCAA

GTCTAGCGCCTGCTGCCATGCGCGGGCGGCAAGCGCGCGCTCGTATGGGTTGAGT

GGGGGACCCCATGGCATGGGGTGGGTGAGCGCGGAGGCGTACATGCCGCAAATG

TCGTAAACGTAGAGGGGCTCTCTGAGTATTCCAAGATATGTAGGGTAGCATCTTC

CACCGCGGATGCTGGCGCGCACGTAATCGTATAGTTCGTGCGAGGGAGCGAGGA

GGTCGGGACCGAGGTTGCTACGGGCGGGCTGCTCTGCTCGGAAGACTATCTGCCT

GAAGATGGCATGTGAGTTGGATGATATGGTTGGACGCTGGAAGACGTTGAAGCT

GGCGTCTGTGAGACCTACCGCGTCACGCACGAAGGAGGCGTAGGAGTCGCGCAG

CTTGTTGACCAGCTCGGCGGTGACCTGCACGTCTAGGGCGCAGTAGTCCAGGGTT

TCCTTGATGATGTCATACTTATCCTGTCCCTTTTTTTTCCACAGCTCGCGGTTGAG

GACAAACTCTTCGCGGTCTTTCCAGTACTCTTGGATCGGAAACCCGTCGGCCTCC

GAACGGTAAGAGCCTAGCATGTAGAACTGGTTGACGGCCTGGTAGGCGCAGCAT

CCCTTTTCTACGGGTAGCGCGTATGCCTGCGCGGCCTTCCGGAGCGAGGTGTGGG

TGAGCGCAAAGGTGTCCCTGACCATGACCAGCATGAAGGGCACGAGCTGCTTCC

CAAAGGCCCCCATCCAAGTATAGGTCTCTACATCGTAGGTGACAAAGAGACGCT

CGGTGCGAGGATGCGAGCCGATCGGGAAGAACTGGATCTCCCGCCACCAATTGG

AGGAGTGGCTATTGATGTGGTGAAAGTAGAAGTCCCTGCGACGGGCCGAACACT

CGTGCTGGCTTTTGTAAAAACGTGCGCAGTACTGGCAGCGGTGCACGGGCTGTAC

ATCCTGCACGAGGTTGACCTGACGACCGCGCACAAGGAAGCAGAGTGGGAATTT

GAGCCCCTCGCCTGGCGGGTTTGGCTGGTGGTCTTCTACTTCGGCTGCTTGTCCTT

GACCGTCTGGCTGCTCGAGGGGAGTTACGGTGGATCGGACCACCACGCCGCGCG

AGCCCAAAGTCCAGATGTCCGCGCGCGGCGGTCGGAGCTTGATGACAACATCGC

GCAGATGGGAGCTGTCCATGGTCTGGAGCTCCCGCGGCGTCAGGTCAGGCGGGA

GCTCCTGCAGGTTTACCTCGCATAGACGGGTCAGGGCGCGGGCTAGATCCAGGT

GATACCTAATTTCCAGGGGCTGGTTGGTGGCGGCGTCGATGGCTTGCAAGAGGCC

GCATCCCCGCGGCGCGACTACGGTACCGCGCGGCGGGCGGTGGGCCGCGGGGT

GTCCTTGGATGATGCATCTAAAAGCGGTGACGCGGGCGAGCCCCCGGAGGTAGG

GGGGGCTCCGGACCCGCCGGGAGAGGGGGCAGGGGCACGTCGGCGCCGCGCGC

GGGCAGGAGCTGGTGCTGCGCGCGTAGGTTGCTGGCGAACGCGACGACGCGGCG

GTTGATCTCCTGAATCTGGCGCCTCTGCGTGAAGACGACGGGCCCGGTGAGCTTG

AaCCTGAAAGAGAGTTCGACAGAATCAATTTCGGTGTCGTTGACGGCGGCCTGGC

GCAAAATCTCCTGCACGTCTCCTGAGTTGTCTTGATAGGCGATCTCGGCCATGAA
```

-continued

```
CTGCTCGATCTCTTCCTCCTGGAGATCTCCGCGTCCGGCTCGCTCCACGGTGGCG
GCGAGGTCGTTGGAAATGCGGGCCATGAGCTGCGAGAAGGCGTTGAGGCCTCCC
TCGTTCCAGACGCGGCTGTAGACCACGCCCCCTTCGGCATCGCGGGCGCGCATGA
CCACCTGCGCGAGATTGAGCTCCACGTGCCGGGCGAAGACGGCGTAGTTTCGCA
GGCGCTGAAAGAGGTAGTTGAGGGTGGTGGCGGTGTGTTCTGCCACGAAGAAGT
ACATAACCCAGCGTCGCAACGTGGATTCGTTGATATCCCCCAAGGCCTCAAGGCG
CTCCATGGCCTCGTAGAAGTCCACGGCGAAGTTGAAAAACTGGGAGTTGCGCGC
CGACACGGTTAACTCCTCCTCCAGAAGACGGATGAGCTCGGCGACAGTGTCGCG
CACCTCGCGCTCAAAGGCTACAGGGGCCTCTTCTTCTTCTTCAATCTCCTCTTCCA
TAAGGGCCTCCCCTTCTTCTTCTTCTGGCGGCGGTGGGGGAGGGGGGACACGGCG
GCGACGACGGCGCACCGGGAGGCGGTCGACAAAGCGCTCGATCATCTCCCCGCG
GCGACGGCGCATGGTCTCGGTGACGGCGCGGCCGTTCTCGCGGGGGCGCAGTTG
GAAGACGCCGCCCGTCATGTCCCGGTTATGGGTTGGCGGGGGGCTGCCATGCGG
CAGGGATACGGCGCTAACGATGCATCTCAACAATTGTTGTGTAGGTACTCCGCCG
CCGAGGGACCTGAGCGAGTCCGCATCGACCGGATCGGAAAACCTCTCGAGAAAG
GCGTCTAACCAGTCACAGTCGCAAGGTAGGCTGAGCACCGTGGCGGGCGGCAGC
GGGCGGCGGTCGGGGTTGTTTCTGGCGGAGGTGCTGCTGATGATGTAATTAAAGT
AGGCGGTCTTGAGACGGCGGATGGTCGACAGAAGCACCATGTCCTTGGGTCCGG
CCTGCTGAATGCGCAGGCGGTCGGCCATGCCCCAGGCTTCGTTTTGACATCGGCG
CAGGTCTTTGTAGTAGTCTTGCATGAGCCTTTCTACCGGCACTTCTTCTTCTCCTT
CCTCTTGTCCTGCATCTCTTGCATCTATCGCTGCGGCGGCGGCGGAGTTTGGCCGT
AGGTGGCGCCCTCTTCCTCCCATGCGTGTGACCCCGAAGCCCCTCATCGGCTGAA
GCAGGGCTAGGTCGGCGACAACGCGCTCGGCTAATATGGCCTGCTGCACCTGCG
TGAGGGTAGACTGGAAGTCATCCATGTCCACAAAGCGGTGGTATGCGCCCGTGTT
GATGGTGTAAGTGCAGTTGGCCATAACGGACCAGTTAACGGTCTGGTGACCCGG
CTGCGAGAGCTCGGTGTACCTGAGACGCGAGTAAGCCCTCGAGTCAAATACGTA
GTCGTTGCAAGTCCGCACCAGGTACTGGTATCCCACCAAAAAGTGCGGCGGCGG
CTGGCGGTAGAGGGGCCAGCGTAGGGTGGCCGGGGCTCCGGGGGCGAGATCTTC
CAACATAAGGCGATGATATCCGTAGATGTACCTGGACATCCAGGTGATGCCGGC
GGCGGTGGTGGAGGCGCGCGGAAAGTCGCGGACGCGGTTCCAGATGTTGCGCAG
CGGCAAAAAGTGCTCCATGGTCGGGACGCTCTGGCCGGTCAGGCGCGCGCAATC
GTTGACGCTCTAGACCGTGCAAAAGGAGAGCCTGTAAGCGGGCACTCTTCCGTG
ATGCGCCCGTGTTGATGGTGTAAGTGCAGTTGGCCATAACGGACCAGTTAACGGT
CTGGTGACCCGGCTGCGAGAGCTCGGTGTACCTGAGACGCGAGTAAGCCCTCGA
GTCAAATACGTAGTCGTTGCAAGTCCGCACCAGGTACTGGTATCCCACCAAAAA
GTGCGGCGGCGGCTGGCGGTAGAGGGGCCAGCGTAGGGTGGCCGGGGCTCCGGG
GGCGAGATCTTCCAACATAAGGCGATGATATCCGTAGATGTACCTGGACATCCA
GGTGATGCCGGCGGCGGTGGTGGAGGCGCGCGGAAAGTCGCGGACGCGGTTCCA
GATGTTGCGCAGCGGCAAAAAGTGCTCCATGGTCGGGACGCTCTGGCCGGTCAG
GCGCGCGCAATCGTTGACGCTCTAGACCGTGCAAAAGGAGAGCCTGTAAGCGGG
CACTCTTCCGTGGCTGGGGCAGGAGGACACGGGCAGCCTGGAGGCAACCCTAAA
```

```
CTACCTGCTGACCAACCGGCGGCAGAAGATCCCCTCGTTGCACAGTTTAAACAGC

GAGGAGGAGCGCATTTTGCGCTACGTGCAGCAGAGCGTGAGCCTTAACCTGATG

CGCGACGGGGTAACGCCCAGCGTGGCGCTGGACATGACCGCGCGCAACATGGAA

CCGGGCATGTATGCCTCAAACCGGCCGTTTATCAACCGCCTAATGGACTACTTGC

ATCGCGCGGCCGCCGTGAACCCCGAGTATTTCACCAATGCCATCTTGAACCCGCA

CTGGCTACCGCCCCTGGTTTCTACACCGGGGATTCGAGGTGCCCGAGGGTAAC

GATGGATTCCTCTGGGACGACATAGACGACAGCGTGTTTTCCCCGCAACCGCAGA

CCCTGCTAGAGTTGCAACAGCGCGAGCAGGCAGAGGCGGCGCTGCGAAAGGAA

AGCTTCCGCAGGCCAAGCAGCTTGTCCGATCTAGGCGCTGCGGCCCCGCGGTCAG

ATGCTAGTAGCCCATTTCCAAGCTTGATAGGGTCTCTTACCAGCACTCGCACCAC

CCGCCCGCGCCTGCTGGGCGAGGAGGAGTACCTAAACAACTCGCTGCTGCAGCC

GCAGCGCGAAAAAAACCTGCCTCCGGCATTTCCCAACAACGGGATAGAGAGCCT

AGTGGACAAGATGAGTAGATGGAAGACGTACGCGCAGGAGCACAGGGACGTGC

CAGGCCCGCGCCCGCCCACCCGTCGTCAAAGGCACGACCGTCAGCGGGGTCTGG

TGTGGGAGGACGATGACTCGGCAGACGACAGCAGCGTCCTGGATTTGGGAGGGA

GTGGCAACCCGTTTGCGCACCTTCGCCCCAGGCTGGGGAGAATGTTTTAAAAAAA

AAAAAaGCATGATGCAAATAAAAAAACTCACCAAGGCCATGGCACCGAGCGTTG

GTTTTCTTGTATTCCCCTTAGTATGCGGCGCGCGGCGATGTATGAGGAAGGTCCT

CCTCCCTCCTACGAGAGTGTGGTGAGCGCGGCGCCAGTGGCGGCGGCGCTGGGT

TCTCCCTTCGATGCTCCCCTGGACCCGCCGTTTGTGCCTCCGCGGTACCTGCGGCC

TACCGGGGGAGAAACAGCATCCGTTACTCTGAGTTGGCACCCCTATTCGACACC

ACCCGTGTGTACCTGGTGGACAACAAGTCAACGGATGTGGCATCCCTGAACTACC

AGAACGACCACAGCAACTTTCTGACCACGGTCATTCAAAACAATGACTACAGCC

CGGGGGAGGCAAGCACACAGACCATCAATCTTGACGACCGGTCGCACTGGGGCG

GCGACCTGAAAACCATCCTGCATACCAACATGCCAAATGTGAACGAGTTCATGTT

TACCAATAAGTTTAAGGCGCGGGTGATGGTGTCGCGCTTGCCTACTAAGGACAAT

CAGGTGGAGCTGAAATACGAGTGGGTGGAGTTCACGCTGCCCGAGGGCAACTAC

TCCGAGACCATGACCATAGACCTTATGAACAACGCGATCGTGGAGCACTACTTG

AAAGTGGGCAGACAGAACGGGGTTCTGGAAAGCGACATCGGGGTAAAGTTTGAC

ACCCGCAACTTCAGACTGGGGTTTGACCCCGTCACTGGTCTTGTCATGCCTGGGG

TATATACAAACGAAGCCTTCCATCCAGACATCATTTTGCTGCCAGGATGCGGGGT

GGACTTCACCCACAGCCGCCTGAGCAACTTGTTGGGCATCCGCAAGCGGCAACC

CTTCCAGGAGGGCTTTAGGATCACCTACGATGATCTGGAGGGTGGTAACATTCCC

GCACTGTTGGATGTGGACGCCTACCAGGCGAGCTTGAAAGATGACACCGAACAG

GGCGGGGTGGCGCAGGCGGCAGCAACAGCAGTGGCAGCGGCGCGGAAGAGAA

CTCCAACGCGGCAGCCGCGGCAATGCAGCCGGTGGAGGACATGAACGATCATGC

CATTCGCGGCGACACCTTTGCCACACGGGCTGAGGAGAAGCGCGCTGAGGCCGA

AGCAGCGGCCGAAGCTGCCGCCCCCGCTGCGCAACCCGAGGTCGAGAAGCCTCA

GAAGAAACCGGTGATCAAACCCCTGACAGAGGACAGCAAGAAACGCAGTTACA

ACCTAATAAGCAATGACAGCACCTTCACCCAGTACCGCAGCTGGTACCTTGCATA
```

-continued

```
CAACTACGGCGACCCTCAGACCGGAATCCGCTCATGGACCCTGCTTTGCACTCCT
GACGTAACCTGCGGCTCGGAGCAGGTCTACTGGTCGTTGCCAGACATGATGCAA
GACCCCGTGACCTTCCGCTCCACGCGCCAGATCAGCAACTTTCCGGTGGTGGGCG
CCGAGCTGTTGCCCGTGCACTCCAAGAGCTTCTACAACGACCAGGCCGTCTACTC
CCAACTCATCCGCCAGTTTACCTCTCTGACCCACGTGTTCAATCGCTTTCCCGAGA
ACCAGATTTTGGCGCGCCCGCCAGCCCCCACCATCACCACCGTCAGTGAAAACGT
TCCTGCTCTCACAGATCACGGGACGCTACCGCTGCGCAACAGCATCGGAGGAGT
CCAGCGAGTGACCATTACTGACGCCAGACGCCGCACCTGCCCCTACGTTTACAAG
GCCCTGGGCATAGTCTCGCCGCGCGTCCTATCGAGCCGCACTTTTTGAGCAAGCA
TGTCCATCCTTATATCGCCCAGCAATAACACAGGCTGGGGCCTGCGCTTCCCAAG
CAAGATGTTTGGCGGGGCCAAGAAGCGCTCCGACCAACACCCAGTGCGCGTGCG
CGGGCACTACCGCGCGCCCTGGGGCGCGCACAAACGCGGCCGCACTGGGCGCAC
CACCGTCGATGACGCCATCGACGCGGTGGTGGAGGAGGCGCGCAACTACACGCC
CACGCCGCCACCAGTGTCCACAGTGGACGCGGCCATTCAGACCGTGGTGCGCGG
AGCCCGGCGCTATGCTAAAATGAAGAGACGGCGGAGGCGCGTAGCACGTCGCCA
CCGCCGCCGACCCGGCACTGCCGCCCAACGCGCGGCGGCGGCCCTGCTTAACCG
CGCACGTCGCACCGGCCGACGGGCGGCCATGCGGGCCGCTCGAAGGCTGGCCGC
GGGTATTGTCACTGTGCCCCCCAGGTCCAGGCGACGAGCGGCCGCCGCAGCAGC
CGCGGCCATTAGTGCTATGACTCAGGGTCGCAGGGGCAACGTGTATTGGGTGCG
CGACTCGGTTAGCGGCCTGCGCGTGCCCGTGCGCACCCGCCCCCCGCGCAACTAG
ATTGCAAGAAAAAACTACTTAGACTCGTACTGTTGTATGTATCCAGCGGCGGCGG
CGCGCAACGAAGCTATGTCCAAGCGCAAAATCAAAGAAGAGATGCTCCAGGTCA
TCGCGCCGGAGATCTATGGCCCCCCGAAGAAGGAAGAGCAGGATTACAAGCCCC
GAAAGCTAAAGCGGGTCAAAAAGAAAAAGAAAGATGATGATGATGAACTTGAC
GACGAGGTGGAACTGCTGCACGCTACCGCGCCCAGGCGACGGGTACAGTGGAAA
GGTCGACGCGTAAAACGTGTTTTGCGACCCGGCACCACCGTAGTCTTTACGCCCG
GTGAGCGCTCCACCCGCACCTACAAGCGCGTGTATGATGAGGTGTACGGCGACG
AGGACCTGCTTGAGCAGGCCAACGAGCGCCTCGGGGAGTTTGCCTACGGAAAGC
GGCATAAGGACATGCTGGCGTTGCCGCTGGACGAGGGCAACCCAACACCTAGCC
TAAAGCCCGTAACACTGCAGCAGGTGCTGCCCGCGCTTGCACCGTCCGAAGAAA
AGCGCGGCCTAAAGCGCGAGTCTGGTGACTTGGCACCCACCGTGCAGCTGATGG
TACCCAAGCGCCAGCGACTGGAAGATGTCTTGGAAAAAATGACCGTGGAACCTG
GGCTGGAGCCCGAGGTCCGCGTGCGGCCAATCAAGCAGGTGGCGCCGGGACTGG
GCGTGCAGACCGTGGACGTTCAGATACCCACTACCAGTAGCACCAGTATTGCCAC
CGCCACAGAGGGCATGGAGACACAAACGTCCCCGGTTGCCTCAGCGGTGGCGGA
TGCCGCGGTGCAGGCGGTCGCTGCGGCCGCGTCCAAGACCTCTACGGAGGTGCA
AACGGACCCGTGGATGTTTCGCGTTTCAGCCCCCCGGCGCCCGCGCcGTTCGAGG
AAGTACGGCGCCGCCAGCGCGCTACTGCCCGAATATGCCCTACATCCTTCCATTG
CGCCTACCCCCGGCTATCGTGGCTACACCTACCGCCCCAGAAGACGAGCAACTAC
CCGACGCCGAACCACCACTGGAACCCGCCGCCGCCGTCGCCGTCGCCAGCCCGT
GCTGGCCCCGATTTCCGTGCGCAGGGTGGCTCGCGAAGGAGGCAGGACCCTGGT
```

```
GCTGCCAACAGCGCGCTACCACCCCAGCATCGTTTAAAAGCCGGTCTTTGTGGTT

CTTGCAGATATGGCCCTCACCTGCCGCCTCCGTTTCCCGGTGCCGGGATTCCGAG

GAAGAATGCACCGTAGGAGGGGCATGGCCGGCCACGGCCTGACGGGCGGCATGC

GTCGTGCGCACCACCGGCGGCGGCGCGCGTCGCACCGTCGCATGCGCGGCGGTA

TCCTGCCCCTCCTTATTCCACTGATCGCCGCGGCGATTGGCGCCGTGCCCGGAAT

TGCATCCGTGGCCTTGCAGGCGCAGAGACACTGATTAAAAACAAGTTGCATGTG

GAAAAATCAAAATAAAAAGTCTGGACTCTCACGCTCGCTTGGTCCTGTAACTATT

TTGTAGAATGGAAGACATCAACTTTGCGTCTCTGGCCCCGCGACACGGCTCGCGC

CCGTTCATGGGAAACTGGCAAGATATCGGCACCAGCAATATGAGCGGTGGCGCC

TTCAGCTGGGGCTCGCTGTGGAGCGGCATTAAAAATTTCGGTTCCACCGTTAAGA

ACTATGGCAGCAAGGCCTGGAACAGCAGCACAGGCCAGATGCTGAGGGATAAGT

TGAAAGAGCAAAATTTCCAACAAAAGGTGGTAGATGGCCTGGCCTCTGGCATTA

GCGGGGTGGTGGACCTGGCCAACCAGGCAGTGCAAAATAAGATTAACAGTAAGC

TTGATCCCCGCCCTCCCGTAGAGGAGCCTCCACCGGCCGTGGAGACAGTGTCTCC

AGAGGGGCGTGGCGAAAAGCGTCCGCGCCCCGACAGGGAAGAAACTCTGGTGA

CGCAAATAGACGAGCCTCCCTCGTACGAGGAGGCACTAAAGCAAGGCCTGCCCA

CCACCCGTCCCATCGCGCCCATGGCTACCGGAGTGCTGGGCCAGCACACACCCGT

AACGCTGGACCTGCCTCCCCCCGCCGACACCCAGCAGAAACCTGTGCTGCCAGG

CCCGACCGCCGTTGTTGTAACCCGTCCTAGCCGCGCGTCCCTGCGCCGCGCCGCC

AGCGGTCCGCGATCGTTGCGGCCCGTAGCCAGTGGCAACTGGCAAAGCACACTG

AACAGCATCGTGGGTCTGGGGGTGCAATCCCTGAAGCGCCGACGATGCTTCTGAT

AGCTAACGTGTCGTATGTGTGTCATGTATGCGTCCATGTCGCCGCCAGAGGAGCT

GCTGAGCCGCCGCGCGCCCGCTTTCCAAGATGGCTACCCCTTCGATGATGCCGCA

GTGGTCTTACATGCACATCTCGGGCCAGGACGCCTCGGAGTACCTGAGCCCCGGG

CTGGTGCAGTTTGCCCGCGCCACCGAGACGTACTTCAGCCTGAATAACAAGTTTA

GAAACCCCACGGTGGCGCCTACGCACGACGTGACCACAGACCGGTCCCAGCGTT

TGACGCTGCGGTTCATCCCTGTGGACCGTGAGGATACTGCGTACTCGTACAAGGC

GCGGTTCACCCTAGCTGTGGGTGATAACCGTGTGCTGGACATGGCTTCCACGTAC

TTTGACATCCGCGGCGTGCTGGACAGGGGCCCTACTTTTAAGCCCTACTCTGGCA

CTGCCTACAACGCCCTGGCTCCCAAGGGTGCCCCAAATCCTTGCGAATGGGATGA

AGCTGCTACTGCTCTTGAAATAAACCTAGAAGAAGAGGACGATGACAACGAAGA

CGAAGTAGACGAGCAAGCTGAGCAGCAAAAAACTCACGTATTTGGGCAGGCGCC

TTATTCTGGTATAAATATTACAAAGGAGGGTATTCAAATAGGTGTCGAAGGTCAA

ACACCTAAATATGCCGATAAAACATTTCAACCTGAACCTCAAATAGGAGAATCTC

AGTGGTACGAAACaGAAATTAATCATGCAGCTGGGAGAGTCCTaAAAAAGACTAC

CCCAATGAAACCATGTTACGGTTCATATGCAAAACCCACAAATGAAATGGAGG

GCAAGGCATTCTTGTAAAGCAACAAAATGGAAAGCTAGAAAGTCAAGTGGAAAT

GCAATTTTTCTCAACTACTGAGGCagCCGCAGGCAATGGTGATAACTTGACTCCTA

AAGTGGTATTGTACAGTGAAGATGTAGATATAGAAACCCCAGACACTCATATTTC

TTACATGCCCACTATTAAGGAAGGTAACTCACGAGAACTAATGGGCCAACAATC
```

```
TATGCCCAACAGGCCTAATTACATTGCTTTTAGGGACAATTTTATTGGTCTAATGT

ATTACAACAGCACGGGTAATATGGGTGTTCTGGCGGGCCAAGCATCGCAGTTGA

ATGCTGTTGTAGATTTGCAAGACAGAAACACAGAGCTTTCATACCAGCTTTTGCT

TGATTCCATTGGTGATAGAACCAGGTACTTTTCTATGTGGAATCAGGCTGTTGAC

AGCTATGATCCAGATGTTAGAATTATTGAAAATCATGGAACTGAAGATGAACTTC

CAAATTACTGCTTTCCACTGGGAGGTGTGATTAATACAGAGACTCTTACCAAGGT

AAAACCTAAAACAGGTCAGGAAAATGGATGGGAAAAGATGCTACAGAATTTTC

AGATAAAAATGAAATAAGAGTTGGAAATAATTTTGCCATGGAAATCAATCTAAA

TGCCAACCTGTGGAGAAATTTCCTGTACTCCAACATAGCGCTGTATTTGCCCGAC

AAGCTAAAGTACAGTCCTTCCAACGTAAAAATTTCTGATAACCCAAACACCTACG

ACTACATGAACAAGCGAGTGGTGGCTCCCGGGcTAGTGGACTGCTACATTAACCT

TGGAGCACGCTGGTCCCTTGACTATATGGACAACGTCAACCCATTTAACCACCAC

CGCAATGCTGGCCTGCGCTACCGCTCAATGTTGCTGGGCAATGGTCGCTATGTGC

CCTTCCACATCCAGGTGCCTCAGAAGTTCTTTGCCATTAAAAACCTCCTTCTCCTG

CCCGGGCTCATACACCTACGAGTGGAACTTCAGGAAGGATGTTAACATGGTTCTGC

AGAGCTCCCTAGGAAATGACCTAAGGGTTGACGGAGCCAGCATTAAGTTTGATA

GCATTTGCCTTTACGCCACCTTCTTCCCCATGGCCCACAACACCGCCTCCACGCTT

GAGGCCATGCTTAGAAACGACACCAACGACCAGTCCTTTAACGACTATCTCTCCG

CCGCCAACATGCTCTACCCTATACCCGCCAACGCTACCAACGTGCCCATATCCAT

CCCCTCCCGCAACTGGGCGGCTTTCCGCGGCTGGGCCTTCACGCGCCTTAAGACT

AAGGAAACCCCATCACTGGGCTCGGGCTACGACCCTTATTACACCTACTCTGGCT

CTATACCCTACCTAGATGGAACCTTTTACCTCAACCACACCTTTAAGAAGGTGGC

CATTACCTTTGACTCTTCTGTCAGCTGGCCTGGCAATGACCGCCTGCTTACCCCCA

ACGAGTTTGAAATTAAGCGCTCAGTTGACGGGGAGGGTTACAACGTTGCCCAGT

GTAACATGACCAAAGACTGGTTCCTGGTACAAATGCTAGCTAACTAtAACATTGG

CTACCAGGGCTTCTATATCCCAGAGAGCTACAAGGACCGCATGTACTCCTTCTTT

AGAAACTTCCAGCCCATGAGCCGTCAGGTGGTGGATGATACTAAATACAAGGAC

TACCAACAGGTGGGCATCCTACACCAACACAACAACTCTGGATTTGTTGGCTACC

TTGCCCCCACCATGCGCGAAGGACAGGCCTACCCTGCTAACTTCCCCTATCCGCT

TATAGGCAAGACCGCAGTTGACAGCATTACCCAGAAAAAGTTTCTTTGCGATCGC

ACCCTTTGGCGCATCCCATTCTCCAGTAACTTTATGTCCATGGGCGCACTCACAG

ACCTGGGCCAAAACCTTCTCTACGCCAACTCCGCCCACGCGCTAGACATGACTTT

TGAGGTGGATCCCATGGACGAGCCCACCCTTCTTTATGTTTTGTTTGAAGTCTTTG

ACGTGGTCCGTGTGCACCAGCCGCACCGCGGCGTCATCGAAACCGTGTACCTGCG

CACGCCCTTCTCGGCCGGCAACGCCACAACATAAAGAAGCAAGCAACATCAACA

ACAGCTGCCGCCAAATAATGTACTAGAGACACTTTCAATAAAGGCAAATGCTTTT

ATTTGTACACTCTCGGGTGATTATTTACCCCCACCCTTGCCGTCTGCGCCGTTTAA

AAATCAAAGGGGTTCTGCCGCGCATCGCTATGCGCCACTGGCAGGGACACGTTG

CGATACTGGTGTTTAGTGCTCCACTTAAACTCAGGCACAACCATCCGCGGCAGCT

CGGTGAAGTTTTCACTCCACAGGCTGCGCACCATCACCAACGCGTTTAGCAGGTC

GGGCGCCGATATCTTGAAGTCGCAGTTGGGGCCTCCGCCCTGCGCGCGCGAGTTG
```

```
CGATACACAGGGTTGCAGCACTGGAACACTATCAGCGCCGGGTGGTGCACGCTG

GCCAGCACGCTCTTGTCGGAGATCAGATCCGCGTCCAGGTCCTCCGCGTTGCTCA

GGGCGAACGGAGTCAACTTTGGTAGCTGCCTTCCCAAAAAGGGCGCGTGCCCAG

GCTTTGAGTTGCACTCGCACCGTAGTGGCATCAAAAGGTGACCGTGCCCGGTCTG

GGCGTTAGGATACAGCGCCTGCATAAAAGCCTTGATCTGCTTAAAAGCCACCTGA

GCCTTTGCGCCTTCAGAGAAGAACATGCCGCAAGACTTGCCGGAAAACTGATTG

GCCGGACAGGCCGCGTCGTGCACGCAGCACCTTGCGTCGGTGTTGGAGATCTGC

ACCACATTTCGGCCCCACCGGTTCTTCACGATCTTGGCCTTGCTAGACTGCTCCTT

CAGCGCGCGCTGCCCGTTTTCGCTCGTCACATCCATTTCAATCACGTGCTCCTTAT

TTATCATAATGCTTCCGTGTAGACACTTAAGCTCGCCTTCGATCTCAGCGCAGCG

GTGCAGCCACAACGCGCAGCCCGTGGGCTCGTGATGCTTGTAGGTCACCTCTGCA

AACGACTGCAGGTACGCCTGCAGGAATCGCCCCATCATCGTCACAAAGGTCTTGT

TGCTGGTGAAGGTCAGCTGCAACCCGCGGTGCTCCTCGTTCAGCCAGGTCTTGCA

TACGGCCGCCAGAGCTTCCACTTGGTCAGGCAGTAGTTTGAAGTTCGCCTTTAGA

TCGTTATCCACGTGGTACTTGTCCATCAGCGCGCGCGCAGCCTCCATGCCCTTCTC

CCACGCAGACACGATCGGCACACTCAGCGGGTTCATCACCGTAATTTCACTTTCC

GCTTCGCTGGGCTCTTCCTCTTCCTCTTGCGTCCGCATACCACGCGCCACTGGGTC

GTCTTCATTCAGCCGCCGCACTGTGCGCTTACCTCCTTTGCCATGCTTGATTAGCA

CCGGTGGGTTGCTGAAACCCACCATTTGTAGCGCCACATCTTCTCTTTCTTCCTCG

CTGTCCACGATTACCTCTGGTGATGGCGGGCGCTCGGGCTTGGGAGAAGGGCGCT

TCTTTTTCTTCTTGGGCGCAATGGCCAAATCCGCCGCCGAGGTCGATGGCCGCGG

GCTGGGTGTGCGCGGCACCAGCGCGTCTTGTGATGAGTCTTCCTCGTCCTCGGAC

TCGATACGCCGCCTCATCCGCTTTTTTGGGGCGCCCGGGGAGGCGGCGGCGACG

GGGACGGGGACGACACGTCCTCCATGGTTGGGGGACGTCGCGCCGCACCGCGTC

CGCGCTCGGGGTGGTTTCGCGCTGCTCCTCTTCCCGACTGGCCATTTCCTTCTCC

TATAGGCAGAAAAAGATCATGGAGTCAGTCGAGAAGAAGGACAGCCTAACCGCC

CCCTCTGAGTTCGCCACCACCGCCTCCACCGATGCCGCCAACGCGCCTACCACCT

TCCCCGTCGAGGCACCCCCGCTTGAGGAGGAGGAAGTGATTATCGAGCAGGACC

CAGGTTTTGTAAGCGAAGACGACGAGGACCGCTCAGTACCAACAGAGGATAAAA

AGCAAGACCAGGACAACGCAGAGGCAAACGAGGAACAAGTCGGGCGGGGGGAC

GAAAGGCATGGCGACTACCTAGATGTGGGAGACGACGTGCTGTTGAAGCATCTG

CAGCGCCAGTGCGCCATTATCTGCGACGCGTTGCAAGAGCGCAGCGATGTGCCC

CTCGCCATAGCGGATGTCAGCCTTGCCTACGAACGCCACCTATTCTCACCGCGCG

TACCCCCCAAACGCCAAGAAAACGGCACATGCGAGCCCAACCCGCGCCTCAACT

TCTACCCCGTATTTGCCGTGCCAGAGGTGCTTGCCACCTATCACATCTTTTTCCAA

AACTGCAAGATACCCCTATCCTGCCGTGCCAACCGCAGCCGAGCGGACAAGCAG

CTGGCCTTGCGGCAGGGCGCTGTCATACCTGATATCGCCTCGCTCAACGAAGTGC

CAAAAATCTTTGAGGGTCTTGGACGCGACGAGAAGCGCGCGGCAAACGCTCTGC

AACAGGAAAACAGCGAAAATGAAAGTCACTCTGGAGTGTTGGTGGAACTCGAGG

GTGACAACGCGCGCCTAGCCGTACTAAAACGCAGCATCGAGGTCACCCACTTTG
```

-continued

```
CCTACCCGGCACTTAACCTACCCCCCAAGGTCATGAGCACAGTCATGAGTGAGCT
GATCGTGCGCCGTGCGCAGCCCCTGGAGAGGGATGCAAATTTGCAAGAACAAAC
AGAGGAGGGCCTACCCGCAGTTGGCGACGAGCAGCTAGCGCGCTGGCTTCAAAC
GCGCGAGCCTGCCGACTTGGAGGAGCGACGCAAACTAATGATGGCCGCAGTGCT
CGTTACCGTGGAGCTTGAGTGCATGCAGCGGTTCTTTGCTGACCCGGAGATGCAG
CGCAAGCTAGAGGAAACATTGCACTACACCTTTCGACAGGGCTACGTACGCCAG
GCCTGCAAGATCTCCAACGTGGAGCTCTGCAACCTGGTCTCCTACCTTGGAATTT
TGCACGAAAACCGCCTTGGGCAAAACGTGCTTCATTCCACGCTCAAGGGCGAGG
CGCGCCGCGACTACGTCCGCGACTGCGTTTACTTATTTCTATGCTACACCTGGCA
GACGGCCATGGGCGTTTGGCAGCAGTGCTTGGAGGAGTGCAACCTCAAGGAGCT
GCAGAAACTGCTAAAGCAAAACTTGAAGGACCTATGGACGGCCTTCAACGAGCG
CTCCGTGGCCGCGCACCTGGCGGACATCATTTTCCCCGAACGCCTGCTTAAAACC
CTGCAACAGGGTCTGCCAGACTTCACCAGTCAAAGCATGTTGCAGAACTTTAGGA
ACTTTATCCTAGAGCGCTCAGGAATCTTGCCCGCCACCTGCTGTGCACTTCCTAG
CGACTTTGTGCCCATTAAGTACCGCGAATGCCCTCCGCCGCTTTGGGGCCACTGC
TACCTTCTGCAGCTAGCCAACTACCTTGCCTACCACTCTGACATAATGGAAGACG
TGAGCGGTGACGGTCTACTGGAGTGTCACTGTCGCTGCAACCTATGCACCCCGCA
CCGCTCCCTGGTTTGCAATTCGCAGCTGCTTAACGAAAGTCAAATTATCGGTACC
TTTGAGCTGCAGGGTCCCTCGCCTGACGAAAAGTCCGCGGCTCCGGGGTTGAAAC
TCACTCCGGGGCTGTGGACGTCGGCTTACCTTCGCAAATTTGTACCTGAGGACTA
CCACGCCCACGAGATTAGGTTCTACGAAGACCAATCCCGCCCGCCtAATGCGGAG
CTTACCGCCTGCGTCATTACCCAGGGCCACATTCTTGGCCAATTGCAAGCCATCA
ACAAAGCCCGCCAAGAGTTTCTGCTACGAAAGGGACGGGGGGTTTACTTGGACC
CCCAGTCCGGCGAGGAGCTCAACCCAATCCCCCCGCCGCCGCAGCCCTATCAGC
AGCAGCCGCGGGCCCTTGCTTCCCAGGATGGCACCCAAAAAGAAGCTGCAGCTG
CCGCCGCCACCCACGGACGAGGAGGAATACTGGGACAGTCAGGCAGAGGAGGTT
TTGGACGAGGAGGAGGAGGACATGATGGAAGACTGGGAGAGCCTAGACGAGGA
AGCTTCCGAGGTCGAAGAGGTGTCAGACGAAACACCGTCACCCTCGGTCGCATT
CCCCTCGCCGGCGCCCCAGAAATCGGCAACCGGTTCCAGCATGGCTACAACCTCC
GCTCCTCAGGCGCCGCCGGCACTGCCCGTTCGCCGACCCAACCGTAGATGGGAC
ACCACTGGAACCAGGGCCGGTAAGTCCAAGCAGCCGCCGCCGTTAGCCCAAGAG
CAACAACAGCGCCAAGGCTACCGCTCATGGCGCGGGCACAAGAACGCCATAGTT
GCTTGCTTGCAAGACTGTGGGGGCAACATCTCCTTCGCCCGCCGCTTTCTTCTCTA
CCATCACGGCGTGGCCTTCCCCCGTAACATCCTGCATTACTACCGTCATCTCTACA
GCCCATACTGCACCGGCGGCAGCGGCAGCAACAGCAGCGGCCACACAGAAGCA
AAGGCGACCGGATAGCAAGACTCTGACAAAGCCCAAGAAATCCACAGCGGCGG
CAGCAGCAGGAGGAGGAGCGCTGCGTCTGGCGCCCAACGAACCCGTATCGACCC
GCGAGCTTAGAAACAGGATTTTTCCCACTCTGTATGCTATATTTCAACAGAGCAG
GGGCCAAGAACAAGAGCTGAAAATAAAAAACAGGTCTCTGCGATCCCTCACCCG
CAGCTGCCTGTATCACAAAAGCGAAGATCAGCTTCGGCGCACGCTGGAAGACGC
GGAGGCTCTCTTCAGTAAATACTGCGCGCTGACTCTTAAGGACTAGTTTCGCGCC
```

-continued

```
CTTTCTCAAATTTAAGCGCGAAAACTACGTCATCTCCAGCGGCCACACCCGGCGC

CAGCACCTGTtGTCAGCGCCATTATGAGCAAGGAAATTCCCACGCCCTACATGTG

GAGTTACCAGCCACAAATGGGACTTGCGGCTGGAGCTGCCCAAGACTACTCAAC

CCGAATAAACTACATGAGCGCGGGACCCCACATGATATCCCGGGTCAACGGAAT aCGCGCCCACCGAAACCGAATTCTCcTGGAACAGGCGGCTATTACCACCACACCT

CGTAATAACCTTAATCCCCGTAGTTGGCCCGCTGCCCTGGTGTACCAGGAAAGTC

CCGCTCCCACCACTGTGGTACTTCCCAGAGACGCCCAGGCCGAAGTTCAGATGAC

TAACTCAGGGGCGCAGCTTGCGGGCGGCTTTCGTCACAGGGTGCGGTCGCCCGG

GCAGGGTATAACTCACCTGACAATCAGAGGGCGAGGTATTCAGCTCAACGACGA

GTCGGTGAGCTCCTCGCTTGGTCTCCGTCCGACGGGACATTTCAGATCGGCGGC

GCCGGCCGctCTTCATTCACGCCTCGTCAGGCAATCCTAACTCTGCAGACCTCGTC

CTCTGAGCCGCGCTCTGGAGGCATTGGAACTCTGCAATTTATTGAGGAGTTTGTG

CCATCGGTCTACTTTAACCCCTTCTCGGGACCTCCCGGCCACTATCCGGATCAATT

TATTCCTAACTTTGACGCGGTAAAGGACTCGGCGGACGGCTACGACTGAATGTTA

AGTGGAGAGGCAGAGCAACTGCGCCTGAAACACCTGGTCCACTGTCGCCGCCAC

AAGTGCTTTGCCCGCGACTCCGGTGAGTTTTGCTACTTTGAATTGCCCGAGGATC

ATATCGAGGGCCCGGCGCACGGCGTCCGGCTTACCGCCCAGGGAGAGCTTGCCC

GTAGCCTGATTCGGGAGTTTACCCAGCGCCCCCTGCTAGTTGAGCGGGACAGGG

GACCCTGTGTTCTCACTGTGATTTGCAACTGTCCTAACCcTGGATTACATCAAGAT

CTTTGTTGCCATCTCTGTGCTGAGTATAATAAATACAGAAATTAAAATATACTGG

GGCTCCTATCGCCATCCTGTAAACGCCACCGTCTTCACCCGCCCAAGCAAACCAA

GGCGAACCTTACCTGGTACTTTTAACATCTCTCCCTCTGTGATTTACAACAGTTTC

AACCCAGACGGAGTGAGTCTACGAGAGAACCTCTCCGAGCTCAGCTACTCCATC

AGAAAAAACACCACCCTCCTTACCTGCCGGGAACGTACGAGTGCGTCACCGGCC

GCTGCACCACACCTACCGCCTGACCGTAAACCAGACTTTTTCCGGACAGACCTCA

ATAACTCTGTTTACCAGAACAGGAGGTGAGCTTAGAAAACCCTTAGGGTATTAG

GCCAAAGGCGCAGCTACTGTGGGGTTTATGAACAATTCAAGCAACTCTACGGGC

TATTCTAATTCAGGTTTCTCTAGAAATGGACGGAATTATTACAGAGCAGCGCCTG

CTAGAAAGACGCAGGGCAGCGGCCGAGCAACAGCGCATGAATCAAGAGCTCCA

AGACATGGTTAACTTGCACCAGTGCAAAAGGGGTATCTTTTGTCTGGTAAAGCAG

GCCAAAGTCACCTACGACAGTAATACCACCGGACACCGCCTTAGCTACAAGTTG

CCAACCAAGCGTCAGAAATTGGTGGTCATGGTGGGAGAAAAGCCCATTACCATA

ACTCAGCACTCGGTAGAAACCGAAGGCTGCATTCACTCACCTTGTCAAGGACCTG

AGGATCTCTGCACCCTTATTAAGACCCTGTGCGGTCTCAAAGATCTTATTCCCTTT

AACTAATAAAAAAAATAATAAAGCATCACTTACTTAAAATCAGTTAGCAAATT

TCTGTCCAGTTTATTCAGCAGCACCTCCTTGCCCTCCTCCCAGCTCTGGTATTGCA

GCTTCCTCCTGGCTGCAAACTTTCTCCACAATCTAAATGGAATGTCAGTTTCCTCC

TGTTCCTGTCCATCCGCACCCACTATCTTCATGTTGTTGCAGATGAAGCGCGCAA

GACCGTCTGAAGATACCTTCAACCCCGTGTATCCATATGACACGGAAACCGGTCC

TCCAACTGTGCCTTTTCTTACTCCTCCCTTTGTATCCCCCAATGGGTTTCAAGAGA
```

-continued

```
GTCCCCCTGGGGTACTCTCTTTGCGCCTATCCGAACCTCTAGTTACCTCCAATGGC
ATGCTTGCGCTCAAAATGGGCAACGGCCTCTCTCTGGACGAGGCCGGCAACCTTA
CCTCCCAAAATGTAACCACTGTGAGCCCACCTCTCAAAAAAACCAAGTCAAACA
TAAACCTGGAAATATCTGCACCCCTCACAGTTACCTCAGAAGCCCTAACTGTGGC
TGCCGCCGCACCTCTAATGGTCGCGGGCAACACACTCACCATGCAATCACAGGCC
CCGCTAACCGTGCACGACTCCAAACTTAGCATTGCCACCCAAGGACCCCTCACAG
TGTCAGAAGGAAAGCTAGCCCTGCAAACATCAGGCCCCCTCACCACCACCGATA
GCAGTACCCTTACTATCACTGCCTCACCCCCTCTAACTACTGCCACTGGTAGCTTG
GGCATTGACTTGAAAGAGCCCATTTATACACAAAATGGAAAACTAGGACTAAAG
TACGGGGCTCCTTTGCATGTAACAGACGACCTAAACACTTTGACCGTAGCAACTG
GTCCAGGTGTGACTATTAATAATACTTCCTTGCAAACTAAAGTTACTGGAGCCTT
GGGTTTTGATTCACAAGGCAATATGCAACTTAATGTAGCAGGAGGACTAAGGAT
TGATTCTCAAAACAGACGCCTTATACTTGATGTTAGTTATCCGTTTGATGCTCAAA
ACCAACTAAATCTAAGACTAGGACAGGGCCCTCTTTTTATAAACTCAGCCCACAA
CTTGGATATTAACTACAACAAAGGCCTTTACTTGTTTACAGCTTCAAACAATTCC
AAAAAGCTTGAGGTTAACCTAAGCACTGCCAAGGGGTTGATGTTTGACGCTACA
GCCATAGCCATTAATGCAGGAGATGGGCTTGAATTTGGTTCACCTAATGCACCAA
ACACAAATCCCCTCAAAACAAAAATTGGCCATGGCCTAGAATTTGATTCAAACA
AGGCTATGGTTCCTAAACTAGGAACTGGCCTTAGTTTTGACAGCACAGGTGCCAT
TACAGTAGGAAACAAAATAATGATAAGCTAACTTTGTGGACCACACCAGCTCC
ATCTCCTAACTGTAGACTAAATGCAGAGAAAGATGCTAAACTCACTTTGGTCTTA
ACAAAATGTGGCAGTCAAATACTTGCTACAGTTTCAGTTTTGGCTGTTAAAGGCA
GTTTGGCTCCAATATCTGGAACAGTTCAAAGTGCTCATCTTATTATAAGATTTGA
CGAAAATGGAGTGCTACTAAACAATTCCTTCCTGGACCCAGAATATTGGAACTTT
AGAAATGGAGATCTTACTGAAGGCACAGCCTATACAAACGCTGTTGGATTTATGC
CTAACCTATCAGCTTATCCAAAATCTCACGGTAAAACTGCCAAAAGTAACATTGT
CAGTCAAGTTTACTTAAACGGAGACAAAACTAAACCTGTAACACTAACCATTAC
ACTAAACGGTACACAGGAAACAGGAGACACAACTCCAAGTGCATACTCTATGTC
ATTTTCATGGGACTGGTCTGGCCACAACTACATTAATGAAATATTTGCCACATCC
TCTTACACTTTTTCATACATTGCCCAAGAATAAAGAATCGTTTGTGTTATGTTTCA
ACGTGTTTATTTTTCAATTGCAGAAAATTTCGAATCATTTTTCATTCAGTAGTATA
GCCCCACCACCACATAGCTTATACAGATCACCGTACCTTAATCAAACTCACAGAA
CCCTAGTATTCAACCTGCCACCTCCCTCCCAACACACAGAGTACACAGTCCTTTC
TCCCCGGCTGGCCTTAAAAAGCATCATATCATGGGTAACAGACATATTCTTAGGT
GTTATATTCCACACGGTTTCCTGTCGAGCCAAACGCTCATCAGTGATATTAATAA
ACTCCCCGGGCAGCTCACTTAAGTTCATGTCGCTGTCCAGCTGCTGAGCCACAGG
CTGCTGTCCAACTTGCGGTTGCTTAACGGGCGGCGAAGGAGAAGTCCACGCCTAC
ATGGGGTAGAGTCATAATCGTGCATCAGGATAGGGCGGTGGTGCTGCAGCAGC
GCGCGAATAAACTGCTGCCGCCGCCGCTCCGTCCTGCAGGAATACAACATGGCA
GTGGTCTCCTCAGCGATGATTCGCACCGCCCGCAGCATAAGGCGCCTTGTCCTCC
GGGCACAGCAGCGCACCCTGATCTCACTTAAATCAGCACAGTAACTGCAGCACA
```

```
GCACCACAATATTGTTCAAAATCCCACAGTGCAAGGCGCTGTATCCAAAGCTCAT

GGCGGGGACCACAGAACCCACGTGGCCATCATACCACAAGCGCAGGTAGATTAA

GTGGCGACCCCTCATAAACACGCTGGACATAAACATTACCTCTTTTGGCATGTTG

TAATTCACCACCTCCCGGTACCATATAAACCTCTGATTAAACATGGCGCCATCCA

CCACCATCCTAAACCAGCTGGCCAAAACCTGCCCGCCGGCTATACACTGCAGGG

AACCGGGACTGGAACAATGACAGTGGAGAGCCCAGGACTCGTAACCATGGATCA

TCATGCTCGTCATGATATCAATGTTGGCACAACACAGGCACACGTGCATACACTT

CCTCAGGATTACAAGCTCCTCCCGCGTTAGAACCATATCCCAGGGAACAACCCAT

TCCTGAATCAGCGTAAATCCCACACTGCAGGGAAGACCTCGCACGTAACTCACGT

TGTGCATTGTCAAAGTGTTACATTCGGGCAGCAGCGGATGATCCTCCAGTATGGT

AGCGCGGGTTTCTGTCTCAAAAGGAGGTAGACGATCCCTACTGTACGGAGTGCG

CCGAGACAACCGAGATCGTGTTGGTCGTAGTGTCATGCCAAATGGAACGCCGGA

CGTAGTCATATTTCCTGAAGCAAAACCAGGTGCGGGCGTGACAAACAGATCTGC

GTCTCCGGTCTCGCCGCTTAGATCGCTCTGTGTAGTAGTTGTAGTATATCCACTCT

CTCAAAGCATCCAGGCGCCCCCTGGCTTCGGGTTCTATGTAAACTCCTTCATGCG

CCGCTGCCCTGATAACATCCACCACCGCAGAATAAGCCACACCCAGCCAACCTA

CACATTCGTTCTGCGAGTCACACACGGGAGGAGCGGGAAGAGCTGGAAGAACCA

TGTTTTTTTTTTATTCCAAAAGATTATCCAAAACCTCAAAATGAAGATCTATTAA

GTGAACGCGCTCCCCTCCGGTGGCGTGGTCAAACTCTACAGCCAAAGAACAGAT

AATGGCATTTGTAAGATGTTGCACAATGGCTTCCAAAAGGCAAACGGCCCTCAC

GTCCAAGTGGACGTAAAGGCTAAACCCTTCAGGGTGAATCTCCTCTATAAACATT

CCAGCACCTTCAACCATGCCCAAATAATTCTCATCTCGCCACCTTCTCAATATATC

TCTAAGCAAATCCCGAATATTAAGTCCGGCCATTGTAAAAATCTGCTCCAGAGCG

CCCTCCACCTTCAGCCTCAAGCAGCGAATCATGATTGCAAAAATTCAGGTTCCTC

ACAGACCTGTATAAGATTCAAAAGCGGAACATTAACAAAAATACCGCGATCCCG

TAGGTCCCTTCGCAGGGCCAGCTGAACATAATCGTGCAGGTCTGCACGGACCAG

CGCGGCCACTTCCCCGCCAGGAACCaTGACAAAAGAACCCACACTGATTATGACA

CGCATACTCGGAGCTATGCTAACCAGCGTAGCCCCGATGTAAGCTTGTTGCATGG

GCGGCGATATAAAATGCAAGGTGCTGCTCAAAAAATCAGGCAAAGCCTCGCGCA

AAAAAGAAAGCACATCGTAGTCATGCTCATGCAGATAAAGGCAGGTAAGCTCCG

GAACCACCACAGAAAAAGACACCATTTTTCTCTCAAACATGTCTGCGGGTTTCTG

CATAAACACAAAATAAAATAACAAAAAAACATTTAAACATTAGAAGCCTGTCTT

ACAACAGGAAAAACAACCCTTATAAGCATAAGACGGACTACGGCCATGCCGGCG

TGACCGTAAAAAAACTGGTCACCGTGATTAAAAAGCACCACCGACAGCTCCTCG

GTCATGTCCGGAGTCATAATGTAAGACTCGGTAAACATCAGGTTGATTCACAT

CGGTCAGTGCTAAAAAGCGACCGAAATAGCCCGGGGGAATACATACCCGCAGGC

GTAGAGACAACATTACAGCCCCCATAGGAGGTATAACAAAATTAATAGGAGAGA

AAAACACATAAACACCTGAAAAACCCTCCTGCCTAGGCAAAATAGCACCCTCCC

GCTCCAGAACAACATACAGCGCTTCCACAGCGGCAGCCATAACAGTCAGCCTTA

CCAGTAAAAAAGAAAACCTATTAAAAAAACACCACTCGACACGGCACCAGCTCA
```

-continued

ATCAGTCACAGTGTAAAAAAGGGCCAAGTGCAGAGCGAGTATATATAGGACTAA

AAAATGACGTAACGGTTAAAGTCCACAAAAAACACCCAGAAAACCGCACGCGA

ACCTACGCCCAGAAACGAAAGCcaaaaaacccacaacttcctcaaatcgtcacttccgttttcccacgttacTTC

TGTGGAATGTGTGTCAGTTAGGGTGTGGAAAGTCCCCAGGCTCCCCAGCAGGCA

GAAGTATGCAAAGCATGCATCTCAATTAGTCAGCAACCAGGTGTGGAAAGTCCC

CAGGCTCCCCAGCAGGCAGAAGTATGCAAAGCATGCAGAAGTATGCAAAGCATG

CATCTCAATTAGTCAGCAACCAGGTGTGGAAAGTCCCCAGGCTCCCCAGCAGGC

AGAAGTATGCAAAGCATGCATCTCAATTAGTCAGCAACCATAGTCCCGCCCCTAA

CTCCGCCCATCCCGCCCCTAACTCCGCCCAGTTCCGCCCATTCTCCGCCCCATGGC

TGACTAATTTTTTTATTTATGCAGAGGCCGAGGCCGCCTCTGCCTCTGAGCTATT

CCAGAAGTAGTGAGGAGGCTTTTTTGGAGGCCTAGGCTTTTGCAAACCTCCGCGG

GGATCCgcaccatggtgagcaagggcgaggaggataacatggccatcatcaaggagttcatgcgcttcaaggtgcacatggag ggctccgtgaacggccacgagttcgagatcgagggcgagggcgagggccgccccta cgagggcacccagaccgccaagctgaa ggtgaccaagggtggcccctgccttcgcctgggacatcctgtcccctcagttcatgtacggctccaaggcctacgtgaagcacccc gccgacatccccgactacttgaagctgtccttccccgagggcttcaagtgggagcgcgtgatgaacttcgaggacggcggcgtggtg accgtgacccaggactcctccctgcaggacggcgagttcatctacaaggtgaagctgcgcggcaccaacttccctccgacggccc cgtaatgcagaagaagaccatgggctgggaggcctcctccgagcggatgtaccccgaggacggcgccctgaagggcgagatcaa gcagaggctgaagctgaaggacggcggccactacgacgctgaggtcaagaccacctacaaggccaagaagcccgtgcagctgcc cggcgcctacaacgtcaacatcaagttggacatcacctcccacaacgaggactacaccatcgtggaacagtacgaacgcgccgagg gccgccactccaccggcggCATGGACGAGCTGTACAAGTAGTTCGAAATGACCGACCAAGC

GACGCCCAACCTGCCATCACGAGATTTCGATTCCACCGCCGCCTTCTATGAAAGG

TTGGGCTTCGGAATCGTTTTCCGGGACGCCGGCTGGATGATCCTCCAGCGCGGGG

ATCTCATGCTGGAGTTCTTCGCCCACCCCAACTTGTTTATTGCAGCTTATAATGGT

TACAAATAAAGCAATAGCATCACAAATTTCACAAATAAAGCATTTTTTTCACTGC

ATTCTAGTTGTGGTTTGTCCAAACTCATCAATGTATCTTATCATGTCTGTATACCG

TCGACCTCTAGCTAGAGgtcacttcccattttaagaaaactacaattcccaacacatacaagttactCCGCCCTA

AAACCTACGTCACCCGCCCCGTTCCCACGCCCCGCGCCACGTCACAAACTCCACC

CCCTCATTATCATATTGGCTTCAATCCAAAATAAGGTATATTATTGATGATGTTAA

TTAATTTAAATCCGCATGCGATATCGAGCTCTCCCGGGAATTCGGATCTGCGACG

CGAGGCTGGATGGCCTTCCCCATTATGATTCTTCTCGcgtttaagggcaccaataactgccttaaaa aaattacgccccgccctgccactcatcgcagtactgttgtaattcattaagcattctgccgacatggaagccatcacaaacggcatgatg aacctgaatcgccagcggcatcagcaccttgtcgccttgcgtataatatttgcccatggtgaaaacgggggcgaagaagttgtccatatt ggccacgtttaaatcaaaactggtgaaactcacccagggattggctgagacgaaaaacatattctcaataaacccctttagggaaatagg ccaggttttcaccgtaacacgccacatcttgcgaatatatgtgtagaaactgccggaaatcgtcgtggtattcactccgagcgatgaaa acgtttcagtttgctcatggaaaacggtgtaacaagggtgaacactatcccatatccaccagctcaccgtctttcattgccatacggaattc cggatgagcattcatcaggcgggcaagaatgtgaataaaggccgataaaacttgtgcttattttctttacggtctttaaaaaggccgta atatccagctgaacggtctggttataggtacattgagcaactgactgaaatgcctcaaaatgttctttacgatgccattgggatatatcaac ggtggtatatccagtgatttttttctccatttagcttcttagctcctgaaaatctcgataactcaaaaaatacgcccggtagtgatcttatttc attatggtgaaagttggaacctcttacgtgccgatcaacgtctcattacgccaaaagttggcccagggcttcccggtatcaacagggac accaggatttatttattctgcgaagtgatcttccgtcacaggtatttattcgcgataagctcatggagcggcgtaaccgtcgcacaggaag gacagagaaagcgcggatctgggaagtgacggacagaacggtcaggacctggattggggaggcggttgccgccgctgctgctga -continued cggtgtgacgttctctgttccggtcacaccacatacgttccgccattcctatgcgatgcacatgctgtatgccggtataccgctgaaagtt ctgcaaagcctgatgggacataagtccatcagttcaacgaagtctacacgaaggttttttgcgctggatgtggctgcccggcaccggg tgcagtttgcgatgccggagtctgatgcggttgcgatgctgaaacaattatcctgagaataaatgccttggccttatatggaaatgtgga actgagtggatatgctgtItttgtctgttaaacagagaagctggctgttatccactgagaagcgaacgaaacagtcgggaaaatctccca ttatcgtagagatccgcattattaatctcaggagcctgtgtagcgtttataggaagtagtgttctgtcatgatgcctgcaagcggtaacgaa aacgatttgaatatgccttcaggaacaatagaaatcttcgtgcggtgttacgttgaagtggagcggattatgtcagcaatggacagaaca acctaatgaacacagaaccatgatgtggtctgtccttttacagccagtagtgctcgccgcagtcgagcgacagggcgaagccctcgag tgagcgaggaagcaccagggaacagcacttatatattctgcttacacacgatgcctgaaaaaacttcccttgggttatccacttatcca cggggatattttttataattattttttttatagtttttagatcttcttttttagagcgccttgtaggcctttatccatgctggttctagagaaggtgttgt gacaaattgcccttcagtgtgacaaatcaccctcaaatgacagtcctgtctgtgacaaattgcccttaaccctgtgacaaattgccctca gaagaagctgtatttcacaaagttatccctgcttattgactctatttatttagtgtgacaatctaaaaacttgtcacacttcacatggatctgtc atggcggaaacagcggttatcaatcacaagaaacgtaaaaatagcccgcgaatcgtccagtcaaacgacctcactgaggcggcatat agtctctcccgggatcaaaaacgtatgctgtatctgttcgttgaccagatcagaaatctgatggcaccctacaggaacatgacggtatc tgcgagatccatgttgctaaatatgctgaaatattcggattgacctctgcggaagccagtaaggatatacggcaggcattgaagagtttc gcggggaaggaagtggttttttatcgccctgaagaggatgccggcgatgaaaaaggctatgaatcttttccttggtttatcaaacgtgcg cacagtccatccagagggctttacagtgtacatatcaacccatatctcattcccttctttatcgggttacagaaccggtttacgcagtttcgg cttagtgaaacaaaagaaatcaccaatccgtatgccatgcgtttatacgaatccctgtgtcagtatcgtaagccggatggctcaggcatc gtctctctgaaaatcgactggatcatagagcgttaccagctgcctcaaagttaccagcgtatgcctgacttccgccgccgcttcctgcag gtctgtgttaatgagatcaacagcagaactccaatgcgcctctcatacattgagaaaagaaaggccgccagacgactcatatcgtattt tccttccgcgatatcacttccatgacgacaggatagtctgagggttatctgtcacagatttgagggtggttcgtcacatttgttctgacctac tgagggtaatttgtcacagttttgctgtttccttcagcctgcatggattactcatactattgaactgtaattataaggaagccaaatttgagg gcagtttgtcacagttgatttccttctattccctcgtcatgtgacctgatatcggggggttagttcgtcatcattgatgagggttgattatcac agtttattactctgaattggctatccgcgtgtgtacctctacctggagttttttcccacggtggatatttcttcttgcgctgagcgtaagagctat ctgacagaacagttcttctttgcttcctcgccagttcgctcgctatgctcggttacacggctgcggcgagcgctagtgataataagtgact gaggtatgtgctcttcttatctccttttgtagtgttgctcttattttaaacaacttttgcggttttttgatgactttgcgatttgttgttgctttgcagt aaattgcaagatttaataaaaaaacgcaaagcaatgattaaaggatgttcagaatgaaactcatggaaacacttaaccagtgcataaac gctggtcatgaaatgacgaaggctatcgccattgcacagtttaatgatgacagcccggaagcgaggaaaataacccggcgctggaga ataggtgaagcagcggatttagttgggggtttcttctcaggctatcagagatgccgagaaagcagggcgactaccgcacccggatatgg aaattcgaggacgggttgagcaacgtgttggtatacaattgaacaaattaatcatatgcgtgatgtgtttggtacgcgattgcgacgtgc tgaagacgtatttccaccggtgatcgggttgctgcccataaaggtggcgtttacaaaacctcagtttctgttcatcttgctcaggatctgg ctctgaaggggctacgtgttttgctcgtgaaggtaacgaccccagggaacagcctcaatgtatcacggatgggtaccagatcttcat attcatgcagaagacactctcctgcctttctatcttggggaaaaggacgatgtcacttatgcaataaagcccacttgctggccggggctt gacattattccttcctgtctggctctgcaccgtattgaaactgagttaatgggcaaatttgatgaaggtaaactgcccaccgatccacacct gatgctccgactggccattgaaactgttgctcatgactatgatgtcatagttattgacagcgcgcctaacctgggtatcggcacgattaat gtcgtatgtgctgctgatgtgctgattgttcccacgcctgctgagttgtttgactacacctccgcactgcagtttacgatatgcttcgtgatc tgctcaagaacgttgatcttaaagggttcgagcctgatgtacgtatttttgcttaccaaatacagcaatagtaatggctctcagtccccgtgg atggaggagcaaattcgggatgcctggggaagcatggttctaaaaaatgttgtacgtgaaacggatgaagttggtaaaggtcagatcc ggatgagaactgtttttgaacaggccattgatcaacgctcttcaactggtgcctggagaaatgctctttctatttgggaacctgtctgcaat gaaattttcgatcgtctgattaaaccacgctgggagattagataatgaagcgtgcgcctgttattccaaaacatacgctcaatactcaacc ggttgaagatacttcgttatcgacaccagctgccccgatggtggattcgttaattgcgcgcgtaggagtaatggctcgcggtaatgccat -continued

```
tactttgcctgtatgtggtcgggatgtgaagtttactcttgaagtgctccggggtgatagtgttgagaagacctctcgggtatggtcaggta atgaacgtgaccaggagctgcttactgaggacgcactggatgatctcatcccttcttttctactgactggtcaacagacaccggcgttcg gtcgaagagtatctggtgtcatagaaattgccgatgggagtcgccgtcgtaaagctgctgcacttaccgaaagtgattatcgtgttctggt tggcgagctggatgatgagcagatggctgcattatccagattgggtaacgattatcgcccaacaagtgcttatgaacgtggtcagcgtt atgcaagccgattgcagaatgaatttgctggaaatatttctgcgctggctgatgcggaaaatatttcacgtaagattattacccgctgtatc aacaccgccaaattgcctaaatcagttgttgctcattactcaccccggtgaactatctgcccggtcaggtgatgcacttcaaaaagcctft acagataaagaggaattacttaagcagcaggcatctaaccttcatgagcagaaaaaagctggggtgatatttgaagctgaagaagttat cactcttttaacttctgtgcttaaaacgtcatctgcatcaagaactagtttaagctcacgacatcagtttgctcctggagcgacagtattgtat aagggcgataaaatggtgcttaacctggacaggtctcgtgttccaactgagtgtatagagaaaattgaggccattcttaaggaacttgaa aagccagcaccctgatgcgaccacgttttagtctacgtttatctgtctttacttaatgtcctagttacaggccagaaagcataactggcctg aatattctctctgggcccactgttccacttgtatcgtcggtctgataatcagactgggaccacggtcccactcgtatcgtcggtctgattatt agtctgggaccacggtcccactcgtatcgtcggtctgattattagtctgggaccacggtcccactcgtatcgtcggtctgataatcagact gggaccacggtcccactcgtatcgtcggtctgattattagtctgggaccatggtcccactcgtatcgtcggtctgattattagtctgggac cacggtcccactcgtatcgtcggtctgattattagtctggaaccacggtcccactcgtatcgtcggtctgattattagtctgggaccacgg tcccactcgtatcgtcggtctgattattagtctgggaccacgatcccactcgtgttgtcggtctgattatcggtctgggaccacggtccca cttgtattgtcgatcagactatcagcgtgagactacgattccatcaatgcctgtcaagggcaagtattgacatgtcgtcgtaacctgtaga acggagtaacctcggtgtgcggttgtatgcctgctgtggattgctgctgtgtcctgcttatccacaacattttgcgcacggttatgtggaca aaatacctggttacccaggccgtgccggcacgttaaccgggCACATTTCCCCGAAAAGTGCCACCTGACG

TCTAAGAAACCATTATTATCATGACATTAACCTATAAAAATAGGCGTATCACGAG

GCCCTTTCGTCTTCAAGaattgGATCCGAATTCCCGGGAGAGCTCGATATCGCATGC

GGATTTAAATTAATTAA
```

REFERENCES

1. Arnold F. H., Design by directed evolution, Acc. Chem. Res., 1998. 31(3): p. 125-31.
2. Baniecki M. L., McGrath W. J., and Mangel W. F., Regulation of a viral proteinase by a peptide and DNA in one-dimensional space: III. atomic resolution structure of the nascent form of the adenovirus proteinase, J. Biol. Chem., 2013. 288(3): p. 2081-91.
3. Benihoud K., Yeh P., and Perricaudet M., Adenoviurs vectors for gene delivery, Curr. Opin. Biotechnol., 1999. 10(5): p. 440-47.
4. Biechele T. L., Adams A. M., and Moon R. T., Transcription-based reporters of Wnt/beta-catenin signaling, Cold Spring Harb. Protoc., 2009. 2009(6): pdb.prot5223.
5. Connolly S. A., Landsburg D. J., Carfi A., Wiley D. C., Cohen G. H., and Eisenberg R. J., Structure-Based Mutagenesis of Herpes Simplex Virus Glycoprotein D Defines Three Critical Regions at the gD-HveA/HVEM Binding Interface, J. Virol., 2003. 77(14): p. 8127-40.
6. Das A. T., Zhou X., Vink M., Klaver B., Verhoef K., Marzio G., and Berkhout B., Viral Evolution as a Tool to Improve the Tetracycline-regulated Gene Expression System, J. Biol. Chem., 2004. 279(18): p. 18776-82.
7. Day R. S. and Ziolowski C. H. J., UV-induced reversion of adenovirus 5ts2 infecting human cells, Photochem. Photobiol., 1981. 34(3): p. 403-06.
8. Dickinson B. C., Packer M. S., Badran A. H., and Liu D. R., A system for the continuous directed evolution of proteases rapidly reveals drug-resistance mutations, Nat. Commun., 2014. 5: p. 5352.
9. Duffy K. E., Quail M. R., Nguyen T. T., Wittrock R. J., Bartus J. O., Halsey W. M., Leary J. J., Bacon T. H., and Sarisky R. T., Assessing the contribution of the herpes simplex virus DNA polymerase to spontaneous mutations, BMC Infect. Dis., 2002. 2:7.
10. Esvelt K. M., Carlson J. C., and Liu D. R., A system for the continuous directed evolution of biomolecules, Nature, 2011. 472(7344): p. 499-503.
11. Flint S. J., Adenoviruses. Encyclopedia of Life Sciences (2001).
12. Gossen M. and Bujard H., Tight control of gene expression in mammalian cells by tetracycline-response promoters, Proc. Natl. Acad. Sci. USA, 1992. 89(12): p. 5547-51.
13. Greber U. F., Webster P., Weber J., and Helenius A., The role of the adenovirus protease on virus entry into cells, EMBO J., 1996. 15(8): p. 1766-77.
14. Grosche P., Sirockin F., Mac Sweeney A., Ramage P., Erbel P., Melkko S., Bemardi A., Hughes N., Ellis D., Combrink K. D., Jarousse N., and Altmann E., Structure-based design and optimization of potent inhibitors of the adenoviral protease, Bioorg. Med. Chem. Lett., 2015. 25(3):p. 438-43
15. Hecht B., Müller G., and Hillen W., Noninducible Tet repressor mutations map from the operator binding motif to the C terminus, J. Bacteriol., 1993. 175(4): p. 1206-10.
16. Iwamoto M., Bjorklund T., Lundberg C., Kirik D., and Wandless T. J., A general chemical method to regulate protein stability in the mammalian central nervous system, Chem. Biol., 2010. 17(9): p. 981-89.

17. Kathman S. G., Xu Z., and Statsyuk, A. V., A fragment-based method to discover irreversible covalent inhibitors of cysteine proteases, J. Med. Chem., 2014. 57(11): p. 4969-74.
18. Kim Y. B., Komor A. C., Levy J. M., Packer M. S., Zhao K. T., and Liu D. R., Increasing the genome-targeting scope and precision of base editing with engineered Cas9-cytidine deaminase fusions, Nat. Biotechnol., 2017. 35(4): p. 371-76.
19. Liu C. C. and Schultz P. G., Adding New Chemistries to the Genetic Code, Annu. Rev. Biochem., 2010. 79: p. 413-44.
20. Muick-Hausl M., Solanki M., Zhang W., Ruzsics Z., and Ehrhardt A., Ad 2.0: a novel recombineering platform for high-throughput generation of tailored adenoviruses, Nucleic Acids Res., 2015. 43(8): e50.
21. Radany E. H., Domfeld K. J., Sanderson R. J., Savage M. K., Majumdar A., Seidman M. M., and Mosbaugh D. W., Increased spontaneous mutation frequency in human cells expressing the page PBS2-encoded inhibitor of uracil-DNA glycosylase, Mutat. Res., 2000. 461(1): p. 41-58.
22. Risso-Ballester J., Cuevas J. M., and Sanjuin R., Genome-wide estimation of the spontaneous mutation rate of human adenovirus 5 by high-fidelity deep sequencing, PLoS Pathog., 2016. 12(11): e1006013.
23. Saribasak H., Saribasak N. N., Ipek F. M., Ellwart J. W., Arakawa H., and Buerstedde J. M., Uracil DNA glycosylase disruption blocks Ig gene conversion and induces transition mutations, J. Immunol., 2006. 176(1): p. 365-71.
24. Uil T. G., Vellinga J., de Vrij J., van den Hengel S. K., Rabelink M. J., Cramer S. J., Eekels J. J., Ariyurek Y., van Galen M., and Hoeben R. C., Directed adenovirus evolution using engineered mutator viral polymerase, Nucleic Acids Res., 2011. 39(5): e30.
25. Wang L., Jackson W. C., Steinbach P. A., and Tsien R. Y., Evolution of new nonantibody proteins via iterative somatic hypermutation, Proc. Natl. Acad. Sci. USA, 2004. 101(48): p. 16745-49.
26. Wang H., Bian X., Xia L., Ding X., Muller R., Zhang Y., Fu J., and Stewart A. F., Improved seamless mutagenesis by recombineering using ccdB for counterselection. Nucleic Acids Res., 2014. 42(5): e37.
27. Williams J. F., Gharpure M., Ustacelebi S., and McDonald S., Isolation of temperature-sensitive mutants of adenovirus type 5, J. Gen. Virol., 1971. 11(2): p. 95-101.
28. Wechman S. L., Rao X. M., McMasters K. M, and Zhou H. S., Adenovirus with DNA packaging gene mutations increased virus release, Viruses, 2016. 8(12).
29. Yueh A. and Schneider R. J., Translation by ribosome shunting on adenovirus and hsp70 mRNAs facilitated by complementarity to 18S rRNA, Genes Dev., 2000. 14(4): p. 414-21.
30. Yoshikawa K., Okazaki I. M., Kinoshita K., Muramatsu M., Nagaoka H., and Honjo T., AID enzyme-induced hypermutation in an actively transcribed gene in fibroblasts, Science, 2002. 296(5575): p. 2033-36.
31. Packer, M. S. & Liu, D. R. Methods for the directed evolution of proteins. Nat. Rev. Genet. 16, 379-394, doi:10.1038/nrg3927 (2015).
32. Gai, S. A. & Wittrup, K. D. Yeast surface display for protein engineering and characterization. Curr. Opin. Struct. Biol. 17, 467-473, doi: 10.1016/j.sbi.2007.08.012 (2007).
33. Romero, P. A. & Arnold, F. H. Exploring protein fitness landscapes by directed evolution. Nat. Rev. Mol. Cell Biol. 10, 866-876, doi:10.1038/nrm2805 (2009).
34. Shaner, N. C. et al. Improved monomeric red, orange and yellow fluorescent proteins derived from *Discosoma* sp. red fluorescent protein. Nat. Biotechnol. 22, 1567-1572, doi:10.1038/nbt1037 (2004).
35. Branon, T. C. et al. Efficient proximity labeling in living cells and organisms with TurboID. Nat. Biotechnol., doi: 10.1038/nbt.4201 (2018).
36. Arzumanyan, G. A., Gabriel, K. N., Ravikumar, A., Javanpour, A. A. & Liu, C. C. Mutually Orthogonal DNA Replication Systems In Vivo. ACS Synth. Biol. 7, 1722-1729, doi: 10.1021/acssynbio.8b00195 (2018).
37. Zetsche, B. et al. Cpf1 is a single RNA-guided endonuclease of a class 2 CRISPR-Cas system. Cell 163, 759-771, doi:10.1016/j.cell.2015.09.038 (2015).
38. Peck, S. H., Chen, I. & Liu, D. R. Directed evolution of a small-molecule-triggered intein with improved splicing properties in mammalian cells. Chem. Biol. 18, 619-630, doi:10.1016/j.chembiol.2011.02.014 (2011).
39. Piatkevich, K. D. et al. A robotic multidimensional directed evolution approach applied to fluorescent voltage reporters. Nat. Chem. Biol. 14, 352-360, doi:10.1038/s41589-018-0004-9 (2018).
40. Banaszynski, L. A., Chen, L. C., Maynard-Smith, L. A., Ooi, A. G. & Wandless, T. J. A rapid, reversible, and tunable method to regulate protein function in living cells using synthetic small molecules. Cell 126, 995-1004, doi:10.1016/j.cell.2006.07.025 (2006).
41. Wang, C. L., Yang, D. C. & Wabl, M. Directed molecular evolution by somatic hypermutation. Protein Eng. Des. Sel. 17, 659-664, doi: 10.1093/protein/gzh080 (2004).
42. Ma, Y. et al. Targeted AID-mediated mutagenesis (TAM) enables efficient genomic diversification in mammalian cells. Nat. Methods 13, 1029-1035, doi:10.1038/nmeth.4027 (2016).
43. Hess, G. T. et al. Directed evolution using dCas9-targeted somatic hypermutation in mammalian cells. Nat. Methods 13, 1036-1042, doi:10.1038/nmeth.4038 (2016).
44. Komor, A. C., Kim, Y. B., Packer, M. S., Zuris, J. A. & Liu, D. R. Programmable editing of a target base in genomic DNA without double-stranded DNA cleavage. Nature 533, 420-424, doi: 10.1038/nature17946 (2016).
45. Lucher, L. A. Abortive adenovirus infection and host range determinants. Curr. Top. Microbiol. Immunol. 199 (Pt 1), 119-152 (1995).
46. Amalfitano, A. & Chamberlain, J. S. Isolation and characterization of packaging cell lines that coexpress the adenovirus E1, DNA polymerase, and preterminal proteins: implications for gene therapy. Gene Ther. 4, 258-263, doi: 10.1038/sj.gt.3300378 (1997).
47. Hoeben, R. C. & Uil, T. G. Adenovirus DNA replication. Cold Spring Harb. Perspect. Biol. 5, a013003, doi: 10.1101/cshperspect.a013003 (2013).
48. Kamtekar, S. et al. Insights into strand displacement and processivity from the crystal structure of the protein-primed DNA polymerase of bacteriophage phi29. Mol. Cell 16, 609-618, doi:10.1016/j.molcel.2004.10.019 (2004).
49. Sanjuin, R., Nebot, M. R., Chirico, N., Mansky, L. M. & Belshaw, R. Viral mutation rates. J. Virol. 84, 9733-9748, doi:10.1128/JVI.00694-10 (2010).
50. Davis, J. N. & van den Pol, A. N. Viral mutagenesis as a means for generating novel proteins. J. Virol. 84, 1625-1630, doi: 10.1128/JVI.01747-09 (2010).
51. Phillips, A. M. et al. Host proteostasis modulates influenza evolution. eLife 6, e28652, doi:10.7554/eLife.28652 (2017).

52. Elahi, S. M., Oualikene, W., Naghdi, L., O'Connor-McCourt, M. & Massie, B. Adenovirus-based libraries: efficient generation of recombinant adenoviruses by positive selection with the adenovirus protease. Gene Ther. 9, 1238-1246, doi:10.1038/sj.gt.3301793 (2002).
53. Webster, A., Leith, I. R. & Hay, R. T. Activation of adenovirus-coded protease and processing of preterminal protein. J. Virol. 68, 7292-7300 (1994).
54. Loew, R., Heinz, N., Hampf, M., Bujard, H. & Gossen, M. Improved Tet-responsive promoters with minimized background expression. BMC Biotechnol. 10, 81, doi: 10.1186/1472-6750-10-81 (2010).
55. Krueger, M., Scholz, O., Wisshak, S. & Hillen, W. Engineered Tet repressors with recognition specificity for the tetO-4C5G operator variant. Gene 404, 93-100, doi: 10.1016/j.gene.2007.09.002 (2007).
56. Hartley, J. L., Temple, G. F. & Brasch, M. A. DNA cloning using in vitro site-specific recombination. Genome Res. 10, 1788-1795, doi:DOI 10.1101/gr. 143000 (2000).
57. Russell, W. C. Update on adenovirus and its vectors. J. Gen. Virol. 81, 2573-2604, doi:10.1099/0022-1317-81-11-2573 (2000).
58. Meyerhans, A. et al. Temporal fluctuations in HIV quasispecies in vivo are not reflected by sequential HIV isolations. Cell 58, 901-910, doi:10.1016/0092-8674(89) 90942-2 (1989).
59. O'Loughlin, T. L., Greene, D. N. & Matsumura, I. Diversification and specialization of HIV protease function during in vitro evolution. Mol. Biol. Evol. 23, 764-772, doi: 10.1093/molbev/msj098 (2006).
60. Meng, F. L. et al. Convergent transcription at intragenic super-enhancers targets AID-initiated genomic instability. Cell 159, 1538-1548, doi:10.1016/j.cell.2014.11.014 (2014).
61. Kim, D. et al. Genome-wide target specificities of CRISPR RNA-guided programmable deaminases. Nat. Biotechnol. 35, 475-480, doi: 10.1038/nbt.3852 (2017).
62. Wang, C. L., Harper, R. A. & Wabl, M. Genome-wide somatic hypermutation. PNAS 101, 7352-7356, doi: 10.1073/pnas.0402009101 (2004).
63. Hubbard, B. P. et al. Continuous directed evolution of DNA-binding proteins to improve TALEN specificity. Nat. Methods. 12, 939-942, doi:10.1038/nmeth.3515 (2015).
64. Badran, A. H. et al. Continuous evolution of *Bacillus thuringiensis* toxins overcomes insect resistance. Nature 533, 58-63, doi:10.1038/nature17938 (2016).
65. Carlson, J. C., Badran, A. H., Guggiana-Nilo, D. A. & Liu, D. R. Negative selection and stringency modulation in phage-assisted continuous evolution. Nat. Chem. Biol. 10, 216-222, doi: 10.1038/nchembio. 1453 (2014).

66. Bryson, D. I. et al. Continuous directed evolution of aminoacyl-tRNA synthetases. Nat. Chem. Biol. 13, 1253-1260, doi:10.1038/nchembio.2474 (2017).

67. Hu, J. H. et al. Evolved Cas9 variants with broad PAM compatibility and high DNA specificity. Nature 556, 57-63, doi:10.1038/nature26155 (2018).

68. Moore, C. L., Papa, L. J., III & Shoulders, M. D. A Processive Protein Chimera Introduces Mutations across Defined DNA Regions In Vivo. J. Am. Chem. Soc., doi:10.1021/jacs.8b04001 (2018).

69. Dull, T. et al. A third-generation lentivirus vector with a conditional packaging system. J. Virol. 72, 8463-8471 (1998).

70. Fallaux, F. J. et al. Characterization of 911: a new helper cell line for the titration and propagation of early region 1-deleted adenoviral vectors. Hum. Gene Ther. 7, 215-222, doi: 10. 1089/hum. 1996.7.2-215 (1996).

71. Li, H. et al. The Sequence Alignment/Map format and SAMtools. Bioinformatics 25, 2078-2079, doi: 10.1093/bioinformatics/btp352 (2009).

72. Li, H. A statistical framework for SNP calling, mutation discovery, association mapping and population genetical parameter estimation from sequencing data. Bioinformatics 27, 2987-2993, doi: 10.1093/bioinformatics/btr509 (2011).

73. Wang, H., Bian, X., Xia, L., Ding, X., Muller, R., Zhang, Y., Fu, J., and Stewart, A. F. (2014) Improved seamless mutagenesis by recombineering using ccdB for counter-selection, Nucleic Acids Res. 42, e37.

74. Suzuki, M., Kondo, S., Pei, Z., Maekawa, A., Saito, I., and Kanegae, Y. (2015) Preferable sites and orientations of transgene inserted in the adenovirus vector genome: The E3 site may be unfavorable for transgene position, Gene Ther. 22, 421-429.

75. de Vega, M., Lizaro, J. M., Salas, M., and Blanco, L. (1998) Mutational analysis of o29 DNA polymerase residues acting as ssDNAligands for 3'-5' exonucleolysis, J. Mol. Biol., 279, 807-822.

76. Biles, B. D., and Connolly, B. A. (2004) Low-fidelity *Pyrococcus furiosus* DNA polymerase mutants useful in error-prone PCR, Nucleic Acids Res., 32, e176-e176.

77. Smith, J. G. (2016) Directed evolution of adenoviruses, Methods Mol. Biol., 1382, 187-196.

78. Luo, J., Deng, Z. L., Luo, X., Tang, N., Song, W. X., Chen, J., Sharff, K. A., Luu, H. H., Haydon, R. C., Kinzler, K. W., Vogelstein, B., and He, T. C. (2007) A protocol for rapid generation of recombinant adenoviruses using the AdEasy system, Nat. Protoc., 2, 1236-1247.

79. Sharan, S. K., Thomason, L. C., Kuznetsov, S. G., and Court, D. L. (2009) Recombineering: a homologous recombination-based method of genetic engineering, Nat. Protoc., 4, 206-223.

80. Landy, A. (1989) Dynamic, structural, and regulatory aspects of Lambda site-specific recombination, Annu. Rev Biochem., 58, 913-949.

81. Warming, S., Costantino, N., Court, D. L., Jenkins, N. A., and Copeland, N. G. (2005) Simple and highly efficient BAC recombineering using galK selection, Nucleic Acids Res., 33, e36.

82. Bett, A. J., Prevec, L., and Graham, F. L. (1993) Packaging capacity and stability of human adenovirus type 5 vectors, J. Virol., 67, 5911-5921.

83. Lichy, J. H., Field, J., Horwitz, M. S., and Hurwitz, J. (1982) Separation of the adenovirus terminal protein precursor from its associated DNA polymerase: role of both proteins in the initiation of adenovirus DNA replication, Proc. Natl. Acad. Sci., 79, 5225-5229.

84. Badran, A. H., and Liu, D. R. (2015) Development of potent in vivo mutagenesis plasmids with broad mutational spectra, Nat. Commun., 6, 8425.

85. Flint, S. J. (2001) Adenoviruses, Encyclopedia of Life Sciences.

86. Stillman, B. W. (1985) Biochemical and genetic analysis of adenovirus DNA replication in vitro. In Genetic Engineering: Principles and Methods (Setlow, J. K., and Hollaender, A., Eds.), pp 1-27, Springer US, Boston, Mass.

87. Rice, S. A., and Klessig, D. F. (1985) Isolation and analysis of adenovirus type 5 mutants containing deletions in the gene encoding the DNA-binding protein, J. Virol., 56, 767-778.

88. Zhou, H., O'Neal, W., Morral, N., and Beaudet, A. L. (1996) Development of a complementing cell line and a system for construction of adenovirus vectors with E1 and E2a deleted, J. Virol., 70, 7030-7038.
89. Maier, O., Galan, D. L., Wodrich, H., and Wiethoff, C. M. (2010) An N-terminal domain of adenovirus protein VI fragments membranes by inducing positive membrane curvature, Virology, 402, 11-19.
90. Blainey, P. C., Graziano, V, Perez-Bemrni, A. J., McGrath, W. J., Flint, S. J., San Martin, C., Xie, X. S., and Mangel, W. F. (2013) Regulation of a Viral Proteinase by a Peptide and DNA in One-dimensional Space: IV. VIRAL PROTEINASE SLIDES ALONG DNA TO LOCATE AND PROCESS ITS SUBSTRATES, J. Biol. Chem., 288, 2092-2102.
91. Dai, X., Wu, L., Sun, R., and Zhou, Z. H. (2017) Atomic structures of minor proteins VI and VII in human adenovirus, J. Virol., 91, e00850-00817.
92. Logan, J., and Shenk, T. (1984) Adenovirus tripartite leader sequence enhances translation of mRNAs late after infection, Proc. Natl. Acad. Sci., 81, 3655-3659.
93. Cuesta, R., Xi, Q., and Schneider, R. J. (2000) Adenovirus-specific translation by displacement of kinase Mnkl from cap-initiation complex eIF4F, Embo J., 19, 3465-3474.
94. Zhao, H., Chen, M., and Pettersson, U. (2014) A new look at adenovirus splicing, Virology, 456-457, 329-341.
95. Lonberg-Holm, K., Crowell, R. L., and Philipson, L. (1976) Unrelated animal viruses share receptors, Nature, 259, 679-681.
96. Von Seggern, D. J., Chiu, C. Y, Fleck, S. K., Stewart, P. L., and Nemerow, G. R. (1999) A helper-independent adenovirus vector with E1, E3, and fiber deleted: structure and infectivity of fiberless particles, J. Virol., 73, 1601-1608.
97. Uil, T. G., de Vrij, J., Vellinga, J., Rabelink, M. J., Cramer, S. J., Chan, O. Y, Pugnali, M., Magnusson, M., Lindholm, L., Boulanger, P., and Hoeben, R. C. (2009) A lentiviral vector-based adenovirus fiber-pseudotyping approach for expedited functional assessment of candidate retargeted fibers, J. Gene. Med., 11, 990-1004.
98. Legrand, V., Spehner, D., Schesinger, Y, Settelen, N., Pavirani, A., and Mehtali, M. (1999) Fiberless recombinant adenoviruses: virus maturation and infectivity in the absence of fiber, J. Virol., 73, 907-919.
99. Persson, R., Wohlfart, C., Svensson, U., and Everitt, E. (1985) Virus-receptor interaction in the adenovirus system: characterization of the positive cooperative binding of virions on HeLa cells, J Virol., 54, 92-97.
100. Von Seggem, D. J., Huang, S., Fleck, S. K., Stevenson, S. C., and Nemerow, G. R. (2000) Adenovirus vector pseudotyping in fiber-expressing cell lines: improved transduction of Epstein-Barr virus-transformed B cells, J. Virol., 74, 354-362.
101. Mangel, W. F., Toledo, D. L., Brown, M. T., Martin, J. H., and McGrath, W. J. (1996) Characterization of three components of human adenovirus proteinase activity in vitro, J. Biol. Chem., 271, 536-543.
102. Cotten, M., and Weber, J. M. (1995) The adenovirus protease is required for virus entry into host cells, Virology, 213, 494-502.
103. Oualikene, W., Lamoureux, L., Weber, J. M., and Massie, B. (2000) Protease-deleted adenovirus vectors and complementing cell lines: potential applications of single-round replication mutants for vaccination and gene therapy, Hum. Gene Ther, 11, 1341-1353.
104. Graziano, V., Luo, G., Blainey, P. C., Perez-Bemi, A. J., McGrath, W. J., Flint, S. J., San Martin, C., Xie, X. S., and Mangel, W. F. (2013) Regulation of a viral proteinase by a peptide and DNA in one-dimensional space: II. ADENOVIRUS PROTEINASE IS ACTIVATED IN AN UNUSUAL ONE-DIMENSIONAL BIOCHEMICAL REACTION, J. Biol. Chem., 288, 2068-2080.
105. Howison, M., Coetzer, M., and Kantor, R. (2018) Measurement error and variant-calling in deep Illumina sequencing of HIV, bioRxiv.
106. Schmitt, M. W., Kennedy, S. R., Salk, J. J., Fox, E. J., Hiatt, J. B., and Loeb, L. A. (2012) Detection of ultra-rare mutations by next-generation sequencing, Proc. Natl. Acad. Sci., 109, 14508-14513.
107. Luria, S. E., and Delbruck, M. (1943) MUTATIONS OF BACTERIA FROM VIRUS SENSITIVITY TO VIRUS RESISTANCE, Genetics, 28, 491-511.
108. Kaplan, L. M., Ariga, H., Hurwitz, J., and Horwitz, M. S. (1979) Complementation of the temperature-sensitive defect in H5ts125 adenovirus DNA replication in vitro, Proc. Natl. Acad. Sci., 76, 5534-5538.
109. Song, B., and Young, C. S. H. (1997) Functional characterization of the Major Late Promoter of mouse adenovirus Type 1, Virology, 235, 109-117.
110. Campeau, E., Ruhl, V. E., Rodier, F., Smith, C. L., Rahmberg, B. L., Fuss, J. O., Campisi, J., Yaswen, P., Cooper, P. K., and Kaufman, P. D. (2009) A versatile viral system for expression and depletion of proteins in mammalian cells, PLoS One, 4, e6529.
111. Martinez, R., Schellenberger, P., Vasishtan, D., Aknin, C., Austin, S., Dacheux, D., Rayne, F., Siebert, A., Ruzsics, Z., Gruenewald, K., and Wodrich, H. (2015) The Amphipathic Helix of Adenovirus Capsid Protein VI Contributes to Penton Release and Postentry Sorting, J. Virol., 89, 2121-2135.
112. Giger, L., Caner, S., Obexer, R., Kast, P., Baker, D., Ban, N., and Hilvert, D. (2013) Evolution of a designed retro-aldolase leads to complete active site remodeling, Nat. Chem. Biol., 9, 494-498.
113. Wang, L., and Tsien, R. Y. (2006) Evolving proteins in mammalian cells using somatic hypermutation, Nat. Protoc., 1, 1346-1350.
114. Dougherty, M. J., and Amold, F. H. (2009) Directed evolution: new parts and optimized function, Curr. Opin. Biotechnol., 20, 486-491.
115. Ptashne, M., and Gann, A. (1997) Transcriptional activation by recruitment, Nature, 386, 569-577.
116. Buskirk, A. R., Kehayova, P. D., Landrigan, A., and Liu, D. R. (2003) In vivo evolution of an RNA-based transcriptional activator, Chem. Biol., 10, 533-540.
117. Collins, C. H., Leadbetter, J. R., and Amold, F. H. (2006) Dual selection enhances the signaling specificity of a variant of the quorum-sensing transcriptional activator LuxR, Nat. Biotechnol., 24, 708-712.
118. Vidal, M., and Legrain, P. (1999) Yeast forward and reverse 'n'-hybrid systems, Nucleic Acids Res., 27, 919-929.
119. Ramos, J. L., Martinez-Bueno, M., Molina-Henares, A. J., Terin, W., Watanabe, K., Zhang, X., Gallegos, M. T., Brennan, R., and Tobes, R. (2005) The TetR family of transcriptional repressors, Microbiol. Mol. Biol. Rev., 69, 326-356.
120. Hirai, H., Tani, T., and Kikyo, N. (2010) Structure and functions of powerful transactivators: VP16, MyoD and FoxA, Int. J. Dev. Biol., 54, 1589-1596.
121. Krueger, C., Schmidt, A., Danke, C., Hillen, W., and Berens, C. (2004) Transactivator mutants with altered 122. Moncivais, K., and Zhang, Z. J. (2012) Tetracycline repressor-based mammalian two-hybrid systems, Methods Mol. Biol., 812, 259-273.
123. Massie, B., and Oualikene, W. (2001) Adenovirus mutants with deleted protease gene, U.S. Pat. No. 6,291,226B1.
124. Meinke, G., Bohm, A., Hauber, J., Pisabarro, M. T., and Buchholz, F. (2016) Cre Recombinase and Other Tyrosine Recombinases, Chem. Rev., 116, 12785-12820.
125. Gaj, T., Mercer, A. C., Gersbach, C. A., Gordley, R. M., and Barbas, C. F. (2011) Structure-guided reprogramming of serine recombinase DNA sequence specificity, Proc. Natl. Acad. Sci., 108, 498-503.
126. Parkitna, J. R., Engblom, D., and Schütz, G. (2009) Generation of Cre recombinase-expressing transgenic mice using bacterial artificial chromosomes, Methods Mol. Biol., 530, 325-342.
127. Chaikind, B., Bessen, J. L., Thompson, D. B., Hu, J. H., and Liu, D. R. (2016) A programmable Cas9-serine recombinase fusion protein that operates on DNA sequences in mammalian cells, Nucleic Acids Res., 44, 9758-9770.
128. Italia, J. S., Zheng, Y., Kelemen, R. E., Erickson, S. B., Addy, P. S., and Chatterjee, A. (2017) Expanding the genetic code of mammalian cells, Biochem. Soc. Trans., 45, 555-562.
129. Meier, J. L., and Stinski, M. F. (1996) Regulation of Human Cytomegalovirus Immediate-Early Gene Expression, Intervirology, 39, 331-342.
130. Babiss, L. E., and Vales, L. D. (1991) Promoter of the adenovirus polypeptide IX gene: similarity to E1B and inactivation by substitution of the simian virus 40 TATA element, J. Virol., 65, 598-605.
131. Helbl, V., and Hillen, W. (1998) Stepwise selection of TetR variants recognizing tet operator 4C with high affinity and specificity, J. Mol. Biol., 276, 313-318.
132. Pfeiffer, F., Grober, C., Blank, M., Hindler, K., Beyer, M., Schultze, J. L., and Mayer, G. (2018) Systematic evaluation of error rates and causes in short samples in next-generation sequencing, Sci. Rep., 8, 10950.
133. Gaj, T., Mercer, A. C., Sirk, S. J., Smith, H. L., and Barbas, C. F. (2013) A comprehensive approach to zinc-finger recombinase customization enables genomic targeting in human cells, Nucleic Acids Res., 41, 3937-3946.
134. Beronja, S., Livshits, G., Williams, S., and Fuchs, E. (2010) Rapid functional dissection of genetic networks via tissue-specific transduction and RNAi in mouse embryos, Nat. Med., 16, 821-827.
135. Chatterjee, A., Guo, J., Lee, H. S., and Schultz, P. G. (2013) A genetically encoded fluorescent probe in mammalian cells, J. Am. Chem. Soc., 135, 12540-12543.
136. Li, H., Handsaker, B., Wysoker, A., Fennell, T., Ruan, J., Homer, N., Marth, G., Abecasis, G., Durbin, R., and 1000 Genome Project Data Processing Subgroup. (2009) The Sequence Alignment/Map format and SAMtools, Bioinformatics, 25, 2078-2079.
137. Li, H. (2011) A statistical framework for SNP calling, mutation discovery, association mapping and population genetical parameter estimation from sequencing data, Bioinformatics, 27, 2987-2993.
138. Tsien, R. Y. (1998) The green fluorescent protein, Annu. Rev. Biochem., 67, 509-544.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

What is claimed is:

1. An engineered, non-naturally occurring adenovirus comprising a modified genome, wherein the modified genome comprises:
   (a) an integration of a polynucleic acid sequence comprising the sequence of a transcribable gene of interest,
   (b) a deletion of the sequence encoding for the adenoviral DNA polymerase,
   (c) a deletion of a sequence encoding for a protein necessary for the production of infectious adenovirus particles, wherein the protein necessary for the production of infectious adenovirus particles is not the adenoviral DNA polymerase or E1, and
   (d) a sequence encoding at least one protein necessary for the production of infectious adenovirus particles.

2. The engineered, non-naturally occurring adenovirus of claim 1, wherein the engineered, non-naturally occurring adenovirus is derived from:
   (a) an adenovirus selected from the genera consisting of Adenovirus, Aviadenovirus, Ichtadenovirus, Mastadenovirus, and Siadenovirus; or
   (b) a human adenovirus selected from the group consisting of HAdV-A, HAdV-B, HAdV-C, HAdV-D, HAdV-E, HAdV-F, and HAdV-G, optionally wherein the HAdV-C adenovirus is selected from the group consisting of HAd2 and HAd5.

3. The engineered, non-naturally occurring adenovirus of claim 1, wherein the sequence encoding for a protein necessary for the production of infectious adenovirus particles comprises the sequence encoding for the adenoviral protease.

4. An engineered, non-naturally occurring mammalian cell comprising a modified genome, wherein the modified genome comprises:
   (a) an integration of a polynucleic acid sequence comprising the sequence of an error-prone adenoviral DNA polymerase, and
   (b) an integration of a polynucleic acid sequence comprising a sequence encoding for a protein necessary for the production of infectious adenovirus particles, wherein the protein necessary for the production of infectious adenovirus particles is not the adenoviral DNA polymerase, and wherein expression of the protein necessary for the production of infectious adenovirus particles is inducible.

5. The engineered, non-naturally occurring mammalian cell of claim 4, wherein the sequence encoding for a protein necessary for the production of infectious adenovirus particles is not the sequence of the adenoviral fiber protein.

6. The engineered, non-naturally occurring mammalian cell of claim 4, wherein the engineered, non-naturally occurring mammalian cell is derived from a human cell, a mouse cell, a rat cell, a cat cell, a dog cell, a pig cell, a guinea pig cell, a hamster cell, a sheep cell, a macaque cell, or a chimpanzee cell, optionally wherein the human cell is a human cell line.

7. The engineered, non-naturally occurring mammalian cell of claim 4, wherein the sequence of the error-prone adenoviral DNA polymerase is derived from a sequence selected from the group consisting of the HAd2 and HAd5 DNA polymerase sequence, optionally wherein the HAd5 DNA polymerase:
   (a) comprises the HAd5 DNA polymerase sequence with at least one mutation selected from the group consisting of T286I, N417A, F421Y, S506T, V585A, and D827A; or
   (b) consists of SEQ ID NO: 27.

8. The engineered, non-naturally occurring mammalian cell of claim 4, wherein the sequence encoding for a protein necessary for the production of infectious adenovirus particles comprises the sequence of the adenoviral protease.

9. A method of performing continuous directed evolution of a polynucleic acid sequence, wherein said polynucleic acid sequence comprises the sequence of a gene of interest, said method comprising:
   (a) contacting a plurality of engineered, non-naturally occurring mammalian cells with a plurality of engineered, non-naturally occurring adenoviruses capable of infecting the mammalian cells, thereby producing a population of infected cells, wherein:
      (i) each engineered, non-naturally occurring adenovirus comprises a modified genome, wherein the modified genome comprises: an integration of a polynucleic acid sequence comprising the sequence of a transcribable gene of interest, a deletion of the sequence encoding for the adenoviral DNA polymerase, and a deletion of a sequence encoding for a protein necessary for the production of infectious adenovirus particles wherein the protein necessary for the production of infectious adenovirus particles is not the adenoviral DNA polymerase; and
      (ii) each engineered, non-naturally occurring mammalian cell comprises a modified genome, wherein the modified genome comprises: an integration of a polynucleic acid sequence comprising the sequence of an error-prone adenoviral DNA polymerase, and an integration of a polynucleic acid sequence comprising the sequence encoding for the protein necessary for the production of infectious adenovirus particles in (a)(i) under the control of a functional couple, optionally wherein the functional couple is a transcriptionally-coupled promoter, and (b) generating infectious adenovirus particles with the infected cells, wherein the generation of the infectious adenovirus particles is increased by the evolution of the polynucleic acid sequence comprising the sequence of the transcribable gene of interest wherein said evolution is driven by the error-prone adenoviral DNA polymerase.

10. The method of claim 9, further comprising screening the infected cells for infectious adenovirus particles.

11. The method of claim 9, wherein the polynucleic acid sequence comprising the sequence of a transcribable gene of interest is a protein coding sequence, wherein expression and translation of the protein coding sequence generates a protein product, optionally wherein the protein product, when unevolved:
  (a) induces the expression of the polynucleic acid sequence comprising the sequence encoding for the protein necessary for the production of infectious adenovirus particles, and wherein the method further comprises contacting the mammalian cells with an agent that decreases the capability of the protein product of inducing expression of the protein necessary for the production of infectious adenovirus particles;
  (b) inhibits the expression of the polynucleic acid sequence comprising the sequence encoding for the protein necessary for the production of infectious adenovirus particles;
  (c) cannot induce the expression of the polynucleic acid sequence comprising the sequence encoding for the protein necessary for the production of infectious adenovirus particles;
  (d) regulates the stability of the protein necessary for the production of infectious adenovirus particles; or
  (e) regulates the subcellular trafficking of the protein necessary for the production of infectious adenovirus particles.

12. The method of claim 9, wherein the sequence encoding for the protein necessary for the production of infectious adenovirus particles further comprises the sequence of an inhibitory tag, wherein the sequence of the protein necessary for the production of infectious adenovirus particles and the sequence of the inhibitory tag are coupled, and wherein:
  (a) translation of the sequence comprising the sequence encoding for the protein necessary for the production of infectious adenovirus particles and the sequence of the inhibitory tag generates a tagged protein; and
  (b) removal of inhibitory tag is dependent upon the evolution of the at least one polynucleic acid sequence comprising the sequence of the gene of interest;

optionally wherein:
  the inhibitory tag is selected from the group consisting of a protein degradation tag or a protein sequestration tag, optionally wherein the protein degradation tag is a degron tag; or
  the gene of interest is a protease.

13. The method of claim 9, wherein:
  (a) the polynucleic acid sequence comprising the sequence of a transcribable gene of interest is a sequence of a non-coding RNA; and/or
  (b) the sequence encoding for the protein necessary for the production of infectious adenovirus particles further comprises a premature stop codon in the sequence encoding for the protein necessary for the production of infectious adenovirus particles.

14. The method of claim 13, wherein the sequence of the gene of interest comprises the sequence of a tRNA or an aminoacyl tRNA synthetase.

15. The method of claim 9, wherein the engineered, non-naturally occurring adenovirus is derived from:
  (a) an adenovirus selected from the genera consisting of Adenovirus, Aviadenovirus, Ichtadenovirus, Mastadenovirus, and Siadenovirus; or
  (b) a human adenovirus selected from the group consisting of HAdV-A, HAdV-B, HAdV-C, HAdV-D, HAdV-E, HAdV-F, and HAdV-G, optionally wherein the HAdV-C adenovirus is selected from the group consisting of HAd2 and HAd5.

16. The method of claim 9, wherein the sequence encoding for a protein necessary for the production of infectious adenovirus particles comprises the sequence encoding for the adenoviral protease.

17. The method of claim 9, wherein the engineered, non-naturally occurring mammalian cell is derived from a human cell, a mouse cell, a rat cell, a cat cell, a dog cell, a pig cell, a guinea pig cell, a hamster cell, a sheep cell, a macaque cell, or a chimpanzee cell, optionally wherein the human cell is a human cell line.

18. The method of claim 9, wherein the sequence of the error-prone adenoviral DNA polymerase is derived from a sequences selected from the group consisting of the HAd2 and HAd5 DNA polymerase sequence, optionally wherein the HAd5 DNA polymerase:
  (a) comprises the HAd5 DNA polymerase sequence with at least one mutation selected from the group consisting of T286I, N417A, F421Y, S506T, V585A, and D827A; or
  (b) consists of SEQ ID NO: 27.

19. The method of claim 9, wherein the error-prone adenoviral DNA polymerase is constitutively expressed in the engineered, non-naturally occurring mammalian cells.

20. The method of claim 9, wherein the method further comprises contacting the engineered, non-naturally occurring mammalian cells with a small molecule that decreases the functionality of the protein necessary for the production of infectious DNA viral particles.

* * * * *

SEQUENCE LISTING

```
<160> NUMBER OF SEQ ID NOS: 210

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1 aaaaaggat ccaccatggg ctccagtg                                          28

<210> SEQ ID NO 2
<211> LENGTH: 40
<212> TYPE: DNA
<213> ORGANISM: Artificial Sequence
<220> FEATURE:
<223> OTHER INFORMATION: Primer

<400> SEQUENCE: 2
aaaaagtcga cttacatgtt tttcaagtga caaaaagaag                            40

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
```
aaaaaagcgg ccgcactctc ttccgcatcg                     30

<210> SEQ ID NO 4
<211> LENGTH: 41
<212> TYPE: DNA
<213> ORGANISM: Artificial Sequence
<220> FEATURE:
<223> OTHER INFORMATION: Primer

<400> SEQUENCE: 4
aaaaaatcta gattacatgt ttttcaagtg acaaaagaa g          41

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
aaaaaagcgg ccgcactctc ttccgcatcg                     30

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
atcgcctgga gaattcactc tcttccgcat cgct                 34

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
ctcactggag cccattgcga ctgtgactgg ttag                 34

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
tggagaagga tccgcactct cttccgcatc gct                  33

<210> SEQ ID NO 9
<211> LENGTH: 44
<212> TYPE: DNA
<213> ORGANISM: Artificial Sequence
<220> FEATURE:
<223> OTHER INFORMATION: Primer

<400> SEQUENCE: 9
atctagagcc ggcgcttaca tgttttttcaa gtgacaaaaa gaag     44

<210> SEQ ID NO 10
<211> LENGTH: 85
<212> TYPE: DNA
<213> ORGANISM: Artificial Sequence

```
<220> FEATURE:
<223> OTHER INFORMATION: Primer

<400> SEQUENCE: 10
atacaaaact acataagacc cccaccttat atattctttc ccaccyttaa gccacgccca    60
ccctcatcag tgccaacata gtaag                                          85

<210> SEQ ID NO 11
<211> LENGTH: 69
<212> TYPE: DNA
<213> ORGANISM: Artificial Sequence
<220> FEATURE:
<223> OTHER INFORMATION: Primer

<400> SEQUENCE: 11
aataagagga agtgaaatct gaataatttt gtgttactca tagcgcgtaa taccgctcat    60
taggcgggc                                                            69

<210> SEQ ID NO 12
<211> LENGTH: 81
<212> TYPE: DNA
<213> ORGANISM: Artificial Sequence
<220> FEATURE:
<223> OTHER INFORMATION: Primer

<400> SEQUENCE: 12
atacaaaact acataagacc cccaccttat atattctttc ccaccyttaa gccacgccca    60
cagatatacg cgttgacatt g                                              81

<210> SEQ ID NO 13
<211> LENGTH: 69
<212> TYPE: DNA
<213> ORGANISM: Artificial Sequence
<220> FEATURE:
<223> OTHER INFORMATION: Primer

<400> SEQUENCE: 13
aataagagga agtgaaatct gaataatttt gtgttactca tagcgcgtaa tagaagccat    60
agagcccac                                                            69

<210> SEQ ID NO 14
<211> LENGTH: 75
<212> TYPE: DNA
<213> ORGANISM: Artificial Sequence
<220> FEATURE:
<223> OTHER INFORMATION: Primer

<400> SEQUENCE: 14 caaaaaccc acaacttcct caaatcgtca cttccgtttt cccacgttac ccctcatcag    60
tgccaacata gtaag                                                     75

<210> SEQ ID NO 15
<211> LENGTH: 67
<212> TYPE: DNA
<213> ORGANISM: Artificial Sequence
<220> FEATURE:
<223> OTHER INFORMATION: Primer

<400> SEQUENCE: 15
agtaacttgt atgtgttggg aattgtagtt ttcttaaaat gggaagtgac ccgctcatta    60
ggcgggc                                                              67
```

```
<210> SEQ ID NO 16
<211> LENGTH: 76
<212> TYPE: DNA
<213> ORGANISM: Artificial Sequence
<220> FEATURE:
<223> OTHER INFORMATION: Primer

<400> SEQUENCE: 16
caaaaaaccc acaacttcct caaatcgtca cttccgtttt cccacgttac ttctgtggaa      60
tgtgtgtcag ttaggg                                                     76

<210> SEQ ID NO 17
<211> LENGTH: 75
<212> TYPE: DNA
<213> ORGANISM: Artificial Sequence
<220> FEATURE:
<223> OTHER INFORMATION: Primer

<400> SEQUENCE: 17
agtaacttgt atgtgttggg aattgtagtt ttcttaaaat gggaagtgac ctctagctag     60
aggtcgacgg tatac                                                     75

<210> SEQ ID NO 18
<211> LENGTH: 75
<212> TYPE: DNA
<213> ORGANISM: Artificial Sequence
<220> FEATURE:
<223> OTHER INFORMATION: Primer

<400> SEQUENCE: 18
tcccgcgctt cttggaactt tacattgtgg gccacaacat caacggccct ccctcatcag     60
tgccaacata gtaag                                                     75

<210> SEQ ID NO 19
<211> LENGTH: 67
<212> TYPE: DNA
<213> ORGANISM: Artificial Sequence
<220> FEATURE:
<223> OTHER INFORMATION: Primer

<400> SEQUENCE: 19
ggcacctcgg aacggttgtt aattacctgg gcggcgagca cgatctcgtc ccgctcatta     60
ggcgggc                                                              67

<210> SEQ ID NO 20
<211> LENGTH: 99
<212> TYPE: DNA
<213> ORGANISM: Artificial Sequence
<220> FEATURE:
<223> OTHER INFORMATION: Primer

<400> SEQUENCE: 20
gcgcggcctt ccggagcgag gtgtgggtga gcgcaaaggt gtccctgacc atgaccagca     60
tgaagggcac gagctgcttc ccaaaggccc ccatccaag                           99

<210> SEQ ID NO 21
<211> LENGTH: 99
<212> TYPE: DNA
<213> ORGANISM: Artificial Sequence
<220> FEATURE:
<223> OTHER INFORMATION: Primer

<400> SEQUENCE: 21
```
cttggatggg ggcctttggg aagcagctcg tgcccttcat gctggtcatg gtcagggaca        60
cctttgcgct cacccacacc tcgctccgga aggccgcgc                              99

<210> SEQ ID NO 22
<211> LENGTH: 75
<212> TYPE: DNA
<213> ORGANISM: Artificial Sequence
<220> FEATURE:
<223> OTHER INFORMATION: Primer

<400> SEQUENCE: 22
ggcaacgcca caacataaag aagcaagcaa catcaacaac agctgccgcc ccctcatcag        60
tgccaacata gtaag                                                        75

<210> SEQ ID NO 23
<211> LENGTH: 67
<212> TYPE: DNA
<213> ORGANISM: Artificial Sequence
<220> FEATURE:
<223> OTHER INFORMATION: Primer

<400> SEQUENCE: 23
tacaaataaa agcatttgcc tttattgaaa gtgtctctag tacattattt ccgctcatta        60
ggcgggc                                                                 67

<210> SEQ ID NO 24
<211> LENGTH: 100
<212> TYPE: DNA
<213> ORGANISM: Artificial Sequence
<220> FEATURE:
<223> OTHER INFORMATION: Primer

<400> SEQUENCE: 24
ggcaacgcca caacataaag aagcaagcaa catcaacaac agctgccgcc aaataatgta        60
ctagagacac tttcaataaa ggcaaatgct tttatttgta                             100

<210> SEQ ID NO 25
<211> LENGTH: 100
<212> TYPE: DNA
<213> ORGANISM: Artificial Sequence
<220> FEATURE:
<223> OTHER INFORMATION: Primer

<400> SEQUENCE: 25
tacaaataaa agcatttgcc tttattgaaa gtgtctctag tacattattt ggcggcagct        60
gttgttgatg ttgcttgctt ctttatgttg tggcgttgcc                             100

<210> SEQ ID NO 26
<211> LENGTH: 3624
<212> TYPE: DNA
<213> ORGANISM: Artificial Sequence
<220> FEATURE:
<223> OTHER INFORMATION: Construct

<400> SEQUENCE: 26
atggccttgg ctcaagctca ccgggcccgt cgtcttcacg cagaggcgcc agattcagga        60
gatcaaccgc cgcgtcgtcg cgttcgccag caacctacgc gcgcagcacc agctcctgcc       120
cgcgcgcggc gccgacgtgc ccctgccccc tctcccggcg ggtccggagc cccccctacc       180
tccgggggct cgcccgcgtc accgcttta gatgcatcat ccaaggacac ccccgcggcc       240

```
caccgcccgc cgcgcggtac cgtagtcgcg ccgcggggat gcggcctctt gcaagccatc    300
gacgccgcca ccaaccagcc cctggaaatt aggtatcacc tggatctagc ccgcgccctg    360
acccgtctat gcgaggtaaa cctgcaggag ctcccgcctg acctgacgcc gcgggagctc    420
cagaccatgg acagctccca tctgcgcgat gttgtcatca agctccgacc gccgcgcgcg    480
gacatctgga ctttgggctc gcgcggcgtg gtggtccgat ccaccgtaac tcccctcgag    540
cagccagacg gtcaaggaca agcagccgaa gtagaagacc accagccaaa cccgccaggc    600
gaggggctca aattcccact ctgcttcctt gtgcgcggtc gtcaggtcaa cctcgtgcag    660
gatgtacagc ccgtgcaccg ctgccagtac tgcgcacgtt tttacaaaag ccagcacgag    720
tgttcggccc gtcgcaggga cttctacttt caccacatca atagccactc ctccaattgg    780
tggcgggaga tccagttctt cccgatcggc tcgcatcctc gcaccgagcg tctctttgtc    840
acctacgatg tagagaccta tacttggatg ggggcctttg ggaagcagct cgtgcccttc    900
atgctggtca tgaagttcgg cggagatgag cctctagtga ctgccgcgcg agacctagcc    960
gcgaaccttg gatgggaccg ctgggaacaa gacccgctta ccttctactg catcaccccca   1020 gaaaaaatgg ccataggtcg ccagtttagg acctttcgcg accacctgca aatgctaatg   1080
gcccgtgacc tgtggagctc attcgtcgct tccaaccctc atcttgcaga ctgggccctt   1140
tcagagcacg ggctcagctc ccctgaagag ctcacctacg aggaacttaa aaaattgcct   1200
tccatcaagg gcatcccgcg cttcttggaa ctttacattg tgggccacaa cattaatggg   1260
tttgacgaga tcgtgctcgc cgcccaggta attaacaacc gttccgaggt gccgggaccc   1320
ttccgcatca cacgcaactt tatgcctcgc gcgggaaaga tactcttcaa cgatgtcacc   1380
ttcgccctgc caaatccgcg ttccaaaaag cgcacggact ttttgctctg ggagcagggc   1440
ggatgcgacg acactgactt caaataccag tacctcaaag tcatggtcag ggacacccttt  1500 gcgctcaccc acacctcgct ccggaaggcc gcgcaggcat acgcgctacc cgtagaaaag   1560
ggatgctgcg cctaccaggc cgtcaaccag ttctacatgc taggctctta ccgttcggag   1620
gccgacgggt ttccgatcca agagtactgg aaagaccgcg aagagtttgt cctcaaccgc   1680
gagctgtgga aaaaaaggg acaggataag tatgacatca tcaaggaaac cctggactac   1740
tgcgccctag acgtgcaggt caccgccgag ctggtcaaca agctgcgcga ctcctacgcc   1800
tccttcgtgc gtgacgcggt aggtctcaca gacgccagct tcaacgtctt ccagcgtcca   1860
accatatcat ccaactcaca tgccatcttc aggcagatag tcttccgagc agagcagccc   1920
gcccgtagca acctcggtcc cgacctcctc gctccctcgc acgaactata cgattacgtg   1980
cgcgccagca tccgcggtgg aagatgctac cctacatatc ttggaatact cagagagccc   2040
ctctacgttt acgacatttg cggcatgtac gcctccgcgc tcacccaccc catgccatgg   2100
ggtcccccac tcaacccata cgagcgcgcg cttgccgccc gcgcatggca gcaggcgcta   2160
gacttgcaag gatgcaagat agactacttc gacgcgcgcc tgctgccgg ggtctttacc    2220 gtggacgcag accccccgga cgagacgcag ctagacccccc taccgccatt ctgctcgcgc   2280
aagggcggcc gcctctgctg gaccaacgag cgcctacgcg gagaggtagc caccagcgtt   2340
gaccttgtca ccctgcacaa ccgcggttgg gcgtgcacc tggtgcccga cgagcgcacc    2400
accgtctttc ccgaatggcg gtgcgttgcg cgcgaatacg tgcagctaaa catcgcggcc   2460
aaggagcgcg ccgatcgcga caaaaaccaa accctgcgct ccatcgccaa gttgctgtcc   2520
aacgccctct acgggtcgtt tgccaccaag cttgacaaca aaaagattgt cttttctgac   2580
cagatggatg cggccaccct caaaggcatc accgcgggcc aggtgaatat caaatcctcc   2640
```

```
tcgtttttgg aaactgacaa tcttagcgca gaagtcatgc ccgctttca gagggagtac    2700 tcaccccaac agctggccct cgcagacagc gatgcgaag agagtgagga cgaacgcgcc    2760 cccacccct tttatagccc cccttcagga acacccggtc acgtggccta cacctacaaa    2820
ccaatcacct tccttgatgc cgaagagggc gacatgtgtc ttcacaccct ggagcgagtg    2880
gaccccctag tggacaacga ccgctacccc tcccacttag cctccttcgt gctggcctgg    2940
acgcgagcct ttgtctcaga gtggtccgag tttctatacg aggaggaccg cggaacaccg    3000
ctcgaggaca ggcctctcaa gtctgtatac ggggacacgg acagccttt cgtcaccgag    3060 cgtggacacc ggctcatgga aaccagaggt aagaaacgca tcaaaaagca tggggggaaac    3120 ctggttttg accccgaacg gccagagctc acctggctcg tggaatgcga gaccgtctgc    3180
ggggcctgcg cgcggatgc ctactccccg gaatcggtat ttctcgcgcc caagctctac    3240
gccctcaaaa gtctgcactg cccctcgtgc ggcgcctcct ccaagggcaa gctgcgcgcc    3300
aagggccacg ccgcggaggg gctggactat gacaccatgg tcaaatgcta cctggccgac    3360
gcgcagggcg aagaccggca gcgcttcagc accagcagga ccagcctcaa gcgcaccctg    3420
gccagcgcgc agcccggagc gcacccctc accgtgaccc agactacgct gacgaggacc    3480
ctgcgcccgt ggaaagacat gaccctggcc cgtctggacg agcaccgact actgccgtac    3540
agcgaaagcc gccccaaccc gcgaaacgag gagatatgct ggatcgagat gccgtaccca    3600
tacgatgttc cggattacgc ttag                                          3624

<210> SEQ ID NO 27
<211> LENGTH: 3624
<212> TYPE: DNA
<213> ORGANISM: Artificial Sequence
<220> FEATURE:
<223> OTHER INFORMATION: Construct

<400> SEQUENCE: 27
atggccttgg ctcaagctca ccgggcccgt cgtcttcacg cagaggcgcc agattcagga     60
gatcaaccgc cgcgtcgtcg cgttcgccag caacctacgc gcgcagcacc agctcctgcc    120
cgcgcgcggc gccgacgtgc ccctgccccc tctcccggcg ggtccggagc cccccctacc    180
tccgggggct cgcccgcgtc accgcttta gatgcatcat ccaaggacac ccccgcggcc    240
caccgcccgc cgcgcggtac cgtagtcgcg ccgcggggat gcggcctctt gcaagccatc    300
gacgccgcca ccaaccagcc cctggaaatt aggtatcacc tggatctagc ccgcgccctg    360
acccgtctat gcgaggtaaa cctgcaggag ctcccgcctg acctgacgcc gcgggagctc    420
cagaccatgg acagctccca tctgcgcgat gttgtcatca agctccgacc gccgcgcgcg    480
gacatctgga ctttgggctc gcgcggcgtg gtggtccgat ccaccgtaac tccctcgag    540 cagccagacg gtcaaggaca agcagccgaa gtagaagacc accagccaaa cccgccaggc    600 gagggctca aattcccact ctgcttcctt gtgcgcggtc gtcaggtcaa cctcgtgcag    660
gatgtacagc ccgtgcaccg ctgccagtac tgcgcacgtt tttacaaaag ccagcacgag    720
tgttcggccc gtcgcaggga cttctacttt caccacatca atagccactc ctccaattgg    780
tggcgggaga tccagttctt cccgatcggc tcgcatcctc gcaccgagcg tctctttgtc    840
acctacgatg tagagaccta tacttggatg ggggcctttg gaagcagct cgtgcccttc    900 atgctggtca tgaagttcgg cggagatgag cctctagtga ctgccgcgcg agacctagcc    960
gcgaaccttg gatgggaccg ctgggaacaa gaccccgctta ccttctactg catcaccca    1020
```

```
gaaaaaatgg ccataggtcg ccagtttagg acctttcgcg accacctgca aatgctaatg    1080
gcccgtgacc tgtggagctc attcgtcgct tccaaccctc atcttgcaga ctgggccctt    1140
tcagagcacg ggctcagctc ccctgaagag ctcacctacg aggaacttaa aaaattgcct    1200
tccatcaagg gcatcccgcg cttcttggaa ctttacattg tgggccacaa cattaatggg    1260
tacgacgaga tcgtgctcgc cgcccaggta attaacaacc gttccgaggt gccgggaccc    1320
ttccgcatca cacgcaactt tatgcctcgc gcgggaaaga tactcttcaa cgatgtcacc    1380
ttcgccctgc caaatccgcg ttccaaaaag cgcacggact ttttgctctg ggagcagggc    1440
ggatgcgacg acactgactt caaataccag tacctcaaag tcatggtcag ggacaccttt    1500
gcgctcaccc acacctcgct ccggaaggcc gcgcaggcat acgcgctacc cgtagaaaag    1560
ggatgctgcg cctaccaggc cgtcaaccag ttctacatgc taggctctta ccgttcggag    1620
gccgacgggt ttccgatcca agagtactgg aaagaccgcg aagagtttgt cctcaaccgc    1680
gagctgtgga aaaaaaggg acaggataag tatgacatca tcaaggaaac cctggactac    1740
tgcgccctag acgtgcaggt caccgccgag ctggtcaaca gctgcgcga ctcctacgcc    1800 tccttcgtgc gtgacgcggt aggtctcaca gacgccagct tcaacgtctt ccagcgtcca    1860
accatatcat ccaactcaca tgccatcttc aggcagatag tcttccgagc agagcagccc    1920
gcccgtagca acctcggtcc cgacctcctc gctccctcgc acgaactata cgattacgtg    1980
cgcgccagca tccgcggtgg aagatgctac cctacatatc ttggaatact cagagagccc    2040
ctctacgttt acgacatttg cggcatgtac gcctccgcgc tcacccaccc catgccatgg    2100 ggtccccac tcaacccata cgagcgcgcg cttgccgccc gcgcatggca gcaggcgcta    2160
gacttgcaag gatgcaagat agactacttc gacgcgcgcc tgctgcccgg ggtctttacc    2220
gtggacgcag accccccgga cgagacgcag ctagaccccc taccgccatt ctgctcgcgc    2280
aagggcggcc gcctctgctg gaccaacgag cgcctacgcg gagaggtagc caccagcgtt    2340
gaccttgtca ccctgcacaa ccgcggttgg cgcgtgcacc tggtgcccga cgagcgcacc    2400
accgtctttc ccgaatggcg gtgcgttgcg cgcgaatacg tgcagctaaa catcgcggcc    2460
aaggagcgcg ccgatcgcgc taagaaccaa acctgcgct ccatcgccaa gttgctgtcc    2520
aacgccctct acgggtcgtt tgccaccaag cttgacaaca aaaagattgt cttttctgac    2580
cagatggatg cggccaccct caaaggcatc accgcgggcc aggtgaatat caaatcctcc    2640 tcgttttttgg aaactgacaa tcttagcgca gaagtcatgc ccgcttttca gagggagtac    2700
tcaccccaac agctggccct cgcagacagc gatgcggaag agagtgagga cgaacgcgcc    2760
cccaccccct tttatagccc cccttcagga acacccggtc acgtggccta cacctacaaa    2820
ccaatcacct tccttgatgc cgaagagggc gacatgtgtc ttcacaccct ggagcgagtg    2880
gaccccctag tggacaacga ccgctacccc tcccacttag cctccttcgt gctggcctgg    2940
acgcgagcct ttgtctcaga gtggtccgag tttctatacg aggaggaccg cggaacaccg    3000
ctcgaggaca ggcctctcaa gtctgtatac ggggacacgg acagccttttt cgtcaccgag    3060 cgtggacacc ggctcatgga aaccagaggt aagaaacgca tcaaaaagca tggggaaac    3120 ctggttttg accccgaacg gccagagctc acctggctcg tggaatgcga gaccgtctgc    3180
ggggcctgcg gcgcggatgc ctactcccg gaatcggtat ttctcgcgcc caagctctac    3240
gccctcaaaa gtctgcactg cccctcgtgc ggcgcctcct ccaagggcaa gctgcgcgcc    3300
aagggccacg ccgcggaggg gctggactat gacaccatgg tcaaatgcta cctggccgac    3360
gcgcagggcg aagaccggca gcgcttcagc accagcagga ccagcctcaa gcgcaccctg    3420
```

```
gccagcgcgc agcccggagc gcacccctte accgtgaccc agactacgct gacgaggacc      3480
ctgcgcccgt ggaaagacat gaccctggcc cgtctggacg agcaccgact actgccgtac      3540
agcgaaagcc gccccaaccc gcgaaacgag gagatatgct ggatcgagat gccgtaccca      3600
tacgatgttc cggattacgc ttag                                             3624

<210> SEQ ID NO 28
<211> LENGTH: 817
<212> TYPE: DNA
<213> ORGANISM: Artificial Sequence
<220> FEATURE:
<223> OTHER INFORMATION: Construct

<400> SEQUENCE: 28
actctcttcc gcatcgctgt ctgcgagggc cagctgttgg gctcgcggtt gaggacaaac        60
tcttcgcggt ctttccagta ctcttggatc ggaaacccgt cggcctccga acaggtactc       120
cgccgccgag ggacctgagc gagtccgcat cgaccggatc ggaaaccctc tcgagaaagg       180
cgtctaacca gtcacagtcg caatgggctc cagtgagcag gaactgaaag ccattgtcaa       240
agatcttggt tgtgggccat attttttggg cacctatgac aagcgctttc caggcttttgt      300 ttctccacac aagctcgcct gcgccatagt caatacggcc ggtcgcgaga ctggggggcgt      360 acactggatg gcctttgcct ggaacccgca ctcaaaaaca tgctacctct ttgagccctt       420
tggcttttct gaccagcgac tcaagcaggt ttaccagttt gagtacgagt cactcctgcg       480
ccgtagcgcc attgcttctt cccccgaccg ctgtataacg ctggaaaagt ccacccaaag       540
cgtacagggg cccaactcgg ccgcctgtgg actattctgc tgcatgtttc tccacgcctt       600
tgccaactgg ccccaaactc ccatggatca caaccccacc atgaacctta ttaccggggt       660
acccaactcc atgctcaaca gtccccaggt acagcccacc ctgcgtcgca accaggaaca       720
gctctacagc ttcctggagc gccactcgcc ctacttccgc agccacagtg cgcagattag       780
gagcgccact tcttttttgtc acttgaaaaa catgtaa                              817

<210> SEQ ID NO 29
<211> LENGTH: 2191
<212> TYPE: DNA
<213> ORGANISM: Artificial Sequence
<220> FEATURE:
<223> OTHER INFORMATION: Construct

<400> SEQUENCE: 29
cctcccacac ataaccagga ggtcagatta tgcagtttaa ggtttacacc tataaaagag        60
agagccgtta tcgtctgttt gtggatgtac agagtgatat tattgacacg cccgggcgac       120
ggatggtgat cccctggcc agtgcacgtc tgctgtcaga taaagtctcc cgtgaacttt        180
acccggtggt gcatatcggg gatgaaagct ggcgcatgat gaccaccgat atggccagtg       240
tgccggtctc cgttatcggg gaagaagtgg ctgatctcag ccaccgcgaa aatgacatca       300
aaaacgccat taacctgatg ttctggggaa tataacccag aagcttagca aaagctaaaa       360
ccaggagcta tttaatggca acagttaacc agctggtacg caaaccacgt gctcgcaaag       420
ttgcgaaaag caacgtgcct gcgctggaag catgcccgca aaaacgtggc gtatgtactc       480
gtgtatatac taccactcct aaaaaaccga actccgcgct gcgtaaagta tgccgtgttc       540
gtctgactaa cggtttcgaa gtgacttcct acatcggtgg tgaaggtcac aacctgcagg       600
agcactccgt gatcctgatc cgtggcggtc gtgttaaaga cctcccgggt gttcgttacc       660
```

| | |
|---|---:|
| acaccgtacg tggtgcgctt gactgctccg gcgttaaaga ccgtaagcag gctcgttcca | 720 |
| agtatggcgt gaagcgtcct aaggcttaat ggttcgcccg cctaatgagc gggcttttt | 780 |
| ttgaattctt ttttaattcg atctgaagat cagcagttca acctgttgat agtacgtact | 840 |
| aagctctcat gtttcacgta ctaagctctc atgtttaacg tactaagctc tcatgtttaa | 900 |
| cgaactaaac cctcatggct aacgtactaa gctctcatgg ctaacgtact aagctctcat | 960 |
| gtttcacgta ctaagctctc atgtttgaac aataaaatta atataaatca gcaacttaaa | 1020 |
| tagcctctaa ggttttaagt tttataagaa aaaaagaat atataaggct tttaaagctt | 1080 |
| ttaaggttta acggttgtgg acaacaagcc agggatgtaa cgcactgaga agcccttaga | 1140 |
| gcctctcaaa gcaattttga gtgacacagg aacacttaac ggctgacatg ggatcccct | 1200 |
| catcagtgcc aacatagtaa gccagtatac actccgctag cgcggccgcc tcgagtttcg | 1260 |
| acctgcagcc tgttgacaat taatcatcgg catagtatat cggcatagta aatacgaca | 1320 |
| aggtgaggaa ctaaccatgg ggatcggcca ttgaacaaga tggattgcac gcaggttctc | 1380 |
| cggccgcttg ggtggagagg ctattcggct atgactgggc acaacagaca atcggctgct | 1440 |
| ctgatgccgc cgtgttccgg ctgtcagcgc aggggcgccc ggttcttttt gtcaagaccg | 1500 |
| acctgtccgg tgccctgaat gaactgcagg acgaggcagc gcggctatcg tggctggcca | 1560 |
| cgacgggcgt tccttgcgca gctgtgctcg acgttgtcac tgaagcggga agggactggc | 1620 |
| tgctattggg cgaagtgccg gggcaggatc tcctgtcatc tcaccttgct cctgccgaga | 1680 |
| aagtatccat catggctgat gcaatgcggc ggctgcatac gcttgatccg gctacctgcc | 1740 |
| cattcgacca ccaagcgaaa catcgcatcg agcgagcacg tactcggatg gaagccggtc | 1800 |
| ttgtcgatca ggatgatctg gacgaagagc atcaggggct cgcgccagcc gaactgttcg | 1860 |
| ccaggctcaa ggcgcgcatg cccgacggcg atgatctcgt cgtgacccat ggcgatgcct | 1920 |
| gcttgccgaa tatcatggtg gaaaatggcc gcttttctgg attcatcgac tgtggccggc | 1980 |
| tgggtgtggc ggaccgctat caggacatag cgttggctac ccgtgatatt gctgaagagc | 2040 |
| ttggcggcga atgggctgac cgcttcctcg tgctttacgg tatcgccgct cccgattcgc | 2100 |
| agcgcatcgc cttctatcgc cttcttgacg agttcttctg aggggatcaa ttctctagag | 2160 |
| ctcgctgatc agcctcgact gtaccgttag c | 2191 |

<210> SEQ ID NO 30
<211> LENGTH: 5978
<212> TYPE: DNA
<213> ORGANISM: Artificial Sequence
<220> FEATURE:
<223> OTHER INFORMATION: Construct

<400> SEQUENCE: 30

| | |
|---|---:|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggacttttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta cccctccgcg gggatcctct agtcagctga cgcgtcctat    960
gtctagactg gacaagagca aagtcataaa ctctgctctg gaattactca atgaagtcgg   1020
tatcgaaggc ctgacgacaa ggaaactcgc tcaaaagctg ggagttgagc agcctaccct   1080
gtactggcac gtgaagaaca gcgggccct gctcgatgcc ctggcaatcg agatgctgga   1140
caggcatcat acccacttct gccccctgga aggcgagtca tggcaagact tctgcggaa    1200
caacgccaag tcattccgct gtgctctcct ctcacatcgc gacggggcta agtgcatct    1260
cggcacccgc ccaacagaga aacagtacga aaccctggaa aatcagctcg cgttcctgtg   1320
tcagcaaggc ttctccctgg agaacgcact gtacgctctg tccgccgtgg gccactttac   1380
actgggctgc gtattggagg atcaggagca tcaagtagca aaagaggaaa gagagacacc   1440
taccaccgat tctatgcccc cacttctgag acaagcaatt gagctgttcg accatcaggg   1500
agccgaacct gccttccttt tcggcctgga actaatcata tgtggcctgg agaaacagct   1560
aaagtgcgaa agcggcgggc cggccgacgc ccttgacgat tttgacttag acatgctccc   1620
agccgatgcc cttgacgact tgaccttga tatgctgcct gctgacgctc ttgacgattt   1680
ggaccttgac atgctccccg ggtaactaga attatctcta gaggatcata atcagccata   1740
ccacatttgt tcgcggccgc cggcaataaa aagacagaat aaaacgcacg ggtgttgggt   1800
cgtttgttcg aattctagca ggcatgctgg ggatgcggtg ggctctatgg cttctgaggc   1860
ggaaagaacc agctggggct ctaggggta tccccacgcg ccctgtagcg gcgcattaag   1920
cgcggcgggt gtggtggtta cgcgcagcgt gaccgctaca cttgccagcg ccctagcgcc   1980
cgctcctttc gctttcttcc cttcctttct cgccacgttc gccggctttc cccgtcaagc   2040
tctaaatcgg gggctccctt tagggttccg atttagtgct ttacggcacc tcgaccccaa   2100
aaaacttgat tagggtgatg gttcacgtag tgggccatcg ccctgataga cggtttttcg   2160
cccttgacg ttggagtcca cgttctttaa tagtggactc ttgttccaaa ctggaacaac   2220
actcaaccct atctcggtct attcttttga tttataaggg attttgccga tttcggccta   2280
ttggttaaaa aatgagctga tttaacaaaa atttaacgcg aattaattct gtggaatgtg   2340
tgtcagttag ggtgtggaaa gtccccaggc tccccagcag gcagaagtat gcaaagcatg   2400
catctcaatt agtcagcaac caggtgtgga agtccccag gctccccagc aggcagaagt   2460
atgcaaagca tgcatctcaa ttagtcagca accatagtcc cgcccctaac tccgcccatc   2520
ccgcccctaa ctccgcccag ttccgcccat tctccgcccc atggctgact aattttttt    2580
atttatgcag aggccgaggc cgcctctgcc tctgagctat tccagaagta gtgaggaggc   2640
ttttttggag gcctaggctt ttgcaaacct ccgcggggat cctctagtca gctgacgcgt   2700
cctatgtcta gactggacaa gagcaaagtc ataaactctg ctctggaatt actcaatgaa   2760
gtcggtatcg aaggcctgac gacaaggaaa ctcgctcaaa agctgggagt tgagcagcct   2820
accctgtact ggcacgtgaa gaacaagcgg gccctgctcg atgccctggc aatcgagatg   2880
```

```
ctggacaggc atcatacccca cttctgcccc ctggaaggcg agtcatggca agactttctg    2940
cggaacaacg ccaagtcatt ccgctgtgct ctcctctcac atcgcgacgg ggctaaagtg    3000
catctcggca cccgcccaac agagaaacag tacgaaaccc tggaaaatca gctcgcgttc    3060
ctgtgtcagc aaggcttctc cctggagaac gcactgtacg ctctgtccgc cgtgggccac    3120
tttacactgg gctgcgtatt ggaggatcag gagcatcaag tagcaaaaga ggaaagagag    3180
acacctacca ccgattctat gcccccactt ctgagacaag caattgagct gttcgaccat    3240
cagggagccg aacctgcctt cctttttcggc ctggaactaa tcatatgtgg cctggagaaa    3300
cagctaaagt gcgaaagcgg cgggccggcc gacgcccttg acgattttga cttagacatg    3360
ctcccagccg atgcccttga cgactttgac cttgatatgc tgcctgctga cgctcttgac    3420
gatttggacc ttgacatgct ccccgggtaa ctagaattat ctctagagga tcataatcag    3480
ccataccaca tttgttcgaa atgaccgacc aagcgacgcc caacctgcca tcacgagatt    3540
tcgattccac cgccgccttc tatgaaaggt tgggcttcgg aatcgttttc cgggacgccg    3600
gctggatgat cctccagcgc ggggatctca tgctggagtt cttcgcccac cccaacttgt    3660
ttattgcagc ttataatggt tacaaataaa gcaatagcat cacaaatttc acaaataaag    3720
catttttttc actgcattct agttgtggtt tgtccaaact catcaatgta tcttatcatg    3780
tctgtatacc gtcgacctct agctagagct tggcgtaatc atggtcatag ctgtttcctg    3840
tgtgaaattg ttatccgctc acaattccac acaacatacg agccggaagc ataaagtgta    3900
aagcctgggg tgcctaatga gtgagctaac tcacattaat tgcgttgcgc tcactgcccg    3960
ctttccagtc gggaaacctg tcgtgccagc tgcattaatg aatcggccaa cgcgcgggga    4020
gaggcggttt gcgtattggg cgctcttccg cttcctcgct cactgactcg ctgcgctcgg    4080
tcgttcggct gcggcgagcg gtatcagctc actcaaaggc ggtaatacgg ttatccacag    4140
aatcagggga taacgcagga aagaacatgt gagcaaaagg ccagcaaaag gccaggaacc    4200
gtaaaaaggc cgcgttgctg gcgtttttcc ataggctccg ccccccctgac gagcatcaca    4260
aaaatcgacg ctcaagtcag aggtggcgaa acccgacagg actataaaga taccaggcgt    4320
ttccccctgg aagctccctc gtgcgctctc ctgttccgac cctgccgctt accggatacc    4380
tgtccgcctt tctcccttcg ggaagcgtgg cgctttctca tagctcacgc tgtaggtatc    4440
tcagttcggt gtaggtcgtt cgctccaagc tgggctgtgt gcacgaaccc cccgttcagc    4500
ccgaccgctg cgccttatcc ggtaactatc gtcttgagtc aacccggta agacacgact    4560
tatcgccact ggcagcagcc actggtaaca ggattagcag agcgaggtat gtaggcggtg    4620
ctacagagtt cttgaagtgg tggcctaact acggctacac tagaagaaca gtatttggta    4680
tctgcgctct gctgaagcca gttaccttcg gaaaaagagt tggtagctct tgatccggca    4740
aacaaaccac cgctggtagc ggtttttttg tttgcaagca gcagattacg cgcagaaaaa    4800
aaggatctca agaagatcct ttgatctttt ctacggggtc tgacgctcag tggaacgaaa    4860
actcacgtta agggattttg gtcatgagat tatcaaaaag gatcttcacc tagatccttt    4920
taaattaaaa atgaagtttt aaatcaatct aaagtatata tgagtaaact tggtctgaca    4980
gttaccaatg cttaatcagt gaggcaccta tctcagcgat ctgtctattt cgttcatcca    5040
tagttgcctg actccccgtc gtgtagataa ctacgatacg ggagggctta ccatctggcc    5100
ccagtgctgc aatgataccg cgagacccac gctcaccggc tccagattta tcagcaataa    5160
accagccagc cggaagggcc gagcgcagaa gtggtcctgc aactttatcc gcctccatcc    5220
agtctattaa ttgttgccgg gaagctagag taagtagttc gccagttaat agtttgcgca    5280
```

```
acgttgttgc cattgctaca ggcatcgtgg tgtcacgctc gtcgtttggt atggcttcat    5340
tcagctccgg ttcccaacga tcaaggcgag ttacatgatc ccccatgttg tgcaaaaaag    5400
cggttagctc cttcggtcct ccgatcgttg tcagaagtaa gttggccgca gtgttatcac    5460
tcatggttat ggcagcactg cataattctc ttactgtcat gccatccgta agatgctttt    5520
ctgtgactgg tgagtactca accaagtcat tctgagaata gtgtatgcgg cgaccgagtt    5580
gctcttgccc ggcgtcaata cgggataata ccgcgccaca tagcagaact ttaaaagtgc    5640
tcatcattgg aaaacgttct cggggcgaaa actctcaag gatcttaccg ctgttgagat     5700
ccagttcgat gtaacccact cgtgcaccca actgatcttc agcatctttt actttcacca    5760
gcgtttctgg gtgagcaaaa acaggaaggc aaaatgccgc aaaaaaggga ataagggcga    5820
cacggaaatg ttgaatactc atactcttcc tttttcaata ttattgaagc atttatcagg    5880
gttattgtct catgagcgga tacatatttg aatgtattta gaaaaataaa caaatagggg    5940
ttccgcgcac atttccccga aaagtgccac ctgacgtc                            5978

<210> SEQ ID NO 31
<211> LENGTH: 5964
<212> TYPE: DNA
<213> ORGANISM: Artificial Sequence
<220> FEATURE:
<223> OTHER INFORMATION: Construct

<400> SEQUENCE: 31
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgccaccat gtgagcaagg gcgaggagga taacatggcc    960
atcatcaagg agttcatgcg cttcaaggtg cacatggagg gctccgtgaa cggccacgag   1020
ttcgagatcg agggcgaggg cgaggggccgc ccctacgagg gcacccagac cgccaagctg   1080
aaggtgacca agggtggccc cctgcccttc gcctgggaca cctgtcccc tcagttcatg    1140 tacggctcca aggcctacgt gaagcacccc gccgacatcc ccgactactt gaagctgtcc    1200
ttccccgagg gcttcaagtg ggagcgcgtg atgaacttcg aggacggcgg cgtggtgacc    1260
gtgacccagg actcctccct gcaggacggc gagttcatct acaaggtgaa gctgcgcggc    1320
```

```
accaacttcc cctccgacgg ccccgtaatg cagaagaaga ccatgggctg ggaggcctcc    1380
tccgagcgga tgtaccccga ggacggcgcc ctgaagggcg agatcaagca gaggctgaag    1440
ctgaaggacg gcggccacta cgacgctgag gtcaagacca cctacaaggc caagaagccc    1500
gtgcagctgc ccgcgccta caacgtcaac atcaagttgg acatcacctc ccacaacgag    1560
gactacacca tcgtggaaca gtacgaacgc gccgagggcc gccactccac cggcggcatg    1620
gacgagctgt acaagtaggc ggccgcatcg ataagcttgt cgacgatatc tctagagggc    1680
ccgtttaaac ccgctgatca gcctcgactg tgccttctag ttgccagcca tctgttgttt    1740
gcccctcccc cgtgccttcc ttgaccctgg aaggtgccac tcccactgtc ctttcctaat    1800
aaaatgagga aattgcatcg cattgtctga gtaggtgtca ttctattctg gggggtgggg    1860
tggggcagga cagcaagggg gaggattggg aagacaatag caggcatgct ggggatgcgg    1920
tgggctctat ggcttctgag gcggaaagaa ccagctgggg ctctagggg tatccccacg    1980 cgccctgtag cggcgcatta agcgcggcgg gtgtggtggt tacgcgcagc gtgaccgcta    2040
cacttgccag cgccctagcg cccgctcctt tcgctttctt cccttccttt ctcgccacgt    2100
tcgccggctt tccccgtcaa gctctaaatc ggggctccc tttagggttc cgatttagtg    2160
ctttacggca cctcgacccc aaaaaacttg attagggtga tggttcacgt agtgggccat    2220
cgccctgata cggtttttcg cccctttga cgttggagtc cacgttcttt aatagtggac    2280
tcttgttcca aactgaaca acactcaacc ctatctcggt ctattctttt gatttataag    2340
ggattttgcc gatttcggcc tattggttaa aaaatgagct gatttaacaa aaatttaacg    2400
cgaattaatt ctgtggaatg tgtgtcagtt agggtgtgga aagtcccag gctccccagc    2460 aggcagaagt atgcaaagca tgcatctcaa ttagtcagca accaggtgtg gaaagtcccc    2520
aggctcccca gcaggcagaa gtatgcaaag catgcatctc aattagtcag caaccatagt    2580
cccgccccta actccgccca tcccgcccct aactccgccc agttccgccc attctccgcc    2640
ccatggctga ctaattttt ttatttatgc agaggccgag gccgcctctg cctctgagct    2700
attccagaag tagtgaggag gcttttttgg aggcctaggc ttttgcaaac ctccgcgggg    2760
atccgcacca tggtgagcaa gggcgaggag gataacatgg ccatcatcaa ggagttcatg    2820
cgcttcaagg tgcacatgga gggctccgtg aacggccacg agttcgagat cgagggcgag    2880
ggcgagggcc gcccctacga gggcacccag accgccaagc tgaaggtgac caagggtggc    2940
cccctgccct tcgcctggga catcctgtcc cctcagttca tgtacggctc caaggcctac    3000
gtgaagcacc ccgccgacat ccccgactac ttgaagctgt ccttccccga ggcttcaag    3060 tgggagcgcg tgatgaactt cgaggacggc ggcgtggtga ccgtgaccca ggactcctcc    3120
ctgcaggacg gcgagttcat ctacaaggtg aagctgcgcg gcaccaactt ccctccgac    3180 ggccccgtaa tgcagaagaa gaccatgggc tgggaggcct cctccgagcg gatgtacccc    3240
gaggacggcg ccctgaaggg cgagatcaag cagaggctga agctgaagga cggcggccac    3300
tacgacgctg aggtcaagac cacctacaag gccaagaagc ccgtgcagct gcccggcgcc    3360
tacaacgtca acatcaagtt ggacatcacc tcccacaacg aggactacac catcgtggaa    3420
cagtacgaac gcgccgaggg ccgccactcc accggcggca tggacgagct gtacaagtag    3480
ttcgaaatga ccgaccaagc gacgcccaac ctgccatcac gagatttcga ttccaccgcc    3540
gccttctatg aaaggttggg cttcggaatc gttttccggg acgccggctg atgatcctc    3600 cagcgcgggg atctcatgct ggagttcttc gcccacccca acttgtttat tgcagcttat    3660
aatggttaca ataaagcaa tagcatcaca aatttcacaa ataaagcatt tttttcactg    3720
```

-continued

```
cattctagtt gtggtttgtc caaactcatc aatgtatctt atcatgtctg tataccgtcg    3780
acctctagct agagcttggc gtaatcatgg tcatagctgt ttcctgtgtg aaattgttat    3840
ccgctcacaa ttccacacaa catacgagcc ggaagcataa agtgtaaagc ctggggtgcc    3900
taatgagtga gctaactcac attaattgcg ttgcgctcac tgcccgcttt ccagtcggga    3960
aacctgtcgt gccagctgca ttaatgaatc ggccaacgcg cggggagagg cggtttgcgt    4020
attgggcgct cttccgcttc ctcgctcact gactcgctgc gctcggtcgt tcggctgcgg    4080
cgagcggtat cagctcactc aaaggcggta atacggttat ccacagaatc aggggataac    4140
gcaggaaaga acatgtgagc aaaaggccag caaaaggcca ggaaccgtaa aaaggccgcg    4200
ttgctggcgt ttttccatag gctccgcccc cctgacgagc atcacaaaaa tcgacgctca    4260
agtcagaggt ggcgaaaccc gacaggacta taaagatacc aggcgtttcc ccctggaagc    4320
tccctcgtgc gctctcctgt tccgaccctg ccgcttaccg gatacctgtc gcctttctc    4380
ccttcgggaa gcgtggcgct ttctcatagc tcacgctgta ggtatctcag ttcggtgtag    4440
gtcgttcgct ccaagctggg ctgtgtgcac gaaccccccg ttcagcccga ccgctgcgcc    4500
ttatccggta actatcgtct tgagtccaac ccggtaagac acgacttatc gccactggca    4560
gcagccactg gtaacaggat tagcagagcg aggtatgtag gcggtgctac agagttcttg    4620
aagtggtggc ctaactacgg ctacactaga agaacagtat ttggtatctg cgctctgctg    4680
aagccagtta ccttcggaaa aagagttggt agctcttgat ccggcaaaca aaccaccgct    4740
ggtagcggtt ttttgtttg caagcagcag attacgcgca gaaaaaaagg atctcaagaa    4800
gatcctttga tcttttctac ggggtctgac gctcagtgga acgaaaactc acgttaaggg    4860
attttggtca tgagattatc aaaaaggatc ttcacctaga tccttttaaa ttaaaaatga    4920
agttttaaat caatctaaag tatatatgag taaacttggt ctgacagtta ccaatgctta    4980
atcagtgagg cacctatctc agcgatctgt ctatttcgtt catccatagt tgcctgactc    5040
cccgtcgtgt agataactac gatacgggag ggcttaccat ctggccccag tgctgcaatg    5100
ataccgcgag acccacgctc accggctcca gatttatcag caataaacca gccagccgga    5160
agggccgagc gcagaagtgg tcctgcaact ttatccgcct ccatccagtc tattaattgt    5220
tgccgggaag ctagagtaag tagttcgcca gttaatagtt tgcgcaacgt tgttgccatt    5280
gctacaggca tcgtggtgtc acgctcgtcg tttggtatgg cttcattcag ctccggttcc    5340
caacgatcaa ggcgagttac atgatccccc atgttgtgca aaaaagcggt tagctccttc    5400
ggtcctccga tcgttgtcag aagtaagttg gccgcagtgt tatcactcat ggttatggca    5460
gcactgcata attctcttac tgtcatgcca tccgtaagat gcttttctgt gactggtgag    5520
tactcaacca agtcattctg agaatagtgt atgcggcgac cgagttgctc ttgcccggcg    5580
tcaatacggg ataataccgc gccacatagc agaactttaa aagtgctcat cattggaaaa    5640
cgttcttcgg ggcgaaaact ctcaaggatc ttaccgctgt tgagatccag ttcgatgtaa    5700
cccactcgtg cacccaactg atcttcagca tcttttactt tcaccagcgt ttctgggtga    5760
gcaaaaacag gaaggcaaaa tgccgcaaaa aagggaataa gggcgacacg gaaatgttga    5820
atactcatac tcttcctttt tcaatattat tgaagcattt atcagggtta ttgtctcatg    5880
agcggataca tatttgaatg tatttagaaa aataaacaaa taggggttcc gcgcacattt    5940
ccccgaaaag tgccacctga cgtc                                          5964
```

<210> SEQ ID NO 32

```
<211> LENGTH: 10765
<212> TYPE: DNA
<213> ORGANISM: Artificial Sequence
<220> FEATURE:
<223> OTHER INFORMATION: Construct
<220> FEATURE:
<221> NAME/KEY: misc_feature
<222> LOCATION: (4978)..(4978)
<223> OTHER INFORMATION: n is a, c, g, or t

<400> SEQUENCE: 32
aattcatggc cttggctcaa gctcaccggg cccgtcgtct tcacgcagag gcgccagatt      60
caggagatca accgccgcgt cgtcgcgttc gccagcaacc tacgcgcgca gcaccagctc     120
ctgcccgcgc gcggcgccga cgtgcccctg cccctctcc cggcgggtcc ggagcccccc      180
ctacctccgg gggctcgccc gcgtcaccgc ttttagatgc atcatccaag gacacccccg     240
cggcccaccg cccgccgcgc ggtaccgtag tcgcgccgcg gggatgcggc ctcttgcaag     300
ccatcgacgc cgccaccaac cagccctgg aaattaggta tcacctggat ctagcccgcg      360
ccctgacccg tctatgcgag gtaaacctgc aggagctccc gcctgacctg acgccgcggg     420
agctccagac catggacagc tcccatctgc gcgatgttgt catcaagctc cgaccgccgc     480
gcgcggacat ctggactttg ggctcgcgcg gcgtggtggt ccgatccacc gtaactcccc     540
tcgagcagcc agacggtcaa ggacaagcag ccgaagtaga agaccaccag ccaaacccgc     600
caggcgaggg gctcaaattc ccactctgct tccttgtgcg cggtcgtcag gtcaacctcg     660
tgcaggatgt acagcccgtg caccgctgcc agtactgcgc acgttttac aaaagccagc      720
acgagtgttc ggcccgtcgc agggacttct actttcacca catcaatagc cactcctcca     780
attggtggcg ggagatccag ttcttcccga tcggctcgca tcctcgcacc gagcgtctct     840
ttgtcaccta cgatgtagag acctatactt ggatgggggc cttgggaag cagctcgtgc      900
ccttcatgct ggtcatgaag ttcggcggag atgagcctct agtgactgcc gcgcgagacc     960
tagccgcgaa ccttggatgg gaccgctggg aacaagaccc gcttaccttc tactgcatca    1020
ccccagaaaa aatggccata ggtcgccagt ttaggacctt tcgcgaccac ctgcaaatgc    1080
taatggcccg tgacctgtgg agctcattcg tcgcttccaa ccctcatctt gcagactggg    1140
cccttttcaga gcacgggctc agctcccctg aagagctcac ctacgaggaa cttaaaaaat   1200
tgccttccat caagggcatc ccgcgcttct tggaacttta cattgtgggc cacaacatta    1260
atgggtttga cgagatcgtg ctcgccgccc aggtaattaa caaccgttcc gaggtgccgg    1320
gacccttccg catcacacgc aactttatgc ctcgcgcggg aaagatactc ttcaacgatg    1380
tcaccttcgc cctgccaaat ccgcgttcca aaaagcgcac ggactttttg ctctgggagc    1440
agggcggatg cgacgacact gacttcaaat accagtacct caaagtcatg gtcagggaca    1500
cctttgcgct cacccacacc tcgctccgga aggccgcgca ggcatacgcg ctaccgtag    1560
aaaagggatg ctgcgcctac caggccgtca accagttcta catgctaggc tcttaccgtt    1620
cggaggccga cgggtttccg atccaagagt actggaaaga ccgcgaagag tttgtcctca    1680
accgcgagct gtggaaaaaa aagggacagg ataagtatga catcatcaag gaaaccctgg    1740
actactgcgc cctagacgtg caggtcaccg ccgagctggt caacaagctg cgcgactcct    1800
acgcctcctt cgtgcgtgac gcggtaggtc tcacagacgc cagcttcaac gtcttccagc    1860
gtccaaccat atcatccaac tcacatgcca tcttcaggca gatagtcttc cgagcagagc    1920
agcccgcccc tagcaacctc ggtccccgacc tcctcgctcc ctcgcacgaa ctatacgatt   1980
acgtgcgcgc cagcatccgc ggtggaagat gctaccctac atatcttgga atactcagag    2040
```

-continued

```
agcccctcta cgtttacgac atttgcggca tgtacgcctc cgcgctcacc caccccatgc    2100 catgggtcc cccactcaac ccatacgagc gcgcgcttgc cgcccgcgca tggcagcagg     2160
cgctagactt gcaaggatgc aagatagact acttcgacgc gcgcctgctg cccggggtct    2220
ttaccgtgga cgcagacccc ccggacgaga cgcagctaga ccccctaccg ccattctgct    2280
cgcgcaaggg cggccgcctc tgctggacca acgagcgcct acgcggagag gtagccacca    2340
gcgttgacct tgtcaccctg cacaaccgcg gttggcgcgt gcacctggtg cccgacgagc    2400
gcaccaccgt cttcccgaa tggcggtgcg ttgcgcgcga atacgtgcag ctaaacatcg     2460
cggccaagga gcgcgccgat cgcgacaaaa accaaaccct gcgctccatc gccaagttgc    2520
tgtccaacgc cctctacggg tcgtttgcca ccaagcttga caacaaaaag attgtctttt    2580
ctgaccagat ggatgcggcc accctcaaag gcatcaccgc gggccaggtg aatatcaaat    2640
cctcctcgtt tttggaaact gacaatctta gcgcagaagt catgcccgct tttcagaggg    2700
agtactcacc ccaacagctg gccctcgcag acagcgatgc ggaagagagt gaggacgaac    2760
gcgcccccac ccccttttat agccccctt caggaacacc cggtcacgtg gcctacacct     2820
acaaaccaat caccttcctt gatgccgaag agggcgacat tgtcttcac accctggagc    2880 gagtggaccc cctagtggac aacgaccgct accctccca cttagcctcc ttcgtgctgg     2940
cctggacgcg agcctttgtc tcagagtggt ccgagtttct atacgaggag gaccgcggaa    3000
caccgctcga ggacaggcct ctcaagtctg tatacgggga cacggacagc ctttcgtca    3060 ccgagcgtgg acaccggctc atggaaacca gaggtaagaa acgcatcaaa aagcatgggg    3120
gaaacctggt ttttgacccc gaacggccag agctcacctg gctcgtggaa tgcgagaccg    3180
tctgcggggc ctgcgcgcg gatgcctact ccccggaatc ggtatttctc gcgcccaagc    3240
tctacgccct caaaagtctg cactgcccct cgtgcggcgc ctcctccaag ggcaagctgc    3300
gcgccaaggg ccacgccgcg gaggggctgg actatgacac catggtcaaa tgctacctgg    3360
ccgacgcgca gggcgaagac cggcagcgct tcagcaccag caggaccagc ctcaagcgca    3420
ccctggccag cgcgcagccc ggagcgcacc ccttcaccgt gacccagact acgctgacga    3480
ggaccctgcg cccgtggaaa gacatgaccc tggcccgtct ggacgagcac cgactactgc    3540
cgtacagcga aagccgcccc aacccgcgaa acgaggagat atgctggatc gagatgccgt    3600
acccatacga tgttccggat tacgcttaga gcacgtgact acatttaaac cctaacaaaa    3660
caaagagatg gggttactct ctaaattta tgggttatgt cattggatgt tatgggtcct    3720
tgccacaaga acacatcata caaaaaatca aagaatgttt tagaaaactt cctattaaca    3780
ggcctattga ttggaaagta tgtcaacgaa ttgtgggtct tttgggtttt gctgccccttt   3840 ttacacaatg tggttatcct gcgttgatgc ctttgtatgc atgtattcaa tctaagcagg    3900
ctttcacttt ctcgccaact tacaaggcct ttctgtgtaa acaatacctg aacctttacc    3960
ccgttgcccg gcaacggcca cctctgtgcc aagtgtttgc tgacgcaacc cccactggct    4020
ggggcttggt catgggccat cagcgcatgc gtggaacctt ttcggctcct ctgccgatcc    4080
atactgcgga actcctagcc gcttgttttg ctcgcagcag gtctggagca aacattatcg    4140
ggactgataa ctctgttgtc ctatcccgca aatatacatc gtttccatgg ctgctaggct    4200
gtgctgccaa ctggatcctg cgcgggacgt ccttttgttta cgtcccgtcg gcgctgaatc    4260
ctgcggacga cccttctcgg ggtcgcttgg gactctctcg tccccttctc cgtctgccgt    4320
tccgaccgac cacggggcgc acctctcttt acgcggactc ccgtctgtg ccttctcatc     4380
```

```
tgccggaccg tgtgcacttc gcttcacctc tgcacgtcgc atggagacca ccgtgaacgc    4440
ccaccaaata ttgcccaagg tcttacataa gaggactctt ggactctcag caatgtcaac    4500
gaccgacctt gaggcatact tcaaagactg tttgtttaaa gactgggagg agttgggga    4560 ggagattagg ttaaaggtct ttgtactagg aggctgtagg cataaattgg tctgcgcacc    4620
agcaccatgt atcactagag cggggtacct ttaagaccaa tgacttacaa ggcagctgta    4680
gatcttagcc acttttaaa agaaaagggg ggacttggaa gggctaattc actcccaacg    4740
aagacaagat ctgcttttg cttgtactgg gtctctctgg ttagaccaga tctgagcctg    4800
ggagctctct ggctaactag ggaacccact gcttaagcct caataaagct tgccttgagt    4860
gcttcaagta gtgtgtgccc gtctgttgtg tgactctggt aactagagat ccctcagacc    4920
cttttagtca gtgtggaaaa tctctagcag tagtagttca tgtcatctta ttattcangt    4980
atttataact tgcaaagaaa tgaatatcag agagtgagag gaacttgttt attgcagctt    5040
ataatggtta caaataaagc aatagcatca caaatttcac aaataaagca ttttttcac    5100 tgcattctag ttgtggtttg tccaaactca tcaatgtatc ttatcatgtc tggctctagc    5160
tatcccgccc ctaactccgc ccagttccgc ccattctccg ccccatggct gactaatttt    5220 tttatttat gcagaggccg aggccgcctc ggcctctgag ctattccaga agtagtgagg    5280 aggcttttt ggaggcctag gcttttgcgt cgagacgtac ccaattcgcc ctatagtgag    5340
tcgtattacg cgcgctcact ggccgtcgtt ttacaacgtc gtgactggga aaaccctggc    5400
gttacccaac ttaatcgcct tgcagcacat ccccctttcg ccagctggcg taatagcgaa    5460
gaggcccgca ccgatcgccc ttcccaacag ttgcgcagcc tgaatggcga atggcgcgac    5520
gcgccctgta gcggcgcatt aagcgcggcg ggtgtggtgg ttacgcgcag cgtgaccgct    5580
acacttgcca gcgccctagc gcccgctcct ttcgctttct tcccttcctt tctcgccacg    5640
ttcgccggct ttccccgtca gctctaaat cgggggctcc ctttagggtt ccgatttagt    5700
gctttacggc acctcgaccc caaaaaactt gattagggtg atggttcacg tagtgggcca    5760
tcgccctgat agacggtttt tcgccctttg acgttggagt ccacgttctt taatagtgga    5820
ctcttgttcc aaactggaac aacactcaac cctatctcgg tctattcttt tgatttataa    5880
gggattttgc cgatttcggc ctattggtta aaaatgagc tgatttaaca aaaatttaac    5940
gcgaatttta acaaaatatt aacgtttaca atttcccagg tggcacttt cggggaaatg    6000 tgcgcggaac ccctatttgt ttatttttct aaatacattc aaatatgtat ccgctcatga    6060
gacaataacc ctgataaatg cttcaataat attgaaaaag gaagagtatg agtattcaac    6120
atttccgtgt cgcccttatt ccctttttg cggcattttg ccttcctgtt tttgctcacc    6180
cagaaacgct ggtgaaagta aaagatgctg aagatcagtt gggtgcacga gtgggttaca    6240
tcgaactgga tctcaacagc ggtaagatcc ttgagagttt tcgccccgaa gaacgttttc    6300
caatgatgag cacttttaaa gttctgctat gtggcgcggt attatcccgt attgacgccg    6360
ggcaagagca actcggtcgc cgcatacact attctcagaa tgacttggtt gagtactcac    6420
cagtcacaga aaagcatctt acggatggca tgacagtaag agaattatgc agtgctgcca    6480
taaccatgag tgataacact gcggccaact tacttctgac aacgatcgga ggaccgaagg    6540
agctaaccgc ttttttgcac aacatggggg atcatgtaac tcgccttgat cgttgggaac    6600
cggagctgaa tgaagccata ccaaacgacg agcgtgacac cacgatgcct gtagcaatgg    6660
caacaacgtt gcgcaaacta ttaactggcg aactacttac tctagcttcc cggcaacaat    6720
taatagactg gatggaggcg gataaagttg caggaccact tctgcgctcg ccccttccgg    6780
```

```
ctggctggtt tattgctgat aaatctggag ccggtgagcg tgggtctcgc ggtatcattg    6840
cagcactggg gccagatggt aagccctccc gtatcgtagt tatctacacg acggggagtc    6900
aggcaactat ggatgaacga atagacaga tcgctgagat aggtgcctca ctgattaagc     6960
attggtaact gtcagaccaa gtttactcat atatacttta gattgattta aaacttcatt    7020
tttaatttaa aaggatctag gtgaagatcc tttttgataa tctcatgacc aaaatccctt    7080
aacgtgagtt ttcgttccac tgagcgtcag accccgtaga aaagatcaaa ggatcttctt    7140
gagatccttt ttttctgcgc gtaatctgct gcttgcaaac aaaaaaacca ccgctaccag    7200
cggtggtttg tttgccggat caagagctac caactctttt tccgaaggta actggcttca    7260
gcagagcgca gataccaaat actgtccttc tagtgtagcc gtagttaggc caccacttca    7320
agaactctgt agcaccgcct acatacctcg ctctgctaat cctgttacca gtggctgctg    7380
ccagtggcga taagtcgtgt cttaccgggt tggactcaag acgatagtta ccggataagg    7440
cgcagcggtc gggctgaacg gggggttcgt gcacacagcc cagcttggag cgaacgacct    7500
acaccgaact gagataccta cagcgtgagc tatgagaaag cgccacgctt cccgaaggga    7560
gaaaggcgga caggtatccg gtaagcggca gggtcggaac aggagagcgc acgagggagc    7620 ttccagggg aaacgcctgg tatctttata gtcctgtcgg gtttcgccac ctctgacttg    7680
agcgtcgatt tttgtgatgc tcgtcagggg gcggagcct atggaaaaac gccagcaacg     7740 cggcctttt acggttcctg ccttttgct ggccttttgc tcacatgttc tttcctgcgt      7800
tatcccctga ttctgtggat aaccgtatta ccgcctttga gtgagctgat accgctcgcc    7860
gcagccgaac gaccgagcgc agcgagtcag tgagcgagga agcggaagag cgcccaatac    7920
gcaaaccgcc tctccccgcg cgttggccga ttcattaatg cagctggcac gacaggtttc    7980
ccgactggaa agcgggcagt gagcgcaacg caattaatgt gagttagctc actcattagg    8040 cacccccaggc tttacacttt atgcttccgg ctcgtatgtt gtgtggaatt gtgagcggat    8100
aacaatttca cacaggaaac agctatgacc atgattacgc caagcgcgca attaaccctc    8160
actaaaggga caaaagctg gagctgcaag cttaatgtag tcttatgcaa tactcttgta     8220
gtcttgcaac atggtaacga tgagttagca acatgcctta caaggagaga aaagcaccg     8280 tgcatgccga ttggtggaag taaggtggta cgatcgtgcc ttattaggaa ggcaacagac    8340
gggtctgaca tggattggac gaaccactga attggaggcg tggcctgggc gggactgggg    8400
agtggcgagc cctcagatcc tgcatataag cagctgcttt ttgcctgtac tgggtctctc    8460
tggttagacc agatctgagc ctgggagctc tctggctaac tagggaaccc actgcttaag    8520
cctcaataaa gcttgccttg agtgcttcaa gtagtgtgtg cccgtctgtt gtgtgactct    8580
ggtaactaga gatccctcag accctttag tcagtgtgga aaatctctag cagtggcgcc     8640
cgaacaggga cctgaaagcg aaagggaaac cagagctctc tcgacgcagg actcggcttg    8700
ctgaagcgcg cacggcaaga ggcgaggggc ggcgactggt gagtacgcca aaatttga      8760 ctagcggagg ctagaaggag agagatgggt gcgagagcgt cagtattaag cgggggagaa    8820
ttagatcgcg atgggaaaaa attcggttaa ggccaggggg aaagaaaaaa tataaattaa    8880
aacatatagt atgggcaagc agggagctag aacgattcgc agttaatcct ggcctgttag    8940
aaacatcaga aggctgtaga caaatactgg gacagctaca accatcccct cagacaggat    9000
cagaagaact tagatcatta tataatacag tagcaaccct ctattgtgtg catcaaagga    9060
tagagataaa agacaccaag gaagctttag acaagataga ggaagagcaa aacaaaagta    9120
```

| | |
|---|---|
| agaccaccgc acagcaagcg gccgctgatc ttcagacctg gaggaggaga tatgagggac | 9180 |
| aattggagaa gtgaattata taaatataaa gtagtaaaaa ttgaaccatt aggagtagca | 9240 |
| cccaccaagg caaagagaag agtggtgcag agagaaaaaa gagcagtggg aataggagct | 9300 |
| ttgttccttg ggttcttggg agcagcagga agcactatgg gcgcagcctc aatgacgctg | 9360 |
| acggtacagg ccagacaatt attgtctggt atagtgcagc agcagaacaa tttgctgagg | 9420 |
| gctattgagg cgcaacagca tctgttgcaa ctcacagtct ggggcatcaa gcagctccag | 9480 |
| gcaagaatcc tggctgtgga agatacctaa aggatcaac agctcctggg gatttggggt | 9540 |
| tgctctggaa aactcatttg caccactgct gtgccttgga atgctagttg gagtaataaa | 9600 |
| tctctggaac agattggaat cacacgacct ggatggagtg ggacagagaa attaacaatt | 9660 |
| acacaagctt aatacactcc ttaattgaag aatcgcaaaa ccagcaagaa aagaatgaac | 9720 |
| aagaattatt ggaattagat aaatgggcaa gtttgtggaa ttggtttaac ataacaaatt | 9780 |
| ggctgtggta tataaaatta ttcataatga tagtaggagg cttggtaggt ttaagaatag | 9840 |
| tttttgctgt actttctata gtgaatagag ttaggcaggg atattcacca ttatcgtttc | 9900 |
| agacccacct cccaaccccg aggggacccg acaggcccga aggaatagaa gaagaaggtg | 9960 |
| gagagagaga cagagacaga tccattcgat tagtgaacgg atctcgacgg tatcggtttt | 10020 |
| aaaagaaaag gggggattgg ggggtacagt gcagggaaa gaatagtaga cataatagca | 10080 |
| acagacatac aaactaaaga attacaaaaa caaattacaa aaattcaaaa ttttatcgat | 10140 |
| aagcttggga gttccgcgtt acataactta cggtaaatgg cccgcctggc tgaccgccca | 10200 |
| acgacccccg cccattgacg tcaataatga cgtatgttcc catagtaacg ccaataggga | 10260 |
| ctttccattg acgtcaatgg gtggagtatt tacggtaaac tgcccacttg gcagtacatc | 10320 |
| aagtgtatca tatgccaagt acgccccta ttgacggtca atgacggtaa atggcccgcc | 10380 |
| tggcattatg cccagtacat gaccttatgg gactttccta cttggcagta catctacgta | 10440 |
| ttagtcatcg ctattaccat ggtgatgcgg ttttggcagt acatcaatgg gcgtggatag | 10500 |
| cggtttgact cacggggatt tccaagtctc caccccattg acgtcaatgg gagtttgttt | 10560 |
| tggcaccaaa atcaacggga ctttccaaaa tgtcgtaaca actccgcccc attgacgcaa | 10620 |
| atgggcggta ggcgtgtacg gtgggaggtc tatataagca gagctcgttt agtgaaccgt | 10680 |
| cagatcgcct ggagacgcca tccacgctgt tttgacctcc atagaagaca ccgacktcta | 10740 |
| gctagaggat cccccgggct gcagg | 10765 |

<210> SEQ ID NO 33
<211> LENGTH: 9536
<212> TYPE: DNA
<213> ORGANISM: Artificial Sequence
<220> FEATURE:
<223> OTHER INFORMATION: Construct

<400> SEQUENCE: 33

| | |
|---|---|
| caggtggcac ttttcgggga aatgtgcgcg gaacccctat ttgtttattt ttctaaatac | 60 |
| attcaaatat gtatccgctc atgagacaat aaccctgata aatgcttcaa taatattgaa | 120 |
| aaaggaagag tatgagtatt caacatttcc gtgtcgccct tattcccttt tttgcggcat | 180 |
| tttgccttcc tgtttttgct cacccagaaa cgctggtgaa agtaaaagat gctgaagatc | 240 |
| agttgggtgc acgagtgggt tacatcgaac tggatctcaa cagcggtaag atccttgaga | 300 |
| gttttcgccc cgaagaacgt tttccaatga tgagcacttt taaagttctg ctatgtggcg | 360 |
| cggtattatc ccgtattgac gccgggcaag agcaactcgg tcgccgcata cactattctc | 420 |

```
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgctttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt cattttaat ttaaaggat ctaggtgaag atccttttg     1080 ataatctcat gaccaaaatc ccttaacgtg agttttcgtt ccactgagcg tcagaccccg   1140
tagaaaagat caaaggatct tcttgagatc ctttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg gaagtaaggt ggtacgatcg   2340
tgccttatta ggaaggcaac agacgggtct gacatggatt ggacgaacca ctgaattgcc   2400
gcattgcaga gatattgtat ttaagtgcct agctcgatac aataaacggg tctctctggt   2460
tagaccagat ctgagcctgg gagctctctg gctaactagg gaacccactg cttaagcctc   2520
aataaagctt gccttgagtg cttcaagtag tgtgtgcccg tctgttgtgt gactctggta   2580
actagagatc cctcagaccc ttttagtcag tgtggaaaat ctctagcagt ggcgcccgaa   2640
cagggacctg aaagcgaaag ggaaaccaga gctctctcga cgcaggactc ggcttgctga   2700
agcgcgcacg gcaagaggcg aggggcggcg actggtgagt acgccaaaaa ttttgactag   2760
```

```
cggaggctag aaggagagag atgggtgcga gagcgtcagt attaagcggg ggagaattag    2820
atcgcgatgg gaaaaaattc ggttaaggcc aggggggaaag aaaaaatata aattaaaaca    2880
tatagtatgg gcaagcaggg agctagaacg attcgcagtt aatcctggcc tgttagaaac    2940
atcagaaggc tgtagacaaa tactgggaca gctacaacca tcccttcaga caggatcaga    3000
agaacttaga tcattatata atacagtagc aaccctctat tgtgtgcatc aaaggataga    3060
gataaaagac accaaggaag ctttagacaa gatagaggaa gagcaaaaca aaagtaagac    3120
caccgcacag caagcggccg ctgatcttca gacctggagg aggagatatg agggacaatt    3180
ggagaagtga attatataaa tataaagtag taaaaattga accattagga gtagcaccca    3240
ccaaggcaaa gagaagagtg gtgcagagag aaaaaagagc agtgggaata ggagctttgt    3300
tccttgggtt cttgggagca gcaggaagca ctatgggcgc agcctcaatg acgctgacgg    3360
tacaggccag acaattattg tctggtatag tgcagcagca gaacaatttg ctgagggcta    3420
ttgaggcgca acagcatctg ttgcaactca cagtctgggg catcaagcag ctccaggcaa    3480
gaatcctggc tgtggaaaga tacctaaagg atcaacagct cctggggatt tggggttgct    3540
ctggaaaact catttgcacc actgctgtgc cttggaatgc tagttggagt aataaatctc    3600
tggaacagat tggaatcaca cgacctggat ggagtgggac agagaaatta acaattacac    3660
aagcttaata cactccttaa ttgaagaatc gcaaaaccag caagaaaaga atgaacaaga    3720
attattggaa ttagataaat gggcaagttt gtggaattgg tttaacataa caaattggct    3780
gtggtatata aaattattca taatgatagt aggaggcttg gtaggtttaa gaatagtttt    3840
tgctgtactt tctatagtga atagagttag gcagggatat tcaccattat cgtttcagac    3900
ccacctccca accccgaggg gacccgacag gcccgaagga atagaagaag aaggtggaga    3960
gagagacaga gacagatcca ttcgattagt gaacggatct cgacggttaa cttttaaaag    4020 aaaaggggggg attgggggggt acagtgcagg ggaaagaata gtagacataa tagcaacaga    4080
catacaaact aaagaattac aaaaacaaat tacaaaaatt caaaattta tcgataagct    4140 tgggagttcc gcgttacata acttacggta aatggcccgc ctggctgacc gcccaacgac    4200
ccccgcccat tgacgtcaat aatgacgtat gttcccatag taacgccaat agggactttc    4260
cattgacgtc aatgggtgga gtatttacgg taaactgccc acttggcagt acatcaagtg    4320
tatcatatgc caagtacgcc ccctattgac gtcaatgacg gtaaatggcc cgcctggcat    4380
tatgcccagt acatgacctt atgggacttt cctacttggc agtacatcta cgtattagtc    4440
atcgctatta ccatggtgat gcggttttgg cagtacatca atgggcgtgg atagcggttt    4500
gactcacggg gatttccaag tctccacccc attgacgtca atgggagttt gttttggcac    4560
caaaatcaac gggactttcc aaaatgtcgt aacaactccg ccccattgac gcaaatgggc    4620
ggtaggcgtg tacggtggga ggtctatata agcagagctc gtttagtgaa ccgtcagatc    4680
gcctggagac gccatccacg ctgttttgac ctccatagaa gacaccgact ctagtccagt    4740
gtggtggaat tctgcagata tcaacaagtt tgtacaaaaa agcaggcttt aaaggaacca    4800
attcagtcga ctggatccgg taccgaattc gcggccgcac tctcttccgc atcgctgtct    4860
gcgagggcca gctgttgggc tcgcggttga ggacaaactc ttcgcggtct ttccagtact    4920
cttggatcgg aaacccgtcg gcctccgaac aggtactccg ccgccgaggg acctgagcga    4980
gtccgcatcg accggatcgg aaaacctctc gagaaaggcg tctaaccagt cacagtcgca    5040
atgggctcca gtgagcagga actgaaagcc attgtcaaag atcttggttg tgggccatat    5100
tttttgggca cctatgacaa gcgctttcca ggctttgttt ctccacacaa gctcgcctgc    5160
```

-continued

```
gccatagtca atacggccgg tcgcgagact gggggcgtac actggatggc ctttgcctgg    5220
aacccgcact caaaaacatg ctacctcttt gagccctttg gcttttctga ccagcgactc    5280
aagcaggttt accagtttga gtacgagtca ctcctgcgcc gtagcgccat tgcttcttcc    5340
cccgaccgct gtataacgct ggaaaagtcc acccaaagcg tacaggggcc caactcggcc    5400
gcctgtggac tattctgctg catgtttctc cacgcctttg ccaactggcc ccaaactccc    5460
atggatcaca accccaccat gaaccttatt accggggtac ccaactccat gctcaacagt    5520
ccccaggtac agcccaccct gcgtcgcaac caggaacagc tctacagctt cctggagcgc    5580
cactcgccct acttccgcag ccacagtgcg cagattagga gcgccacttc tttttgtcac    5640
ttgaaaaaca tgtaatctag acccagcttt cttgtacaaa gtggttgata tccagcacag    5700
tggcggccgc tcgacaatca acctctggat tacaaaattt gtgaaagatt gactggtatt    5760
cttaactatg ttgctccttt tacgctatgt ggatacgctg ctttaatgcc tttgtatcat    5820
gctattgctt cccgtatggc tttcattttc tcctccttgt ataaatcctg gttgctgtct    5880
ctttatgagg agttgtggcc cgttgtcagg caacgtggcg tggtgtgcac tgtgtttgct    5940
gacgcaaccc ccactggttg gggcattgcc accacctgtc agctcctttc cgggactttc    6000
gctttccccc tccctattgc cacggcggaa ctcatcgccg cctgccttgc ccgctgctgg    6060
acagggctcg gctgttggg cactgacaat tccgtggtgt tgtcggggaa gctgacgtcc    6120
tttccatggc tgctcgcctg tgttgccacc tggattctgc gcgggacgtc cttctgctac    6180
gtcccttcgg ccctcaatcc agcggacctt ccttcccgcg gcctgctgcc ggctctgcgg    6240
cctcttccgc gtcttcgcct tcgccctcag acagtcgga tctcccttg gccgcctcc    6300
ccgcctggaa ttctgcagat atccggacta gtgatctctc gaggttaacg aattctaccg    6360
ggtaggggag gcgcttttcc caaggcagtc tggagcatgc gctttagcag ccccgctggg    6420
cacttggcgc tacacaagtg gcctctggcc tcgcacacat tccacatcca ccggtaggcg    6480
ccaaccggct ccgttctttg gtggccccctt cgcgccacct tctactcctc ccctagtcag    6540
gaagttcccc cccgcccgc agctcgcgtc gtgcaggacg tgacaaatgg aagtagcacg    6600
tctcactagt ctcgtgcaga tggacagcac cgctgagcaa tggaagcggg taggcctttg    6660
gggcagcggc caatagcagc tttgctcctt cgctttctgg gctcagaggc tgggaagggg    6720
tgggtccggg ggcgggctca ggggcgggct caggggcggg gcgggcgccc gaaggtcctc    6780
cggaggcccg gcattctgca cgcttcaaaa gcgcacgtct gccgcgctgt tctcctcttc    6840
ctcatctccg ggccttttcga cctgcatccc gccaccatga aaaagcctga actcaccgcg    6900
acgtctgtcg agaagtttct gatcgaaaag ttcgacagcg tctccgacct gatgcagctc    6960
tcggagggcg aagaatctcg tgctttcagc ttcgatgtag gagggcgtgg atatgtcctg    7020
cgggtaaata gctgcgccga tggtttctac aaagatcgtt atgtttatcg gcactttgca    7080
tcggccgcgc tcccgattcc ggaagtgctt gacattgggg aattcagcga gagcctgacc    7140
tattgcatct cccgccgtgc acagggtgtc acgttgcaag acctgcctga aaccgaactg    7200
cccgctgttc tgcagccggt cgcggaggcc atggatgcga tcgctgcggc cgatcttagc    7260
cagacgagcg ggttcggccc attcggaccg caaggaatcg gtcaatacac tacatggcgt    7320
gatttcatat gcgcgattgc tgatccccat gtgtatcact ggcaaactgt gatggacgac    7380
accgtcagtg cgtccgtcgc gcaggctctc gatgagctga tgctttgggc cgaggactgc    7440
cccgaagtcc ggcacctcgt gcacgcggat ttcggctcca acaatgtcct gacggacaat    7500
```

| | | | | | |
|---|---|---|---|---|---|
| ggccgcataa | cagcggtcat | tgactggagc | gaggcgatgt | tcggggattc | ccaatacgag | 7560 |
| gtcgccaaca | tcttcttctg | gaggccgtgg | ttggcttgta | tggagcagca | gacgcgctac | 7620 |
| ttcgagcgga | ggcatccgga | gcttgcagga | tcgccgcggc | tccggggcgt | atatgctccg | 7680 |
| cattggtctt | gaccaactct | atcagagctt | ggttgacggc | aatttcgatg | atgcagcttg | 7740 |
| ggcgcagggt | cgatgcgacg | caatcgtccg | atccggagcc | gggactgtcg | ggcgtacaca | 7800 |
| aatcgcccgc | agaagcgcgg | ccgtctggac | cgatggctgt | gtagaagtac | tcgccgatag | 7860 |
| tggaaaccga | cgccccagca | ctcgtccgag | ggcaaaggaa | tagagtagat | gccgaccgaa | 7920 |
| caagagctga | tttcgagaac | gcctcagcca | gcaactcgcg | cgagcctagc | aaggcaaatg | 7980 |
| cgagagaacg | gccttacgct | tggtggcaca | gttctcgtcc | acagttcgct | aagctcgctc | 8040 |
| ggctgggtcg | cgggagggcc | ggtcgcagtg | attcaggccc | ttctggattg | tgttggtccc | 8100 |
| cagggcacga | ttgtcatgcc | cacgcactcg | ggtgatctga | ctgatcccgc | agattggaga | 8160 |
| tcgccgcccg | tgcctgccga | ttgggtgcag | atccgtcgag | ggcccggtac | ctttaagacc | 8220 |
| aatgacttac | aaggcagctg | tagatcttag | ccacttttta | aaagaaaagg | ggggactgga | 8280 |
| agggctagct | cactcccaac | gaagacaaga | tctgcttttt | gcttgtactg | ggtctctctg | 8340 |
| gttagaccag | atctgagcct | gggagctctc | tggctgccta | gggaacccac | tgcttaagcc | 8400 |
| tcaataaagc | ttgccttgag | tgcttcaagt | agtgtgtgcc | cgtctgttgt | gtgactctgg | 8460 |
| taactagaga | tccctcagac | ccttttagtc | agtgtggaaa | atctctagca | gtagtagttc | 8520 |
| atgtcatctt | attattcagt | atttataact | tgcaaagaaa | tgaatatcag | agagtgagag | 8580 |
| gaacttgttt | attgcagctt | ataatggtta | caaataaagc | aatagcatca | caaatttcac | 8640 |
| aaataaagca | tttttttcac | tgcattctag | ttgtggtttg | tccaaactca | tcaatgtatc | 8700 |
| ttatcatgtc | tggctctagc | tatcccgccc | ctaactccgc | ccagttccgc | ccattctccg | 8760 |
| ccccatggct | gactaatttt | ttttatttat | gcagaggccg | aggccgcctc | ggcctctgag | 8820 |
| ctattccaga | agtagtgagg | aggcttttt | ggaggcctag | gcttttgcgt | cgagacgtac | 8880 |
| ccaattcgcc | ctatagtgag | tcgtattacg | cgcgctcact | ggccgtcgtt | ttacaacgtc | 8940 |
| gtgactggga | aaaccctggc | gttacccaac | ttaatcgcct | tgcagcacat | ccccctttcg | 9000 |
| ccagctggcg | taatagcgaa | gaggcccgca | ccgatcgccc | ttcccaacag | ttgcgcagcc | 9060 |
| tgaatggcga | atggcgcgac | gcgccctgta | gcggcgcatt | aagcgcggcg | ggtgtggtgg | 9120 |
| ttacgcgcag | cgtgaccgct | acacttgcca | gcgccctagc | gcccgctcct | ttcgctttct | 9180 |
| tcccttcctt | tctcgccacg | ttcgccggct | ttccccgtca | agctctaaat | cgggggctcc | 9240 |
| ctttagggtt | ccgatttagt | gctttacggc | acctcgaccc | caaaaaactt | gattagggtg | 9300 |
| atggttcacg | tagtgggcca | tcgccctgat | agacggtttt | tcgccctttg | acgttggagt | 9360 |
| ccacgttctt | taatagtgga | ctcttgttcc | aaactggaac | aacactcaac | cctatctcgg | 9420 |
| tctattcttt | tgatttataa | gggattttgc | cgatttcggc | ctattggtta | aaaaatgagc | 9480 |
| tgatttaaca | aaaatttaac | gcgaatttta | acaaaatatt | aacgtttaca | atttcc | 9536 |

<210> SEQ ID NO 34
<211> LENGTH: 8717
<212> TYPE: DNA
<213> ORGANISM: Artificial Sequence
<220> FEATURE:
<223> OTHER INFORMATION: Construct

<400> SEQUENCE: 34

| | | | | | |
|---|---|---|---|---|---|
| tggaagggct | aattcactcc | caaagaagac | aagatatcct | tgatctgtgg | atctaccaca | 60 |

```
cacaaggcta cttccctgat tagcagaact acacaccagg gccagggatc agatatccac    120
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag gactttccg     360 ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600 agacccttt  agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga gggcggcga  ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca ggggggaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttgctgt    1860 actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga actacaaaaa caaattacaa aaattcaaaa ttttcgggtt tattacaggg   2160
acagcagaga tccagtttat cgatgaggcc ctttcgtctt cactcgagtt tactccctat   2220
cagtgataga gaacgtatga agagtttact ccctatcagt gatagagaac gtatgcagac   2280
tttactccct atcagtgata gagaacgtat aaggagttta ctccctatca gtgatagaga   2340
acgtatgacc agtttactcc ctatcagtga tagagaacgt atctacagtt tactccctat   2400
```

```
cagtgataga gaacgtatat ccagtttact ccctatcagt gatagagaac gtatgtcgag    2460
gtaggcgtgt acggtgggcg cctataaaag cagagctcgt ttagtgaacc gtcagatcgc    2520
ctggagcaat tccacaacac ttttgtctta tacttggatc cgcactctct tccgcatcgc    2580
tgtctgcgag ggccagctgt tgggctcgcg gttgaggaca aactcttcgc ggtcttccca    2640
gtactcttgg atcggaaacc cgtcggcctc cgaacaggta ctccgccgcc gagggacctg    2700
agcgagtccg catcgaccgg atcggaaaac ctctcgagaa aggcgtctaa ccagtcacag    2760
tcgcaatggg ctccagtgag caggaactga aagccattgt caaagatctt ggttgtgggc    2820
catattttt gggcacctat gacaagcgct ttccaggctt tgtttctcca cacaagctcg    2880
cctgcgccat agtcaatacg gccggtcgcg agactggggg cgtacactgg atggcctttg    2940
cctggaaccc gcactcaaaa acatgctacc tctttgagcc ctttggcttt tctgaccagc    3000
gactcaagca ggtttaccag tttgagtacg agtcactcct gcgccgtagc gccattgctt    3060
cttcccccga ccgctgtata acgctggaaa agtccaccca aagcgtacag ggcccaact    3120
cggccgcctg tggactattc tgctgcatgt ttctccacgc ctttgccaac tggccccaaa    3180
ctcccatgga tcacaacccc accatgaacc ttattaccgg ggtacccaac tccatgctca    3240
acagtcccca ggtacagccc accctgcgtc gcaaccagga acagctctac agcttcctgg    3300
agcgccactc gccctacttc cgcagccaca gtgcgcagat taggagcgcc acttcttttt    3360
gtcacttgaa aaacatgtaa gcgccggctc tagatcgcga acgcgtgaat tctaccgggt    3420
aggggaggcg cttttcccaa ggcagtctgg agcatgcgct ttagcagccc cgctgggcac    3480
ttggcgctac acaagtggcc tctggcctcg cacacattcc acatccaccg gtaggcgcca    3540
accggctccg ttctttggtg gccccttcgc gccaccttct actcctcccc tagtcaggaa    3600
gttccccccc gccccgcagc tcgcgtcgtg caggacgtga caaatggaag tagcacgtct    3660
cactagtctc gtgcagatgg acagcaccgc tgagcaatgg aagcgggtag gcctttgggg    3720
cagcggccaa tagcagcttt gctccttcgc tttctgggct cagaggctgg aaggggtgg    3780
gtccgggggc gggctcaggg gcgggctcag gggcggggcg ggcgcccgaa ggtcctccgg    3840
aggcccggca ttctgcacgc ttcaaaagcg cacgtctgcc gcgctgttct cctcttcctc    3900
atctccgggc cttttcgacct gcagcccaag cttaccatga ccgagtacaa gcccacggtg    3960
cgcctcgcca cccgcgacga cgtccccagg gccgtacgca ccctcgccgc gcgttcgcc    4020
gactacccg ccacgcgcca caccgtcgat ccggaccgcc acatcgagcg ggtcaccgag    4080
ctgcaagaac tcttcctcac gcgcgtcggg ctcgacatcg gcaaggtgtg ggtcgcggac    4140
gacggcgccg cggtggcggt ctggaccacg ccggagagcg tcgaagcggg ggcggtgttc    4200
gccgagatcg gcccgcgcat ggccgagttg agcggttccc ggctggccgc gcagcaacag    4260
atggaaggcc tcctggcgcc gcaccggccc aaggagcccg cgtggttcct ggccaccgtc    4320
ggcgtctcgc ccgaccacca gggcaagggt ctgggcagcg ccgtcgtgct ccccggagtg    4380
gaggcggcca gcgcgccgg ggtgcccgcc ttcctggaga cctccgcgcc ccgcaacctc    4440
cccttctacg agcggctcgg cttcaccgtc accgccgacg tcgaggtgcc cgaaggaccg    4500
cgcacctggt gcatgacccg caagcccggt gcctgacggg gcgcgtctgg aacaatcaac    4560
ctctggatta caaaatttgt gaaagattga ctggtattct taactatgtt gctccttta    4620
cgctatgtgg atacgctgct ttaatgcctt tgtatcatgc tattgcttcc cgtatggctt    4680
tcattttctc ctccttgtat aaatcctggt tgctgtctct ttatgaggag ttgtggcccg    4740
ttgtcaggca acgtggcgtg gtgtgcactg tgtttgctga cgcaacccc actggttggg    4800
```

```
gcattgccac cacctgtcag ctcctttccg ggactttcgc tttcccctc cctattgcca    4860
cggcggaact catcgccgcc tgccttgccc gctgctggac aggggctcgg ctgttgggca    4920
ctgacaattc cgtggtgttg tcggggaagc tgacgtcctt tccatggctg ctcgcctgtg    4980
ttgccacctg gattctgcgc gggacgtcct tctgctacgt cccttcggcc ctcaatccag    5040
cggaccttcc ttcccgcggc ctgctgccgg ctctgcggcc tcttccgcgt cttcgccttc    5100
gccctcagac gagtcggatc tccctttggg ccgcctcccc gcctggaatt aattctgcag    5160
tcgagaccta gaaaacatg gagcaatcac aagtagcaat acagcagcta ccaatgctga    5220
ttgtgcctgg ctagaagcac aagaggagga ggaggtgggt ttttccagtc cacctcagg     5280
taccttaag accaatgact tacaaggcag ctgtagatct tagccactt ttaaaagaaa      5340
agagggact ggaagggcta attcactccc aacgaagaca agatatcctt gatctgtgga     5400
tctaccacac acaaggctac ttccctgatt agcagaacta cacaccaggg ccagggtca    5460
gatatccact gacctttgga tggtgctaca agctagtacc agttgagcca gataaggtag    5520
aagaggccaa taaggagag aacaccagct tgttacaccc tgtgagcctg catgggatgg     5580
atgacccgga gagaagtg ttagagtgga ggtttgacag ccgcctagca tttcatcacg      5640
tggcccgaga gctgcatccg gagtacttca agaactgctg atatcgagct tgctacaagg    5700
gactttccgc tggggacttt ccagggaggc gtggcctggg cgggactggg gagtggcgag    5760
ccctcagatc ctgcatataa gcagctgctt tttgcctgta ctgggtctct ctggttagac    5820
cagatctgag cctgggagct ctctggctaa ctagggaacc cactgcttaa gcctcaataa    5880
agcttgcctt gagtgcttca agtagtgtgt gcccgtctgt tgtgtgactc tggtaactag    5940
agatccctca gacccttta gtcagtgtgg aaaatctcta gcagtagtag ttcatgtcat    6000
cttattattc agtattata acttgcaaag aaatgaatat cagagagtga gaggccttga     6060
cattgctagc gttttaccgt cgacctctag ctagagcttg gcgtaatcat ggtcatagct    6120
gtttcctgtg tgaaattgtt atccgctcac aattccacac aacatacgag ccggaagcat    6180
aaagtgtaaa gcctggggtg cctaatgagt gagctaactc acattaattg cgttgcgctc    6240
actgcccgct ttccagtcgg gaaacctgtc gtgccagctg cattaatgaa tcggccaacg    6300
cgcggggaga ggcggtttgc gtattgggcg ctcttccgct tcctcgctca ctgactcgct    6360
gcgctcggtc gttcggctgc ggcgagcggt atcagctcac tcaaaggcgg taatacggtt    6420
atccacagaa tcaggggata acgcaggaaa gaacatgtga gcaaaaggcc agcaaaaggc    6480
caggaaccgt aaaaaggccg cgttgctggc gtttttccat aggctccgcc ccctgacga    6540
gcatcacaaa aatcgacgct caagtcagag gtggcgaaac ccgacaggac tataaagata    6600
ccaggcgttt ccccctggaa gctccctcgt gcgctctcct gttccgaccc tgccgcttac    6660
cggatacctg tccgcctttc tcccttcggg aagcgtggcg ctttctcata gctcacgctg    6720
taggtatctc agttcggtgt aggtcgttcg ctccaagctg ggctgtgtgc acgaaccccc    6780
cgttcagccc gaccgctgcg ccttatccgg taactatcgt cttgagtcca acccggtaag    6840
acacgactta tcgccactgg cagcagccac tggtaacagg attagcagag cgaggtatgt    6900
aggcggtgct acagagttct tgaagtggtg gcctaactac ggctacacta agaacagt     6960
atttggtatc tgcgctctgc tgaagccagt taccttcgga aaagagttg gtagctcttg     7020
atccggcaaa caaccaccg ctggtagcgg ttttttgtt tgcaagcagc agattacgcg      7080
cagaaaaaa ggatctcaag aagatccttt gatctttct acggggtctg acgctcagtg     7140
```

| | |
|---|---|
| gaacgaaaac tcacgttaag ggattttggt catgagatta tcaaaaagga tcttcaccta | 7200 |
| gatcctttta aattaaaaat gaagttttaa atcaatctaa agtatatatg agtaaacttg | 7260 |
| gtctgacagt taccaatgct taatcagtga ggcacctatc tcagcgatct gtctatttcg | 7320 |
| ttcatccata gttgcctgac tccccgtcgt gtagataact acgatacggg agggcttacc | 7380 |
| atctggcccc agtgctgcaa tgataccgcg agacccacgc tcaccggctc cagatttatc | 7440 |
| agcaataaac cagccagccg gaagggccga gcgcagaagt ggtcctgcaa ctttatccgc | 7500 |
| ctccatccag tctattaatt gttgccggga agctagagta agtagttcgc cagttaatag | 7560 |
| tttgcgcaac gttgttgcca ttgctacagg catcgtggtg tcacgctcgt cgtttggtat | 7620 |
| ggcttcattc agctccggtt cccaacgatc aaggcgagtt acatgatccc ccatgttgtg | 7680 |
| caaaaaagcg gttagctcct tcggtcctcc gatcgttgtc agaagtaagt tggccgcagt | 7740 |
| gttatcactc atggttatgg cagcactgca taattctctt actgtcatgc catccgtaag | 7800 |
| atgcttttcg taagttggcc gcagtgttat cactcatggt tatggcagca ctgcataatt | 7860 |
| ctcttactgt catgccatcc gtaagatgct tttctgtgac tggtgagtac tcaaccaagt | 7920 |
| cattctgaga atagtgtatg cggcgaccga gttgctcttg cccggcgtca atacgggata | 7980 |
| ataccgcgcc acatagcaga actttaaaag tgctcatcat tggaaaacgt tcttcggggc | 8040 |
| gaaaactctc aaggatctta ccgctgttga gatccagttc gatgtaaccc actcgtgcac | 8100 |
| ccaactgatc ttcagcatct tttactttca ccagcgtttc tgggtgagca aaaacaggaa | 8160 |
| ggcaaaatgc cgcaaaaaag ggaataaggg cgacacggaa atgttgaata ctcatactct | 8220 |
| tcctttttca atattattga agcatttatc agggttattg tctcatgagc ggatacatat | 8280 |
| ttgaatgtat ttagaaaaat aaacaaatag gggttccgcg cacatttccc cgaaaagtgc | 8340 |
| cacctgacgt cgacggatcg ggagatcaac ttgtttattg cagcttataa tggttacaaa | 8400 |
| taaagcaata gcatcacaaa tttcacaaat aaagcatttt tttcactgca ttctagttgt | 8460 |
| ggtttgtcca aactcatcaa tgtatcttat catgtctgga tcaactggat aactcaagct | 8520 |
| aaccaaaatc atcccaaact tcccacccca taccctatta ccactgccaa ttacctagtg | 8580 |
| gtttcattta ctctaaacct gtgattcctc tgaattattt tcattttaaa gaaattgtat | 8640 |
| ttgttaaata tgtactacaa acttagtagt ttttaaagaa attgtatttg ttaaatatgt | 8700 |
| actacaaact tagtagt | 8717 |

<210> SEQ ID NO 35
<211> LENGTH: 38585
<212> TYPE: DNA
<213> ORGANISM: Artificial Sequence
<220> FEATURE:
<223> OTHER INFORMATION: Construct

<400> SEQUENCE: 35

| | |
|---|---|
| catcatcaat aatataccct attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt tccgcgttc | 420 |
| cgggtcaaag ttggcgtttt attattatag tcagtcgaag cttggatccg gtacctctag | 480 |

```
aattctcgag cggccgctag cgacatcgga tctcccgatc ccctatggtg cactctcagt    540
acaatctgct ctgatgccgc atagttaagc cagtatctgc tccctgcttg tgtgttggag    600
gtcgctgagt agtgcgcgag caaaatttaa gctacaacaa ggcaaggctt gaccgacaat    660
tgcatgaaga atctgcttag ggttaggcgt tttgcgctgc ttcgcgatgt acgggccaga    720
tatacgcgtt gacattgatt attgactagt tattaatagt aatcaattac ggggtcatta    780
gttcatagcc catatatgga gttccgcgtt acataactta cggtaaatgg cccgcctggc    840
tgaccgccca acgaccccg cccattgacg tcaataatga cgtatgttcc catagtaacg    900
ccaataggga ctttccattg acgtcaatgg gtggactatt tacggtaaac tgcccacttg    960
gcagtacatc aagtgtatca tatgccaagt acgccccta ttgacgtcaa tgacggtaaa    1020
tggcccgcct ggcattatgc ccagtacatg accttatggg actttcctac ttggcagtac    1080
atctacgtat tagtcatcgc tattaccatg gtgatgcggt tttggcagta catcaatggg    1140
cgtggatagc ggtttgactc acggggattt ccaagtctcc accccattga cgtcaatggg    1200
agtttgtttt ggcaccaaaa tcaacgggac tttccaaaat gtcgtaacaa ctccgcccca    1260
ttgacgcaaa tgggcggtag gcgtgtacgg tgggaggtct atataagcag agctctctgg    1320
ctaactagag aacccactgc ttactggctt atcgaaatta atacgactca ctatagggag    1380
acccaagctg gctagttaag ctatcaacaa gtttgtacaa aaaagcaggc tttaaggaa    1440 ccaattcagt cgactggatc cggtaccacc atgttcctga actgctgccc aggttgctgt    1500
atggagcctg aattcaccat ggtgagcaag ggcgaggagc tgttcaccgg ggtggtgccc    1560
atcctggtcg agctggacgg cgacgtaaac ggccacaagt tcagcgtgtc cggcgagggc    1620
gagggcgatg ccacctacgg caagctgacc ctgaagttca tctgcaccac cggcaagctg    1680
cccgtgccct ggcccaccct cgtgaccacc ctgacctggg gcgtgcagtg cttcgcccgc    1740
taccccgacc acatgaagca gcacgacttc ttcaagtccg ccatgcccga aggctacgtc    1800
caggagcgca ccatcttctt caaggacgac ggcaactaca agacccgcgc cgaggtgaag    1860
ttcgagggcg acaccctggt gaaccgcatc gagctgaagg gcatcgactt caaggaggac    1920
ggcaacatcc tggggcacaa gctggagtac aacgccatca gcgacaacgt ctatatcacc    1980
gccgacaagc agaagaacgg catcaaggcc aacttcaaga tccgccacaa catcgaggac    2040
ggcagcgtgc agctcgccga ccactaccag cagaacaccc ccatcggcga cggccccgtg    2100
ctgctgcccg acaaccacta cctgagcacc cagtccaagc tgagcaaaga ccccaacgag    2160
aagcgcgatc acatggtcct gctggagttc gtgaccgccg ccgggatcac tctcggcatg    2220
gacgagctgt acaaggtcga ctatccgtac gacgtaccag actacgcata accgcggccg    2280
cactcgagat atctagaccc agctttcttg tacaaagtgg ttgatctaga gggccgcgg    2340 ttcgaaggta agcctatccc taaccctctc ctcggtctcg attctacgcg taccggttag    2400
taatgagttt aaacggggga ggctaactga aacacggaag gagacaatac cggaaggaac    2460
ccgcgctatg acggcaataa aaagacagaa taaaacgcac gggtgttggg tcgtttgttc    2520
ataaacgcgg ggttcggtcc cagggctggc actctgtcga taccccaccg agaccccatt    2580
ggggccaata cgcccgcgtt tcttcctttt ccccacccca cccccaagt tcgggtgaag    2640 gcccagggct cgcagccaac gtcggggcgg caggccctgc catagcagat ccgattcgac    2700
agatcactga aatgtgtggg cgtggcttaa gggtgggaaa gaatatataa ggtgggggtc    2760
ttatgtagtt ttgtatctgt tttgcagcag ccgccgccgc catgagcacc aactcgtttg    2820
```

| | |
|---|---|
| atggaagcat tgtgagctca tatttgacaa cgcgcatgcc cccatgggcc ggggtgcgtc | 2880 |
| agaatgtgat gggctccagc attgatggtc gccccgtcct gcccgcaaac tctactacct | 2940 |
| tgacctacga gaccgtgtct ggaacgccgt tggagactgc agcctccgcc gccgcttcag | 3000 |
| ccgctgcagc caccgcccgc gggattgtga ctgactttgc tttcctgagc ccgcttgcaa | 3060 |
| gcagtgcagc ttcccgttca tccgcccgcg atgacaagtt gacggctctt ttggcacaat | 3120 |
| tggattcttt gacccgggaa cttaatgtcg tttctcagca gctgttggat ctgcgccagc | 3180 |
| aggtttctgc cctgaaggct tcctcccctc ccaatgcggt ttaaaacata aataaaaaac | 3240 |
| cagactctgt ttggatttgg atcaagcaag tgtcttgctg tctttattta ggggttttgc | 3300 |
| gcgcgcggta ggcccgggac cagcggtctc ggtcgttgag ggtcctgtgt attttttcca | 3360 |
| ggacgtggta aaggtgactc tggatgttca gatacatggg cataagcccg tctctgggt | 3420 |
| ggaggtagca ccactgcaga gcttcatgct gcggggtggt gttgtagatg atccagtcgt | 3480 |
| agcaggagcg ctgggcgtgg tgcctaaaaa tgtctttcag tagcaagctg attgccaggg | 3540 |
| gcaggccctt ggtgtaagtg tttacaaagc ggttaagctg ggatgggtgc atacgtgggg | 3600 |
| atatgagatg catcttggac tgtattttta ggttggctat gttccagcc atatccctcc | 3660 |
| ggggattcat gttgtgcaga accaccagca cagtgtatcc ggtgcacttg ggaaatttgt | 3720 |
| catgtagctt agaaggaaat gcgtggaaga acttggagac gcccttgtga cctccaagat | 3780 |
| tttccatgca ttcgtccata atgatggcaa tgggcccacg ggcggcggcc tgggcgaaga | 3840 |
| tatttctggg atcactaacg tcatagttgt gttccaggat gagatcgtca taggccattt | 3900 |
| ttacaaagcg cgggcggagg gtgccagact gcggtataat ggttccatcc ggcccagggg | 3960 |
| cgtagttacc ctcacagatt tgcatttccc acgctttgag ttcagatggg gggatcatgt | 4020 |
| ctacctgcgg ggcgatgaag aaaacggttt ccggggtagg ggagatcagc tgggaagaaa | 4080 |
| gcaggttcct gagcagctgc gacttaccgc agccggtggg cccgtaaatc acacctatta | 4140 |
| ccggctgcaa ctggtagtta agagagctgc agctgccgtc atccctgagc agggggggcca | 4200 |
| cttcgttaag catgtccctg actcgcatgt tttccctgac caaatccgcc agaaggcgct | 4260 |
| cgccgcccag cgatagcagt tcttgcaagg aagcaaagtt tttcaacggt ttgagaccgt | 4320 |
| ccgccgtagg catgcttttg agcgtttgac caagcagttc caggcggtcc cacagctcgg | 4380 |
| tcacctgctc tacggcatct cgatccagca tatctcctcg tttcgcgggt tggggcggct | 4440 |
| ttcgctgtac ggcagtagtc ggtgctcgtc cagacgggcc agggtcatgt ctttccacgg | 4500 |
| gcgcagggtc ctcgtcagcg tagtctgggt cacggtgaag gggtgcgctc cgggctgcgc | 4560 |
| gctggccagg gtgcgcttga ggctggtcct gctggtgctg aagcgctgcc ggtcttcgcc | 4620 |
| ctgcgcgtcg gccaggtagc atttgaccat ggtgtcatag tccagcccct ccgcggcgtg | 4680 |
| gcccttggcg cgcagcttgc ccttggagga ggcgccgcac gagggcagt gcagactttt | 4740 |
| gagggcgtag agcttgggcg cgagaaatac cgattccggg gagtaggcat ccgcgccgca | 4800 |
| ggccccgcag acggtctcgc attccacgag ccaggtgagc tctggccgtt cggggtcaaa | 4860 |
| aaccaggttt cccccatgct ttttgatgcg tttcttacct ctggtttcca tgagccggtg | 4920 |
| tccacgctcg gtgacgaaaa ggctgtccgt gtccccgtat acagacttga gaggcctgtc | 4980 |
| ctcgagcggt gttccgcggt cctcctcgta tagaaactcg gaccactctg agacaaaggc | 5040 |
| tcgcgtccag gccagcacga aggaggctaa gtgggagggg tagcggtcgt tgtccactag | 5100 |
| ggggtccact cgctccaggg tgtgaagaca catgtcgccc tcttcggcat caaggaaggt | 5160 |
| gattggtttg taggtgtagg ccacgtgacc gggtgttcct gaagggggc tataaaaggg | 5220 |

```
ggtgggggcg cgttcgtcct cactctcttc cgcatcgctg tctgcgaggg ccagctgttg    5280
gggtgagtac tccctctgaa aagcgggcat gacttctgcg ctaagattgt cagttttcaa    5340
aaacgaggag gatttgatat tcacctggcc cgcggtgatg cctttgaggg tggccgcatc    5400
catctggtca gaaaagacaa tcttttttgtt gtcaagcttg gtggcaaacg acccgtagag    5460
ggcgttggac agcaacttgg cgatggagcg cagggtttgg tttttgtcgc gatcggcgcg    5520
ctccttggcc gcgatgttta gctgcacgta ttcgcgcgca acgcaccgcc attcgggaaa    5580
gacggtggtg cgctcgtcgg gcaccaggtg cacgcgccaa ccgcggttgt gcagggtgac    5640
aaggtcaacg ctggtggcta cctctccgcg taggcgctcg ttggtccagc agaggcggcc    5700
gcccttgcgc gagcagaatg gcggtagggg gtctagctgc gtctcgtccg ggggtctgc    5760
gtccacggta aagaccccgg gcagcaggcg cgcgtcgaag tagtctatct tgcatccttg    5820
caagtctagc gcctgctgcc atgcgcgggc ggcaagcgcg cgctcgtatg ggttgagtgg    5880
gggaccccat ggcatggggt gggtgagcgc ggaggcgtac atgccgcaaa tgtcgtaaac    5940
gtagaggggc tctctgagta ttccaagata tgtagggtag catcttccac cgcggatgct    6000
ggcgcgcacg taatcgtata gttcgtgcga gggagcgagg aggtcgggac cgaggttgct    6060
acgggcgggc tgctctgctc ggaagactat ctgcctgaag atggcatgtg agttggatga    6120
tatggttgga cgctggaaga cgttgaagct ggcgtctgtg agacctaccg cgtcacgcac    6180
gaaggaggcg taggagtcgc gcagcttgtt gaccagctcg gcggtgacct gcacgtctag    6240
ggcgcagtag tccagggttt ccttgatgat gtcatactta tcctgtccct ttttttttcca    6300
cagctcgcgg ttgaggacaa actcttcgcg gtctttccag tactcttgga tcggaaaccc    6360
gtcggcctcc gaacggtaag agcctagcat gtagaactgg ttgacggcct ggtaggcgca    6420
gcatcccttt tctacgggta gcgcgtatgc ctgcgcggcc ttccggagcg aggtgtgggt    6480
gagcgcaaag gtgtccctga ccatgaccag catgaagggc acgagctgct tcccaaaggc    6540
ccccatccaa gtataggtct ctacatcgta ggtgacaaag agacgctcgg tgcgaggatg    6600
cgagccgatc gggaagaact ggatctcccg ccaccaattg gaggagtggc tattgatgtg    6660
gtgaaagtag aagtccctgc gacgggccga acactcgtgc tggcttttgt aaaaacgtgc    6720
gcagtactgg cagcggtgca cgggctgtac atcctgcacg aggttgacct gacgaccgcg    6780
cacaaggaag cagagtggga atttgagccc ctcgcctggc gggtttggct ggtggtcttc    6840
tacttcggct gcttgtcctt gaccgtctgg ctgctcgagg ggagttacgg tggatcggac    6900
caccacgccg cgcgagccca aagtccagat gtccgcgcgc ggcggtcgga gcttgatgac    6960
aacatcgcgc agatgggagc tgtccatggt ctggagctcc gcggcgtca ggtcaggcgg    7020
gagctcctgc aggtttacct cgcatagacg ggtcagggcg cgggctagat ccaggtgata    7080
cctaatttcc aggggctggt tggtggcggc gtcgatggct tgcaagaggc cgcatccccg    7140
cggcgcgact acggtaccgc gcggcgggcg gtggccgcg ggggtgtcct tggatgatgc    7200
atctaaaagc ggtgacgcgg gcgagccccc ggaggtaggg ggggctccgg acccgccggg    7260
agaggggggca ggggcacgtc ggcgccgcgc gcgggcagga gctggtgctg cgcgcgtagg    7320
ttgctggcga acgcgacgac gcggcggttg atctcctgaa tctggcgcct ctgcgtgaag    7380
acgacgggcc cggtgagctt gaacctgaaa gagagttcga cagaatcaat ttcggtgtcg    7440
ttgacgcgg cctggcgcaa aatctcctgc acgtctcctg agttgtcttg ataggcgatc    7500
tcggccatga actgctcgat ctcttcctcc tggagatctc cgcgtccggc tcgctccacg    7560
```

```
gtggcggcga ggtcgttgga aatgcgggcc atgagctgcg agaaggcgtt gaggcctccc    7620
tcgttccaga cgcggctgta gaccacgccc ccttcggcat cgcgggcgcg catgaccacc    7680
tgcgcgagat tgagctccac gtgccgggcg aagacggcgt agtttcgcag gcgctgaaag    7740
aggtagttga gggtggtggc ggtgtgttct gccacgaaga agtacataac ccagcgtcgc    7800
aacgtggatt cgttgatatc ccccaaggcc tcaaggcgct ccatggcctc gtagaagtcc    7860
acggcgaagt tgaaaaactg ggagttgcgc gccgacacgg ttaactcctc ctccagaaga    7920
cggatgagct cggcgacagt gtcgcgcacc tcgcgctcaa aggctacagg ggcctcttct    7980
tcttcttcaa tctcctcttc cataaggggc tccccttctt cttcttctgg cggcggtggg    8040
ggagggggga cacggcggcg acgacggcgc accgggaggc ggtcgacaaa gcgctcgatc    8100
atctccccgc ggcgacggcg catggtctcg gtgacggcgc ggccgttctc gcggggggcgc    8160 agttggaaga cgccgcccgt catgtcccgg ttatgggttg gcgggggggct gccatgcggc    8220 agggatacgg cgctaacgat gcatctcaac aattgttgtg taggtactcc gccgccgagg    8280
gacctgagcg agtccgcatc gaccggatcg gaaaacctct cgagaaaggc gtctaaccag    8340
tcacagtcgc aaggtaggct gagcaccgtg gcgggcggca gcgggcggcg gtcggggttg    8400
tttctggcgg aggtgctgct gatgatgtaa ttaaagtagg cggtcttgag acggcggatg    8460
gtcgacagaa gcaccatgtc cttgggtccg gcctgctgaa tgcgcaggcg gtcggccatg    8520
ccccaggctt cgttttgaca tcggcgcagg tctttgtagt agtcttgcat gagcctttct    8580
accggcactt cttcttctcc ttcctcttgt cctgcatctc ttgcatctat cgctgcggcg    8640
gcggcggagt ttggccgtag gtggcgccct cttcctccca tgcgtgtgac cccgaagccc    8700
ctcatcggct gaagcagggc taggtcggcg acaacgcgct cggctaatat ggcctgctgc    8760
acctgcgtga gggtagactg gaagtcatcc atgtccacaa agcggtggta tgcgcccgtg    8820
ttgatggtgt aagtgcagtt ggccataacg gaccagttaa cggtctggtg acccggctgc    8880
gagagctcgg tgtacctgag acgcgagtaa gccctcgagt caaatacgta gtcgttgcaa    8940
gtccgcacca ggtactggta tcccaccaaa aagtgcggcg gcggctggcg gtagagggggc    9000 cagcgtaggg tggccggggc tccggggggcg agatcttcca acataaggcg atgatatccg    9060
tagatgtacc tggacatcca ggtgatgccg gcggcggtgg tggaggcgcg cggaaagtcg    9120
cggacgcggt tccagatgtt gcgcagcggc aaaaagtgct ccatggtcgg gacgctctgg    9180
ccggtcaggc gcgcgcaatc gttgacgctc tagaccgtgc aaaaggagag cctgtaagcg    9240
ggcactcttc cgtggtctgg tggataaatt cgcaagggta tcatggcgga cgaccggggt    9300
tcgagccccg tatccggccg tccgccgtga tccatgcggt taccgcccgc gtgtcgaacc    9360
caggtgtgcg acgtcagaca acggggggagt gctccttttg gcttccttcc aggcgcggcg    9420
gctgctgcgc tagcttttt ggccactggc cgcgcgcagc gtaagcggtt aggctggaaa    9480
gcgaaagcat taagtggctc gctccctgta gccgagggt tattttccaa gggttgagtc    9540
gcgggacccc cggttcgagt ctcggaccgg ccggactgcg cgaacgggg gtttgcctcc    9600 ccgtcatgca agacccgct tgcaaattcc tccggaaaca gggacgagcc cctttttttgc    9660 ttttcccaga tgcatccggt gctgcggcag atgcgccccc ctcctcagca gcggcaagag    9720
caagagcagc ggcagacatg cagggcaccc tcccctcctc ctaccgcgtc aggagggggcg    9780 acatccgcgg ttgacgcggc agcagatggt gattacgaac cccgcgcgcg ccgggcccgg    9840
cactacctgg acttggagga gggcgagggc ctggcgcggc taggagcgcc ctctcctgag    9900
cggcacccaa gggtgcagct gaagcgtgat acgcgtgagg cgtacgtgcc gcggcagaac    9960
```

```
ctgtttcgcg accgcgaggg agaggagccc gaggagatgc gggatcgaaa gttccacgca    10020
gggcgcgagc tgcggcatgg cctgaatcgc gagcggttgc tgcgcgagga ggactttgag    10080
cccgacgcgc gaaccgggat tagtcccgcg cgcgcacacg tggcggccgc cgacctggta    10140
accgcatacg agcagacggt gaaccaggag attaactttc aaaaaagctt taacaaccac    10200
gtgcgtacgc ttgtggcgcg cgaggaggtg gctataggac tgatgcatct gtgggacttt    10260
gtaagcgcgc tggagcaaaa cccaaatagc aagccgctca tggcgcagct gttccttata    10320
gtgcagcaca gcagggacaa cgaggcattc agggatgcgc tgctaaacat agtagagccc    10380
gagggccgct ggctgctcga tttgataaac atcctgcaga gcatagtggt gcaggagcgc    10440
agcttgagcc tggctgacaa ggtggccgcc atcaactatt ccatgcttag cctgggcaag    10500
ttttacgccc gcaagatata ccatacccct tacgttccca tagacaagga ggtaaagatc    10560
gaggggttct acatgcgcat ggcgctgaag gtgcttacct tgagcgacga cctgggcgtt    10620
tatcgcaacg agcgcatcca caaggccgtg agcgtgagcc ggcggcgcga gctcagcgac    10680
cgcgagctga tgcacagcct gcaaagggcc ctggctggca cgggcagcgg cgatagagag    10740
gccgagtcct actttgacgc gggcgctgac ctgcgctggg ccccaagccg acgcgccctg    10800
gaggcagctg gggccggacc tgggctggcg gtggcacccg cgcgcgctgg caacgtcggc    10860
ggcgtggagg aatatgacga ggacgatgag tacgagccag aggacggcga gtactaagcg    10920
gtgatgtttc tgatcagatg atgcaagacg caacggaccc ggcggtgcgg gcggcgctgc    10980
agagccagcc gtccggcctt aactccacgg acgactggcg ccaggtcatg gaccgcatca    11040
tgtcgctgac tgcgcgcaat cctgacgcgt tccggcagca gccgcaggcc aaccggctct    11100
ccgcaattct ggaagcggtg gtcccggcgc gcgcaaaccc cacgcacgag aaggtgctgg    11160
cgatcgtaaa cgcgctggcc gaaaacaggg ccatccggcc cgacgaggcc ggcctggtct    11220
acgacgcgct gcttcagcgc gtggctcgtt acaacagcgg caacgtgcag accaacctgg    11280
accggctggt gggggatgtg cgcgaggccg tggcgcagcg tgagcgcgcg cagcagcagg    11340
gcaacctggg ctccatggtt gcactaaacg ccttcctgag tacacagccc gccaacgtgc    11400
cgcggggaca ggaggactac accaactttg tgagcgcact gcggctaatg gtgactgaga    11460
caccgcaaag tgaggtgtac cagtctgggc cagactattt tttccagacc agtagacaag    11520
gcctgcagac cgtaaacctg agccaggctt tcaaaaactt gcaggggctg tgggggggtgc    11580 gggctcccac aggcgaccgc gcgaccgtgt ctagcttgct gacgcccaac tcgcgcctgt    11640
tgctgctgct aatagcgccc ttcacggaca gtggcagcgt gtcccgggac acatacctag    11700
gtcacttgct gacactgtac cgcgaggcca taggtcaggc gcatgtggac gagcatactt    11760
tccaggagat tacaagtgtc agccgcgcgc tgggcagga ggacacgggc agcctggagg    11820
caaccctaaa ctacctgctg accaaccggc ggcagaagat cccctcgttg cacagtttaa    11880
acagcgagga ggagcgcatt ttgcgctacg tgcagcagag cgtgagcctt aacctgatgc    11940 gcgacgggt aacgcccagc gtggcgctgg acatgaccgc gcgcaacatg gaaccgggca    12000
tgtatgcctc aaaccggccg tttatcaacc gcctaatgga ctacttgcat cgcgcggccg    12060
ccgtgaaccc cgagtatttc accaatgcca tcttgaaccc gcactggcta ccgccccctg    12120
gtttctacac cggggggattc gaggtgcccg agggtaacga tggattcctc tgggacgaca    12180
tagacgacag cgtgttttcc ccgcaaccgc agacctgct agagttgcaa cagcgcgagc    12240
aggcagaggc ggcgctgcga aaggaaagct tccgcaggcc aagcagcttg tccgatctag    12300
```

```
gcgctgcggc cccgcggtca gatgctagta gcccatttcc aagcttgata gggtctctta   12360
ccagcactcg caccacccgc ccgcgcctgc tgggcgagga ggagtaccta aacaactcgc   12420
tgctgcagcc gcagcgcgaa aaaaacctgc ctccggcatt tcccaacaac gggatagaga   12480
gcctagtgga caagatgagt agatggaaga cgtacgcgca ggagcacagg gacgtgccag   12540
gcccgcgccc gcccacccgt cgtcaaaggc acgaccgtca gcggggtctg tgtgtgggagg  12600
acgatgactc ggcagacgac agcagcgtcc tggatttggg agggagtggc aacccgtttg   12660
cgcaccttcg ccccaggctg gggagaatgt tttaaaaaaa aaaaagcat  gatgcaaaat   12720
aaaaaactca ccaaggccat ggcaccgagc gttggttttc ttgtattccc cttagtatgc   12780
ggcgcgcggc gatgtatgag gaaggtcctc ctccctccta cgagagtgtg gtgagcgcgg   12840
cgccagtggc ggcggcgctg ggttctccct tcgatgctcc cctggacccg ccgtttgtgc   12900
ctccgcggta cctgcggcct accggggga gaaacagcat ccgttactct gagttggcac    12960
ccctattcga caccacccgt gtgtacctgg tggacaacaa gtcaacggat gtggcatccc   13020
tgaactacca gaacgaccac agcaactttc tgaccacggt cattcaaaac aatgactaca   13080
gcccggggga ggcaagcaca cagaccatca atcttgacga ccggtcgcac tggggcggcg   13140
acctgaaaac catcctgcat accaacatgc caaatgtgaa cgagttcatg tttaccaata   13200
agtttaaggc gcgggtgatg gtgtcgcgct tgcctactaa ggacaatcag gtggagctga   13260
aatacgagtg ggtggagttc acgctgcccg agggcaacta ctccgagacc atgaccatag   13320
accttatgaa caacgcgatc gtggagcact acttgaaagt gggcagacag aacggggttc   13380
tggaaagcga catcggggta aagtttgaca cccgcaactt cagactgggg tttgaccccg   13440
tcactggtct tgtcatgcct ggggtatata caaacgaagc cttccatcca gacatcattt   13500
tgctgccagg atgcggggtg gacttcaccc acagccgcct gagcaacttg ttgggcatcc   13560
gcaagcggca acccttccag gagggcttta ggatcaccta cgatgatctg gagggtggta   13620
acattcccgc actgttggat gtggacgcct accaggcgag cttgaaagat gacaccgaac   13680
agggcggggg tggcgcaggc ggcagcaaca gcagtggcag cggcgcggaa gagaactcca   13740
acgcggcagc cgcggcaatg cagccggtgg aggacatgaa cgatcatgcc attcgcggcg   13800
acacctttgc cacacgggct gaggagaagc gcgctgaggc cgaagcagcg gccgaagctg   13860
ccgcccccgc tgcgcaaccc gaggtcgaga gcctcagaa  gaaaccggtg atcaaacccc   13920
tgacagagga cagcaagaaa cgcagttaca acctaataag caatgacagc accttcaccc   13980
agtaccgcag ctggtacctt gcatacaact acggcgaccc tcagaccgga atccgctcat   14040
ggaccctgct ttgcactcct gacgtaacct gcggctcgga gcaggtctac tggtcgttgc   14100
cagacatgat gcaagacccc gtgaccttcc gctccacgcg ccagatcagc aactttccgg   14160
tggtgggcgc cgagctgttg cccgtgcact ccaagagctt ctacaacgac caggccgtct   14220
actcccaact catccgccag tttacctctc tgacccacgt gttcaatcgc tttcccgaga   14280
accagatttt ggcgcgcccg ccagccccca ccatcaccac cgtcagtgaa aacgttcctg   14340
ctctcacaga tcacgggacg ctaccgctgc gcaacagcat cggaggagtc cagcgagtga   14400
ccattactga cgccagacgc gcacctgcc  cctacgttta caaggccctg gcatagtct   14460
cgccgcgcgt cctatcgagc cgcactttt  gagcaagcat gtccatcctt atatcgccca   14520
gcaataacac aggctgggc  ctgcgcttcc caagcaagat gtttggcggg gccaagaagc   14580
gctccgacca cacccagtg  cgcgtgcgcg ggcactaccg cgcgccctgg ggcgcgcaca   14640
aacgcggccg cactgggcgc accaccgtcg atgacgccat cgacgcggtg gtggaggagg   14700
```

```
cgcgcaacta cacgcccacg ccgccaccag tgtccacagt ggacgcggcc attcagaccg   14760
tggtgcgcgg agcccggcgc tatgctaaaa tgaagagacg gcggaggcgc gtagcacgtc   14820
gccaccgccg ccgacccggc actgccgccc aacgcgcggc ggcggcccctg cttaaccgcg  14880 cacgtcgcac cggccgacgg gcggccatgc gggccgctcg aaggctggcc gcgggtattg   14940
tcactgtgcc ccccaggtcc aggcgacgag cggccgccgc agcagccgcg gccattagtg   15000
ctatgactca gggtcgcagg ggcaacgtgt attgggtgcg cgactcggtt agcggcctgc   15060
gcgtgcccgt gcgcacccgc ccccgcgca actagattgc aagaaaaaac tacttagact    15120
cgtactgttg tatgtatcca gcggcggcgg cgcgcaacga agctatgtcc aagcgcaaaa   15180
tcaaagaaga gatgctccag gtcatcgcgc cggagatcta tggccccccg aagaaggaag   15240
agcaggatta caagccccga aagctaaagc gggtcaaaaa gaaaagaaa gatgatgatg    15300 atgaacttga cgacgaggtg gaactgctgc acgctaccgc gcccaggcga cgggtacagt   15360
ggaaaggtcg acgcgtaaaa cgtgttttgc gacccggcac caccgtagtc tttacgcccg   15420
gtgagcgctc cacccgcacc tacaagcgcg tgtatgatga ggtgtacggc gacgaggacc   15480
tgcttgagca ggccaacgag cgcctcgggg agtttgccta cggaaagcgg cataaggaca   15540
tgctggcgtt gccgctggac gagggcaacc caacacctag cctaaagccc gtaacactgc   15600
agcaggtgct gcccgcgctt gcaccgtccg aagaaaagcg cggcctaaag cgcgagtctg   15660
gtgacttggc acccaccgtg cagctgatgg tacccaagcg ccagcgactg gaagatgtct   15720
tggaaaaaat gaccgtggaa cctgggctgg agcccgaggt ccgcgtgcgg ccaatcaagc   15780
aggtggcgcc gggactgggc gtgcagaccg tggacgttca gatacccact accagtagca   15840
ccagtattgc caccgccaca gagggcatgg agacacaaac gtccccggtt gcctcagcgg   15900
tggcggatgc cgcggtgcag gcggtcgctg cggccgcgtc caagacctct acggaggtgc   15960
aaacggaccc gtggatgttt cgcgtttcag cccccccggcg cccgcgccgt tcgaggaagt   16020
acggcgccgc cagcgcgcta ctgcccgaat atgccctaca tccttccatt gcgcctaccc   16080
ccggctatcg tggctacacc taccgcccca agagacgagc aactaccga cgccgaacca   16140 ccactggaac ccgccgccgc cgtcgccgtc gccagcccgt gctggccccg atttccgtgc   16200
gcagggtggc tcgcgaagga ggcaggacc tggtgctgcc aacagcgcgc taccaccca   16260 gcatcgttta aaagccggtc tttgtggttc ttgcagatat ggccctcacc tgccgcctcc   16320
gtttcccggt gccgggattc cgaggaagaa tgcaccgtag gagggcatg gccggccacg    16380 gcctgacggg cggcatgcgt cgtgcgcacc accggcgcg gcgcgcgtcg caccgtcgca    16440
tgcgcggcgg tatcctgccc ctccttattc cactgatcgc cgcggcgatt ggcgccgtgc   16500
ccggaattgc atccgtggcc ttgcaggcgc agagacactg attaaaaaca agttgcatgt   16560
ggaaaaatca aaataaaaag tctggactct cacgctcgct tggtcctgta actattttgt   16620
agaatggaag acatcaactt tgcgtctctg gccccgcgac acggctcgcg cccgttcatg   16680
ggaaactggc aagatatcgg caccagcaat atgagcggtg gcgccttcag ctggggctcg   16740
ctgtggagcg gcattaaaaa tttcggttcc accgttaaga actatggcag caaggcctgg   16800
aacagcagca caggccagat gctgagggat aagttgaaag agcaaaattt ccaacaaaag   16860
gtggtagatg gcctggcctc tggcattagc ggggtggtgg acctggccaa ccaggcagtg   16920
caaaataaga ttaacagtaa gcttgatccc cgccctcccg tagaggagcc tccaccggcc   16980
gtggagacag tgtctccaga ggggcgtggc gaaaagcgtc cgcgccccga cagggaagaa   17040
```

```
actctggtga cgcaaataga cgagcctccc tcgtacgagg aggcactaaa gcaaggcctg    17100
cccaccaccc gtcccatcgc gcccatggct accggagtgc tgggccagca cacacccgta    17160
acgctggacc tgcctccccc cgccgacacc cagcagaaac ctgtgctgcc aggcccgacc    17220
gccgttgttg taacccgtcc tagccgcgcg tccctgcgcc gcgccgccag cggtccgcga    17280
tcgttgcggc ccgtagccag tggcaactgg caaagcacac tgaacagcat cgtgggtctg    17340
ggggtgcaat ccctgaagcg ccgacgatgc ttctgatagc taacgtgtcg tatgtgtgtc    17400
atgtatgcgt ccatgtcgcc gccagaggag ctgctgagcc gccgcgcgcc cgctttccaa    17460
gatggctacc ccttcgatga tgccgcagtg gtcttacatg cacatctcgg gccaggacgc    17520
ctcggagtac ctgagccccg ggctggtgca gtttgcccgc gccaccgaga cgtacttcag    17580
cctgaataac aagtttagaa accccacggt ggcgcctacg cacgacgtga ccacagaccg    17640
gtcccagcgt ttgacgctgc ggttcatccc tgtggaccgt gaggatactg cgtactcgta    17700
caaggcgcgg ttcaccctag ctgtgggtga taaccgtgtg ctggacatgg cttccacgta    17760
cttggacatc cgcggcgtgc tggacagggg ccctactttt aagccctact ctggcactgc    17820
ctacaacgcc ctggctccca agggtgcccc aaatccttgc gaatgggatg aagctgctac    17880
tgctcttgaa ataaacctag aagaagagga cgatgacaac gaagacgaag tagacgagca    17940
agctgagcag caaaaaactc acgtatttgg gcaggcgcct tattctggta taaatattac    18000
aaaggagggt attcaaatag gtgtcgaagg tcaaacacct aaatatgccg ataaaacatt    18060
tcaacctgaa cctcaaatag gagaatctca gtggtacgaa acagaaatta atcatgcagc    18120
tgggagagtc ctaaaaaaga ctaccccaat gaaaccatgt tacggttcat atgcaaaacc    18180
cacaaatgaa aatggagggc aaggcattct tgtaaagcaa caaaatggaa agctagaaag    18240
tcaagtggaa atgcaatttt tctcaactac tgaggcagcc gcaggcaatg gtgataactt    18300
gactcctaaa gtggtattgt acagtgaaga tgtagatata gaaaccccag acactcatat    18360
ttcttacatg cccactatta aggaaggtaa ctcacgagaa ctaatgggcc aacaatctat    18420
gcccaacagg cctaattaca ttgcttttag ggacaatttt attggtctaa tgtattacaa    18480
cagcacgggt aatatgggtg ttctggcggg ccaagcatcg cagttgaatg ctgttgtaga    18540
tttgcaagac agaaacacag agctttcata ccagcttttg cttgattcca ttggtgatag    18600
aaccaggtac ttttctatgt ggaatcaggc tgttgacagc tatgatccag atgttagaat    18660
tattgaaaat catggaactg aagatgaact tccaaattac tgctttccac tgggaggtgt    18720
gattaataca gagactctta ccaaggtaaa acctaaaaca ggtcaggaaa atggatggga    18780
aaaagatgct acagaatttt cagataaaaa tgaaataaga gttggaaata ttttgccat     18840 ggaaatcaat ctaaatgcca acctgtggag aaatttcctg tactccaaca tagcgctgta    18900
tttgcccgac aagctaaagt acagtccttc caacgtaaaa atttctgata acccaaacac    18960
ctacgactac atgaacaagc gagtggtggc tcccgggcta gtggactgct acattaacct    19020
tggagcacgc tggtcccttg actatatgga caacgtcaac ccatttaacc accaccgcaa    19080
tgctggcctg cgctaccgct caatgttgct gggcaatggt cgctatgtgc ccttccacat    19140
ccaggtgcct cagaagttct ttgccattaa aaacctcctt ctcctgccgg gctcatacac    19200
ctacgagtgg aacttcagga aggatgttaa catggttctg cagagctccc taggaaatga    19260
cctaagggtt gacggagcca gcattaagtt tgatagcatt tgcctttacg ccaccttctt    19320
ccccatggcc cacaacaccg cctccacgct tgaggccatg cttagaaacg acaccaacga    19380
ccagtccttt aacgactatc tctccgccgc caacatgctc taccctatac ccgccaacgc    19440
```

```
taccaacgtg cccatatcca tccccctcccg caactgggcg gctttccgcg gctgggcctt    19500
cacgcgcctt aagactaagg aaaccccatc actgggctcg ggctacgacc cttattacac    19560
ctactctggc tctataccct acctagatgg aaccttttac ctcaaccaca cctttaagaa    19620
ggtggccatt acctttgact cttctgtcag ctggcctggc aatgaccgcc tgcttacccc    19680
caacgagttt gaaattaagc gctcagttga cggggagggt tacaacgttg cccagtgtaa    19740
catgaccaaa gactggttcc tggtacaaat gctagctaac tataacattg ctaccaggg    19800 cttctatatc ccagagagct acaaggaccg catgtactcc ttctttagaa acttccagcc    19860
catgagccgt caggtggtgg atgatactaa atacaaggac taccaacagg tgggcatcct    19920
acaccaacac aacaactctg gatttgttgg ctaccttgcc cccaccatgc gcgaaggaca    19980
ggcctaccct gctaacttcc cctatccgct tataggcaag accgcagttg acagcattac    20040
ccagaaaaag tttctttgcg atcgcaccct ttggcgcatc ccattctcca gtaactttat    20100
gtccatgggc gcactcacag acctgggcca aaaccttctc tacgccaact ccgcccacgc    20160
gctagacatg acttttgagg tggatcccat ggacgagccc acccttcttt atgttttgtt    20220
tgaagtcttt gacgtggtcc gtgtgcacca gccgcaccgc ggcgtcatcg aaaccgtgta    20280
cctgcgcacg cccttctcgg ccggcaacgc cacaacataa agaagcaagc aacatcaaca    20340
acagctgccg ccaaataatg tactagagac actttcaata aaggcaaatg cttttatttg    20400
tacactctcg ggtgattatt taccccaccc cttgccgtct gcgccgttta aaaatcaaag    20460
gggttctgcc gcgcatcgct atgcgccact ggcaggaca cgttgcgata ctggtgttta    20520
gtgctccact taaactcagg cacaaccatc cgcggcagct cggtgaagtt ttcactccac    20580
aggctgcgca ccatcaccaa cgcgtttagc aggtcgggcg ccgatatctt gaagtcgcag    20640
ttggggcctc cgccctgcgc gcgcgagttg cgatacacag ggttgcagca ctggaacact    20700
atcagcgccg ggtggtgcac gctgccagc acgctcttgt cggagatcag atccgcgtcc    20760
aggtcctccg cgttgctcag ggcgaacgga gtcaactttg gtagctgcct tcccaaaaag    20820
ggcgcgtgcc caggctttga gttgcactcg caccgtagtg gcatcaaaag gtgaccgtgc    20880
ccggtctggg cgttaggata cagcgcctgc ataaaagcct tgatctgctt aaaagccacc    20940
tgagcctttg cgccttcaga gaagaacatg ccgcaagact tgccggaaaa ctgattggcc    21000
ggacaggccg cgtcgtgcac gcagcaccct tgcgtcggtgt tggagatctg caccacattt    21060
cggccccacc ggttcttcac gatcttggcc ttgctagact gctccttcag cgcgcgctgc    21120
ccgttttcgc tcgtcacatc catttcaatc acgtgctcct tatttatcat aatgcttccg    21180
tgtagacact taagctcgcc ttcgatctca gcgcagcggt gcagccacaa cgcgcagccc    21240
gtgggctcgt gatgcttgta ggtcacctct gcaaacgact gcaggtacgc ctgcaggaat    21300
cgccccatca tcgtcacaaa ggtcttgttg ctggtgaagg tcagctgcaa cccgcggtgc    21360
tcctcgttca gccaggtctt gcatacggcc gccagagctt ccactggtc aggcagtagt    21420 ttgaagttcg ccttttagatc gttatccacg tggtacttgt ccatcagcgc gcgcgcagcc    21480
tccatgccct tctcccacgc agacacgatc ggcacactca gcgggttcat caccgtaatt    21540
tcactttccg cttcgctggg ctcttcctct tcctcttgcg tccgcatacc acgcgccact    21600
gggtcgtctt cattcagccg ccgcactgtg cgcttacctc ctttgccatg cttgattagc    21660
accggtgggt tgctgaaacc caccatttgt agcgccacat cttctctttc ttcctcgctg    21720
tccacgatta cctctggtga tggcgggcgc tcgggcttgg gagaagggcg cttctttttc    21780
```

```
ttcttgggcg caatggccaa atccgccgcc gaggtcgatg gccgcgggct gggtgtgcgc   21840
ggcaccagcg cgtcttgtga tgagtcttcc tcgtcctcgg actcgatacg ccgcctcatc   21900
cgcttttttg ggggcgcccg gggaggcggc ggcgacgggg acggggacga cacgtcctcc   21960
atggttgggg gacgtcgcgc cgcaccgcgt ccgcgctcgg gggtggtttc gcgctgctcc   22020
tcttcccgac tggccatttc cttctcctat aggcagaaaa agatcatgga gtcagtcgag   22080
aagaaggaca gcctaaccgc cccctctgag ttcgccacca ccgcctccac cgatgccgcc   22140
aacgcgccta ccaccttccc cgtcgaggca cccccgcttg aggaggagga agtgattatc   22200
gagcaggacc caggttttgt aagcgaagac gacgaggacc gctcagtacc aacagaggat   22260
aaaaagcaag accaggacaa cgcagaggca aacgaggaac aagtcgggcg ggggacgaa    22320 aggcatggcg actacctaga tgtgggagac gacgtgctgt tgaagcatct gcagcgccag   22380
tgcgccatta tctgcgacgc gttgcaagag cgcagcgatg tgcccctcgc catagcggat   22440
gtcagccttg cctacgaacg ccacctattc tcaccgcgcg tacccccaa acgccaagaa   22500 aacggcacat gcgagcccaa cccgcgcctc aacttctacc ccgtatttgc cgtgccagag   22560
gtgcttgcca cctatcacat cttttttccaa aactgcaaga taccccctatc ctgccgtgcc   22620 aaccgcagcc gagcggacaa gcagctggcc ttgcggcagg cgctgtcat acctgatatc   22680 gcctcgctca acgaagtgcc aaaaatcttt gagggtcttg gacgcgacga gaagcgcgcg   22740
gcaaacgctc tgcaacagga aaacagcgaa aatgaaagtc actctggagt gttggtggaa   22800
ctcgagggtg acaacgcgcg cctagccgta ctaaaacgca gcatcgaggt cacccacttt   22860
gcctacccgg cacttaacct accccccaag gtcatgagca cagtcatgag tgagctgatc   22920
gtgcgccgtg cgcagcccct ggagagggat gcaaatttgc aagaacaaac agaggagggc   22980
ctacccgcag ttggcgacga gcagctagcg cgctggcttc aaacgcgcga gcctgccgac   23040
ttggaggagc gacgcaaact aatgatggcc gcagtgctcg ttaccgtgga gcttgagtgc   23100
atgcagcggt tctttgctga cccggagatg cagcgcaagc tagaggaaac attgcactac   23160
acctttcgac agggctacgt acgccaggcc tgcaagatct ccaacgtgga gctctgcaac   23220
ctggtctcct accttggaat tttgcacgaa accgccttg gcaaaacgt gcttcattcc    23280 acgctcaagg gcgaggcgcg ccgcgactac gtccgcgact gcgtttactt atttctatgc   23340
tacacctggc agacggccat gggcgtttgg cagcagtgct tggaggagtg caacctcaag   23400
gagctgcaga aactgctaaa gcaaaacttg aaggacctat ggacggcctt caacgagcgc   23460
tccgtggccc cgcacctggc ggacatcatt ttccccgaac gcctgcttaa aaccctgcaa   23520
cagggtctgc cagacttcac cagtcaaagc atgttgcaga actttaggaa ctttatccta   23580
gagcgctcag gaatcttgcc cgccaccgtc tgtgcacttc ctagcgactt tgtgcccatt   23640
aagtaccgcg aatgccctcc gccgctttgg ggccactgct accttctgca gctagccaac   23700
taccttgcct accactctga cataatggaa gacgtgagcg gtgacggtct actggagtgt   23760
cactgtcgct gcaacctatg caccccgcac cgctccctgg tttgcaattc gcagctgctt   23820
aacgaaagtc aaattatcgg tacctttgag ctgcagggtc cctcgcctga cgaaaagtcc   23880
gcggctccgg ggttgaaact cactccgggg ctgtggacgt cggcttacct tcgcaaattt   23940
gtacctgagg actaccacgc ccacgagatt aggttctacg aagaccaatc ccgcccgcct   24000
aatgcggagc ttaccgcctg cgtcattacc caggcccaca ttcttggcca attgcaagcc   24060
atcaacaaag cccgccaaga gtttctgcta cgaaagggac ggggggttta cttggacccc   24120
cagtccggcg aggagctcaa cccaatcccc ccgccgccgc agccctatca gcagcagccg   24180
```

```
cgggcccttg cttcccagga tggcacccaa aaagaagctg cagctgccgc cgccacccac  24240
ggacgaggag gaatactggg acagtcaggc agaggaggtt ttggacgagg aggaggagga  24300
catgatggaa gactgggaga gcctagacga ggaagcttcc gaggtcgaag aggtgtcaga  24360
cgaaacaccg tcaccctcgg tcgcattccc ctcgccggcg ccccagaaat cggcaaccgg  24420
ttccagcatg gctacaacct ccgctcctca ggcgccgccg gcactgcccg ttcgccgacc  24480
caaccgtaga tgggacacca ctggaaccag ggccggtaag tccaagcagc cgccgccgtt  24540
agcccaagag caacaacagc gccaaggcta ccgctcatgg cgcgggcaca agaacgccat  24600
agttgcttgc ttgcaagact gtggggcaa catctccttc gcccgccgct ttcttctcta  24660
ccatcacggc gtggccttcc cccgtaacat cctgcattac taccgtcatc tctacagccc  24720
atactgcacc ggcggcagcg gcagcaacag cagcggccac acagaagcaa aggcgaccgg  24780
atagcaagac tctgacaaag cccaagaaat ccacagcggc ggcagcagca ggaggaggag  24840
cgctgcgtct ggcgcccaac gaacccgtat cgacccgcga gcttagaaac aggattttc  24900 ccactctgta tgctatattt caacagagca ggggccaaga acaagagctg aaaataaaaa  24960
acaggtctct gcgatccctc acccgcagct gcctgtatca caaaagcgaa gatcagcttc  25020
ggcgcacgct ggaagacgcg gaggctctct tcagtaaata ctgcgcgctg actcttaagg  25080
actagtttcg cgccctttct caaatttaag cgcgaaaact acgtcatctc cagcggccac  25140
acccggcgcc agcacctgtt gtcagcgcca ttatgagcaa ggaaattccc acgccctaca  25200
tgtggagtta ccagccacaa atgggacttg cggctggagc tgcccaagac tactcaaccc  25260 gaataaaacta catgagcgcg ggaccccaca tgatatcccg ggtcaacgga atacgcgccc  25320
accgaaaccg aattctcctg gaacaggcgg ctattaccac cacacctcgt aataaccta  25380 atccccgtag ttggcccgct gccctggtgt accaggaaag tcccgctccc accactgtgg  25440
tacttcccag agacgcccag gccgaagttc agatgactaa ctcaggggcg cagcttgcgg  25500
gcggctttcg tcacagggtg cggtcgcccg ggcagggtat aactcacctg acaatcagag  25560
ggcgaggtat tcagctcaac gacgagtcgg tgagctcctc gcttggtctc cgtccggacg  25620
ggacatttca gatcggcggc gccggccgct cttcattcac gcctcgtcag gcaatcctaa  25680
ctctgcagac ctcgtcctct gagccgcgct ctggaggcat tggaactctg caatttattg  25740
aggagtttgt gccatcggtc tactttaacc ccttctcggg acctcccggc cactatccgg  25800
atcaatttat tcctaacttt gacgcggtaa aggactcggc ggacggctac gactgaatgt  25860
taagtggaga ggcagagcaa ctgcgcctga acacctggt ccactgtcgc cgccacaagt  25920
gctttgcccg cgactccggt gagttttgct actttgaatt gcccgaggat catatcgagg  25980
gcccggcgca cggcgtccgg cttaccgccc agggagagct tgcccgtagc ctgattcggg  26040
agtttaccca gcgcccctg ctagttgagc gggacagggg accctgtgtt ctcactgtga  26100
tttgcaactg tcctaaccct ggattacatc aagatctttg ttgccatctc tgtgctgagt  26160
ataataaata cagaaattaa aatatactgg ggctcctatc gccatcctgt aaacgccacc  26220
gtcttcaccc gcccaagcaa accaaggcga accttacctg gtactttaa catctctccc  26280 tctgtgattt acaacagttt caacccagac ggagtgagtc tacgagagaa cctctccgag  26340
ctcagctact ccatcagaaa aaacaccacc ctccttacct gccgggaacg tacgagtgcg  26400
tcaccggccg ctgcaccaca cctaccgcct gaccgtaaac cagactttt ccggacagac  26460 ctcaataact ctgtttacca gaacaggagg tgagcttaga aaacccttag ggtattaggc  26520
```

```
caaaggcgca gctactgtgg ggtttatgaa caattcaagc aactctacgg gctattctaa    26580
ttcaggtttc tctagaaatg gacggaatta ttacagagca gcgcctgcta gaaagacgca    26640
gggcagcggc cgagcaacag cgcatgaatc aagagctcca agacatggtt aacttgcacc    26700
agtgcaaaag gggtatcttt tgtctggtaa agcaggccaa agtcacctac gacagtaata    26760
ccaccggaca ccgccttagc tacaagttgc caaccaagcg tcagaaattg gtggtcatgg    26820
tgggagaaaa gcccattacc ataactcagc actcggtaga aaccgaaggc tgcattcact    26880
caccttgtca aggacctgag gatctctgca cccttattaa gaccctgtgc ggtctcaaag    26940
atcttattcc ctttaactaa taaaaaaaaa taataaagca tcacttactt aaaatcagtt    27000
agcaaatttc tgtccagttt attcagcagc acctccttgc cctcctccca gctctggtat    27060
tgcagcttcc tcctggctgc aaactttctc cacaatctaa atggaatgtc agtttcctcc    27120
tgttcctgtc catccgcacc cactatcttc atgttgttgc agatgaagcg cgcaagaccg    27180
tctgaagata ccttcaaccc cgtgtatcca tatgacacgg aaaccggtcc tccaactgtg    27240
cctttttctta ctcctccctt tgtatccccc aatgggtttc aagagagtcc cctgggggta    27300
ctctctttgc gcctatccga acctctagtt acctccaatg gcatgcttgc gctcaaaatg    27360
ggcaacggcc tctctctgga cgaggccggc aaccttacct cccaaaatgt aaccactgtg    27420
agcccacctc tcaaaaaaac caagtcaaac ataaacctgg aaatatctgc acccctcaca    27480
gttacctcag aagccctaac tgtggctgcc gccgcacctc taatggtcgc gggcaacaca    27540
ctcaccatgc aatcacaggc cccgctaacc gtgcacgact ccaaacttag cattgccacc    27600
caaggacccc tcacagtgtc agaaggaaag ctagccctgc aaacatcagg cccccctcacc    27660
accaccgata gcagtaccct tactatcact gcctcacccc ctctaactac tgccactggt    27720
agcttgggca ttgacttgaa agagcccatt tatacacaaa atggaaaact aggactaaag    27780
tacggggctc ctttgcatgt aacagacgac ctaaacactt tgaccgtagc aactggtcca    27840
ggtgtgacta ttaataatac ttccttgcaa actaaagtta ctggagcctt gggttttgat    27900
tcacaaggca atatgcaact taatgtagca ggaggactaa ggattgattc tcaaaacaga    27960
cgccttatac ttgatgttag ttatccgttt gatgctcaaa accaactaaa tctaagacta    28020
ggacagggcc ctctttttat aaactcagcc cacaacttgg atattaacta caacaaaggc    28080
ctttacttgt ttacagcttc aaacaattcc aaaaagcttg aggttaacct aagcactgcc    28140
aaggggttga tgtttgacgc tacagccata gccattaatg caggagatgg gcttgaattt    28200
ggttcaccta atgcaccaaa cacaaatccc ctcaaaacaa aaattggcca tggcctagaa    28260
tttgattcaa acaaggctat ggttcctaaa ctaggaactg gccttagttt tgacagcaca    28320
ggtgccatta cagtaggaaa caaaaataat gataagctaa cttttgtggac cacaccagct    28380
ccatctccta actgtagact aaatgcagag aaagatgcta aactcacttt ggtcttaaca    28440
aaatgtggca gtcaaatact tgctacagtt tcagttttgg ctgttaaagg cagtttggct    28500
ccaatatctg gaacagttca aagtgctcat cttattataa gatttgacga aaatggagtg    28560
ctactaaaca attccttcct ggacccagaa tattggaact ttagaaatgg agatcttact    28620
gaaggcacag cctatacaaa cgctgttgga tttatgccta acctatcagc ttatccaaaa    28680
tctcacggta aaactgccaa aagtaacatt gtcagtcaag tttacttaaa cggagacaaa    28740
actaaacctg taacactaac cattacacta aacggtacac aggaaacagg agacacaact    28800
ccaagtgcat actctatgtc attttcatgg gactggtctg gccacaacta cattaatgaa    28860
atatttgcca catcctctta cactttttca tacattgccc aagaataaag aatcgtttgt    28920
```

```
gttatgtttc aacgtgttta tttttcaatt gcagaaaatt tcgaatcatt tttcattcag   28980
tagtatagcc ccaccaccac atagcttata cagatcaccg taccttaatc aaactcacag   29040
aaccctagta ttcaacctgc cacctccctc caacacaca gagtacacag tcctttctcc    29100
ccggctggcc ttaaaaagca tcatatcatg ggtaacagac atattcttag gtgttatatt   29160
ccacacggtt tcctgtcgag ccaaacgctc atcagtgata ttaataaact ccccgggcag   29220
ctcacttaag ttcatgtcgc tgtccagctg ctgagccaca ggctgctgtc caacttgcgg   29280
ttgcttaacg ggcggcgaag gagaagtcca cgcctacatg ggggtagagt cataatcgtg   29340
catcaggata gggcggtggt gctgcagcag gcgcgcgaata aactgctgcc gccgccgctc   29400
cgtcctgcag gaatacaaca tggcagtggt ctcctcagcg atgattcgca ccgcccgcag   29460
cataaggcgc cttgtcctcc gggcacagca gcgcaccctg atctcactta aatcagcaca   29520
gtaactgcag cacagcacca caatattgtt caaaatccca cagtgcaagg cgctgtatcc   29580
aaagctcatg gcggggacca cagaacccac gtggccatca taccacaagc gcaggtagat   29640
taagtggcga ccccctcataa acacgctgga cataaacatt acctcttttg gcatgttgta   29700
attcaccacc tcccggtacc atataaacct ctgattaaac atggcgccat ccaccaccat   29760
cctaaaccag ctggccaaaa cctgcccgcc ggctatacac tgcagggaac cgggactgga   29820
acaatgacag tggagagccc aggactcgta accatggatc atcatgctcg tcatgatatc    29880
aatgttggca caacacaggc acacgtgcat acacttcctc aggattacaa gctcctcccg   29940
cgttagaacc atatcccagg gaacaaccca ttcctgaatc agcgtaaatc ccacactgca   30000
gggaagacct cgcacgtaac tcacgttgtg cattgtcaaa gtgttacatt cgggcagcag   30060
cggatgatcc tccagtatgg tagcgcgggt ttctgtctca aaaggaggta gacgatccct   30120
actgtacgga gtgcgccgag acaaccgaga tcgtgttggt cgtagtgtca tgccaaatgg   30180
aacgccggac gtagtcatat ttcctgaagc aaaaccaggt gcgggcgtga caaacagatc   30240
tgcgtctccg gtctcgccgc ttagatcgct ctgtgtagta gttgtagtat atccactctc   30300
tcaaagcatc caggcgcccc ctggcttcgg gttctatgta aactccttca tgcgccgctg   30360
ccctgataac atccaccacc gcagaataag ccacacccag ccaacctaca cattcgttct   30420
gcgagtcaca cacggagga gcgggaagag ctggaagaac catgttttttt ttttatcc     30480 aaaagattat ccaaaacctc aaaatgaaga tctattaagt gaacgcgctc ccctccggtg   30540
gcgtggtcaa actctacagc caaagaacag ataatggcat ttgtaagatg ttgcacaatg   30600
gcttccaaaa ggcaaacggc cctcacgtcc aagtggacgt aaaggctaaa cccttcaggg   30660
tgaatctcct ctataaacat tccagcacct tcaaccatgc ccaaataatt ctcatctcgc   30720
caccttctca atatatctct aagcaaatcc gaatattaa gtccggccat tgtaaaaatc    30780
tgctccagag cgccctccac cttcagcctc aagcagcgaa tcatgattgc aaaaattcag   30840
gttcctcaca gacctgtata agattcaaaa gcggaacatt aacaaaaata ccgcgatccc   30900
gtaggtccct tcgcagggcc agctgaacat aatcgtgcag gtctgcacgg accagcgcgg   30960
ccacttcccc gccaggaacc atgacaaaag aacccacact gattatgaca cgcatactcg   31020
gagctatgct aaccagcgta gccccgatgt aagcttgttg catgggcggc gatataaaat   31080
gcaaggtgct gctcaaaaaa tcaggcaaag cctcgcgcaa aaagaaagc acatcgtagt    31140 catgctcatg cagataaagg caggtaagct ccggaaccac cacagaaaaa gacaccattt   31200
ttctctcaaa catgtctgcg ggtttctgca taaacacaaa ataaaataac aaaaaaacat   31260
```

-continued

```
ttaaacatta gaagcctgtc ttacaacagg aaaaacaacc cttataagca taagacggac   31320
tacggccatg ccggcgtgac cgtaaaaaaa ctggtcaccg tgattaaaaa gcaccaccga   31380
cagctcctcg gtcatgtccg gagtcataat gtaagactcg gtaaacacat caggttgatt   31440
cacatcggtc agtgctaaaa agcgaccgaa atagcccggg ggaatacata cccgcaggcg   31500
tagagacaac attacagccc ccataggagg tataacaaaa ttaataggag agaaaaacac   31560
ataaacacct gaaaaccct cctgcctagg caaaatagca ccctcccgct ccagaacaac   31620
atacagcgct tccacagcgg cagccataac agtcagcctt accagtaaaa aagaaaacct   31680
attaaaaaaa caccactcga cacggcacca gctcaatcag tcacagtgta aaaaagggcc   31740
aagtgcagag cgagtatata taggactaaa aaatgacgta acggttaaag tccacaaaaa   31800
acacccagaa aaccgcacgc gaacctacgc ccagaaacga aagccaaaaa acccacaact   31860
tcctcaaatc gtcacttccg ttttcccacg ttacgtcact tcccattta agaaaactac   31920
aattcccaac acatacaagt tactccgccc taaaacctac gtcacccgcc ccgttcccac   31980
gccccgcgcc acgtcacaaa ctccaccccc tcattatcat attggcttca atccaaaata   32040
aggtatatta ttgatgatgt taattaattt aaatcccgcat gcgatatcga gctctcccgg   32100
gaattcggat ctgcgacgcg aggctggatg gccttcccca ttatgattct tctcgcgttt   32160
aagggcacca ataactgcct taaaaaaatt acgccccgcc ctgccactca tcgcagtact   32220
gttgtaattc attaagcatt ctgccgacat ggaagccatc acaaacggca tgatgaacct   32280
gaatcgccag cggcatcagc accttgtcgc cttgcgtata atatttgccc atggtgaaaa   32340
cgggggcgaa gaagttgtcc atattggcca cgtttaaatc aaaactggtg aaactcaccc   32400
agggattggc tgagacgaaa aacatattct caataaaccc tttagggaaa taggccaggt   32460
tttcaccgta acacgccaca tcttgcgaat atatgtgtag aaactgccgg aaatcgtcgt   32520
ggtattcact ccagagcgat gaaaacgttt cagtttgctc atggaaaacg gtgtaacaag   32580
ggtgaacact atcccatatc accagctcac cgtctttcat tgccatacgg aattccggat   32640
gagcattcat caggcgggca agaatgtgaa taaaggccgg ataaaacttg tgcttatttt   32700
tctttacggt ctttaaaaag gccgtaatat ccagctgaac ggtctggtta taggtacatt   32760
gagcaactga ctgaaatgcc tcaaaatgtt ctttacgatg ccattgggat atatcaacgg   32820
tggtatatcc agtgattttt ttctccattt tagcttcctt agctcctgaa atctctgata   32880
actcaaaaaa tacgcccggt agtgatctta tttcattatg gtgaaagttg gaacctctta   32940
cgtgccgatc aacgtctcat tttcgccaaa agttggccca gggcttcccg gtatcaacag   33000
ggacaccagg atttatttat tctgcgaagt gatcttccgt cacaggtatt tattcgcgat   33060
aagctcatgg agcggcgtaa ccgtcgcaca ggaaggacag agaaagcgcg gatctgggaa   33120
gtgacggaca gaacggtcag gacctggatt ggggaggcgg ttgccgccgc tgctgctgac   33180
ggtgtgacgt tctctgttcc ggtcacacca catacgttcc gccattccta tgcgatgcac   33240
atgctgtatg ccggtatacc gctgaaagtt ctgcaaagcc tgatgggaca taagtccatc   33300
agttcaacgg aagtctacac gaaggttttt gcgctggatg tggctgcccg gcaccgggtg   33360
cagtttgcga tgccggagtc tgatgcggtt gcgatgctga acaattatc ctgagaataa   33420
atgccttggc ctttatatgg aaatgtggaa ctgagtggat atgctgtttt tgtctgttaa   33480
acagagaagc tggctgttat ccactgagaa gcgaacgaaa cagtcgggaa aatctcccat   33540
tatccgtagag atccgcatta ttaatctcag gagcctgtgt agcgtttata ggaagtagtg   33600
ttctgtcatg atgcctgcaa gcggtaacga aaacgatttg aatatgcctt caggaacaat   33660
```

```
agaaatcttc gtgcggtgtt acgttgaagt ggagcggatt atgtcagcaa tggacagaac   33720
aacctaatga acacagaacc atgatgtggt ctgtccttt  acagccagta gtgctcgccg   33780
cagtcgagcg acagggcgaa gccctcgagt gagcgaggaa gcaccaggga acagcactta   33840
tatattctgc ttacacacga tgcctgaaaa aacttcctt  ggggttatcc acttatccac   33900
ggggatattt ttataattat ttttttata  gttttagat  cttctttttt agagcgcctt   33960
gtaggccttt atccatgctg gttctagaga aggtgttgtg acaaattgcc ctttcagtgt   34020
gacaaatcac cctcaaatga cagtcctgtc tgtgacaaat tgcccttaac cctgtgacaa   34080
attgccctca gaagaagctg ttttttcaca aagttatccc tgcttattga ctctttttta   34140
tttagtgtga caatctaaaa acttgtcaca cttcacatgg atctgtcatg gcggaaacag   34200
cggttatcaa tcacaagaaa cgtaaaaata gcccgcgaat cgtccagtca aacgacctca   34260
ctgaggcggc atatagtctc tcccgggatc aaaaacgtat gctgtatctg ttcgttgacc   34320
agatcagaaa atctgatggc accctacagg aacatgacgg tatctgcgag atccatgttg   34380
ctaaatatgc tgaaatattc ggattgacct ctgcggaagc cagtaaggat atacggcagg   34440
cattgaagag tttcgcgggg aaggaagtgg tttttatcg  ccctgaagag gatgccggcg   34500
atgaaaaagg ctatgaatct tttccttggt ttatcaaacg tgcgcacagt ccatccagag   34560
ggctttacag tgtacatatc aacccatatc tcattccctt ctttatcggg ttacagaacc   34620
ggtttacgca gtttcggctt agtgaaacaa agaaatcac  caatccgtat gccatgcgtt   34680
tatacgaatc cctgtgtcag tatcgtaagc cggatggctc aggcatcgtc tctctgaaaa   34740
tcgactggat catagagcgt taccagctgc ctcaaagtta ccagcgtatg cctgacttcc   34800
gccgccgctt cctgcaggtc tgtgttaatg agatcaacag cagaactcca atgcgcctct   34860
catacattga gaaaaagaaa ggccgccaga cgactcatat cgtattttcc ttccgcgata   34920
tcacttccat gacgacagga tagtctgagg gttatctgtc acagatttga gggtggttcg   34980
tcacatttgt tctgacctac tgagggtaat ttgtcacagt tttgctgttt ccttcagcct   35040
gcatggattt tctcatactt tttgaactgt aattttaag  gaagccaaat ttgagggcag   35100
tttgtcacag ttgatttcct tctctttccc ttcgtcatgt gacctgatat cggggggtag   35160
ttcgtcatca ttgatgaggg ttgattatca cagtttatta ctctgaattg gctatccgcg   35220
tgtgtacctc tacctggagt ttttcccacg gtggatattt cttcttgcgc tgagcgtaag   35280
agctatctga cagaacagtt cttctttgct tcctcgccag ttcgctcgct atgctcggtt   35340
acacggctgc ggcgagcgct agtgataata agtgactgag gtatgtgctc ttcttatctc   35400
cttttgtagt gttgctctta ttttaaacaa ctttgcggtt ttttgatgac tttgcgattt   35460
tgttgttgct ttgcagtaaa ttgcaagatt taataaaaaa acgcaaagca atgattaaag   35520
gatgttcaga atgaaactca tggaaacact taaccagtgc ataaacgctg gtcatgaaat   35580
gacgaaggct atcgccattg cacagtttaa tgatgacagc ccgaagcga  ggaaaataac   35640
ccggcgctgg agaataggtg aagcagcgga tttagttggg gtttcttctc aggctatcag   35700
agatgccgag aaagcagggc gactaccgca cccggatatg gaaattcgag acgggttga   35760
gcaacgtgtt ggttatacaa ttgaacaaat taatcatatg cgtgatgtgt ttggtacgcg   35820
attgcgacgt gctgaagacg tatttccacc ggtgatcggg gttgctgccc ataaaggtgg   35880
cgtttacaaa acctcagttt ctgttcatct tgctcaggat ctggctctga ggggctacg   35940
tgttttgctc gtggaaggta cgaccccca  gggaacagcc tcaatgtatc acggatgggt   36000
```

```
accagatctt catattcatg cagaagacac tctcctgcct ttctatcttg ggaaaagga    36060
cgatgtcact tatgcaataa agcccacttg ctggccgggg cttgacatta ttccttcctg   36120
tctggctctg caccgtattg aaactgagtt aatgggcaaa tttgatgaag gtaaactgcc   36180
caccgatcca cacctgatgc tccgactggc cattgaaact gttgctcatg actatgatgt   36240
catagttatt gacagcgcgc ctaacctggg tatcggcacg attaatgtcg tatgtgctgc   36300
tgatgtgctg attgttccca cgcctgctga gttgtttgac tacacctccg cactgcagtt   36360
tttcgatatg cttcgtgatc tgctcaagaa cgttgatctt aaagggttcg agcctgatgt   36420
acgtattttg cttaccaaat acagcaatag taatggctct cagtcccgt ggatggagga    36480
gcaaattcgg gatgcctggg aagcatggt tctaaaaaat gttgtacgtg aaacggatga    36540
agttggtaaa ggtcagatcc ggatgagaac tgttttgaa caggccattg atcaacgctc     36600
ttcaactggt gcctggagaa atgctctttc tatttgggaa cctgtctgca atgaaatttt   36660
cgatcgtctg attaaaccac gctgggagat tagataatga agcgtgcgcc tgttattcca   36720
aaacatacgc tcaatactca accggttgaa gatacttcgt tatcgacacc agctgccccg   36780
atggtggatt cgttaattgc gcgcgtagga gtaatggctc gcggtaatgc cattactttg   36840
cctgtatgtg gtcgggatgt gaagtttact cttgaagtgc tccggggtga tagtgttgag   36900
aagacctctc gggtatggtc aggtaatgaa cgtgaccagg agctgcttac tgaggacgca   36960
ctggatgatc tcatcccttc ttttctactg actggtcaac agacaccggc gttcggtcga   37020
agagtatctg gtgtcataga aattgccgat gggagtcgcc gtcgtaaagc tgctgcactt   37080
accgaaagtg attatcgtgt tctggttggc gagctggatg atgagcagat ggctgcatta   37140
tccagattgg gtaacgatta tcgcccaaca agtgcttatg aacgtggtca gcgttatgca   37200
agccgattgc agaatgaatt tgctggaaat atttctgcgc tggctgatgc ggaaaatatt   37260
tcacgtaaga ttattacccg ctgtatcaac accgccaaat tgcctaaatc agttgttgct   37320
cttttttctc accccggtga actatctgcc cggtcaggtg atgcacttca aaaagccttt   37380
acagataaag aggaattact taagcagcag gcatctaacc ttcatgagca gaaaaaagct   37440
ggggtgatat ttgaagctga agaagttatc actcttttaa cttctgtgct taaaacgtca   37500
tctgcatcaa gaactagttt aagctcacga catcagtttg ctcctggagc gacagtattg   37560
tataagggcg ataaaatggt gcttaacctg gacaggtctc gtgttccaac tgagtgtata   37620
gagaaaattg aggccattct taaggaactt gaaaagccag caccctgatg cgaccacgtt   37680
ttagtctacg tttatctgtc tttacttaat gtcctttgtt acaggccaga agcataact    37740
ggcctgaata ttctctctgg gcccactgtt ccacttgtat cgtcggtctg ataatcagac   37800
tgggaccacg gtcccactcg tatcgtcggt ctgattatta gtctgggacc acggtcccac   37860
tcgtatcgtc ggtctgatta ttagtctggg accacggtcc cactcgtatc gtcggtctga   37920
taatcagact gggaccacgg tcccactcgt atcgtcggtc tgattattag tctgggacca   37980
tggtcccact cgtatcgtcg gtctgattat tagtctggga ccacggtccc actcgtatcg   38040
tcggtctgat tattagtctg gaaccacggt cccactcgta tcgtcggtct gattattagt   38100
ctggaccac ggtcccactc gtatcgtcgg tctgattatt agtctgggac cacgatccca    38160
ctcgtgttgt cggtctgatt atcggtctgg gaccacggtc ccacttgtat tgtcgatcag   38220
actatcagcg tgagactacg attccatcaa tgcctgtcaa gggcaagtat tgacatgtcg   38280
tcgtaacctg tagaacggag taacctcggt gtgcggttgt atgcctgctg tggattgctg   38340
ctgtgtcctg cttatccaca acatttgcg cacggttatg tggacaaaat acctggttac     38400
```

```
ccaggccgtg ccggcacgtt aaccgggcac atttccccga aaagtgccac ctgacgtcta   38460
agaaaccatt attatcatga cattaaccta taaaaatagg cgtatcacga ggcccttcg    38520 tcttcaagaa ttggatccga attcccggga gagctcgata tcgcatgcgg atttaaatta  38580
attaa                                                               38585
```

<210> SEQ ID NO 36
<211> LENGTH: 37233
<212> TYPE: DNA
<213> ORGANISM: Artificial Sequence
<220> FEATURE:
<223> OTHER INFORMATION: Construct

<400> SEQUENCE: 36

```
catcatcaat aatataccttt attttggatt gaagccaata tgataatgag ggggtggagt    60
ttgtgacgtg gcgcggggcg tgggaacggg gcgggtgacg tagtagtgtg gcggaagtgt    120
gatgttgcaa gtggcggaa acacatgtaa gcgacggatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccatttcgc gggaaaactg aataagagga    300
agtgaaatct gaataatttt gtgttactca tagcgcgtaa tagaagccat agagcccacc   360
gcatccccag catgcctgct agaattcgaa caaacgaccc aacacccgtg cgttttattc   420
tgtcttttta ttgccggcgg ccgcgaacaa atgtggtatg gctgattatg atcctctaga   480
gataattcta gttacccggg gagcatgtca aggtccaaat cgtcaagagc gtcagcaggc   540
agcatatcaa ggtcaaagtc gtcaagggca tcggctggga gcatgtctaa gtcaaaatcg   600
tcaagggcgt cggccggccc gccgcttcg cactttagct gtttctccag gccacatatg   660
attagttcca ggccgaaaag gaaggcaggt tcggctccct gatggtcgaa cagctcaatt   720
gcttgtctca gaagtgggggg catagaatcg gtggtaggtg tctctcttc ctcttttgct   780 acttgatgct cctgatcctc caatacgcag cccagtgtaa agtggccac ggcggacaga   840 gcgtacagtg cgttctccag ggagaagcct tgctgacaca ggaacgcgag ctgattttcc    900
agggtttcgt actgtttctc tgttgggcgg gtgccgagat gcactttagc cccgtcgcga   960
tgtgagagga gagcacagcg gaatgacttg gcgttgttcc gcagaaagtc ttgccatgac   1020
tcgccttcca gggggcagaa gtgggtatga tgcctgtcca gcatctcgat tgccagggca   1080
tcgagcaggg cccgcttgtt cttcacgtgc cagtacaggg taggctgctc aactcccagc   1140
ttttgagcga gtttccttgt cgtcaggcct tcgataccga cttcattgag taattccaga   1200
gcagagttta tgactttgct cttgtccagt ctagacatag gacgcgtcag ctgactagag   1260 gatcccgcg gagggtacc aagcttaagt ttaaacgcta gcagcttgg gtctccctat    1320 agtgagtcgt attaatttcg ataagccagt aagcagtggg ttctctagtt agccagagag   1380
ctctgcttat atagacctcc caccgtacac gcctaccgcc catttgcgtc aatgggcgg    1440 agttgttacg acattttgga aagtcccgtt gattttggtg ccaaaacaaa ctcccattga   1500
cgtcaatggg gtggagactt ggaaatcccc gtgagtcaaa ccgctatcca cgcccattga   1560
tgtactgcca aaaccgcatc accatggtaa tagcgatgac taatacgtag atgtactgcc   1620
aagtaggaaa gtcccataag gtcatgtact gggcataatg ccaggcgggc catttaccgt   1680
cattgacgtc aataggggc gtacttggca tatgatacac ttgatgtact gccaagtggg   1740
cagtttaccg taaatactcc acccattgac gtcaatggaa agtccctatt ggcgttacta   1800
```

```
tgggaacata cgtcattatt gacgtcaatg ggcggggtc gttgggcggt cagccaggcg    1860
ggccatttac cgtaagttat gtaacgcgga actccatata tgggctatga actaatgacc    1920
ccgtaattga ttactattaa taactagtca ataatcaatg tcaacgcgta tatctgtggg    1980
cgtggcttaa gggtgggaaa gaatatataa ggtgggggtc ttatgtagtt ttgtatctgt    2040
tttgcagcag ccgccgccgc catgagcacc aactcgtttg atggaagcat tgtgagctca    2100
tatttgacaa cgcgcatgcc cccatgggcc ggggtgcgtc agaatgtgat gggctccagc    2160
attgatggtc gccccgtcct gcccgcaaac tctactacct tgacctacga gaccgtgtct    2220
ggaacgccgt tggagactgc agcctccgcc gccgcttcag ccgctgcagc caccgcccgc    2280
gggattgtga ctgactttgc tttcctgagc ccgcttgcaa gcagtgcagc ttcccgttca    2340
tccgcccgcg atgacaagtt gacggctctt ttggcacaat tggattcttt gacccgggaa    2400
cttaatgtcg tttctcagca gctgttggat ctgcgccagc aggtttctgc cctgaaggct    2460
tcctcccctc ccaatgcggt ttaaaacata aataaaaaac cagactctgt ttggatttgg    2520
atcaagcaag tgtcttgctg tctttattta ggggttttgc gcgcgcggta ggcccgggac    2580
cagcggtctc ggtcgttgag ggtcctgtgt attttttcca ggacgtggta aaggtgactc    2640
tggatgttca gatacatggg cataagcccg tctctggggt ggaggtagca ccactgcaga    2700
gcttcatgct gcggggtggt gttgtagatg atccagtcgt agcaggagcg ctgggcgtgg    2760
tgcctaaaaa tgtcttttcag tagcaagctg attgccaggg gcaggccctt ggtgtaagtg    2820
tttacaaagc ggttaagctg ggatgggtgc atacgtgggg atatgagatg catcttggac    2880
tgtattttta ggttggctat gttcccagcc atatccctcc ggggattcat gttgtgcaga    2940
accaccagca cagtgtatcc ggtgcacttg ggaaatttgt catgtagctt agaaggaaat    3000
gcgtggaaga acttggagac gcccttgtga cctccaagat tttccatgca ttcgtccata    3060
atgatggcaa tgggcccacg ggcggcggcc tgggcgaaga tatttctggg atcactaacg    3120
tcatagttgt gttccaggat gagatcgtca taggccattt ttacaaagcg cgggcggagg    3180
gtgccagact gcggtataat ggttccatcc ggcccagggg cgtagttacc ctcacagatt    3240
tgcatttccc acgctttgag ttcagatggg gggatcatgt ctacctgcgg ggcgatgaag    3300
aaaacggttt ccggggtagg ggagatcagc tgggaagaaa gcaggttcct gagcagctgc    3360
gacttaccgc agccgtgggg cccgtaaatc acacctatta ccggctgcaa ctggtagtta    3420
agagagctgc agctgccgtc atccctgagc aggggggcca cttcgttaag catgtccctg    3480
actcgcatgt tttccctgac caaatccgcc agaaggcgct cgccgcccag cgatagcagt    3540
tcttgcaagg aagcaaagtt tttcaacggt ttgagaccgt ccgccgtagg catgcttttg    3600
agcgtttgac caagcagttc caggcggtcc cacagctcgg tcacctgctc tacggcatct    3660
cgatccagca tatctcctcg tttcgcgggt tggggcggct ttcgctgtac ggcagtagtc    3720
ggtgctcgtc cagacgggcc agggtcatgt cttttccacgg gcgcagggtc ctcgtcagcg    3780
tagtctgggt cacggtgaag gggtgcgctc cgggctgcgc gctggccagg gtgcgcttga    3840
ggctggtcct gctggtgctg aagcgctgcc ggtcttcgcc ctgcgcgtcg gccaggtagc    3900
atttgaccat ggtgtcatag tccagcccct ccgcggcgtg gccttggcg cgcagcttgc    3960
ccttggagga ggcgccgcac gagggggcagt gcagacttt gagggcgtag agcttgggcg    4020
cgagaaatac cgattccggg gagtaggcat ccgcgccgca ggccccgcag acggtctcgc    4080
attccacgag ccaggtgagc tctggccgtt cggggtcaaa aaccaggttt ccccccatgct    4140
ttttgatgcg tttcttacct ctggtttcca tgagccggtg tccacgctcg gtgacgaaaa    4200
```

```
ggctgtccgt gtccccgtat acagacttga gaggcctgtc ctcgagcggt gttccgcggt    4260
cctcctcgta tagaaactcg gaccactctg agacaaaggc tcgcgtccag gccagcacga    4320
aggaggctaa gtgggagggg tagcggtcgt tgtccactag ggggtccact cgctccaggg    4380
tgtgaagaca catgtcgccc tcttcggcat caaggaaggt gattggtttg taggtgtagg    4440
ccacgtgacc gggtgttcct gaaggggggc tataaaaggg ggtgggggcg cgttcgtcct    4500
cactctcttc cgcatcgctg tctgcgaggg ccagctgttg gggtgagtac tccctctgaa    4560
aagcgggcat gacttctgcg ctaagattgt cagtttccaa aaacgaggag gatttgatat    4620
tcacctggcc cgcggtgatg cctttgaggg tggccgcatc catctggtca gaaaagacaa    4680 tcttttttgtt gtcaagcttg gtggcaaacg accgctagag ggcgttggac agcaacttgg    4740
cgatggagcg cagggtttgg tttttgtcgc gatcggcgcg ctccttggcc gcgatgttta    4800
gctgcacgta ttcgcgcgca acgcaccgcc attcgggaaa gacggtggtg cgctcgtcgg    4860
gcaccaggtg cacgcgccaa ccgcggttgt gcagggtgac aaggtcaacg ctggtggcta    4920
cctctccgcg taggcgctcg ttggtccagc agaggcggcc gcccttgcgc gagcagaatg    4980
gcggtagggg gtctagctgc gtctcgtccg ggggtctgc gtccacggta aagacccc gg    5040 gcagcaggcg cgcgtcgaag tagtctatct tgcatccttg caagtctagc gcctgctgcc    5100
atgcgcgggc ggcaagcgcg cgctcgtatg ggttgagtgg gggacccat ggcatggggt    5160 gggtgagcgc ggaggcgtac atgccgcaaa tgtcgtaaac gtagaggggc tctctgagta    5220
ttccaagata tgtagggtag catcttccac cgcggatgct ggcgcgcacg taatcgtata    5280
gttcgtgcga gggagcgagg aggtcgggac cgaggttgct acgggcgggc tgctctgctc    5340
ggaagactat ctgcctgaag atggcatgtg agttggatga tatggttgga cgctggaaga    5400
cgttgaagct ggcgtctgtg agacctaccg cgtcacgcac gaaggaggcg taggagtcgc    5460
gcagcttgtt gaccagctcg gcggtgacct gcacgtctag ggcgcagtag tccagggttt    5520
ccttgatgat gtcatactta tcctgtccct tttttttcca cagctcgcgg ttgaggacaa    5580
actcttcgcg gtctttccag tactcttgga tcggaaaccc gtcggcctcc gaacggtaag    5640
agcctagcat gtagaactgg ttgacggcct ggtaggcgca gcatcccttt tctacgggta    5700
gcgcgtatgc ctgcgcggcc ttccggagcg aggtgtgggt gagcgcaaag gtgtccctga    5760
ccatgaccag catgaagggc acgagctgct tcccaaaggc ccccatccaa gtataggtct    5820
ctacatcgta ggtgacaaag agacgctcgg tgcgaggatg cgagccgatc gggaagaact    5880
ggatctcccg ccaccaattg gaggagtggc tattgatgtg gtgaaagtag aagtccctgc    5940
gacgggccga acactcgtgc tggctttttgt aaaaacgtgc gcagtactgg cagcggtgca    6000
cgggctgtac atcctgcacg aggttgacct gacgaccgcg cacaaggaag cagagtggga    6060
atttgagccc ctcgcctggc gggtttggct ggtggtcttc tacttcggct gcttgtcctt    6120
gaccgtctgg ctgctcgagg ggagttacgg tggatcggac caccacgccg cgcgagccca    6180
aagtccagat gtccgcgcgc ggcggtcgga gcttgatgac aacatcgcgc agatgggagc    6240
tgtccatggt ctggagctcc cgcggcgtca ggtcaggcgg gagctcctgc aggtttacct    6300
cgcatagacg ggtcagggcg cgggctagat ccaggtgata cctaatttcc aggggctggt    6360
tggtggcggc gtcgatggct tgcaagaggc cgcatccccg cggcgcgact acggtaccgc    6420
gcggcgggcg gtgggccgcg ggggtgtcct tggatgatgc atctaaaagc ggtgacgcgg    6480
gcgagccccc ggaggtaggg ggggctccgg acccgccggg agaggggca ggggcacgtc    6540
```

```
ggcgccgcgc gcgggcagga gctggtgctg cgcgcgtagg ttgctggcga acgcgacgac    6600
gcggcggttg atctcctgaa tctggcgcct ctgcgtgaag acgacgggcc cggtgagctt    6660
gaacctgaaa gagagttcga cagaatcaat ttcggtgtcg ttgacggcgg cctggcgcaa    6720
aatctcctgc acgtctcctg agttgtcttg ataggcgatc tcggccatga actgctcgat    6780
ctcttcctcc tggagatctc cgcgtccggc tcgctccacg gtgcggcga ggtcgttgga     6840 aatgcgggcc atgagctgcg agaaggcgtt gaggcctccc tcgttccaga cgcggctgta    6900
gaccacgccc ccttcggcat cgcgggcgcg catgaccacc tgcgcgagat tgagctccac    6960
gtgccgggcg aagacggcgt agtttcgcag gcgctgaaag aggtagttga gggtggtggc    7020
ggtgtgttct gccacgaaga agtacataac ccagcgtcgc aacgtggatt cgttgatatc    7080
ccccaaggcc tcaaggcgct ccatggcctc gtagaagtcc acggcgaagt tgaaaaactg    7140
ggagttgcgc gccgacacgg ttaactcctc ctccagaaga cggatgagct cggcgacagt    7200
gtcgcgcacc tcgcgctcaa aggctacagg ggcctcttct tcttcttcaa tctcctcttc    7260
cataagggcc tccccttctt cttcttctgg cggcggtggg ggagggggga cacggcggcg    7320
acgacggcgc accggaggc ggtcgacaaa gcgctcgatc atctccccgc ggcgacggcg     7380
catggtctcg gtgacggcgc ggccgttctc gcggggggcg agttggaaga cgccgcccgt    7440
catgtcccgg ttatgggttg gcggggggct gccatgcggc agggatacgg cgctaacgat    7500
gcatctcaac aattgttgtg taggtactcc gccgccgagg gacctgagcg agtccgcatc    7560
gaccggatcg gaaaacctct cgagaaaggc gtctaaccag tcacagtcgc aaggtaggct    7620
gagcaccgtg gcgggcggca gcgggcggcg gtcggggttg tttctggcgg aggtgctgct    7680
gatgatgtaa ttaaagtagg cggtcttgag acggcggatg gtcgacagaa gcaccatgtc    7740
cttgggtccg gcctgctgaa tgcgcaggcg gtcggccatg ccccaggctt cgttttgaca    7800
tcggcgcagg tctttgtagt agtcttgcat gagcctttct accggcactt cttcttctcc    7860
ttcctcttgt cctgcatctc ttgcatctat cgctgcggcg gcggcggagt ttggccgtag    7920
gtggcgccct cttcctccca tgcgtgtgac cccgaagccc ctcatcggct gaagcagggc    7980
taggtcggca caacgcgct cggctaatat ggctgctgc acctgcgtga gggtagactg      8040
gaagtcatcc atgtccacaa agcggtggta tgcgcccgtg ttgatggtgt aagtgcagtt    8100
ggccataacg gaccagttaa cggtctggtg acccggctgc gagagctcgg tgtacctgag    8160
acgcgagtaa gccctcgagt caaatacgta gtcgttgcaa gtccgcacca ggtactggta    8220
tcccaccaaa aagtgcggcg gcggctggcg gtagaggggc cagcgtaggg tggccggggc    8280
tccgggggcg agatcttcca acataaggcg atgatatccg tagatgtacc tggacatcca    8340
ggtgatgccg gcgcggtgg tggaggcgcg cggaaagtcg cggacgcggt tccagatgtt     8400
gcgcagcggc aaaaagtgct ccatggtcgg gacgctctgg ccggtcaggc gcgcgcaatc    8460
gttgacgctc tagaccgtgc aaaaggagag cctgtaagcg ggcactcttc cgtgatgcgc    8520
ccgtgttgat ggtgtaagtg cagttggcca taacggacca gttaacgtc tggtgacccg     8580 gctgcgagag ctcggtgtac ctgagacgcg agtaagccct cgagtcaaat acgtagtcgt    8640
tgcaagtccg caccaggtac tggtatccca ccaaaaagtg cggcggcggc tggcggtaga    8700
ggggccagcg tagggtggcc ggggctccgg ggcgagatc ttccaacata aggcgatgat     8760
atccgtagat gtacctggac atccaggtga tgccggcggc ggtggtggag gcgcgcggaa    8820
agtcgcggac gcggttccag atgttgcgca gcggcaaaaa gtgctccatg gtcgggacgc    8880
tctggccggt caggcgcgcg caatcgttga cgctctagac cgtgcaaaag gagagcctgt    8940
```

```
aagcgggcac tcttccgtgg ctggggcagg aggacacggg cagcctggag gcaaccctaa    9000
actacctgct gaccaaccgg cggcagaaga tcccctcgtt gcacagttta aacagcgagg    9060
aggagcgcat tttgcgctac gtgcagcaga gcgtgagcct taacctgatg cgcgacgggg    9120
taacgcccag cgtggcgctg acatgaccg cgcgcaacat ggaacgggc atgtatgcct     9180
caaaccggcc gtttatcaac cgcctaatgg actacttgca tcgcgcggcc gccgtgaacc   9240
ccgagtattt caccaatgcc atcttgaacc cgcactggct accgccccct ggtttctaca   9300
ccggggggatt cgaggtgccc gagggtaacg atggattcct ctgggacgac atagacgaca  9360
gcgtgtttc cccgcaaccg cagaccctgc tagagttgca acagcgcgag caggcagagg    9420
cggcgctgcg aaaggaaagc ttccgcaggc caagcagctt gtccgatcta ggcgctgcgg   9480
ccccgcggtc agatgctagt agcccatttc caagcttgat agggtctctt accagcactc   9540
gcaccacccg cccgcgcctg ctgggcgagg aggagtacct aaacaactcg ctgctgcagc   9600
cgcagcgcga aaaaaacctg cctccggcat ttcccaacaa cgggatagag agcctagtgg   9660
acaagatgag tagatggaag acgtacgcgc aggagcacag ggacgtgcca ggcccgcgcc   9720
cgcccacccg tcgtcaaagg cacgaccgtc agcggggtct ggtgtgggag gacgatgact   9780
cggcagacga cagcagcgtc ctggatttgg gagggagtgg caacccgttt gcgcaccttc   9840
gccccaggct ggggagaatg ttttaaaaaa aaaaaaagca tgatgcaaaa taaaaaactc   9900
accaaggcca tggcaccgag cgttggtttt cttgtattcc ccttagtatg cggcgcgcgg   9960
cgatgtatga ggaaggtcct cctccctcct acgagagtgt ggtgagcgcg cgcgccagtgg  10020
cggcggcgct gggttctccc ttcgatgctc ccctggaccc gccgtttgtg cctccgcggt   10080
acctgcggcc taccggggg agaaacagca tccgttactc tgagttggca ccctattcg    10140
acaccacccg tgtgtacctg gtggacaaca agtcaacgga tgtggcatcc ctgaactacc   10200
agaacgacca cagcaacttt ctgaccacgt tcattcaaaa caatgactac agcccggggg   10260
aggcaagcac acagaccatc aatcttgacg accggtcgca ctggggcggc gacctgaaaa   10320
ccatcctgca taccaacatg ccaaatgtga acgagttcat gtttaccaat aagtttaagg   10380
cgcgggtgat ggtgtcgcgc ttgcctacta aggacaatca ggtggagctg aaatacgagt   10440
gggtggagtt cacgctgccc gagggcaact actccgagac catgaccata gaccttatga   10500
acaacgcgat cgtggagcac tacttgaaag tgggcagaca gaacgggttc tggaaagcg    10560
acatcggggt aaagtttgac acccgcaact tcagactggg gtttgacccc gtcactggtc   10620
ttgtcatgcc tgggtatat acaaacgaag ccttccatcc agacatcatt ttgctgccag    10680
gatgcgggt ggacttcacc cacagccgcc tgagcaactt gttgggcatc cgcaagcggc   10740
aaccccttcca ggagggcttt aggatcacct acgatgatct ggaggtggt aacattcccg   10800
cactgttgga tgtggacgcc taccaggcga gcttgaaaga tgacaccgaa cagggcgggg   10860
gtggcgcagg cggcagcaac agcagtggca gggcgcgga agagaactcc aacgcggcag   10920
ccgcggcaat gcagccggtg gaggacatga acgatcatgc cattcgcggc gacaccttg    10980
ccacacgggc tgaggagaag cgcgctgagg ccgaagcagc ggccgaagct gccgcccccg   11040
ctgcgcaacc cgaggtcgag aagcctcaga agaaaccggt gatcaaaccc ctgacagagg   11100
acagcaagaa acgcagttac aacctaataa gcaatgacag caccttcacc cagtaccgca   11160
gctggtacct tgcatacaac tacggcgacc ctcagaccgg aatccgctca tggaccctgc   11220
tttgcactcc tgacgtaacc tgcggctcgg agcaggtcta ctggtcgttg ccagacatga   11280
```

```
tgcaagaccc cgtgaccttc cgctccacgc gccagatcag caactttccg gtggtgggcg   11340
ccgagctgtt gcccgtgcac tccaagagct tctacaacga ccaggccgtc tactcccaac   11400
tcatccgcca gtttacctct ctgacccacg tgttcaatcg ctttcccgag aaccagattt   11460
tggcgcgccc gccagccccc accatcacca ccgtcagtga aaacgttcct gctctcacag   11520
atcacgggac gctaccgctg cgcaacagca tcggaggagt ccagcgagtg accattactg   11580
acgccagacg ccgcacctgc ccctacgttt acaaggccct gggcatagtc tcgccgcgcg   11640
tcctatcgag ccgcactttt tgagcaagca tgtccatcct tatatcgccc agcaataaca   11700
caggctgggg cctgcgcttc caagcaaga tgtttggcgg ggccaagaag cgctccgacc   11760
aacacccagt gcgcgtgcgc gggcactacc gcgcgccctg gggcgcgcac aaacgcggcc   11820
gcactgggcg caccaccgtc gatgacgcca tcgacgcggt ggtggaggag gcgcgcaact   11880
acacgcccac gccgccacca gtgtccacag tggacgcggc cattcagacc gtggtgcgcg   11940
gagcccggcg ctatgctaaa atgaagagac ggcggaggcg cgtagcacgt cgccaccgcc   12000
gccgacccgg cactgccgcc caacgcgcgg cggcggccct gcttaaccgc gcacgtcgca   12060
ccggccgacg ggcggccatg cgggccgctc gaaggctggc cgcgggtatt gtcactgtgc   12120
cccccaggtc caggcgacga gcggccgccg cagcagccgc ggccattagt gctatgactc   12180
agggtcgcag gggcaacgtg tattgggtgc gcgactcggt tagcggcctg cgcgtgcccg   12240
tgcgcacccg ccccccgcgc aactagattg caagaaaaaa ctactagac tcgtactgtt   12300 gtatgtatcc agcggcggcg gcgcgcaacg aagctatgtc caagcgcaaa atcaaagaag   12360
agatgctcca ggtcatcgcg ccggagatct atggcccccc gaagaaggaa gagcaggatt   12420
acaagccccg aaagctaaag cgggtcaaaa agaaaaagaa agatgatgat gatgaacttg   12480
acgacgaggt ggaactgctg cacgctaccg cgcccaggcg acgggtacag tggaaaggtc   12540
gacgcgtaaa acgtgttttg cgacccggca ccaccgtagt ctttacgccc ggtgagcgct   12600
ccacccgcac ctacaagcgc gtgtatgatg aggtgtacgg cgacgaggac ctgcttgagc   12660
aggccaacga gcgcctcggg gagtttgcct acggaaagcg gcataaggac atgctggcgt   12720
tgccgctgga cgagggcaac ccaacaccta gcctaaagcc cgtaacactg cagcaggtgc   12780 tgccccgcgct tgcaccgtcc gaagaaaagc gcggcctaaa gcgcgagtct ggtgacttgg   12840
cacccaccgt gcagctgatg gtacccaagc gccagcgact ggaagatgtc ttggaaaaaa   12900
tgaccgtgga acctgggctg gagcccgagg tccgcgtgcg gccaatcaag caggtggcgc   12960
cgggactggg cgtgcagacc gtggacgttc agatacccac taccagtagc accagtattg   13020
ccaccgccac agagggcatg gagacacaaa cgtccccggt tgcctcagcg gtggcggatg   13080
ccgcggtgca ggcggtcgct gcggccgcgt ccaagacctc tacggaggtg caaacggacc   13140
cgtggatgtt tcgcgtttca gccccccggc gcccgcgccg ttcgaggaag tacggcgccg   13200
ccagcgcgct actgccccgaa tatgccctac atccttccat tgcgcctacc cccgctatc   13260 gtggctacac ctaccgcccc agaagacgag caactacccg acgccgaacc accactggaa   13320
cccgccgccg ccgtcgccgt cgccagcccg tgctggcccc gatttccgtg cgcagggtgg   13380
ctcgcgaagg aggcaggacc ctggtgctgc aacagcgcg ctaccacccc agcatcgttt   13440
aaaagccggt cttttgtggtt cttgcagata tggccctcac ctgccgcctc cgtttcccgg   13500
tgccgggatt ccgaggaaga atgcaccgta ggagggcat ggccggccac ggcctgacgg   13560
gcggcatgcg tcgtgcgcac caccggcggc ggcgcgcgtc gcaccgtcgc atgcgcggcg   13620
gtatcctgcc cctccttatt ccactgatcg ccgcggcgat tggcgccgtg cccggaattg   13680
```

```
catccgtggc cttgcaggcg cagagacact gattaaaaac aagttgcatg tggaaaaatc    13740
aaaataaaaa gtctggactc tcacgctcgc ttggtcctgt aactattttg tagaatggaa    13800
gacatcaact ttgcgtctct ggccccgcga cacggctcgc gcccgttcat gggaaactgg    13860
caagatatcg gcaccagcaa tatgagcggt ggcgccttca gctggggctc gctgtggagc    13920
ggcattaaaa atttcggttc caccgttaag aactatggca gcaaggcctg aacagcagc     13980 acaggccaga tgctgaggga taagttgaaa gagcaaaatt tccaacaaaa ggtggtagat    14040
ggcctggcct ctggcattag cggggtggtg gacctggcca accaggcagt gcaaaataag    14100
attaacagta agcttgatcc ccgccctccc gtagaggagc ctccaccggc cgtggagaca    14160
gtgtctccag aggggcgtgg cgaaaagcgt ccgcgccccg acaggaagaa aactctggtg    14220
acgcaaatag acgagcctcc ctcgtacgag gaggcactaa agcaaggcct gcccaccacc    14280
cgtcccatcg cgcccatggc taccggagtg ctgggccagc acacacccgt aacgctggac    14340
ctgcctcccc ccgccgacac ccagcagaaa cctgtgctgc caggcccgac cgccgttgtt    14400
gtaacccgtc ctagccgcgc gtccctgcgc cgcgccgcca gcggtccgcg atcgttgcgg    14460
cccgtagcca gtggcaactg gcaaagcaca ctgaacagca tcgtgggtct gggggtgcaa    14520
tccctgaagc gccgacgatg cttctgatag ctaacgtgtc gtatgtgtgt catgtatgcg    14580
tccatgtcgc cgccagagga gctgctgagc cgccgcgcgc ccgctttcca agatggctac    14640
cccttcgatg atgccgcagt ggtcttacat gcacatctcg ggccaggacg cctcggagta    14700
cctgagcccc gggctggtgc agtttgcccg cgccaccgag acgtacttca gcctgaataa    14760
caagtttaga accccacggg tggcgcctac gcacgacgtg accacagacc ggtcccagcg    14820
tttgacgctg cggttcatcc ctgtggaccg tgaggatact cgtactcgt acaaggcgcg     14880 gttcacccta gctgtgggtg ataaccgtgt gctggacatg gcttccacgt actttgacat    14940
ccgcggcgtg ctggacaggg gccctacttt taagccctac tctggcactg cctacaacgc    15000
cctggctccc aagggtgccc caaatccttg cgaatgggat gaagctgcta ctgctcttga    15060
aataaaccta gaagaagagg acgatgacaa cgaagacgaa gtagacgagc aagctgagca    15120
gcaaaaaact cacgtatttg ggcaggcgcc ttattctggt ataaatatta caaaggaggg    15180
tattcaaata ggtgtcgaag gtcaaacacc taaatatgcc gataaaacat ttcaacctga    15240
acctcaaata ggagaatctc agtggtacga aacagaaatt aatcatgcag ctgggagagt    15300
cctaaaaaag actaccccaa tgaaaccatg ttacggttca tatgcaaaac ccacaaatga    15360
aaatggaggg caaggcattc ttgtaaagca acaaaatgga aagctagaaa gtcaagtgga    15420
aatgcaattt ttctcaacta ctgaggcagc cgcaggcaat ggtgataact tgactcctaa    15480
agtggtattg tacagtgaag atgtagatat agaaacccca gacactcata tttcttacat    15540
gcccactatt aaggaaggta actcacgaga actaatgggc caacaatcta tgcccaacag    15600
gcctaattac attgctttta gggacaattt tattggtcta atgtattaca acagcacggg    15660
taatatgggt gttctggcgg gccaagcatc gcagttgaat gctgttgtag atttgcaaga    15720
cagaaacaca gagctttcat accagctttt gcttgattcc attggtgata gaaccaggta    15780
cttttctatg tggaatcagg ctgttgacag ctatgatcca gatgttagaa ttattgaaaa    15840
tcatggaact gaagatgaac ttccaaatta ctgctttcca ctgggaggtg tgattaatac    15900
agagactctt accaaggtaa aacctaaaac aggtcaggaa aatggatggg aaaaagatgc    15960
tacagaattt tcagataaaa atgaaataag agttggaaat aatttgcca tggaaatcaa     16020
```

```
tctaaatgcc aacctgtgga gaaatttcct gtactccaac atagcgctgt atttgcccga    16080
caagctaaag tacagtcctt ccaacgtaaa aatttctgat aacccaaaca cctacgacta    16140
catgaacaag cgagtggtgg ctcccgggct agtggactgc tacattaacc ttggagcacg    16200
ctggtccctt gactatatgg acaacgtcaa cccatttaac caccaccgca atgctggcct    16260
gcgctaccgc tcaatgttgc tgggcaatgg tcgctatgtg cccttccaca tccaggtgcc    16320
tcagaagttc tttgccatta aaaacctcct tctcctgccg ggctcataca cctacgagtg    16380
gaacttcagg aaggatgtta acatggttct gcagagctcc ctaggaaatg acctaagggt    16440
tgacggagcc agcattaagt ttgatagcat ttgcctttac gccaccttct tccccatggc    16500
ccacaacacc gcctccacgc ttgaggccat gcttagaaac gacaccaacg accagtcctt    16560
taacgactat ctctccgccg ccaacatgct ctaccctata cccgccaacg ctaccaacgt    16620
gcccatatcc atccctcc gcaactgggc ggctttccgc ggctgggcct tcacgcgcct    16680
taagactaag gaaaccccat cactgggctc gggctacgac ccttattaca cctactctgg    16740
ctctataccc tacctagatg gaaccttta cctcaaccac accttaaga aggtggccat    16800
taccttgac tcttctgtca gctggcctgg caatgaccgc ctgcttaccc caacgagtt    16860
tgaaattaag cgctcagttg acggggaggg ttacaacgtt gcccagtgta acatgaccaa    16920
agactggttc ctggtacaaa tgctagctaa ctataacatt ggctaccagg gcttctatat    16980
cccagagagc tacaaggacc gcatgtactc cttctttaga aacttccagc ccatgagccg    17040
tcaggtggtg gatgatacta aatacaagga ctaccaacag gtgggcatcc tacaccaaca    17100
caacaactct ggatttgttg gctaccttgc ccccaccatg cgcgaaggac aggcctaccc    17160
tgctaacttc ccctatccgc ttataggcaa gaccgcagtt gacagcatta cccagaaaaa    17220
gtttctttgc gatcgcaccc tttgcgcat cccattctcc agtaactta tgtccatggg    17280
cgcactcaca gacctgggcc aaaaccttct ctacgccaac tccgcccacg cgctagacat    17340
gactttgag gtggatccca tggacgagcc caccttctt tatgttttgt ttgaagtctt    17400
tgacgtggtc cgtgtgcacc agccgcaccg cggcgtcatc gaaaccgtgt acctgcgcac    17460
gcccttctcg gccggcaacg ccacaacata aagaagcaag caacatcaac aacagctgcc    17520
gccaaataat gtactagaga cactttcaat aaaggcaaat gcttttattt gtacactctc    17580
gggtgattat ttacccccac ccttgccgtc tgcgccgttt aaaaatcaaa ggggttctgc    17640
cgcgcatcgc tatgcgccac tggcagggac acgttgcgat actggtgttt agtgctccac    17700
ttaaactcag gcacaaccat ccgcggcagc tcggtgaagt tttcactcca caggctgcgc    17760
accatcacca acgcgtttag caggtcgggc gccgatatct tgaagtcgca gttggggcct    17820
ccgccctgcg cgcgcgagtt gcgatacaca gggttcagc actggaacac tatcagcgcc    17880
gggtggtgca cgctggccag cacgctcttg tcggagatca gatccgcgtc caggtcctcc    17940
gcgttgctca gggcgaacgg agtcaacttt ggtagctgcc ttcccaaaaa gggcgcgtgc    18000
ccaggctttg agttgcactc gcaccgtagt ggcatcaaaa ggtgaccgtg cccggtctgg    18060
gcgttaggat acagcgcctg cataaaagcc ttgatctgct aaaagccac ctgagccttt    18120
gcgccttcag agaagaacat gccgcaagac ttgccgaaaa actgattggc cggacaggcc    18180
gcgtcgtgca cgcagcacct tgcgtcggtg ttggagatct gcaccacatt tcggcccac    18240
cggttcttca cgatcttggc cttgctagac tgctccttca gcgcgcgctg cccgttttcg    18300
ctcgtcacat ccatttcaat cacgtgctcc ttatttatca taatgcttcc gtgtagacac    18360
ttaagctcgc cttcgatctc agcgcagcgg tgcagccaca acgcgcagcc cgtgggctcg    18420
```

```
tgatgcttgt aggtcacctc tgcaaacgac tgcaggtacg cctgcaggaa tcgccccatc    18480
atcgtcacaa aggtcttgtt gctggtgaag gtcagctgca acccgcggtg ctcctcgttc    18540
agccaggtct tgcatacggc cgccagagct tccacttggt caggcagtag tttgaagttc    18600
gcctttagat cgttatccac gtggtacttg tccatcagcg cgcgcgcagc ctccatgccc    18660
ttctcccacg cagacacgat cggcacactc agcgggttca tcaccgtaat ttcactttcc    18720
gcttcgctgg gctcttcctc ttcctcttgc gtccgcatac cacgcgccac tgggtcgtct    18780
tcattcagcc gccgcactgt gcgcttacct cctttgccat gcttgattag caccggtggg    18840
ttgctgaaac ccaccatttg tagcgccaca tcttctcttt cttcctcgct gtccacgatt    18900
acctctggtg atggcgggcg ctcgggcttg ggagaagggc gcttcttttt cttcttgggc    18960
gcaatggcca atccgccgc cgaggtcgat ggccgcgggc tgggtgtgcg cggcaccagc    19020
gcgtcttgtg atgagtcttc ctcgtcctcg gactcgatac gccgcctcat ccgctttttt    19080
gggggcgccc ggggaggcgg cggcgacggg gacgggacg acacgtcctc catggttggg    19140
ggacgtcgcg ccgcaccgcg tccgcgctcg ggggtggttt cgcgctgctc ctcttcccga    19200
ctggccattt ccttctcccta taggcagaaa aagatcatgg agtcagtcga gaagaaggac    19260
agcctaaccg cccccctctga gttcgccacc accgcctcca ccgatgccgc caacgcgcct    19320
accaccttcc ccgtcgaggc accccgcctt gaggaggagg aagtgattat cgagcaggac    19380
ccaggttttg taagcgaaga cgacgaggac cgctcagtac caacagagga taaaaagcaa    19440
gaccaggaca acgcagaggc aaacgaggaa caagtcgggc gggggacga aaggcatggc    19500 gactacctag atgtgggaga cgacgtgctg ttgaagcatc tgcagcgcca gtgcgccatt    19560
atctgcgacg cgttgcaaga gcgcagcgat gtgccctcg ccatagcgga tgtcagcctt    19620
gcctacgaac gccacctatt ctcaccgcgc gtaccccca aacgccaaga aaacggcaca    19680
tgcgagccca acccgcgcct caacttctac cccgtatttg ccgtgccaga ggtgcttgcc    19740
acctatcaca tcttttttcca aaactgcaag ataccctat cctgccgtgc caaccgcagc    19800
cgagcggaca agcagctggc cttgcggcag ggcgctgtca tacctgatat cgcctcgctc    19860
aacgaagtgc caaaaatctt tgagggtctt ggacgcgacg agaagcgcgc ggcaaacgct    19920
ctgcaacagg aaaacagcga aaatgaaagt cactctggag tgttggtgga actcgagggt    19980
gacaacgcgc gcctagccgt actaaaacgc agcatcgagg tcacccactt tgcctacccg    20040
gcacttaacc tacccccaa ggtcatgagc acagtcatga gtgagctgat cgtgcgccgt    20100
gcgcagcccc tggagaggga tgcaaatttg caagaacaaa cagaggaggg cctacccgca    20160
gttggcgacg agcagctagc gcgctggctt caaacgcgcg agcctgccga cttggaggag    20220
cgacgcaaac taatgatggc cgcagtgctc gttaccgtgg agcttgagtg catgcagcgg    20280
ttctttgctg acccggagat gcagcgcaag ctagaggaaa cattgcacta cacctttcga    20340
cagggctacg tacgccaggc ctgcaagatc tccaacgtgg agctctgcaa cctggtctcc    20400
taccttggaa ttttgcacga aaaccgcctt gggcaaaacg tgcttcattc cacgctcaag    20460
ggcgaggcgc gccgcgacta cgtccgcgac tgcgtttact tatttctatg ctacacctgg    20520
cagacggcca tgggcgtttg gcagcagtgc ttggaggagt gcaacctcaa ggagctgcag    20580
aaactgctaa agcaaaactt gaaggaccta tggacggcct tcaacgagcg ctccgtggcc    20640
gcgcacctgg cggacatcat tttccccgaa cgcctgctta aaccctgca acagggtctg    20700 ccagacttca ccagtcaaag catgttgcag aactttagga actttatcct agagcgctca    20760
```

```
ggaatcttgc ccgccacctg ctgtgcactt cctagcgact ttgtgcccat taagtaccgc   20820
gaatgccctc cgccgctttg gggccactgc taccttctgc agctagccaa ctaccttgcc   20880
taccactctg acataatgga agacgtgagc ggtgacggtc tactggagtg tcactgtcgc   20940
tgcaacctat gcaccccgca ccgctccctg gtttgcaatt cgcagctgct taacgaaagt   21000
caaattatcg gtacctttga gctgcagggt ccctcgcctg acgaaaagtc cgcggctccg   21060
gggttgaaac tcactccggg gctgtggacg tcggcttacc ttcgcaaatt tgtacctgag   21120
gactaccacg cccacgagat taggttctac gaagaccaat cccgcccgcc taatgcggag   21180
cttaccgcct gcgtcattac ccagggccac attcttggcc aattgcaagc catcaacaaa   21240
gcccgccaag agtttctgct acgaaaggga cgggggtttt acttggaccc ccagtccggc   21300
gaggagctca acccaatccc cccgccgccg cagccctatc agcagcagcc gcgggccctt   21360
gcttcccagg atggcaccca aaagaagct gcagctgccg ccgccaccca cggacgagga   21420
ggaatactgg gacagtcagg cagaggaggt tttggacgag gaggaggagg acatgatgga   21480
agactgggag agcctagacg aggaagcttc cgaggtcgaa gaggtgtcag acgaaacacc   21540
gtcaccctcg gtcgcattcc cctcgccggc gccccagaaa tcggcaaccg gttccagcat   21600
ggctacaacc tccgctcctc aggcgccgcc ggcactgccc gttcgccgac ccaaccgtag   21660
atgggacacc actggaacca gggccggtaa gtccaagcag ccgccgccgt tagcccaaga   21720
gcaacaacag cgccaaggct accgctcatg gcgcgggcac aagaacgcca tagttgcttg   21780
cttgcaagac tgtgggggca acatctcctt cgcccgccgc tttcttctct accatcacgg   21840
cgtggccttc ccccgtaaca tcctgcatta ctaccgtcat ctctacagcc catactgcac   21900
cggcggcagc ggcagcaaca gcagcggcca cacagaagca aaggcgaccg gatagcaaga   21960
ctctgacaaa gcccaagaaa tccacagcgg cggcagcagc aggaggagga gcgctgcgtc   22020
tggcgcccaa cgaacccgta tcgacccgcg agcttagaaa caggatttttt cccactctgt   22080 atgctatatt tcaacagagc aggggccaag aacaagagct gaaaataaaa aacaggtctc   22140
tgcgatccct cacccgcagc tgcctgtatc acaaaagcga agatcagctt cggcgcacgc   22200
tggaagacgc ggaggctctc ttcagtaaat actgcgcgct gactcttaag gactagtttc   22260
gcgccctttc tcaaatttaa gcgcgaaaac tacgtcatct ccagcggcca cacccggcgc   22320
cagcacctgt tgtcagcgcc attatgagca aggaaattcc cacgccctac atgtggagtt   22380
accagccaca aatgggactt gcggctggag ctgcccaaga ctactcaacc cgaataaact   22440
acatgagcgc gggaccccac atgatatccc gggtcaacgg aatacgcgcc caccgaaacc   22500
gaattctcct ggaacaggcg gctattacca ccacacctcg taataacctt aatccccgta   22560
gttggcccgc tgcctggtg taccaggaaa gtcccgctcc caccactgtg gtacttccca   22620
gagacgccca ggccgaagtt cagatgacta actcaggggc gcagcttgcg ggcggctttc   22680
gtcacagggt gcggtcgccc gggcagggta taactcacct gacaatcaga gggcgaggta   22740
ttcagctcaa cgacgagtcg gtgagctcct cgcttggtct ccgtccggac gggacatttc   22800
agatcggcgg cgccggccgc tcttcattca cgcctcgtca ggcaatccta actctgcaga   22860
cctcgtcctc tgagccgcgc tctgaggca ttggaactct gcaatttatt gaggagtttg   22920
tgccatcggt ctactttaac cccttctcgg gacctccgg ccactatccg gatcaattta   22980
ttcctaactt tgacgcggta aaggactcgg cggacggcta cgactgaatg ttaagtggag   23040
aggcagagca actgcgcctg aaacacctgg tccactgtcg ccgccacaag tgctttgccc   23100
gcgactccgg tgagttttgc tactttgaat tgcccgagga tcatatcgag ggcccggcgc   23160
```

```
acggcgtccg gcttaccgcc cagggagagc ttgcccgtag cctgattcgg gagtttaccc    23220 agcgcccct  gctagttgag cgggacaggg gaccctgtgt tctcactgtg atttgcaact    23280
gtcctaaccc tggattacat caagatcttt gttgccatct ctgtgctgag tataataaat    23340
acagaaatta aatatactg  gggctcctat cgccatcctg taaacgccac cgtcttcacc    23400
cgcccaagca aaccaaggcg aaccttacct ggtactttta acatctctcc ctctgtgatt    23460
tacaacagtt tcaacccaga cggagtgagt ctacgagaga acctctccga gctcagctac    23520
tccatcagaa aaaacaccac cctccttacc tgccgggaac gtacgagtgc gtcaccggcc    23580
gctgcaccac acctaccgcc tgaccgtaaa ccagactttt tccggacaga cctcaataac    23640
tctgtttacc agaacaggag gtgagcttag aaaaccctta gggtattagg ccaaaggcgc    23700
agctactgtg gggtttatga acaattcaag caactctacg ggctattcta attcaggttt    23760
ctctagaaat ggacggaatt attacagagc agcgcctgct agaaagacgc agggcagcgg    23820
ccgagcaaca gcgcatgaat caagagctcc aagacatggt taacttgcac cagtgcaaaa    23880
ggggtatctt ttgtctggta aagcaggcca aagtcaccta cgacagtaat accaccggac    23940
accgccttag ctacaagttg ccaaccaagc gtcagaaatt ggtggtcatg gtgggagaaa    24000
agcccattac cataactcag cactcggtag aaaccgaagg ctgcattcac tcaccttgtc    24060
aaggacctga ggatctctgc acccttatta agacccgtgt cggtctcaaa gatcttattc    24120
cctttaacta ataaaaaaaa ataataaagc atcacttact taaaatcagt tagcaaattt    24180
ctgtccagtt tattcagcag cacctccttg ccctcctccc agctctggta ttgcagcttc    24240
ctcctggctg caaactttct ccacaatcta aatggaatgt cagtttcctc ctgttcctgt    24300
ccatccgcac ccactatctt catgttgttg cagatgaagc gcgcaagacc gtctgaagat    24360
accttcaacc ccgtgtatcc atatgacacg gaaaccggtc ctccaactgt gccttttctt    24420
actcctccct ttgtatcccc caatgggttt caagagagtc cccctggggt actctctttg    24480
cgcctatccg aacctctagt tacctccaat ggcatgcttg cgctcaaaat gggcaacggc    24540
ctctctctgg acgaggccgg caaccttacc tcccaaaatg taaccactgt gagcccacct    24600
ctcaaaaaaa ccaagtcaaa cataaacctg gaaatatctg caccccctcac agttacctca    24660 gaagccctaa ctgtggctgc cgccgcacct ctaatggtcg cgggcaacac actcaccatg    24720
caatcacagg ccccgctaac cgtgcacgac tccaaactta gcattgccac ccaaggaccc    24780
ctcacagtgt cagaaggaaa gctagccctg caaacatcag ccccctcac caccaccgat    24840 agcagtaccc ttactatcac tgcctcaccc cctctaacta ctgccactgg tagcttgggc    24900
attgacttga aagagcccat ttatacacaa aatggaaaac taggactaaa gtacggggct    24960
cctttgcatg taacagacga cctaaacact ttgaccgtag caactggtcc aggtgtgact    25020
attaataata cttccttgca aactaaagtt actggagcct gggtttttga ttcacaaggc    25080
aatatgcaac ttaatgtagc aggaggacta aggattgatt ctcaaaacag acgccttata    25140
cttgatgtta gttatccgtt tgatgctcaa aaccaactaa atctaagact aggacagggc    25200 cctctttttta taaactcagc ccacaacttg gatattaact acaacaaagg cctttacttg    25260
tttacagctt caaacaattc caaaaagctt gaggttaacc taagcactgc caaggggttg    25320
atgtttgacg ctacagccat agccattaat gcaggagatg ggcttgaatt tggttcacct    25380
aatgcaccaa acacaaatcc cctcaaaaca aaaattggcc atggcctaga atttgattca    25440
aacaaggcta tggttcctaa actaggaact ggccttagtt ttgacagcac aggtgccatt    25500
```

```
acagtaggaa acaaaaataa tgataagcta actttgtgga ccacaccagc tccatctcct    25560
aactgtagac taaatgcaga gaaagatgct aaactcactt tggtcttaac aaaatgtggc    25620
agtcaaatac ttgctacagt ttcagttttg gctgttaaag gcagtttggc tccaatatct    25680
ggaacagttc aaagtgctca tcttattata agatttgacg aaaatggagt gctactaaac    25740
aattccttcc tggacccaga atattggaac tttagaaatg gagatcttac tgaaggcaca    25800
gcctatacaa acgctgttgg atttatgcct aacctatcag cttatccaaa atctcacggt    25860
aaaactgcca aaagtaacat tgtcagtcaa gtttacttaa acggagacaa aactaaacct    25920
gtaacactaa ccattacact aaacggtaca caggaaacag gagacacaac tccaagtgca    25980
tactctatgt cattttcatg ggactggtct ggccacaact acattaatga aatatttgcc    26040
acatcctctt acactttttc atacattgcc caagaataaa gaatcgtttg tgttatgttt    26100
caacgtgttt attttttcaat tgcagaaaat ttcgaatcat ttttcattca gtagtatagc    26160
cccaccacca catagcttat acagatcacc gtaccttaat caaactcaca gaaccctagt    26220
attcaacctg ccacctccct cccaacacac agagtacaca gtcctttctc cccggctggc    26280
cttaaaaagc atcatatcat gggtaacaga catattctta ggtgttatat tccacacggt    26340
ttcctgtcga gccaaacgct catcagtgat attaataaac tccccgggca gctcacttaa    26400
gttcatgtcg ctgtccagct gctgagccac aggctgctgt ccaacttgcg gttgcttaac    26460
gggcggcgaa ggagaagtcc acgcctacat gggggtagag tcataatcgt gcatcaggat    26520
agggcggtgg tgctgcagca gcgcgcgaat aaactgctgc cgccgccgct ccgtcctgca    26580
ggaatacaac atggcagtgg tctcctcagc gatgattcgc accgcccgca gcataaggcg    26640
ccttgtcctc cgggcacagc agcgcaccct gatctcactt aaatcagcac agtaactgca    26700
gcacagcacc acaatattgt tcaaaatccc acagtgcaag gcgctgtatc caaagctcat    26760
ggcggggacc acagaaccca cgtggccatc ataccacaag cgcaggtaga ttaagtggcg    26820
acccctcata aacacgctgg acataaacat tacctctttt ggcatgttgt aattcaccac    26880
ctcccggtac catataaacc tctgattaaa catggcgcca tccaccacca tcctaaacca    26940
gctggccaaa acctgcccgc cggctataca ctgcagggaa ccgggactgg aacaatgaca    27000
gtggagagcc caggactcgt aaccatggat catcatgctc gtcatgatat caatgttggc    27060
acaacacagg cacacgtgca tacacttcct caggattaca agctcctccc gcgttagaac    27120
catatcccag ggaacaaccc attcctgaat cagcgtaaat cccacactgc agggaagacc    27180
tcgcacgtaa ctcacgttgt gcattgtcaa agtgttacat tcgggcagca gcggatgatc    27240
ctccagtatg gtagcgcggg tttctgtctc aaaaggaggt agacgatccc tactgtacgg    27300
agtgcgccga acaaccgag atcgtgttgg tcgtagtgtc atgccaaatg gaacgccgga    27360
cgtagtcata tttcctgaag caaaaccagg tgcgggcgtg acaaacagat ctgcgtctcc    27420
ggtctcgccg cttagatcgc tctgtgtagt agttgtagta tatccactct ctcaaagcat    27480
ccaggcgccc cctggcttcg ggttctatgt aaactccttc atgcgccgct gccctgataa    27540
catccaccac cgcagaataa gccacaccca gccaacctac acattcgttc tgcgagtcac    27600
acacgggagg agcgggaaga gctggaagaa ccatgttttt tttttttattc caaaagatta    27660 tccaaaacct caaaatgaag atctattaag tgaacgcgct cccctccggt ggcgtggtca    27720
aactctacag ccaaagaaca gataatggca tttgtaagat gttgcacaat ggcttccaaa    27780
aggcaaacgg ccctcacgtc caagtggacg taaaggctaa accttcagg gtgaatctcc    27840 tctataaaca ttccagcacc ttcaaccatg cccaaataat tctcatctcg ccaccttctc    27900
```

```
aatatatctc taagcaaatc ccgaatatta agtccggcca ttgtaaaaat ctgctccaga   27960
gcgccctcca ccttcagcct caagcagcga atcatgattg caaaaattca ggttcctcac   28020
agacctgtat aagattcaaa agcggaacat taacaaaaat accgcgatcc cgtaggtccc   28080
ttcgcagggc cagctgaaca taatcgtgca ggtctgcacg gaccagcgcg gccacttccc   28140
cgccaggaac catgacaaaa gaacccacac tgattatgac acgcatactc ggagctatgc   28200
taaccagcgt agccccgatg taagcttgtt gcatgggcgg cgatataaaa tgcaaggtgc   28260
tgctcaaaaa atcaggcaaa gcctcgcgca aaaagaaag cacatcgtag tcatgctcat    28320
gcagataaag gcaggtaagc tccggaacca ccacagaaaa agacaccatt tttctctcaa   28380
acatgtctgc gggtttctgc ataaacacaa aataaaataa caaaaaaaca tttaaacatt   28440
agaagcctgt cttacaacag gaaaacaac ccttataagc ataagacgga ctacggccat    28500
gccggcgtga ccgtaaaaaa actggtcacc gtgattaaaa agcaccaccg acagctcctc   28560
ggtcatgtcc ggagtcataa tgtaagactc ggtaaacaca tcaggttgat tcacatcggt   28620
cagtgctaaa aagcgaccga aatagcccgg gggaatacat acccgcaggc gtagagacaa   28680
cattacagcc cccataggag gtataacaaa attaatagga gagaaaaaca cataaacacc   28740
tgaaaaaccc tcctgcctag gcaaaatagc accctcccgc tccagaacaa catacagcgc   28800
ttccacagcg gcagccataa cagtcagcct taccagtaaa aagaaaacc tattaaaaaa    28860 acaccactcg acacggcacc agctcaatca gtcacagtgt aaaaagggc caagtgcaga    28920 gcgagtatat ataggactaa aaaatgacgt aacggttaaa gtccacaaaa acacccaga    28980 aaaccgcacg cgaacctacg cccagaaacg aaagccaaaa aacccacaac ttcctcaaat   29040
cgtcacttcc gttttcccac gttacttctg tggaatgtgt gtcagttagg gtgtggaaag   29100
tccccaggct ccccagcagg cagaagtatg caaagcatgc atctcaatta gtcagcaacc   29160
aggtgtggaa agtccccagg ctccccagca ggcagaagta tgcaaagcat gcagaagtat   29220
gcaaagcatg catctcaatt agtcagcaac caggtgtgga aagtccccag gctccccagc   29280
aggcagaagt atgcaaagca tgcatctcaa ttagtcagca accatagtcc cgcccctaac   29340
tccgcccatc ccgcccctaa ctccgcccag ttccgcccat tctccgcccc atggctgact   29400
aatttttttt atttatgcag aggccgaggc cgcctctgcc tctgagctat tccagaagta   29460
gtgaggaggc ttttttggag gcctaggctt ttgcaaacct ccgcggggat ccgcaccatg   29520
gtgagcaagg gcgaggagga taacatggcc atcatcaagg agttcatgcg cttcaaggtg   29580
cacatggagg gctccgtgaa cggccacgag ttcgagatcg agggcgaggg cgagggccgc   29640
ccctacgagg gcacccagac cgccaagctg aaggtgacca agggtggccc cctgcccttc   29700
gcctgggaca tcctgtcccc tcagttcatg tacggctcca aggcctacgt gaagcacccc   29760
gccgacatcc ccgactactt gaagctgtcc ttccccgagg gcttcaagtg ggagcgcgtg   29820
atgaacttcg aggacggcgg cgtggtgacc gtgacccagg actcctccct gcaggacggc   29880
gagttcatct acaaggtgaa gctgcgcggc accaacttcc cctccgacgg ccccgtaatg   29940
cagaagaaga ccatgggctg ggaggcctcc tccgagcgga tgtacccga ggacggcgcc    30000 ctgaagggcg agatcaagca gaggctgaag ctgaaggacg gcggccacta cgacgctgag   30060
gtcaagacca cctacaaggc caagaagccc gtgcagctgc ccggcgccta caacgtcaac   30120
atcaagttgg acatcaccct ccacaacgag gactacacca tcgtggaaca gtacgaacgc   30180
gccgagggcc gccactccac cggcggcatg gacgagctgt acaagtagtt cgaaatgacc   30240
```

```
gaccaagcga cgcccaacct gccatcacga gatttcgatt ccaccgccgc cttctatgaa    30300
aggttgggct tcggaatcgt tttccgggac gccggctgga tgatcctcca gcgcgggat    30360
ctcatgctgg agttcttcgc ccacccaac ttgtttattg cagcttataa tggttacaaa    30420
taaagcaata gcatcacaaa tttcacaaat aaagcatttt tttcactgca ttctagttgt    30480
ggtttgtcca aactcatcaa tgtatcttat catgtctgta taccgtcgac ctctagctag    30540
aggtcacttc ccattttaag aaaactacaa ttcccaacac atacaagtta ctccgcccta    30600
aaacctacgt cacccgcccc gttcccacgc cccgcgccac gtcacaaact ccacccctc    30660
attatcatat tggcttcaat ccaaaataag gtatattatt gatgatgtta attaatttaa    30720
atccgcatgc gatatcgagc tctcccggga attcggatct gcgacgcgag gctggatggc    30780
cttccccatt atgattcttc tcgcgtttaa gggcaccaat aactgcctta aaaaaattac    30840
gccccgccct gccactcatc gcagtactgt tgtaattcat taagcattct gccgacatgg    30900
aagccatcac aaacggcatg atgaacctga atcgccagcg gcatcagcac cttgtcgcct    30960
tgcgtataat atttgcccat ggtgaaaacg ggggcgaaga agttgtccat attggccacg    31020
tttaaatcaa aactggtgaa actcacccag ggattggctg agacgaaaaa catattctca    31080
ataaaccctt tagggaaata ggccaggttt tcaccgtaac acgccacatc ttgcgaatat    31140
atgtgtagaa actgccggaa atcgtcgtgg tattcactcc agagcgatga aaacgtttca    31200
gtttgctcat ggaaaacggt gtaacaaggg tgaacactat cccatatcac cagctcaccg    31260
tctttcattg ccatacgaa ttccggatga gcattcatca ggcgggcaag aatgtgaata    31320
aaggccggat aaaacttgtg cttatttttc tttacggtct ttaaaaaggc cgtaatatcc    31380
agctgaacgg tctggttata ggtacattga gcaactgact gaaatgcctc aaaatgttct    31440
ttacgatgcc attgggatat atcaacggtg gtatatccag tgatttttt ctccatttta    31500
gcttccttag ctcctgaaaa tctcgataac tcaaaaaata cgcccggtag tgatcttatt    31560
tcattatggt gaaagttgga acctcttacg tgccgatcaa cgtctcattt cgccaaaag    31620
ttggcccagg cttcccggt atcaacaggg acaccaggat ttatttattc tgcgaagtga    31680
tcttccgtca caggtattta ttcgcgataa gctcatggag cggcgtaacc gtcgcacagg    31740
aaggacagag aaagcgcgga tctgggaagt gacggacaga acggtcagga cctggattgg    31800
ggaggcggtt gccgccgctg ctgctgacgg tgtgacgttc tctgttccgg tcacaccaca    31860
tacgttccgc cattcctatg cgatgcacat gctgtatgcc ggtataccgc tgaaagttct    31920
gcaaagcctg atgggacata agtccatcag ttcaacggaa gtctacacga aggttttgc    31980
gctggatgtg gctgcccggc accgggtgca gtttgcgatg ccggagtctg atgcggttgc    32040
gatgctgaaa caattatcct gagaataaat gccttggcct ttatatggaa atgtggaact    32100
gagtggatat gctgtttttg tctgttaaac agagaagctg gctgttatcc actgagaagc    32160
gaacgaaaca gtcgggaaaa tctcccatta tcgtagagat ccgcattatt aatctcagga    32220
gcctgtgtag cgtttatagg aagtagtgtt ctgtcatgat gcctgcaagc ggtaacgaaa    32280
acgatttgaa tatgccttca ggaacaatag aaatcttcgt gcggtgttac gttgaagtgg    32340
agcggattat gtcagcaatg gacagaacaa cctaatgaac acagaaccat gatgtggtct    32400
gtccttttac agccagtagt gctcgccgca gtcgagcgac agggcgaagc cctcgagtga    32460
gcgaggaagc accagggaac agcacttata tattctgctt acacacgatg cctgaaaaaa    32520
cttcccttgg ggttatccac ttatccacgg ggatattttt ataattattt tttttatagt    32580
ttttagatct tctttttag agcgccttgt aggcctttat ccatgctggt tctagagaag    32640
```

```
gtgttgtgac aaattgccct ttcagtgtga caaatcaccc tcaaatgaca gtcctgtctg   32700
tgacaaattg cccttaaccc tgtgacaaat tgccctcaga agaagctgtt ttttcacaaa   32760
gttatccctg cttattgact ctttttttatt tagtgtgaca atctaaaaac ttgtcacact   32820
tcacatggat ctgtcatggc ggaaacagcg gttatcaatc acaagaaacg taaaaatagc   32880
ccgcgaatcg tccagtcaaa cgacctcact gaggcggcat atagtctctc ccgggatcaa   32940
aaacgtatgc tgtatctgtt cgttgaccag atcagaaaat ctgatggcac cctacaggaa   33000
catgacggta tctgcgagat ccatgttgct aaatatgctg aaatattcgg attgacctct   33060
gcggaagcca gtaaggatat acggcaggca ttgaagagtt tcgcggggaa ggaagtggtt   33120
ttttatcgcc ctgaagagga tgccggcgat gaaaaaggct atgaatcttt tccttggttt   33180
atcaaacgtg cgcacagtcc atccagaggg ctttacagtg tacatatcaa cccatatctc   33240
attcccttct ttatcgggtt acagaaccgg tttacgcagt ttcggcttag tgaaacaaaa   33300
gaaatcacca atccgtatgc catgcgttta tacgaatccc tgtgtcagta tcgtaagccg   33360
gatggctcag gcatcgtctc tctgaaaatc gactggatca tagagcgtta ccagctgcct   33420
caaagttacc agcgtatgcc tgacttccgc cgccgcttcc tgcaggtctg tgttaatgag   33480
atcaacagca gaactccaat gcgcctctca tacattgaga aaagaaagg ccgccagacg   33540 actcatatcg tattttcctt ccgcgatatc acttccatga cgacaggata gtctgagggt   33600
tatctgtcac agatttgagg gtggttcgtc acatttgttc tgacctactg agggtaattt   33660
gtcacagttt tgctgtttcc ttcagcctgc atggattttc tcatactttt tgaactgtaa   33720
tttttaagga agccaaattt gagggcagtt tgtcacagtt gatttccttc tctttcccctt   33780 cgtcatgtga cctgatatcg ggggttagtt cgtcatcatt gatgagggtt gattatcaca   33840
gtttattact ctgaattggc tatccgcgtg tgtacctcta cctggagttt ttcccacggt   33900
ggatatttct tcttgcgctg agcgtaagag ctatctgaca gaacagttct tctttgcttc   33960
ctcgccagtt cgctcgctat gctcggttac acggctgcgg cgagcgctag tgataataag   34020
tgactgaggt atgtgctctt cttatctcct tttgtagtgt tgctcttatt ttaaacaact   34080
ttgcggtttt ttgatgactt tgcgattttg ttgttgcttt gcagtaaatt gcaagattta   34140
ataaaaaaac gcaaagcaat gattaaagga tgttcagaat gaaactcatg gaaacactta   34200
accagtgcat aaacgctggt catgaaatga cgaaggctat cgccattgca cagtttaatg   34260
atgacagccc ggaagcgagg aaaataaccc ggcgctggag aataggtgaa gcagcggatt   34320
tagttggggt ttcttctcag gctatcagag atgccgagaa agcagggcga ctaccgcacc   34380
cggatatgga aattcgagga cgggttgagc aacgtgttgg ttatacaatt gaacaaatta   34440
atcatatgcg tgatgtgttt ggtacgcgat tgcgacgtgc tgaagacgta tttccaccgg   34500
tgatcggggt tgctgcccat aaaggtggcg tttacaaaac ctcagtttct gttcatcttg   34560
ctcaggatct ggctctgaag gggctacgtg ttttgctcgt ggaaggtaac gaccccccagg   34620 gaacagcctc aatgtatcac ggatgggtac cagatcttca tattcatgca gaagacactc   34680
tcctgccttt ctatcttggg gaaaaggacg atgtcactta tgcaataaag cccacttgct   34740
ggccggggct tgacattatt ccttcctgtc tggctctgca ccgtattgaa actgagttaa   34800
tgggcaaatt tgatgaaggt aaactgccca ccgatccaca cctgatgctc cgactggcca   34860
ttgaaactgt tgctcatgac tatgatgtca tagttattga cagcgcgcct aacctgggta   34920
tcggcacgat taatgtcgta tgtgctgctg atgtgctgat tgttcccacg cctgctgagt   34980
```

```
tgtttgacta cacctccgca ctgcagtttt tcgatatgct tcgtgatctg ctcaagaacg    35040
ttgatcttaa agggttcgag cctgatgtac gtattttgct taccaaatac agcaatagta    35100
atggctctca gtccccgtgg atggaggagc aaattcggga tgcctgggga agcatggttc    35160
taaaaaatgt tgtacgtgaa acggatgaag ttggtaaagg tcagatccgg atgagaactg    35220
tttttgaaca ggccattgat caacgctctt caactggtgc ctggagaaat gctctttcta    35280
tttgggaacc tgtctgcaat gaaattttcg atcgtctgat taaaccacgc tgggagatta    35340
gataatgaag cgtgcgcctg ttattccaaa acatacgctc aatactcaac cggttgaaga    35400
tacttcgtta tcgacaccag ctgccccgat ggtggattcg ttaattgcgc gcgtaggagt    35460
aatggctcgc ggtaatgcca ttactttgcc tgtatgtggt cgggatgtga agtttactct    35520
tgaagtgctc cggggtgata tgttgagaa gacctctcgg gtatggtcag gtaatgaacg    35580
tgaccaggag ctgcttactg aggacgcact ggatgatctc atcccttctt ttctactgac    35640
tggtcaacag acaccggcgt tcggtcgaag agtatctggt gtcatagaaa ttgccgatgg    35700
gagtcgccgt cgtaaagctg ctgcacttac cgaaagtgat tatcgtgttc tggttggcga    35760
gctggatgat gagcagatgg ctgcattatc cagattgggt aacgattatc gcccaacaag    35820
tgcttatgaa cgtggtcagc gttatgcaag ccgattgcag aatgaatttg ctggaaatat    35880
ttctgcgctg gctgatgcgg aaaatatttc acgtaagatt attacccgct gtatcaacac    35940
cgccaaattg cctaaatcag ttgttgctct tttttctcac cccggtgaac tatctgcccg    36000
gtcaggtgat gcacttcaaa aagcctttac agataaagag gaattactta agcagcaggc    36060
atctaacctt catgagcaga aaaaagctgg ggtgatattt gaagctgaag aagttatcac    36120
tcttttaact tctgtgctta aaacgtcatc tgcatcaaga actagtttaa gctcacgaca    36180
tcagtttgct cctggagcga cagtattgta aagggcgat aaaatggtgc ttaacctgga    36240
caggtctcgt gttccaactg agtgtataga gaaaattgag gccattctta aggaacttga    36300
aaagccagca ccctgatgcg accacgtttt agtctacgtt tatctgtctt tacttaatgt    36360
cctttgttac aggccagaaa gcataactgg cctgaatatt ctctctgggc ccactgttcc    36420
acttgtatcg tcggtctgat aatcagactg ggaccacggt cccactcgta tcgtcggtct    36480
gattattagt ctgggaccac ggtcccactc gtatcgtcgg tctgattatt agtctgggac    36540
cacggtccca ctcgtatcgt cggtctgata atcagactgg gaccacggtc ccactcgtat    36600
cgtcggtctg attattagtc tgggaccatg gtcccactcg tatcgtcggt ctgattatta    36660
gtctgggacc acggtcccac tcgtatcgtc ggtctgatta ttagtctgga accacggtcc    36720
cactcgtatc gtcggtctga ttattagtct gggaccacgg tcccactcgt atcgtcggtc    36780
tgattattag tctgggacca cgatcccact cgtgttgtcg gtctgattat cggtctggga    36840
ccacggtccc acttgtattg tcgatcagac tatcagcgtg agactacgat tccatcaatg    36900
cctgtcaagg gcaagtattg acatgtcgtc gtaacctgta gaacggagta acctcggtgt    36960
gcggttgtat gcctgctgtg gattgctgct gtgtcctgct tatccacaac attttgcgca    37020
cggttatgtg gacaaaatac ctggttaccc aggccgtgcc ggcacgttaa ccgggcacat    37080
ttccccgaaa agtgccacct gacgtctaag aaaccattat tatcatgaca ttaacctata    37140
aaaataggcg tatcacgagg cccttcgtc ttcaagaatt ggatccgaat tcccgggaga    37200
gctcgatatc gcatgcggat ttaaattaat taa                                37233
```

<210> SEQ ID NO 37  
<211> LENGTH: 30

<212> TYPE: DNA
<213> ORGANISM: Artificial Sequence
<220> FEATURE:
<223> OTHER INFORMATION: Primer

<400> SEQUENCE: 37
aaaaaaggat ccaccatggg ctccagtgag        30

<210> SEQ ID NO 38
<211> LENGTH: 40
<212> TYPE: DNA
<213> ORGANISM: Artificial Sequence
<220> FEATURE:
<223> OTHER INFORMATION: Primer

<400> SEQUENCE: 38
aaaaagtcga cttacatgtt tttcaagtga caaaaagaag        40

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
aaaaaagcgg ccgcactctc ttccgcatcg        30

<210> SEQ ID NO 40
<211> LENGTH: 41
<212> TYPE: DNA
<213> ORGANISM: Artificial Sequence
<220> FEATURE:
<223> OTHER INFORMATION: Primer

<400> SEQUENCE: 40
aaaaaatcta gattacatgt ttttcaagtg acaaaaagaa g        41

<210> SEQ ID NO 41
<211> LENGTH: 34
<212> TYPE: DNA
<213> ORGANISM: Artificial Sequence
<220> FEATURE:
<223> OTHER INFORMATION: Primer

<400> SEQUENCE: 41
atcgcctgga gaattcactc tcttccgcat cgct        34

<210> SEQ ID NO 42
<211> LENGTH: 34
<212> TYPE: DNA
<213> ORGANISM: Artificial Sequence
<220> FEATURE:
<223> OTHER INFORMATION: Primer

<400> SEQUENCE: 42
ctcactggag cccattgcga ctgtgactgg ttag        34

<210> SEQ ID NO 43
<211> LENGTH: 226
<212> TYPE: DNA
<213> ORGANISM: Artificial Sequence
<220> FEATURE:
<223> OTHER INFORMATION: Primer

<400> SEQUENCE: 43

```
aaaaaagaat tcactctctt ccgcatcgct gtctgcgagg gccagctgtt gggctcgcgg    60
ttgaggacaa actcttcgcg gtcttttccag tactcttgga tcggaaaccc gtcggcctcc   120
gaacaggtac tccgccgccg agggacctga gcgagtccgc atcgaccgga tcggaaaacc   180
tctcgagaaa ggcgtctaac cagtcacagt cgcaggatcc tttttt                  226
```

```
<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
atgggctcca gtgagcag                                                  18

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
gaattctcca ggcgatctg                                                 19

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
aaaaaagcgg ccgcactctc ttccgcatcg                                     30

<210> SEQ ID NO 47
<211> LENGTH: 41
<212> TYPE: DNA
<213> ORGANISM: Artificial Sequence
<220> FEATURE:
<223> OTHER INFORMATION: Primer

<400> SEQUENCE: 47
aaaaaatcta gattacatgt ttttcaagtg acaaaaagaa g                        41

<210> SEQ ID NO 48
<211> LENGTH: 33
<212> TYPE: DNA
<213> ORGANISM: Artificial Sequence
<220> FEATURE:
<223> OTHER INFORMATION: Primer

<400> SEQUENCE: 48
tggagaagga tccgcactct cttccgcatc gct                                 33

<210> SEQ ID NO 49
<211> LENGTH: 44
<212> TYPE: DNA
<213> ORGANISM: Artificial Sequence
<220> FEATURE:
<223> OTHER INFORMATION: Primer

<400> SEQUENCE: 49
atctagagcc ggcgcttaca tgtttttcaa gtgacaaaaa gaag                     44
```

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
aaaaaaagcg gccgccgcca ccatggtgag                             30

<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
aaaaaagaat tccggccgct ttacttgtac                             30

<210> SEQ ID NO 52
<211> LENGTH: 31
<212> TYPE: DNA
<213> ORGANISM: Artificial Sequence
<220> FEATURE:
<223> OTHER INFORMATION: Primer

<400> SEQUENCE: 52
aaaaaagcgg ccgcgcacca tggtgagcaa g                           31

<210> SEQ ID NO 53
<211> LENGTH: 35
<212> TYPE: DNA
<213> ORGANISM: Artificial Sequence
<220> FEATURE:
<223> OTHER INFORMATION: Primer

<400> SEQUENCE: 53
aaaaaactcg agactacttg tacagctcgt ccatg                       35

<210> SEQ ID NO 54
<211> LENGTH: 37
<212> TYPE: DNA
<213> ORGANISM: Artificial Sequence
<220> FEATURE:
<223> OTHER INFORMATION: Primer

<400> SEQUENCE: 54
aaaaaagtcg acatgtctag actggacaag agcaaag                     37

<210> SEQ ID NO 55
<211> LENGTH: 34
<212> TYPE: DNA
<213> ORGANISM: Artificial Sequence
<220> FEATURE:
<223> OTHER INFORMATION: Primer

<400> SEQUENCE: 55
aaaaaaggat ccttacccgg ggagcatgtc aagg                        34

<210> SEQ ID NO 56
<211> LENGTH: 30
<212> TYPE: DNA
<213> ORGANISM: Artificial Sequence
<220> FEATURE:

<223> OTHER INFORMATION: Primer

<400> SEQUENCE: 56
aaaaaagcgg ccgcactctc ttccgcatcg                                      30

<210> SEQ ID NO 57
<211> LENGTH: 41
<212> TYPE: DNA
<213> ORGANISM: Artificial Sequence
<220> FEATURE:
<223> OTHER INFORMATION: Primer

<400> SEQUENCE: 57
aaaaaatcta gattacatgt ttttcaagtg acaaaaagaa g                         41

<210> SEQ ID NO 58
<211> LENGTH: 42
<212> TYPE: DNA
<213> ORGANISM: Artificial Sequence
<220> FEATURE:
<223> OTHER INFORMATION: Primer

<400> SEQUENCE: 58
taatctagac ccagctttct tgtacaaagt tggcattata ag                        42

<210> SEQ ID NO 59
<211> LENGTH: 75
<212> TYPE: DNA
<213> ORGANISM: Artificial Sequence
<220> FEATURE:
<223> OTHER INFORMATION: Primer

<400> SEQUENCE: 59
agaaagctgg gtctagatta cttatcgtcg tcatccttgt aatccatgtt tttcaagtga     60
caaaaagaag tggcg                                                      75

<210> SEQ ID NO 60
<211> LENGTH: 37
<212> TYPE: DNA
<213> ORGANISM: Artificial Sequence
<220> FEATURE:
<223> OTHER INFORMATION: Primer

<400> SEQUENCE: 60
agtcgactgg atccggtacc gccgcatcaa cgagctc                              37

<210> SEQ ID NO 61
<211> LENGTH: 37
<212> TYPE: DNA
<213> ORGANISM: Artificial Sequence
<220> FEATURE:
<223> OTHER INFORMATION: Primer

<400> SEQUENCE: 61
gagagtgcgg ccgcgaattc gaggcccaga gggtacc                              37

<210> SEQ ID NO 62
<211> LENGTH: 16
<212> TYPE: DNA
<213> ORGANISM: Artificial Sequence
<220> FEATURE:
<223> OTHER INFORMATION: Primer

<400> SEQUENCE: 62
gaattcgcgg ccgcac                                                     16

-continued

<210> SEQ ID NO 63
<211> LENGTH: 19
<212> TYPE: DNA
<213> ORGANISM: Artificial Sequence
<220> FEATURE:
<223> OTHER INFORMATION: Primer

<400> SEQUENCE: 63
ggtaccggat ccagtcgac                                                      19

<210> SEQ ID NO 64
<211> LENGTH: 45
<212> TYPE: DNA
<213> ORGANISM: Artificial Sequence
<220> FEATURE:
<223> OTHER INFORMATION: Primer

<400> SEQUENCE: 64
cagtgagcag gaatagaaag ccattgtcaa agatcttggt tgtgg                         45

<210> SEQ ID NO 65
<211> LENGTH: 42
<212> TYPE: DNA
<213> ORGANISM: Artificial Sequence
<220> FEATURE:
<223> OTHER INFORMATION: Primer

<400> SEQUENCE: 65
ctttgacaat ggctttctat tcctgctcac tggagcccat tg                            42

<210> SEQ ID NO 66
<211> LENGTH: 75
<212> TYPE: DNA
<213> ORGANISM: Artificial Sequence
<220> FEATURE:
<223> OTHER INFORMATION: Primer

<400> SEQUENCE: 66
atacaaaact acataagacc cccaccttat atattctttc ccacccttaa ccctcatcag         60
tgccaacata gtaag                                                          75

<210> SEQ ID NO 67
<211> LENGTH: 67
<212> TYPE: DNA
<213> ORGANISM: Artificial Sequence
<220> FEATURE:
<223> OTHER INFORMATION: Primer

<400> SEQUENCE: 67
aataagagga agtgaaatct gaataatttt gtgttactca tagcgcgtaa ccgctcatta         60
ggcgggc                                                                   67

<210> SEQ ID NO 68
<211> LENGTH: 67
<212> TYPE: DNA
<213> ORGANISM: Artificial Sequence
<220> FEATURE:
<223> OTHER INFORMATION: Primer

<400> SEQUENCE: 68
tggaactaat catatgtggc ctggagaaac agctaaagtg cgaaagcggc ccgctcatta         60
ggcgggc                                                                   67

<210> SEQ ID NO 69
<211> LENGTH: 75
<212> TYPE: DNA
<213> ORGANISM: Artificial Sequence
<220> FEATURE:
<223> OTHER INFORMATION: Primer

<400> SEQUENCE: 69
cgcgaacaaa tgtggtatgg ctgattatga tcctctagag ataattctag ccctcatcag    60
tgccaacata gtaag                                                     75

<210> SEQ ID NO 70
<211> LENGTH: 81
<212> TYPE: DNA
<213> ORGANISM: Artificial Sequence
<220> FEATURE:
<223> OTHER INFORMATION: Primer

<400> SEQUENCE: 70
atacaaaact acataagacc cccaccttat atattctttc ccaccettaa gccacgccca    60 cagatatacg cgttgacatt g                                              81

<210> SEQ ID NO 71
<211> LENGTH: 69
<212> TYPE: DNA
<213> ORGANISM: Artificial Sequence
<220> FEATURE:
<223> OTHER INFORMATION: Primer

<400> SEQUENCE: 71
aataagagga agtgaaatct gaataatttt gtgttactca tagcgcgtaa tagaagccat    60
agagcccac                                                            69

<210> SEQ ID NO 72
<211> LENGTH: 75
<212> TYPE: DNA
<213> ORGANISM: Artificial Sequence
<220> FEATURE:
<223> OTHER INFORMATION: Primer

<400> SEQUENCE: 72 caaaaaccc acaacttcct caaatcgtca cttccgtttt cccacgttac ccctcatcag     60
tgccaacata gtaag                                                     75

<210> SEQ ID NO 73
<211> LENGTH: 67
<212> TYPE: DNA
<213> ORGANISM: Artificial Sequence
<220> FEATURE:
<223> OTHER INFORMATION: Primer

<400> SEQUENCE: 73
agtaacttgt atgtgttggg aattgtagtt ttcttaaaat gggaagtgac ccgctcatta    60
ggcgggc                                                              67

<210> SEQ ID NO 74
<211> LENGTH: 76
<212> TYPE: DNA
<213> ORGANISM: Artificial Sequence
<220> FEATURE:
<223> OTHER INFORMATION: Primer

<400> SEQUENCE: 74

```
caaaaaaccc acaacttcct caaatcgtca cttccgtttt cccacgttac ttctgtggaa    60
tgtgtgtcag ttaggg                                                    76

<210> SEQ ID NO 75
<211> LENGTH: 75
<212> TYPE: DNA
<213> ORGANISM: Artificial Sequence
<220> FEATURE:
<223> OTHER INFORMATION: Primer

<400> SEQUENCE: 75
agtaacttgt atgtgttggg aattgtagtt ttcttaaaat gggaagtgac ctctagctag    60
aggtcgacgg tatac                                                     75

<210> SEQ ID NO 76
<211> LENGTH: 75
<212> TYPE: DNA
<213> ORGANISM: Artificial Sequence
<220> FEATURE:
<223> OTHER INFORMATION: Primer

<400> SEQUENCE: 76
tcccgcgctt cttggaactt tacattgtgg gccacaacat caacggccct ccctcatcag    60
tgccaacata gtaag                                                     75

<210> SEQ ID NO 77
<211> LENGTH: 67
<212> TYPE: DNA
<213> ORGANISM: Artificial Sequence
<220> FEATURE:
<223> OTHER INFORMATION: Primer

<400> SEQUENCE: 77
ggcacctcgg aacggttgtt aattacctgg gcggcgagca cgatctcgtc ccgctcatta    60
ggcgggc                                                              67

<210> SEQ ID NO 78
<211> LENGTH: 99
<212> TYPE: DNA
<213> ORGANISM: Artificial Sequence
<220> FEATURE:
<223> OTHER INFORMATION: Primer

<400> SEQUENCE: 78
gcgcggcctt ccggagcgag gtgtgggtga gcgcaaaggt gtccctgacc atgaccagca    60
tgaagggcac gagctgcttc ccaaaggccc ccatccaag                           99

<210> SEQ ID NO 79
<211> LENGTH: 99
<212> TYPE: DNA
<213> ORGANISM: Artificial Sequence
<220> FEATURE:
<223> OTHER INFORMATION: Primer

<400> SEQUENCE: 79
cttggatggg ggcctttggg aagcagctcg tgcccttcat gctggtcatg gtcagggaca    60
cctttgcgct cacccacacc tcgctccgga aggccgcgc                           99

<210> SEQ ID NO 80
<211> LENGTH: 75
<212> TYPE: DNA
```

```
<213> ORGANISM: Artificial Sequence
<220> FEATURE:
<223> OTHER INFORMATION: Primer

<400> SEQUENCE: 80
ggcaacgcca caacataaag aagcaagcaa catcaacaac agctgccgcc ccctcatcag      60
tgccaacata gtaag                                                      75

<210> SEQ ID NO 81
<211> LENGTH: 67
<212> TYPE: DNA
<213> ORGANISM: Artificial Sequence
<220> FEATURE:
<223> OTHER INFORMATION: Primer

<400> SEQUENCE: 81
tacaaataaa agcatttgcc tttattgaaa gtgtctctag tacattattt ccgctcatta     60
ggcgggc                                                               67

<210> SEQ ID NO 82
<211> LENGTH: 100
<212> TYPE: DNA
<213> ORGANISM: Artificial Sequence
<220> FEATURE:
<223> OTHER INFORMATION: Primer

<400> SEQUENCE: 82
ggcaacgcca caacataaag aagcaagcaa catcaacaac agctgccgcc aaataatgta     60
ctagagacac tttcaataaa ggcaaatgct tttatttgta                          100

<210> SEQ ID NO 83
<211> LENGTH: 100
<212> TYPE: DNA
<213> ORGANISM: Artificial Sequence
<220> FEATURE:
<223> OTHER INFORMATION: Primer

<400> SEQUENCE: 83
tacaaataaa agcatttgcc tttattgaaa gtgtctctag tacattattt ggcggcagct     60
gttgttgatg ttgcttgctt ctttatgttg tggcgttgcc                          100

<210> SEQ ID NO 84
<211> LENGTH: 10765
<212> TYPE: DNA
<213> ORGANISM: Artificial Sequence
<220> FEATURE:
<223> OTHER INFORMATION: Vector
<220> FEATURE:
<221> NAME/KEY: misc_feature
<222> LOCATION: (4978)..(4978)
<223> OTHER INFORMATION: n is a, c, g, or t

<400> SEQUENCE: 84
aattcatggc cttggctcaa gctcaccggg cccgtcgtct tcacgcagag gcgccagatt     60
caggagatca accgccgcgt cgtcgcgttc gccagcaacc tacgcgcgca gcaccagctc   120
ctgcccgcgc gcggcgccga cgtgcccctg cccctctcc cggcgggtcc ggagcccccc    180
ctacctccgg gggctcgccc gcgtcaccgc ttttagatgc atcatccaag gacaccccg    240 cggcccaccg cccgccgcgc ggtaccgtag tcgcgccgcg gggatgcggc ctcttgcaag   300
ccatcgacgc cgccaccaac cagccccctgg aaattaggta tcacctggat ctagcccgcg   360
ccctgacccg tctatgcgag gtaaacctgc aggagctccc gcctgacctg acgccgcggg   420
```

```
agctccagac catggacagc tcccatctgc gcgatgttgt catcaagctc cgaccgccgc     480
gcgcggacat ctggactttg ggctcgcgcg gcgtggtggt ccgatccacc gtaactcccc     540
tcgagcagcc agacggtcaa ggacaagcag ccgaagtaga agaccaccag ccaaacccgc     600
caggcgaggg gctcaaattc ccactctgct tccttgtgcg cggtcgtcag gtcaacctcg     660
tgcaggatgt acagcccgtg caccgctgcc agtactgcgc acgttttac aaaagccagc      720
acgagtgttc ggcccgtcgc agggacttct actttcacca catcaatagc cactcctcca     780
attggtggcg ggagatccag ttcttcccga tcggctcgca tcctcgcacc gagcgtctct     840
ttgtcaccta cgatgtagag acctatactt ggatgggggc cttgggaag cagctcgtgc       900
ccttcatgct ggtcatgaag ttcggcggag atgagcctct agtgactgcc gcgcgagacc     960
tagccgcgaa ccttggatgg gaccgctggg aacaagaccc gcttaccttc tactgcatca    1020
ccccagaaaa aatggccata ggtcgccagt ttaggacctt tcgcgaccac ctgcaaatgc    1080
taatggcccg tgacctgtgg agctcattcg tcgcttccaa ccctcatctt gcagactggg    1140
ccctttcaga gcacgggctc agctcccctg aagagctcac ctacgaggaa cttaaaaaat    1200
tgccttccat caagggcatc ccgcgcttct tggaacttta cattgtgggc cacaacatta    1260
atgggtttga cgagatcgtg ctcgccgccc aggtaattaa caaccgttcc gaggtgccgg    1320
gaccccttccg catcacacgc aactttatgc ctcgcgcggg aaagatactc ttcaacgatg   1380
tcaccttcgc cctgccaaat ccgcgttcca aaaagcgcac ggacttttg ctctgggagc      1440
agggcggatg cgacgacact gacttcaaat accagtacct caaagtcatg gtcagggaca    1500
cctttgcgct cacccacacc tcgctccgga aggccgcgca ggcatacgcg ctacccgtag    1560
aaaagggatg ctgcgcctac caggccgtca accagttcta catgctaggc tcttaccgtt    1620
cggaggccga cgggtttccg atccaagagt actggaaaga ccgcgaagag tttgtcctca    1680
accgcgagct gtggaaaaaa aagggacagg ataagtatga catcatcaag gaaaccctgg    1740
actactgcgc cctagacgtg caggtcaccg ccgagctggt caacaagctg cgcgactcct    1800
acgcctcctt cgtgcgtgac gcggtaggtc tcacagacgc cagcttcaac gtcttccagc    1860
gtccaaccat atcatccaac tcacatgcca tcttcaggca gatagtcttc cgagcagagc    1920
agcccgcccg tagcaacctc ggtcccgacc tcctcgctcc ctcgcacgaa ctatacgatt    1980
acgtgcgcgc cagcatccgc ggtggaagat gctaccctac atatcttgga atactcagag    2040
agccctcta cgtttacgac atttgcggca tgtacgcctc cgcgctcacc caccccatgc     2100
catgggtcc cccactcaac ccatacgagc gcgcgcttgc cgcccgcgca tggcagcagg     2160
cgctagactt gcaaggatgc aagatagact acttcgacgc gcgcctgctg cccggggtct    2220
ttaccgtgga cgcagacccc ccggacgaga cgcagctaga ccccctaccg ccattctgct    2280
cgcgcaaggg cggccgcctc tgctggacca acgagcgcct acgcggagag gtagccacca    2340
gcgttgacct tgtcaccctg cacaaccgcg gttggcgcgt gcacctggtg cccgacgagc    2400
gcaccaccgt cttttcccgaa tggcggtgcg ttgcgcgcga atacgtgcag ctaaacatcg    2460
cggccaagga gcgcgccgat cgcgacaaaa accaaaccct gcgctccatc gccaagttgc    2520
tgtccaacgc cctctacggg tcgtttgcca ccaagcttga caacaaaaag attgtctttt    2580
ctgaccagat ggatgcggcc accctcaaag gcatcaccgc gggccaggtg aatatcaaat    2640
cctcctcgtt tttggaaact gacaatctta gcgcagaagt catgcccgct tttcagaggg    2700
agtactcacc ccaacagctg gccctcgcag acagcgatgc ggaagagagt gaggacgaac    2760
```

```
gcgccccac  cccctttat  agcccccctt  caggaacacc  cggtcacgtg  gcctacacct   2820
acaaaccaat  caccttcctt  gatgccgaag  agggcgacat  gtgtcttcac  accctggagc   2880
gagtggaccc  cctagtggac  aacgaccgct  acccctccca  cttagcctcc  ttcgtgctgg   2940
cctggacgcg  agcctttgtc  tcagagtggt  ccgagtttct  atacgaggag  accgcggaa    3000
caccgctcga  ggacaggcct  ctcaagtctg  tatacgggga  cacggacagc  cttttcgtca   3060
ccgagcgtgg  acaccggctc  atggaaacca  gaggtaagaa  acgcatcaaa  aagcatgggg   3120
gaaacctggt  ttttgacccc  gaacggccag  agctcacctg  gctcgtggaa  tgcgagaccg   3180
tctgcggggc  ctgcgcgcg   gatgcctact  ccccggaatc  ggtatttctc  gcgcccaagc   3240
tctacgccct  caaaagtctg  cactgcccct  cgtgcggcgc  ctcctccaag  ggcaagctgc   3300
gcgccaaggg  ccacgccgcg  gaggggctgg  actatgacac  catggtcaaa  tgctacctgg   3360
ccgacgcgca  gggcgaagac  cggcagcgct  tcagcaccag  caggaccagc  ctcaagcgca   3420
ccctggccag  cgcgcagccc  ggagcgcacc  ccttcaccgt  gacccagact  acgctgacga   3480
ggaccctgcg  cccgtggaaa  gacatgaccc  tggcccgtct  ggacgagcac  cgactactgc   3540
cgtacagcga  aagccgcccc  aacccgcgaa  acgaggagat  atgctggatc  gagatgccgt   3600
acccatacga  tgttccggat  tacgcttaga  gcacgtgact  acatttaaac  cctaacaaaa   3660
caaagagatg  gggttactct  ctaaatttta  tgggttatgt  cattggatgt  tatgggtcct   3720
tgccacaaga  acacatcata  caaaaaatca  aagaatgttt  tagaaaactt  cctattaaca   3780
ggcctattga  ttggaaagta  tgtcaacgaa  ttgtgggtct  tttgggtttt  gctgccccctt  3840
ttacacaatg  tggttatcct  gcgttgatgc  ctttgtatgc  atgtattcaa  tctaagcagg   3900
cttttcacttt  ctcgccaact  tacaaggcct  ttctgtgtaa  acaatacctg  aacctttacc   3960
ccgttgcccg  gcaacggcca  cctctgtgcc  aagtgtttgc  tgacgcaacc  cccactggct   4020
ggggcttggt  catgggccat  cagcgcatgc  gtggaacctt  ttcggctcct  ctgccgatcc   4080
atactgcgga  actcctagcc  gcttgttttg  ctcgcagcag  gtctggagca  aacattatcg   4140
ggactgataa  ctctgttgtc  ctatcccgca  aatatacatc  gtttccatgg  ctgctaggct   4200
gtgctgccaa  ctggatcctg  cgcgggacgt  ccttttgttta  cgtcccgtcg  gcgctgaatc   4260
ctgcggacga  cccttctcgg  ggtcgcttgg  gactctctcg  tcccccttctc  cgtctgccgt   4320
tccgaccgac  cacggggcgc  acctctcttt  acgcggactc  cccgtctgtg  ccttctcatc   4380
tgccggaccg  tgtgcacttc  gcttcacctc  tgcacgtcgc  atggagacca  ccgtgaacgc   4440
ccaccaaata  ttgcccaagg  tcttacataa  gaggactctt  ggactctcag  caatgtcaac   4500
gaccgacctt  gaggcatact  tcaaagactg  tttgtttaaa  gactgggagg  agttggggga   4560
ggagattagg  ttaaaggtct  ttgtactagg  aggctgtagg  cataaattgg  tctgcgcacc   4620
agcaccatgt  atcactagag  cggggtacct  ttaagaccaa  tgacttacaa  ggcagctgta   4680
gatcttagcc  acttttaaa   agaaaagggg  ggacttggaa  gggctaattc  actcccaacg   4740
aagacaagat  ctgctttttg  cttgtactgg  gtctctctgg  ttagaccaga  tctgagcctg   4800
ggagctctct  ggctaactag  ggaacccact  gcttaagcct  caataaagct  tgccttgagt   4860
gcttcaagta  gtgtgtgccc  gtctgttgtg  tgactctggt  aactagagat  ccctcagacc   4920
cttttagtca  gtgtggaaaa  tctctagcag  tagtagttca  tgtcatctta  ttattcangt   4980
atttataact  tgcaaagaaa  tgaatatcag  agagtgagag  gaacttgttt  attgcagctt   5040
ataatggtta  caaataaagc  aatagcatca  caaattccac  aaataaagca  ttttttttcac  5100
tgcattctag  ttgtggtttg  tccaaactca  tcaatgtatc  ttatcatgtc  tggctctagc   5160
```

```
tatcccgccc ctaactccgc ccagttccgc ccattctccg ccccatggct gactaatttt      5220
ttttatttat gcagaggccg aggccgcctc ggcctctgag ctattccaga agtagtgagg      5280 aggcttttt ggaggcctag gcttttgcgt cgagacgtac ccaattcgcc ctatagtgag       5340
tcgtattacg cgcgctcact ggccgtcgtt ttacaacgtc gtgactggga aaaccctggc     5400
gttacccaac ttaatcgcct tgcagcacat ccccctttcg ccagctggcg taatagcgaa      5460
gaggcccgca ccgatcgccc ttcccaacag ttgcgcagcc tgaatggcga atggcgcgac     5520
gcgccctgta gcggcgcatt aagcgcggcg ggtgtggtgg ttacgcgcag cgtgaccgct     5580
acacttgcca gcgccctagc gcccgctcct ttcgctttct tcccttcctt tctcgccacg     5640
ttcgccggct ttccccgtca gctctaaatc gggggctcc ctttagggtt ccgatttagt       5700
gctttacggc acctcgaccc caaaaaactt gattagggtg atggttcacg tagtgggcca     5760
tcgccctgat agacggtttt tcgccctttg acgttggagt ccacgttctt taatagtgga    5820
ctcttgttcc aaactggaac aacactcaac cctatctcgg tctattcttt tgatttataa     5880
gggattttgc cgatttcggc ctattggtta aaaaatgagc tgatttaaca aaaatttaac     5940
gcgaatttta acaaaatatt aacgtttaca atttcccagg tggcactttt cggggaaatg    6000
tgcgcggaac ccctatttgt ttattttct aaatacattc aaatatgtat ccgctcatga      6060
gacaataacc ctgataaatg cttcaataat attgaaaaag gaagagtatg agtattcaac     6120
atttccgtgt cgcccttatt cccttttttg cggcattttg ccttcctgtt tttgctcacc     6180
cagaaacgct ggtgaaagta aaagatgctg aagatcagtt gggtgcacga gtgggttaca    6240
tcgaactgga tctcaacagc ggtaagatcc ttgagagttt tcgccccgaa gaacgttttc     6300
caatgatgag cacttttaaa gttctgctat gtggcgcggt attatcccgt attgacgccg     6360
ggcaagagca actcggtcgc cgcatacact attctcagaa tgacttggtt gagtactcac     6420
cagtcacaga aaagcatctt acggatggca tgacagtaag agaattatgc agtgctgcca     6480
taaccatgag tgataacact gcggccaact tacttctgac aacgatcgga ggaccgaagg     6540
agctaaccgc ttttttgcac aacatggggg atcatgtaac tcgccttgat cgttgggaac    6600
cggagctgaa tgaagccata ccaaacgacg agcgtgacac cacgatgcct gtagcaatgg    6660
caacaacgtt gcgcaaacta ttaactggcg aactacttac tctagcttcc cggcaacaat     6720
taatagactg gatggaggcg gataaagttg caggaccact tctgcgctcg gcccttccgg     6780
ctggctggtt tattgctgat aaatctggag ccggtgagcg tgggtctcgc ggtatcattg    6840
cagcactggg gccagatggt aagccctccc gtatcgtagt tatctacacg acggggagtc    6900
aggcaactat ggatgaacga atagacaga tcgctgagat aggtgcctca ctgattaagc      6960
attggtaact gtcagaccaa gtttactcat atatacttta gattgattta aaacttcatt    7020
tttaatttaa aaggatctag gtgaagatcc ttttttgataa tctcatgacc aaaatccctt     7080
aacgtgagtt ttcgttccac tgagcgtcag accccgtaga aaagatcaaa ggatcttctt     7140
gagatccttt ttttctgcgc gtaatctgct gcttgcaaac aaaaaaacca ccgctaccag     7200
cggtggtttg tttgccggat caagagctac caactctttt tccgaaggta actggcttca     7260
gcagagcgca gataccaaat actgtccttc tagtgtagcc gtagttaggc caccacttca    7320
agaactctgt agcaccgcct acatacctcg ctctgctaat cctgttacca gtggctgctg     7380
ccagtggcga taagtcgtgt cttaccgggt tggactcaag acgatagtta ccggataagg     7440
cgcagcggtc gggctgaacg ggggggttcgt gcacacagcc cagcttggag cgaacgacct    7500
```

```
acaccgaact gagatacct a cagcgtgagc tatgagaaag cgccacgctt cccgaaggga    7560
gaaaggcgga caggtatccg gtaagcggca gggtcggaac aggagagcgc acagagggagc   7620 ttccagggg  aaacgcctgg tatctttata gtcctgtcgg gtttcgccac ctctgacttg    7680
agcgtcgatt tttgtgatgc tcgtcagggg ggcggagcct atggaaaaac gccagcaacg   7740
cggccttttt acggttcctg gccttttgct ggccttttgc tcacatgttc tttcctgcgt    7800 tatccctga ttctgtggat aaccgtatta ccgcctttga gtgagctgat accgctcgcc    7860
gcagccgaac gaccgagcgc agcgagtcag tgagcgagga agcggaagag cgcccaatac   7920
gcaaaccgcc tctccccgcg cgttggccga ttcattaatg cagctggcac gacaggtttc    7980
ccgactggaa agcgggcagt gagcgcaacg caattaatgt gagttagctc actcattagg   8040
caccccaggc tttacacttt atgcttccgg ctcgtatgtt gtgtggaatt gtgagcggat    8100
aacaatttca cacaggaaac agctatgacc atgattacgc caagcgcgca attaaccctc    8160 actaaggga acaaaagctg gagctgcaag cttaatgtag tcttatgcaa tactcttgta    8220
gtcttgcaac atggtaacga tgagttagca acatgcctta caaggagaga aaaagcaccg   8280
tgcatgccga ttggtggaag taaggtggta cgatcgtgcc ttattaggaa ggcaacagac   8340
gggtctgaca tggattggac gaaccactga attggaggcg tggcctgggc gggactgggg   8400
agtggcgagc cctcagatcc tgcatataag cagctgcttt ttgcctgtac tgggtctctc    8460
tggttagacc agatctgagc ctgggagctc tctggctaac tagggaaccc actgcttaag   8520
cctcaataaa gcttgccttg agtgcttcaa gtagtgtgtg cccgtctgtt gtgtgactct    8580
ggtaactaga gatccctcag acccttttag tcagtgtgga aaatctctag cagtggcgcc    8640
cgaacaggga cctgaaagcg aaagggaaac cagagctctc tcgacgcagg actcggcttg   8700
ctgaagcgcg cacggcaaga ggcgaggggc ggcgactggt gagtacgcca aaaattttga   8760
ctagcggagg ctagaaggag agagatgggt gcgagagcgt cagtattaag cgggggagaa    8820
ttagatcgcg atgggaaaaa attcggttaa ggccaggggg aaagaaaaaa tataaattaa    8880
aacatatagt atgggcaagc agggagctag aacgattcgc agttaatcct ggcctgttag   8940
aaacatcaga aggctgtaga caaatactgg gacagctaca accatccctt cagacaggat    9000
cagaagaact tagatcatta tataatacag tagcaaccct ctattgtgtg catcaaagga   9060
tagagataaa agacaccaag gaagctttag acaagataga ggaagagcaa acaaaagta    9120 agaccaccgc acagcaagcg gccgctgatc ttcagacctg gaggaggaga tatgagggac   9180
aattggagaa gtgaattata taaatataaa gtagtaaaaa ttgaaccatt aggagtagca   9240
cccaccaagg caaagagaag agtggtgcag agagaaaaaa gagcagtggg aataggagct    9300
ttgttccttg ggttcttggg agcagcagga agcactatgg gcgcagcctc aatgacgctg    9360
acggtacagg ccagacaatt attgtctggt atagtgcagc agcagaacaa tttgctgagg   9420
gctattgagg cgcaacagca tctgttgcaa ctcacagtct ggggcatcaa gcagctccag   9480
gcaagaatcc tggctgtgga agataccta aaggatcaac agctcctggg gatttggggt    9540
tgctctggaa aactcatttg caccactgct gtgccttgga atgctagttg gagtaataaa    9600
tctctggaac agattggaat cacacgacct ggatggagtg gacagagaa attaacaatt    9660 acacaagctt aatacactcc ttaattgaag aatcgcaaaa ccagcaagaa aagaatgaac   9720
aagaattatt ggaattagat aaatgggcaa gtttgtggaa ttggtttaac ataacaaatt    9780
ggctgtggta tataaaatta ttcataatga tagtaggagg cttggtaggt ttaagaatag   9840
tttttgctgt actttctata gtgaatagag ttaggcaggg atattcacca ttatcgtttc    9900
```

```
agacccacct cccaaccccg aggggacccg acaggcccga aggaatagaa gaagaaggtg    9960
gagagagaga cagagacaga tccattcgat tagtgaacgg atctcgacgg tatcggtttt   10020
aaaagaaaag gggggattgg ggggtacagt gcagggaaa gaatagtaga cataatagca   10080
acagacatac aaactaaaga attacaaaaa caaattacaa aaattcaaaa ttttatcgat   10140
aagcttggga gttccgcgtt acataactta cggtaaatgg cccgcctggc tgaccgccca   10200
acgaccccg cccattgacg tcaataatga cgtatgttcc catagtaacg ccaatagggga   10260
ctttccattg acgtcaatgg gtggagtatt tacggtaaac tgcccacttg gcagtacatc   10320
aagtgtatca tatgccaagt acgccccta ttgacggtca atgacggtaa atggcccgcc   10380
tggcattatg cccagtacat gaccttatgg gactttccta cttggcagta catctacgta   10440
ttagtcatcg ctattaccat ggtgatgcgg ttttggcagt acatcaatgg gcgtggatag   10500
cggtttgact cacggggatt tccaagtctc cacccattg acgtcaatgg gagtttgttt   10560
tggcaccaaa atcaacggga ctttccaaaa tgtcgtaaca actccgcccc attgacgcaa   10620
atgggcggta ggcgtgtacg gtgggaggtc tatataagca gagctcgttt agtgaaccgt   10680
cagatcgcct ggagacgcca tccacgctgt tttgacctcc atagaagaca ccgacktcta   10740
gctagaggat cccccgggct gcagg                                         10765

<210> SEQ ID NO 85
<211> LENGTH: 10765
<212> TYPE: DNA
<213> ORGANISM: Artificial Sequence
<220> FEATURE:
<223> OTHER INFORMATION: Vector
<220> FEATURE:
<221> NAME/KEY: misc_feature
<222> LOCATION: (4978)..(4978)
<223> OTHER INFORMATION: n is a, c, g, or t

<400> SEQUENCE: 85
aattcatggc cttggctcaa gctcaccggg cccgtcgtct tcacgcagag gcgccagatt     60
caggagatca accgccgcgt cgtcgcgttc gccagcaacc tacgcgcgca gcaccagctc    120
ctgcccgcgc gcggcgccga cgtgcccctg cccctctcc cggcgggtcc ggagccccc    180
ctacctccgg gggctcgccc gcgtcaccgc ttttagatgc atcatccaag gacacccccg    240
cggcccaccg cccgccgcgc ggtaccgtag tcgcgccgcg gggatgcggc ctcttgcaag    300
ccatcgacgc cgccaccaac cagcccctgg aaattaggta tcacctggat ctagcccgcg    360
ccctgacccg tctatgcgag gtaaacctgc aggagctccc gcctgacctg acgccgcggg    420
agctccagac catggacagc tcccatctgc gcgatgttgt catcaagctc cgaccgccgc    480
gcgcggacat ctggactttg ggctcgcgcg gcgtggtggt ccgatccacc gtaactcccc    540
tcgagcagcc agacggtcaa ggacaagcag ccgaagtaga agaccaccag ccaaacccgc    600
caggcgaggg gctcaaattc ccactctgct tccttgtgcg cggtcgtcag gtcaacctcg    660
tgcaggatgt acagcccgtg caccgctgcc agtactgcgc acgtttttac aaaagccagc    720
acgagtgttc ggcccgtcgc agggacttct actttcacca catcaatagc cactcctcca    780
attggtggcg ggagatccag ttcttcccga tcggctcga tcctcgcacc gagcgtctct    840
ttgtcaccta cgatgtagag acctatactt ggatggggc ctttgggaag cagctcgtgc    900
ccttcatgct ggtcatgaag ttcggcgag atgagcctct agtgactgcc gcgcgagacc    960
tagccgcgaa ccttggatgg gaccgctggg aacaagaccc gcttaccttc tactgcatca   1020
```

-continued

```
ccccagaaaa aatggccata ggtcgccagt ttaggacctt tcgcgaccac ctgcaaatgc    1080
taatggcccg tgacctgtgg agctcattcg tcgcttccaa ccctcatctt gcagactggg    1140 cccttcaga gcacgggctc agctcccctg aagagctcac ctacgaggaa cttaaaaaat    1200
tgccttccat caagggcatc ccgcgcttct tggaacttta cattgtgggc acaacatta    1260 atgggtacga cgagatcgtg ctcgccgccc aggtaattaa caaccgttcc gaggtgccgg    1320 gaccctccg catcacacgc aactttatgc ctcgcgcggg aaagatactc ttcaacgatg    1380
tcaccttcgc cctgccaaat ccgcgttcca aaaagcgcac ggactttttg ctctgggagc    1440
agggcggatg cgacgacact gacttcaaat accagtacct caaagtcatg gtcagggaca    1500
cctttgcgct cacccacacc tcgctccgga aggccgcgca ggcatacgcg ctaccgtag    1560 aaaaggatg ctgcgcctac caggccgtca accagttcta catgctaggc tcttaccgtt    1620
cggaggccga cgggtttccg atccaagagt actggaaaga ccgcgaagag tttgtcctca    1680
accgcgagct gtggaaaaaa aagggacagg ataagtatga catcatcaag gaaaccctgg    1740
actactgcgc cctagacgtg caggtcaccg ccgagctggt caacaagctg cgcgactcct    1800
acgcctcctt cgtgcgtgac gcggtaggtc tcacagacgc cagcttcaac gtcttccagc    1860
gtccaaccat atcatccaac tcacatgcca tcttcaggca gatagtcttc cgagcagagc    1920
agcccgcccg tagcaacctc ggtcccgacc tcctcgctcc ctcgcacgaa ctatacgatt    1980
acgtgcgcgc cagcatccgc ggtggaagat gctaccctac atatcttgga atactcagag    2040
agcccctcta cgtttacgac atttgcggca tgtacgcctc cgcgctcacc caccccatgc    2100 catgggtcc cccactcaac ccatacgagc gcgcgcttgc cgcccgcgca tggcagcagg    2160
cgctagactt gcaaggatgc aagatagact acttcgacgc gcgcctgctg cccggggtct    2220
ttaccgtgga cgcagacccc ccggacgaga cgcagctaga cccctaccg ccattctgct    2280 cgcgcaaggg cggccgcctc tgctggacca acgagcgcct acgcggagag gtagccacca    2340
gcgttgacct tgtcaccctg cacaaccgcg gttggcgcgt gcacctggtg cccgacgagc    2400
gcaccaccgt cttccccgaa tggcggtgcg ttgcgcgcga atacgtgcag ctaaacatcg    2460
cggccaagga gcgcgccgat cgcgctaaga accaaaccct gcgctccatc gccaagttgc    2520
tgtccaacgc cctctacggg tcgtttgcca ccaagcttga caacaaaaag attgtctttt    2580
ctgaccagat ggatgcggcc accctcaaag gcatccaccgc gggccaggtg aatatcaaat    2640
cctcctcgtt tttgaaaact gacaatctta gcgcagaagt catgcccgct tttcagaggg    2700
agtactcacc ccaacagctg gccctcgcag acagcgatgc ggaagagagt gaggacgaac    2760
gcgcccccac ccccttttat agcccccctt caggaacacc cggtcacgtg gcctacacct    2820
acaaaccaat caccttcctt gatgccgaag agggcgacat gtgtcttcac accctggagc    2880
gagtggaccc cctagtggac aacgaccgct accccctccca cttagcctcc ttcgtgctgg    2940
cctggacgcg agcctttgtc tcagagtggt ccgagtttct atacgaggag gaccgcggaa    3000
caccgctcga ggacaggcct ctcaagtctg tatacgggga cacggacagc cttttcgtca    3060
ccgagcgtgg acaccggctc atggaaacca gaggtaagaa acgcatcaaa aagcatgggg    3120
gaaacctggt ttttgaccccc gaacggccag agctcacctg gctcgtggaa tgcgagaccg    3180
tctgcggggc ctgcggcgcg gatgcctact ccccggaatc ggtatttctc gcgcccaagc    3240
tctacgccct caaaagtctg cactgcccct cgtgcggcgc ctcctccaag ggcaagctgc    3300
gcgccaaggg ccacgccgcg gagggctgg actatgacac catggtcaaa tgctacctgg    3360
ccgacgcgca gggcgaagac cggcagcgct tcagcaccag caggaccagc ctcaagcgca    3420
```

```
ccctggccag cgcgcagccc ggagcgcacc ccttcaccgt gacccagact acgctgacga    3480
ggaccctgcg cccgtggaaa gacatgaccc tggcccgtct ggacgagcac cgactactgc    3540
cgtacagcga aagccgcccc aacccgcgaa acgaggagat atgctggatc gagatgccgt    3600
acccatacga tgttccggat tacgcttaga gcacgtgact acatttaaac cctaacaaaa    3660
caaagagatg gggttactct ctaaatttta tgggttatgt cattggatgt tatgggtcct    3720
tgccacaaga acacatcata caaaaaatca aagaatgttt tagaaaactt cctattaaca    3780
ggcctattga ttggaaagta tgtcaacgaa ttgtgggtct tttgggtttt gctgccoctt    3840
ttacacaatg tggttatcct gcgttgatgc ctttgtatgc atgtattcaa tctaagcagg    3900
cttteacttt ctcgccaact tacaaggcct ttctgtgtaa acaataccty aacctttacc    3960
ccgttgcccg gcaacggcca cctctgtgcc aagtgtttgc tgacgcaacc cccactggct    4020
ggggcttggt catgggccat cagcgcatgc gtggaacctt ttcggctcct ctgccgatcc    4080
atactgcgga actcctagcc gcttgttttg ctcgcagcag gtctggagca acattatcg    4140
ggactgataa ctctgttgtc ctatcccgca aatatacatc gtttccatgg ctgctaggct    4200
gtgctgccaa ctggatcctg cgcgggacgt cctttgttta cgtcccgtcg gcgctgaatc    4260
ctgcggacga cccttctcgg ggtcgcttgg gactctctcg tccccttctc cgtctgccgt    4320
tccgaccgac cacggggcgc acctctcttt acgcggactc cccgtctgtg ccttctcatc    4380
tgccggaccg tgtgcacttc gcttcacctc tgcacgtcgc atggagacca ccgtgaacgc    4440
ccaccaaata ttgcccaagg tcttacataa gaggactctt ggactctcag caatgtcaac    4500
gaccgacctt gaggcatact tcaaagactg tttgtttaaa gactgggagg agttggggga    4560
ggagattagg ttaaaggtct ttgtactagg aggctgtagg cataaattgg tctgcgcacc    4620
agcaccatgt atcactagag cggggtacct ttaagaccaa tgacttacaa ggcagctgta    4680
gatcttagcc actttttaaa agaaaagggg ggacttggaa gggctaattc actcccaacg    4740
aagacaagat ctgcttttg cttgtactgg gtctctctgg ttagaccaga tctgagcctg    4800
ggagctctct ggctaactag ggaacccact gcttaagcct caataaagct tgccttgagt    4860
gcttcaagta gtgtgtgccc gtctgttgtg tgactctggt aactagagat ccctcagacc    4920
cttttagtca gtgtggaaaa tctctagcag tagtagttca tgtcatctta ttattcangt    4980
atttataact tgcaaagaaa tgaatatcag agagtgagag gaacttgttt attgcagctt    5040
ataatggtta caaataaagc aatagcatca caaatttcac aaataaagca ttttttttcac    5100
tgcattctag ttgtggtttg tccaaactca tcaatgtatc ttatcatgtc tggctctagc    5160
tatcccgccc ctaactccgc ccagttccgc ccattctccg ccccatggct gactaatttt    5220
ttttatttat gcagaggccg aggccgcctc ggcctctgag ctattccaga agtagtgagg    5280
aggcttttttt ggaggcctag gcttttgcgt cgagacgtac ccaattcgcc ctatagtgag    5340
tcgtattacg cgcgctcact ggccgtcgtt ttacaacgtc gtgactggga aaaccctggc    5400
gttacccaac ttaatcgcct tgcagcacat cccccttttcg ccagctggcg taatagcgaa    5460
gaggcccgca ccgatcgccc ttcccaacag ttgcgcagcc tgaatggcga atggcgcgac    5520
gcgccctgta gcggcgcatt aagcgcggcg ggtgtggtgg ttacgcgcag cgtgaccgct    5580
acacttgcca gcgccctagc gcccgctcct ttcgctttct tcccttcctt tctcgccacg    5640
ttcgccggct ttccccgtca gctctaaat cgggggctcc ctttagggtt ccgatttagt    5700
gctttacggc acctcgaccc caaaaaactt gattagggtg atggttcacg tagtgggcca    5760
```

```
tcgccctgat agacggtttt tcgcccttg  acgttggagt ccacgttctt taatagtgga      5820
ctcttgttcc aaactggaac aacactcaac cctatctcgg tctattcttt tgatttataa      5880
gggattttgc cgatttcggc ctattggtta aaaatgagc  tgatttaaca aaaatttaac     5940
gcgaatttta acaaaatatt aacgttaca  atttcccagg tggcactttt cggggaaatg     6000
tgcgcggaac ccctatttgt ttattttct  aaatacattc aaatatgtat ccgctcatga     6060
gacaataacc ctgataaatg cttcaataat attgaaaaag gaagagtatg agtattcaac     6120
atttccgtgt cgcccttatt ccctttttg  cggcattttg ccttcctgtt tttgctcacc     6180
cagaaacgct ggtgaaagta aaagatgctg aagatcagtt gggtgcacga gtgggttaca     6240
tcgaactgga tctcaacagc ggtaagatcc ttgagagttt tcgccccgaa gaacgttttc     6300
caatgatgag cacttttaaa gttctgctat gtggcgcggt attatcccgt attgacgccg     6360
ggcaagagca actcggtcgc cgcatacact attctcagaa tgacttggtt gagtactcac     6420
cagtcacaga aaagcatctt acggatggca tgacagtaag agaattatgc agtgctgcca     6480
taaccatgag tgataacact gcggccaact tacttctgac aacgatcgga ggaccgaagg     6540
agctaaccgc ttttttgcac aacatggggg atcatgtaac tcgccttgat cgttgggaac     6600
cggagctgaa tgaagccata ccaaacgacg agcgtgacac cacgatgcct gtagcaatgg     6660
caacaacgtt gcgcaaacta ttaactggcg aactacttac tctagcttcc cggcaacaat     6720
taatagactg gatggaggcg gataaagttg caggaccact tctgcgctcg gcccttccgg     6780
ctggctggtt tattgctgat aaatctggag ccggtgagcg tgggtctcgc ggtatcattg     6840
cagcactggg gccagatggt aagccctccc gtatcgtagt tatctacacg acggggagtc     6900
aggcaactat ggatgaacga atagacaga  tcgctgagat aggtgcctca ctgattaagc     6960
attggtaact gtcagaccaa gtttactcat atatacttta gattgattta aaacttcatt     7020
tttaatttaa aaggatctag gtgaagatcc tttttgataa tctcatgacc aaaatccctt     7080
aacgtgagtt ttcgttccac tgagcgtcag accccgtaga aaagatcaaa ggatcttctt     7140
gagatccttt ttttctgcgc gtaatctgct gcttgcaaac aaaaaaacca ccgctaccag     7200
cggtggtttg tttgccggat caagagctac caactctttt tccgaaggta actggcttca     7260
gcagagcgca gataccaaat actgtccttc tagtgtagcc gtagttaggc caccacttca     7320
agaactctgt agcaccgcct acatacccg  ctctgctaat cctgttacca gtggctgctg     7380
ccagtggcga taagtcgtgt cttaccgggt tggactcaag acgatagtta ccggataagg     7440
cgcagcggtc gggctgaacg gggggttcgt gcacacagcc cagcttggag cgaacgacct     7500
acaccgaact gagatacta  cagcgtgagc tatgagaaag cgccacgctt cccgaaggga     7560
gaaaggcgga caggtatccg gtaagcggca gggtcggaac aggagagcgc acgagggagc     7620
ttccaggggg aaacgcctgg tatctttata gtcctgtcgg gtttcgccac ctctgacttg     7680
agcgtcgatt tttgtgatgc tcgtcagggg ggcggagcct atggaaaaac gccagcaacg     7740
cggcctttt  acggttcctg gccttttgct ggccttttgc tcacatgttc tttcctgcgt     7800
tatcccctga ttctgtggat aaccgtatta ccgcctttga gtgagctgat accgctcgcc     7860
gcagccgaac gaccgagcgc agcgagtcag tgagcgagga agcggaagag cgcccaatac     7920
gcaaaccgcc tctccccgcg cgttggccga ttcattaatg cagctggcac gacaggtttc     7980
ccgactggaa agcgggcagt gagcgcaacg caattaatgt gagttagctc actcattagg     8040
cacccccagg ctttacactt tatgcttccg gctcgtatgt tgtgtggaatt gtgagcggat     8100
aacaatttca cacaggaaac agctatgacc atgattacgc caagcgcgca attaaccctc     8160
```

```
actaaaggga caaaagctg gagctgcaag cttaatgtag tcttatgcaa tactcttgta    8220
gtcttgcaac atggtaacga tgagttagca acatgcctta caaggagaga aaaagcaccg    8280
tgcatgccga ttggtggaag taaggtggta cgatcgtgcc ttattaggaa ggcaacagac    8340
gggtctgaca tggattggac gaaccactga attggaggcg tggcctgggc gggactgggg    8400
agtggcgagc cctcagatcc tgcatataag cagctgcttt ttgcctgtac tgggtctctc    8460
tggttagacc agatctgagc ctgggagctc tctggctaac tagggaaccc actgcttaag    8520
cctcaataaa gcttgccttg agtgcttcaa gtagtgtgtg cccgtctgtt gtgtgactct    8580
ggtaactaga gatccctcag accctttttag tcagtgtgga aaatctctag cagtggcgcc    8640
cgaacaggga cctgaaagcg aaagggaaac cagagctctc tcgacgcagg actcggcttg    8700
ctgaagcgcg cacggcaaga ggcgaggggc ggcgactggt gagtacgcca aaattttga    8760
ctagcggagg ctagaaggag agagatgggt gcgagagcgt cagtattaag cggggagaa    8820
ttagatcgcg atgggaaaaa attcggttaa ggccaggggg aaagaaaaaa tataaattaa    8880
aacatatagt atgggcaagc agggagctag aacgattcgc agttaatcct ggcctgttag    8940
aaacatcaga aggctgtaga caaatactgg gacagctaca accatccctt cagacaggat    9000
cagaagaact tagatcatta tataatacag tagcaaccct ctattgtgtg catcaaagga    9060
tagagataaa agacaccaag gaagctttag acaagataga ggaagagcaa acaaaagta    9120
agaccaccgc acagcaagcg gccgctgatc ttcagacctg gaggaggaga tatgagggac    9180
aattggagaa gtgaattata taatataaa gtagtaaaaa ttgaaccatt aggagtagca    9240
cccaccaagg caaagagaag agtggtgcag agagaaaaaa gagcagtggg aataggagct    9300
ttgttccttg ggttcttggg agcagcagga agcactatgg gcgcagcctc aatgacgctg    9360
acggtacagg ccagacaatt attgtctggt atagtgcagc agcagaacaa tttgctgagg    9420
gctattgagg cgcaacagca tctgttgcaa ctcacagtct ggggcatcaa gcagctccag    9480
gcaagaatcc tggctgtgga agataccta aaggatcaac agctcctggg gatttggggt    9540
tgctctggaa aactcatttg caccactgct gtgccttgga atgctagttg gagtaataaa    9600
tctctggaac agattggaat cacacgacct ggatggagtg ggacagagaa attaacaatt    9660
acacaagctt aatacactcc ttaattgaag aatcgcaaaa ccagcaagaa aagaatgaac    9720
aagaattatt ggaattagat aaatgggcaa gtttgtggaa ttggtttaac ataacaaatt    9780
ggctgtggta tataaaatta ttcataatga tagtaggagg cttggtaggt ttaagaatag    9840
tttttgctgt actttctata gtgaatagag ttaggcaggg atattcacca ttatcgtttc    9900
agacccacct cccaaccccg aggggacccg acaggcccga aggaatagaa gaagaaggtg    9960
gagagagaga cagagacaga tccattcgat tagtgaacgg atctcgacgg tatcggtttt   10020
aaaagaaaag gggggattgg ggggtacagt gcagggaaa gaatagtaga cataatagca   10080
acagacatac aaactaaaga attacaaaaa caaattacaa aaattcaaaa ttttatcgat   10140
aagcttggga gttccgcgtt acataactta cggtaaatgg cccgcctggc tgaccgccca   10200
acgaccccg cccattgacg tcaataatga cgtatgttcc catagtaacg ccaatagggga   10260
ctttccattg acgtcaatgg gtggagtatt tacggtaaac tgcccacttg gcagtacatc   10320
aagtgtatca tatgccaagt acgccccta ttgacggtca atgacggtaa atggcccgcc   10380
tggcattatg cccagtacat gaccttatgg actttcccta cttggcagta catctacgta   10440
ttagtcatcg ctattaccat ggtgatgcgg ttttggcagt acatcaatgg gcgtggatag   10500
```

-continued

| | |
|---|---|
| cggtttgact cacggggatt tccaagtctc cacccattg acgtcaatgg gagtttgttt | 10560 |
| tggcaccaaa atcaacggga ctttccaaaa tgtcgtaaca actccgcccc attgacgcaa | 10620 |
| atgggcggta ggcgtgtacg gtgggaggtc tatataagca gagctcgttt agtgaaccgt | 10680 |
| cagatcgcct ggagacgcca tccacgctgt tttgacctcc atagaagaca ccgacktcta | 10740 |
| gctagaggat ccccggggct gcagg | 10765 |

<210> SEQ ID NO 86
<211> LENGTH: 3357
<212> TYPE: DNA
<213> ORGANISM: Artificial Sequence
<220> FEATURE:
<223> OTHER INFORMATION: Vector

<400> SEQUENCE: 86

| | |
|---|---|
| atcgcctgga gaattcactc tcttccgcat cgctgtctgc gagggccagc tgttgggctc | 60 |
| gcggttgagg acaaactctt cgcggtcttt ccagtactct tggatcggaa acccgtcggc | 120 |
| ctccgaacag gtactccgcc gccgaggac ctgagcgagt ccgcatcgac cggatcggaa | 180 |
| aacctctcga gaaaggcgtc taaccagtca cagtcgcaat gggctccagt gagcaggaac | 240 |
| tgaaagccat tgtcaaagat cttggttgtg ggccatattt tttgggcacc tatgacaagc | 300 |
| gctttccagg ctttgtttct ccacacaagc tcgcctgcgc catagtcaat acggccggtc | 360 |
| gcgagactgg gggcgtacac tggatggcct ttgcctggaa cccgcactca aaaacatgct | 420 |
| acctctttga gccctttggc ttttctgacc agcgactcaa gcaggtttac cagtttgagt | 480 |
| acgagtcact cctgcgccgt agcgccattg cttcttcccc cgaccgctgt ataacgctgg | 540 |
| aaaagtccac ccaaagcgta caggggccca actcggccgc tgtggacta ttctgctgca | 600 |
| tgtttctcca cgcctttgcc aactggcccc aaactcccat ggatcacaac cccaccatga | 660 |
| accttattac cggggtaccc aactccatgc tcaacagtcc ccaggtacag cccacccctgc | 720 |
| gtcgcaacca ggaacagctc tacagcttcc tggagcgcca ctcgccctac ttccgcagcc | 780 |
| acagtgcgca gattaggagc gccacttctt tttgtcactt gaaaaacatg taagtcgacg | 840 |
| atatctctag aggatcataa tcagccatac cacatttgta gaggttttac ttgctttaaa | 900 |
| aaacctccca cacctccccc tgaacctgaa acataaaatg aatgcaattg ttgttgttaa | 960 |
| cttgtttatt gcagcttata atggttacaa ataaagcaat agcatcacaa atttcacaaa | 1020 |
| taaagcattt ttttcactgc ctcgagcttc ctcgctcact gactcgctgc gctcggtcgt | 1080 |
| tcggctgcgg cgagcggtat cagctcactc aaaggcggta atacggttat ccacagaatc | 1140 |
| aggggataac gcaggaaaga acatgtgagc aaaaggccag caaaaggcca ggaaccgtaa | 1200 |
| aaaggccgcg ttgctggcgt ttttccatag gctccgcccc cctgacgagc atcacaaaaa | 1260 |
| tcgacgctca agtcagaggt ggcgaaaccc gacaggacta taaagatacc aggcgtttcc | 1320 |
| ccctggaagc tccctcgtgc gctctcctgt tccgaccctg ccgcttaccg gatacctgtc | 1380 |
| cgcctttctc ccttcgggaa gcgtggcgct ttctcatagc tcacgctgta ggtatctcag | 1440 |
| ttcggtgtag gtcgttcgct ccaagctggg ctgtgtgcac gaaccccccg ttcagcccga | 1500 |
| ccgctgcgcc ttatccggta actatcgtct tgagtccaac ccggtaagac acgacttatc | 1560 |
| gccactggca gcagccactg gtaacaggat tagcagagcg aggtatgtag gcggtgctac | 1620 |
| agagttcttg aagtggtggc ctaactacgg ctacactaga agaacagtat ttggtatctg | 1680 |
| cgctctgctg aagccagtta ccttcggaaa aagagttggt agctcttgat ccggcaaaca | 1740 |
| aaccaccgct ggtagcggtg gtttttttgt ttgcaagcag cagattacgc gcagaaaaaa | 1800 |

```
aggatctcaa gaagatcctt tgatcttttc tacggggtct gacgctcagt ggaacgaaaa   1860
ctcacgttaa gggattttgg tcatgagatt atcaaaaagg atcttcacct agatcctttt   1920
aaattaaaaa tgaagtttta aatcaatcta agtatatat gagtaaactt ggtctgacag    1980
ttaccaatgc ttaatcagtg aggcacctat ctcagcgatc tgtctatttc gttcatccat   2040
agttgcctga ctccccgtcg tgtagataac tacgatacgg gagggcttac catctggccc   2100
cagtgctgca atgataccgc gagacccacg ctcaccggct ccagatttat cagcaataaa   2160
ccagccagcc ggaagggccg agcgcagaag tggtcctgca actttatccg cctccatcca   2220
gtctattaat tgttgccggg aagctagagt aagtagttcg ccagttaata gtttgcgcaa   2280
cgttgttgcc attgctacag gcatcgtggt gtcacgctcg tcgtttggta tggcttcatt   2340
cagctccggt tcccaacgat caaggcgagt tacatgatcc cccatgttgt gcaaaaaagc   2400
ggttagctcc ttcggtcctc cgatcgttgt cagaagtaag ttggccgcag tgttatcact   2460
catggttatg gcagcactgc ataattctct tactgtcatg ccatccgtaa gatgcttttc   2520
tgtgactggt gagtactcaa ccaagtcatt ctgagaatag tgtatgcggc gaccgagttg   2580
ctcttgcccg gcgtcaacac gggataatac cgcgccacat agcagaactt aaaagtgct   2640 catcattgga aaacgttctt cggggcgaaa actctcaagg atcttaccgc tgttgagatc   2700
cagttcgatg taacccactc gtgcacccaa ctgatcttca gcatctttta ctttcaccag   2760
cgtttctggg tgagcaaaaa caggaaggca aaatgccgca aaaagggaa taagggcgac    2820 acggaaatgt tgaatactca tactcttcct ttttcaatat tattgaagca tttatcaggg   2880
ttattgtctc atgagcggat acatatttga atgtatttag aaaaataaac aataggggt    2940 tccgcgcaca tttccccgaa aagtgccacc tgacgtctaa gaaaccatta ttatcatgac   3000
attaacctat aaaaataggc gtatcacgag gccctttcgt cttcactcga gtttactccc   3060
tatcagtgat agagaacgta tgtcgagttt actccctatc agtgatagag aacgatgtcg   3120
agtttactcc ctatcagtga tagagaacgt atgtcgagtt tactccctat cagtgataga   3180
gaacgtatgt cgagtttact ccctatcagt gatagagaac gtatgtcgag tttatcccta   3240
tcagtgatag agaacgtatg tcgagtttac tccctatcag tgatagagaa cgtatgtcga   3300
ggtaggcgtg tacggtggga ggcctatata agcagagctc gtttagtgaa ccgtcag      3357
```

<210> SEQ ID NO 87  
<211> LENGTH: 9546  
<212> TYPE: DNA  
<213> ORGANISM: Artificial Sequence  
<220> FEATURE:  
<223> OTHER INFORMATION: Vector
<400> SEQUENCE: 87

```
aggtggcact tttcggggaa atgtgcgcgg aacccctatt tgtttatttt tctaaataca     60
ttcaaatatg tatccgctca tgagacaata accctgataa atgcttcaat aatattgaaa    120
aaggaagagt atgagtattc aacatttccg tgtcgccctt attcccttt ttgcggcatt     180 ttgccttcct gtttttgctc acccagaaac gctggtgaaa gtaaaagatg ctgaagatca    240
gttgggtgca cgagtgggtt acatcgaact ggatctcaac agcggtaaga tccttgagag    300
ttttcgcccc gaagaacgtt ttccaatgat gagcactttt aaagttctgc tatgtggcgc    360
ggtattatcc cgtattgacg ccgggcaaga gcaactcggt cgccgcatac actattctca    420
gaatgacttg gttgagtact caccagtcac agaaaagcat cttacggatg gcatgacagt    480
```

-continued

```
aagagaatta tgcagtgctg ccataaccat gagtgataac actgcggcca acttacttct    540
gacaacgatc ggaggaccga aggagctaac cgctttttg cacaacatgg gggatcatgt     600
aactcgcctt gatcgttggg aaccggagct gaatgaagcc ataccaaacg acgagcgtga    660
caccacgatg cctgtagcaa tggcaacaac gttgcgcaaa ctattaactg gcgaactact    720
tactctagct tcccggcaac aattaataga ctggatggag gcggataaag ttgcaggacc    780
acttctgcgc tcggcccttc cggctggctg gtttattgct gataaatctg gagccggtga    840
gcgtgggtct cgcggtatca ttgcagcact ggggccagat ggtaagccct cccgtatcgt    900
agttatctac acgacgggga gtcaggcaac tatggatgaa cgaaatagac agatcgctga    960
gataggtgcc tcactgatta agcattggta actgtcagac caagtttact catatatact   1020
ttagattgat ttaaaacttc attttaatt taaaaggatc taggtgaaga tccttttga    1080 taatctcatg accaaaatcc cttaacgtga gttttcgttc cactgagcgt cagacccgt    1140 agaaaagatc aaaggatctt cttgagatcc ttttttctg cgcgtaatct gctgcttgca    1200 aacaaaaaa ccaccgctac cagcggtggt ttgtttgccg gatcaagagc taccaactct   1260
ttttccgaag gtaactggct tcagcagagc gcagatacca aatactgttc ttctagtgta   1320
gccgtagtta ggccaccact tcaagaactc tgtagcaccg cctacatacc tcgctctgct   1380
aatcctgtta ccagtggctg ctgccagtgg cgataagtcg tgtcttaccg ggttggactc   1440
aagacgatag ttaccggata aggcgcagcg gtcgggctga acgggggggtt cgtgcacaca   1500 gcccagcttg gagcgaacga cctacaccga actgagatac ctacagcgtg agctatgaga   1560
aagcgccacg cttcccgaag ggagaaaggc ggacaggtat ccggtaagcg gcagggtcgg   1620
aacaggagag cgcacgaggg agcttccagg gggaaacgcc tggtatcttt atagtcctgt   1680
cgggtttcgc cacctctgac ttgagcgtcg attttgtga tgctcgtcag ggggggcggag    1740 cctatggaaa aacgccagca acgcggcctt tttacggttc ctggcctttt gctggccttt   1800
tgctcacatg ttctttcctg cgttatcccc tgattctgtg ataaccgta ttaccgcctt    1860 tgagtgagct gataccgctc gccgcagccg aacgaccgag cgcagcgagt cagtgagcga   1920
ggaagcggaa gagcgcccaa tacgcaaacc gcctctcccc gcgcgttggc cgattcatta   1980
atgcagctgg cacgacaggt ttcccgactg gaaagcgggc agtgagcgca acgcaattaa   2040
tgtgagttag ctcactcatt aggcacccca ggctttacac tttatgcttc cggctcgtat   2100
gttgtgtgga attgtgagcg gataacaatt tcacacagga aacagctatg accatgatta   2160
cgccaagcgc gcaattaacc ctcactaaag ggaacaaaag ctggagctgc aagcttaatg   2220
tagtcttatg caatactctt gtagtcttgc aacatggtaa cgatgagtta gcaacatgcc   2280
ttacaaggag agaaaaagca ccgtgcatgc cgattggtgg aagtaaggtg gtacgatcgt   2340
gccttattag gaaggcaaca gacgggtctg acatggattg gacgaaccac tgaattgccg   2400
cattgcagag atattgtatt taagtgccta gctcgataca taaacgggtc tctctggtta   2460
gaccagatct gagcctggga gctctctggc taactaggga acccactgct taagcctcaa   2520
taaagcttgc cttgagtgct tcaagtagtg tgtgcccgtc tgttgtgtga ctctggtaac   2580
tagagatccc tcagaccctt ttagtcagtg tggaaaatct ctagcagtgg cgcccgaaca   2640
gggacttgaa agcgaaaggg aaaccagagg agctctctcg acgcaggact cggcttgctg   2700
aagcgcgcac ggcaagaggc gaggggcggc gactggtgag tacgccaaaa attttgacta   2760
gcggaggcta aaggagaga gatgggtgcg agagcgtcag tattaagcgg gggagaatta   2820
gatcgcgatg ggaaaaaatt cggttaaggc caggggggaaa gaaaaaatat aaattaaaac   2880
```

```
atatagtatg ggcaagcagg gagctagaac gattcgcagt taatcctggc ctgttagaaa    2940
catcagaagg ctgtagacaa atactgggac agctacaacc atcccttcag acaggatcag    3000
aagaacttag atcattatat aatacagtag caaccctcta ttgtgtgcat caaaggatag    3060
agataaaaga caccaaggaa gctttagaca agatagagga agagcaaaac aaaagtaaga    3120
ccaccgcaca gcaagcggcc gctgatcttc agacctggag gaggagatat gagggacaat    3180
tggagaagtg aattatataa atataaagta gtaaaaattg aaccattagg agtagcaccc    3240
accaaggcaa agagaagagt ggtgcagaga gaaaaaagag cagtgggaat aggagctttg    3300
ttccttgggt tcttgggagc agcaggaagc actatgggcg cagcgtcaat gacgctgacg    3360
gtacaggcca gacaattatt gtctggtata gtgcagcagc agaacaattt gctgagggct    3420
attgaggcgc aacagcatct gttgcaactc acagtctggg gcatcaagca gctccaggca    3480
agaatcctgg ctgtggaaag atacctaaag gatcaacagc tcctggggat ttggggttgc    3540
tctggaaaac tcatttgcac cactgctgtg ccttggaatg ctagttggag taataaatct    3600
ctggaacaga tttggaatca cacgacctgg atggagtggg acagagaaat taacaattac    3660
acaagcttaa tacactcctt aattgaagaa tcgcaaaacc agcaagaaaa gaatgaacaa    3720
gaattattgg aattagataa atgggcaagt ttgtggaatt ggtttaacat aacaaattgg    3780
ctgtggtata taaaattatt cataatgata gtaggaggct tggtaggttt aagaatagtt    3840
tttgctgtac tttctatagt gaatagagtt aggcagggat attcaccatt atcgtttcag    3900
acccacctcc caaccccgag gggacccgac aggcccgaag gaatagaaga agaaggtgga    3960
gagagagaca gagacagatc cattcgatta gtgaacggat ctcgacggta tcggttaact    4020
tttaaaagaa aagggggat tgggggac agtgcagggg aaagaatagt agacataata    4080
gcaacagaca tacaaactaa agaattacaa aaacaaatta caaaattcaa aattttatcg    4140
ataagcttgg gagttccgcg ttacataact tacggtaaat ggcccgcctg gctgaccgcc    4200
caacgacccc cgcccattga cgtcaataat gacgtatgtt cccatagtaa cgccaatagg    4260
gactttccat tgacgtcaat gggtggagta tttacggtaa actgcccact tggcagtaca    4320
tcaagtgtat catatgccaa gtacgccccc tattgacgtc aatgacggta aatggcccgc    4380
ctggcattat gcccagtaca tgaccttatg ggactttcct acttggcagt acatctacgt    4440
attagtcatc gctattacca tggtgatgcg gttttggcag tacatcaatg ggcgtggata    4500
gcggtttgac tcacggggat ttccaagtct ccaccccatt gacgtcaatg ggagtttgtt    4560
ttggcaccaa aatcaacggg actttccaaa atgtcgtaac aactccgccc cattgacgca    4620
aatgggcggt aggcgtgtac ggtgggaggt ctatataagc agagctcgtt tagtgaaccg    4680
tcagatcgcc tggagacgcc atccacgctg ttttgacctc catagaagac accgactcta    4740
gtccagtgtg gtggaattct gcagatatca acaagtttgt acaaaaaagc aggctttaaa    4800
ggaaccaatt cagtcgactg gatccggtac cgaattcgcg gccgcactct cttccgcatc    4860
gctgtctgcg agggccagct gttgggctcg cggttgagga caaactcttc gcggtctttc    4920
cagtactctt ggatcggaaa cccgtcggcc tccgaacagg tactccgccc cagagggacc    4980
tgagcgagtc cgcatcgacc ggatcggaaa acctctcgag aaaggcgtct aaccagtcac    5040
agtcgcaatg ggctccagtg agcaggaact gaaagccatt gtcaaagatc ttggttgtgg    5100
gccatatttt ttgggcacct atgacaagcg ctttccaggc tttgtttctc cacacaagct    5160
cgcctgcgcc atagtcaata cggccggtcg cgagactggg ggcgtacact ggatggcctt    5220
```

```
tgcctggaac ccgcactcaa aaacatgcta cctctttgag ccctttggct tttctgacca    5280
gcgactcaag caggtttacc agtttgagta cgagtcactc ctgcgccgta gcgccattgc    5340
ttcttccccc gaccgctgta taacgctgga aaagtccacc caaagcgtac aggggcccaa    5400
ctcggccgcc tgtggactat tctgctgcat gtttctccac gcctttgcca actgccccaa    5460
aactcccatg gatcacaacc ccaccatgaa ccttattacc ggggtaccca actccatgct    5520
caacagtccc caggtacagc ccaccctgcg tcgcaaccag gaacagctct acagcttcct    5580
ggagcgccac tcgccctact ccgcagccaa cagtgcgcag attaggagcg ccacttcttt    5640
ttgtcacttg aaaaacatgt aatctagacc cagctttctt gtacaaagtg gttgatatcc    5700
agcacagtgg cggccgctcg acaatcaacc tctggattac aaaatttgtg aaagattgac    5760
tggtattctt aactatgttg ctccttttac gctatgtgga tacgctgctt taatgccttt    5820
gtatcatgct attgcttccc gtatggcttt cattttctcc tccttgtata atcctggtt    5880 gctgtctctt tatgaggagt tgtggcccgt tgtcaggcaa cgtggcgtgg tgtgcactgt    5940
gtttgctgac gcaacccccca ctggttgggg cattgccacc acctgtcagc tcctttccgg    6000
gactttcgct ttcccccctcc ctattgccac ggcggaactc atcgccgcct gccttgcccg    6060
ctgctggaca ggggctcggc tgttgggcac tgacaattcc gtggtgttgt cggggaagct    6120
gacgtccttt ccatggctgc tcgcctgtgt tgccacctgg attctgcgcg gacgtccttt    6180
ctgctacgtc ccttcggccc tcaatccagc ggaccttcct tcccgcggcc tgctgccggc    6240
tctgcggcct cttccgcgtc ttcgccttcg ccctcagacg agtcggatct ccctttgggc    6300
cgcctccccg cctggaattc tgcagatatc cggactagtg atctctcgag gttaacgaat    6360
tctaccgggt aggggaggcg cttttcccaa ggcagtctgg agcatgcgct ttagcagccc    6420
cgctgggcac ttggcgctac acaagtggcc tctggcctcg cacacattcc acatccaccg    6480
gtaggcgcca accggctccg ttctttggtg ccccttcgc gccaccttct actcctcccc    6540
tagtcaggaa gttcccccccc gccccgcagc tcgcgtcgtg caggacgtga caaatgaag    6600 tagcacgtct cactagtctc gtgcagatgg acagcaccgc tgagcaatgg aagcgggtag    6660
gcctttgggg cagcggccaa tagcagcttt gctccttcgc tttctgggct cagaggctgg    6720 gaagggtgg gtccggggc gggctcaggg gcgggctcag gggcggggcg gcgcccgaa    6780 ggtcctccgg aggcccggca ttctgcacgc ttcaaaagcg cacgtctgcc gcgctgttct    6840
cctcttcctc atctccgggc ctttcgacct gcatcccgcc accatgaaaa agcctgaact    6900
caccgcgacg tctgtcgaga agtttctgat cgaaaagttc gacagcgtct ccgacctgat    6960
gcagctctcg gagggcgaag aatctcgtgc tttcagcttc gatgtaggag ggcgtggata    7020
tgtcctgcgg gtaaatagct gcgccgatgg tttctacaaa gatcgttatg tttatcggca    7080
ctttgcatcg gccgcgctcc cgattccgga agtgcttgac attggggaat tcagcgagag    7140
cctgacctat tgcatctccc gccgtgcaca gggtgtcacg ttgcaagacc tgcctgaaac    7200
cgaactgccc gctgttctgc agccggtcgc ggaggccatg gatgcgatcg ctgcggccga    7260
tcttagccag acgagcgggt tcggcccatt cggaccgcaa ggaatcggtc aatacactac    7320
atggcgtgat ttcatatgcg cgattgctga tccccatgtg tatcactggc aaactgtgat    7380
ggacgacacc gtcagtgcgt ccgtcgcgca ggctctcgat gagctgatgc tttgggccga    7440
ggactgcccc gaagtccggc acctcgtgca cgcggatttc ggctccaaca atgtcctgac    7500
ggacaatggc cgcataacag cggtcattga ctggagcgag gcgatgttcg ggattccca    7560 atacgaggtc gccaacatct tcttctggag gccgtggttg gcttgtatgg agcagcagac    7620
```

-continued

```
gcgctacttc gagcggaggc atccggagct tgcaggatcg ccgcggctcc gggcgtatat    7680
gctccgcatt ggtcttgacc aactctatca gagcttggtt gacggcaatt tcgatgatgc    7740
agcttgggcg cagggtcgat gcgacgcaat cgtccgatcc ggagccggga ctgtcgggcg    7800
tacacaaatc gcccgcagaa gcgcggccgt ctggaccgat ggctgtgtag aagtactcgc    7860
cgatagtgga aaccgacgcc ccagcactcg tccgagggca aggaataga gtagatgccg    7920
accgaacaag agctgatttc gagaacgcct cagccagcaa ctcgcgcgag cctagcaagg    7980
caaatgcgag agaacggcct tacgcttggt ggcacagttc tcgtccacag ttcgctaagc    8040
tcgctcggct gggtcgcggg agggccggtc gcagtgattc aggcccttct ggattgtgtt    8100
ggtccccagg gcacgattgt catgcccacg cactcgggtg atctgactga tcccgcagat    8160
tggagatcgc cgcccgtgcc tgccgattgg gtgcagatcc gtcgagggcc cggtacccttt   8220
aagaccaatg acttacaagg cagctgtaga tcttagccac ttttttaaaag aaaagggggg   8280
actggaaggg ctagctcact cccaacgaag acaagatctg cttttttgctt gtactgggtc   8340
tctctggtta gaccagatct gagcctggga gctctctggc taactaggga acccactgct   8400
taagcctcaa taaagcttgc cttgagtgct tcaagtagtg tgtgcccgtc tgttgtgtga    8460
ctctggtaac tagagatccc tcagaccctt ttagtcagtg tggaaaatct ctagcagtag    8520
tagttcatgt catcttatta ttcagtattt ataacttgca aagaaatgaa tatcagagag    8580
tgagaggaac ttgtttattg cagcttataa tggttacaaa taaagcaata gcatcacaaa    8640
tttcacaaat aaagcatttt tttcactgca ttctagttgt ggtttgtcca aactcatcaa    8700
tgtatcttat catgtctggc tctagctatc ccgcccctaa ctccgcccat cccgccccta    8760
actccgccca gttccgccca ttctccgccc catggctgac taattttttt tatttatgca    8820
gaggccgagg ccgcctcggc ctctgagcta ttccagaagt agtgaggagg cttttttgga    8880
ggcctaggga cgtacccaat tcgccctata gtgagtcgta ttacgcgcgc tcactggccg    8940
tcgttttaca acgtcgtgac tgggaaaacc ctggcgttac ccaacttaat cgccttgcag    9000
cacatccccc tttcgccagc tggcgtaata gcgaagaggc ccgcaccgat cgcccttccc    9060
aacagttgcg cagcctgaat ggcgaatggg acgcgccctg tagcggcgca ttaagcgcgg    9120
cgggtgtggt ggttacgcgc agcgtgaccg ctacacttgc cagcgcccta gcgcccgctc    9180
ctttcgcttt cttcccttcc tttctcgcca cgttcgccgg ctttccccgt caagctctaa    9240
atcgggggct ccctttaggg ttccgattta gtgctttacg gcacctcgac cccaaaaaac    9300
ttgattaggg tgatggttca cgtagtgggc catcgccctg atagacggtt tttcgccctt    9360
tgacgttgga gtccacgttc tttaatagtg gactcttgtt ccaaactgga acaacactca    9420
accctatctc ggtctattct tttgatttat aagggatttt gccgatttcg cctattggt    9480
taaaaaatga gctgatttaa caaaaattta acgcgaattt taacaaaata ttaacgctta    9540
caattt                                                               9546
```

<210> SEQ ID NO 88
<211> LENGTH: 8632
<212> TYPE: DNA
<213> ORGANISM: Artificial Sequence
<220> FEATURE:
<223> OTHER INFORMATION: Vector

<400> SEQUENCE: 88

```
tggaagggct aattcactcc caaagaagac aagatatcct tgatctgtgg atctaccaca      60
```

-continued

| | | | | |
|---|---|---|---|---|
| cacaaggcta | cttccctgat | tagcagaact | acacaccagg | gccagggtc agatatccac | 120 |
| tgacctttgg | atggtgctac | aagctagtac | cagttgagcc | agataaggta gaagaggcca | 180 |
| ataaaggaga | gaacaccagc | ttgttacacc | ctgtgagcct | gcatgggatg gatgacccgg | 240 |
| agagagaagt | gttagagtgg | aggtttgaca | gccgcctagc | atttcatcac gtggcccgag | 300 |
| agctgcatcc | ggagtacttc | aagaactgct | gatatcgagc | ttgctacaag ggactttccg | 360 |
| ctggggactt | tccagggagg | cgtggcctgg | gcgggactgg | ggagtggcga gccctcagat | 420 |
| cctgcatata | agcagctgct | ttttgcctgt | actgggtctc | tctggttaga ccagatctga | 480 |
| gcctgggagc | tctctggcta | actagggaac | ccactgctta | agcctcaata aagcttgcct | 540 |
| tgagtgcttc | aagtagtgtg | tgcccgtctg | ttgtgtgact | ctggtaacta gagatccctc | 600 |
| agacccttt | agtcagtgtg | gaaaatctct | agcagtggcg | cccgaacagg gacttgaaag | 660 |
| cgaaagggaa | accagaggag | ctctctcgac | gcaggactcg | gcttgctgaa gcgcgcacgg | 720 |
| caagaggcga | ggggcggcga | ctggtgagta | cgccaaaaat | tttgactagc ggaggctaga | 780 |
| aggagagaga | tgggtgcgag | agcgtcagta | ttaagcgggg | gagaattaga tcgcgatggg | 840 |
| aaaaaattcg | gttaaggcca | gggggaaaga | aaaaatataa | attaaaacat atagtatggg | 900 |
| caagcaggga | gctagaacga | ttcgcagtta | atcctggcct | gttagaaaca tcagaaggct | 960 |
| gtagacaaat | actgggacag | ctacaaccat | cccttcagac | aggatcagaa gaacttagat | 1020 |
| cattatataa | tacagtagca | accctctatt | gtgtgcatca | aaggatagag ataaaagaca | 1080 |
| ccaaggaagc | tttagacaag | atagaggaag | agcaaaacaa | aagtaagacc accgcacagc | 1140 |
| aagcggccgg | ccgctgatct | tcagacctgg | aggaggagat | atgagggaca attggagaag | 1200 |
| tgaattatat | aaatataaag | tagtaaaaat | tgaaccatta | ggagtagcac ccaccaaggc | 1260 |
| aaagagaaga | gtggtgcaga | gagaaaaaag | agcagtggga | ataggagctt tgttccttgg | 1320 |
| gttcttggga | gcagcaggaa | gcactatggg | cgcagcgtca | atgacgctga cggtacaggc | 1380 |
| cagacaatta | ttgtctggta | tagtgcagca | gcagaacaat | ttgctgaggg ctattgaggc | 1440 |
| gcaacagcat | ctgttgcaac | tcacagtctg | gggcatcaag | cagctccagg caagaatcct | 1500 |
| ggctgtggaa | agatacctaa | aggatcaaca | gctcctgggg | atttggggtt gctctggaaa | 1560 |
| actcatttgc | accactgctg | tgccttggaa | tgctagttgg | agtaataaat ctctggaaca | 1620 |
| gatttggaat | cacacgacct | ggatggagtg | ggacagagaa | attaacaatt acacaagctt | 1680 |
| aatacactcc | ttaattgaag | aatcgcaaaa | ccagcaagaa | aagaatgaac aagaattatt | 1740 |
| ggaattagat | aaatgggcaa | gtttgtggaa | ttggtttaac | ataacaaatt ggctgtggta | 1800 |
| tataaaatta | ttcataatga | tagtaggagg | cttggtaggt | ttaagaatag ttttgctgt | 1860 |
| actttctata | gtgaatagag | ttaggcaggg | atattcacca | ttatcgtttc agacccacct | 1920 |
| cccaaccccg | aggggacccg | acaggcccga | aggaatagaa | gaagaaggtg gagagagaga | 1980 |
| cagagacaga | tccattcgat | tagtgaacgg | atctcgacgg | tatcgccttt aaaagaaaag | 2040 |
| gggggattgg | ggggtacagt | gcaggggaaa | gaatagtaga | cataatagca acagacatac | 2100 |
| aaactaaaga | actacaaaaa | caaattacaa | aaattcaaaa | ttttcgggtt tattacaggg | 2160 |
| acagcagaga | tccagtttat | cgatgaggcc | ctttcgtctt | cactcgagtt tactccctat | 2220 |
| cagtgataga | gaacgtatga | agagtttact | ccctatcagt | gatagagaac gtatgcagac | 2280 |
| tttactccct | atcagtgata | gagaacgtat | aaggagttta | ctccctatca gtgatagaga | 2340 |
| acgtatgacc | agtttactcc | ctatcagtga | tagagaacgt | atctacagtt tactccctat | 2400 |
| cagtgataga | gaacgtatat | ccagtttact | ccctatcagt | gatagagaac gtatgtcgag | 2460 |

-continued

```
gtaggcgtgt acggtgggcg cctataaaag cagagctcgt ttagtgaacc gtcagatcgc   2520
ctggagcaat tccacaacac ttttgtctta tacttggatc cgcactctct tccgcatcgc   2580
tgtctgcgag ggccagctgt tgggctcgcg gttgaggaca aactcttcgc ggtctttcca   2640
gtactcttgg atcggaaacc cgtcggcctc cgaacaggta ctccgccgcc gagggacctg   2700
agcgagtccg catcgaccgg atcggaaaac ctctcgagaa aggcgtctaa ccagtcacag   2760
tcgcaatggg ctccagtgag caggaactga aagccattgt caaagatctt ggttgtgggc   2820
catattttt gggcacctat gacaagcgct ttccaggctt tgtttctcca cacaagctcg   2880
cctgcgccat agtcaatacg gccggtcgcg agactggggg cgtacactgg atggcctttg   2940
cctggaaccc gcactcaaaa acatgctacc tctttgagcc cttttggcttt tctgaccagc   3000
gactcaagca ggtttaccag tttgagtacg agtcactcct cgccgtagc gccattgctt   3060
cttccccga ccgctgtata acgctggaaa agtccaccca aagcgtacag ggcccaact    3120
cggccgcctg tggactattc tgctgcatgt ttctccacgc ctttgccaac tggcccaaa   3180
ctcccatgga tcacaacccc accatgaacc ttattaccgg ggtacccaac tccatgctca   3240
acagtcccca ggtacagccc accctgcgtc gcaaccagga acagctctac agcttcctgg   3300
agcgccactc gccctacttc cgcagccaca gtgcgcagat taggagcgcc acttcttttt   3360
gtcacttgaa aaacatgtaa gcgccggtc tagatcgcga acgcgtgaat tctaccgggt   3420
agggggaggcg cttttcccaa ggcagtctgg agcatgcgct ttagcagccc cgctgggcac   3480
ttggcgctac acaagtggcc tctgcctcg cacacattcc acatccaccg gtaggcgcca   3540
accggctccg ttctttggtg gccccttcgc gccaccttct actcctcccc tagtcaggaa   3600
gttccccccc gccccgcagc tcgcgtcgtg caggacgtga caaatggaag tagcacgtct   3660
cactagtctc gtgcagatgg acagcaccgc tgagcaatgg aagcgggtag gcctttgggg   3720
cagcggccaa tagcagcttt gctccttcgc tttctgggct cagaggctgg aaggggtgg   3780
gtccgggggc gggctcaggg gcgggctcag gggcggggcg ggcgcccgaa ggtcctccgg   3840
aggcccggca ttctgcacgc ttcaaaagcg cacgtctgcc gcgctgttct cctcttcctc   3900
atctccgggc ctttcgacct gcagcccaag cttaccatga ccgagtacaa gcccacggtg   3960
cgcctcgcca cccgcgacga cgtccccagg gccgtacgca ccctcgccgc gcgttcgcc   4020
gactaccccg ccacgcgcca caccgtcgat ccggaccgcc acatcgagcg ggtcaccgag   4080
ctgcaagaac tcttcctcac gcgcgtcggg ctcgacatcg gcaaggtgtg ggtcgcggac   4140
gacggcgccg cggtggcggt ctggaccacg ccggagagcg tcgaagcggg ggcggtgttc   4200
gccgagatcg gcccgcgcat ggccgagttg agcggttccc ggctggccgc gcagcaacag   4260
atggaaggcc tcctggcgcc gcaccggccc aaggagcccg cgtggttcct ggccaccgtc   4320
ggcgtctcgc ccgaccacca gggcaagggt ctgggcagcg ccgtcgtgct ccccggagtg   4380
gaggcggcca gcgcgccgg ggtgcccgcc ttcctggaga cctccgcgcc ccgcaacctc   4440
cccttctacg agcggctcgg cttcaccgtc accgccgacg tcgaggtgcc cgaaggaccg   4500
cgcacctggt gcatgacccg caagcccggt gcctgacggg gcgcgtctgg aacaatcaac   4560
ctctggatta caaaatttgt gaaagattga ctggtattct taactatgtt gctccttta   4620
cgctatgtgg atacgctgct ttaatgcctt tgtatcatgc tattgcttcc cgtatggctt   4680
tcattttctc ctccttgtat aaatcctggt tgctgtctct ttatgaggag ttgtggcccg   4740
ttgtcaggca acgtggcgtg gtgtgcactg tgtttgctga cgcaaccccc actggttggg   4800
```

```
gcattgccac cacctgtcag ctcctttccg ggactttcgc tttccccctc cctattgcca    4860
cggcggaact catcgccgcc tgccttgccc gctgctggac aggggctcgg ctgttgggca    4920
ctgacaattc cgtggtgttg tcggggaagc tgacgtcctt tccatggctg ctcgcctgtg    4980
ttgccacctg gattctgcgc gggacgtcct tctgctacgt cccttcggcc ctcaatccag    5040
cggaccttcc ttcccgcggc ctgctgccgg ctctgcggcc tcttccgcgt cttcgccttc    5100
gccctcagac gagtcggatc tccctttggg ccgcctcccc gcctggaatt aattctgcag    5160
tcgagaccta gaaaacatg gagcaatcac aagtagcaat acagcagcta ccaatgctga    5220
ttgtgcctgg ctagaagcac aagaggagga ggaggtgggt ttttccagtc cacctcagg    5280 taccttaag accaatgact acaaggcag ctgtagatct tagccacttt ttaaaagaaa    5340 agagggact ggaagggcta attcactccc aacgaagaca agatatcctt gatctgtgga    5400
tctaccacac acaaggctac ttccctgatt agcagaacta cacaccaggg ccaggggtca    5460
gatatccact gacctttgga tggtgctaca agctagtacc agttgagcca gataaggtag    5520
aagaggccaa taaggagag aacaccagct tgttacaccc tgtgagcctg catgggatgg    5580
atgacccgga gagagaagtg ttagagtgga ggtttgacag ccgcctagca tttcatcacg    5640
tggcccgaga gctgcatccg gagtacttca agaactgctg atatcgagct tgctacaagg    5700
gactttccgc tggggacttt ccagggaggc gtggcctggg cgggactggg gagtggcgag    5760
ccctcagatc ctgcatataa gcagctgctt tttgcctgta ctgggtctct ctggttagac    5820
cagatctgag cctgggagct ctctggctaa ctagggaacc cactgcttaa gcctcaataa    5880
agcttgcctt gagtgcttca agtagtgtgt gcccgtctgt tgtgtgactc tggtaactag    5940
agatccctca gaccctttta gtcagtgtgg aaaatctcta gcagtagtag ttcatgtcat    6000
cttattattc agtatttata acttgcaaag aaatgaatat cagagagtga gaggccttga    6060
cattgctagc gttttaccgt cgacctctag ctagagcttg gcgtaatcat ggtcatagct    6120
gtttcctgtg tgaaattgtt atccgctcac aattccacac aacatacgag ccggaagcat    6180
aaagtgtaaa gcctggggtg cctaatgagt gagctaactc acattaattg cgttgcgctc    6240
actgcccgct ttccagtcgg gaaacctgtc gtgccagctg cattaatgaa tcggccaacg    6300
cgcggggaga ggcggtttgc gtattgggcg ctcttccgct tcctcgctca ctgactcgct    6360
gcgctcggtc gttcggctgc ggcgagcggt atcagctcac tcaaaggcgg taatacggtt    6420
atccacagaa tcaggggata acgcaggaaa gaacatgtga gcaaaaggcc agcaaaaggc    6480
caggaaccgt aaaaaggccg cgttgctggc gttttccat aggctccgcc ccctgacga    6540 gcatcacaaa aatcgacgct caagtcagag gtggcgaaac ccgacaggac tataaagata    6600
ccaggcgttt cccctggaa gctccctcgt gcgctctcct gttccgaccc tgccgcttac    6660
cggatacctg tccgccttc tcccttcggg aagcgtggcg ctttctcata gctcacgctg    6720
taggtatctc agttcggtgt aggtcgttcg ctccaagctg ggctgtgtgc acgaaccccc    6780
cgttcagccc gaccgctgcg ccttatccgg taactatcgt cttgagtcca acccggtaag    6840
acacgactta tcgccactgg cagcagccac tggtaacagg attagcagag cgaggtatgt    6900
aggcggtgct acagagttct tgaagtggtg gcctaactac ggctacacta gaagaacagt    6960
atttggtatc tgcgctctgc tgaagccagt taccttcgga aaaagagttg gtagctcttg    7020
atccggcaaa caaaccaccg ctggtagcgg tttttttgtt tgcaagcagc agattacgcg    7080
cagaaaaaaa ggatctcaag aagatccttt gatcttttct acggggtctg acgctcagtg    7140
gaacgaaaac tcacgttaag ggattttggt catgagatta tcaaaaagga tcttcaccta    7200
```

```
gatcctttta aattaaaaat gaagttttaa atcaatctaa agtatatatg agtaaacttg    7260
gtctgacagt taccaatgct taatcagtga ggcacctatc tcagcgatct gtctatttcg    7320
ttcatccata gttgcctgac tccccgtcgt gtagataact acgatacggg agggcttacc    7380
atctggcccc agtgctgcaa tgataccgcg agacccacgc tcaccggctc cagatttatc    7440
agcaataaac cagccagccg aagggccga gcgcagaagt ggtcctgcaa ctttatccgc    7500
ctccatccag tctattaatt gttgccggga agctagagta agtagttcgc cagttaatag    7560
tttgcgcaac gttgttgcca ttgctacagg catcgtggtg tcacgctcgt cgtttggtat    7620
ggcttcattc agctccggtt cccaacgatc aaggcgagtt acatgatccc ccatgttgtg    7680
caaaaaagcg gttagctcct tcggtcctcc gatcgttgtc agaagtaagt tggccgcagt    7740
gttatcactc atggttatgg cagcactgca taattctctt actgtcatgc catccgtaag    7800
atgcttttct gtgactggtg agtactcaac caagtcattc tgagaatagt gtatgcggcg    7860
accgagttgc tcttgcccgg cgtcaatacg ggataatacc gcgccacata gcagaacttt    7920
aaaagtgctc atcattggaa aacgttcttc ggggcgaaaa ctctcaagga tcttaccgct    7980
gttgagatcc agttcgatgt aacccactcg tgcacccaac tgatcttcag catcttttac    8040
tttcaccagc gtttctgggt gagcaaaaac aggaaggcaa aatgccgcaa aaaagggaat    8100
aagggcgaca cggaaatgtt gaatactcat actcttcctt tttcaatatt attgaagcat    8160
ttatcagggt tattgtctca tgagcggata catatttgaa tgtatttaga aaaataaaca    8220
aataggggtt ccgcgcacat ttccccgaaa agtgccacct gacgtcgacg gatcgggaga    8280
tcaacttgtt tattgcagct tataatggtt acaaataaag caatagcatc acaaatttca    8340
caaataaagc atttttttca ctgcattcta gttgtggttt gtccaaactc atcaatgtat    8400
cttatcatgt ctggatcaac tggataactc aagctaacca aaatcatccc aaacttccca    8460 ccccatatccc tattaccact gccaattacc tagtggttc atttactcta aacctgtgat    8520
tcctctgaat tattttcatt ttaaagaaat tgtatttgtt aaatatgtac tacaaactta    8580
gtagttttta agaaattgt atttgttaaa tatgtactac aaacttagta gt    8632
```

<210> SEQ ID NO 89
<211> LENGTH: 8536
<212> TYPE: DNA
<213> ORGANISM: Artificial Sequence
<220> FEATURE:
<223> OTHER INFORMATION: Vector

<400> SEQUENCE: 89

```
tggaagggct aattcactcc caaagaagac aagatatcct tgatctgtgg atctaccaca      60
cacaaggcta cttccctgat tagcagaact acacaccagg gccagggtc agatatccac     120 tgacctttgg atggtgctac aagctagtac cagttgagcc agataaggta gagaggcca     180 ataaaggaga gaacaccagc ttgttacacc ctgtgagcct gcatgggatg atgacccgg     240 agagagaagt gttagagtgg aggtttgaca gccgcctagc atttcatcac gtggcccgag     300
agctgcatcc ggagtacttc aagaactgct gatatcgagc ttgctacaag gactttccg     360 ctggggactt tccagggagg cgtggcctgg gcggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata aagcttgcct     540
tgagtgcttc aagtagtgtg tgcccgtctg ttgtgtgact ctggtaacta gagatccctc     600
```

```
agacccttttt agtcagtgtg aaaatctctc agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaatataa attaaaacat atagtatggg     900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttgctgt    1860 actttctata gtgaatagag ttaggcaggg atattcacca ttatcgtttc agacccacct   1920
cccaaccccg aggggacccg acaggcccga aggaataga a gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga actacaaaaa caaattacaa aaattcaaaa ttttcgggtt tattacaggg   2160
acagcagaga tccagtttat cgatgaggcc ctttcgtctt cactcgagtt tactccctat   2220
cagtgataga gaacgtatga agagtttact ccctatcagt gatagagaac gtatgcagac   2280
tttactccct atcagtgata gagaacgtat aaggagttta ctccctatca gtgatagaga   2340
acgtatgacc agtttactcc ctatcagtga tagagaacgt atctacagtt tactccctat   2400
cagtgataga gaacgtatat ccagtttact ccctatcagt gatagagaac gtatgtcgag   2460
gtaggcgtgt acggtgggcg cctataaaag cagagctcgt ttagtgaacc gtcagatcgc   2520
ctggagcaat tccacaacac ttttgtctta tacttggatc cgggcccgcg gccgccgcca   2580
ccatggtgag caagggcgag gagctgttca ccggggtggt gcccatcctg gtcgagctgg   2640
acggcgacgt aaacggccac aagttcagcg tgtccggcga gggcgagggc gatgccacct   2700
acggcaagct gaccctgaag ttcatctgca ccaccggcaa gctgcccgtg ccctggccca   2760
ccctcgtgac caccctgacc tacggcgtgc agtgcttcag ccgctacccc gaccacatga   2820
agcagcacga cttcttcaag tccgccatgc ccgaaggcta cgtccaggag cgcaccatct   2880
tcttcaagga cgacggcaac tacaagaccc gcgccgaggt gaagttcgag ggcgacaccc   2940
tggtgaaccg catcgagctg aagggcatcg acttcaagga ggacggcaac atcctggggc   3000
```

-continued

```
acaagctgga gtacaactac aacagccaca acgtctatat catggccgac aagcagaaga    3060
acggcatcaa ggtgaacttc aagatccgcc acaaacatcga ggacggcagc gtgcagctcg    3120
ccgaccacta ccagcagaac accccccatcg gcgacggccc cgtgctgctg cccgacaacc    3180
actacctgag cacccagtcc gccctgagca agacccccaa cgagaagcgc gatcacatgg    3240
tcctgctgga gttcgtgacc gccgccggga tcactctcgg catggacgag ctgtacaagt    3300
aaagcggccg gaattctacc gggtagggga ggcgcttttc ccaaggcagt ctggagcatg    3360
cgctttagca gccccgctgg gcacttggcg ctacacaagt ggcctctggc ctcgcacaca    3420
ttccacatcc accggtaggc gccaaccggc tccgttcttt ggtggcccct cgcgccacc     3480 ttctactcct cccctagtca ggaagttccc ccccgccccg cagctcgcgt cgtgcaggac    3540
gtgacaaatg gaagtagcac gtctcactag tctcgtgcag atggacagca ccgctgagca    3600
atggaagcgg gtaggccttt ggggcagcgg ccaatagcag ctttgctcct tcgctttctg    3660
ggctcagagg ctgggaaggg gtgggtccgg gggcgggctc aggggcgggc tcaggggcgg    3720
ggcgggcgcc cgaaggtcct ccggaggccc ggcattctgc acgcttcaaa agcgcacgtc    3780
tgccgcgctg ttctcctctt cctcatctcc gggccttttcg acctgcagcc caagcttacc    3840
atgaccgagt acaagcccac ggtgcgcctc gccacccgcg acgacgtccc cagggccgta    3900
cgcaccctcg ccgccgcgtt cgccgactac cccgccacgc gccacaccgt cgatccggac    3960
cgccacatcg agcgggtcac cgagctgcaa gaactcttcc tcacgcgcgt cgggctcgac    4020
atcggcaagt gtgggtcgc ggacgacggc gccgcgtgg cggtctggac cacgccggag    4080
agcgtcgaag cggggggcggt gttcgccgag atcggcccgc gcatggccga gttgagcggt    4140
tcccggctgg ccgcgcagca acagatggaa ggcctcctgg cgccgcaccg gcccaaggag    4200
cccgcgtggt tcctggccac cgtcggcgtc tcgcccgacc accagggcaa gggtctgggc    4260
agcgccgtcg tgctccccgg agtggaggcg gccgagcgcg ccggggtgcc cgccttcctg    4320
gagacctccg cgccccgcaa cctccccttc tacgagcggc tcggcttcac cgtcaccgcc    4380
gacgtcgagg tgcccgaagg accgcgcacc tggtgcatga cccgcaagcc cggtgcctga    4440
cggggcgcgt ctggaacaat caacctctgg attacaaaat ttgtgaaaga ttgactggta    4500
ttcttaacta tgttgctcct tttacgctat gtggatacgc tgctttaatg cctttgtatc    4560
atgctattgc ttcccgtatg gctttcattt tctcctcctt gtataaatcc tggttgctgt    4620
ctctttatga ggagttgtgg cccgttgtca ggcaacgtgg cgtggtgtgc actgtgtttg    4680
ctgacgcaac ccccactggt tggggcattg ccaccacctg tcagctcctt ccgggacttt    4740
tcgctttccc cctccctatt gccacggcgg aactcatcgc cgcctgcctt gcccgctgct    4800 ggacagggc tcgctgttg gcactgaca attccgtggt gttgtcgggg aagctgacgt    4860 ccttccatg gctgctcgcc tgtgttgcca cctggattct gcgcgggacg tccttctgct    4920
acgtcccttc ggccctcaat ccagcggacc ttccttcccg cggcctgctg ccggctctgc    4980
ggcctcttcc gcgtcttcgc cttcgccctc agacgagtcg gatctccctt tgggccgcct    5040
ccccgcctgg aattaattct gcagtcgaga cctagaaaaa catggagcaa tcacaagtag    5100
caatacagca gctaccaatg ctgattgtgc ctggctagaa gcacagagg aggaggaggt    5160 gggttttttcc agtcacacct caggtacctt taagaccaat gacttacaag gcagctgtag    5220
atcttagcca cttttttaaaa gaaagagggg gactggaagg gctaattcac tcccaacgaa    5280
gacaagatat ccttgatctg tggatctacc acacacaagg ctacttccct gattagcaga    5340
```

```
actacacacc agggccaggg gtcagatatc cactgacctt tggatggtgc tacaagctag    5400
taccagttga gccagataag gtagaagagg ccaataaagg agagaacacc agcttgttac    5460
accctgtgag cctgcatggg atggatgacc cggagagaga agtgttagag tggaggtttg    5520
acagccgcct agcatttcat cacgtggccc gagagctgca tccggagtac ttcaagaact    5580
gctgatatcg agcttgctac aagggacttt ccgctgggga ctttccaggg aggcgtggcc    5640
tgggcgggac tggggagtgg cgagccctca gatcctgcat ataagcagct gcttttttgcc   5700 tgtactgggt ctctctggtt agaccagatc tgagcctggg agctctctgg ctaactaggg    5760
aacccactgc ttaagcctca ataaagcttg ccttgagtgc ttcaagtagt gtgtgcccgt    5820
ctgttgtgtg actctggtaa ctagagatcc ctcagaccct tttagtcagt gtggaaaatc    5880
tctagcagta gtagttcatg tcatcttatt attcagtatt tataacttgc aaagaaatga    5940
atatcagaga gtgagaggcc ttgacattgc tagcgtttta ccgtcgacct ctagctagag    6000
cttggcgtaa tcatggtcat agctgttttc tgtgtgaaat tgttatccgc tcacaattcc    6060
acacaacata cgagccggaa gcataaagtg taaagcctgg ggtgcctaat gagtgagcta    6120
actcacatta attgcgttgc gctcactgcc cgctttccag tcgggaaacc tgtcgtgcca    6180
gctgcattaa tgaatcggcc aacgcgcggg gagaggcggt ttgcgtattg ggcgctcttc    6240
cgcttcctcg ctcactgact cgctgcgctc ggtcgttcgg ctgcggcgag cggtatcagc    6300
tcactcaaag gcggtaatac ggttatccac agaatcaggg gataacgcag gaaagaacat    6360
gtgagcaaaa ggccagcaaa aggccaggaa ccgtaaaaag gccgcgttgc tggcgttttt    6420
ccataggctc cgcccccctg acgagcatca caaaaatcga cgctcaagtc agaggtggcg    6480
aaacccgaca ggactataaa gataccaggc gtttccccct ggaagctccc tcgtgcgctc    6540
tcctgttccg accctgccgc ttaccggata cctgtccgcc tttctccctt cgggaagcgt    6600
ggcgctttct catagctcac gctgtaggta tctcagttcg gtgtaggtcg ttcgctccaa    6660
gctgggctgt gtgcacgaac ccccgttca gcccgaccgc tgcgccttat ccggtaacta    6720
tcgtcttgag tccaacccgg taagacacga cttatcgcca ctggcagcag ccactggtaa    6780
caggattagc agagcgaggt atgtaggcgg tgctacagag ttcttgaagt ggtggcctaa    6840
ctacggctac actagaagaa cagtatttgg tatctgcgct ctgctgaagc cagttacctt    6900
cggaaaaaga gttggtagct cttgatccgg caaacaaacc accgctggta gcggtttttt    6960
tgtttgcaag cagcagatta cgcgcagaaa aaaaggatct caagaagatc ctttgatctt    7020
ttctacgggg tctgacgctc agtggaacga aaactcacgt taagggattt tggtcatgag    7080
attatcaaaa aggatcttca cctagatcct ttaaattaa aaatgaagtt ttaaatcaat    7140
ctaaagtata tatgagtaaa cttggtctga cagttaccaa tgcttaatca gtgaggcacc    7200
tatctcagcg atctgtctat ttcgttcatc catagttgcc tgactccccg tcgtgtagat    7260
aactacgata cgggagggct taccatctgg ccccagtgct gcaatgatac cgcgagaccc    7320
acgctcaccg gctccagatt tatcagcaat aaaccagcca gccggaaggg ccgagcgcag    7380
aagtggtcct gcaactttat ccgcctccat ccagtctatt aattgttgcc gggaagctag    7440
agtaagtagt tcgccagtta atagtttgcg caacgttgtt gccattgcta caggcatcgt    7500
ggtgtcacgc tcgtcgtttg gtatggcttc attcagctcc ggttcccaac gatcaaggcg    7560
agttacatga tcccccatgt tgtgcaaaaa agcggttagc tccttcggtc ctccgatcgt    7620
tgtcagaagt aagttggccg cagtgttatc actcatggtt atggcagcac tgcataattc    7680
tcttactgtc atgccatccg taagatgctt ttctgtgact ggtgagtact caaccaagtc    7740
```

```
attctgagaa tagtgtatgc ggcgaccgag ttgctcttgc ccggcgtcaa tacgggataa     7800
taccgcgcca catagcagaa ctttaaaagt gctcatcatt ggaaaacgtt cttcggggcg     7860
aaaactctca aggatcttac cgctgttgag atccagttcg atgtaaccca ctcgtgcacc     7920
caactgatct tcagcatctt ttactttcac cagcgtttct gggtgagcaa aaacaggaag     7980
gcaaaatgcc gcaaaaaagg gaataagggc gacacggaaa tgttgaatac tcatactctt     8040
cctttttcaa tattattgaa gcatttatca gggttattgt ctcatgagcg gatacatatt     8100
tgaatgtatt tagaaaaata acaaataggg gttccgcgc acatttcccc gaaaagtgcc     8160
acctgacgtc gacggatcgg gagatcaact tgtttattgc agcttataat ggttacaaat     8220
aaagcaatag catcacaaat ttcacaaata aagcattttt ttcactgcat tctagttgtg     8280
gtttgtccaa actcatcaat gtatcttatc atgtctggat caactggata actcaagcta     8340
accaaaatca tcccaaactt cccacccat accctattac cactgccaat tacctagtgg     8400
tttcatttac tctaaacctg tgattcctct gaattatttt cattttaaag aaattgtatt     8460
tgttaaatat gtactacaaa cttagtagtt tttaaagaaa ttgtatttgt taaatatgta     8520
ctacaaactt agtagt                                                     8536

<210> SEQ ID NO 90
<211> LENGTH: 6011
<212> TYPE: DNA
<213> ORGANISM: Artificial Sequence
<220> FEATURE:
<223> OTHER INFORMATION: Vector

<400> SEQUENCE: 90
gcgcgcgttg acattgatta ttgactagtt attaatagta atcaattacg gggtcattag       60
ttcatagccc atatatggag ttccgcgtta cataacttac ggtaaatggc ccgcctggct      120
gaccgcccaa cgacccccgc ccattgacgt caataatgac gtatgttccc atagtaacgc      180
caatagggac tttccattga cgtcaatggg tggactattt acggtaaact gcccacttgg      240
cagtacatca agtgtatcat atgccaagta cgccccctat tgacgtcaat gacggtaaat      300
ggcccgcctg gcattatgcc cagtacatga ccttatggga ctttcctact tggcagtaca      360
tctacgtatt agtcatcgct attaccatgg tgatgcggtt ttggcagtac atcaatgggc      420
gtggatagcg gtttgactca cggggatttc caagtctcca ccccattgac gtcaatggga      480
gtttgttttg gcaccaaaat caacgggact ttccaaaatg tcgtaacaac tccgccccat      540
tgacgcaaat gggcggtagg cgtgtacggt gggaggtcta tataagcaga gctctctggc      600
taactagaga acccactgct tactggctta tcgaaattaa tacgactcac tatagggaga      660
cccaagcttg cattcctgca ggtcgacatg tctagactgg acaagagcaa agtcataaac      720
tctgctctgg aattactcaa tgaagtcggt atcgaaggcc tgacgacaag gaaactcgct      780
caaaagctgg gagttgagca gcctaccctg tactggcacg tgaagaacaa gcgggccctg      840
ctcgatgccc tggcaatcga gatgctggac aggcatcata cccacttctg cccctggaa       900 ggcgagtcat ggcaagactt tctgcggaac aacgccaagt cattccgctg tgctctcctc      960
tcacatcgcg acggggctaa agtgcatctc ggcacccgcc caacagagaa acagtacgaa     1020
accctggaaa atcagctcgc gttcctgtgt cagcaaggct tctccctgga gaacgcactg     1080
tacgctctgt ccgccgtggg ccactttaca ctgggctgcg tattggagga tcaggagcat     1140
caagtagcaa aagaggaaag agagacacct accaccgatt ctatgccccc acttctgaga     1200
```

```
caagcaattg agctgttcga ccatcaggga gccgaacctg ccttcctttt cggcctggaa    1260
ctaatcatat gtggcctgga gaaacagcta aagtgcgaaa gcggcgggcc ggccgacgcc    1320
cttgacgatt ttgacttaga catgctccca gccgatgccc ttgacgactt tgaccttgat    1380
atgctgcctg ctgacgctct tgacgatttg gaccttgaca tgctccccgg gtaaggatcc    1440
gaacaaaaac tcatctcaga agaggatctg aatatgcata ccggtcatca tcaccatcac    1500
cattgagttt gatccccggg aattcagaca tgataagata cattgatgag tttggacaaa    1560
ccacaactag aatgcagtga aaaaaatgct ttatttgtga aatttgtgat gctattgctt    1620
tatttgtaac cattataagc tgcaataaac aagttgggt  gggcgaagaa ctccagcatg    1680
agatccccgc gctggaggat catccagccg gcgtcccgga aaacgattcc gaagcccaac    1740
ctttcataga aggcggcggt ggaatcgaaa tctcgtagca cgtgtcagtc ctgctcctcg    1800
gccacgaagt gcacgcagtt gccggccggg tcgcgcaggg cgaactcccg ccccacggc    1860 tgctcgccga tctcggtcat ggccggcccg gaggcgtccc ggaagttcgt ggacacgacc    1920
tccgaccact cggcgtacag ctcgtccagg ccgcgcaccc acacccaggc cagggtgttg    1980
tccggcacca cctggtcctg gaccgcgctg atgaacaggg tcacgtcgtc ccggaccaca    2040
ccggcgaagt cgtcctccac gaagtcccgg gagaacccga gccggtcggt ccagaactcg    2100
accgctccgg cgacgtcgcg cgcggtgagc accggaacgg cactggtcaa cttggccatg    2160
gtttagttcc tcaccttgtc gtattatact atgccgatat actatgccga tgattaattg    2220
tcaacacgtg ctgatcagat ccgaaaatgg atatacaagc tcccgggagc ttttttgcaaa   2280 agcctaggcc tccaaaaaag cctcctcact acttctggaa tagctcagag gcagaggcgg    2340
cctcggcctc tgcataaata aaaaaaatta gtcagccatg gggcggagaa tgggcggaac    2400
tgggcggagt taggggcggg atgggcggag ttaggggcgg gactatggtt gctgactaat    2460
tgagatgcat gctttgcata cttctgcctg ctggggagcc tggggacttt ccacacctgg    2520
ttgctgacta attgagatgc atgctttgca tacttctgcc tgctggggag cctggggact    2580
ttccacaccc tcgtcgagct agcttcgtga ggctccggtg cccgtcagtg gcagagcgc    2640 acatcgccca cagtccccga gaagttgggg ggaggggtcg gcaattgaac cggtgcctag    2700
agaaggtggc gcggggtaaa ctgggaaagt gatgtcgtgt actggctccg ccttttttccc   2760 gagggtgggg gagaaccgta tataagtgca gtagtcgccg tgaacgttct ttttcgcaac    2820
gggtttgccg ccagaacaca ggtaagtgcc gtgtgtggtt cccgcgggcc tggcctcttt    2880
acgggttatg gcccttgcgt gccttgaatt acttccacct ggctccagta cgtgattctt    2940
gatcccgagc tggagccagg ggcgggcctt gcgctttagg agccccttcg cctcgtgctt    3000
gagttgaggc ctggcctggg cgctgggcc gccgcgtgcg aatctggtgg caccttcgcg    3060
cctgtctcgc tgctttcgat aagtctctag ccatttaaaa ttttgatga cctgctgcga    3120 cgctttttt  ctggcaagat agtcttgtaa atgcgggcca ggatctgcac actggtattt    3180 cggttttgg  gccgcggcc ggcgacgggg cccgtgcgtc ccagcgcaca tgttcggcga    3240
ggcggggcct gcgagcgcgg ccaccgagaa tcggacgggg gtagtctcaa gctggccggc    3300
ctgctctggt gcctggcctc gcgccgccgt gtatcgcccc gccctgggcg caaggctgg    3360 cccggtcggc accagttgcg tgagcggaaa gatggccgct tccggccct gctccagggg    3420 gctcaaaatg gaggacgcgg cgctcgggag agcgggcggg tgagtcaccc acacaaagga    3480
aaagggcctt tccgtcctca gccgtcgctt catgtgactc cacggagtac cgggcgccgt    3540
ccaggcacct cgattagttc tggagctttt ggagtacgtc gtctttaggt tggggggagg    3600
```

```
ggttttatgc gatggagttt ccccacactg agtgggtgga gactgaagtt aggccagctt      3660
ggcacttgat gtaattctcg ttggaatttg ccctttttga gtttggatct tggttcattc      3720
tcaagcctca gacagtggtt caaagttttt ttcttccatt tcaggtgtcg tgaacacgtg      3780
gtcgcggccg cgcaccatgg tgagcaaggg cgaggaggat aacatggcca tcatcaagga      3840
gttcatgcgc ttcaaggtgc acatggaggg ctccgtgaac ggccacgagt tcgagatcga      3900
gggcgagggc gagggccgcc cctacgaggg cacccagacc gccaagctga aggtgaccaa      3960
gggtggcccc ctgcccttcg cctgggacat cctgtcccct cagttcatgt acggctccaa      4020
ggcctacgtg aagcaccccg ccgacatccc cgactacttg aagctgtcct tccccgaggg      4080
cttcaagtgg gagcgcgtga tgaacttcga ggacggcggc gtggtgaccg tgacccagga      4140
ctcctccctg caggacggcg agttcatcta caaggtgaag ctgcgcggca ccaacttccc      4200
ctccgacggc cccgtaatgc agaagaagac catgggctgg gaggcctcct ccgagcggat      4260 gtacccgag gacggcgccc tgaagggcga gatcaagcag aggctgaagc tgaaggacgg      4320
cggccactac gacgctgagg tcaagaccac ctacaaggcc aagaagcccg tgcagctgcc      4380
cggcgcctac aacgtcaaca tcaagttgga catcacctcc cacaacgagg actacaccat      4440
cgtggaacag tacgaacgcg ccgagggccg ccactccacc ggcggcatgg acgagctgta      4500
caagtagtct cgagagatct ggccggctgg gccgtttcg aaggtaagcc tatccctaac      4560
cctctcctcg gtctcgattc tacgcgtacc ggtcatcatc accatcacca ttgagtttaa      4620
acccgctgat cagcctcgac tgtgccttct agttgccagc catctgttgt ttgcccctcc      4680
cccgtgcctt ccttgaccct ggaaggtgcc actcccactg tcctttccta ataaaatgag      4740
gaaattgcat cgcattgtct gagtaggtgt cattctattc tggggggtgg ggtggggcag      4800
gacagcaagg gggaggattg ggaagacaat agcaggcatg ctggggatgc ggtgggctct      4860
atggcttctg aggcggaaag aaccagtggc ggtaatacgg ttatccacag aatcaggga      4920 taacgcagga aagaacatgt gagcaaaagg ccagcaaaag gccaggaacc gtaaaaaggc      4980
cgcgttgctg gcgttttcc ataggctccg cccccctgac gagcatcaca aaatcgacg      5040 ctcaagtcag aggtggcgaa acccgacagg actataaaga taccaggcgt ttccccctgg      5100
aagctccctc gtgcgctctc ctgttccgac cctgccgctt accggatacc tgtccgcctt      5160
tctcccttcg ggaagcgtgg cgctttctca tagctcacgc tgtaggtatc tcagttcggt      5220
gtaggtcgtt cgctccaagc tgggctgtgt gcacgaaccc ccgttcagc ccgaccgctg      5280 cgccttatcc ggtaactatc gtcttgagtc caacccggta agacacgact tatcgccact      5340
ggcagcagcc actggtaaca ggattagcag agcgaggtat gtaggcggtg ctacagagtt      5400
cttgaagtgg tggcctaact acggctacac tagaaggaca gtatttggta tctgcgctct      5460
gctgaagcca gttaccttcg gaaaaagagt tggtagctct tgatccggca aacaaaccac      5520
cgctggtagc ggtggttttt tgtttgcaa gcagcagatt acgcgcagaa aaaaggatc      5580 tcaagaagat cctttgatct tttctacggg gtctgacgct cagtggaacg aaaactcacg      5640
ttaagggatt ttggtcatga cattaaccta taaaaatagg cgtatcacga ggccctttcg      5700
tctcgcgcgt ttcggtgatg acggtgaaaa cctctgacac atgcagctcc cggagacggt      5760
cacagcttgt ctgtaagcgg atgccggag cagacaagcc cgtcagggcg cgtcagcggg      5820
tgttggcggg tgtcggggct ggcttaacta tgcggcatca gagcagattg tactgagagt      5880
gcaccatata tgcggtgtga aataccgcac agatgcgtaa ggagaaaata ccgcatcagg      5940
```

```
cgccattcgc cattcaggct gcgcaactgt tgggaagggc gatcggtgcg ggcctcttcg      6000
ctattacgcc a                                                           6011

<210> SEQ ID NO 91
<211> LENGTH: 2191
<212> TYPE: DNA
<213> ORGANISM: Artificial Sequence
<220> FEATURE:
<223> OTHER INFORMATION: Vector

<400> SEQUENCE: 91
cctcccacac ataaccagga ggtcagatta tgcagtttaa ggtttacacc tataaaagag        60
agagccgtta tcgtctgttt gtggatgtac agagtgatat tattgacacg cccgggcgac       120
ggatggtgat cccctggcc agtgcacgtc tgctgtcaga taaagtctcc cgtgaacttt        180
acccggtggt gcatatcggg gatgaaagct ggcgcatgat gaccaccgat atggccagtg       240
tgccggtctc cgttatcggg gaagaagtgg ctgatctcag ccaccgcgaa aatgacatca       300
aaaacgccat taacctgatg ttctggggaa tataacccag aagcttagca aaagctaaaa       360
ccaggagcta tttaatggca acagttaacc agctggtacg caaaccacgt gctcgcaaag       420
ttgcgaaaag caacgtgcct gcgctggaag catgcccgca aaaacgtggc gtatgtactc       480
gtgtatatac taccactcct aaaaaaccga actccgcgct gcgtaaagta tgccgtgttc       540
gtctgactaa cggtttcgaa gtgacttcct acatcggtgg tgaaggtcac aacctgcagg       600
agcactccgt gatcctgatc cgtggcggtc gtgttaaaga cctcccgggt gttcgttacc       660
acaccgtacg tggtgcgctt gactgctccg gcgttaaaga ccgtaagcag gctcgttcca       720
agtatggcgt gaagcgtcct aaggcttaat ggttcgcccg cctaatgagc gggctttttt       780
ttgaattctt ttttaattcg atctgaagat cagcagttca acctgttgat agtacgtact       840
aagctctcat gtttcacgta ctaagctctc atgtttaacg tactaagctc tcatgtttaa       900
cgaactaaac cctcatggct aacgtactaa gctctcatgg ctaacgtact aagctctcat       960
gtttcacgta ctaagctctc atgtttgaac aataaaatta atataaatca gcaacttaaa      1020
tagcctctaa ggttttaagt tttataagaa aaaaagaat atataaggct tttaaagctt       1080
ttaaggttta acggttgtgg acaacaagcc agggatgtaa cgcactgaga agcccttaga      1140
gcctctcaaa gcaattttga gtgacacagg aacacttaac ggctgacatg ggatccccct      1200
catcagtgcc aacatagtaa gccagtatac actccgctag cgcggccgcc tcgagtttcg      1260
acctgcagcc tgttgacaat taatcatcgg catagtatat cggcatagta taatacgaca      1320
aggtgaggaa ctaaaccatg ggatcggcca ttgaacaaga tggattgcac gcaggttctc      1380
cggccgcttg ggtggagagg ctattcggct atgactgggc acaacagaca atcggctgct      1440
ctgatgccgc cgtgttccgg ctgtcagcgc agggcgcc ggttcttttt gtcaagaccg      1500
acctgtccgg tgccctgaat gaactgcagg acgaggcagc gcggctatcg tggctggcca      1560
cgacgggcgt tccttgcgca gctgtgctcg acgttgtcac tgaagcggga agggactggc      1620
tgctattggg cgaagtgccg gggcaggatc tcctgtcatc tcaccttgct cctgccgaga      1680
aagtatccat catggctgat gcaatgcggc ggctgcatac gcttgatccg gctacctgcc      1740
cattcgacca ccaagcgaaa catcgcatcg agcgagcacg tactcggatg aagccggtc       1800 ttgtcgatca ggatgatctg gacgaagagc atcaggggct cgcgccagcc gaactgttcg      1860
ccaggctcaa ggcgcgcatg cccgacggcg atgatctcgt cgtgacccat ggcgatgcct      1920
gcttgccgaa tatcatggtg gaaaatggcc gcttttctgg attcatcgac tgtggccggc      1980
```

```
tgggtgtggc ggaccgctat caggacatag cgttggctac ccgtgatatt gctgaagagc   2040
ttggcggcga atgggctgac cgcttcctcg tgctttacgg tatcgccgct cccgattcgc   2100
agcgcatcgc cttctatcgc cttcttgacg agttcttctg aggggatcaa ttctctagag   2160
ctcgctgatc agcctcgact gtaccgttag c                                 2191

<210> SEQ ID NO 92
<211> LENGTH: 5964
<212> TYPE: DNA
<213> ORGANISM: Artificial Sequence
<220> FEATURE:
<223> OTHER INFORMATION: Vector

<400> SEQUENCE: 92
gacggatcgg gagatctccc gatccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgcaccatg gtgagcaagg gcgaggagga taacatggcc    960
atcatcaagg agttcatgcg cttcaaggtg cacatggagg gctccgtgaa cggccacgag   1020
ttcgagatcg agggcgaggg cgagggccgc ccctacgagg gcacccagac cgccaagctg   1080
aaggtgacca agggtggccc cctgcccttc gcctgggaca tcctgtcccc tcagttcatg   1140
tacggctcca aggcctacgt gaagcacccc gccgacatcc ccgactactt gaagctgtcc   1200
ttccccgagg gcttcaagtg ggagcgcgtg atgaacttcg aggacggcgg cgtggtgacc   1260
gtgacccagg actcctccct gcaggacggc gagttcatct acaaggtgaa gctgcgcggc   1320
accaacttcc cctccgacgg ccccgtaatg cagaagaaga ccatgggctg ggaggcctcc   1380
tccgagcgga tgtaccccga ggacggcgcc ctgaagggcg agatcaagca gaggctgaag   1440
ctgaaggacg gcggccacta cgacgctgag gtcaagacca cctacaaggc caagaagccc   1500
gtgcagctgc ccggcgccta caacgtcaac atcaagttgg acatcacctc ccacaacgag   1560
gactacacca tcgtggaaca gtacgaacgc gccgagggcc gccactccac cggcggcatg   1620
gacgagctgt acaagtaggc ggccgcatcg ataagcttgt cgacgatatc tctagagggc   1680
ccgtttaaac ccgctgatca gcctcgactg tgccttctag ttgccagcca tctgttgttt   1740
gcccctcccc cgtgccttcc ttgaccctgg aaggtgccac tcccactgtc ctttcctaat   1800
```

```
aaaatgagga aattgcatcg cattgtctga gtaggtgtca ttctattctg gggggtgggg    1860
tggggcagga cagcaagggg gaggattggg aagacaatag caggcatgct ggggatgcgg    1920
tgggctctat ggcttctgag gcggaaagaa ccagctgggg ctctagggggg tatccccacg   1980 cgccctgtag cggcgcatta agcgcggcgg gtgtggtggt tacgcgcagc gtgaccgcta    2040
cacttgccag cgccctagcg cccgctcctt tcgctttctt cccttccttt ctcgccacgt    2100
tcgccggctt tccccgtcaa gctctaaatc ggggctccc tttagggttc cgatttagtg     2160
ctttacggca cctcgacccc aaaaaacttg attagggtga tggttcacgt agtgggccat    2220
cgccctgata gacggttttt cgcccttga cgttggagtc cacgttcttt aatagtggac     2280
tcttgttcca aactggaaca acactcaacc ctatctcggt ctattctttt gatttataag    2340
ggattttgcc gatttcggcc tattggttaa aaaatgagct gatttaacaa aaatttaacg    2400
cgaattaatt ctgtggaatg tgtgtcagtt agggtgtgga aagtccccag gctccccagc    2460
aggcagaagt atgcaaagca tgcatctcaa ttagtcagca accaggtgtg aaagtcccc     2520 aggctcccca gcaggcagaa gtatgcaaag catgcatctc aattagtcag caaccatagt    2580
cccgccccta actccgccca tcccgcccct aactccgccc agttccgccc attctccgcc    2640
ccatggctga ctaatttttt ttatttatgc agaggccgag gccgcctctg cctctgagct    2700
attccagaag tagtgaggag gcttttttgg aggcctaggc ttttgcaaac ctccgcgggg    2760
atccgcacca tggtgagcaa gggcgaggag gataacatgg ccatcatcaa ggagttcatg    2820
cgcttcaagg tgcacatgga gggctccgtg aacggccacg agttcgagat cgagggcgag    2880
ggcgagggcc gccctacga gggcacccag accgccaagc tgaaggtgac caagggtggc     2940
cccctgccct cgcctggga catcctgtcc cctcagttca tgtacggctc caaggcctac    3000
gtgaagcacc ccgccgacat ccccgactac ttgaagctgt ccttccccga gggcttcaag    3060
tgggagcgcg tgatgaactt cgaggacggc ggcgtggtga ccgtgaccca ggactcctcc    3120
ctgcaggacg gcgagttcat ctacaaggtg aagctgcgcg gcaccaactt cccctccgac    3180
ggccccgtaa tgcagaagaa gaccatgggc tgggaggcct cctccgagcg gatgtacccc    3240
gaggacggcg ccctgaaggg cgagatcaag cagaggctga agctgaagga cggcggccac    3300
tacgacgctg aggtcaagac cacctacaag gccaagaagc ccgtgcagct gcccggcgcc    3360
tacaacgtca acatcaagtt ggacatcacc tcccacaacg aggactacac catcgtggaa    3420
cagtacgaac gcgccgaggg ccgccactcc accggcggca tggacgagct gtacaagtag    3480
ttcgaaatga ccgaccaagc gacgcccaac ctgccatcac gagatttcga ttccaccgcc    3540
gccttctatg aaaggttggg cttcggaatc gttttccggg acgccggctg gatgatcctc    3600
cagcgcgggg atctcatgct ggagttcttc gcccaccca acttgtttat tgcagcttat     3660
aatggttaca ataaagcaa tagcatcaca aatttcacaa ataaagcatt ttttttcactg    3720 cattctagtt gtggtttgtc caaactcatc aatgtatctt atcatgtctg tataccgtcg    3780
acctctagct agagcttggc gtaatcatgg tcatagctgt ttcctgtgtg aaattgttat    3840
ccgctcacaa ttccacacaa catacgagcc ggaagcataa agtgtaaagc ctggggtgcc    3900
taatgagtga gctaactcac attaattgcg ttgcgctcac tgcccgcttt ccagtcggga    3960
aacctgtcgt gccagctgca ttaatgaatc ggccaacgcg cggggagagg cggtttgcgt    4020
attgggcgct cttccgcttc ctcgctcact gactcgctgc gctcggtcgt tcggctgcgg    4080
cgagcggtat cagctcactc aaaggcggta atacggttat ccacagaatc aggggataac    4140
gcaggaaaga acatgtgagc aaaaggccag caaaaggcca ggaaccgtaa aaaggccgcg    4200
```

```
ttgctggcgt ttttccatag gctccgcccc cctgacgagc atcacaaaaa tcgacgctca    4260
agtcagaggt ggcgaaaccc gacaggacta taaagatacc aggcgtttcc ccctggaagc    4320
tccctcgtgc gctctcctgt tccgaccctg ccgcttaccg gatacctgtc cgcctttctc    4380
ccttcgggaa gcgtggcgct ttctcatagc tcacgctgta ggtatctcag ttcggtgtag    4440
gtcgttcgct ccaagctggg ctgtgtgcac gaaccccccg ttcagcccga ccgctgcgcc    4500
ttatccggta actatcgtct tgagtccaac ccggtaagac acgacttatc gccactggca    4560
gcagccactg gtaacaggat tagcagagcg aggtatgtag gcggtgctac agagttcttg    4620
aagtggtggc ctaactacgg ctacactaga agaacagtat ttggtatctg cgctctgctg    4680
aagccagtta ccttcggaaa aagagttggt agctcttgat ccggcaaaca aaccaccgct    4740
ggtagcggtt ttttgtttg caagcagcag attacgcgca gaaaaaaagg atctcaagaa    4800
gatcctttga tcttttctac ggggtctgac gctcagtgga acgaaaactc acgttaaggg    4860
attttggtca tgagattatc aaaaaggatc ttcacctaga tccttttaaa ttaaaaatga    4920
agttttaaat caatctaaag tatatatgag taaacttggt ctgacagtta ccaatgctta    4980
atcagtgagg cacctatctc agcgatctgt ctatttcgtt catccatagt tgcctgactc    5040
cccgtcgtgt agataactac gatacgggag ggcttaccat ctggccccag tgctgcaatg    5100
ataccgcgag acccacgctc accggctcca gatttatcag caataaacca gccagccgga    5160
agggccgagc gcagaagtgg tcctgcaact ttatccgcct ccatccagtc tattaattgt    5220
tgccgggaag ctagagtaag tagttcgcca gttaatagtt tgcgcaacgt tgttgccatt    5280
gctacaggca tcgtggtgtc acgctcgtcg tttggtatgg cttcattcag ctccggttcc    5340
caacgatcaa ggcgagttac atgatccccc atgttgtgca aaaaagcggt tagctccttc    5400
ggtcctccga tcgttgtcag aagtaagttg gccgcagtgt tatcactcat ggttatggca    5460
gcactgcata attctcttac tgtcatgcca tccgtaagat gcttttctgt gactggtgag    5520
tactcaacca agtcattctg agaatagtgt atgcggcgac cgagttgctc ttgcccggcg    5580
tcaatacggg ataataccgc gccacatagc agaactttaa aagtgctcat cattggaaaa    5640
cgttcttcgg ggcgaaaact ctcaaggatc ttaccgctgt tgagatccag ttcgatgtaa    5700
cccactcgtg cacccaactg atcttcagca tcttttactt tcaccagcgt ttctgggtga    5760
gcaaaaacag gaaggcaaaa tgccgcaaaa aagggaataa gggcgacacg gaaatgttga    5820
atactcatac tcttcctttt tcaatattat tgaagcattt atcagggtta ttgtctcatg    5880
agcggataca tatttgaatg tatttagaaa aataaacaaa tagggggttcc gcgcacattt    5940 ccccgaaaag tgccacctga cgtc                                          5964
```

<210> SEQ ID NO 93
<211> LENGTH: 5999
<212> TYPE: DNA
<213> ORGANISM: Artificial Sequence
<220> FEATURE:
<223> OTHER INFORMATION: Vector

<400> SEQUENCE: 93

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
```

```
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgcaccatg gtgagcaagg gcgaggagga taacatggcc    960
atcatcaagg agttcatgcg cttcaaggtg cacatggagg gctccgtgaa cggccacgag    1020
ttcgagatcg agggcgaggg cgagggccgc ccctacgagg gcacccagac cgccaagctg    1080
aaggtgacca agggtggccc cctgcccttc gcctgggaca cctgtcccc tcagttcatg    1140 tacggctcca aggcctacgt gaagcacccc gccgacatcc ccgactactt gaagctgtcc    1200
ttccccgagg gcttcaagtg ggagcgcgtg atgaacttcg aggacggcgg cgtggtgacc    1260
gtgacccagg actcctccct gcaggacggc gagttcatct acaaggtgaa gctgcgcggc    1320
accaacttcc cctccgacgg ccccgtaatg cagaagaaga ccatgggctg ggaggcctcc    1380
tccgagcgga tgtaccccga ggacggcgcc ctgaagggcg agatcaagca gaggctgaag    1440
ctgaaggacg gcggccacta cgacgctgag gtcaagacca cctacaaggc caagaagccc    1500
gtgcagctgc ccggcgccta caacgtcaac atcaagttgg acatcaccct ccacaacgag    1560
gactacacca tcgtggaaca gtacgaacgc gccgagggcc gccactccac cggcggcatg    1620
gacgagctgt acaagtaggc ggccgcatcg ataagcttgt cgacgatatc tctagagggc    1680
ccgtttaaac ccgctgatca gcctcgactg tgccttctag ttgccagcca tctgttgttt    1740
gcccctcccc cgtgccttcc ttgaccctgg aaggtgccac tcccactgtc ctttcctaat    1800
aaaatgagga aattgcatcg cattgtctga gtaggtgtca ttctattctg ggggtgggg    1860 tggggcagga cagcaagggg gaggattggg aagacaatag caggcatgct ggggatgcgg    1920
tgggctctat ggcttctgag gcggaaagaa ccagctgggg ctctaggggg tatccccacg    1980
cgccctgtag cggcgcatta agcgcggcgg gtgtggtggt tacgcgcagc gtgaccgcta    2040
cacttgccag cgccctagcg cccgctcctt tcgctttctt cccttccttt ctcgccacgt    2100
tcgccggctt tccccgtcaa gctctaaatc ggggggctccc tttagggttc cgatttagtg    2160
ctttacggca cctcgacccc aaaaaacttg attagggtga tggttcacgt agtgggccat    2220
cgccctgata cacggttttt cgccctttga cgttggagtc cacgttcttt aatagtggac    2280
tcttgttcca aactggaaca acactcaacc ctatctcggt ctattctttt gatttataag    2340
ggattttgcc gatttcggcc tattggttaa aaaatgagct gatttaacaa aatttaacg    2400 cgaattaatt ctgtggaatg tgtgtcagtt agggtgtgga aagtccccag gctccccagc    2460
aggcagaagt atgcaaagca tgcatctcaa ttagtcagca accaggtgtg gaaagtcccc    2520 aggctccccca gcaggcagaa gtatgcaaag catgcatctc aattagtcag caaccatagt    2580
cccgccccta actccgccca tcccgcccct aactccgccc agttccgccc attctccgcc    2640
```

```
ccatggctga ctaattttt ttatttatgc agaggccgag gccgcctctg cctctgagct    2700
attccagaag tagtgaggag gcttttttgg aggcctaggc ttttgcaaac ctccgcgggg    2760
atccaccggt cgccaccatg gtgagcaagg gcgaggagct gttcaccggg gtggtgccca    2820
tcctggtcga gctggacggc gacgtaaacg gccacaagtt cagcgtgtcc ggcgagggcg    2880
agggcgatgc cacctacggc aagctgaccc tgaagttcat ctgcaccacc ggcaagctgc    2940
ccgtgccctg gcccaccctc gtgaccaccc tgacctacgg cgtgcagtgc ttcagccgct    3000
accccgacca catgaagcag cacgacttct tcaagtccgc catgcccgaa ggctacgtcc    3060
aggagcgcac catcttcttc aaggacgacg gcaactacaa gacccgcgcc gaggtgaagt    3120
tcgagggcga caccctggtg aaccgcatcg agctgaaggg catcgacttc aaggaggacg    3180
gcaacatcct ggggcacaag ctggagtaca actacaacag ccacaacgtc tatatcatgg    3240
ccgacaagca gaagaacggc atcaaggtga acttcaagat ccgccacaac atcgaggacg    3300
gcagcgtgca gctcgccgac cactaccagc agaacacccc catcggcgac ggccccgtgc    3360
tgctgcccga caaccactac ctgagcaccc agtccgccct gagcaaagac cccaacgaga    3420
agcgcgatca catggtcctg ctggagttcg tgaccgccgc cgggatcact ctcggcatgg    3480
acgagctgta caagtaaagc ggccgcatcg ataagttcga atgaccgac caagcgacgc    3540 ccaacctgcc atcacgagat ttcgattcca ccgccgcctt ctatgaaagg ttgggcttcg    3600
gaatcgtttt ccgggacgcc ggctggatga tcctccagcg cggggatctc atgctggagt    3660
tcttcgccca ccccaacttg tttattgcag cttataatgg ttacaaataa agcaatagca    3720
tcacaaattt cacaaataaa gcatttttt cactgcattc tagttgtggt ttgtccaaac    3780
tcatcaatgt atcttatcat gtctgtatac cgtcgacctc tagctagagc ttggcgtaat    3840
catggtcata gctgtttcct gtgtgaaatt gttatccgct cacaattcca cacaacatac    3900
gagccggaag cataaagtgt aaagcctggg gtgcctaatg agtgagctaa ctcacattaa    3960
ttgcgttgcg ctcactgccc gctttccagt cgggaaacct gtcgtgccag ctgcattaat    4020
gaatcggcca acgcgcgggg agaggcggtt tgcgtattgg gcgctcttcc gcttcctcgc    4080
tcactgactc gctgcgctcg tcgttcggc tgcggcgagc ggtatcagct cactcaaagg    4140
cggtaatacg gttatccaca gaatcagggg ataacgcagg aaagaacatg tgagcaaaag    4200
gccagcaaaa ggccaggaac cgtaaaaagg ccgcgttgct ggcgttttc cataggctcc    4260 gcccccctga cgagcatcac aaaaatcgac gctcaagtca gaggtggcga aacccgacag    4320
gactataaag ataccaggcg tttccccctg gaagctccct cgtgcgctct cctgttccga    4380
ccctgccgct taccggatac ctgtccgcct ttctcccttc gggaagcgtg gcgctttctc    4440
atagctcacg ctgtaggtat ctcagttcgg tgtaggtcgt tcgctccaag ctgggctgtg    4500
tgcacgaacc ccccgttcag cccgaccgct gcgccttatc cggtaactat cgtcttgagt    4560
ccaacccggt aagacacgac ttatcgccac tggcagcagc cactggtaac aggattagca    4620
gagcgaggta tgtaggcggt gctacagagt tcttgaagtg gtggcctaac tacggctaca    4680
ctagaagaac agtatttggt atctgcgctc tgctgaagcc agttaccttc ggaaaaagag    4740
ttggtagctc ttgatccggc aaacaaacca ccgctggtag cggtttttt gtttgcaagc    4800 agcagattac gcgcagaaaa aaaggatctc aagaagatcc tttgatcttt tctacggggt    4860
ctgacgctca gtggaacgaa aactcacgtt aagggatttt ggtcatgaga ttatcaaaaa    4920
ggatcttcac ctagatcctt ttaaattaaa aatgaagttt taaatcaatc taaagtatat    4980
```

```
atgagtaaac ttggtctgac agttaccaat gcttaatcag tgaggcacct atctcagcga    5040
tctgtctatt tcgttcatcc atagttgcct gactcccgt cgtgtagata actacgatac    5100
gggagggctt accatctggc cccagtgctg caatgatacc gcgagaccca cgctcaccgg    5160
ctccagattt atcagcaata aaccagccag ccggaagggc cgagcgcaga agtggtcctg    5220
caactttatc cgcctccatc cagtctatta attgttgccg ggaagctaga gtaagtagtt    5280
cgccagttaa tagtttgcgc aacgttgttg ccattgctac aggcatcgtg gtgtcacgct    5340
cgtcgtttgg tatggcttca ttcagctccg gttcccaacg atcaaggcga gttacatgat    5400
cccccatgtt gtgcaaaaaa gcggttagct ccttcggtcc tccgatcgtt gtcagaagta    5460
agttggccgc agtgttatca ctcatggtta tggcagcact gcataattct cttactgtca    5520
tgccatccgt aagatgcttt tctgtgactg gtgagtactc aaccaagtca ttctgagaat    5580
agtgtatgcg gcgaccgagt tgctcttgcc cggcgtcaat acgggataat accgcgccac    5640
atagcagaac tttaaaagtg ctcatcattg gaaaacgttc ttcggggcga aaactctcaa    5700
ggatcttacc gctgttgaga tccagttcga tgtaacccac tcgtgcaccc aactgatctt    5760
cagcatcttt tactttcacc agcgtttctg ggtgagcaaa aacaggaagg caaaatgccg    5820
caaaaaaggg aataagggcg acacggaaat gttgaatact catactcttc ctttttcaat    5880
attattgaag catttatcag ggttattgtc tcatgagcgg atacatattt gaatgtattt    5940
agaaaaataa acaaataggg gttccgcgca catttccccg aaaagtgcca cctgacgtc    5999
```

<210> SEQ ID NO 94
<211> LENGTH: 5978
<212> TYPE: DNA
<213> ORGANISM: Artificial Sequence
<220> FEATURE:
<223> OTHER INFORMATION: Vector

<400> SEQUENCE: 94

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta cccctccgcg gggatcctct agtcagctga cgcgtcctat     960
gtctagactg gacaagagca aagtcataaa ctctgctctg gaattactca atgaagtcgg    1020
tatcgaaggc ctgacgacaa ggaaactcgc tcaaaagctg ggagttgagc agcctaccct    1080
```

```
gtactggcac gtgaagaaca agcgggccct gctcgatgcc ctggcaatcg agatgctgga   1140
caggcatcat acccacttct gcccctgga aggcgagtca tggcaagact ttctgcggaa    1200
caacgccaag tcattccgct gtgctctcct ctcacatcgc gacggggcta aagtgcatct   1260
cggcacccgc ccaacagaga aacagtacga aaccctggaa atcagctcg  cgttcctgtg   1320 tcagcaaggc ttctccctgg agaacgcact gtacgctctg tccgccgtgg gccactttac   1380
actgggctgc gtattggagg atcaggagca tcaagtagca aaagaggaaa gagagacacc   1440
taccaccgat tctatgcccc cacttctgag acaagcaatt gagctgttcg accatcaggg   1500
agccgaacct gccttccttt tcggcctgga actaatcata tgtggcctgg agaaacagct   1560
aaagtgcgaa agcggcgggc cggccgacgc ccttgacgat tttgacttag acatgctccc   1620
agccgatgcc cttgacgact ttgacccttga tatgctgcct gctgacgctc ttgacgattt   1680
ggaccttgac atgctccccg ggtaactaga attatctcta gaggatcata atcagccata   1740
ccacatttgt tcgcggccgc cggcaataaa aagacagaat aaaacgcacg ggtgtttggt    1800
cgtttgttcg aattctagca ggcatgctgg ggatgcggtg ggctctatgg cttctgaggc   1860
ggaaagaacc agctggggct ctaggggta tccccacgcg ccctgtagcg gcgcattaag   1920
cgcggcgggt gtggtggtta cgcgcagcgt gaccgctaca cttgccagcg ccctagcgcc   1980
cgctcctttc gctttcttcc cttcctttct cgccacgttc gccggctttc cccgtcaagc   2040
tctaaatcgg gggctccctt tagggttccg atttagtgct ttacggcacc tcgaccccaa   2100
aaaacttgat tagggtgatg gttcacgtag tgggccatcg ccctgataga cggttttttcg   2160 ccctttgacg ttggagtcca cgttctttaa tagtggactc ttgttccaaa ctggaacaac   2220
actcaaccct atctcggtct attcttttga ttttataaggg attttgccga tttcggccta   2280
ttggttaaaa aatgagctga tttaacaaaa atttaacgcg aattaattct gtggaatgtg   2340
tgtcagttag ggtgtggaaa gtccccaggc tccccagcag gcagaagtat gcaaagcatg   2400
catctcaatt agtcagcaac caggtgtgga aagtccccag gctccccagc aggcagaagt   2460
atgcaaagca tgcatctcaa ttagtcagca accatagtcc cgcccctaac tccgcccatc   2520
ccgcccctaa ctccgcccag ttccgcccat tctccgcccc atggctgact aatttttttt   2580
atttatgcag aggccgaggc cgcctctgcc tctgagctat tccagaagta gtgaggaggc   2640
ttttttggag gcctaggctt ttgcaaacct ccgcgggat  cctctagtca gctgacgcgt   2700
cctatgtcta gactggacaa gagcaaagtc ataaactctg ctctggaatt actcaatgaa   2760
gtcggtatcg aaggcctgac gacaaggaaa ctcgctcaaa agctgggagt tgagcagcct   2820
accctgtact ggcacgtgaa gaacaagcgg gccctgctcg atgccctggc aatcgagatg   2880
ctggacaggc atcatacccca cttctgcccc ctggaaggcg agtcatggca agactttctg   2940
cggaacaacg ccaagtcatt ccgctgtgct ctcctctcac atcgcgacgg ggctaaagtg   3000
catctcggca cccgcccaac agagaaacag tacgaaaccc tggaaaatca gctcgcgttc   3060
ctgtgtcagc aaggcttctc cctggagaac gcactgtacg ctctgtccgc cgtgggccac   3120
tttacactgg gctgcgtatt ggaggatcag gagcatcaag tagcaaaaga ggaaagagag   3180
acacctacca ccgattctat gccccactt  ctgagacaag caattgagct gttcgaccat   3240
cagggagccg aacctgcctt ccttttcggc ctggaactaa tcatatgtgg cctggagaaa   3300
cagctaaagt gcgaaagcgg cgggccgcc  gacgcccttg acgatttga  cttagacatg   3360 ctcccagccg atgcccttga cgactttgac cttgatatgc tgcctgctga cgctcttgac   3420
```

```
gatttggacc ttgacatgct ccccgggtaa ctagaattat ctctagagga tcataatcag    3480
ccataccaca tttgttcgaa atgaccgacc aagcgacgcc caacctgcca tcacgagatt    3540
tcgattccac cgccgccttc tatgaaaggt tgggcttcgg aatcgttttc cgggacgccg    3600
gctggatgat cctccagcgc ggggatctca tgctggagtt cttcgcccac cccaacttgt    3660
ttattgcagc ttataatggt tacaaataaa gcaatagcat cacaaatttc acaaataaag    3720 cattttttc actgcattct agttgtggtt tgtccaaact catcaatgta tcttatcatg    3780
tctgtatacc gtcgacctct agctagagct tggcgtaatc atggtcatag ctgtttcctg    3840
tgtgaaattg ttatccgctc acaattccac acaacatacg agccggaagc ataaagtgta    3900
aagcctgggg tgcctaatga gtgagctaac tcacattaat tgcgttgcgc tcactgcccg    3960
ctttccagtc gggaaacctg tcgtgccagc tgcattaatg aatcggccaa cgcgcgggga    4020
gaggcggttt gcgtattggg cgctcttccg cttcctcgct cactgactcg ctgcgctcgg    4080
tcgttcggct gcggcgagcg gtatcagctc actcaaaggc ggtaatacgg ttatccacag    4140
aatcagggga taacgcagga agaacatgt gagcaaaagg ccagcaaaag gccaggaacc    4200
gtaaaaaggc cgcgttgctg cgttttttcc ataggctccg cccccctgac gagcatcaca    4260
aaaatcgacg ctcaagtcag aggtggcgaa acccgacagg actataaaga taccaggcgt    4320
ttccccctgg aagctccctc gtgcgctctc ctgttccgac cctgccgctt accggatacc    4380
tgtccgcctt tctcccttcg ggaagcgtgg cgctttctca tagctcacgc tgtaggtatc    4440
tcagttcggt gtaggtcgtt cgctccaagc tgggctgtgt gcacgaaccc cccgttcagc    4500
ccgaccgctg cgccttatcc ggtaactatc gtcttgagtc aacccggta agacacgact    4560 tatcgccact ggcagcagcc actggtaaca ggattagcag agcgaggtat gtaggcggtg    4620
ctacagagtt cttgaagtgg tggcctaact acggctacac tagaagaaca gtatttggta    4680
tctgcgctct gctgaagcca gttaccttcg gaaaaagagt tggtagctct tgatccggca    4740
aacaaaccac cgctggtagc ggttttttg tttgcaagca gcagattacg cgcagaaaaa    4800
aaggatctca agaagatcct ttgatctttt ctacgggtc tgacgctcag tggaacgaaa    4860
actcacgtta agggattttg gtcatgagat tatcaaaaag gatcttcacc tagatccttt    4920
taaattaaaa atgaagtttt aaatcaatct aaagtatata tgagtaaact tggtctgaca    4980
gttaccaatg cttaatcagt gaggcaccta tctcagcgat ctgtctattt cgttcatcca    5040
tagttgcctg actccccgtc gtgtagataa ctacgatacg ggagggctta ccatctggcc    5100
ccagtgctgc aatgataccg cgagacccac gctcaccggc tccagattta tcagcaataa    5160
accagccagc cggaagggcc gagcgcagaa gtggtcctgc aactttatcc gcctccatcc    5220
agtctattaa ttgttgccgg gaagctgag taagtagttc gccagttaat agtttgcgca    5280
acgttgttgc cattgctaca ggcatcgtgg tgtcacgctc gtcgtttggt atggcttcat    5340
tcagctccgg ttcccaacga tcaaggcgag ttacatgatc ccccatgttg tgcaaaaaag    5400
cggttagctc cttcggtcct ccgatcgttg tcagaagtaa gttggccgca gtgttatcac    5460
tcatggttat ggcagcactg cataattctc ttactgtcat gccatccgta agatgctttt    5520
ctgtgactgt tgagtactca accaagtcat tctgagaata gtgtatgcgg cgaccgagtt    5580
gctcttgccc ggcgtcaata cgggataata ccgcgccaca tagcagaact ttaaaagtgc    5640
tcatcattgg aaaacgttct tcggggcgaa aactctcaag gatcttaccg ctgttgagat    5700
ccagttcgat gtaacccact cgtgcaccca actgatcttc agcatctttt actttcacca    5760
gcgtttctgg gtgagcaaaa acaggaaggc aaaatgccgc aaaaaaggga ataagggcga    5820
```

```
cacggaaatg ttgaatactc atactcttcc tttttcaata ttattgaagc atttatcagg    5880
gttattgtct catgagcgga tacatatttg aatgtattta gaaaaataaa caaataggg     5940 ttccgcgcac atttccccga aaagtgccac ctgacgtc                            5978
```

<210> SEQ ID NO 95
<211> LENGTH: 5978
<212> TYPE: DNA
<213> ORGANISM: Artificial Sequence
<220> FEATURE:
<223> OTHER INFORMATION: Vector

<400> SEQUENCE: 95

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacgggtc attagttcat agcccatata      300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta cccctccgcg gggatcctct agtcagctga cgcgtcctat     960
gtctagactg gacaagagca aagtcataaa ctctgctctg gaattactca atgaagtcgg    1020
tatcgaaggc ctgacgacaa ggaaactcgc tcaaaagctg ggagctgcgc agaagaccct    1080
gtactggcac gtgaagaaca gcgggcccct gctcgatgcc ctggcaatcg atgctggac    1140 caggcatcat acccacttct gccccctgga aggcgagtca tggcaagact ttctgcggaa    1200
caacgccaag tcattccgct gtgctctcct ctcacatcgc gacggggcta aagtgcatct    1260
cggcacccgc caacagaga acagtacga accctggaa atcagctcg cgttcctgtg      1320 tcagcaaggc ttctccctgg agaacgcact gtacgctctg tccgccgtgg gccactttac    1380
actgggctgc gtattggagg atcaggagca tcaagtagca aaagaggaaa gagagacacc    1440
taccaccgat tctatgcccc cacttctgag acaagcaatt gagctgttcg accatcaggg    1500
agccgaacct gccttccttt tcggcctgga actaatcata tgtggcctgg agaaacagct    1560
aaagtgcgaa agcggcgggc cggccgacgc ccttgacgat tttgacttag acatgctccc    1620
agccgatgcc cttgacgact ttgaccttga tatgctgcct gctgacgctc ttgacgattt    1680
ggaccttgac atgctccccg gtaactagaa ttatctcta gaggatcata atcagccata    1740
ccacatttgt tcgcggccgc cggcaataaa aagacagaat aaaacgcacg ggtgttgggt    1800
cgtttgttcg aattctagca ggcatgctgg ggatgcggtg ggctctatgg cttctgaggc    1860
```

```
ggaaagaacc agctggggct ctaggggta tccccacgcg ccctgtagcg gcgcattaag    1920
cgcggcgggt gtggtggtta cgcgcagcgt gaccgctaca cttgccagcg ccctagcgcc    1980
cgctcctttc gctttcttcc cttcctttct cgccacgttc gccggctttc cccgtcaagc    2040
tctaaatcgg gggctcccct tagggttccg atttagtgct ttacggcacc tcgaccccaa    2100
aaaacttgat tagggtgatg gttcacgtag tgggccatcg ccctgataga cggttttcg    2160
ccctttgacg ttggagtcca cgttctttaa tagtggactc ttgttccaaa ctggaacaac    2220
actcaaccct atctcggtct attcttttga tttataaggg attttgccga tttcggccta    2280
ttggttaaaa aatgagctga tttaacaaaa atttaacgcg aattaattct gtggaatgtg    2340
tgtcagttag ggtgtggaaa gtccccaggc tccccagcag gcagaagtat gcaaagcatg    2400
catctcaatt agtcagcaac caggtgtgga aagtccccag gctccccagc aggcagaagt    2460
atgcaaagca tgcatctcaa ttagtcagca accatagtcc cgcccctaac tccgcccatc    2520
ccgcccctaa ctccgcccag ttccgcccat tctccgcccc atggctgact aatttttttt    2580
atttatgcag aggccgaggc cgcctctgcc tctgagctat tccagaagta gtgaggaggc    2640
tttttttggag gcctaggctt ttgcaaacct ccgcggggat cctctagtca gctgacgcgt    2700
cctatgtcta gactggacaa gagcaaagtc ataaactctg ctctggaatt actcaatgaa    2760
gtcggtatcg aaggcctgac gacaaggaaa ctcgctcaaa gctgggagt tgagcagcct    2820
accctgtact ggcacgtgaa gaacaagcgg gccctgctcg atgccctggc aatcgagatg    2880
ctggacaggc atcatcccca cttctgcccc ctggaaggcg agtcatggca agactttctg    2940
cggaacaacg ccaagtcatt ccgctgtgct ctcctctcac atcgcgacgg ggctaaagtg    3000
catctcggca cccgcccaac agagaaacag tacgaaaccc tggaaaatca gctcgcgttc    3060
ctgtgtcagc aaggcttctc cctggagaac gcactgtacg ctctgtccgc cgtgggccac    3120
tttacactgg gctgcgtatt ggaggatcag gagcatcaag tagcaaaaga ggaaagagag    3180
acacctacca ccgattctat gccccacctt ctgagacaag caattgagct gttcgaccat    3240
cagggagccg aacctgcctt ccttttcggc ctggaactaa tcatatgtgg cctggagaaa    3300
cagctaaagt gcgaaagcgg cgggccggcc gacgcccttg acgattttga cttagacatg    3360
ctcccagccg atgcccttga cgactttgac cttgatatgc tgcctgctga cgctcttgac    3420
gatttggacc ttgacatgct ccccgggtaa ctagaattat ctctagagga tcataatcag    3480
ccataccaca tttgttcgaa atgaccgacc aagcgacgcc caacctgcca tcacgagatt    3540
tcgattccac cgccgccttc tatgaaaggt tgggcttcgg aatcgttttc cgggacgccg    3600
gctggatgat cctccagcgc ggggatctca tgctggagtt cttcgcccac cccaacttgt    3660
ttattgcagc ttataatggt tacaaataaa gcaatagcat cacaaatttc acaaataaag    3720
cattttttc actgcattct agttgtggtt tgtccaaact catcaatgta tcttatcatg    3780
tctgtatacc gtcgacctct agctagagct tggcgtaatc atggtcatag ctgtttcctg    3840
tgtgaaattg ttatccgctc acaattccac acaacatacg agccggaagc ataaagtgta    3900
aagcctgggg tgcctaatga gtgagctaac tcacattaat tgcgttgcgc tcactgcccg    3960
ctttccagtc gggaaacctg tcgtgccagc tgcattaatg aatcggccaa cgcgcgggga    4020
gaggcggttt gcgtattggg cgctcttccg cttcctcgct cactgactcg ctgcgctcgg    4080
tcgttcggct gcggcgagcg gtatcagctc actcaaaggc ggtaatacgg ttatccacag    4140
aatcagggga taacgcagga aagaacatgt gagcaaaagg ccagcaaaag gccaggaacc    4200
gtaaaaaggc cgcgttgctg gcgtttttcc ataggctccg ccccctgac gagcatcaca    4260
```

-continued

```
aaaatcgacg ctcaagtcag aggtggcgaa acccgacagg actataaaga taccaggcgt    4320
ttccccctgg aagctccctc gtgcgctctc ctgttccgac cctgccgctt accggatacc    4380
tgtccgcctt tctcccttcg ggaagcgtgg cgctttctca tagctcacgc tgtaggtatc    4440
tcagttcggt gtaggtcgtt cgctccaagc tgggctgtgt gcacgaaccc cccgttcagc    4500
ccgaccgctg cgccttatcc ggtaactatc gtcttgagtc caacccggta agacacgact    4560
tatcgccact ggcagcagcc actggtaaca ggattagcag agcgaggtat gtaggcggtg    4620
ctacagagtt cttgaagtgg tggcctaact acggctacac tagaagaaca gtatttggta    4680
tctgcgctct gctgaagcca gttaccttcg aaaaagagt tggtagctct tgatccggca    4740
aacaaaccac cgctggtagc ggttttttg tttgcaagca gcagattacg cgcagaaaaa    4800
aaggatctca agaagatcct ttgatctttt ctacggggtc tgacgctcag tggaacgaaa    4860
actcacgtta agggattttg gtcatgagat tatcaaaaag gatcttcacc tagatccttt    4920
taaattaaaa atgaagtttt aaatcaatct aaagtatata tgagtaaact tggtctgaca    4980
gttaccaatg cttaatcagt gaggcaccta tctcagcgat ctgtctattt cgttcatcca    5040
tagttgcctg actccccgtc gtgtagataa ctacgatacg ggagggctta ccatctggcc    5100
ccagtgctgc aatgataccg cgagacccac gctcaccggc tccagattta tcagcaataa    5160
accagccagc cggaagggcc gagcgcagaa gtggtcctgc aactttatcc gcctccatcc    5220
agtctattaa ttgttgccgg gaagctagag taagtagttc gccagttaat agtttgcgca    5280
acgttgttgc cattgctaca ggcatcgtgg tgtcacgctc gtcgtttggt atggcttcat    5340
tcagctccgg ttcccaacga tcaaggcgag ttacatgatc ccccatgttg tgcaaaaaag    5400
cggttagctc cttcggtcct ccgatcgttg tcagaagtaa gttggccgca gtgttatcac    5460
tcatggttat ggcagcactg cataattctc ttactgtcat gccatccgta agatgctttt    5520
ctgtgactgg tgagtactca accaagtcat tctgagaata gtgtatgcgg cgaccgagtt    5580
gctcttgccc ggcgtcaata cgggataata ccgcgccaca tagcagaact ttaaaagtgc    5640
tcatcattgg aaaacgttct tcggggcgaa aactctcaag gatcttaccg ctgttgagat    5700
ccagttcgat gtaaccccact cgtgcaccca actgatcttc agcatctttt actttcacca    5760
gcgtttctgg gtgagcaaaa acaggaaggc aaaatgccgc aaaaaaggga taagggcga    5820 cacggaaatg ttgaatactc atactcttcc tttttcaata ttattgaagc atttatcagg    5880
gttattgtct catgagcgga tacatatttg aatgtattta gaaaaataaa caaatagggg    5940
ttccgcgcac atttccccga aaagtgccac ctgacgtc                           5978
```

<210> SEQ ID NO 96
<211> LENGTH: 8075
<212> TYPE: DNA
<213> ORGANISM: Artificial Sequence
<220> FEATURE:
<223> OTHER INFORMATION: Vector

<400> SEQUENCE: 96

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
```

```
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca acaagtttgt acaaaaaagc tgaacgagaa acgtaaaatg atataaatat    960
caatatatta aattagattt tgcataaaaa acagactaca taatactgta aaacacaaca   1020
tatccagtca ctatggcggc cgcttttcgac ctgcagcctg ttgacaatta atcatcggca   1080
tagtatatcg gcatagtata atacgacaag gtgaggaact aaaccatggg atcggccatt   1140
gaacaagatg gattgcacgc aggttctccg gccgcttggg tggagaggct attcggctat   1200
gactgggcac aacagacaat cggctgctct gatgccgccg tgttccggct gtcagcgcag   1260
gggcgcccgg ttcttttgt caagaccgac ctgtccggtg ccctgaatga actgcaggac   1320
gaggcagcgc ggctatcgtg gctggccacg acgggcgttc cttgcgcagc tgtgctcgac   1380
gttgtcactg aagcgggaag ggactggctg ctattgggcg aagtgccggg gcaggatctc   1440
ctgtcatctc accttgctcc tgccgagaaa gtatccatca tggctgatgc aatgcggcgg   1500
ctgcatacgc ttgatccggc tacctgccca ttcgaccacc aagcgaaaca tcgcatcgag   1560
cgagcacgta ctcggatgga agccggtctt gtcgatcagg atgatctgga cgaagagcat   1620
caggggctcg cgccagccga actgttcgcc aggctcaagg cgcgcatgcc cgacggcgat   1680
gatctcgtcg tgacccatgg cgatgcctgc ttgccgaata tcatggtgga aaatggccgc   1740
ttttctggat tcatcgactg tggccggctg ggtgtggcgg accgctatca ggacatagcg   1800
ttggctaccc gtgatattgc tgaagagctt ggcggcgaat gggctgaccg cttcctcgtg   1860
ctttacggta tcgccgctcc cgattcgcag cgcatcgcct tctatcgcct tcttgacgag   1920
ttcttctgag gggatcaatt ctctagagct cgctgatcag cctcgacgcg gccgcattag   1980 gcacccagg ctttacactt tatgcttccg gctcgtataa tgtgtggatt ttgagttagg   2040
atccggcgag atttcagga gctaaggaag ctaaaatgga gaaaaaatc actggatata   2100 ccaccgttga tatcccaa tggcatcgta aagaacattt tgaggcattt cagtcagttg   2160
ctcaatgtac ctataaccag accgttcagc tggatattac ggcctttta aagaccgtaa   2220 agaaaaataa gcacaagttt tatccggcct ttattcacat tcttgcccgc ctgatgaatg   2280
ctcatccgga attccgtatg gcaatgaaag acggtgagct ggtgatatgg gatagtgttc   2340
acccttgtta caccgttttc catgagcaaa ctgaaacgtt ttcatcgctc tggagtgaat   2400
accacgacga tttccggcag tttctacaca tatattcgca agatgtggcg tgttacggtg   2460
aaaacctggc ctatttccct aaagggttta ttgagaatat gttttcgtc tcagccaatc   2520 cctgggtgag tttcaccagt tttgatttaa acgtggccaa tatggacaac ttcttcgccc   2580
ccgttttcac catgggcaaa tattatacgc aaggcgacaa ggtgctgatg ccgctggcga   2640
ttcaggttca tcatgccgtc tgtgatggct tccatgtcgg cagaatgctt aatgaattac   2700
```

```
aacagtactg cgatgagtgg cagggcgggg cgtaaagatc tggatccggc ttactaaaag   2760
ccagataaca gtatgcgtat ttgcgcgctg attttttgcgg tataagaata tatactgata   2820
tgtatacccg aagtatgtca aaaagaggtg tgctatgaag cagcgtatta cagtgacagt   2880
tgacagcgac agctatcagt tgctcaaggc atatatgatg tcaatatctc cggtctggta   2940
agcacaacca tgcagaatga agcccgtcgt ctgcgtgccg aacgctggaa agcggaaaat   3000
caggaaggga tggctgaggt cgcccggttt attgaaatga acggctcttt tgctgacgag   3060
aacagggact ggtgaaatgc agtttaaggt ttacacctat aaaagagaga gccgttatcg   3120
tctgtttgtg gatgtacaga gtgatattat tgacacgccc gggcgacgga tggtgatccc   3180
cctggccagt gcacgtctgc tgtcagataa agtctcccgt gaactttacc cggtggtgca   3240
tatcggggat gaaagctggc gcatgatgac caccgatatg gccagtgtgc cggtctccgt   3300
tatcggggaa gaagtggctg atctcagcca ccgcgaaaat gacatcaaaa acgccattaa   3360
cctgatgttc tggggaatat aaatgtcagg ctccgttata cacagccagt ctgcaggtcg   3420
accatagtga ctggatatgt tgtgttttac agtattatgt agtctgtttt ttatgcaaaa   3480
tctaatttaa tatattgata tttatatcat tttacgtttc tcgttcagct ttcttgtaca   3540
aagtggttga tctagagggc ccgcggttcg aaggtaagcc tatccctaac cctctcctcg   3600
gtctcgattc tacgcgtacc ggtcatcatc accatcacca ttgagtttaa acccgctgat   3660
cagcctcgac tgtgccttct agttgccagc catctgttgt ttgcccctcc ccgtgccttt   3720
ccttgaccct ggaaggtgcc actcccactg tcctttccta ataaaatgag gaaattgcat   3780
cgcattgtct gagtaggtgt cattctattc tggggggtgg ggtggggcag gacagcaagg   3840
gggaggattg ggaagacaat agcaggcatg ctggggatgc ggtgggctct atggcttctg   3900
aggcggaaag aaccagctgg ggctctaggg ggtatcccca cgcgccctgt agcggcgcat   3960
taagcgcggc gggtgtggtg gttacgcgca gcgtgaccgc tacacttgcc agcgccctag   4020
cgcccgctcc tttcgctttc ttcccttcct ttctcgccac gttcgccggc tttccccgtc   4080
aagctctaaa tcgggggctc cctttagggt tccgatttag tgctttacgg cacctcgacc   4140
ccaaaaaact tgattagggt gatggttcac gtagtgggcc atcgccctga tagacggttt   4200
ttcgcccttt gacgttggag tccacgttct ttaatagtgg actcttgttc caaactggaa   4260
caacactcaa ccctatctcg gtctattctt ttgatttata agggattttg ccgatttcgg   4320
cctattggtt aaaaaatgag ctgatttaac aaaaatttaa cgcgaattaa ttctgtggaa   4380
tgtgtgtcag ttagggtgtg gaaagtcccc aggctcccca gcaggcagaa gtatgcaaag   4440
catgcatctc aattagtcag caaccaggtg tggaaagtcc ccaggctccc cagcaggcag   4500
aagtatgcaa agcatgcatc tcaattagtc agcaaccata gtcccgcccc taactccgcc   4560
catcccgccc ctaactccgc ccagttccgc ccattctccg ccccatggct gactaatttt   4620
ttttatttat gcagaggccg aggccgcctc tgcctctgag ctattccaga agtagtgagg   4680 aggcttttttt ggaggcctag gcttttgcaa aaagctcccg ggagcttgta tatccatttt   4740
cggatctgat caagagacag gatgaggatc gtttcgcatg attgaacaag atggattgca   4800
cgcaggttct ccggccgctt gggtggagag gctattcggc tatgactggg cacaacagac   4860
aatcggctgc tctgatgccg ccgtgttccg gctgtcagcg caggggcgcc cggttctttt   4920
tgtcaagacc gacctgtccg gtgccctgaa tgaactgcag gacgaggcag cgcggctatc   4980
gtggctggcc acgacgggcg ttccttgcgc agctgtgctc gacgttgtca ctgaagcggg   5040
```

```
aagggactgg ctgctattgg gcgaagtgcc ggggcaggat ctcctgtcat ctcaccttgc    5100
tcctgccgag aaagtatcca tcatggctga tgcaatgcgg cggctgcata cgcttgatcc    5160
ggctacctgc ccattcgacc accaagcgaa acatcgcatc gagcgagcac gtactcggat    5220
ggaagccggt cttgtcgatc aggatgatct ggacgaagag catcaggggc tcgcgccagc    5280
cgaactgttc gccaggctca aggcgcgcat gcccgacggc gaggatctcg tcgtgaccca    5340
tggcgatgcc tgcttgccga atatcatggt ggaaaatggc cgcttttctg gattcatcga    5400
ctgtggccgg ctgggtgtgg cggaccgcta tcaggacata gcgttggcta cccgtgatat    5460
tgctgaagag cttggcggcg aatgggctga ccgcttcctc gtgctttacg gtatcgccgc    5520
tcccgattcg cagcgcatcg ccttctatcg ccttcttgac gagttcttct gagcgggact    5580
ctggggttcg cgaaatgacc gaccaagcga cgcccaacct gccatcacga gatttcgatt    5640
ccaccgccgc cttctatgaa aggttgggct tcggaatcgt tttccgggac gccggctgga    5700
tgatcctcca gcgcggggat ctcatgctgg agttcttcgc ccaccccaac ttgtttattg    5760
cagcttataa tggttacaaa taaagcaata gcatcacaaa tttcacaaat aaagcatttt    5820
tttcactgca ttctagttgt ggtttgtcca aactcatcaa tgtatcttat catgtctgta    5880
taccgtcgac ctctagctag agcttggcgt aatcatggtc atagctgttt cctgtgtgaa    5940
attgttatcc gctcacaatt ccacacaaca tacgagccgg aagcataaag tgtaaagcct    6000
ggggtgccta atgagtgagc taactcacat taattgcgtt gcgctcactg cccgctttcc    6060
agtcgggaaa cctgtcgtgc cagctgcatt aatgaatcgg ccaacgcgcg gggagaggcg    6120
gtttgcgtat tgggcgctct tccgcttcct cgctcactga ctcgctgcgc tcggtcgttc    6180
ggctgcggcg agcggtatca gctcactcaa aggcggtaat acggttatcc acagaatcag    6240
gggataacgc aggaaagaac atgtgagcaa aaggccagca aaaggccagg aaccgtaaaa    6300
aggccgcgtt gctggcgttt ttccataggc tccgcccccc tgacgagcat cacaaaaatc    6360
gacgctcaag tcagaggtgg cgaaacccga caggactata aagataccag gcgtttcccc    6420
ctggaagctc cctcgtgcgc tctcctgttc cgaccctgcc gcttaccgga tacctgtccg    6480
cctttctccc ttcgggaagc gtggcgcttt ctcatagctc acgctgtagg tatctcagtt    6540
cggtgtaggt cgttcgctcc aagctgggct gtgtgcacga accccccgtt cagcccgacc    6600
gctgcgcctt atccggtaac tatcgtcttg agtccaaccc ggtaagacac gacttatcgc    6660
cactggcagc agccactggt aacaggatta gcagagcgag gtatgtaggc ggtgctacag    6720
agttcttgaa gtggtggcct aactacggct acactagaag aacagtattt ggtatctgcg    6780
ctctgctgaa gccagttacc ttcggaaaaa gagttggtag ctcttgatcc ggcaaacaaa    6840
ccaccgctgg tagcggtggt ttttttgttt gcaagcagca gattacgcgc agaaaaaaag    6900
gatctcaaga agatcctttg atcttttcta cggggtctga cgctcagtgg aacgaaaact    6960
cacgttaagg gattttggtc atgagattat caaaaaggat cttcacctag atccttttaa    7020
attaaaaatg aagttttaaa tcaatctaaa gtatatatga gtaaacttgg tctgacagtt    7080
accaatgctt aatcagtgag gcacctatct cagcgatctg tctatttcgt tcatccatag    7140
ttgcctgact ccccgtcgtg tagataacta cgatacggga gggcttacca tctggcccca    7200
gtgctgcaat gataccgcga gacccacgct caccggctcc agatttatca gcaataaacc    7260
agccagccgg aagggccgag cgcagaagtg gtcctgcaac tttatccgcc tccatccagt    7320
ctattaattg ttgccgggaa gctagagtaa gtagttcgcc agttaatagt ttgcgcaacg    7380
ttgttgccat tgctacaggc atcgtggtgt cacgctcgtc gtttggtatg gcttcattca    7440
```

```
gctccggttc caacgatcag aggcgagtta catgatcccc catgttgtgc aaaaaagcgg    7500
ttagctcctt cggtcctccg atcgttgtca gaagtaagtt ggccgcagtg ttatcactca    7560
tggttatggc agcactgcat aattctctta ctgtcatgcc atccgtaaga tgcttttctg    7620
tgactggtga gtactcaacc aagtcattct gagaatagtg tatgcggcga ccgagttgct    7680
cttgcccggc gtcaatacgg gataataccg cgccacatag cagaacttta aaagtgctca    7740
tcattggaaa acgttcttcg gggcgaaaac tctcaaggat cttaccgctg ttgagatcca    7800
gttcgatgta acccactcgt gcacccaact gatcttcagc atcttttact ttcaccagcg    7860
tttctgggtg agcaaaaaca ggaaggcaaa atgccgcaaa aaagggaata agggcgacac    7920
ggaaatgttg aatactcata ctcttccttt tcaatatta ttgaagcatt tatcagggtt    7980
attgtctcat gagcggatac atatttgaat gtatttagaa aaataaacaa ataggggttc    8040
cgcgcacatt tccccgaaaa gtgccacctg acgtc                               8075
```

<210> SEQ ID NO 97
<211> LENGTH: 39773
<212> TYPE: DNA
<213> ORGANISM: Artificial Sequence
<220> FEATURE:
<223> OTHER INFORMATION: Vector

<400> SEQUENCE: 97

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccatttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagtcgaag cttggatccg gtacctctag    480
aattctcgag cggccgctag cgacatcgga tctcccgatc ccctatggtg cactctcagt    540
acaatctgct ctgatgccgc atagttaagc cagtatctgc tccctgcttg tgtgttggag    600
gtcgctgagt agtgcgcgag caaaatttaa gctacaacaa ggcaaggctt gaccgacaat    660
tgcatgaaga atctgcttag ggttaggcgt tttgcgctgc ttcgcgatgt acgggccaga    720
tatacgcgtt gacattgatt attgactagt tattaatagt aatcaattac ggggtcatta    780
gttcatagcc catatatgga gttccgcgtt acataactta cggtaaatgg cccgcctggc    840
tgaccgccca acgacccccg cccattgacg tcaataatga cgtatgttcc catagtaacg    900
ccaataggga ctttccattg acgtcaatgg gtggactatt tacggtaaac tgcccacttg    960
gcagtacatc aagtgtatca tatgccaagt acgccccta ttgacgtcaa tgacggtaaa   1020
tggcccgcct ggcattatgc ccagtacatg accttatggg actttcctac ttggcagtac   1080
atctacgtat tagtcatcgc tattaccatg gtgatgcggt tttggcagta catcaatggg   1140
cgtggatagc ggtttgactc acggggattt ccaagtctcc accccattga cgtcaatggg   1200
agtttgtttt ggcaccaaaa tcaacgggac tttccaaaat gtcgtaacaa ctccgcccca   1260
ttgacgcaaa tgggcggtag gcgtgtacgg tgggaggtct atataagcag agctctctgg   1320
ctaactagag aacccactgc ttactggctt atcgaaatta atacgactca ctatagggag   1380
```

-continued

```
acccaagctg gctagttaag ctatcaacaa gtttgtacaa aaaagcaggc tttaaaggaa     1440
ccaattcagt cgactggatc cggtaccacc atgttcctga actgctgccc aggttgctgt     1500
atggagcctg aattcaccat ggtgagcaag ggcgaggagc tgttcaccgg ggtggtgccc     1560
atcctggtcg agctggacgg cgacgtaaac ggccacaagt tcagcgtgtc cggcgagggc     1620
gagggcgatg ccacctacgg caagctgacc ctgaagttca tctgcaccac cggcaagctg     1680
cccgtgccct ggcccaccct cgtgaccacc ctgacctggg cgtgcagtg cttcgcccgc      1740 taccccgacc acatgaagca gcacgacttc ttcaagtccg ccatgcccga aggctacgtc     1800
caggagcgca ccatcttctt caaggacgac ggcaactaca agacccgcgc cgaggtgaag     1860
ttcgagggcg acaccctggt gaaccgcatc gagctgaagg gcatcgactt caaggaggac     1920
ggcaacatcc tggggcacaa gctggagtac aacgccatca gcgacaacgt ctatatcacc     1980
gccgacaagc agaagaacgg catcaaggcc aacttcaaga tccgccacaa catcgaggac     2040
ggcagcgtgc agctcgccga ccactaccag cagaacaccc ccatcggcga cggccccgtg     2100
ctgctgcccg acaaccacta cctgagcacc cagtccaagc tgagcaaaga ccccaacgag     2160
aagcgcgatc acatggtcct gctggagttc gtgaccgccg ccgggatcac tctcggcatg     2220
gacgagctgt acaaggtcga ctatccgtac gacgtaccag actacgcata accgcggccg     2280
cactcgagat atctagaccc agctttcttg tacaaagtgg ttgatctaga gggcccgcgg     2340
ttcgaaggta agcctatccc taaccctctc ctcggtctcg attctacgcg taccggttag     2400
taatgagttt aaacggggga ggctaactga acacggaag gagacaatac cggaaggaac      2460
ccgcgctatg acggcaataa aaagacagaa taaaacgcac gggtgttggg tcgtttgttc      2520
ataaacgcgg ggttcggtcc cagggctggc actctgtcga taccccaccg agacccatt      2580 ggggccaata cgcccgcgtt tcttccttt ccccaccca ccccccaagt tcgggtgaag        2640
gcccagggct cgcagccaac gtcggggcgg caggccctgc catagcagat ccgattcgac     2700
agatcactga aatgtgtggg cgtggcttaa gggtgggaaa gaatatataa ggtgggggtc     2760
ttatgtagtt ttgtatctgt tttgcagcag ccgccgccgc catgagcacc aactcgtttg     2820
atggaagcat tgtgagctca tatttgacaa cgcgcatgcc cccatgggcc ggggtgcgtc     2880
agaatgtgat gggctccagc attgatggtc gccccgtcct gcccgcaaac tctactacct     2940
tgacctacga gaccgtgtct ggaacgccgt tggagactgc agcctccgcc gccgcttcag     3000
ccgctgcagc caccgcccgc gggattgtga ctgactttgc tttcctgagc ccgcttgcaa     3060
gcagtgcagc ttcccgttca tccgcccgcg atgacaagtt gacggctctt ttggcacaat     3120
tggattcttt gacccgggaa cttaatgtcg tttctcagca gctgttggat ctgcgccagc     3180
aggtttctgc cctgaaggct tcctcccctc ccaatgcggt ttaaaacata aataaaaaac     3240
cagactctgt ttggatttgg atcaagcaag tgtcttgctg tctttattta ggggttttgc     3300
gcgcgcggta ggcccgggac cagcggtctc ggtcgttgag ggtcctgtgt atttttcca     3360 ggacgtggta aaggtgactc tggatgttca gatacatggg cataagcccg tctctggggt     3420
ggaggtagca ccactgcaga gcttcatgct gcggggtggt gttgtagatg atccagtcgt     3480
agcaggagcg ctgggcgtgg tgcctaaaaa tgtctttcag tagcaagctg attgccaggg     3540
gcaggccctt ggtgtaagtg tttacaaagc ggttaagctg ggatgggtgc atacgtgggg     3600
atatgagatg catcttggac tgtatttta ggttggctat gttccagcc atatccctcc       3660 ggggattcat gttgtgcaga accaccagca cagtgtatcc ggtgcacttg ggaaatttgt     3720
catgtagctt agaaggaaat gcgtggaaga acttggagac gcccttgtga cctccaagat     3780
```

```
tttccatgca ttcgtccata atgatggcaa tgggcccacg ggcggcggcc tgggcgaaga    3840
tatttctggg atcactaacg tcatagttgt gttccaggat gagatcgtca taggccattt    3900
ttacaaagcg cgggcggagg gtgccagact gcggtataat ggttccatcc ggcccagggg    3960
cgtagttacc ctcacagatt tgcatttccc acgctttgag ttcagatggg gggatcatgt    4020
ctacctgcgg ggcgatgaag aaaacggttt ccggggtagg ggagatcagc tgggaagaaa    4080
gcaggttcct gagcagctgc gacttaccgc agccggtggg cccgtaaatc acacctatta    4140
ccggctgcaa ctggtagtta agagagctgc agctgccgtc atccctgagc agggggggcca   4200 cttcgttaag catgtccctg actcgcatgt tttccctgac caaatccgcc agaaggcgct    4260
cgccgcccag cgatagcagt tcttgcaagg aagcaaagtt tttcaacggt ttgagaccgt    4320
ccgccgtagg catgcttttg agcgtttgac caagcagttc caggcggtcc cacagctcgg    4380
tcacctgctc tacggcatct cgatccagca tatctcctcg tttcgcgggt tggggcggct    4440
ttcgctgtac ggcagtagtc ggtgctcgtc cagacgggcc aggtcatgt ctttccacgg     4500 gcgcagggtc ctcgtcagcg tagtctgggt cacggtgaag gggtgcgctc cgggctgcgc    4560
gctggccagg gtgcgcttga ggctggtcct gctggtgctg aagcgctgcc ggtcttcgcc    4620
ctgcgcgtcg gccaggtagc atttgaccat ggtgtcatag tccagcccct ccgcggcgtg    4680
gcccttggcg cgcagcttgc ccttggagga ggcgccgcac gaggggcagt gcagactttt    4740
gagggcgtag agcttgggcg cgagaaatac cgattccggg gagtaggcat ccgcgccgca    4800
ggccccgcag acggtctcgc attccacgag ccaggtgagc tctggccgtt cggggtcaaa    4860
aaccaggttt ccccccatgct ttttgatgcg tttcttacct ctggtttcca tgagccggtg    4920
tccacgctcg gtgacgaaaa ggctgtccgt gtccccgtat acagacttga gaggcctgtc    4980
ctcgagcggt gttccgcggt cctcctcgta tagaaactcg gaccactctg agacaaaggc    5040
tcgcgtccag gccagcacga aggaggctaa gtgggagggg tagcggtcgt tgtccactag    5100
ggggtccact cgctccaggg tgtgaagaca catgtcgccc tcttcggcat caaggaaggt    5160
gattggtttg taggtgtagg ccacgtgacc gggtgttcct gaaggggggc tataaaaggg    5220
ggtgggggcg cgttcgtcct cactctcttc cgcatcgctg tctgcgaggg ccagctgttg    5280
gggtgagtac tccctctgaa aagcgggcat gacttctgcg ctaagattgt cagtttccaa    5340
aaacgaggag gatttgatat tcacctggcc cgcggtgatg cctttgaggg tggccgcatc    5400
catctggtca gaaaagacaa tcttttttgtt gtcaagcttg gtggcaaacg acccgtagag    5460
ggcgttggac agcaacttgg cgatggagcg cagggtttgg tttttgtcgc gatcggcgcg    5520
ctccttggcc gcgatgttta gctgcacgta ttcgcgcgca acgcaccgcc attcgggaaa    5580
gacggtggtg cgctcgtcgg gcaccaggtg cacgcgccaa ccgcggttgt gcagggtgac    5640
aaggtcaacg ctggtggcta cctctccgcg taggcgctcg ttggtccagc agaggcggcc    5700
gcccttgcgc gagcagaatg gcggtagggg gtctagctgc gtctcgtccg ggggtctgc    5760 gtccacggta aagaccccgg gcagcaggcg cgcgtcgaag tagtctatct tgcatccttg    5820
caagtctagc gcctgctgcc atgcgcgggc ggcaagcgcg cgctcgtatg ggttgagtgg    5880
gggaccccat ggcatggggt gggtgagcgc ggaggcgtac atgccgcaaa tgtcgtaaac    5940 gtagagggc tctctgagta ttccaagata tgtagggtag catcttccac cgcggatgct     6000
ggcgcgcacg taatcgtata gttcgtgcga gggagcgagg aggtcgggac cgaggttgct    6060
acgggcgggc tgctctgctc ggaagactat ctgcctgaag atggcatgtg agttggatga    6120
```

-continued

```
tatggttgga cgctggaaga cgttgaagct ggcgtctgtg agacctaccg cgtcacgcac    6180
gaaggaggcg taggagtcgc gcagcttgtt gaccagctcg gcggtgacct gcacgtctag    6240
ggcgcagtag tccagggttt ccttgatgat gtcatactta tcctgtccct ttttttttcca   6300 cagctcgcgg ttgaggacaa actcttcgcg gtctttccag tactcttgga tcggaaaccc    6360
gtcggcctcc gaacggtaag agcctagcat gtagaactgg ttgacggcct ggtaggcgca    6420
gcatcccttt tctacgggta gcgcgtatgc ctgcgcggcc ttccgagcg aggtgtgggt     6480 gagcgcaaag gtgtccctga ccatgacttt gaggtactgg tatttgaagt cagtgtcgtc    6540
gcatccgccc tgctcccaga gcaaaaagtc cgtgcgcttt ttggaacgcg gatttggcag    6600
ggcgaaggtg acatcgttga agagtatctt tcccgcgcga ggcataaagt tgcgtgtgat    6660
gcggaagggt cccggcacct cggaacggtt gttaattacc tgggcggcga gcacgatctc    6720
gtcaaagccg ttgatgttgt ggcccacaat gtaaagttcc aagaagcgcg ggatgccctt    6780 gatgaaggc aattttttaa gttcctcgta ggtgagctct tcaggggagc tgagcccgtg     6840
ctctgaaagg gcccagtctg caagatgagg gttggaagcg acgaatgagc tccacaggtc    6900
acgggccatt agcatttgca ggtggtcgcg aaaggtccta aactggcgac ctatggccat    6960
tttttctggg gtgatgcagt agaaggtaag cgggtcttgt tcccagcggt cccatccaag    7020
gttcgcggct aggtctcgcg cggcagtcac tagaggctca tctccgccga acttcatgac    7080
cagcatgaag ggcacgagct gcttcccaaa ggccccatc caagtatagg tctctacatc     7140
gtaggtgaca aagagacgct cggtgcgagg atgcgagccg atcgggaaga actggatctc    7200
ccgccaccaa ttgaggagt ggctattgat gtggtgaaag tagaagtccc tgcgacgggc     7260
cgaacactcg tgctggcttt tgtaaaaacg tgcgcagtac tggcagcggt gcacgggctg    7320
tacatcctgc acgaggttga cctgacgacc gcgcacaagg aagcagagtg ggaatttgag    7380
cccctcgcct ggcgggtttg gctggtggtc ttctacttcg gctgcttgtc cttgaccgtc    7440
tggctgctcg aggggagtta cggtggatcg gaccaccacg ccgcgcgagc caaagtccga   7500
gatgtccgcg cgcggcggtc ggagcttgat gacaacatcg cgcagatggg agctgtccat   7560
ggtctggagc tccgcggcg tcaggtcagg cgggagctcc tgcaggttta cctcgcatag    7620
acgggtcagg gcgcgggcta gatccaggtg ataccctaatt tccaggggct ggttggtggc   7680
ggcgtcgatg gcttgcaaga ggccgcatcc ccgcggcgcg actacggtac cgcgcggcgg    7740
gcggtgggcc gcggggggtgt ccttggatga tgcatctaaa agcggtgacg cgggcgagcc   7800
cccggaggta gggggggctc cggacccgcc gggagagggg gcaggggcac gtcggcgccg   7860
cgcgcgggca ggagctggtg ctgcgcgcgt aggttgctgg cgaacgcgac gacgcggcgg    7920
ttgatctcct gaatctggcg cctctgcgtg aagacgacgg gccggtgag cttgaacctg     7980 aaagagagtt cgacagaatc aatttcggtg tcgttgacgg cggcctggcg caaaatctcc    8040
tgcacgtctc ctgagttgtc ttgataggcg atctcggcca tgaactgctc gatctcttcc    8100
tcctggagat ctccgcgtcc ggctcgctcc acggtgcgg cgaggtcgtt ggaaatgcgg     8160
gccatgagct gcgagaaggc gttgaggcct ccctcgttcc agacgcggct gtagaccacg    8220
cccccttcgg catcgcgggc gcgcatgacc acctgcgcga gattgagctc cacgtgccgg    8280
gcgaagacgg cgtagtttcg caggcgctga aagaggtagt tgagggtggt ggcggtgtgt    8340
tctgccacga agaagtacat aacccagcgt cgcaacgtgg attcgttgat atccccccaag   8400 gcctcaaggc gctccatggc ctcgtagaag tccacgcgca agttgaaaaa ctgggagttg    8460
cgcgccgaca cggttaactc ctcctccaga agacggatga gctcggcgac agtgtcgcgc    8520
```

```
acctcgcgct caaaggctac aggggcctct tcttcttctt caatctcctc ttccataagg   8580
gcctccccett cttcttcttc tggcggcggt gggggagggg ggacacggcg gcgacgacgg   8640
cgcaccggga ggcggtcgac aaagcgctcg atcatctccc cgcggcgacg gcgcatggtc   8700
tcggtgacgg cgcggccgtt ctcgcggggg cgcagttgga agacgccgcc cgtcatgtcc   8760
cggttatggg ttggcggggg gctgccatgc ggcagggata cggcgctaac gatgcatctc   8820
aacaattgtt gtgtaggtac tccgccgccg agggacctga gcgagtccgc atcgaccgga   8880
tcggaaaacc tctcgagaaa ggcgtctaac cagtcacagt cgcaaggtag gctgagcacc   8940
gtggcgggcg gcagcgggcg gcggtcgggg ttgtttctgg cggaggtgct gctgatgatg   9000
taattaaagt aggcggtctt gagacggcgg atggtcgaca gaagcaccat gtccttgggt   9060
ccggcctgct gaatgcgcag gcggtcggcc atgccccagg cttcgttttg acatcggcgc   9120
aggtctttgt agtagtcttg catgagcctt tctaccggca cttcttcttc tccttcctct   9180
tgtcctgcat ctcttgcatc tatcgctgcg gcggcggcgg agtttggccg taggtggcgc   9240
cctcttcctc ccatgcgtgt gaccccgaag cccctcatcg gctgaagcag ggctaggtcg   9300
gcgacaacgc gctcggctaa tatggcctgc tgcacctgcg tgagggtaga ctggaagtca   9360
tccatgtcca caaagcggtg gtatgcgccc gtgttgatgg tgtaagtgca gttggccata   9420
acggaccagt taacggtctg gtgacccggc tgcgagagct cggtgtacct gagacgcgag   9480
taagccctcg agtcaaatac gtagtcgttg caagtccgca ccaggtactg gtatcccacc   9540
aaaaagtgcg gcggcggctg gcggtagagg ggccagcgta gggtggccgg ggctccgggg   9600
gcgagatctt ccaacataag gcgatgatat ccgtagatgt aacctggacat ccaggtgatg   9660
ccggcggcgg tggtggaggc gcgcggaaag tcgcggacgc ggttccagat gttgcgcagc   9720
ggcaaaaagt gctccatggt cgggacgctc tggccggtca ggcgcgcgca atcgttgacg   9780
ctctagaccg tgcaaaagga gagcctgtaa gcgggcactc ttccgtggtc tggtggataa   9840
attcgcaagg gtatcatggc ggacgaccgg ggttcgagcc ccgtatccgg ccgtccgccg   9900
tgatccatgc ggttaccgcc cgcgtgtcga acccaggtgt gcgacgtcag acaacggggg   9960
agtgctcctt ttggcttcct tccaggcgcg gcggctgctg cgctagcttt tttggccact  10020
ggccgcgcgc agcgtaagcg gttaggctgg aaagcgaaag cattaagtgg ctcgctccct  10080
gtagccggag ggttatttc caagggttga gtcgcgggac ccccggttcg agtctcggac  10140
cggccggact gcggcgaacg ggggtttgcc tccccgtcat gcaagacccc gcttgcaaat  10200
tcctccggaa acagggacga gccccttttt tgcttttccc agatgcatcc ggtgctgcgg  10260
cagatgcgcc cccctcctca gcagcggcaa gagcaagagc agcggcagac atgcagggca  10320
ccctcccctc ctcctaccgc gtcaggaggg gcgacatccg cggttgacgc ggcagcagat  10380
ggtgattacg aaccccgcg gcgccgggcc cggcactacc tggacttgga ggagggcgag  10440
ggcctggcgc ggctaggagc gccctctcct gagcggcacc caagggtgca gctgaagcgt  10500
gatacgcgtg aggcgtacgt gccgcggcag aacctgtttc gcgaccgcga gggagaggag  10560
cccgaggaga tgcgggatcg aaagttccac gcagggcgcg agctgcggca tggcctgaat  10620
cgcgagcggt tgctgcgcga ggaggacttt gagcccgacg cgcgaaccgg gattagtccc  10680
gcgcgcgcac acgtggcggc cgccgacctg gtaaccgcat acgagcagac ggtgaaccag  10740
gagattaact ttcaaaaaag ctttaacaac cacgtgcgta cgcttgtggc gcgcgaggag  10800
gtggctatag gactgatgca tctgtgggac tttgtaagcg cgctggagca aacccaaat  10860
```

```
agcaagccgc tcatggcgca gctgttcctt atagtgcagc acagcaggga caacgaggca   10920
ttcagggatg cgctgctaaa catagtagag cccgagggcc gctggctgct cgatttgata   10980
aacatcctgc agagcatagt ggtgcaggag cgcagcttga gcctggctga caaggtggcc   11040
gccatcaact attccatgct tagcctgggc aagttttacg cccgcaagat ataccatacc   11100
ccttacgttc ccatagacaa ggaggtaaag atcgaggggt tctacatgcg catggcgctg   11160
aaggtgctta ccttgagcga cgacctgggc gtttatcgca acgagcgcat ccacaaggcc   11220
gtgagcgtga gccggcggcg cgagctcagc gaccgcgagc tgatgcacag cctgcaaagg   11280
gccctggctg cacgggcag cggcgataga gaggccgagt cctactttga cgcgggcgct   11340
gacctgcgct gggccccaag ccgacgcgcc ctggaggcag ctggggccgg acctgggctg   11400
gcggtggcac ccgcgcgcgc tggcaacgtc ggcggcgtgg aggaatatga cgaggacgat   11460
gagtacgagc cagaggacgg cgagtactaa gcggtgatgt ttctgatcag atgatgcaag   11520
acgcaacgga cccggcggtg cgggcggcgc tgcagagcca gccgtccggc cttaactcca   11580
cggacgactg gcgccaggtc atggaccgca tcatgtcgct gactgcgcgc aatcctgacg   11640
cgttccggca gcagccgcag gccaaccggc tctccgcaat tctggaagcg gtggtcccgg   11700
cgcgcgcaaa ccccacgcac gagaaggtgc tggcgatcgt aaacgcgctg ccgaaaaaca   11760
gggccatccg gcccgacgag gccggcctgg tctacgacgc gctgcttcag cgcgtggctc   11820
gttacaacag cggcaacgtg cagaccaacc tggaccggct ggtgggggat gtgcgcgagg   11880
ccgtggcgca gcgtgagcgc gcgcagcagc agggcaacct gggctccatg gttgcactaa   11940
acgccttcct gagtacacag cccgccaacg tgccgcgggg acaggaggac tacaccaact   12000
ttgtgagcgc actgcggcta atggtgactg agacaccgca aagtgaggtg taccagtctg   12060
ggccagacta ttttttccag accagtagac aaggcctgca gaccgtaaac ctgagccagg   12120
ctttcaaaaa cttgcagggg ctgtgggggg tgcgggctcc cacaggcgac cgcgcgaccg   12180
tgtctagctt gctgacgccc aactcgcgcc tgttgctgct gctaatagcg cccttcacgg   12240
acagtggcag cgtgtcccgg gacacatacc taggtcactt gctgacactg taccgcgagg   12300
ccataggtca ggcgcatgtg gacgagcata cttttccagga gattacaagt gtcagccgcg   12360
cgctggggca ggaggacacg ggcagcctgg aggcaaccct aaactacctg ctgaccaacc   12420
ggcggcagaa gatcccctcg ttgcacagtt taaacagcga ggaggagcgc attttgcgct   12480
acgtgcagca gagcgtgagc cttaacctga tgcgcgacgg ggtaacgccc agcgtggcgc   12540
tggacatgac cgcgcgcaac atggaaccgg gcatgtatgc ctcaaaccgg ccgtttatca   12600
accgcctaat ggactacttg catcgcgcgg ccgccgtgaa cccgagtat ttcaccaatg   12660
ccatcttgaa cccgcactgg ctaccgcccc ctggtttcta caccggggga ttcgaggtgc   12720
ccgagggtaa cgatggattc ctctgggacg acatagcga cagcgtgttt tccccgcaac   12780
cgcagaccct gctagagttg caacagcgcg agcaggcaga ggcggcgctg cgaaaggaaa   12840
gcttccgcag gccaagcagc ttgtccgatc taggcgctgc ggccccgcgg tcagatgcta   12900
gtagcccatt tccaagcttg ataggtctc ttaccagcac tcgcaccacc cgcccgcgcc   12960
tgctgggcga ggaggagtac ctaaacaact cgctgctgca gccgcagcgc gaaaaaaacc   13020
tgcctccggc atttcccaac aacgggatag agagcctagt ggacaagatg agtagatgga   13080
agacgtacgc gcaggagcac agggacgtgc caggccgcg cccgcccacc cgtcgtcaaa   13140
ggcacgaccg tcagcggggt ctggtgtggg aggacgatga ctcggcagac gacagcagcg   13200
tcctggattt gggagggagt ggcaacccgt ttgcgcacct tcgccccagg ctggggagaa   13260
```

```
tgttttaaaa aaaaaaaaag catgatgcaa aataaaaaac tcaccaaggc catggcaccg    13320
agcgttggtt ttcttgtatt ccccttagta tgcggcgcgc ggcgatgtat gaggaaggtc    13380
ctcctccctc ctacgagagt gtggtgagcg cggcgccagt ggcggcggcg ctgggttctc    13440
ccttcgatgc tcccctggac ccgccgtttg tgcctccgcg gtacctgcgg cctaccgggg    13500
ggagaaacag catccgttac tctgagttgg caccnctatt cgacaccacc cgtgtgtacc    13560
tggtggacaa caagtcaacg gatgtggcat ccctgaacta ccagaacgac cacagcaact    13620
ttctgaccac ggtcattcaa aacaatgact acagcccggg ggaggcaagc acacagacca    13680
tcaatcttga cgaccggtcg cactgggcg gcgacctgaa aaccatcctg cataccaaca    13740
tgccaaatgt gaacgagttc atgtttacca ataagtttaa ggcgcgggtg atggtgtcgc    13800
gcttgcctac taaggacaat caggtggagc tgaaatacga gtgggtggag ttcacgctgc    13860
ccgagggcaa ctactccgag accatgacca tagaccttat gaacaacgcg atcgtggagc    13920
actacttgaa agtgggcaga cagaacgggg ttctggaaag cgacatcggg gtaaagtttg    13980
acacccgcaa cttcagactg gggtttgacc ccgtcactgg tcttgtcatg cctggggtat    14040
atacaaacga agccttccat ccagacatca ttttgctgcc aggatgcggg gtggacttca    14100
cccacagccg cctgagcaac ttgttgggca tccgcaagcg gcaacccttc caggagggct    14160
ttaggatcac ctacgatgat ctggagggtg gtaacattcc cgcactgttg gatgtggacg    14220
cctaccaggc gagcttgaaa gatgacaccg aacagggcgg gggtggcgca ggcggcagca    14280
acagcagtgg cagcggcgcg gaagagaact ccaacgcggc agccgcggca atgcagccgg    14340
tggaggacat gaacgatcat gccattcgcg gcgacacctt tgccacacgg gctgaggaga    14400
agcgcgctga ggccgaagca gcggccgaag ctgccgcccc cgctgcgcaa cccgaggtcg    14460
agaagcctca gaagaaaccg gtgatcaaac ccctgacaga ggacagcaag aaacgcagtt    14520
acaacctaat aagcaatgac agcaccttca cccagtaccg cagctggtac cttgcataca    14580
actacggcga ccctcagacc ggaatccgct catggaccct gctttgcact cctgacgtaa    14640
cctgcggctc ggagcaggtc tactggtcgt tgccagacat gatgcaagac cccgtgacct    14700
tccgctccac gcgccagatc agcaacttc cggtggtggg cgccgagctg ttgcccgtgc    14760
actccaagag cttctacaac gaccaggccg tctactccca actcatccgc cagttttacct    14820 ctctgaccca cgtgttcaat cgcttttccg agaaccagat tttggcgcgc ccgccagccc    14880
ccaccatcac caccgtcagt gaaaacgttc ctgctctcac agatcacggg acgctaccgc    14940
tgcgcaacag catcggagga gtccagcgag tgaccattac tgacgccaga cgccgcacct    15000
gcccctacgt ttacaaggcc ctgggcatag tctcgccgcg cgtcctatcg agccgcactt    15060
tttgagcaag catgtccatc cttatatcgc ccagcaataa cacaggctgg ggcctgcgct    15120
tcccaagcaa gatgtttggc ggggccaaga agcgctccga ccaacaccca gtgcgcgtgc    15180
gcgggcacta ccgcgcgccc tgggcgcgc acaaacgcgg ccgcactggg cgcaccaccg    15240
tcgatgacgc catcgacgcg gtggtggagg aggcgcgcaa ctacacgccc acgccgccac    15300
cagtgtccac agtggacgcg gccattcaga ccgtggtgcg cggagcccgg cgctatgcta    15360
aaatgaagag acggcggagg cgcgtagcac gtcgccaccg ccgccgaccc ggcactgccg    15420
cccaacgcgc ggcggcggcc ctgcttaacc gcgcacgtcg caccggccga cgggcggcca    15480
tgcgggccgc tcgaaggctg gccgcgggta ttgtcactgt gccccccagg tccaggcgac    15540
gagcggccgc cgcagcagcc gcggccatta gtgctatgac tcagggtcgc aggggcaacg    15600
```

```
tgtattgggt gcgcgactcg gttagcggcc tgcgcgtgcc cgtgcgcacc cgcccccgc    15660 gcaactagat tgcaagaaaa aactacttag actcgtactg ttgtatgtat ccagcggcgg    15720
cggcgcgcaa cgaagctatg tccaagcgca aaatcaaaga agagatgctc caggtcatcg    15780
cgccggagat ctatggcccc ccgaagaagg aagagcagga ttacaagccc cgaaagctaa    15840
agcgggtcaa aaagaaaaag aaagatgatg atgatgaact tgacgacgag gtggaactgc    15900
tgcacgctac cgcgcccagg cgacgggtac agtggaaagg tcgacgcgta aaacgtgttt    15960
tgcgacccgg caccaccgta gtctttacgc ccggtgagcg ctccacccgc acctacaagc    16020
gcgtgtatga tgaggtgtac ggcgacgagg acctgcttga gcaggccaac gagcgcctcg    16080
gggagtttgc ctacggaaag cggcataagg acatgctggc gttgccgctg gacgagggca    16140
acccaacacc tagcctaaag cccgtaacac tgcagcaggt gctgcccgcg cttgcaccgt    16200
ccgaagaaaa gcgcggccta agcgcgagt ctggtgactt ggcacccacc gtgcagctga    16260
tggtacccaa gcgccagcga ctggaagatg tcttggaaaa aatgaccgtg gaacctgggc    16320
tggagcccga ggtccgcgtg cggccaatca agcaggtggc gccgggactg ggcgtgcaga    16380
ccgtggacgt tcagataccc actaccagta gcaccagtat tgccaccgcc acagagggca    16440
tggagacaca aacgtccccg gttgcctcag cggtggcgga tgccgcggtg caggcggtcg    16500
ctgcggccgc gtccaagacc tctacggagg tgcaaacgga cccgtggatg tttcgcgttt    16560
cagccccccg gcgcccgcgc cgttcgagga agtacggcgc cgccagcgcg ctactgcccg    16620
aatatgccct acatccttcc attgcgccta ccccggcta tcgtggctac acctaccgcc    16680
ccagaagacg agcaactacc cgacgccgaa ccaccactgg aacccgccgc cgccgtcgcc    16740
gtcgccagcc cgtgctggcc ccgatttccg tgcgcagggt ggctcgcgaa ggaggcagga    16800
ccctggtgct gccaacagcg cgctaccacc ccagcatcgt ttaaaagccg gtctttgtgg    16860
ttcttgcaga tatggccctc acctgccgcc tccgtttccc ggtgccggga ttccgaggaa    16920
gaatgcaccg taggagggc atggccggcc acggcctgac gggcggcatg cgtcgtgcgc    16980
accaccggcg gcggcgcgcg tcgcaccgtc gcatgcgcgg cggtatcctg cccctcctta    17040
ttccactgat cgccgcggcg attggcgccg tgcccggaat tgcatccgtg gccttgcagg    17100
cgcagagaca ctgattaaaa acaagttgca tgtggaaaaa tcaaaataaa aagtctggac    17160
tctcacgctc gcttggtcct gtaactattt tgtagaatgg aagacatcaa ctttgcgtct    17220
ctggccccgc gacacggctc gcgcccgttc atgggaaact ggcaagatat cggcaccagc    17280
aatatgagcg gtggcgcctt cagctggggc tcgctgtgga gcggcattaa aaatttcggt    17340
tccaccgtta agaactatgg cagcaaggcc tggaacagca gcacaggcca gatgctgagg    17400
gataagttga agagcaaaa tttccaacaa aaggtggtag atggcctggc ctctggcatt    17460
agcggggtgg tggacctggc caaccaggca gtgcaaaata agattaacag taagcttgat    17520
ccccgccctc ccgtagagga gcctccaccg gccgtggaga cagtgtctcc agaggggcgt    17580
ggcgaaaagc gtccgcgccc cgacagggaa gaaactctgg tgacgcaaat agacgagcct    17640
ccctcgtacg aggaggcact aaagcaaggc ctgcccacca cccgtcccat cgcgcccatg    17700
gctaccggag tgctgggcca gcacacaccc gtaacgctgg acctgcctcc ccccgccgac    17760
acccagcaga aacctgtgct gccaggcccg accgccgttg ttgtaacccg tcctagccgc    17820
gcgtccctgc gccgcgccgc cagcggtccg cgatcgttgc ggcccgtagc cagtggcaac    17880
tggcaaagca cactgaacag catcgtgggt ctggggggtgt aatccctgaa gcgccgacga    17940
tgcttctgat agctaacgtg tcgtatgtgt gtcatgtatg cgtccatgtc gccgccagag    18000
```

```
gagctgctga gccgccgcgc gcccgctttc caagatggct acccccttcga tgatgccgca   18060 gtggtcttac atgcacatct cgggccagga cgcctcggag tacctgagcc ccgggctggt   18120
gcagtttgcc cgcgccaccg agacgtactt cagcctgaat aacaagttta gaaacccccac  18180 ggtggcgcct acgcacgacg tgaccacaga ccggtcccag cgtttgacgc tgcggttcat   18240
ccctgtggac cgtgaggata ctgcgtactc gtacaaggcg cggttcaccc tagctgtggg   18300
tgataaccgt gtgctggaca tggcttccac gtactttgac atccgcggcg tgctggacag   18360
gggccctact tttaagccct actctggcac tgcctacaac gccctggctc caagggtgc   18420 cccaaatcct tgcgaatggg atgaagctgc tactgctctt gaaataaacc tagaagaaga   18480
ggacgatgac aacgaagacg aagtagacga gcaagctgag cagcaaaaaa ctcacgtatt   18540
tgggcaggcg ccttattctg gtataaatat tacaaaggag ggtattcaaa taggtgtcga   18600
aggtcaaaca cctaaatatg ccgataaaac atttcaacct gaacctcaaa taggagaatc   18660
tcagtggtac gaaacagaaa ttaatcatgc agctgggaga gtcctaaaaa agactacccc   18720
aatgaaacca tgttacggtt catatgcaaa acccacaaat gaaaatggag ggcaaggcat   18780
tcttgtaaag caacaaaatg gaaagctaga agtcaagtg gaaatgcaat ttttctcaac   18840
tactgaggca gccgcaggca atggtgataa cttgactcct aaagtggtat tgtacagtga   18900
agatgtagat atagaaaccc cagacactca tatttcttac atgcccacta ttaaggaagg   18960
taactcacga gaactaatgg gccaacaatc tatgcccaac aggcctaatt acattgcttt   19020
tagggacaat tttattggtc taatgtatta caacagcacg ggtaatatgg gtgttctggc   19080
gggccaagca tcgcagttga atgctgttgt agatttgcaa gacagaaaca cagagctttc   19140
ataccagctt ttgcttgatt ccattggtga tagaaccagg tactttttcta tgtggaatca   19200 ggctgttgac agctatgatc cagatgttag aattattgaa aatcatggaa ctgaagatga   19260
acttccaaat tactgctttc cactgggagg tgtgattaat acagagactc ttaccaaggt   19320
aaaacctaaa acaggtcagg aaaatggatg ggaaaaagat gctacagaat tttcagataa   19380
aaatgaaata agagttggaa ataattttgc catggaaatc aatctaaatg ccaacctgtg   19440
gagaaatttc ctgtactcca acatagcgct gtatttgccc gacaagctaa agtacagtcc   19500
ttccaacgta aaaatttctg ataacccaaa cacctacgac tacatgaaca agcgagtggt   19560
ggctcccggg ctagtggact gctacattaa ccttggagca cgctggtccc ttgactatat   19620
ggacaacgtc aacccattta accaccaccg caatgctggc ctgcgctacc gctcaatgtt   19680
gctgggcaat ggtcgctatg tgcccttcca catccaggtg cctcagaagt ctttttgccat  19740 taaaaacctc cttctcctgc cgggctcata cacctacgag tggaacttca ggaaggatgt   19800
taacatggtt ctgcagagct ccctaggaaa tgacctaagg gttgacggag ccagcattaa   19860
gtttgatagc atttgccttt acgccacctt cttccccatg gcccacaaca ccgcctccac   19920
gcttgaggcc atgcttagaa acgacaccaa cgaccagtcc tttaacgact atctctccgc   19980
cgccaacatg ctctacccta tacccgccaa cgctaccaac gtgcccatat ccatcccctc   20040
ccgcaactgg gcggctttcc gcggctgggc cttcacgcgc cttaagacta aggaaacccc  20100
atcactgggc tcgggctacg accttatta cacctactct ggctctatac cctacctaga   20160
tggaaccttt tacctcaacc acacctttaa gaaggtggcc attacctttg actcttctgt   20220
cagctggcct ggcaatgacc gcctgctac ccccaacgag tttgaaatta gcgctcagt   20280 tgacggggag ggttacaacg ttgcccagtg taacatgacc aaagactggt tcctggtaca   20340
```

```
aatgctagct aactataaca ttggctacca gggcttctat atcccagaga gctacaagga    20400
ccgcatgtac tccttcttta gaaacttcca gcccatgagc cgtcaggtgg tggatgatac    20460
taaatacaag gactaccaac aggtgggcat cctacaccaa cacaacaact ctggatttgt    20520
tggctacctt gcccccacca tgcgcgaagg acaggcctac cctgctaact tcccctatcc    20580
gcttataggc aagaccgcag ttgacagcat tacccagaaa aagtttcttt gcgatcgcac    20640
cctttggcgc atcccattct ccagtaactt tatgtccatg ggcgcactca cagacctggg    20700
ccaaaacctt ctctacgcca actccgccca cgcgctagac atgactttg aggtggatcc     20760
catggacgag cccacccttc tttatgtttt gtttgaagtc tttgacgtgg tccgtgtgca    20820
ccagccgcac cgcggcgtca tcgaaaccgt gtacctgcgc acgcccttct cggccggcaa    20880
cgccacaaca taagaagca agcaacatca acaacagctg ccgccatggg ctccagtgag     20940
caggaactga aagccattgt caaagatctt ggttgtgggc catattttt gggcacctat      21000
gacaagcgct ttccaggctt tgtttctcca cacaagctcg cctgcgccat agtcaatacg    21060
gccggtcgcg agactggggg cgtacactgg atggcctttg cctggaaccc gcactcaaaa    21120
acatgctacc tctttgagcc cttttggcttt tctgaccagc gactcaagca ggtttaccag   21180
tttgagtacg agtcactcct gcgccgtagc gccattgctt cttcccccga ccgctgtata    21240
acgctggaaa agtccaccca aagcgtacag gggcccaact cggccgcctg tggactattc    21300
tgctgcatgt ttctccacgc ctttgccaac tggccccaaa ctcccatgga tcacaacccc   21360
accatgaacc ttattaccgg ggtacccaac tccatgctca acagtcccca ggtacagccc    21420
accctgcgtc gcaaccagga acagctctac agcttcctgg agcgccactc gccctacttc    21480
cgcagccaca gtgcgcagat taggagcgcc acttcttttt gtcacttgaa aaacatgtaa    21540
aaataatgta ctagagacac tttcaataaa ggcaaatgct tttatttgta cactctcggg    21600
tgattattta ccccccaccct tgccgtctgc gccgttttaaa aatcaaaggg gttctgccgc    21660
gcatcgctat gcgccactgg cagggacacg ttgcgatact ggtgtttagt gctccactta    21720
aactcaggca caaccatccg cggcagctcg gtgaagtttt cactccacag gctgcgcacc    21780
atcaccaacg cgtttagcag gtcgggcgcc gatatcttga agtcgcagtt ggggcctccg    21840
ccctgcgcgc gcgagttgcg atacacaggg ttgcagcact ggaacactat cagcgccggg    21900
tggtgcacgc tggccagcac gctcttgtcg gagatcagat ccgcgtccag gtcctccgcg    21960
ttgctcaggg cgaacggagt caactttggt agctgccttc ccaaaaaggg cgcgtgccca    22020
ggctttgagt tgcactcgca ccgtagtggc atcaaaaggt gaccgtgccc ggtctgggcg    22080
ttaggataca gcgcctgcat aaaagccttg atctgcttaa aagccacctg agcctttgcg    22140
ccttcagaga agaacatgcc gcaagacttg ccggaaaact gattggccgg acaggccgcg    22200
tcgtgcacgc agcaccttgc gtcggtgttg gagatctgca ccacatttcg gccccaccgg    22260
ttcttcacga tcttggcctt gctagactgc tccttcagcg cgcgctgccc gttttcgctc    22320
gtcacatcca tttcaatcac gtgctcctta tttatcataa tgcttccgtg tagacactta    22380
agctcgcctt cgatctcagc gcagcggtgc agccacaacg cgcagcccgt gggctcgtga    22440
tgcttgtagg tcacctctgc aaacgactgc aggtacgcct gcaggaatcg ccccatcatc    22500
gtcacaaagg tcttgttgct ggtgaaggtc agctgcaacc cgcggtgctc ctcgttcagc    22560
caggtcttgc atacggccgc cagagcttcc acttggtcag gcagtagttt gaagttcgcc    22620
tttagatcgt tatccacgtg gtacttgtcc atcagcgcgc gcgcagcctc catgcccttc    22680
tcccacgcag acacgatcgg cacactcagc gggttcatca ccgtaatttc actttccgct    22740
```

```
tcgctgggct cttcctcttc ctcttgcgtc cgcataccac gcgccactgg gtcgtcttca    22800
ttcagccgcc gcactgtgcg cttacctcct ttgccatgct tgattagcac cggtgggttg    22860
ctgaaaccca ccatttgtag cgccacatct tctctttctt cctcgctgtc cacgattacc    22920
tctggtgatg gcgggcgctc gggcttggga aagggcgct tctttttctt cttgggcgca    22980
atggccaaat ccgccgccga ggtcgatggc cgcgggctgg gtgtgcgcgg caccagcgcg    23040
tcttgtgatg agtcttcctc gtcctcggac tcgatacgcc gcctcatccg cttttttggg    23100
ggcgcccggg gaggcggcgg cgacggggac ggggacgaca cgtcctccat ggttggggga    23160
cgtcgcgccg caccgcgtcc gcgctcgggg gtggtttcgc gctgctcctc ttcccgactg    23220
gccatttcct tctcctatag gcagaaaaag atcatggagt cagtcgagaa gaaggacagc    23280
ctaaccgccc cctctgagtt cgccaccacc gcctccaccg atgccgccaa cgcgcctacc    23340
accttccccg tcgaggcacc cccgcttgag gaggaggaag tgattatcga gcaggaccca    23400
ggttttgtaa gcaagacga cgaggaccgc tcagtaccaa cagaggataa aaagcaagac    23460
caggacaacg cagaggcaaa cgaggaacaa gtcgggcggg gggacgaaag gcatggcgac    23520
tacctagatg tgggagacga cgtgctgttg aagcatctgc agcgccagtg cgccattatc    23580
tgcgacgcgt tgcaagagcg cagcgatgtg cccctcgcca tagcggatgt cagccttgcc    23640
tacgaacgcc acctattctc accgcgcgta ccccccaaac gccaagaaaa cggcacatgc    23700
gagcccaacc cgcgcctcaa cttctacccc gtatttgccg tgccagaggt gcttgccacc    23760
tatcacatct ttttccaaaa ctgcaagata cccctatcct gccgtgccaa ccgcagccga    23820
gcggacaagc agctggcctt gcggcagggc gctgtcatac ctgatatcgc ctcgctcaac    23880
gaagtgccaa aaatctttga gggtcttgga cgcgacgaga agcgcgcggc aaacgctctg    23940
caacaggaaa acagcgaaaa tgaaagtcac tctggagtgt tggtggaact cgagggtgac    24000
aacgcgcgcc tagccgtact aaaacgcagc atcgaggtca cccactttgc ctacccggca    24060
cttaacctac cccccaaggt catgagcaca gtcatgagtg agctgatcgt gcgccgtgcg    24120
cagcccctgg agagggatgc aaatttgcaa gaacaaacag aggagggcct acccgcagtt    24180
ggcgacgagc agctagcgcg ctggcttcaa acgcgcgagc ctgccgactt ggaggagcga    24240
cgcaaactaa tgatggccgc agtgctcgtt accgtggagc ttgagtgcat gcagcggttc    24300
tttgctgacc cggagatgca gcgcaagcta gaggaaacat tgcactacac ctttcgacag    24360
ggctacgtac gccaggcctg caagatctcc aacgtggagc tctgcaacct ggtctcctac    24420
cttggaattt tgcacgaaaa ccgccttggg caaaacgtgc ttcattccac gctcaagggc    24480
gaggcgcgcc gcgactacgt ccgcgactgc gtttacttat ttctatgcta cacctggcag    24540
acggccatgg gcgtttggca gcagtgcttg gaggagtgca acctcaagga gctgcagaaa    24600
ctgctaaagc aaaacttgaa ggacctatgg acggccttca cgagcgctc cgtggccgcg    24660 cacctggcgg acatcatttt ccccgaacgc ctgcttaaaa ccctgcaaca gggtctgcca    24720
gacttcacca gtcaaagcat gttgcagaac tttaggaact ttatcctaga gcgctcagga    24780
atcttgcccg ccacctgctg tgcacttcct agcgactttg tgcccattaa gtaccgcgaa    24840
tgccctccgc cgctttgggg ccactgctac cttctgcagc tagccaacta ccttgcctac    24900
cactctgaca taatggaaga cgtgagcggt gacggtctac tggagtgtca ctgtcgctgc    24960
aacctatgca ccccgcaccg ctccctggtt tgcaattcgc agctgcttaa cgaaagtcaa    25020
attatcggta cctttgagct gcagggtccc tcgcctgacg aaaagtccgc ggctccgggg    25080
```

```
ttgaaactca ctccggggct gtggacgtcg gcttaccttc gcaaatttgt acctgaggac   25140
taccacgccc acgagattag gttctacgaa gaccaatccc gcccgcctaa tgcggagctt   25200
accgcctgcg tcattaccca gggccacatt cttggccaat gcaagccat caacaaagcc    25260 cgccaagagt ttctgctacg aaagggacgg ggggtttact tggacccca gtccggcgag    25320 gagctcaacc caatccccc gccgccgcag ccctatcagc agcagccgcg ggcccttgct    25380
tcccaggatg gcacccaaaa agaagctgca gctgccgccg ccacccacgg acgaggagga    25440
atactgggac agtcaggcag aggaggtttt ggacgaggag gaggaggaca tgatggaaga    25500 ctggagagc ctagacgagg aagcttccga ggtcgaagag gtgtcagacg aaacaccgtc     25560
accctcggtc gcattcccct cgccggcgcc ccagaaatcg gcaaccggtt ccagcatggc    25620
tacaacctcc gctcctcagg cgccgccggc actgcccgtt cgccgaccca accgtagatg    25680
ggacaccact ggaaccaggg ccggtaagtc caagcagccg ccgccgttag cccaagagca    25740
acaacagcgc caaggctacc gctcatggcg cgggcacaag aacgccatag ttgcttgctt    25800
gcaagactgt gggggcaaca tctccttcgc ccgccgcttt cttctctacc atcacggcgt    25860
ggccttcccc cgtaacatcc tgcattacta ccgtcatctc tacagcccat actgcaccgg    25920
cggcagcggc agcaacagca gcggccacac agaagcaaag gcgaccggat agcaagactc    25980
tgacaaagcc caagaaatcc acagcggcgg cagcagcagg aggaggagcg ctgcgtctgg    26040
cgcccaacga acccgtatcg acccgcgagc ttagaaacag gattttccc actctgtatg     26100 ctatatttca acagagcagg ggccaagaac aagagctgaa aataaaaaac aggtctctgc    26160
gatccctcac ccgcagctgc ctgtatcaca aaagcgaaga tcagcttcgg cgcacgctgg    26220
aagacgcgga ggctctcttc agtaaatact gcgcgctgac tcttaaggac tagtttcgcg    26280
ccctttctca aatttaagcg cgaaaactac gtcatctcca gcggccacac ccggcgccag    26340
cacctgttgt cagcgccatt atgagcaagg aaattcccac gccctacatg tggagttacc    26400
agccacaaat gggacttgcg gctggagctg cccaagacta ctcaacccga ataaactaca    26460
tgagcgcggg accccacatg atatcccggg tcaacggaat acgcgcccac cgaaaccgaa    26520
ttctcctgga acaggcggct attaccacca cacctcgtaa taaccttaat ccccgtagtt    26580
ggcccgctgc cctggtgtac caggaaagtc ccgctcccac cactgtggta cttcccagag    26640
acgcccaggc cgaagttcag atgactaact caggggcgca gcttgcgggc ggctttcgtc    26700
acagggtgcg gtcgcccggg cagggtataa ctcacctgac aatcagaggg cgaggtattc    26760
agctcaacga cgagtcggtg agctcctcgc ttggtctccg tccggacggg acatttcaga    26820
tcggcggcgc cggccgctct tcattcacgc ctcgtcaggc aatcctaact ctgcagacct    26880
cgtcctctga gccgcgctct ggaggcattg gaactctgca atttattgag gagtttgtgc    26940
catcggtcta ctttaaccc ttctcgggac ctcccggcca ctatccggat caatttattc      27000
ctaactttga cgcggtaaag gactcggcgg acggctacga ctgaatgtta agtggagagg    27060
cagagcaact gcgcctgaaa cacctggtcc actgtcgccg ccacaagtgc tttgcccgcg     27120
actccggtga gttttgctac tttgaattgc ccgaggatca tatcgagggc ccggcgcacg    27180
gcgtccggct taccgcccag ggagagcttg cccgtagcct gattcgggag tttacccagc    27240 gcccctgct agttgagcgg acaggggac cctgtgttct cactgtgatt tgcaactgtc       27300
ctaaccctgg attacatcaa gatctttgtt gccatctctg tgctgagtat aataaataca    27360
gaaattaaaa tatactgggg ctcctatcgc catcctgtaa acgccaccgt cttcacccgc    27420
ccaagcaaac caaggcgaac cttacctggt acttttaaca tctctccctc tgtgatttac    27480
```

```
aacagtttca acccagacgg agtgagtcta cgagagaacc tctccgagct cagctactcc   27540
atcagaaaaa acaccaccct ccttacctgc cgggaacgta cgagtgcgtc accggccgct   27600
gcaccacacc taccgcctga ccgtaaacca gactttttcc ggacagacct caataactct   27660
gtttaccaga acaggaggtg agcttagaaa acccttaggg tattaggcca aaggcgcagc   27720
tactgtgggg tttatgaaca attcaagcaa ctctacgggc tattctaatt caggtttctc   27780
tagaaatgga cggaattatt acagagcagc gcctgctaga aagacgcagg gcagcggccg   27840
agcaacagcg catgaatcaa gagctccaag acatggttaa cttgcaccag tgcaaaaggg   27900
gtatcttttg tctggtaaag caggccaaag tcacctacga cagtaatacc accgacacc    27960
gccttagcta caagttgcca accaagcgtc agaaattggt ggtcatggtg ggagaaaagc   28020
ccattaccat aactcagcac tcggtagaaa ccgaaggctg cattcactca ccttgtcaag   28080
gacctgagga tctctgcacc cttattaaga ccctgtgcgg tctcaaagat cttattccct   28140
ttaactaata aaaaaaaata ataaagcatc acttacttaa aatcagttag caaatttctg   28200
tccagtttat tcagcagcac ctccttgccc tcctcccagc tctggtattg cagcttcctc   28260
ctggctgcaa actttctcca caatctaaat ggaatgtcag tttcctcctg ttcctgtcca   28320
tccgcaccca ctatcttcat gttgttgcag atgaagcgcg caagaccgtc tgaagatacc   28380
ttcaaccccg tgtatccata tgacacggaa accggtcctc caactgtgcc ttttcttact   28440
cctcccttg tatcccccaa tgggtttcaa gagagtcccc ctggggtact ctctttgcgc   28500
ctatccgaac ctctagttac ctccaatggc atgcttgcgc tcaaaatggg caacggcctc   28560
tctctggacg aggccggcaa ccttacctcc caaaatgtaa ccactgtgag cccacctctc   28620
aaaaaaacca agtcaaacat aaacctggaa atatctgcac ccctcacagt tacctcagaa   28680
gccctaactg tggctgccgc cgcacctcta atggtcgcgg gcaacacact caccatgcaa   28740
tcacaggccc cgctaaccgt gcacgactcc aaacttagca ttgccaccca aggacccctc   28800
acagtgtcag aaggaaagct agccctgcaa acatcaggcc ccctcaccac caccgatagc   28860
agtaccctta ctatcactgc ctcacccccct ctaactactg ccactggtag cttgggcatt   28920
gacttgaaag agcccattta tacacaaaat ggaaaactag gactaaagta cggggctcct   28980
ttgcatgtaa cagacgacct aaacactttg accgtagcaa ctggtccagg tgtgactatt   29040
aataatactt ccttgcaaac taagttact ggagccttgg gttttgattc acaaggcaat   29100
atgcaactta atgtagcagg aggactaagg attgattctc aaaacagacg cctatactt    29160
gatgttagtt atccgtttga tgctcaaaac caactaaatc taagactagg acagggccct   29220
cttttttataa actcagccca caacttggat attaactaca acaaaggcct ttacttgttt   29280
acagcttcaa acaattccaa aaagcttgag gttaacctaa gcactgccaa ggggttgatg   29340
tttgacgcta cagccatagc cattaatgca ggagatgggc ttgaatttgg ttcacctaat   29400
gcaccaaaca caaatcccct caaaacaaaa attggccatg gcctagaatt tgattcaaac   29460
aaggctatgg ttcctaaact aggaactggc cttagttttg acagcacagg tgccattaca   29520
gtaggaaaca aaaataatga taagctaact ttgtggacca caccagctcc atctcctaac   29580
tgtagactaa atgcagagaa agatgctaaa ctcactttgg tcttaacaaa atgtggcagt   29640
caaatacttg ctacagtttc agttttggct gttaaaggca gtttggctcc aatatctgga   29700
acagttcaaa gtgctcatct tattataaga tttgacgaaa atggagtgct actaaacaat   29760
tccttcctgg acccagaata ttggaacttt agaaatggag atcttactga aggcacagcc   29820
```

```
tatacaaacg ctgttggatt tatgcctaac ctatcagctt atccaaaatc tcacggtaaa    29880
actgccaaaa gtaacattgt cagtcaagtt tacttaaacg gagacaaaac taaacctgta    29940
acactaacca ttacactaaa cggtacacag gaaacaggag acacaactcc aagtgcatac    30000
tctatgtcat tttcatggga ctggtctggc cacaactaca ttaatgaaat atttgccaca    30060
tcctcttaca ctttttcata cattgcccaa gaataaagaa tcgtttgtgt tatgtttcaa    30120
cgtgtttatt tttcaattgc agaaaatttc gaatcatttt tcattcagta gtatagcccc    30180
accaccacat agcttataca gatcaccgta ccttaatcaa actcacagaa ccctagtatt    30240
caacctgcca cctccctccc aacacacaga gtacacagtc ctttctcccc ggctggcctt    30300
aaaaagcatc atatcatggg taacagacat attcttaggt gttatattcc acacggtttc    30360
ctgtcgagcc aaacgctcat cagtgatatt aataaactcc ccgggcagct cacttaagtt    30420
catgtcgctg tccagctgct gagccacagg ctgctgtcca acttgcggtt gcttaacggg    30480
cggcgaagga gaagtccacg cctacatggg ggtagagtca taatcgtgca tcaggatagg    30540
gcggtggtgc tgcagcagcg cgcgaataaa ctgctgccgc cgccgctccg tcctgcagga    30600
atacaacatg gcagtggtct cctcagcgat gattcgcacc gcccgcagca taaggcgcct    30660
tgtcctccgg gcacagcagc gcaccctgat ctcacttaaa tcagcacagt aactgcagca    30720
cagcaccaca atattgttca aaatcccaca gtgcaaggcg ctgtatccaa agctcatggc    30780
ggggaccaca gaacccacgt ggccatcata ccacaagcgc aggtagatta gtggcgacc    30840 cctcataaac acgctggaca taaacattac ctcttttggc atgttgtaat tcaccacctc    30900
ccggtaccat ataaacctct gattaaacat ggcgccatcc accaccatcc taaaccagct    30960
ggccaaaacc tgcccgccgg ctatacactg cagggaaccg ggactggaac aatgacagtg    31020
gagagcccag gactcgtaac catggatcat catgctcgtc atgatatcaa tgttggcaca    31080
acacaggcac acgtgcatac acttcctcag gattacaagc tcctcccgcg ttagaaccat    31140
atcccaggga acaacccatt cctgaatcag cgtaaatccc acactgcagg gaagacctcg    31200
cacgtaactc acgttgtgca ttgtcaaagt gttacattcg ggcagcagcg gatgatcctc    31260
cagtatggta gcgcgggttt ctgtctcaaa aggaggtaga cgatccctac tgtacggagt    31320
gcgccgagac aaccgagatc gtgttggtcg tagtgtcatg ccaaatggaa cgccggacgt    31380
agtcatattt cctgaagcaa aaccaggtgc gggcgtgaca aacagatctg cgtctccggt    31440
ctcgccgctt agatcgctct gtgtagtagt tgtagtatat ccactctctc aaagcatcca    31500
ggcgccccct ggcttcgggt tctatgtaaa ctccttcatg cgccgctgcc ctgataacat    31560
ccaccaccgc agaataagcc acacccagcc aacctacaca ttcgttctgc gagtcacaca    31620
cgggaggagc gggaagagct ggaagaacca tgttttttttt tttattccaa agatattacc    31680
aaaacctcaa aatgaagatc tattaagtga acgcgctccc ctccggtggc gtggtcaaac    31740
tctacagcca aagaacagat aatggcattt gtaagatgtt gcacaatggc ttccaaaagg    31800
caaacggccc tcacgtccaa gtggacgtaa aggctaaacc cttcagggtg aatctcctct    31860
ataaacattc cagcaccttc aaccatgccc aaataattct catctcgcca ccttctcaat    31920
atatctctaa gcaaatcccg aatattaagt ccggccattg taaaaatctg ctccagagcg    31980
ccctccacct tcagcctcaa gcagcgaatc atgattgcaa aaattcaggt tcctcacaga    32040
cctgtataag attcaaaagc ggaacattaa caaaaatacc gcgatcccgt aggtcccttc    32100
gcagggccag ctgaacataa tcgtgcaggt ctgcacggac cagcgcggcc acttccccgc    32160
caggaaccat gacaaaagaa cccacactga ttatgacacg catactcgga gctatgctaa    32220
```

```
ccagcgtagc cccgatgtaa gcttgttgca tgggcggcga tataaaatgc aaggtgctgc    32280
tcaaaaaatc aggcaaagcc tcgcgcaaaa aagaaagcac atcgtagtca tgctcatgca    32340
gataaaggca ggtaagctcc ggaaccacca cagaaaaaga caccattttt ctctcaaaca    32400
tgtctgcggg tttctgcata aacacaaaat aaaataacaa aaaaacattt aaacattaga    32460
agcctgtctt acaacaggaa aaacaaccct tataagcata agacggacta cggccatgcc    32520
ggcgtgaccg taaaaaaact ggtcaccgtg attaaaaagc accaccgaca gctcctcggt    32580
catgtccgga gtcataatgt aagactcggt aaacacatca ggttgattca catcggtcag    32640
tgctaaaaag cgaccgaaat agcccggggg aatacatacc cgcaggcgta gagacaacat    32700
tacagccccc ataggaggta taacaaaatt aataggagag aaaaacacat aaacacctga    32760
aaaaccctcc tgcctaggca aaatagcacc ctcccgctcc agaacaacat acagcgcttc    32820
cacagcggca gccataacag tcagccttac cagtaaaaaa gaaaacctat taaaaaaaca    32880
ccactcgaca cggcaccagc tcaatcagtc acagtgtaaa aaagggccaa gtgcagagcg    32940
agtatatata ggactaaaaa atgacgtaac ggttaaagtc cacaaaaaac acccagaaaa    33000
ccgcacgcga acctacgccc agaaacgaaa gccaaaaaac ccacaacttc ctcaaatcgt    33060
cacttccgtt ttcccacgtt acgtcacttc ccattttaag aaaactacaa ttcccaacac    33120
atacaagtta ctccgcccta aaacctacgt cacccgcccc gttcccacgc cccgcgccac    33180
gtcacaaact ccaccccctc attatcatat tggcttcaat ccaaaataag gtatattatt    33240
gatgatgtta attaatttaa atccgcatgc gatatcgagc tctcccggga attcggatct    33300
gcgacgcgag gctggatggc cttccccatt atgattcttc tcgcgtttaa gggcaccaat    33360
aactgcctta aaaaaattac gccccgccct gccactcatc gcagtactgt tgtaattcat    33420
taagcattct gccgacatgg aagccatcac aaacggcatg atgaacctga atcgccagcg    33480
gcatcagcac cttgtcgcct tgcgtataat atttgcccat ggtgaaaacg ggggcgaaga    33540
agttgtccat attggccacg tttaaatcaa aactggtgaa actcacccag ggattggctg    33600
agacgaaaaa catattctca ataaaccctt tagggaaata ggccaggttt tcaccgtaac    33660
acgccacatc ttgcgaatat atgtgtagaa actgccggaa atcgtcgtgg tattcactcc    33720
agagcgatga aaacgtttca gtttgctcat ggaaaacggt gtaacaaggg tgaacactat    33780
cccatatcac cagctcaccg tctttcattg ccatacggaa ttccggatga gcattcatca    33840
ggcgggcaag aatgtgaata aaggccggat aaaacttgtg cttattttc tttacggtct    33900 ttaaaaaggc cgtaatatcc agctgaacgg tctggttata ggtacattga gcaactgact    33960
gaaatgcctc aaaatgttct ttacgatgcc attgggatat atcaacggtg gtatatccag    34020 tgatttttt ctccatttta gcttccttag ctcctgaaaa tctcgataac tcaaaaaata    34080
cgcccggtag tgatcttatt tcattatggt gaaagttgga acctcttacg tgccgatcaa    34140
cgtctcattt tcgccaaaag ttggcccagg cttcccggt atcaacaggg acaccaggat    34200
ttatttattc tgcgaagtga tcttccgtca caggtattta ttcgcgataa gctcatggag    34260
cggcgtaacc gtcgcacagg aaggacagag aaagcgcgga tctgggaagt gacggacaga    34320
acggtcagga cctggattgg ggaggcggtt gccgccgctg ctgctgacgg tgtgacgttc    34380
tctgttccgg tcacaccaca tacgttccgc cattcctatg cgatgcacat gctgtatgcc    34440
ggtataccgc tgaaagttct gcaaagcctg atgggacata agtccatcag ttcaacggaa    34500
gtctacacga aggtttttgc gctggatgtg gctgcccggc accgggtgca gtttgcgatg    34560
```

```
ccggagtctg atgcggttgc gatgctgaaa caattatcct gagaataaat gccttggcct    34620
ttatatggaa atgtggaact gagtggatat gctgttttg tctgttaaac agagaagctg     34680
gctgttatcc actgagaagc gaacgaaaca gtcgggaaaa tctcccatta tcgtagagat    34740
ccgcattatt aatctcagga gcctgtgtag cgtttatagg aagtagtgtt ctgtcatgat    34800
gcctgcaagc ggtaacgaaa acgatttgaa tatgccttca ggaacaatag aaatcttcgt    34860
gcggtgttac gttgaagtgg agcggattat gtcagcaatg gacagaacaa cctaatgaac    34920
acagaaccat gatgtggtct gtccttttac agccagtagt gctcgccgca gtcgagcgac    34980
agggcgaagc cctcgagtga gcgaggaagc accagggaac agcacttata tattctgctt    35040
acacacgatg cctgaaaaaa cttcccttgg ggttatccac ttatccacgg ggatattttt    35100
ataattattt tttttatagt ttttagatct tcttttttag agcgccttgt aggccttat     35160 ccatgctggt tctagagaag gtgttgtgac aaattgccct ttcagtgtga caaatcaccc    35220
tcaaatgaca gtcctgtctg tgacaaattg cccttaaccc tgtgacaaat tgccctcaga    35280
agaagctgtt ttttcacaaa gttatccctg cttattgact cttttttatt tagtgtgaca    35340
atctaaaaac ttgtcacact tcacatggat ctgtcatggc ggaaacagcg gttatcaatc    35400
acaagaaacg taaaaatagc ccgcgaatcg tccagtcaaa cgacctcact gaggcggcat    35460
atagtctctc ccgggatcaa aaacgtatgc tgtatctgtt cgttgaccag atcagaaaat    35520
ctgatggcac cctacaggaa catgacggta tctgcgagat ccatgttgct aaatatgctg    35580
aaatattcgg attgacctct gcggaagcca gtaaggatat acggcaggca ttgaagagtt    35640
tcgcggggaa ggaagtggtt ttttatcgcc ctgaagagga tgccggcgat gaaaaaggct    35700
atgaatcttt tccttggttt atcaaacgtg cgcacagtcc atccagaggg ctttacagtg    35760
tacatatcaa cccatatctc attcccttct ttatcgggtt acagaaccgg tttacgcagt    35820
ttcggcttag tgaaacaaaa gaaatcacca atccgtatgc catgcgttta tacgaatccc    35880
tgtgtcagta tcgtaagccg gatggctcag gcatcgtctc tctgaaaatc gactggatca    35940
tagagcgtta ccagctgcct caaagttacc agcgtatgcc tgacttccgc cgccgcttcc    36000
tgcaggtctg tgttaatgag atcaacagca gaactccaat gcgcctctca tacattgaga    36060
aaaagaaagg ccgccagacg actcatatcg tattttcctt ccgcgatatc acttccatga    36120
cgacaggata gtctgagggt tatctgtcac agatttgagg gtggttcgtc acatttgttc    36180
tgacctactg agggtaattt gtcacagttt tgctgtttcc ttcagcctgc atggattttc    36240
tcatactttt tgaactgtaa tttttaagga agccaaattt gagggcagtt tgtcacagtt    36300
gatttccttc tctttcctt cgtcatgtga cctgatatcg ggggttagtt cgtcatcatt    36360
gatgagggtt gattatcaca gtttattact ctgaattggc tatccgcgtg tgtacctcta    36420
cctggagttt ttcccacggt ggatatttct tcttgcgctg agcgtaagag ctatctgaca    36480
gaacagttct tctttgcttc ctcgccagtt cgctcgctat gctcggttac acggctgcgg    36540
cgagcgctag tgataataag tgactgaggt atgtgctctt cttatctcct tttgtagtgt    36600
tgctcttatt ttaaacaact ttgcggtttt ttgatgactt tgcgattttg ttgttgcttt    36660
gcagtaaatt gcaagattta ataaaaaaac gcaaagcaat gattaaagga tgttcagaat    36720
gaaactcatg gaaacactta accagtgcat aaacgctggt catgaaatga cgaaggctat    36780
cgccattgca cagtttaatg atgacagccc ggaagcgagg aaaataaccc ggcgctggag    36840
aataggtgaa gcagcggatt tagttggggt tccttctcag gctatcagag atgccgagaa    36900
agcagggcga ctaccgcacc cggatatgga aattcgagga cggggttgagc aacgtgttgg    36960
```

```
ttatacaatt gaacaaatta atcatatgcg tgatgtgttt ggtacgcgat tgcgacgtgc   37020
tgaagacgta tttccaccgg tgatcggggt tgctgcccat aaaggtggcg tttacaaaac   37080
ctcagtttct gttcatcttg ctcaggatct ggctctgaag gggctacgtg ttttgctcgt   37140
ggaaggtaac gaccccagg gaacagcctc aatgtatcac ggatgggtac cagatcttca    37200
tattcatgca gaagacactc tcctgccttt ctatcttggg gaaaaggacg atgtcactta   37260
tgcaataaag cccacttgct ggccggggct tgacattatt ccttcctgtc tggctctgca   37320
ccgtattgaa actgagttaa tgggcaaatt tgatgaaggt aaactgccca ccgatccaca   37380
cctgatgctc cgactggcca ttgaaactgt tgctcatgac tatgatgtca tagttattga   37440
cagcgcgcct aacctgggta tcggcacgat taatgtcgta tgtgctgctg atgtgctgat   37500
tgttcccacg cctgctgagt tgtttgacta cacctccgca ctgcagtttt tcgatatgct   37560
tcgtgatctg ctcaagaacg ttgatcttaa agggttcgag cctgatgtac gtattttgct   37620
taccaaatac agcaatagta atggctctca gtccccgtgg atggaggagc aaattcggga   37680
tgcctgggga agcatggttc taaaaaatgt tgtacgtgaa acggatgaag ttggtaaagg   37740
tcagatccgg atgagaactg tttttgaaca ggccattgat caacgctctt caactggtgc   37800
ctggagaaat gctctttcta tttgggaacc tgtctgcaat gaaattttcg atcgtctgat   37860
taaaccacgc tgggagatta gataatgaag cgtgcgcctg ttattccaaa acatacgctc   37920
aatactcaac cggttgaaga tacttcgtta tcgacaccag ctgccccgat ggtggattcg   37980
ttaattgcgc gcgtaggagt aatggctcgc ggtaatgcca ttactttgcc tgtatgtggt   38040
cgggatgtga agtttactct tgaagtgctc cggggtgata gtgttgagaa gacctctcgg   38100
gtatggtcag gtaatgaacg tgaccaggag ctgcttactg aggacgcact ggatgatctc   38160
atcccttctt ttctactgac tggtcaacag acaccggcgt tcggtcgaag agtatctggt   38220
gtcatagaaa ttgccgatgg gagtcgccgt cgtaaagctg ctgcacttac cgaaagtgat   38280
tatcgtgttc tggttggcga gctggatgat gagcagatgg ctgcattatc cagattgggt   38340
aacgattatc gcccaacaag tgcttatgaa cgtggtcagc gttatgcaag ccgattgcag   38400
aatgaatttg ctggaaatat ttctgcgctg gctgatgcga aaaatatttc acgtaagatt   38460
attacccgct gtatcaacac cgccaaattg cctaaatcag ttgttgctct ttttttctcac   38520 cccggtgaac tatctgcccg tcaggtgat gcacttcaaa aagcctttac agataaagag    38580
gaattactta agcagcaggc atctaacctt catgagcaga aaaaagctgg ggtgatattt   38640
gaagctgaag aagttatcac tcttttaact tctgtgctta aaacgtcatc tgcatcaaga   38700
actagtttaa gctcacgaca tcagtttgct cctggagcga cagtattgta taagggcgat   38760
aaaatggtgc ttaacctgga caggtctcgt gttccaactg agtgtataga gaaaattgag   38820
gccattctta aggaacttga aaagccagca ccctgatgcg accacgtttt agtctacgtt   38880
tatctgtctt tacttaatgt cctttgttac aggccagaaa gcataactgg cctgaatatt   38940
ctctctgggc ccactgttcc acttgtatcg tcggtctgat aatcagactg ggaccacggt   39000
cccactcgta tcgtcggtct gattattagt ctgggaccac ggtcccactc gtatcgtcgg   39060
tctgattatt agtctgggac cacgtcccca ctcgtatcgt cggtctgata atcagactgg   39120
gaccacggtc ccactcgtat cgtcggtctg attattagtc tgggaccatg gtcccactcg   39180 tatcgtcgg ctgattatta gtctgggacc acgtcccac tcgtatcgtc ggtctgatta     39240
ttagtctgga accacggtcc cactcgtatc gtcggtctga ttattagtct gggaccacgg   39300
```

| | |
|---|---|
| tcccactcgt atcgtcggtc tgattattag tctgggacca cgatcccact cgtgttgtcg | 39360 |
| gtctgattat cggtctggga ccacggtccc acttgtattg tcgatcagac tatcagcgtg | 39420 |
| agactacgat tccatcaatg cctgtcaagg gcaagtattg acatgtcgtc gtaacctgta | 39480 |
| gaacggagta acctcggtgt gcggttgtat gcctgctgtg gattgctgct gtgtcctgct | 39540 |
| tatccacaac attttgcgca cggttatgtg gacaaaatac ctggttaccc aggccgtgcc | 39600 |
| ggcacgttaa ccgggcacat ttccccgaaa agtgccacct gacgtctaag aaaccattat | 39660 |
| tatcatgaca ttaacctata aaaataggcg tatcacgagg cccttttcgtc ttcaagaatt | 39720 |
| ggatccgaat tcccgggaga gctcgatatc gcatgcggat ttaaattaat taa | 39773 |

<210> SEQ ID NO 98
<211> LENGTH: 39231
<212> TYPE: DNA
<213> ORGANISM: Artificial Sequence
<220> FEATURE:
<223> OTHER INFORMATION: Vector

<400> SEQUENCE: 98

| | |
|---|---|
| catcatcaat aatataccttt attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tagaagccat agagcccacc | 360 |
| gcatccccag catgcctgct agaattcgaa caaacgaccc aacaccgtg cgttttattc | 420 |
| tgtcttttta ttgccggcgg ccgcgaacaa atgtggtatg gctgattatg atcctctaga | 480 |
| gataattcta gttacccggg gagcatgtca aggtccaaat cgtcaagagc gtcagcaggc | 540 |
| agcatatcaa ggtcaaagtc gtcaagggca tcggctggga gcatgtctaa gtcaaaatcg | 600 |
| tcaagggcgt cggccggccc gccgcttttcg cactttagct gtttctccag gccacatatg | 660 |
| attagttcca ggccgaaaag gaaggcaggt tcggctccct gatggtcgaa cagctcaatt | 720 |
| gcttgtctca gaagtggggg catagaatcg gtggtaggtg tctctctttc ctcttttgct | 780 |
| acttgatgct cctgatcctc caatacgcag cccagtgtaa agtggccac ggcggacaga | 840 |
| gcgtacagtg cgttctccag ggagaagcct tgctgacaca ggaacgcgag ctgatttttcc | 900 |
| agggtttcgt actgtttctc tgttgggcgg gtgccgagat gcactttagc cccgtcgcga | 960 |
| tgtgagagga gagcacagcg gaatgacttg gcgttgttcc gcagaaagtc ttgccatgac | 1020 |
| tcgccttcca gggggcagaa gtgggtatga tgcctgtcca gcatctcgat tgccagggca | 1080 |
| tcgagcaggg cccgcttgtt cttcacgtgc cagtacaggg taggctgctc aactcccagc | 1140 |
| ttttgagcga gtttccttgt cgtcaggcct tcgataccga cttcattgag taattccaga | 1200 |
| gcagagttta tgactttgct cttgtccagt ctagacatag gacgcgtcag ctgactagag | 1260 |
| gatccccgcg gaggggtacc aagcttaagt ttaaacgcta gccagcttgg gtctccctat | 1320 |
| agtgagtcgt attaatttcg ataagccagt aagcagtggg ttctctagtt agccagagag | 1380 |
| ctctgcttat atagacctcc caccgtacac gcctaccgcc catttgcgtc aatgggcgg | 1440 |
| agttgttacg acattttgga aagtcccgtt gattttggtg ccaaaacaaa ctcccattga | 1500 |
| cgtcaatggg gtggagactt ggaaatcccc gtgagtcaaa ccgctatcca cgcccattga | 1560 |
| tgtactgcca aaaccgcatc accatggtaa tagcgatgac taatacgtag atgtactgcc | 1620 |

```
aagtaggaaa gtcccataag gtcatgtact gggcataatg ccaggcgggc catttaccgt    1680
cattgacgtc aataggggc gtacttggca tatgatacac ttgatgtact gccaagtggg     1740
cagtttaccg taaatactcc acccattgac gtcaatggaa agtccctatt ggcgttacta    1800
tgggaacata cgtcattatt gacgtcaatg gcgggggtc gttgggcggt cagccaggcg     1860
ggccatttac cgtaagttat gtaacgcgga actccatata tgggctatga actaatgacc    1920
ccgtaattga ttactattaa taactagtca ataatcaatg tcaacgcgta tatctgtggg    1980
cgtggcttaa gggtgggaaa gaatatataa ggtgggggtc ttatgtagtt ttgtatctgt    2040
tttgcagcag ccgccgccgc catgagcacc aactcgtttg atggaagcat tgtgagctca    2100
tatttgacaa cgcgcatgcc cccatgggcc ggggtgcgtc agaatgtgat gggctccagc    2160
attgatggtc gccccgtcct gcccgcaaac tctactacct tgacctacga gaccgtgtct    2220
ggaacgccgt tggagactgc agcctccgcc gccgcttcag ccgctgcagc caccgcccgc    2280
gggattgtga ctgactttgc ttcctgagcc ccgcttgcaa gcagtgcagc ttcccgttca    2340
tccgcccgcg atgacaagtt gacggctctt ttggcacaat tggattcttt gacccgggaa    2400
cttaatgtcg tttctcagca gctgttggat ctgcgccagc aggtttctgc cctgaaggct    2460
tcctcccctc ccaatgcggt ttaaaacata aataaaaaac cagactctgt ttggatttgg    2520
atcaagcaag tgtcttgctg tctttattta ggggttttgc gcgcgcggta ggcccgggac    2580
cagcggtctc ggtcgttgag ggtcctgtgt atttttttcca ggacgtggta aaggtgactc    2640
tggatgttca gatacatggg cataagcccg tctctggggt ggaggtagca ccactgcaga    2700
gcttcatgct gcggggtggt gttgtagatg atccagtcgt agcaggagcg ctgggcgtgg    2760
tgcctaaaaa tgtcttttcag tagcaagctg attgccaggg gcaggccctt ggtgtaagtg    2820
tttacaaagc ggttaagctg ggatgggtgc atacgtgggg atatgagatg catcttggac    2880
tgtattttta ggttggctat gttcccagcc atatccctcc ggggattcat gttgtgcaga    2940
accaccagca cagtgtatcc ggtgcacttg ggaaatttgt catgtagctt agaaggaaat    3000
gcgtggaaga acttggagac gcccttgtga cctccaagat tttccatgca ttcgtccata    3060
atgatggcaa tgggcccacg ggcggcggcc tgggcgaaga tatttctggg atcactaacg    3120
tcatagttgt gttccaggat gagatcgtca taggccattt ttacaaagcg cgggcggagg    3180
gtgccagact gcggtataat ggttccatcc ggcccagggg cgtagttacc ctcacagatt    3240
tgcatttccc acgctttgag ttcagatggg gggatcatgt ctacctgcgg ggcgatgaag    3300
aaaacggttt ccggggtagg ggagatcagc tgggaagaaa gcaggttcct gagcagctgc    3360
gacttaccgc agccggtggg cccgtaaatc acacctatta ccggctgcaa ctggtagtta    3420
agagagctgc agctgccgtc atccctgagc aggggggcca cttcgttaag catgtccctg    3480
actcgcatgt tttccctgac caaatccgcc agaaggcgct cgccgcccag cgatagcagt    3540
tcttgcaagg aagcaaagtt tttcaacggt ttgagaccgt ccgccgtagg catgcttttg    3600
agcgtttgac caagcagttc caggcggtcc cacagctcgg tcacctgctc tacggcatct    3660
cgatccagca tatctcctcg tttcgcgggt tggggcggct ttcgctgtac ggcagtagtc    3720
ggtgctcgtc cagacgggcc aggtcatgt ctttccacgg gcgcagggtc ctcgtcagcg    3780
tagtctgggt cacggtgaag gggtgcgctc cgggctgcgc gctggccagg gtgcgcttga    3840
ggctggtcct gctggtgctg aagcgctgcc ggtcttcgcc ctgcgcgtcg gccaggtagc    3900
atttgaccat ggtgtcatag tccagcccct ccgcggcgtg gcccttggcg cgcagcttgc    3960
```

```
ccttggagga ggcgccgcac gagggcagt gcagactttt gagggcgtag agcttgggcg     4020
cgagaaatac cgattccggg gagtaggcat ccgcgccgca ggccccgcag acggtctcgc     4080
attccacgag ccaggtgagc tctggccgtt cggggtcaaa aaccaggttt ccccatgct     4140
ttttgatgcg tttcttacct ctggtttcca tgagccggtg tccacgctcg gtgacgaaaa     4200
ggctgtccgt gtccccgtat acagacttga gaggcctgtc ctcgagcggt gttccgcggt     4260
cctcctcgta tagaaactcg gaccactctg agacaaaggc tcgcgtccag gccagcacga     4320
aggaggctaa gtgggagggg tagcggtcgt tgtccactag ggggtccact cgctccaggg     4380
tgtgaagaca catgtcgccc tcttcggcat caaggaaggt gattggtttg taggtgtagg     4440
ccacgtgacc gggtgttcct gaagggggc tataaaaggg ggtgggggcg cgttcgtcct     4500
cactctcttc cgcatcgctg tctgcgaggg ccagctgttg gggtgagtac tccctctgaa     4560
aagcgggcat gacttctgcg ctaagattgt cagtttccaa aaacgaggag gatttgatat     4620
tcacctggcc cgcggtgatg cctttgaggg tggccgcatc catctggtca gaaaagacaa     4680
tcttttgtt gtcaagcttg gtggcaaacg acccgtagag ggcgttggac agcaacttgg     4740
cgatggagcg caggggtttgg ttttttgtcgc gatcggcgcg ctccttggcc gcgatgttta     4800
gctgcacgta ttcgcgcgca acgcaccgcc attcgggaaa gacggtggtg cgctcgtcgg     4860
gcaccaggtg cacgcgccaa ccgcggttgt gcagggtgac aaggtcaacg ctggtggcta     4920
cctctccgcg taggcgctcg ttggtccagc agaggcggcc gcccttgcgc gagcagaatg     4980
gcggtagggg gtctagctgc gtctcgtccg ggggtctgc gtccacggta aagaccccgg     5040
gcagcaggcg cgcgtcgaag tagtctatct tgcatccttg caagtctagc gcctgctgcc     5100
atgcgcgggc ggcaagcgcg cgctcgtatg ggttgagtgg gggacccccat ggcatggggt     5160
gggtgagcgc ggaggcgtac atgccgcaaa tgtcgtaaac gtagaggggc tctctgagta     5220
ttccaagata tgtagggtag catcttccac cgcggatgct ggcgcgcacg taatcgtata     5280
gttcgtgcga gggagcgagg aggtcgggac cgaggttgct acgggcgggc tgctctgctc     5340
ggaagactat ctgcctgaag atggcatgtg agttggatga tatggttgga cgctggaaga     5400
cgttgaagct ggcgtctgtg agacctaccg cgtcacgcac gaaggaggcg taggagtcgc     5460
gcagcttgtt gaccagctcg gcggtgacct gcacgtctag ggcgcagtag tccagggttt     5520
ccttgatgat gtcatactta tcctgtccct ttttttttcca cagctcgcgg ttgaggacaa     5580
actcttcgcg gtctttccag tactcttgga tcggaaaccc gtcggcctcc gaacggtaag     5640
agcctagcat gtagaactgg ttgacggcct ggtaggcgca gcatcccttt tctacgggta     5700
gcgcgtatgc ctgcgcggcc ttccggagcg aggtgtgggt gagcgcaaag gtgtccctga     5760
ccatgaccag catgaagggc acgagctgct tcccaaaggc ccccatccaa gtataggtct     5820
ctacatcgta ggtgacaaag agacgctcgg tgcgaggatg cgagccgatc gggaagaact     5880
ggatctcccg ccaccaattg gaggagtggc tattgatgtg gtgaaagtag aagtccctgc     5940
gacgggccga acactcgtgc tggcttttgt aaaaacgtgc gcagtactgg cagcggtgca     6000
cgggctgtac atcctgcacg aggttgacct gacgaccgcg cacaaggaag cagagtggga     6060
atttgagccc ctcgcctggc gggttggct gtggtcttc tacttcggct gcttgtcctt     6120
gaccgtctgg ctgctcgagg ggagttacgg tggatcggac caccacgccg cgcgagccca     6180
aagtccagat gtccgcgcgc ggcggtcgga gcttgatgac aacatcgcgc agatgggagc     6240
tgtccatggt ctggagctcc cgcggcgtca ggtcaggcgg gagctcctgc aggtttacct     6300
cgcatagacg ggtcagggcg cgggctagat ccaggtgata cctaatttcc agggggctggt     6360
```

```
tggtggcggc gtcgatggct tgcaagaggc cgcatcccg cggcgcgact acggtaccgc   6420
gcggcgggcg gtgggccgcg ggggtgtcct tggatgatgc atctaaaagc ggtgacgcgg   6480
gcgagccccc ggaggtaggg ggggctccgg acccgccggg agaggggca ggggcacgtc    6540 ggcgccgcgc gcgggcagga gctggtgctg cgcgcgtagg ttgctggcga acgcgacgac   6600
gcggcggttg atctcctgaa tctggcgcct ctgcgtgaag acgacgggcc cggtgagctt   6660
gaacctgaaa gagagttcga cagaatcaat ttcggtgtcg ttgacggcgg cctgcgcaa    6720 aatctcctgc acgtctcctg agttgtcttg ataggcgatc tcggccatga actgctcgat   6780
ctcttcctcc tggagatctc cgcgtccggc tcgctccacg gtggcggcga ggtcgttgga   6840
aatgcgggcc atgagctgcg agaaggcgtt gaggcctccc tcgttccaga cgcggctgta   6900
gaccacgccc ccttcggcat cgcgggcgcg catgaccacc tgcgcgagat tgagctccac   6960
gtgccgggcg aagacggcgt agtttcgcag gcgctgaaag aggtagttga gggtggtggc   7020
ggtgtgttct gccacgaaga agtacataac ccagcgtcgc aacgtggatt cgttgatatc   7080
ccccaaggcc tcaaggcgct ccatggcctc gtagaagtcc acgcgaagt tgaaaaactg     7140 ggagttgcgc gccgacacgg ttaactcctc ctccagaaga cggatgagct cggcgacagt   7200
gtcgcgcacc tcgcgctcaa aggctacagg ggcctcttct tcttcttcaa tctcctcttc   7260
cataagggcc tccccttctt cttcttctgg cggcggtggg ggagggggga cacgcggcg    7320 acgacggcgc accgggaggc ggtcgacaaa gcgctcgatc atctccccgc ggcgacggcg   7380
catggtctcg gtgacggcgc ggccgttctc gcggggggcgc agttggaaga cgccgcccgt   7440
catgtcccgg ttatgggttg gcggggggct gccatgcggc agggatacgg cgctaacgat   7500
gcatctcaac aattgttgtg taggtactcc gccgccgagg gacctgagcg agtccgcatc   7560
gaccggatcg gaaaacctct cgagaaaggc gtctaaccag tcacagtcgc aaggtaggct   7620
gagcaccgtg gcgggcggca gcgggcggcg gtcggggttg tttctggcgg aggtgctgct   7680
gatgatgtaa ttaaagtagg cggtcttgag acggcggatg gtcgacagaa gcaccatgtc   7740
cttgggtccg gcctgctgaa tgcgcaggcg gtcggccatg ccccaggctt cgttttgaca    7800
tcggcgcagg tctttgtagt agtcttgcat gagcctttct accggcactt cttcttctcc   7860
ttcctcttgt cctgcatctc ttgcatctat cgctgcggcg gcggcggagt ttggccgtag   7920
gtggcgccct cttcctccca tgcgtgtgac cccgaagccc ctcatcggct gaagcagggc   7980
taggtcggcg acaacgcgct cggctaatat ggcctgctgc acctgcgtga gggtagactg   8040
gaagtcatcc atgtccacaa agcggtggta tgcgcccgtg ttgatggtgt aagtgcagtt   8100
ggccataacg gaccagttaa cggtctggtg acccggctgc gagagctcgg tgtacctgag   8160
acgcgagtaa gccctcgagt caaatacgta gtcgttgcaa gtccgcacca ggtactggta   8220
tcccaccaaa aagtgcggcg gcggctggcg gtagaggggc cagcgtaggg tggccggggc   8280
tccgggggcg agatcttcca acataaggcg atgatatccg tagatgtacc tggacatcca   8340
ggtgatgccg gcggcggtgg tggaggcgcg cggaaagtcg cggacgcggt tccagatgtt   8400
gcgcagcggc aaaaagtgct ccatggtcgg gacgctctgg ccggtcaggc gcgcgcaatc   8460
gttgacgctc tagaccgtgc aaaaggagag cctgtaagcg ggcactcttc cgtggtctgg   8520
tggataaatt cgcaagggta tcatggcgga cgaccggggt tcgagccccg tatccggccg   8580
tccgccgtga tccatgcggt taccgcccgc gtgtcgaacc caggtgtgcg acgtcagaca   8640
acgggggagt gctccttttg gcttccttcc aggcgcggcg gctgctgcgc tagctttttt   8700
```

```
ggccactggc cgcgcgcagc gtaagcggtt aggctggaaa gcgaaagcat taagtggctc    8760
gctccctgta gccggagggt tatttttccaa gggttgagtc gcgggacccc cggttcgagt   8820
ctcggaccgg ccggactgcg gcgaacgggg gtttgcctcc ccgtcatgca agaccccgct    8880
tgcaaattcc tccggaaaca gggacgagcc ccttttttgc ttttcccaga tgcatccggt    8940
gctgcggcag atgcgccccc ctcctcagca gcggcaagag caagagcagc ggcagacatg    9000
cagggcaccc tcccctcctc ctaccgcgtc aggaggggcg acatccgcgg ttgacgcggc    9060
agcagatggt gattacgaac ccccgcggcg ccgggcccgg cactacctgg acttggagga    9120
gggcgagggc ctggcgcggc taggagcgcc ctctcctgag cggcacccaa gggtgcagct    9180
gaagcgtgat acgcgtgagg cgtacgtgcc gcggcagaac ctgtttcgcg accgcgaggg    9240
agaggagccc gaggagatgc gggatcgaaa gttccacgca gggcgcgagc tgcggcatgg    9300
cctgaatcgc gagcggttgc tgcgcgagga ggactttgag cccgacgcgc gaaccgggat    9360
tagtcccgcg cgcgcacacg tggcggccgc cgacctggta accgcatacg agcagacggt    9420
gaaccaggag attaactttc aaaaaagctt taacaaccac gtgcgtacgc ttgtggcgcg    9480
cgaggaggtg gctataggac tgatgcatct gtgggacttt gtaagcgcgc tggagcaaaa    9540
cccaaatagc aagccgctca tggcgcagct gttccttata gtgcagcaca gcagggacaa    9600
cgaggcattc agggatgcgc tgctaaacat agtagagccc gagggccgct ggctgctcga    9660
tttgataaac atcctgcaga gcatagtggt gcaggagcgc agcttgagcc tggctgacaa    9720
ggtggccgcc atcaactatt ccatgcttag cctgggcaag ttttacgccc gcaagatata    9780
ccatacccct tacgttccca tagacaagga ggtaaagatc gaggggttct acatgcgcat    9840
ggcgctgaag gtgcttacct tgagcgacga cctgggcgtt tatcgcaacg agcgcatcca    9900
caaggccgtg agcgtgagcc ggcggcgcga gctcagcgac cgcgagctga tgcacagcct    9960
gcaaagggcc ctggctggca cgggcagcgg cgatagagag gccgagtcct actttgacgc    10020
gggcgctgac ctgcgctggg ccccaagccg acgcgccctg gaggcagctg gggccggacc    10080
tgggctggcg gtggcacccg cgcgcgctgg caacgtcggc ggcgtggagg aatatgacga    10140
ggacgatgag tacgagccag aggacggcga gtactaagcg gtgatgtttc tgatcagatg    10200
atgcaagacg caacggaccc ggcggtgcgg gcggcgctgc agagccagcc gtccggcctt    10260
aactccacgg acgactggcg ccaggtcatg gaccgcatca tgtcgctgac tgcgcgcaat    10320
cctgacgcgt tccggcagca gccgcaggcc aaccggctct ccgcaattct ggaagcggtg    10380
gtcccggcgc gcgcaaaccc cacgcacgag aaggtgctgg cgatcgtaaa cgcgctggcc    10440
gaaaacaggg ccatccggcc cgacgaggcc ggcctggtct acgacgcgct gcttcagcgc    10500
gtggctcgtt acaacagcgg caacgtgcag accaacctgg accggctggt gggggatgtg    10560
cgcgaggccg tggcgcagcg tgagcgcgcg cagcagcagg gcaacctggg ctccatggtt    10620
gcactaaacg ccttcctgag tacacagccc gccaacgtgc cgcggggaca ggaggactac    10680
accaactttg tgagcgcact gcggctaatg gtgactgaga caccgcaaag tgaggtgtac    10740
cagtctgggc cagactattt tttccagacc agtagacaag gcctgcagac cgtaaacctg    10800
agccaggctt tcaaaaactt gcaggggctg tgggggtgc gggctcccac aggcgaccgc    10860
gcgaccgtgt ctagcttgct gacgcccaac tcgcgcctgt tgctgctgct aatagcgccc    10920
ttcacggaca gtggcagcgt gtcccgggac acatacctag gtcacttgct gacactgtac    10980
cgcgaggcca taggtcaggc gcatgtggac gagcatactt tccaggagat tacaagtgtc    11040
agccgcgcgc tggggcagga ggacacgggc agcctggagg caaccctaaa ctacctgctg    11100
```

-continued

```
accaaccggc ggcagaagat cccctcgttg cacagtttaa acagcgagga ggagcgcatt    11160
ttgcgctacg tgcagcagag cgtgagcctt aacctgatgc gcgacggggt aacgcccagc    11220
gtggcgctgg acatgaccgc gcgcaacatg gaaccgggca tgtatgcctc aaaccggccg    11280
tttatcaacc gcctaatgga ctacttgcat cgcgcggccg ccgtgaaccc cgagtatttc    11340
accaatgcca tcttgaaccc gcactggcta ccgcccccctg gtttctacac cgggggattc    11400
gaggtgcccg agggtaacga tggattcctc tgggacgaca tagacgacag cgtgttttcc    11460
ccgcaaccgc agaccctgct agagttgcaa cagcgcgagc aggcagaggc ggcgctgcga    11520
aaggaaagct tccgcaggcc aagcagcttg tccgatctag cgcgctgcggc cccgcggtca    11580
gatgctagta gcccatttcc aagcttgata gggtctctta ccagcactcg caccacccgc    11640
ccgcgcctgc tgggcgagga ggagtaccta aacaactcgc tgctgcagcc gcagcgcgaa    11700
aaaaacctgc ctccggcatt tcccaacaac gggatagaga gcctagtgga caagatgagt    11760
agatggaaga cgtacgcgca ggagcacagg gacgtgccag gccgcgcccc gcccacccgt    11820
cgtcaaaggc acgaccgtca gcggggtctg gtgtgggagg acgatgactc ggcagacgac    11880
agcagcgtcc tggatttggg agggagtggc aacccgtttg cgcaccttcg ccccaggctg    11940
gggagaatgt tttaaaaaaa aaaaaagcat gatgcaaaat aaaaaactca ccaaggccat    12000
ggcaccgagc gttggtttc ttgtattccc cttagtatgc ggcgcgcggc gatgtatgag    12060
gaaggtcctc ctccctccta cgagagtgtg gtgagcgcgg cgccagtggc ggcggcgctg    12120
ggttctccct tcgatgctcc cctggacccg ccgtttgtgc ctccgcggta cctgcggcct    12180
accgggggga gaaacagcat ccgttactct gagttggcac ccctattcga caccacccgt    12240
gtgtacctgg tggacaacaa gtcaacggat gtggcatccc tgaactacca gaacgaccac    12300
agcaactttc tgaccacggt cattcaaaac aatgactaca gcccggggga ggcaagcaca    12360
cagaccatca atcttgacga ccggtcgcac tggggcggcg acctgaaaac catcctgcat    12420
accaacatgc caaatgtgaa cgagttcatg tttaccaata gtttaaggc gcgggtgatg    12480
gtgtcgcgct tgcctactaa ggacaatcag gtggagctga atacgagtg ggtggagttc    12540
acgctgcccg agggcaacta ctccgagacc atgaccatag accttatgaa caacgcgatc    12600
gtggagcact acttgaaagt gggcagacag aacggggttc tggaaagcga catcggggta    12660
aagtttgaca cccgcaactt cagactgggg tttgaccccg tcactggtct tgtcatgcct    12720
ggggtatata caaacgaagc cttccatcca gacatcattt tgctgccagg atgcgggtg    12780
gacttcaccc cagccgcct gagcaacttg ttgggcatcc gcaagcggca acccttccag    12840
gagggcttta ggatcaccta cgatgatctg gagggtggta acattccgc actgttggat    12900
gtggacgcct accaggcgag cttgaaagat gacaccgaac agggcgggg tggcgcaggc    12960
ggcagcaaca gcagtggcag cggcgcggaa gagaactcca acgcggcagc cgcggcaatg    13020
cagccggtgg aggacatgaa cgatcatgcc attcgcggcg acacctttgc cacacgggct    13080
gaggagaagc gcgctgaggc cgaagcagcg gccgaagctg ccgcccccgc tgcgcaaccc    13140
gaggtcgaga agcctcagaa gaaaccggtg atcaaacccc tgacagagga cagcaagaaa    13200
cgcagttaca acctaataag caatgacagc accttcaccc agtaccgcag ctggtacctt    13260
gcatacaact acggcgaccc tcagaccgga atccgctcat ggaccctgct ttgcactcct    13320
gacgtaacct gcggctcgga gcaggtctac tggtcgttgc cagacatgat gcaagacccc    13380
gtgaccttcc gctccacgcg ccagatcagc aactttccgg tggtgggcgc cgagctgttg    13440
```

```
cccgtgcact ccaagagctt ctacaacgac caggccgtct actcccaact catccgccag    13500
tttacctctc tgacccacgt gttcaatcgc tttcccgaga accagatttt ggcgcgcccg    13560
ccagccccca ccatcaccac cgtcagtgaa acgttcctg  ctctcacaga tcacgggacg    13620
ctaccgctgc gcaacagcat cggaggagtc cagcgagtga ccattactga cgccagacgc    13680
cgcacctgcc cctacgttta caaggccctg ggcatagtct cgccgcgcgt cctatcgagc    13740 cgcactttt  gagcaagcat gtccatcctt atatcgccca gcaataacac aggctggggc    13800
ctgcgcttcc caagcaagat gtttggcggg gccaagaagc gctccgacca acacccagtg    13860
cgcgtgcgcg ggcactaccg cgcgccctgg ggcgcgcaca acgcggccg  cactgggcgc    13920 accaccgtcg atgacgccat cgacgcgtg  gtggaggagg cgcgcaacta cacgcccacg    13980
ccgccaccag tgtccacagt ggacgcggcc attcagaccg tggtgcgcgg agcccggcgc    14040
tatgctaaaa tgaagagacg gcggaggcgc gtagcacgtc gccaccgccg ccgacccggc    14100
actgccgccc aacgcgcggc ggcggcccctg cttaaccgcg cacgtcgcac cggccgacgg    14160
gcggccatgc gggccgctcg aaggctggcc gcgggtattg tcactgtgcc ccccaggtcc    14220
aggcgacgag cggccgccgc agcagccgcg gccattagtg ctatgactca gggtcgcagg    14280
ggcaacgtgt attgggtgcg cgactcggtt agcggcctgc gcgtgcccgt gcgcacccgc    14340
cccccgcgca actagattgc aagaaaaaac tacttagact cgtactgttg tatgtatcca    14400
gcggcggcgg cgcgcaacga agctatgtcc aagcgcaaaa tcaaagaaga gatgctccag    14460
gtcatcgcgc cggagatcta tggccccccg aagaaggaag agcaggatta caagccccga    14520
aagctaaagc gggtcaaaaa gaaaagaaa  gatgatgatg atgaacttga cgacgaggtg    14580
gaactgctgc acgctaccgc gcccaggcga cgggtacagt ggaaaggtcg acgcgtaaaa    14640
cgtgttttgc gacccggcac caccgtagtc tttacgcccg tgagcgctc  cacccgcacc    14700 tacaagcgcg tgtatgatga ggtgtacggc gacgaggacc tgcttgagca ggccaacgag    14760
cgcctcgggg agtttgccta cggaaagcgg cataaggaca tgctggcgtt gccgctggac    14820
gagggcaacc caacacctag cctaaagccc gtaacactgc agcaggtgct gcccgcgctt    14880
gcaccgtccg aagaaaagcg cggcctaaag cgcgagtctg gtgacttggc acccaccgtg    14940
cagctgatgg tacccaagcg ccagcgactg gaagatgtct tggaaaaaat gaccgtggaa    15000
cctgggctgg agcccgaggt ccgcgtgcgg ccaatcaagc aggtggcgcc gggactgggc    15060
gtgcagaccg tggacgttca gataccact  accagtagca ccagtattgc caccgccaca    15120
gagggcatgg agacacaaac gtccccggtt gcctcagcgg tggcggatgc cgcggtgcag    15180
gcggtcgctg cggccgcgtc caagacctct acggaggtgc aaacggaccc gtggatgttt    15240
cgcgtttcag cccccccggcg cccgcgccgt tcgaggaagt acggcgccgc cagcgcgcta    15300
ctgcccgaat atgccctaca tccttccatt gcgcctaccc ccggctatcg tggctacacc    15360
taccgcccca gaagacgagc aactacccga cgccgaacca ccactggaac ccgccgccgc    15420
cgtcgccgtc gccagcccgt gctggcccg  atttccgtgc gcagggtggc tcgcgaagga    15480
ggcaggaccc tggtgctgcc aacagcgcgc taccacccca gcatcgttta aagccggtc    15540 tttgtggttc ttgcagatat ggccctcacc tgccgcctcc gtttcccggt gccgggattc    15600
cgaggaagaa tgcaccgtag gagggcatg  gccggccacg gcctgacggg cggcatgcgt    15660
cgtgcgcacc accggcggcg gcgcgcgtcg caccgtcgca tgcgcggcgg tatcctgccc    15720
ctccttattc cactgatcgc cgcggcgatt ggcgccgtgc ccggaattgc atccgtggcc    15780
ttgcaggcgc agagacactg attaaaaaca agttgcatgt ggaaaaatca aaataaaaag    15840
```

```
tctggactct cacgctcgct tggtcctgta actattttgt agaatggaag acatcaactt    15900
tgcgtctctg gccccgcgac acggctcgcg cccgttcatg ggaaactggc aagatatcgg    15960
caccagcaat atgagcggtg gcgccttcag ctggggctcg ctgtggagcg gcattaaaaa    16020
tttcggttcc accgttaaga actatggcag caaggcctgg aacagcagca caggccagat    16080
gctgagggat aagttgaaag agcaaaattt ccaacaaaag gtggtagatg gcctggcctc    16140
tggcattagc ggggtggtgg acctggccaa ccaggcagtg caaaataaga ttaacagtaa    16200
gcttgatccc cgccctcccg tagaggagcc tccaccggcc gtggagacag tgtctccaga    16260
ggggcgtggc gaaaagcgtc cgcgcccga caggaagaa actctggtga cgcaaataga     16320
cgagcctccc tcgtacgagg aggcactaaa gcaaggcctg cccaccaccc gtcccatcgc    16380
gcccatggct accggagtgc tgggccagca cacacccgta acgctggacc tgcctccccc    16440
cgccgacacc cagcagaaac ctgtgctgcc aggcccgacc gccgttgttg taacccgtcc    16500
tagccgcgcg tccctgcgcc gcgccgccag cggtccgcga tcgttgcggc ccgtagccag    16560
tggcaactgg caaagcacac tgaacagcat cgtgggtctg ggggtgcaat ccctgaagcg    16620
ccgacgatgc ttctgatagc taacgtgtcg tatgtgtgtc atgtatgcgt ccatgtcgcc    16680
gccagaggag ctgctgagcc gccgcgcgcc cgctttccaa gatggctacc ccttcgatga    16740
tgccgcagtg gtcttacatg cacatctcgg gccaggacgc ctcggagtac ctgagccccg    16800
ggctggtgca gtttgcccgc gccaccgaga cgtacttcag cctgaataac aagtttagaa    16860
accccacggt ggcgcctacg cacgacgtga ccacagaccg gtcccagcgt ttgacgctgc    16920
ggttcatccc tgtggaccgt gaggatactg cgtactcgta caaggcgcgg ttcaccctag    16980
ctgtgggtga taccgtgtg ctggacatgg cttccacgta ctttgacatc cgcggcgtgc     17040
tggacagggg ccctactttt aagccctact ctggcactgc ctacaacgcc ctggctccca    17100
agggtgcccc aaatccttgc gaatgggatg aagctgctac tgctcttgaa ataaacctag    17160
aagaagagga cgatgacaac gaagacgaag tagacgagca agctgagcag caaaaaactc    17220
acgtatttgg gcaggcgcct tattctggta taaatattac aaaggagggt attcaaaatag   17280 gtgtcgaagg tcaaacacct aaatatgccg ataaaacatt tcaacctgaa cctcaaatag    17340
gagaatctca gtggtacgaa acagaaatta atcatgcagc tgggagagtc ctaaaaaaga    17400
ctaccccaat gaaaccatgt tacgggttcat atgcaaaacc cacaaatgaa aatggagggc    17460
aaggcattct tgtaaagcaa caaaatggaa agctagaaag tcaagtggaa atgcaatttt    17520
tctcaactac tgaggcagcc gcaggcaatg gtgataactt gactcctaaa gtggtattgt    17580
acagtgaaga tgtagatata gaaaccccag acactcatat ttcttacatg cccactatta    17640
aggaaggtaa ctcacgagaa ctaatgggcc aacaatctat gcccaacagg cctaattaca    17700
ttgcttttag ggacaatttt attggtctaa tgtattacaa cagcacgggt aatatgggtg    17760
ttctggcggg ccaagcatcg cagttgaatg ctgttgtaga tttgcaagac agaaacacag    17820
agctttcata ccagctttttg cttgattcca ttggtgatag aaccaggtac ttttctatgt    17880
ggaatcaggc tgttgacagc tatgatccag atgttagaat tattgaaaat catgggactg     17940
aagatgaact tccaaattac tgcttttccac tgggaggtgt gattaataca gagactctta    18000
ccaaggtaaa acctaaaaca ggtcaggaaa atggatggga aaagatgct acagaatttt      18060 cagataaaaa tgaaataaga gttggaaata attttgccat ggaatcaat ctaaatgcca     18120 acctgtggag aaatttcctg tactccaaca tagcgctgta tttgcccgac aagctaaagt    18180
```

```
acagtccttc caacgtaaaa atttctgata acccaaacac ctacgactac atgaacaagc   18240
gagtggtggc tcccgggcta gtggactgct acattaacct tggagcacgc tggtcccttg   18300
actatatgga caacgtcaac ccatttaacc accaccgcaa tgctggcctg cgctaccgct   18360
caatgttgct gggcaatggt cgctatgtgc ccttccacat ccaggtgcct cagaagttct   18420
ttgccattaa aaacctcctt ctcctgccgg gctcatacac ctacgagtgg aacttcagga   18480
aggatgttaa catggttctg cagagctccc taggaaatga cctaagggtt gacggagcca   18540
gcattaagtt tgatagcatt tgcctttacg ccaccttctt ccccatggcc cacaacaccg   18600
cctccacgct tgaggccatg cttagaaacg acaccaacga ccagtccttt aacgactatc   18660
tctccgccgc caacatgctc taccctatac ccgccaacgc taccaacgtg cccatatcca   18720
tcccctcccg caactgggcg gctttccgcg gctgggcctt cacgcgcctt aagactaagg   18780 aaacccatc actgggctcg ggctacgacc cttattacac ctactctggc tctatacccct   18840 acctagatgg aaccttttac ctcaaccaca cctttaagaa ggtggccatt acctttgact   18900
cttctgtcag ctggcctggc aatgaccgcc tgcttacccc caacgagttt gaaattaagc   18960
gctcagttga cggggagggt tacaacgttg cccagtgtaa catgaccaaa gactggttcc   19020
tggtacaaat gctagctaac tataacattg gctaccaggg cttctatatc ccagagagct   19080
acaaggaccg catgtactcc ttctttagaa acttccagcc catgagccgt caggtggtgg   19140
atgatactaa atacaaggac taccaacagg tgggcatcct acaccaacac aacaactctg   19200
gatttgttgg ctaccttgcc cccaccatgc gcgaaggaca ggcctaccct gctaacttcc   19260
cctatccgct tataggcaag accgcagttg acagcattac ccagaaaaag tttctttgcg   19320
atcgcaccct ttggcgcatc ccattctcca gtaactttat gtccatgggc gcactcacag   19380
acctgggcca aaaccttctc tacgccaact ccgcccacgc gctagacatg acttttgagg   19440
tggatcccat ggacgagccc acccttcttt atgtttttgtt tgaagtcttt gacgtggtcc   19500
gtgtgcacca gccgcaccgc ggcgtcatcg aaaccgtgta cctgcgcacg cccttctcgg   19560
ccggcaacgc cacaacataa agaagcaagc aacatcaaca acagctgccg ccaaataatg   19620
tactagagac actttcaata aaggcaaatg ctttttattg tacactctcg ggtgattatt   19680 taccccacc cttgccgtct gcgccgttta aaaatcaaag gggttctgcc gcgcatcgct   19740
atgcgccact ggcagggaca cgttgcgata ctggtgttta gtgctccact taaactcagg   19800
cacaaccatc cgcggcagct cggtgaagtt ttcactccac aggctgcgca ccatcaccaa   19860
cgcgtttagc aggtcgggcg ccgatatctt gaagtcgcag ttggggcctc cgccctgcgc   19920
gcgcgagttg cgatacacag ggttgcagca ctggaacact atcagcgccg ggtggtgcac   19980
gctggccagc acgctcttgt cggagatcag atccgcgtcc aggtcctccg cgttgctcag   20040
ggcgaacgga gtcaactttg gtagctgcct tcccaaaaag ggcgcgtgcc caggctttga   20100
gttgcactcg caccgtagtg gcatcaaaag gtgaccgtgc ccggtctggg cgttaggata   20160
cagcgcctgc ataaaagcct tgatctgctt aaaagccacc tgagcctttg cgccttcaga   20220
gaagaacatg ccgcaagact tgccggaaaa ctgattggcc ggacaggccg cgtcgtgcac   20280
gcagcacctt gcgtcggtgt tggagatctg caccacattt cggccccacc ggttcttcac   20340
gatcttggcc ttgctagact gctccttcag cgcgcgctgc ccgttttcgc tcgtcacatc   20400
catttcaatc acgtgctcct tatttatcat aatgcttccg tgtagacact taagctcgcc   20460
ttcgatctca gcgcagcggt gcagccacaa cgcgcagccc gtgggctcgt gatgcttgta   20520
ggtcacctct gcaaacgact gcaggtacgc ctgcaggaat cgccccatca tcgtcacaaa   20580
```

```
ggtcttgttg ctggtgaagg tcagctgcaa cccgcggtgc tcctcgttca gccaggtctt    20640
gcatacggcc gccagagctt ccacttggtc aggcagtagt ttgaagttcg cctttagatc    20700
gttatccacg tggtacttgt ccatcagcgc gcgcgcagcc tccatgccct tctcccacgc    20760
agacacgatc ggcacactca gcgggttcat caccgtaatt tcactttccg cttcgctggg    20820
ctcttcctct tcctcttgcg tccgcatacc acgcgccact gggtcgtctt cattcagccg    20880
ccgcactgtg cgcttacctc ctttgccatg cttgattagc accggtgggt tgctgaaacc    20940
caccatttgt agcgccacat cttctctttc ttcctcgctg tccacgatta cctctggtga    21000
tggcgggcgc tcgggcttgg gagaagggcg cttcttttc ttcttgggcg caatggccaa    21060
atccgccgcc gaggtcgatg ccgcgggct gggtgtgcgc ggcaccagcg cgtcttgtga     21120
tgagtcttcc tcgtcctcgg actcgatacg ccgcctcatc cgcttttttg ggggcgcccg    21180
gggaggcggc ggcgacgggg acggggacga cacgtcctcc atggttgggg gacgtcgcgc    21240
cgcaccgcgt ccgcgctcgg gggtggtttc gcgctgctcc tcttcccgac tggccatttc    21300
cttctcctat aggcagaaaa agatcatgga gtcagtcgag aagaaggaca gcctaaccgc    21360
cccctctgag ttcgccacca ccgcctccac cgatgccgcc aacgcgccta ccaccttccc    21420
cgtcgaggca ccccgcttg aggaggagga agtgattatc gagcaggacc caggttttgt     21480
aagcgaagac gacgaggacc gctcagtacc aacagaggat aaaaagcaag accaggacaa    21540
cgcagaggca aacgaggaac aagtcgggcg gggggacgaa aggcatggcg actacctaga    21600
tgtgggagac gacgtgctgt tgaagcatct gcagcgccag tgcgccatta tctgcgacgc    21660
gttgcaagag cgcagcgatg tgcccctcgc catagcggat gtcagccttg cctacgaacg    21720
ccacctattc tcaccgcgcg tacccccccaa acgccaagaa aacggcacat gcgagcccaa    21780
cccgcgcctc aacttctacc ccgtatttgc cgtgccagag gtgcttgcca cctatcacat    21840
ctttttccaa aactgcaaga tacccctatc ctgccgtgcc aaccgcagcc gagcggacaa    21900
gcagctggcc ttgcggcagg gcgctgtcat acctgatatc gcctcgctca acgaagtgcc    21960
aaaaatcttt gagggtcttg gacgcgacga gaagcgcgcg gcaaacgctc tgcaacagga    22020
aaacagcgaa aatgaaagtc actctggagt gttggtggaa ctcgagggtg acaacgcgcg    22080
cctagccgta ctaaaacgca gcatcgaggt cacccacttt gcctaccgg cacttaacct     22140 accccccaag gtcatgagca cagtcatgag tgagctgatc gtgcgccgtg cgcagccct    22200 ggagagggat gcaaatttgc aagaacaaac agaggagggc ctacccgcag ttggcgacga    22260
gcagctagcg cgctggcttc aaacgcgcga gcctgccgac ttggaggagc gacgcaaact    22320
aatgatggcc gcagtgctcg ttaccgtgga gcttgagtgc atgcagcggt tctttgctga    22380 cccgagatg cagcgcaagc tagaggaaac attgcactac acctttcgac agggctacgt     22440
acgccaggcc tgcaagatct ccaacgtgga gctctgcaac ctggtctcct accttggaat    22500
tttgcacgaa aaccgccttg gcaaaaacgt gcttcattcc acgctcaagg gcgaggcgcg    22560
ccgcgactac gtccgcgact gcgtttactt atttctatgc tacacctggc agacggccat    22620
gggcgtttgg cagcagtgct tggaggagtg caacctcaag gagctgcaga aactgctaaa    22680
gcaaaacttg aaggacctat ggacggcctt caacgagcgc tccgtggccg cgcacctggc    22740
ggacatcatt ttccccgaac gcctgcttaa accctgcaa cagggtctgc cagacttcac     22800
cagtcaaagc atgttgcaga actttaggaa ctttatccta gagcgctcag gaatcttgcc    22860
cgccacctgc tgtgcacttc ctagcgactt tgtgcccatt aagtaccgcg aatgccctcc    22920
```

```
gccgctttgg ggccactgct accttctgca gctagccaac taccttgcct accactctga   22980
cataatggaa gacgtgagcg gtgacggtct actggagtgt cactgtcgct gcaacctatg   23040
caccccgcac cgctccctgg tttgcaattc gcagctgctt aacgaaagtc aaattatcgg   23100
tacctttgag ctgcagggtc cctcgcctga cgaaaagtcc gcggctccgg ggttgaaact   23160
cactccgggg ctgtggacgt cggcttacct tcgcaaattt gtacctgagg actaccacgc   23220
ccacgagatt aggttctacg aagaccaatc ccgcccgcct aatgcggagc ttaccgcctg   23280
cgtcattacc cagggccaca ttcttggcca attgcaagcc atcaacaaag cccgccaaga   23340
gtttctgcta cgaaagggac gggggggttta cttggacccc cagtccggcg aggagctcaa   23400
cccaatcccc ccgccgccgc agccctatca gcagcagccg cgggcccttg cttcccagga   23460
tggcacccaa aaagaagctg cagctgccgc cgccacccac ggacgaggag gaatactggg   23520
acagtcaggc agaggaggtt ttggacgagg aggaggagga catgatggaa gactgggaga   23580
gcctagacga ggaagcttcc gaggtcgaag aggtgtcaga cgaaacaccg tcaccctcgg   23640
tcgcattccc ctcgccggcg ccccagaaat cggcaaccgg ttccagcatg ctacaacct   23700
ccgctcctca ggcgccgccg gcactgcccg ttcgccgacc caaccgtaga tgggacacca   23760
ctggaaccag ggccggtaag tccaagcagc cgccgccgtt agcccaagag caacaacagc   23820
gccaaggcta ccgctcatgg cgcgggcaca agaacgccat agttgcttgc ttgcaagact   23880
gtgggggcaa catctccttc gcccgccgct ttcttctcta ccatcacggc gtggccttcc   23940
cccgtaacat cctgcattac taccgtcatc tctacagccc atactgcacc ggcggcagcg   24000
gcagcaacag cagcggccac acagaagcaa aggcgaccgg atagcaagac tctgacaaag   24060
cccaagaaat ccacagcggc ggcagcagca ggaggaggag cgctgcgtct ggcgcccaac   24120
gaacccgtat cgaccgcga gcttagaaac aggattttc ccactctgta tgctatattt   24180
caacagagca ggggccaaga acaagagctg aaaataaaaa acaggtctct gcgatccctc   24240
acccgcagct gcctgtatca caaaagcgaa gatcagcttc ggcgcacgct ggaagacgcg   24300
gaggctctct tcagtaaata ctgcgcgctg actcttaagg actagtttcg cgccctttct   24360
caaatttaag cgcgaaaact acgtcatctc cagcggccac acccggcgcc agcacctgtt   24420
gtcagcgcca ttatgagcaa ggaaattccc acgccctaca tgtggagtta ccagccacaa   24480
atgggacttg cggctggagc tgcccaagac tactcaaccc gaataaacta catgagcgcg   24540
ggaccccaca tgatatcccg ggtcaacgga atacgcgccc accgaaaccg aattctcctg   24600
gaacaggcgg ctattaccac cacacctcgt aataaccta atccccgtag ttggcccgct   24660
gccctggtgt accaggaaag tcccgctccc accactgtgg tacttcccag agacgcccag   24720
gccgaagttc agatgactaa ctcaggggcg cagcttgcgg gcggctttcg tcacagggtg   24780
cggtcgcccg ggcagggtat aactcacctg acaatcagag ggcgaggtat tcagctcaac   24840
gacgagtcgg tgagctcctc gcttggtctc cgtccggacg ggacatttca gatcggcggc   24900
gccggccgct cttcattcac gcctcgtcag gcaatcctaa ctctgcagac ctcgtcctct   24960
gagccgcgct ctggaggcat tggaactctg caatttattg aggagtttgt gccatcggtc   25020
tactttaacc ccttctcggg acctcccggc cactatccgg atcaatttat tcctaacttt   25080
gacgcggtaa aggactcggc ggacggctac gactgaatgt taagtggaga ggcagagcaa   25140
ctgcgcctga aacacctggt ccactgtcgc cgccacaagt gctttgcccg cgactccggt   25200
gagttttgct actttgaatt gcccgaggat catatcgagg gccgcgcca ggcgtccgg   25260
cttaccgccc agggagagct tgcccgtagc ctgattcggg agtttaccca gcgccccctg   25320
```

```
ctagttgagc gggacagggg accctgtgtt ctcactgtga tttgcaactg tcctaaccct   25380
ggattacatc aagatctttg ttgccatctc tgtgctgagt ataataaata cagaaattaa   25440
aatatactgg ggctcctatc gccatcctgt aaacgccacc gtcttcaccc gcccaagcaa   25500
accaaggcga accttacctg gtacttttaa catctctccc tctgtgattt acaacagttt   25560
caacccagac ggagtgagtc tacgagagaa cctctccgag ctcagctact ccatcagaaa   25620
aaacaccacc ctccttacct gccgggaacg tacgagtgcg tcaccggccg ctgcaccaca   25680
cctaccgcct gaccgtaaac cagactttt ccggacagac ctcaataact ctgtttacca   25740
gaacaggagg tgagcttaga aaacccttag ggtattaggc caaaggcgca gctactgtgg   25800
ggtttatgaa caattcaagc aactctacgg gctattctaa ttcaggtttc tctagaaatg   25860
gacggaatta ttacagagca gcgcctgcta gaaagacgca gggcagcggc cgagcaacag   25920
cgcatgaatc aagagctcca agacatggtt aacttgcacc agtgcaaaag gggtatcttt   25980
tgtctggtaa agcaggccaa agtcacctac gacagtaata ccaccggaca ccgccttagc   26040
tacaagttgc caaccaagcg tcagaaattg gtggtcatgg tgggagaaaa gcccattacc   26100
ataactcagc actcggtaga aaccgaaggc tgcattcact caccttgtca aggacctgag   26160
gatctctgca cccttattaa gaccctgtgc ggtctcaaag atcttattcc ctttaactaa   26220 taaaaaaaa taataaagca tcacttactt aaaatcagtt agcaaatttc tgtccagttt   26280
attcagcagc acctccttgc cctcctccca gctctggtat tgcagcttcc tcctggctgc   26340
aaactttctc cacaatctaa atggaatgtc agtttcctcc tgttcctgtc catccgcacc   26400
cactatcttc atgttgttgc agatgaagcg cgcaagaccg tctgaagata ccttcaaccc   26460
cgtgtatcca tatgacacgg aaaccggtcc tccaactgtg cctttcctta ctcctccctt   26520
tgtatccccc aatgggtttc aagagagtcc ccctggggta ctctctttgc gcctatccga   26580
acctctagtt acctccaatg gcatgcttgc gctcaaaatg gcaacggcc tctctctgga   26640 cgaggccggc aaccttacct cccaaaatgt aaccactgtg agcccacctc tcaaaaaaac   26700
caagtcaaac ataaacctgg aaatatctgc acccctcaca gttacctcag aagccctaac   26760
tgtggctgcc gccgcacctc taatggtcgc gggcaacaca ctcaccatgc aatcacaggc   26820
cccgctaacc gtgcacgact ccaaacttag cattgccacc caaggacccc tcacagtgtc   26880
agaaggaaag ctagccctgc aaacatcagg cccccctcacc accaccgata gcagtaccct   26940
tactatcact gcctcacccc ctctaactac tgccactggt agcttgggca ttgacttgaa   27000
agagcccatt tatacacaaa atggaaaact aggactaaag tacggggctc ctttgcatgt   27060
aacagacgac ctaaacactt tgaccgtagc aactggtcca ggtgtgacta ttaataatac   27120
ttccttgcaa actaaagtta ctggagcctt gggttttgat tcacaaggca atatgcaact   27180
taatgtagca ggaggactaa ggattgattc tcaaaacaga cgccttatac ttgatgttag   27240
ttatccgttt gatgctcaaa accaactaaa tctaagacta ggacagggcc ctctttttat   27300
aaactcagcc cacaacttgg atattaacta caacaaaggc ctttacttgt ttacagcttc   27360
aaacaattcc aaaagcttg aggttaacct aagcactgcc aaggggttga tgtttgacgc   27420
tacagccata gccattaatg caggagatgg gcttgaattt ggttcaccta atgcaccaaa   27480
cacaaatccc ctcaaaacaa aaattggcca tggcctagaa tttgattcaa acaaggctat   27540
ggttcctaaa ctaggaactg gccttagttt tgacagcaca ggtgccatta cagtaggaaa   27600
caaaaataat gataagctaa ctttgtggac cacaccagct ccatctccta actgtagact   27660
```

```
aaatgcagag aaagatgcta aactcacttt ggtcttaaca aaatgtggca gtcaaatact      27720
tgctacagtt tcagttttgg ctgttaaagg cagtttggct ccaatatctg aacagttca      27780 aagtgctcat cttattataa gatttgacga aaatggagtg ctactaaaca attccttcct      27840
ggacccagaa tattggaact ttagaaatgg agatcttact gaaggcacag cctatacaaa      27900
cgctgttgga tttatgccta acctatcagc ttatccaaaa tctcacggta aaactgccaa      27960
aagtaacatt gtcagtcaag tttacttaaa cggagacaaa actaaacctg taacactaac      28020
cattacacta aacggtacac aggaaacagg agacacaact ccaagtgcat actctatgtc      28080
attttcatgg gactggtctg ccacaacta cattaatgaa atatttgcca catcctctta      28140 cacttttttca tacattgccc aagaataaag aatcgtttgt gttatgtttc aacgtgttta      28200
tttttcaatt gcagaaaatt tcgaatcatt tttcattcag tagtatagcc ccaccaccac      28260
atagcttata cagatcaccg taccttaatc aaactcacag aaccctagta ttcaacctgc      28320
cacctccctc ccaacacaca gagtacacag tcctttctcc ccggctggcc ttaaaaagca      28380
tcatatcatg ggtaacagac atattcttag gtgttatatt ccacacggtt tcctgtcgag      28440
ccaaacgctc atcagtgata ttaataaact ccccgggcag ctcacttaag ttcatgtcgc      28500
tgtccagctg ctgagccaca ggctgctgtc caacttgcgg ttgcttaacg ggcggcgaag      28560
gagaagtcca cgcctacatg ggggtagagt cataatcgtg catcaggata gggcggtggt      28620
gctgcagcag cgcgcgaata aactgctgcc gccgccgctc cgtcctgcag gaatacaaca      28680
tggcagtggt ctcctcagcg atgattcgca ccgcccgcag cataaggcgc cttgtcctcc      28740
gggcacagca gcgcaccctg atctcactta aatcagcaca gtaactgcag cacagcacca      28800
caatattgtt caaaatccca cagtgcaagg cgctgtatcc aaagctcatg gcggggacca      28860
cagaacccac gtggccatca taccacaagc gcaggtagat taagtggcga cccctcataa      28920
acacgctgga cataaacatt acctcttttg gcatgttgta attcaccacc tcccggtacc      28980
atataaacct ctgattaaac atggcgccat ccaccaccat cctaaaccag ctggccaaaa      29040
cctgcccgcc ggctatacac tgcagggaac cgggactgga acaatgacag tggagagccc      29100
aggactcgta accatggatc atcatgctcg tcatgatatc aatgttggca caacacaggc      29160
acacgtgcat acacttcctc aggattacaa gctcctcccg cgttagaacc atatcccagg      29220
gaacaaccca ttcctgaatc agcgtaaatc ccacactgca gggaagacct cgcacgtaac      29280
tcacgttgtg cattgtcaaa gtgttacatt cgggcagcag cggatgatcc tccagtatgg      29340
tagcgcgggt ttctgtctca aaaggaggta gacgatccct actgtacgga gtgcgccgag      29400
acaaccgaga tcgtgttggt cgtagtgtca tgccaaatgg aacgccggac gtagtcatat      29460
ttcctgaagc aaaaccaggt gcgggcgtga caaacagatc tgcgtctccg gtctcgccgc      29520
ttagatcgct ctgtgtagta gttgtagtat atccactctc tcaaagcatc caggcgcccc      29580
ctggcttcgg gttctatgta aactccttca tgcgccgctg ccctgataac atccaccacc      29640
gcagaataag ccacacccag ccaacctaca cattcgttct gcgagtcaca cacgggagga      29700
gcgggaagag ctggaagaac catgtttttt tttttattcc aaaagattat ccaaaacctc      29760
aaaatgaaga tctattaagt gaacgcgctc ccctccggtg gcgtggtcaa actctacagc      29820
caaagaacag ataatggcat tgtaagatg ttgcacaatg gcttccaaaa ggcaaacggc      29880
cctcacgtcc aagtggacgt aaaggctaaa cccttcaggg tgaatctcct ctataaacat      29940
tccagcacct tcaccatgc ccaaataatt ctcatctcgc caccttctca atatatctct      30000
aagcaaatcc cgaatattaa gtccggccat tgtaaaaatc tgctccagag cgccctccac      30060
```

```
cttcagcctc aagcagcgaa tcatgattgc aaaaattcag gttcctcaca gacctgtata   30120
agattcaaaa gcggaacatt aacaaaaata ccgcgatccc gtaggtccct tcgcagggcc   30180
agctgaacat aatcgtgcag gtctgcacgg accagcgcgg ccacttcccc gccaggaacc   30240
atgacaaaag aacccacact gattatgaca cgcatactcg gagctatgct aaccagcgta   30300
gccccgatgt aagcttgttg catgggcggc gatataaaat gcaaggtgct gctcaaaaaa   30360
tcaggcaaag cctcgcgcaa aaagaaagc acatcgtagt catgctcatg cagataaagg    30420
caggtaagct ccggaaccac cacagaaaaa gacaccattt ttctctcaaa catgtctgcg   30480
ggtttctgca taaacacaaa ataaaataac aaaaaaacat ttaaacatta gaagcctgtc   30540
ttacaacagg aaaaacaacc cttataagca taagacggac tacgccatg ccggcgtgac    30600 cgtaaaaaaa ctggtcaccg tgattaaaaa gcaccaccga cagctcctcg gtcatgtccg   30660
gagtcataat gtaagactcg gtaaacacat caggttgatt cacatcggtc agtgctaaaa   30720
agcgaccgaa atagcccggg ggaatacata cccgcaggcg tagagacaac attacagccc   30780
ccataggagg tataacaaaa ttaataggag agaaaaacac ataaacacct gaaaaaccct   30840
cctgcctagg caaaatagca ccctcccgct ccagaacaac atacagcgct tccacagcgg   30900
cagccataac agtcagcctt accagtaaaa aagaaaacct attaaaaaaa caccactcga   30960
cacggcacca gctcaatcag tcacagtgta aaaaagggcc aagtgcagag cgagtatata   31020
taggactaaa aaatgacgta acggttaaag tccacaaaaa acacccagaa aaccgcacgc   31080
gaacctacgc ccagaaacga aagccaaaaa acccacaact tcctcaaatc gtcacttccg   31140
ttttcccacg ttacttctgt ggaatgtgtg tcagttaggg tgtggaaagt ccccaggctc   31200
cccagcaggc agaagtatgc aaagcatgca tctcaattag tcagcaacca ggtgtggaaa   31260
gtccccaggc tccccagcag gcagaagtat gcaaagcatg catctcaatt agtcagcaac   31320
catagtcccg cccctaactc cgcccatccc gcccctaact ccgcccagtt ccgcccattc   31380
tccgccccat ggctgactaa ttttttttat ttatgcagag gccgaggccg cctctgcctc   31440
tgagctattc cagaagtagt gaggaggctt ttttggaggc ctaggctttt gcaaacctcc   31500
gcggggatcc gcaccatggt gagcaagggc gaggaggata acatgccat catcaaggag   31560 ttcatgcgct tcaaggtgca catggagggc tccgtgaacg gccacgagtt cgagatcgag   31620
ggcgagggcg agggccgccc ctacgagggc acccagaccg ccaagctgaa ggtgaccaag   31680 ggtggcccc tgcccttcgc ctgggacatc ctgtcccctc agttcatgta cggctccaag   31740
gcctacgtga agcaccccgc cgacatcccc gactacttga agctgtcctt ccccgagggc   31800
ttcaagtggg agcgcgtgat gaacttcgag gacggcggcg tggtgaccgt gacccaggac   31860
tcctccctgc aggacggcga gttcatctac aaggtgaagc tgcgcggcac caacttcccc   31920
tccgacggcc ccgtaatgca gaagaagacc atgggctggg aggcctcctc cgagcggatg   31980 tacccccgagg acggcgccct gaagggcgag atcaagcaga ggctgaagct gaaggacggc   32040
ggccactacg acgctgaggt caagaccacc tacaaggcca agaagcccgt gcagctgccc   32100
ggcgcctaca acgtcaacat caagttggac atcacctccc acaacgagga ctacaccatc   32160
gtggaacagt acgaacgcgc cgagggccgc cactccaccg gcggcatgga cgagctgtac   32220
aagtagttcg aaatgaccga ccaagcgacg cccaacctgc catcacgaga tttcgattcc   32280
accgccgcct tctatgaaag gttgggcttc ggaatcgttt tccggacgc cggctggatg   32340 atcctccagc gcggggatct catgctggag ttcttcgccc accccaactt gtttattgca   32400
```

```
gcttataatg gttacaaata aagcaatagc atcacaaatt tcacaaataa agcatttttt    32460
tcactgcatt ctagttgtgg tttgtccaaa ctcatcaatg tatcttatca tgtctgtata    32520
ccgtcgacct ctagctagag gtcacttccc attttaagaa aactacaatt cccaacacat    32580
acaagttact ccgccctaaa acctacgtca cccgccccgt tcccacgccc cgcgccacgt    32640
cacaaactcc accccctcat tatcatattg gcttcaatcc aaaataaggt atattattga    32700
tgatgttaat taatttaaat ccgcatgcga tatcgagctc tcccgggaat tcggatctgc    32760
gacgcgaggc tggatggcct tccccattat gattcttctc gcgtttaagg gcaccaataa    32820
ctgccttaaa aaaattacgc cccgccctgc cactcatcgc agtactgttg taattcatta    32880
agcattctgc cgacatggaa gccatcacaa acggcatgat gaacctgaat cgccagcggc    32940
atcagcacct tgtcgccttg cgtataatat ttgcccatgg tgaaaacggg ggcgaagaag    33000
ttgtccatat tggccacgtt taaatcaaaa ctggtgaaac tcacccaggg attggctgag    33060
acgaaaaaca tattctcaat aaacccttta gggaaatagg ccaggttttc accgtaacac    33120
gccacatctt gcgaatatat gtgtagaaac tgccggaaat cgtcgtggta ttcactccag    33180
agcgatgaaa acgtttcagt ttgctcatgg aaaacggtgt aacaagggtg aacactatcc    33240 catatccacca gctcaccgtc tttcattgcc atacggaatt ccggatgagc attcatcagg    33300
cgggcaagaa tgtgaataaa ggccggataa aacttgtgct tatttttctt tacggtcttt    33360
aaaaaggccg taatatccag ctgaacggtc tggtttatagg tacattgagc aactgactga    33420
aatgcctcaa aatgttcttt acgatgccat gggatatat caacggtggt atatccagtg    33480 attttttttct ccattttagc ttccttagct cctgaaaatc tcgataactc aaaaaatacg    33540
cccggtagtg atcttatttc attatggtga agttggaac ctcttacgtg ccgatcaacg    33600
tctcattttc gccaaaagtt ggcccagggc ttccggtat caacagggac accaggattt    33660
atttattctg cgaagtgatc ttccgtcaca ggtatttatt cgcgataagc tcatggagcg    33720
gcgtaaccgt cgcacaggaa ggacagagaa agcgcggatc tgggaagtga cggacagaac    33780
ggtcaggacc tggattgggg aggcggttgc cgccgctgct gctgacggtg tgacgttctc    33840
tgttccggtc acaccacata cgttccgcca ttcctatgcg atgcacatgc tgtatgccgg    33900
tataccgctg aaagttctgc aaagcctgat gggacataag tccatcagtt caacggaagt    33960
ctacacgaag gttttttgcgc tggatgtggc tgcccggcac cgggtgcagt ttgcgatgcc    34020
ggagtctgat gcggttgcga tgctgaaaca attatcctga gaataaatgc cttggccttt    34080
atatggaaat gtggaactga gtggatatgc tgttttttgtc tgttaaacag agaagctggc    34140
tgttatccac tgagaagcga acgaaacagt cgggaaaatc tcccattatc gtagagatcc    34200
gcattattaa tctcaggagc ctgtgtagcg tttataggaa gtagtgttct gtcatgatgc    34260
ctgcaagcgg taacgaaaac gatttgaata tgccttcagg aacaatagaa atcttcgtgc    34320
ggtgttacgt tgaagtggag cggattatgt cagcaatgga cagaacaacc taatgaacac    34380
agaaccatga tgtggtctgt ccttttacag ccagtagtgc tcgccgcagt cgagcgacag    34440
ggcgaagccc tcgagtgagc gaggaagcac cagggaacag cacttatata ttctgcttac    34500
acacgatgcc tgaaaaaact tcccttgggg ttatccactt atccacgggg atattttat     34560 aattattttt tttatagttt ttagatcttc tttttagag cgccttgtag gcctttatcc    34620
atgctggttc tagagaaggt gttgtgcaaa attgcccttt cagtgtgaca aatcaccctc    34680
aaatgacagt cctgtctgtg acaaattgcc cttaaccctg tgacaaattg ccctcagaag    34740
aagctgtttt ttcacaaagt tatccctgct tattgactct tttttattta gtgtgacaat    34800
```

```
ctaaaaactt gtcacacttc acatggatct gtcatggcgg aaacagcggt tatcaatcac   34860
aagaaacgta aaaatagccc gcgaatcgtc cagtcaaacg acctcactga ggcggcatat   34920
agtctctccc gggatcaaaa acgtatgctg tatctgttcg ttgaccagat cagaaaatct   34980
gatggcaccc tacaggaaca tgacggtatc tgcgagatcc atgttgctaa atatgctgaa   35040
atattcggat tgacctctgc ggaagccagt aaggatatac ggcaggcatt gaagagtttc   35100
gcggggaagg aagtggtttt ttatcgccct gaagaggatg ccggcgatga aaaaggctat   35160
gaatcttttc cttggtttat caaacgtgcg cacagtccat ccagagggct ttacagtgta   35220
catatcaacc catatctcat tcccttcttt atcgggttac agaaccggtt tacgcagttt   35280
cggcttagtg aaacaaaaga aatcaccaat ccgtatgcca tgcgtttata cgaatccctg   35340
tgtcagtatc gtaagccgga tggctcaggc atcgtctctc tgaaaatcga ctggatcata   35400
gagcgttacc agctgcctca aagttaccag cgtatgcctg acttccgccg ccgcttcctg   35460
caggtctgtg ttaatgagat caacagcaga actccaatgc gcctctcata cattgagaaa   35520
aagaaaggcc gccagacgac tcatatcgta ttttccttcc gcgatatcac ttccatgacg   35580
acaggatagt ctgagggtta tctgtcacag atttgagggt ggttcgtcac atttgttctg   35640
acctactgag ggtaatttgt cacagttttg ctgtttcctt cagcctgcat ggattttctc   35700
atactttttg aactgtaatt tttaaggaag ccaaatttga gggcagtttg tcacagttga   35760
tttccttctc tttcccttcg tcatgtgacc tgatatcggg ggttagttcg tcatcattga   35820
tgagggttga ttatcacagt ttattactct gaattggcta tccgcgtgtg tacctctacc   35880
tggagttttt cccacggtgg atatttcttc ttgcgctgag cgtaagagct atctgacaga   35940
acagttcttc tttgcttcct cgccagttcg ctcgctatgc tcggttacac ggctgcggcg   36000
agcgctagtg ataataagtg actgaggtat gtgctcttct tatctccttt tgtagtgttg   36060
ctcttatttt aaacaactt tgcggttttt tgatgacttg cgattttgtt gttgctttgc   36120
agtaaattgc aagatttaat aaaaaaacgc aaagcaatga ttaaaggatg ttcagaatga   36180
aactcatgga aacacttaac cagtgcataa acgctggtca tgaaatgacg aaggctatcg   36240
ccattgcaca gtttaatgat gacagcccgg aagcgaggaa aataacccgg cgctggaaaa   36300
taggtgaagc agcggattta gttggggttt cttctcaggc tatcagagat gccgagaaag   36360
cagggcgact accgcacccg gatatggaaa ttcgaggacg ggttgagcaa cgtgttggtt   36420
atacaattga acaaattaat catatgcgtg atgtgtttgg tacgcgattg cgacgtgctg   36480
aagacgtatt tccaccggtg atcggggttg ctgcccataa aggtggcgtt tacaaaacct   36540
cagtttctgt tcatcttgct caggatctgg ctctgaaggg gctacgtgtt ttgctcgtgg   36600
aaggtaacga cccccaggga acagcctcaa tgtatcacgg atgggtacca gatcttcata   36660
ttcatgcaga agacactctc ctgcctttct atcttgggga aaaggacgat gtcacttatg   36720
caataaagcc cacttgctgg ccggggcttg acattattcc ttcctgtctg gctctgcacc   36780
gtattgaaac tgagttaatg ggcaaatttg atgaaggtaa actgcccacc gatccacacc   36840
tgatgctccg actggccatt gaaactgttc ctcatgacta tgatgtcata gttattgaca   36900
gcgcgcctaa cctgggtatc ggcacgatta atgtcgtatg tgctgctgat gtgctgattg   36960 ttccccacgcc tgctgagttg tttgactaca cctccgcact gcagttttc gatatgcttc   37020 gtgatctgct caagaacgtt gatcttaaag ggttcgagcc tgatgtacgt attttgctta   37080
ccaaatacag caatagtaat ggctctcagt ccccgtggat ggaggagcaa attcgggatg   37140
```

-continued

```
cctgggaag catggttcta aaaaatgttg tacgtgaaac ggatgaagtt ggtaaaggtc    37200
agatccggat gagaactgtt tttgaacagg ccattgatca acgctcttca actggtgcct    37260
ggagaaatgc tctttctatt tgggaacctg tctgcaatga aattttcgat cgtctgatta    37320
aaccacgctg ggagattaga taatgaagcg tgcgcctgtt attccaaaac atacgctcaa    37380
tactcaaccg gttgaagata cttcgttatc gacaccagct gccccgatgg tggattcgtt    37440
aattgcgcgc gtaggagtaa tggctcgcgg taatgccatt actttgcctg tatgtggtcg    37500
ggatgtgaag tttactcttg aagtgctccg gggtgatagt gttgagaaga cctctcgggt    37560
atggtcaggt aatgaacgtg accaggagct gcttactgag gacgcactgg atgatctcat    37620
cccttctttt ctactgactg gtcaacagac accggcgttc ggtcgaagag tatctggtgt    37680
catagaaatt gccgatggga gtcgccgtcg taaagctgct gcacttaccg aaagtgatta    37740
tcgtgttctg gttggcgagc tggatgatga gcagatggc gcattatcca gattgggtaa     37800
cgattatcgc ccaacaagtg cttatgaacg tggtcagcgt tatgcaagcc gattgcagaa    37860
tgaatttgct ggaaatattt ctgcgctggc tgatgcggaa aatatttcac gtaagattat    37920
tacccgctgt atcaacaccg ccaaattgcc taaatcagtt gttgctcttt tttctcaccc    37980
cggtgaacta tctgcccggt caggtgatgc acttcaaaaa gcctttacag ataaagagga    38040
attacttaag cagcaggcat ctaaccttca tgagcagaaa aaagctgggg tgatatttga    38100
agctgaagaa gttatcactc tttttaacttc tgtgcttaaa acgtcatctg catcaagaac    38160
tagtttaagc tcacgacatc agtttgctcc tggagcgaca gtattgtata agggcgataa    38220
aatggtgctt aacctggaca ggtctcgtgt tccaactgag tgtatagaga aaattgaggc    38280
cattcttaag gaacttgaaa agccagcacc ctgatgcgac cacgttttag tctacgttta    38340
tctgtcttta cttaatgtcc tttgttacag gccagaaagc ataactggcc tgaatattct    38400
ctctgggccc actgttccac ttgtatcgtc ggtctgataa tcagactggg accacggtcc    38460
cactcgtatc gtcggtctga ttattagtct gggaccacgg tcccactcgt atcgtcggtc    38520
tgattattag tctgggacca cggtcccact cgtatcgtcg gtctgataat cagactggga    38580
ccacggtccc actcgtatcg tcggtctgat tattagtctg gaccatggt cccactcgta     38640 tcgtcggtct gattattagt ctgggaccac ggtcccactc gtatcgtcgg tctgattatt    38700
agtctggaac cacggtccca ctcgtatcgt cggtctgatt attagtctgg gaccacggtc    38760
ccactcgtat cgtcggtctg attattagtc tgggaccacg atcccactcg tgttgtcggt    38820
ctgattatcg gtctgggacc acggtcccac ttgtattgtc gatcagacta tcagcgtgag    38880
actacgattc catcaatgcc tgtcaagggc aagtattgac atgtcgtcgt aacctgtaga    38940
acggagtaac ctcggtgtgc ggttgtatgc ctgctgtgga ttgctgctgt gtcctgctta    39000
tccacaacat tttgcgcacg gttatgtgga caaaatacct ggttacccag gccgtgccgg    39060
cacgttaacc gggcacattt ccccgaaaag tgccacctga cgtctaagaa accattatta    39120
tcatgacatt aacctataaa aataggcgta tcacgaggcc ctttcgtctt caagaattgg    39180
atccgaattc ccgggagagc tcgatatcgc atgcggattt aaattaatta a             39231
```

<210> SEQ ID NO 99
<211> LENGTH: 39266
<212> TYPE: DNA
<213> ORGANISM: Artificial Sequence
<220> FEATURE:
<223> OTHER INFORMATION: Vector

<400> SEQUENCE: 99

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tagaagccat agagcccacc     360
gcatccccag catgcctgct agaattcgaa caaacgaccc aacacccgtg cgttttattc     420
tgtcttttta ttgccggcgg ccgcgaacaa atgtggtatg gctgattatg atcctctaga     480
gataattcta gttacccggg gagcatgtca aggtccaaat cgtcaagagc gtcagcaggc     540
agcatatcaa ggtcaaagtc gtcaagggca tcggctggga gcatgtctaa gtcaaaatcg     600
tcaagggcgt cggccggccc gccgctttcg cactttagct gtttctccag gccacatatg     660
attagttcca ggccgaaaag gaaggcaggt tcggctccct gatggtcgaa cagctcaatt     720
gcttgtctca gaagtggggg catagaatcg gtggtaggtg tctctctttc ctcttttgct     780
acttgatgct cctgatcctc caatacgcag cccagtgtaa agtggcccac ggcggacaga     840
gcgtacagtg cgttctccag ggagaagcct tgctgacaca ggaacgcgag ctgatttcc      900
agggtttcgt actgtttctc tgttgggcgg gtgccgagat gcactttagc cccgtcgcga     960
tgtgagagga gagcacagcg gaatgacttg gcgttgttcc gcagaaagtc ttgccatgac    1020
tcgccttcca gggggcagaa gtgggtatga tgcctgtcca gcatctcgat tgccagggca    1080
tcgagcaggg cccgcttgtt cttcacgtgc cagtacaggg tcttctgcgc agctcccagc    1140
ttttgagcga gtttccttgt cgtcaggcct tcgataccga cttcattgag taattccaga    1200
gcagagttta tgactttgct cttgtccagt ctagacatag gacgcgtcag ctgactagag    1260
gatccccgcg gagggtacc aagcttaagt ttaaacgcta gccagcttgg gtctccctat    1320
agtgagtcgt attaatttcg ataagccagt aagcagtggg ttctctagtt agccagagag    1380
ctctgcttat atagacctcc caccgtacac gcctaccgcc catttgcgtc aatggggcgg    1440
agttgttacg acattttgga aagtcccgtt gatttggtg ccaaaacaaa ctcccattga    1500
cgtcaatggg gtggagactt ggaaatcccc gtgagtcaaa ccgctatcca cgcccattga    1560
tgtactgcca aaaccgcatc accatggtaa tagcgatgac taatacgtag atgtactgcc    1620
aagtaggaaa gtcccataag gtcatgtact gggcataatg ccaggcgggc catttaccgt    1680
cattgacgtc aataggggc gtacttggca tatgatacac ttgatgtact gccaagtggg    1740
cagtttaccg taaatactcc acccattgac gtcaatggaa agtccctatt ggcgttacta    1800
tgggaacata cgtcattatt gacgtcaatg ggcggggtc gttgggcggt cagccaggcg    1860
ggccatttac cgtaagttat gtaacgcgga actccatata tgggctatga actaatgacc    1920
ccgtaattga ttactattaa taactagtca ataatcaatg tcaacgcgta tatctgtggg    1980
cgtggcttaa gggtgggaaa gaatatataa ggtgggggtc ttatgtagtt ttgtatctgt    2040
tttgcagcag ccgccgccgc catgagcacc aactcgtttg atggaagcat tgtgagctca    2100
tatttgacaa cgcgcatgcc cccatgggcc ggggtgcgtc agaatgtgat gggctccagc    2160
attgatggtc gccccgtcct gcccgcaaac tctactacct tgacctacga gaccgtgtct    2220
ggaacgccgt tggagactgc agcctccgcc gccgcttcag ccgctgcagc caccgccgc    2280
gggattgtga ctgactttgc tttcctgagc ccgcttgcaa gcagtgcagc ttcccgttca    2340
```

```
tccgcccgcg atgacaagtt gacggctctt ttggcacaat tggattcttt gacccgggaa    2400
cttaatgtcg tttctcagca gctgttggat ctgcgccagc aggtttctgc cctgaaggct    2460
tcctcccctc ccaatgcggt ttaaaacata aataaaaaac cagactctgt ttggatttgg    2520
atcaagcaag tgtcttgctg tctttattta ggggttttgc gcgcgcggta ggcccgggac    2580
cagcggtctc ggtcgttgag ggtcctgtgt atttttcca ggacgtggta aaggtgactc     2640
tggatgttca gatacatggg cataagcccg tctctggggt ggaggtagca ccactgcaga    2700
gcttcatgct gcggggtggt gttgtagatg atccagtcgt agcaggagcg ctgggcgtgg    2760
tgcctaaaaa tgtctttcag tagcaagctg attgccaggg gcaggccctt ggtgtaagtg    2820
tttacaaagc ggttaagctg ggatgggtgc atacgtgggg atatgagatg catcttggac    2880 tgtatttta ggttggctat gttcccagcc atatccctcc ggggattcat gttgtgcaga     2940
accaccagca cagtgtatcc ggtgcacttg ggaaatttgt catgtagctt agaaggaaat    3000
gcgtggaaga acttggagac gcccttgtga cctccaagat tttccatgca ttcgtccata    3060
atgatggcaa tgggcccacg ggcggcggcc tgggcgaaga tatttctggg atcactaacg    3120
tcatagttgt gttccaggat gagatcgtca taggccattt ttacaaagcg cgggcggagg    3180
gtgccagact gcggtataat ggttccatcc ggcccagggg cgtagttacc ctcacagatt    3240
tgcatttccc acgctttgag ttcagatggg gggatcatgt ctacctgcgg ggcgatgaag    3300
aaaacggttt ccggggtagg ggagatcagc tgggaagaaa gcaggttcct gagcagctgc    3360
gacttaccgc agccggtggg cccgtaaatc acacctatta ccggctgcaa ctggtagtta    3420
agagagctgc agctgccgtc atccctgagc agggggggcca cttcgttaag catgtccctg    3480
actcgcatgt tttccctgac caaatccgcc agaaggcgct cgccgcccag cgatagcagt    3540
tcttgcaagg aagcaaagtt tttcaacggt ttgagaccgt ccgccgtagg catgcttttg    3600
agcgtttgac caagcagttc caggcggtcc cacagctcgg tcacctgctc tacggcatct    3660
cgatccagca tatctcctcg tttgcgggt tggggcggct ttcgctgtac ggcagtagtc      3720
ggtgctcgtc cagacgggcc aggtcatgt cttttccacgg gcgcagggtc ctcgtcagcg     3780
tagtctgggt cacggtgaag gggtgcgctc cgggctgcgc gctggccagg gtgcgcttga    3840
ggctggtcct gctggtgctg aagcgctgcc ggtcttcgcc ctgcgcgtcg gccaggtagc    3900
atttgaccat ggtgtcatag tccagcccct ccgcggcgtg gcccttggcg cgcagcttgc    3960
ccttggagga ggcgccgcac gagggggcagt gcagacttttt gagggcgtag agcttgggcg    4020
cgagaaatac cgattccggg gagtaggcat ccgcgccgca ggccccgcag acggtctcgc    4080
attccacgag ccaggtgagc tctggccgtt cggggtcaaa aaccaggttt ccccccatgct    4140 ttttgatgcg tttcttacct ctggtttcca tgagccggtg tccacgctcg gtgacgaaaa    4200
ggctgtccgt gtccccgtat acagacttga gaggcctgtc ctcgagcggt gttccgcggt    4260
cctcctcgta tagaaactcg gaccactctg agacaaaggc tcgcgtccag gccagcacga    4320
aggaggctaa gtgggagggg tagcggtcgt tgtccactag ggggtccact cgctccaggg    4380
tgtgaagaca catgtcgccc tcttcggcat caaggaaggt gattggtttg taggtgtagg    4440
ccacgtgacc gggtgttcct gaaggggggc tataaaaggg ggtgggggcg cgttcgtcct    4500
cactctcttc cgcatcgctg tctgcgaggg ccagctgttg gggtgagtac tccctctgaa    4560
aagcgggcat gacttctgcg ctaagattgt cagtttccaa aaacgaggag gatttgatat    4620
tcacctggcc cgcggtgatg cctttgaggg tggccgcatc catctggtca gaaaagacaa    4680
tctttttgtt gtcaagcttg gtggcaaacg accccgtagag ggcgttggac agcaacttgg    4740
```

```
cgatggagcg cagggtttgg tttttgtcgc gatcggcgcg ctccttggcc gcgatgttta    4800
gctgcacgta ttcgcgcgca acgcaccgcc attcgggaaa gacggtggtg cgctcgtcgg    4860
gcaccaggtg cacgcgccaa ccgcggttgt gcagggtgac aaggtcaacg ctggtggcta    4920
cctctccgcg taggcgctcg ttggtccagc agaggcggcc gcccttgcgc gagcagaatg    4980
gcggtagggg gtctagctgc gtctcgtccg ggggtctgc gtccacggta aagaccccgg    5040
gcagcaggcg cgcgtcgaag tagtctatct tgcatccttg caagtctagc gcctgctgcc    5100
atgcgcgggc ggcaagcgcg cgctcgtatg ggttgagtgg gggacccat ggcatggggt    5160
gggtgagcgc ggaggcgtac atgccgcaaa tgtcgtaaac gtagaggggc tctctgagta    5220
ttccaagata tgtagggtag catcttccac cgcggatgct ggcgcgcacg taatcgtata    5280
gttcgtgcga gggagcgagg aggtcgggac cgaggttgct acgggcgggc tgctctgctc    5340
ggaagactat ctgcctgaag atggcatgtg agttggatga tatggttgga cgctggaaga    5400
cgttgaagct ggcgtctgtg agacctaccg cgtcacgcac gaaggaggcg taggagtcgc    5460
gcagcttgtt gaccagctcg gcggtgacct gcacgtctag ggcgcagtag tccagggttt    5520
ccttgatgat gtcatactta tcctgtccct ttttttccca cagctcgcgg ttgaggacaa    5580
actcttcgcg gtcttcccag tactcttgga tcggaaaccc gtcggcctcc gaacggtaag    5640
agcctagcat gtagaactgg ttgacggcct ggtaggcgca gcatcccttt tctacgggta    5700
gcgcgtatgc ctgcgcggcc ttccggagcg aggtgtgggt gagcgcaaag gtgtccctga    5760
ccatgaccag catgaagggc acgagctgct tcccaaaggc ccccatccaa gtataggtct    5820
ctacatcgta ggtgacaaag agacgctcgg tgcgaggatg cgagccgatc gggaagaact    5880
ggatctcccg ccaccaattg gaggagtggc tattgatgtg gtgaaagtag aagtccctgc    5940
gacgggccga acactcgtgc tggcttttgt aaaaacgtgc gcagtactgg cagcggtgca    6000
cgggctgtac atcctgcacg aggttgacct gacgaccgcg cacaaggaag cagagtggga    6060
atttgagccc ctcgcctggc gggtttggct ggtggtcttc tacttcggct gcttgtcctt    6120
gaccgtctgg ctgctcgagg ggagttacgg tggatcggac caccacgccg cgcgagccca    6180
aagtccagat gtccgcgcgc ggcggtcgga gcttgatgac aacatcgcgc agatgggagc    6240
tgtccatggt ctggagctcc cgcggcgtca ggtcaggcgg gagctcctgc aggtttacct    6300
cgcatagacg ggtcagggcg cgggctagat ccaggtgata cctaatttcc aggggctggt    6360
tggtggcggc gtcgatggct tgcaagaggc cgcatccccg cggcgcgact acggtaccgc    6420
gcggcgggcg gtgggccgcg ggggtgtcct tggatgatga atctaaaagc ggtgacgcgg    6480
gcgagccccc ggaggtaggg ggggctccgg acccgccggg agaggggca ggggcacgtc    6540
ggcgccgcgc gcgggcagga gctggtgctg cgcgcgtagg ttgctggcga acgcgacgac    6600
gcggcggttg atctcctgaa tctggcgcct ctgcgtgaag acgacgggcc cggtgagctt    6660
gaacctgaaa gagagttcga cagaatcaat ttcggtgtcg ttgacggcgg cctgcgcaa    6720
aatctcctgc acgtctcctg agttgtcttg ataggcgatc tcggccatga actgctcgat    6780
ctcttcctcc tggagatctc cgcgtccggc tcgctccacg gtggcggcga gtcgttgga    6840
aatgcgggcc atgagctgcg agaaggcgtt gaggcctccc tcgttccaga gcggctgta    6900
gaccacgccc ccttcggcat cgcgggcgcg catgaccacc tgcgcgagat tgagctccac    6960
gtgccgggca aagacggcgt agtttcgcag gcgctgaaag aggtagttga gggtggtggc    7020
ggtgtgttct gccacgaaga agtacataac ccagcgtcgc aacgtggatt cgttgatatc    7080
```

-continued

```
ccccaaggcc tcaaggcgct ccatggcctc gtagaagtcc acggcgaagt tgaaaaactg    7140
ggagttgcgc gccgacacgg ttaactcctc ctccagaaga cggatgagct cggcgacagt    7200
gtcgcgcacc tcgcgctcaa aggctacagg ggcctcttct tcttcttcaa tctcctcttc    7260
cataagggcc tccccttctt cttcttctgg cggcggtggg ggaggggga cacgcggcg     7320 acgacggcgc accgggaggc ggtcgacaaa gcgctcgatc atctcccgc ggcgacggcg    7380 catggtctcg gtgacggcgc ggccgttctc gcggggggcg agttggaaga cgccgcccgt   7440
catgtcccgg ttatgggttg gcggggggct gccatgcggc agggatacgg cgctaacgat   7500
gcatctcaac aattgttgtg taggtactcc gccgccgagg gacctgagcg agtccgcatc   7560
gaccggatcg gaaaacctct cgagaaaggc gtctaaccag tcacagtcgc aaggtaggct   7620
gagcaccgtg gcgggcggca gcgggcgcg gtcggggttg tttctggcgg aggtgctgct    7680
gatgatgtaa ttaaagtagg cggtcttgag acggcggatg gtcgacagaa gcaccatgtc   7740
cttgggtccg gcctgctgaa tgcgcaggcg gtcggccatg ccccaggctt cgttttgaca   7800
tcggcgcagg tctttgtagt agtcttgcat gagcctttct accggcactt cttcttctcc   7860
ttcctcttgt cctgcatctc ttgcatctat cgctgcggcg gcggcggagt ttggccgtag   7920
gtggcgccct cttcctccca tgcgtgtgac cccgaagccc ctcatcggct gaagcagggc   7980
taggtcggcg acaacgcgct cggctaatat ggcctgctgc acctgcgtga gggtagactg   8040
gaagtcatcc atgtccacaa agcggtggta tgcgcccgtg ttgatggtgt aagtgcagtt   8100
ggccataacg gaccagttaa cggtctggtg accggctgc gagagctcgg tgtacctgag     8160
acgcgagtaa gccctcgagt caaatacgta gtcgttgcaa gtccgcacca ggtactggta   8220
tcccaccaaa aagtgcggcg gcggctggcg gtagagggc cagcgtaggg tggccggggc     8280 tccggggcg agatcttcca acataaggcg atgatatccg tagatgtacc tggacatcca    8340
ggtgatgccg gcggcggtgg tggaggcgcg cggaaagtcg cggacgcggt tccagatgtt   8400
gcgcagcgga aaaagtgct ccatggtcgg gacgctctgg ccggtcaggc gcgcgcaatc     8460
gttgacgctc tagaccgtgc aaaaggagag cctgtaagcg ggcactcttc cgtggtctgg   8520
tggataaatt cgcaagggta tcatggcgga cgaccggggt tcgagccccg tatccggccg   8580
tccgccgtga tccatgcggt taccgcccgc gtgtcgaacc caggtgtgcg acgtcagaca   8640 acggggagt gctccttttg gcttccttcc aggcgcggcg gctgctgcgc tagcttttt     8700 ggccactggc cgcgcgcagc gtaagcggtt aggctggaaa gcgaaagcat taagtggctc    8760 gctcctgta gccggagggt tattttccaa gggttgagtc gcgggacccc cggttcgagt    8820
ctcggaccgg ccggactgcg gcgaacgggg gtttgcctcc ccgtcatgca agaccccgct   8880
tgcaaattcc tccggaaaca gggacgagcc ccttttttgc ttttcccaga tgcatccggt   8940
gctgcggcag atgcgcccc ctcctcagca gcggcaagag caagagcagc ggcagacatg     9000
cagggcaccc tcccctcctc ctaccgcgtc aggagggcg acatccgcgg ttgacgcggc    9060
agcagatggt gattacgaac ccccgcgcg ccgggcccgg cactacctgg acttggagga     9120
gggcgagggc ctggcgcggc taggagcgcc ctctcctgag cggcacccaa gggtgcagct   9180
gaagcgtgat acgcgtgagg cgtacgtgcc gcggcagaac ctgtttcgcg accgcgaggg   9240
agaggagccc gaggagatgc gggatcgaaa gttccacgca gggcgcgagc tgcggcatgg   9300
cctgaatcgc gagcggttgc tgcgcgagga ggactttgag cccgacgcgc gaaccgggat   9360
tagtcccgcg cgcgcacacg tggcggccgc cgacctggta accgcatacg agcagacggt   9420
gaaccaggag attaactttc aaaaaagctt taacaaccac gtgcgtacgc ttgtggcgcg   9480
```

```
cgaggaggtg gctataggac tgatgcatct gtgggacttt gtaagcgcgc tggagcaaaa    9540
cccaaatagc aagccgctca tggcgcagct gttccttata gtgcagcaca gcagggacaa    9600
cgaggcattc agggatgcgc tgctaaacat agtagagccc gagggccgct ggctgctcga    9660
tttgataaac atcctgcaga gcatagtggt gcaggagcgc agcttgagcc tggctgacaa    9720
ggtggccgcc atcaactatt ccatgcttag cctgggcaag ttttacgccc gcaagatata    9780 ccataccect tacgttccca tagacaagga ggtaaagatc gaggggttct acatgcgcat    9840
ggcgctgaag gtgcttacct tgagcgacga cctgggcgtt tatcgcaacg agcgcatcca    9900
caaggccgtg agcgtgagcc ggcggcgcga gctcagcgac cgcgagctga tgcacagcct    9960
gcaaagggcc ctggctggca cgggcagcgg cgatagagag gccgagtcct actttgacgc   10020
gggcgctgac ctgcgctggg ccccaagccg acgcgccctg gaggcagctg gggccggacc   10080
tgggctggcg gtggcacccg cgcgcgctgg caacgtcggc ggcgtggagg aatatgacga   10140
ggacgatgag tacgagccag aggacggcga gtactaagcg gtgatgtttc tgatcagatg   10200
atgcaagacg caacggaccc ggcggtgcgg gcggcgctgc agagccagcc gtccggcctt   10260
aactccacgg acgactggcg ccaggtcatg gaccgcatca tgtcgctgac tgcgcgcaat   10320
cctgacgcgt tccggcagca gccgcaggcc aaccggctct ccgcaattct ggaagcggtg   10380
gtcccggcgc gcgcaaaccc cacgcacgag aaggtgctgg cgatcgtaaa cgcgctggcc   10440
gaaaacaggg ccatccggcc cgacgaggcc ggcctggtct acgacgcgct gcttcagcgc   10500
gtggctcgtt acaacagcgg caacgtgcag accaacctgg accggctggt gggggatgtg   10560
cgcgaggccg tggcgcagcg tgagcgcgcg cagcagcagg gcaacctggg ctccatggtt   10620
gcactaaacg ccttcctgag tacacagccc gccaacgtgc cgcggggaca ggaggactac   10680
accaactttg tgagcgcact gcggctaatg gtgactgaga caccgcaaag tgaggtgtac   10740
cagtctgggc cagactattt tttccagacc agtagacaag gcctgcagac cgtaaacctg   10800
agccaggctt tcaaaaactt gcaggggctg tgggggtgc gggctccac aggcgaccgc   10860 gcgaccgtgt ctagcttgct gacgcccaac tcgcgcctgt tgctgctgct aatagcgccc   10920
ttcacggaca gtggcagcgt gtcccgggac acatacctag gtcacttgct gacactgtac   10980
cgcgaggcca taggtcaggc gcatgtggac gagcatactt tccaggagat tacaagtgtc   11040
agccgcgcgc tggggcagga ggacacgggc agcctggagg caaccctaaa ctacctgctg   11100
accaaccggc ggcagaagat cccctcgttg cacagtttaa acagcgagga ggagcgcatt   11160
ttgcgctacg tgcagcagag cgtgagcctt aacctgatgc gcgacggggt aacgcccagc   11220
gtggcgctgg acatgaccgc gcgcaacatg gaacgggca tgtatgcctc aaaccggccg   11280
tttatcaacc gcctaatgga ctacttgcat cgcgcggccg ccgtgaaccc cgagtatttc   11340
accaatgcca tcttgaaccc gcactggcta ccgccccctg gtttctacac cggggggattc   11400 gaggtgcccg agggtaacga tggattcctc tgggacgaca tagacgacag cgtgttttcc   11460
ccgcaaccgc agaccctgct agagttgcaa cagcgcgagc aggcagaggc ggcgctgcga   11520
aaggaaagct tccgcaggcc aagcagcttg tccgatctag gcgctgcggc cccgcggtca   11580
gatgctagta gcccatttcc aagcttgata gggtctctta ccagcactcg cacccaccgc   11640
ccgcgcctgc tgggcgagga ggagtaccta aacaactcgc tgctgcagcc gcagcgcgaa   11700
aaaaacctgc ctccggcatt tcccaacaac gggatagaga gcctagtgga caagatgagt   11760
agatggaaga cgtacgcgca ggagcacagg gacgtgccag gcccgcgccc gcccaccgt   11820
```

```
cgtcaaaggc acgaccgtca gcggggtctg gtgtgggagg acgatgactc ggcagacgac   11880
agcagcgtcc tggatttggg agggagtggc aacccgtttg cgcaccttcg ccccaggctg   11940
gggagaatgt tttaaaaaaa aaaaaagcat gatgcaaaat aaaaaactca ccaaggccat   12000
ggcaccgagc gttggttttc ttgtattccc cttagtatgc ggcgcgcggc gatgtatgag   12060
gaaggtcctc ctccctccta cgagagtgtg gtgagcgcgg cgccagtggc ggcggcgctg   12120
ggttctccct tcgatgctcc cctgacccg ccgtttgtgc ctccgcggta cctgcggcct   12180
accgggggga gaaacagcat ccgttactct gagttggcac ccctattcga caccacccgt   12240
gtgtacctgg tggacaacaa gtcaacggat gtggcatccc tgaactacca gaacgaccac   12300
agcaactttc tgaccacggt cattcaaaac aatgactaca gcccggggga ggcaagcaca   12360
cagaccatca atcttgacga ccggtcgcac tggggcggcg acctgaaaac catcctgcat   12420
accaacatgc caaatgtgaa cgagttcatg tttaccaata agtttaaggc gcgggtgatg   12480
gtgtcgcgct tgcctactaa ggacaatcag gtggagctga atacgagtg ggtggagttc   12540 acgctgcccg agggcaacta ctccgagacc atgaccatag accttatgaa caacgcgatc   12600
gtggagcact acttgaaagt gggcagacag aacggggttc tggaaagcga catcggggta   12660
aagtttgaca cccgcaactt cagactgggg tttgaccccg tcactggtct tgtcatgcct   12720
ggggtatata caaacgaagc cttccatcca gacatcattt tgctgccagg atgcggggtg   12780
gacttcaccc cagccgcct gagcaacttg ttgggcatcc gcaagcggca acccttccag   12840
gagggcttta ggatcaccta cgatgatctg gagggtggta acattccgc actgttggat   12900 gtggacgcct accaggcgag cttgaaagat gacaccgaac agggcggggg tggcgcaggc   12960
ggcagcaaca gcagtggcag cggcgcggaa gagaactcca acgcggcagc cgcggcaatg   13020
cagccggtgg aggacatgaa cgatcatgcc attcgcggcg acacctttgc cacacgggct   13080
gaggagaagc gcgctgaggc cgaagcagcg gccgaagctg ccgcccccgc tgcgcaaccc   13140
gaggtcgaga agcctcagaa gaaaccggtg atcaaaccc tgacagagga cagcaagaaa   13200
cgcagttaca acctaataag caatgacagc accttcaccc agtaccgcag ctggtacctt   13260
gcatacaact acgcgacccc tcagaccgga atccgctcat ggaccctgct ttgcactcct   13320
gacgtaacct gcggctcgga gcaggtctac tggtcgttgc cagacatgat gcaagacccc   13380
gtgaccttcc gctccacgcg ccagatcagc aactttccgg tggtgggcgc cgagctgttg   13440
cccgtgcact ccaagagctt ctacaacgac caggccgtct actcccaact catccgccag   13500
tttacctctc tgacccacgt gttcaatcgc tttcccgaga accagatttt ggcgcgcccg   13560
ccagccccca ccatcaccac cgtcagtgaa aacgttcctg ctctcacaga tcacgggacg   13620
ctaccgctgc gcaacagcat cggaggagtc cagcgagtga ccattactga cgccagacgc   13680
cgcacctgcc cctacgttta caaggccctg ggcatagtct cgccgcgcgt cctatcgagc   13740
cgcacttttt gagcaagcat gtccatcctt atatcgccca gcaataacac aggctggggc   13800
ctgcgcttcc caagcaagat gtttggcggg gccaagaagc gctccgacca acacccagtg   13860
cgcgtgcgcg ggcactaccg cgcgccctgg ggcgcgcaca aacgcggccg cactgggcgc   13920
accaccgtcg atgacgccat cgacgcggtg gtggaggagg cgcgcaacta cacgcccacg   13980
ccgccaccag tgtccacagt ggacgcggcc attcagaccg tggtgcgcgg agcccggcgc   14040
tatgctaaaa tgaagagacg gcggaggcgc gtagcacgtc gccaccgccg ccgacccggc   14100
actgccgccc aacgcgcggc ggcggccctg cttaaccgcg cacgtcgcac cggccgacgg   14160
gcggccatgc gggccgctcg aaggctggcc gcgggtattg tcactgtgcc ccccaggtcc   14220
```

```
aggcgacgag cggccgccgc agcagccgcg gccattagtg ctatgactca gggtcgcagg   14280
ggcaacgtgt attgggtgcg cgactcggtt agcggcctgc gcgtgcccgt gcgcacccgc   14340
cccccgcgca actagattgc aagaaaaaac tacttagact cgtactgttg tatgtatcca   14400
gcggcggcgg cgcgcaacga agctatgtcc aagcgcaaaa tcaaagaaga gatgctccag   14460
gtcatcgcgc cggagatcta tggccccccg aagaaggaag agcaggatta caagccccga   14520
aagctaaagc gggtcaaaaa gaaaagaaa gatgatgatg atgaacttga cgacgaggtg   14580
gaactgctgc acgctaccgc gcccaggcga cgggtacagt ggaaaggtcg acgcgtaaaa   14640
cgtgttttgc gacccggcac caccgtagtc tttacgcccg tgagcgctc cacccgcacc   14700 tacaagcgcg tgtatgatga ggtgtacggc gacgaggacc tgcttgagca ggccaacgag   14760
cgcctcgggg agtttgccta cggaaagcgg cataaggaca tgctggcgtt gccgctggac   14820
gagggcaacc caacacctag cctaaagccc gtaacactgc agcaggtgct gcccgcgctt   14880
gcaccgtccg aagaaaagcg cggcctaaag cgcgagtctg tgacttggc acccaccgtg   14940 cagctgatgg tacccaagcg ccagcgactg gaagatgtct tggaaaaaat gaccgtggaa   15000
cctgggctgg agcccgaggt ccgcgtgcgg ccaatcaagc aggtggcgcc gggactgggc   15060
gtgcagaccg tggacgttca gatacccact accagtagca ccagtattgc caccgccaca   15120
gagggcatga agacacaaac gtccccggtt gcctcagcgg tggcggatgc cgcggtgcag   15180
gcggtcgctg cggccgcgtc caagacctct acggaggtgc aaacggaccc gtggatgttt   15240
cgcgtttcag ccccccggcg cccgcgccgt tcgaggaagt acggcgccgc cagcgcgcta   15300
ctgcccgaat atgccctaca tccttccatt gcgcctaccc ccggctatcg tggctacacc   15360
taccgcccca aagacgagc aactaccga cgccgaacca ccactggaac ccgccgccgc   15420
cgtcgccgtc gccagcccgt gctggcccg atttccgtgc gcagggtggc tcgcgaagga   15480
ggcaggaccc tggtgctgcc aacagcgcgc taccaccca gcatcgttta aaagccggtc   15540
tttgtggttc ttgcagatat ggccctcacc tgccgcctcc gtttcccggt gccgggattc   15600
cgaggaagaa tgcaccgtag gaggggcatg gccggccacg gcctgacggg cggcatgcgt   15660
cgtgcgcacc accggcggcg gcgcgcgtcg caccgtcgca tgcgcggcgg tatcctgccc   15720
ctccttattc cactgatcgc cgcggcgatt ggcgccgtgc ccggaattgc atccgtggcc   15780
ttgcaggcgc agagacactg attaaaaaca agttgcatgt ggaaaaatca aataaaaag   15840 tctggactct cacgctcgct tggtcctgta actattttgt agaatggaag acatcaactt   15900
tgcgtctctg gccccgcgac acggctcgcg cccgttcatg ggaaactggc aagatatcgg   15960
caccagcaat atgagcggtg gcgccttcag ctggggctcg ctgtggagcg gcattaaaaa   16020
tttcggttcc accgttaaga actatggcag caaggcctgg aacagcagca caggccagat   16080
gctgagggat aagttgaaag agcaaaattt ccaacaaaag gtggtagatg gcctggcctc   16140
tggcattagc ggggtggtgg acctggccaa ccagcagtg caaaataaga ttaacagtaa   16200
gcttgatccc cgccctcccg tagaggagcc tccaccggcc gtggagacag tgtctccaga   16260
ggggcgtggc gaaaagcgtc cgcgccccga cagggaagaa actctggtga cgcaaataga   16320
cgagcctccc tcgtacgagg aggcactaaa gcaaggcctg cccaccaccc gtcccatcgc   16380
gcccatggct accggagtgc tgggccagca cacaccgta acgctggacc tgcctcccc   16440 cgccgacacc cagcagaaac ctgtgctgcc aggcccgacc gccgttgttg taacccgtcc   16500
tagccgcgcg tccctgcgcc gcgccgccag cggtccgcga tcgttgcggc ccgtagccag   16560
```

```
tggcaactgg caaagcacac tgaacagcat cgtgggtctg ggggtgcaat ccctgaagcg    16620
ccgacgatgc ttctgatagc taacgtgtcg tatgtgtgtc atgtatgcgt ccatgtcgcc    16680
gccagaggag ctgctgagcc gccgcgcgcc cgctttccaa gatggctacc ccttcgatga    16740
tgccgcagtg gtcttacatg cacatctcgg gccaggacgc ctcggagtac ctgagccccg    16800
ggctggtgca gtttgcccgc gccaccgaga cgtacttcag cctgaataac aagtttagaa    16860
accccacggt ggcgcctacg cacgacgtga ccacagaccg gtcccagcgt ttgacgctgc    16920
ggttcatccc tgtggaccgt gaggatactg cgtactcgta caaggcgcgg ttcaccctag    16980
ctgtgggtga taaccgtgtg ctggacatgg cttccacgta ctttgacatc cgcggcgtgc    17040
tggacagggg ccctactttt aagccctact ctggcactgc ctacaacgcc ctggctccca    17100
agggtgcccc aaatccttgc gaatgggatg aagctgctac tgctcttgaa ataaacctag    17160
aagaagagga cgatgacaac gaagacgaag tagacgagca agctgagcag caaaaaactc    17220
acgtatttgg gcaggcgcct tattctggta taaatattac aaaggagggt attcaaatag    17280
gtgtcgaagg tcaaacacct aaatatgccg ataaaacatt tcaacctgaa cctcaaatag    17340
gagaatctca gtggtacgaa acagaaatta atcatgcagc tgggagagtc ctaaaaaaga    17400
ctaccccaat gaaaccatgt tacgttcat atgcaaaacc cacaaatgaa aatggagggc    17460
aaggcattct tgtaaagcaa caaaatggaa agctagaaag tcaagtggaa atgcaatttt    17520
tctcaactac tgaggcagcc gcaggcaatg gtgataactt gactcctaaa gtggtattgt    17580
acagtgaaga tgtagatata gaaccccag acactcatat ttcttacatg cccactatta    17640
aggaaggtaa ctcacgagaa ctaatgggcc aacaatctat gcccaacagg cctaattaca    17700
ttgcttttag ggacaatttt attggtctaa tgtattacaa cagcacgggt aatatgggtg    17760
ttctggcggg ccaagcatcg cagttgaatg ctgttgtaga tttgcaagac agaaacacag    17820
agctttcata ccagcttttg cttgattcca ttggtgatag aaccaggtac ttttctatgt    17880
ggaatcaggc tgttgacagc tatgatccag atgttagaat tattgaaaat catgaactg    17940 aagatgaact tccaaattac tgctttccac tgggaggtgt gattaataca gagactctta    18000
ccaaggtaaa acctaaaaca ggtcaggaaa atggatggga aaaagatgct acagaatttt    18060
cagataaaaa tgaaataaga gttggaaata attttgccat ggaaatcaat ctaaatgcca    18120
acctgtggag aaatttcctg tactccaaca tagcgctgta tttgcccgac aagctaaagt    18180
acagtccttc caacgtaaaa atttctgata acccaaacac ctacgactac atgaacaagc    18240
gagtggtggc tcccgggcta gtggactgct acattaacct tggagcacgc tggtcccttg    18300
actatatgga caacgtcaac ccatttaacc accaccgcaa tgctggcctg cgctaccgct    18360
caatgttgct gggcaatggt cgctatgtgc ccttccacat ccaggtgcct cagaagttct    18420
ttgccattaa aaacctcctt ctcctgccgg gctcatacac ctacgagtgg aacttcagga    18480
aggatgttaa catggttctg cagagctccc taggaaatga cctaagggtt gacggagcca    18540
gcattaagtt tgatagcatt tgcctttacg ccaccttctt ccccatggcc cacaacaccg    18600
cctccacgct tgaggccatg cttagaaacg acaccaacga ccagtccttt aacgactatc    18660
tctccgccgc caacatgctc taccctatac ccgccaacgc taccaacgtg cccatatcca    18720 tccctcccg caactgggcg ctttccgcg ctgggccttc acgcgcctt aagactaagg    18780 aaacccatc actgggctcg ggctacgacc cttattacac ctactctggc tctatccct    18840 acctagatgg aaccttttac ctcaaccaca cctttaagaa ggtggccatt accttgact    18900 cttctgtcag ctggcctggc aatgaccgcc tgcttacccc caacgagttt gaaattaagc    18960
```

```
gctcagttga cggggagggt tacaacgttg cccagtgtaa catgaccaaa gactggttcc   19020
tggtacaaat gctagctaac tataacattg gctaccaggg cttctatatc ccagagagct   19080
acaaggaccg catgtactcc ttctttagaa acttccagcc catgagccgt caggtggtgg   19140
atgatactaa atacaaggac taccaacagg tgggcatcct acaccaacac aacaactctg   19200
gatttgttgg ctaccttgcc cccaccatgc gcgaaggaca ggcctaccct gctaacttcc   19260
cctatccgct tataggcaag accgcagttg acagcattac ccagaaaaag tttctttgcg   19320
atcgcaccct ttggcgcatc ccattctcca gtaactttat gtccatgggc gcactcacag   19380
acctgggcca aaaccttctc tacgccaact ccgcccacgc gctagacatg acttttgagg   19440
tggatcccat ggacgagccc acccttcttt atgttttgtt tgaagtcttt gacgtggtcc   19500
gtgtgcacca gccgcaccgc ggcgtcatcg aaaccgtgta cctgcgcacg cccttctcgg   19560
ccggcaacgc cacaacataa agaagcaagc aacatcaaca acagctgccg ccaaataatg   19620
tactagagac actttcaata aaggcaaatg cttttatttg tacactctcg ggtgattatt   19680
tacccccacc cttgccgtct gcgccgttta aaaatcaaag gggttctgcc gcgcatcgct   19740
atgcgccact ggcagggaca cgttgcgata ctggtgttta gtgctccact taaactcagg   19800
cacaaccatc cgcggcagct cggtgaagtt ttcactccac aggctgcgca ccatcaccaa   19860
cgcgtttagc aggtcgggcg ccgatatctt gaagtcgcag ttggggcctc cgccctgcgc   19920
gcgcgagttg cgatacacag ggttgcagca ctggaacact atcagcgccg ggtggtgcac   19980
gctggccagc acgctcttgt cggagatcag atccgcgtcc aggtcctccg cgttgctcag   20040
ggcgaacgga gtcaactttg gtagctgcct tcccaaaaag ggcgcgtgcc caggctttga   20100
gttgcactcg caccgtagtg gcatcaaaag gtgaccgtgc ccggtctggg cgttaggata   20160
cagcgcctgc ataaaagcct tgatctgctt aaaagccacc tgagcctttg cgccttcaga   20220
gaagaacatg ccgcaagact tgccggaaaa ctgattggcc ggacaggccg cgtcgtgcac   20280
gcagcacctt gcgtcggtgt tggagatctg caccacattt cggcccacc ggttcttcac   20340
gatcttggcc ttgctagact gctccttcag cgcgcgctgc ccgttttcgc tcgtcacatc   20400
catttcaatc acgtgctcct tatttatcat aatgcttccg tgtagacact taagctcgcc   20460
ttcgatctca gcgcagcggt gcagccacaa cgcgcagccc gtgggctcgt gatgcttgta   20520
ggtcacctct gcaaacgact gcaggtacgc ctgcaggaat cgccccatca tcgtcacaaa   20580
ggtcttgttg ctggtgaagg tcagctgcaa cccgcggtgc tcctcgttca gccaggtctt   20640
gcatacggcc gccagagctt ccacttggtc aggcagtagt ttgaagttcg cctttagatc   20700
gttatccacg tggtacttgt ccatcagcgc gcgcgcagcc tccatgccct tctcccacgc   20760
agacacgatc ggcacactca gcgggttcat caccgtaatt tcactttccg cttcgctggg   20820
ctcttcctct tcctcttgcg tccgcatacc acgcgccact gggtcgtctt cattcagccg   20880
ccgcactgtg cgcttacctc cttttgccatg cttgattagc accggtgggt tgctgaaacc   20940
caccatttgt agcgccacat cttctctttc ttcctcgctg tccacgatta cctctggtga   21000
tggcgggcgc tcgggcttgg gagaagggcg cttctttttc ttcttgggcg caatggccaa   21060
atccgccgcc gaggtcgatg gccgcgggct gggtgtgcgc ggcaccagcg cgtcttgtga   21120
tgagtcttcc tcgtcctcgg actcgatacg ccgcctcatc cgcttttttg ggggcgcccg   21180
gggaggcggc ggcgacgggg acgggacga cacgtcctcc atggttgggg acgtcgcgc   21240
cgcaccgcgt ccgcgctcgg gggtggtttc gcgctgctcc tcttcccgac tggccatttc   21300
```

```
cttctcctat aggcagaaaa agatcatgga gtcagtcgag aagaaggaca gcctaaccgc  21360
cccctctgag ttcgccacca ccgcctccac cgatgccgcc aacgcgccta ccaccttccc  21420
cgtcgaggca cccccgcttg aggaggagga agtgattatc gagcaggacc caggttttgt  21480
aagcgaagac gacgaggacc gctcagtacc aacagaggat aaaaagcaag accaggacaa  21540
cgcagaggca aacgaggaac aagtcgggcg ggggacgaa aggcatggcg actacctaga  21600
tgtgggagac gacgtgctgt tgaagcatct gcagcgccag tgcgccatta tctgcgacgc  21660
gttgcaagag cgcagcgatg tgcccctcgc catagcggat gtcagccttg cctacgaacg  21720
ccacctattc tcaccgcgcg tacccccaa acgccaagaa aacggcacat gcgagcccaa  21780
cccgcgcctc aacttctacc ccgtatttgc cgtgccagag gtgcttgcca cctatcacat  21840 cttttttccaa aactgcaaga tacccctatc ctgccgtgcc aaccgcagcc gagcggacaa  21900
gcagctggcc ttgcggcagg gcgctgtcat acctgatatc gcctcgctca acgaagtgcc  21960
aaaaatcttt gagggtcttg gacgcgacga gaagcgcgcg gcaaacgctc tgcaacagga  22020
aaacagcgaa aatgaaagtc actctggagt gttggtggaa ctcgagggtg acaacgcgcg  22080
cctagccgta ctaaaacgca gcatcgaggt cacccacttt gcctaccgg cacttaacct  22140 accccccaag gtcatgagca cagtcatgag tgagctgatc gtgcgccgtg cgcagccct  22200 ggagagggat gcaaatttgc aagaacaaac agaggagggc ctacccgcag ttggcgacga  22260
gcagctagcg cgctggcttc aaacgcgcga gcctgccgac ttggaggagc gacgcaaact  22320
aatgatggcc gcagtgctcg ttaccgtgga gcttgagtgc atgcagcggt tctttgctga  22380
cccggagatg cagcgcaagc tagaggaaac attgcactac ccctttcgac agggctacgt  22440
acgccaggcc tgcaagatct ccaacgtgga gctctgcaac ctggtctcct accttggaat  22500
tttgcacgaa aaccgccttg ggcaaaacgt gcttcattcc acgctcaagg gcgaggcgcg  22560
ccgcgactac gtccgcgact gcgtttactt atttctatgc tacacctggc agacggccat  22620
gggcgtttgg cagcagtgct tggaggagtg caacctcaag gagctgcaga aactgctaaa  22680
gcaaaacttg aaggacctat ggacggcctt caacgagcgc tccgtggccg cgcacctggc  22740
ggacatcatt ttccccgaac gcctgcttaa aaccctgcaa cagggtctgc cagacttcac  22800
cagtcaaagc atgttgcaga actttaggaa ctttatccta gagcgctcag gaatcttgcc  22860
cgccacctgc tgtgcacttc ctagcgactt tgtgcccatt aagtaccgcg aatgccctcc  22920
gccgctttgg ggccactgct accttctgca gctagccaac taccttgcct accactctga  22980
cataatggaa gacgtgagcg gtgacggtct actggagtgt cactgtcgct gcaacctatg  23040
caccccgcac cgctccctgg tttgcaattc gcagctgctt aacgaaagtc aaattatcgg  23100
tacctttgag ctgcagggtc cctcgcctga cgaaaagtcc gcggctccgg ggttgaaact  23160
cactccgggg ctgtggacgt cggcttacct tcgcaaattt gtacctgagg actaccacgc  23220
ccacgagatt aggttctacg aagaccaatc ccgcccgcct aatgcggagc ttaccgcctg  23280
cgtcattacc cagggccaca ttcttggcca attgcaagcc atcaacaaag cccgccaaga  23340
gtttctgcta cgaaagggac ggggggttta cttggacccc cagtccggcg aggagctcaa  23400
cccaatcccc ccgccgccgc agccctatca gcagcagccg cgggcccttg cttcccagga  23460
tggcacccaa aaagaagctg cagctgccgc cgccacccac ggacgaggag gaatactggg  23520
acagtcaggc agaggaggtt ttggacgagg aggaggagga catgatggaa gactgggaga  23580
gcctagacga ggaagcttcc gaggtcgaag aggtgtcaga cgaaacaccg tcaccctcgg  23640
tcgcattccc ctcgccggcg ccccagaaat cggcaaccgg ttccagcatg gctacaacct  23700
```

```
ccgctcctca ggcgccgccg gcactgcccg ttcgccgacc caaccgtaga tgggacacca   23760
ctggaaccag ggccggtaag tccaagcagc cgccgccgtt agcccaagag caacaacagc   23820
gccaaggcta ccgctcatgg cgcgggcaca agaacgccat agttgcttgc ttgcaagact   23880
gtgggggcaa catctccttc gcccgccgct ttcttctcta ccatcacggc gtggccttcc   23940
cccgtaacat cctgcattac taccgtcatc tctacagccc atactgcacc ggcggcagcg   24000
gcagcaacag cagcggccac acagaagcaa aggcgaccgg atagcaagac tgacaaag    24060 cccaagaaat ccacagcggc ggcagcagca ggaggaggag cgctgcgtct ggcgcccaac   24120
gaacccgtat cgaccgcga gcttagaaac aggatttttc ccactctgta tgctatattt   24180
caacagagca ggggccaaga acaagagctg aaaataaaaa acaggtctct gcgatccctc   24240
acccgcagct gcctgtatca caaaagcgaa gatcagcttc ggcgcacgct ggaagacgcg   24300
gaggctctct tcagtaaata ctgcgcgctg actcttaagg actagtttcg cgcccttttct  24360 caaatttaag cgcgaaaact acgtcatctc cagcggccac acccggcgcc agcacctgtt   24420
gtcagcgcca ttatgagcaa ggaaattccc acgccctaca tgtggagtta ccagccacaa   24480
atgggacttg cggctggagc tgcccaagac tactcaaccc gaataaacta catgagcgcg   24540 ggacccccaca tgatatcccg ggtcaacgga atacgcgccc accgaaaccg aattctcctg   24600
gaacaggcgg ctattaccac cacacctcgt aataacctta atccccgtag ttggcccgct   24660
gccctggtgt accaggaaag tcccgctccc accactgtgg tacttcccag agacgcccag   24720
gccgaagttc agatgactaa ctcaggggcg cagcttgcgg gcggctttcg tcacagggtg   24780
cggtcgcccg ggcagggtat aactcacctg acaatcagag ggcgaggtat tcagctcaac   24840
gacgagtcgg tgagctcctc gcttggtctc cgtccggacg ggacatttca gatcggcggc   24900
gccggccgct cttcattcac gcctcgtcag gcaatcctaa ctctgcagac ctcgtcctct   24960
gagccgcgct ctggaggcat tggaactctg caatttattg aggagtttgt gccatcggtc   25020
tactttaacc ccttctcggg acctcccggc cactatccgg atcaatttat tcctaacttt   25080
gacgcggtaa aggactcggc ggacggctac gactgaatgt taagtggaga ggcagagcaa   25140
ctgcgcctga aacacctggt ccactgtcgc cgccacaagt gctttgcccg cgactccggt   25200
gagttttgct actttgaatt gcccgaggat catatcgagg gcccggcgca cggcgtccgg   25260
cttaccgccc agggagagct tgcccgtagc ctgattcggg agtttaccca cgcccccctg   25320
ctagttgagc gggacagggg accctgtgtt ctcactgtga tttgcaactg tcctaaccct   25380
ggattacatc aagatctttg ttgccatctc tgtgctgagt ataataaata cagaaattaa   25440
aatatactgg ggctcctatc gccatcctgt aaacgccacc gtcttcaccc gcccaagcaa   25500
accaaggcga accttacctg gtacttttaa catctctccc tctgtgattt acaacagttt   25560
caacccagac ggagtgagtc tacgagagaa cctctccgag ctcagctact ccatcagaaa   25620
aaacaccacc ctccttacct gccgggaacg tacgagtgcg tcaccggccg ctgcaccaca   25680
cctaccgcct gaccgtaaac cagactttttt ccggacagac ctcaataact ctgtttacca   25740
gaacaggagg tgagcttaga aaaccccttag ggtattaggc caaaggcgca gctactgtgg   25800
ggtttatgaa caattcaagc aactctacgg gctattctaa ttcaggtttc tctagaaatg   25860
gacggaatta ttacagagca gcgcctgcta gaaagacgca gggcagcggc cgagcaacag   25920
cgcatgaatc aagagctcca agacatggtt aacttgcacc agtgcaaaag gggtatcttt   25980
tgtctggtaa agcaggccaa agtcacctac gacagtaata ccaccggaca ccgccttagc   26040
```

```
tacaagttgc caaccaagcg tcagaaattg gtggtcatgg tgggagaaaa gcccattacc  26100
ataactcagc actcggtaga aaccgaaggc tgcattcact caccttgtca aggacctgag  26160
gatctctgca cccttattaa gaccctgtgc ggtctcaaag atcttattcc ctttaactaa  26220
taaaaaaaaa taataaagca tcacttactt aaaatcagtt agcaaatttc tgtccagttt  26280
attcagcagc acctccttgc cctcctccca gctctggtat tgcagcttcc tcctggctgc  26340
aaactttctc cacaatctaa atggaatgtc agtttcctcc tgttcctgtc catccgcacc  26400
cactatcttc atgttgttgc agatgaagcg cgcaagaccg tctgaagata ccttcaaccc  26460
cgtgtatcca tatgacacgg aaaccggtcc tccaactgtg cctttttctta ctcctcccct  26520 tgtatccccc aatgggtttc aagagagtcc ccctgggta ctctctttgc gcctatccga  26580
acctctagtt acctccaatg gcatgcttgc gctcaaaatg ggcaacggcc tctctctgga  26640
cgaggccggc aaccttacct cccaaaatgt aaccactgtg agcccacctc tcaaaaaaac  26700
caagtcaaac ataaacctgg aaatatctgc acccctcaca gttacctcag aagccctaac  26760
tgtggctgcc gccgcacctc taatggtcgc gggcaacaca ctcaccatgc aatcacaggc  26820
cccgctaacc gtgcacgact ccaaacttag cattgccacc caaggacccc tcacagtgtc  26880
agaaggaaag ctagccctgc aaacatcagg ccccctcacc accaccgata gcagtaccct  26940
tactatcact gcctcacccc ctctaactac tgccactggt agcttgggca ttgacttgaa  27000
agagcccatt tatacacaaa atggaaaact aggactaaag tacggggctc ctttgcatgt  27060
aacagacgac ctaaacactt tgaccgtagc aactggtcca ggtgtgacta ttaataatac  27120
ttccttgcaa actaaagtta ctggagcctt gggtttttgat tcacaaggca atatgcaact  27180
taatgtagca ggaggactaa ggattgattc tcaaaacaga cgccttatac ttgatgttag  27240
ttatccgttt gatgctcaaa accaactaaa tctaagacta ggacagggcc ctctttttat  27300
aaactcagcc cacaacttgg atattaacta caacaaaggc ctttacttgt ttacagcttc  27360
aaacaattcc aaaaagcttg aggttaacct aagcactgcc aaggggttga tgtttgacgc  27420
tacagccata gccattaatg caggagatgg gcttgaattt ggttcaccta atgcaccaaa  27480
cacaaatccc ctcaaaacaa aaattggcca tggcctagaa tttgattcaa caaggctat  27540 ggttcctaaa ctaggaactg gccttagttt tgacagcaca ggtgccatta cagtaggaaa  27600
caaaaataat gataagctaa cttttgtggac cacaccagct ccatctccta actgtagact  27660
aaatgcagag aaagatgcta aactcacttt ggtcttaaca aaatgtggca gtcaaatact  27720
tgctacagtt tcagttttgg ctgttaaagg cagtttggct ccaatatctg aacagttca  27780 aagtgctcat cttattataa gatttgacga aaatggagtg ctactaaaca attccttcct  27840
ggacccagaa tattggaact ttagaaatgg agatcttact gaaggcacag cctatacaaa  27900
cgctgttgga tttatgccta acctatcagc ttatccaaaa tctcacggta aaactgccaa  27960
aagtaacatt gtcagtcaag tttacttaaa cggagacaaa actaaacctg taacactaac  28020
cattacacta aacggtacac aggaaacagg agacacaact ccaagtgcat actctatgtc  28080
attttcatgg gactggtctg gccacaacta cattaatgaa atatttgcca catcctctta  28140
cactttttca tacattgccc aagaataaag aatcgtttgt gttatgtttc aacgtgttta  28200
tttttcaatt gcagaaaatt tcgaatcatt tttcattcag tagtatagcc ccaccaccac  28260
atagcttata cagatcaccg taccttaatc aaactcacag aacccctagta ttcaacctgc  28320 cacctccctc ccaacacaca gagtacacag tcctttctcc ccggctggcc ttaaaaagca  28380
tcatatcatg ggtaacagac atattcttag gtgttatatt ccacacggtt tcctgtcgag  28440
```

```
ccaaacgctc atcagtgata ttaataaact ccccgggcag ctcacttaag ttcatgtcgc    28500
tgtccagctg ctgagccaca ggctgctgtc aacttgcgg ttgcttaacg ggcggcgaag    28560
gagaagtcca cgcctacatg ggggtagagt cataatcgtg catcaggata gggcggtggt    28620
gctgcagcag cgcgcgaata aactgctgcc gccgccgctc cgtcctgcag gaatacaaca    28680
tggcagtggt ctcctcagcg atgattcgca ccgcccgcag cataaggcgc cttgtcctcc    28740
gggcacagca gcgcacccctg atctcactta aatcagcaca gtaactgcag cacagccaca   28800
caatattgtt caaaatccca cagtgcaagg cgctgtatcc aaagctcatg gcggggacca    28860
cagaacccac gtggccatca taccacaagc gcaggtagat taagtggcga cccctcataa    28920
acacgctgga cataaacatt acctcttttg gcatgttgta attcaccacc tcccggtacc    28980
atataaacct ctgattaaac atggcgccat ccaccaccat cctaaaccag ctggccaaaa    29040
cctgcccgcc ggctatacac tgcagggaac cgggactgga acaatgacag tggagagccc    29100
aggactcgta accatggatc atcatgctcg tcatgatatc aatgttggca caacacaggc    29160
acacgtgcat acacttcctc aggattacaa gctcctcccg cgttagaacc atatcccagg    29220
gaacaaccca ttcctgaatc agcgtaaatc ccacactgca gggaagacct cgcacgtaac    29280
tcacgttgtg cattgtcaaa gtgttacatt cgggcagcag cggatgatcc tccagtatgg    29340
tagcgcgggt ttctgtctca aaaggaggta gacgatccct actgtacgga gtgcgccgag    29400
acaaccgaga tcgtgttggt cgtagtgtca tgccaaatgg aacgccggac gtagtcatat    29460
ttcctgaagc aaaaccaggt gcgggcgtga caaacagatc tgcgtctccg gtctcgccgc    29520
ttagatcgct ctgtgtagta gttgtagtat atccactctc tcaaagcatc caggcgcccc    29580
ctggcttcgg gttctatgta aactccttca tgcgccgctg ccctgataac atccaccacc    29640
gcagaataag ccacacccag ccaacctaca cattcgttct gcgagtcaca cacgggagga    29700 gcggaagag ctggaagaac catgtttttt tttttattcc aaaagattat ccaaaacctc    29760
aaaatgaaga tctattaagt gaacgcgctc ccctccggtg gcgtggtcaa actctacagc    29820
caaagaacag ataatggcat ttgtaagatg ttgcacaatg gcttccaaaa ggcaaacggc    29880
cctcacgtcc aagtggacgt aaaggctaaa cccttcaggg tgaatctcct ctataaacat    29940
tccagcacct tcaaccatgc ccaaataatt ctcatctcgc caccttctca atatatctct    30000
aagcaaatcc cgaatattaa gtccggccat tgtaaaaatc tgctccagag cgccctccac    30060
cttcagcctc aagcagcgaa tcatgattgc aaaaattcag gttcctcaca gacctgtata    30120
agattcaaaa gcggaacatt aacaaaaata ccgcgatccc gtaggtccct tcgcagggcc    30180
agctgaacat aatcgtgcag gtctgcacgg accagcgcgg ccacttcccc gccaggaacc    30240
atgacaaaag aacccacact gattatgaca cgcatactcg gagctatgct aaccagcgta    30300
gccccgatgt aagcttgttg catgggcggc gatataaaat gcaaggtgct gctcaaaaaa    30360
tcaggcaaag cctcgcgcaa aaaagaaagc acatcgtagt catgctcatg cagatcaagg   30420
caggtaagct ccggaaccac cacagaaaaa gacaccattt ttctctcaaa catgtctgcg    30480
ggtttctgca taaacacaaa ataaaataac aaaaaaacat ttaaacatta gaagcctgtc    30540
ttacaacagg aaaaacaacc cttataagca taagacggac tacggccatg ccggcgtgac    30600
cgtaaaaaaa ctggtcaccg tgattaaaaa gcaccaccga cagctcctcg gtcatgtccg    30660
gagtcataat gtaagactcg gtaaacacat caggttgatt cacatcggtc agtgctaaaa    30720
agcgaccgaa atagcccggg ggaatacata cccgcaggcg tagagacaac attacagccc    30780
```

```
ccataggagg tataacaaaa ttaataggag agaaaaacac ataaacacct gaaaaaccct    30840
cctgcctagg caaaatagca ccctcccgct ccagaacaac atacagcgct tccacagcgg    30900
cagccataac agtcagcctt accagtaaaa aagaaaacct attaaaaaaa caccactcga    30960
cacggcacca gctcaatcag tcacagtgta aaaaagggcc aagtgcagag cgagtatata    31020
taggactaaa aaatgacgta acggttaaag tccacaaaaa acacccagaa aaccgcacgc    31080
gaacctacgc ccagaaacga aagccaaaaa acccacaact tcctcaaatc gtcacttccg    31140
ttttcccacg ttacttctgt ggaatgtgtg tcagttaggg tgtggaaagt ccccaggctc    31200
cccagcaggc agaagtatgc aaagcatgca tctcaattag tcagcaacca ggtgtggaaa    31260
gtccccaggc tccccagcag gcagaagtat gcaaagcatg catctcaatt agtcagcaac    31320
catagtcccg cccctaactc cgcccatccc gcccctaact ccgcccagtt ccgcccattc    31380
tccgccccat ggctgactaa ttttttttat ttatgcagag gccgaggccg cctctgcctc    31440
tgagctattc cagaagtagt gaggaggctt ttttggaggc ctaggctttt gcaaacctcc    31500
gcggggatcc accggtcgcc accatggtga gcaagggcga ggagctgttc accggggtgg    31560
tgcccatcct ggtcgagctg gacggcgacg taaacggcca caagttcagc gtgtccggcg    31620
agggcgaggc gatgccacc tacggcaagc tgaccctgaa gttcatctgc accaccggca    31680
agctgcccgt gccctggccc accctcgtga ccaccctgac ctacggcgtg cagtgcttca    31740
gccgctaccc cgaccacatg aagcagcacg acttcttcaa gtccgccatg cccgaaggct    31800
acgtccagga gcgcaccatc ttcttcaagg acgacggcaa ctacaagacc cgcgccgagg    31860
tgaagttcga gggcgacacc ctggtgaacc gcatcgagct gaagggcatc gacttcaagg    31920
aggacggcaa catcctgggg cacaagctgg agtacaacta caacagccac aacgtctata    31980
tcatggccga caagcagaag aacggcatca aggtgaactt caagatccgc cacaacatcg    32040
aggacggcag cgtgcagctc gccgaccact accagcagaa cacccccatc ggcgacggcc    32100
ccgtgctgct gcccgacaac cactacctga gcacccagtc cgccctgagc aaagacccca    32160
acgagaagcg cgatcacatg gtcctgctgg agttcgtgac cgccgccggg atcactctcg    32220
gcatggacga gctgtacaag taaagcggcc gcatcgataa gttcgaaatg accgaccaag    32280
cgacgcccaa cctgccatca cgagatttcg attccaccgc cgccttctat gaaaggttgg    32340
gcttcggaat cgttttccgg gacgccggct ggatgatcct ccagcgcggg gatctcatgc    32400
tggagttctt cgcccacccc aacttgttta ttgcagctta taatggttac aaataaagca    32460
atagcatcac aaatttcaca aataaagcat ttttttcact gcattctagt tgtggtttgt    32520
ccaaactcat caatgtatct tatcatgtct gtataccgtc gacctctagc tagaggtcac    32580
ttcccatttt aagaaaacta caattcccaa cacatacaag ttactccgcc ctaaaaccta    32640
cgtcacccgc cccgttccca cgccccgcgc cacgtcacaa actccacccc ctcattatca    32700
tattggcttc aatccaaaat aaggtatatt attgatgatg ttaattaatt taaatccgca    32760
tgcgatatcg agctctcccg ggaattcgga tctgcgacgc gaggctggat ggccttcccc    32820
attatgattc ttctcgcgtt taagggcacc aataactgcc ttaaaaaaat tacgccccgc    32880
cctgccactc atcgcagtac tgttgtaatt cattaagcat tctgccgaca tggaagccat    32940
cacaaacggc atgatgaacc tgaatcgcca gcggcatcag caccttgtcg ccttgcgtat    33000
aatatttgcc catggtgaaa acggggggga agaagttgtc catattggcc acgtttaaat    33060
caaaactggt gaaactcacc cagggattgg ctgagacgaa aaacatattc tcaataaacc    33120
ctttagggaa ataggccagg ttttcaccgt aacacgccac atcttgcgaa tatatgtgta    33180
```

```
gaaactgccg gaaatcgtcg tggtattcac tccagagcga tgaaaacgtt tcagtttgct  33240
catggaaaac ggtgtaacaa gggtgaacac tatcccatat caccagctca ccgtctttca  33300
ttgccatacg gaattccgga tgagcattca tcaggcgggc aagaatgtga ataaaggccg  33360
gataaaactt gtgcttattt ttctttacgg tcttaaaaa ggccgtaata tccagctgaa   33420
cggtctggtt ataggtacat tgagcaactg actgaaatgc ctcaaaatgt tctttacgat  33480
gccattggga tatatcaacg gtggtatatc cagtgatttt tttctccatt ttagcttcct  33540
tagctcctga aaatctcgat aactcaaaaa atacgcccgg tagtgatctt atttcattat  33600
ggtgaaagtt ggaacctctt acgtgccgat caacgtctca ttttcgccaa aagttggccc  33660
agggcttccc ggtatcaaca gggacaccag gatttattta ttctgcgaag tgatcttccg  33720
tcacaggtat ttattcgcga taagctcatg gagcggcgta accgtcgcac aggaaggaca  33780
gagaaagcgc ggatctggga agtgacggac agaacggtca ggacctggat tggggaggcg  33840
gttgccgccg ctgctgctga cggtgtgacg ttctctgttc cggtcacacc acatacgttc  33900
cgccattcct atgcgatgca catgctgtat gccggtatac cgctgaaagt tctgcaaagc  33960
ctgatgggac ataagtccat cagttcaacg gaagtctaca cgaaggtttt tgcgctggat  34020
gtggctgccc ggcaccgggt gcagtttgcg atgccggagt ctgatgcggt tgcgatgctg  34080
aaacaattat cctgagaata aatgccttgg cctttatatg gaaatgtgga actgagtgga  34140
tatgctgttt ttgtctgtta aacagagaag ctggctgtta tccactgaga agcgaacgaa  34200
acagtcggga aaatctccca ttatcgtaga gatccgcatt attaatctca ggagcctgtg  34260
tagcgtttat aggaagtagt gttctgtcat gatgcctgca agcggtaacg aaaacgattt  34320
gaatatgcct tcaggaacaa tagaaatctt cgtgcggtgt tacgttgaag tggagcggat  34380
tatgtcagca atggacagaa caacctaatg aacacagaac catgatgtgg tctgtccttt  34440
tacagccagt agtgctcgcc gcagtcgagc gacagggcga agccctcgag tgagcgagga  34500
agcaccaggg aacagcactt atatattctg cttacacacg atgcctgaaa aaacttccct  34560
tggggttatc cacttatcca cggggatatt tttataatta tttttttat agttttaga   34620
tcttcttttt tagagcgcct tgtaggcctt tatccatgct ggttctagag aaggtgttgt  34680
gacaaattgc cctttcagtg tgacaaatca ccctcaaatg acagtcctgt ctgtgacaaa  34740
ttgcccttaa ccctgtgaca aattgccctc agaagaagct gttttttcac aaagttatcc  34800
ctgcttattg actctttttt atttagtgtg acaatctaaa aacttgtcac acttcacatg  34860
gatctgtcat ggcggaaaca gcggttatca atcacaagaa acgtaaaaat agcccgcgaa  34920
tcgtccagtc aaacgacctc actgaggcgg catatagtct ctcccgggat caaaaacgta  34980
tgctgtatct gttcgttgac cagatcagaa atctgatgg caccctacag gaacatgacg   35040
gtatctgcga gatccatgtt gctaaatatg ctgaaatatt cggattgacc tctgcggaag  35100
ccagtaagga tatacggcag gcattgaaga gtttcgcggg gaaggaagtg gttttttatc  35160
gccctgaaga ggatgccggc gatgaaaaag gctatgaatc ttttccttgg tttatcaaac  35220
gtgcgcacag tccatccaga gggctttaca gtgtacatat caacccatat ctcattccct  35280
tctttatcgg gttacagaac cggtttacgc agtttcggct tagtgaaaca aaagaaatca  35340
ccaatccgta tgccatgcgt ttatacgaat ccctgtgtca gtatcgtaag ccggatggct  35400
caggcatcgt ctctctgaaa atcgactgga tcatagagcg ttaccagctg cctcaaagtt  35460
accagcgtat gcctgacttc cgccgccgct tcctgcaggt ctgtgttaat gagatcaaca  35520
```

```
gcagaactcc aatgcgcctc tcatacattg agaaaaagaa aggccgccag acgactcata   35580 tcgtatttc cttccgcgat atcacttcca tgacgacagg atagtctgag ggttatctgt    35640
cacagatttg agggtggttc gtcacatttg ttctgaccta ctgagggtaa tttgtcacag   35700
ttttgctgtt tccttcagcc tgcatggatt ttctcatact ttttgaactg taatttttaa   35760
ggaagccaaa tttgagggca gtttgtcaca gttgatttcc ttctctttcc cttcgtcatg   35820
tgacctgata tcggggggtta gttcgtcatc attgatgagg gttgattatc acagtttatt   35880
actctgaatt ggctatccgc gtgtgtacct ctacctggag ttttcccac ggtggatatt    35940 tcttcttgcg ctgagcgtaa gagctatctg acagaacagt tcttctttgc ttcctcgcca   36000
gttcgctcgc tatgctcggt tacacggctg cggcgagcgc tagtgataat aagtgactga   36060
ggtatgtgct cttcttatct cctttttgtag tgttgctctt attttaaaca actttgcggt   36120
tttttgatga ctttgcgatt ttgttgttgc tttgcagtaa attgcaagat ttaataaaaa   36180
aacgcaaagc aatgattaaa ggatgttcag aatgaaactc atggaaacac ttaaccagtg   36240
cataaacgct ggtcatgaaa tgacgaaggc tatcgccatt gcacagttta atgatgacag   36300
cccggaagcg aggaaaataa cccggcgctg gagaataggt gaagcagcgg atttagttgg   36360
ggtttcttct caggctatca gagatgccga gaaagcaggg cgactaccgc acccggatat   36420
ggaaattcga ggacggggttg agcaacgtgt tggttataca attgaacaaa ttaatcatat   36480
gcgtgatgtg tttggtacgc gattgcgacg tgctgaagac gtatttccac cggtgatcgg   36540
ggttgctgcc cataaaggtg gcgtttacaa aacctcagtt tctgttcatc ttgctcagga   36600
tctggctctg aaggggctac gtgttttgct cgtggaaggt aacgaccccc agggaacagc   36660
ctcaatgtat cacggatggg taccagatct tcatattcat gcagaagaca ctctcctgcc   36720
tttctatctt ggggaaaagg acgatgtcac ttatgcaata aagcccactt gctggccggg   36780
gcttgacatt attccttcct gtctggctct gcaccgtatt gaaactgagt taatgggcaa   36840
atttgatgaa ggtaaactgc ccaccgatcc acacctgatg ctccgactgg ccattgaaac   36900
tgttgctcat gactatgatg tcatagttat tgacagcgcg cctaacctgg gtatcggcac   36960
gattaatgtc gtatgtgctg ctgatgtgct gattgttccc acgcctgctg agttgtttga   37020
ctacacctcc gcactgcagt ttttcgatat gcttcgtgat ctgctcaaga acgttgatct   37080
taaagggttc gagcctgatg tacgtatttt gcttaccaaa tacagcaata gtaatggctc   37140
tcagtccccg tggatggagg agcaaattcg ggatgcctgg ggaagcatgg ttctaaaaaa   37200
tgttgtacgt gaaacggatg aagttggtaa aggtcagatc cggatgagaa ctgttttga    37260 acaggccatt gatcaacgct cttcaactgg tgcctggaga aatgctcttt ctatttggga   37320
acctgtctgc aatgaaattt tcgatcgtct gattaaacca cgctgggaga ttagataatg   37380
aagcgtgcgc ctgttattcc aaaacatacg ctcaatactc aaccggttga agatacttcg   37440
ttatcgacac cagctgcccc gatggtggat tcgttaattg cgcgcgtagg agtaatggct   37500
cgcggtaatg ccattacttt gcctgtatgt ggtcgggatg tgaagtttac tcttgaagtg   37560
ctccggggtg atagtgttga aagacctct cgggtatggt caggtaatga acgtgaccag   37620
gagctgctta ctgaggacgc actgatgat ctcatccctt cttttctact gactggtcaa    37680
cagacaccgg cgttcggtcg aagagtatct ggtgtcatag aaattgccga tgggagtcgc   37740
cgtcgtaaag ctgctgcact taccgaaagt gattatcgtg ttctggttgg cgagctggat   37800
gatgagcaga tggctgcatt atccagattg ggtaacgatt atcgcccaac aagtgcttat   37860
gaacgtggtc agcgttatgc aagccgattg cagaatgaat ttgctggaaa tatttctgcg   37920
```

```
ctggctgatg cggaaaatat ttcacgtaag attattaccc gctgtatcaa caccgccaaa    37980
ttgcctaaat cagttgttgc tcttttttct caccccggtg aactatctgc ccggtcaggt    38040
gatgcacttc aaaaagcctt tacagataaa gaggaattac ttaagcagca ggcatctaac    38100
cttcatgagc agaaaaaagc tggggtgata tttgaagctg aagaagttat cactctttta    38160
acttctgtgc ttaaaacgtc atctgcatca agaactagtt taagctcacg acatcagttt    38220
gctcctggag cgacagtatt gtataagggc gataaaatgg tgcttaacct ggacaggtct    38280
cgtgttccaa ctgagtgtat agagaaaatt gaggccattc ttaaggaact gaaaagcca     38340 gcaccctgat gcgaccacgt tttagtctac gtttatctgt ctttacttaa tgtcctttgt    38400
tacaggccag aaagcataac tggcctgaat attctctctg ggcccactgt tccacttgta    38460
tcgtcggtct gataatcaga ctgggaccac ggtcccactc gtatcgtcgg tctgattatt    38520
agtctgggac cacggtccca ctcgtatcgt cggtctgatt attagtctgg gaccacggtc    38580
ccactcgtat cgtcggtctg ataatcagac tgggaccacg gtcccactcg tatcgtcggt    38640
ctgattatta gtctgggacc atggtcccac tcgtatcgtc ggtctgatta ttagtctggg    38700
accacggtcc cactcgtatc gtcggtctga ttattagtct ggaaccacgg tcccactcgt    38760
atcgtcggtc tgattattag tctgggacca cggtcccact cgtatcgtcg gtctgattat    38820
tagtctggga ccacgatccc actcgtgttg tcggtctgat tatcggtctg ggaccacggt    38880
cccacttgta ttgtcgatca gactatcagc gtgagactac gattccatca atgcctgtca    38940
agggcaagta ttgacatgtc gtcgtaacct gtagaacgga gtaacctcgg tgtgcggttg    39000
tatgcctgct gtggattgct gctgtgtcct gcttatccac aacattttgc gcacggttat    39060
gtggacaaaa tacctggtta cccaggccgt gccggcacgt taaccgggca catttccccg    39120
aaaagtgcca cctgacgtct aagaaaccat tattatcatg acattaacct ataaaaatag    39180
gcgtatcacg aggcccttc gtcttcaaga attggatccg aattcccggg agagctcgat     39240
atcgcatgcg gatttaaatt aattaa                                         39266
```

<210> SEQ ID NO 100
<211> LENGTH: 41275
<212> TYPE: DNA
<213> ORGANISM: Artificial Sequence
<220> FEATURE:
<223> OTHER INFORMATION: Vector

<400> SEQUENCE: 100

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tagaagccat agagcccacc     360
gcatccccag catgcctgct attgtcttcc caatcctccc ccttgctgtc ctgccccacc     420 ccaccccca gaatagaatg acacctactc agacaatgcg atgcaatttc ctcattttat      480
taggaaagga cagtgggagt ggcaccttcc agggtcaagg aaggcacggg ggaggggcaa     540
acaacagatg gctggcaact agaaggcaca gtcgaggctg atcagcgggt ttaaactcaa     600
tggtgatggt gatgatgacc ggtacgcgta gaatcgagac cgaggagagg gttagggata     660
```

```
ggcttacctt cgaaccgcgg gccctctaga tcaaccactt tgtacaagaa agctgaacga    720
gaaacgtaaa atgatataaa tatcaatata ttaaattaga ttttgcataa aaaacagact    780
acataatact gtaaaacaca acatatccag tcactatggt cgacctgcag actggctgtg    840
tataacggag cctgacattt atattcccca gaacatcagg ttaatggcgt ttttgatgtc    900
attttcgcgg tggctgagat cagccacttc ttccccgata acggagaccg gcacactggc    960
catatcggtg gtcatcatgc gccagctttc atccccgata tgcaccaccg ggtaaagttc   1020
acgggagact ttatctgaca gcagacgtgc actggccagg gggatcacca tccgtcgccc   1080
gggcgtgtca ataatatcac tctgtacatc cacaaacaga cgataacggc tctctctttt   1140
ataggtgtaa accttaaact gcatttcacc agtccctgtt ctcgtcagca aaagagccgt   1200
tcatttcaat aaaccgggcg acctcagcca tcccttcctg attttccgct ttccagcgtt   1260
cggcacgcag acgacgggct tcattctgca tggttgtgct taccagaccg agatattga    1320 catcatatat gccttgagca actgatagct gtcgctgtca actgtcactg taatacgctg   1380
cttcatagca caccctcttt tgacatactt cgggtataca tatcagtata tattcttata   1440
ccgcaaaaat cagcgcgcaa atacgcatac tgttatctgg cttttagtaa gccggatcca   1500
gatctttacg ccccgccctg ccactcatcg cagtactgtt gtaattcatt aagcattctg   1560
ccgacatgga agccatcaca gacggcatga tgaacctgaa tcgccagcgg catcagcacc   1620
ttgtcgcctt gcgtataata tttgcccatg gtgaaacgg gggcgaagaa gttgtccata   1680
ttggccacgt ttaaatcaaa actggtgaaa ctcacccagg gattggctga cgaaaaac    1740 atattctcaa taacccattt agggaaatag gccaggtttt caccgtaaca cgccacatct   1800
tgcgaatata tgtgtagaaa ctgccggaaa tcgtcgtggt attcactcca gagcgatgaa   1860
aacgtttcag tttgctcatg gaaacggtg taacaagggt gaacactatc ccatatcacc    1920
agctcaccgt ctttcattgc catacggaat tccggatgag cattcatcag gcgggcaaga   1980
atgtgaataa aggccggata aaacttgtgc ttattttct ttacggtctt taaaaaggcc    2040
gtaatatcca gctgaacggt ctggttatag gtacattgag caactgactg aaatgcctca   2100
aaatgttctt tacgatgcca ttgggatata tcaacggtgg tatatccagt gattttttc     2160 tccatttag cttccttagc tcctgaaaat ctcgccggat cctaactcaa aatccacaca    2220
ttatacgagc cggaagcata aagtgtaaag cctggggtgc ctaatgcggc gcgtcgagg    2280 ctgatcagcg agctctagag aattgatccc ctcagaagaa ctcgtcaaga aggcgataga   2340
aggcgatgcg ctgcgaatcg ggagcggcga taccgtaaag cacgaggaag cggtcagccc   2400
attcgccgcc aagctcttca gcaatatcac gggtagccaa cgctatgtcc tgatagcggt   2460
ccgccacacc cagccggcca cagtcgatga atccagaaaa gcggccattt tccaccatga   2520
tattcggcaa gcaggcatcg ccatgggtca cgacgagatc atcgccgtcg gcatgcgcg    2580 ccttgagcct ggcgaacagt tcggctggcg cgagcccctg atgctcttcg tccagatcat   2640
cctgatcgac aagaccggct tccatccgag tacgtgctcg ctcgatgcga tgtttcgctt    2700
ggtggtcgaa tgggcaggta gccggatcaa gcgtatgcag ccgccgcatt gcatcagcca   2760
tgatggatac tttctcggca ggagcaaggt gagatgacag gagatcctgc cccggcactt   2820
cgcccaatag cagccagtcc cttcccgctt cagtgacaac gtcgagcaca gctgcgcaag   2880
gaacgcccgt cgtggccagc cacgatagcc gcgctgcctc gtcctgcagt tcattcaggg   2940
caccggacag gtcggtcttg acaaaaagaa ccgggcgccc ctgcgctgac agccggaaca   3000
cggcggcatc agagcagccg attgtctgtt gtgcccagtc atagccgaat agcctctcca   3060
```

```
cccaagcggc cggagaacct gcgtgcaatc catcttgttc aatggccgat cccatggttt   3120
agttcctcac cttgtcgtat tatactatgc cgatatacta tgccgatgat taattgtcaa   3180
caggctgcag gtcgaaagcg gccgccatag tgactggata tgttgtgttt tacagtatta   3240
tgtagtctgt tttttatgca aaatctaatt taatatattg atatttatat cattttacgt   3300
ttctcgttca gcttttttgt acaaacttgt tgatagctta actagccagc ttgggtctcc   3360
ctatagtgag tcgtattaat ttcgataagc cagtaagcag tgggttctct agttagccag   3420
agagctctgc ttatatagac ctcccaccgt acacgcctac cgcccatttg cgtcaatggg   3480
gcggagttgt tacgacattt tggaaagtcc cgttgatttt ggtgccaaaa caaactccca   3540
ttgacgtcaa tggggtggag acttggaaat ccccgtgagt caaaccgcta ccacgcccca   3600
ttgatgtact gccaaaaccg catcaccatg gtaatagcga tgactaatac gtagatgtac   3660
tgccaagtag gaaagtccca taaggtcatg tactgggcat aatgccaggc gggccattta   3720
ccgtcattga cgtcaatagg gggcgtactt ggcatatgat acacttgatg tactgccaag   3780
tgggcagttt accgtaaata ctccacccat tgacgtcaat ggaaagtccc tattggcgtt   3840
actatgggaa catacgtcat tattgacgtc aatgggcggg ggtcgttggg cggtcagcca   3900
ggcgggccat ttaccgtaag ttatgtaacg cggaactcca tatatgggct atgaactaat   3960
gaccccgtaa ttgattacta ttaataacta gtcaataatc aatgtcaacg cgtatatctg   4020 gcccgtggc ttaagggtgg aaagaatat ataaggtggg ggtcttatgt agttttgtat   4080
ctgttttgca gcagccgccg ccgccatgag caccaactcg tttgatggaa gcattgtgag   4140
ctcatatttg acaacgcgca tgccccatg gccggggtg cgtcagaatg tgatgggctc   4200
cagcattgat ggtcgccccg tcctgcccgc aaactctact accttgacct acgagaccgt   4260
gtctggaacg ccgttggaga ctgcagcctc cgccgccgct tcagccgctg cagccaccgc   4320
ccgcgggatt gtgactgact ttgctttcct gagcccgctt gcaagcagtg cagcttcccg   4380
ttcatccgcc cgcgatgaca agttgacggc tcttttggca caattggatt ctttgacccg   4440
ggaacttaat gtcgtttctc agcagctgtt ggatctgcgc cagcaggttt ctgccctgaa   4500
ggcttcctcc cctcccaatg cggtttaaaa cataaataaa aaaccagact ctgtttggat   4560
ttggatcaag caagtgtctt gctgtctta tttaggggtt ttgcgcgcgc ggtaggcccg   4620
ggaccagcgg tctcggtcgt tgagggtcct gtgtattttt tccaggacgt ggtaaaggtg   4680
actctggatg ttcagataca tgggcataag cccgtctctg gggtggaggt agcaccactg   4740
cagagcttca tgctgcgggg tggtgttgta gatgatccag tcgtagcagg agcgctgggc   4800
gtggtgccta aaaatgtctt tcagtagcaa gctgattgcc aggggcaggc ccttggtgta   4860
agtgtttaca aagcggttaa gctgggatgg gtgcatacgt ggggatatga gatgcatctt   4920
ggactgtatt tttaggttgg ctatgttccc agccatatcc ctccggggat tcatgttgtg   4980
cagaaccacc agcacagtgt atccggtgca cttgggaaat tgtcatgta gcttagaagg   5040 aaatgcgtgg aagaacttgg agacgccctt gtgacctcca agattttcca tgcattcgtc   5100
cataatgatg gcaatgggcc cacgggcggc ggcctgggcg aagatatttc tgggatcact   5160
aacgtcatag ttgtgttcca ggatgagatc gtcataggcc attttacaa agcgcgggcg   5220 gagggtgcca gactgcggta taatggttcc atccggccca ggggcgtagt taccctcaca   5280
gatttgcatt tcccacgctt tgagttcaga tggggggatc atgtctacct gcggggcgat   5340
gaagaaaacg gtttccgggg taggggagat cagctgggaa gaaagcaggt tcctgagcag   5400
```

```
ctgcgactta ccgcagccgg tgggcccgta aatcacacct attaccggct gcaactggta    5460
gttaagagag ctgcagctgc cgtcatccct gagcaggggg gccacttcgt taagcatgtc    5520
cctgactcgc atgttttccc tgaccaaatc cgccagaagg cgctcgccgc ccagcgatag    5580
cagttcttgc aaggaagcaa agttttcaa cggtttgaga ccgtccgccg taggcatgct     5640
tttgagcgtt tgaccaagca gttccaggcg gtcccacagc tcggtcacct gctctacggc    5700
atctcgatcc agcatatctc ctcgtttcgc gggttggggc ggctttcgct gtacggcagt    5760
agtcggtgct cgtccagacg ggccagggtc atgtctttcc acgggcgcag ggtcctcgtc    5820
agcgtagtct gggtcacggt gaaggggtgc gctccgggct gcgcgctggc cagggtgcgc    5880
ttgaggctgg tcctgctggt gctgaagcgc tgccggtctt cgccctgcgc gtcggccagg    5940
tagcatttga ccatggtgtc atagtccagc ccctccgcgg cgtggcccct ggcgcgcagc    6000
ttgcccttgg aggaggcgcc gcacgagggg cagtgcagac ttttgagggc gtagagcttg    6060
ggcgcgagaa ataccgattc cggggagtag gcatccgcgc gcaggcccc gcagacggtc     6120 tcgcattcca cgagccaggt gagctctggc cgttcggggt caaaaaccag gtttccccca    6180 tgcttttga tgcgtttctt acctctggtt tccatgagcc ggtgtccacg ctcggtgacg     6240
aaaaggctgt ccgtgtcccc gtatacagac ttgagaggcc tgtcctcgag cggtgttccg    6300
cggtcctcct cgtatagaaa ctcggaccac tctgagacaa aggctcgcgt ccaggccagc    6360
acgaaggagg ctaagtggga gggtagcgg tcgttgtcca ctaggggtc cactcgctcc       6420 agggtgtgaa gacacatgtc gccctcttcg gcatcaagga aggtgattgg tttgtaggtg    6480
taggccacgt gaccgggtgt tcctgaaggg gggctataaa aggggtggg ggcgcgttcg     6540 tcctcactct cttccgcatc gctgtctgcg agggccagct gttggggtga gtactccctc    6600
tgaaaagcgg gcatgacttc tgcgctaaga ttgtcagttt ccaaaaacga ggaggatttg    6660
atattcacct ggcccgcggt gatgcctttg agggtggccg catccatctg gtcagaaaag    6720
acaatctttt tgttgtcaag cttggtggca acgacccgt agagggcgtt ggacagcaac      6780
ttggcgatgg agcgcagggt ttggttttg tcgcgatcgg cgcgctcctt ggccgcgatg      6840
tttagctgca cgtattcgcg cgcaacgcac cgccattcgg gaaagacggt ggtgcgctcg    6900
tcgggcacca ggtgcacgcg ccaaccgcgg ttgtgcaggg tgacaaggtc aacgctggtg    6960
gctacctctc cgcgtaggcg ctcgttggtc cagcagaggc ggccgcccct gcgcgagcag    7020
aatggcggta gggggtctag ctgcgtctcg tccgggggt ctgcgtccac ggtaaagacc      7080
ccgggcagca ggcgcgcgtc gaagtagtct atcttgcatc cttgcaagtc tagcgcctgc    7140
tgccatgcgc gggcggcaag cgcgcgctcg tatgggttga gtgggggacc ccatggcatg    7200
gggtgggtga gcgcggaggc gtacatgccg caaatgtcgt aaacgtagag gggctctctg    7260
agtattccaa gatatgtagg gtagcatctt ccaccgcgga tgctggcgcg cacgtaatcg    7320
tatagttcgt gcgagggagc gaggaggtcg ggaccgaggt tgctacgggc gggctgctct    7380
gctcggaaga ctatctgcct gaagatggca tgtgagttgg atgatatggt tggacgctgg    7440
aagacgttga agctggcgtc tgtgagacct accgcgtcac gcacgaagga ggcgtaggag    7500
tcgcgcagct tgttgaccag ctcggcgtg acctgcacgt ctaggcgca gtagtccagg       7560 gtttccttga tgatgtcata cttatcctgt ccctttttt tccacagctc gcggttgagg      7620
acaaactctt cgcggtcttt ccagtactct tggatcggaa accgtcggc ctccgaacgg      7680 taagagccta gcatgtagaa ctggttgacg gcctggtagg cgcagcatcc cttttctacg    7740
ggtagcgcgt atgcctgcgc ggccttccgg agcgaggtgt gggtgagcgc aaaggtgtcc    7800
```

```
ctgaccatga ccagcatgaa gggcacgagc tgcttcccaa aggcccccat ccaagtatag    7860
gtctctacat cgtaggtgac aaagagacgc tcggtgcgag gatgcgagcc gatcgggaag    7920
aactggatct cccgccacca attggaggag tggctattga tgtggtgaaa gtagaagtcc    7980
ctgcgacggg ccgaacactc gtgctggctt ttgtaaaaac gtgcgcagta ctggcagcgg    8040
tgcacgggct gtacatcctg cacgaggttg acctgacgac cgcgcacaag gaagcagagt    8100
gggaatttga gccccctcgcc tggcgggttt ggctggtggt cttctacttc ggctgcttgt    8160
ccttgaccgt ctggctgctc gagggagtt acggtggatc ggaccaccac gccgcgcgag    8220
cccaaagtcc agatgtccgc gcgcggcggt cggagcttga tgacaacatc gcgcagatgg    8280
gagctgtcca tggtctggag ctcccgcggc gtcaggtcag gcgggagctc ctgcaggttt    8340
acctcgcata gacgggtcag ggcgcgggct agatccaggt gatacctaat ttccaggggc    8400
tggttggtgg cggcgtcgat ggcttgcaag aggccgcatc cccgcggcgc gactacggta    8460
ccgcgcggcg ggcggtgggc gcgcggggtg tccttggatg atgcatctaa aagcggtgac    8520
gcgggcgagc ccccggaggt agggggggct ccggacccgc cgggagaggg ggcaggggca    8580
cgtcggcgcc gcgcgcgggc aggagctggt gctgcgcgcg taggttgctg gcgaacgcga    8640
cgacgcggcg gttgatctcc tgaatctggc gcctctgcgt gaagacgacg ggcccggtga    8700
gcttgaacct gaaagagagt tcgacagaat caatttcggt gtcgttgacg gcggcctggc    8760
gcaaaatctc ctgcacgtct cctgagttgt cttgataggc gatctcggcc atgaactgct    8820
cgatctcttc ctcctggaga tctccgcgtc cggctcgctc cacggtggcg gcgaggtcgt    8880
tggaaatgcg ggccatgagc tgcgagaagg cgttgaggcc tccctcgttc cagacgcggc    8940
tgtagaccac gccccccttcg gcatcgcggg cgcgcatgac cacctgcgcg agattgagct    9000
ccacgtgccg ggcgaagacg gcgtagtttc gcaggcgctg aaagaggtag ttgagggtgg    9060
tggcggtgtg ttctgccacg aagaagtaca taacccagcg tcgcaacgtg gattcgttga    9120
tatcccccaa ggcctcaagg cgctccatgg cctcgtagaa gtccacggcg aagttgaaaa    9180
actgggagtt gcgcgccgac acggttaact cctcctccag aagacggatg agctcggcga    9240
cagtgtcgcg cacctcgcgc tcaaaggcta caggggcctc ttcttcttct tcaatctcct    9300
cttccataag ggcctcccct tcttcttctt ctggcggcgg tggggagggg gggacacggc    9360
ggcgacgacg gcgcaccggg aggcggtcga caaagcgctc gatcatctcc ccgcggcgac    9420
ggcgcatggt ctcggtgacg gcgcggccgt tctcgcgggg gcgcagttgg aagacgccgc    9480
ccgtcatgtc ccggttatgg gttggcgggg ggctgccatg cggcagggat acggcgctaa    9540
cgatgcatct caacaattgt tgtgtaggta ctccgccgcc gagggacctg agcgagtccg    9600
catcgaccgg atcggaaaac ctctcgagaa aggcgtctaa ccagtcacag tgcaaggta    9660 ggctgagcac cgtggcgggc ggcagcgggc ggcggtcggg gttgtttctg gcggaggtgc    9720
tgctgatgat gtaattaaag taggcggtct tgagacggcg gatggtcgac agaagcacca    9780
tgtccttggg tccggcctgc tgaatgcgca ggcggtcggc catgcccag gcttcgtttt    9840 gacatcggcg caggtctttg tagtagtctt gcatgagcct ttctaccggc acttcttctt    9900
ctccttcctc ttgtcctgca tctcttgcat ctatcgctgc ggcggcggcg gagtttggcc    9960
gtaggtggcg ccctcttcct cccatgcgtg tgaccccgaa gcccctcatc ggctgaagca    10020
gggctaggtc ggcgacaacg cgctcggcta atatggcctg ctgcacctgc gtgagggtag    10080
actggaagtc atccatgtcc acaaagcggt ggtatgcgcc cgtgttgatg gtgtaagtgc    10140
```

```
agttggccat aacggaccag ttaacggtct ggtgacccgg ctgcgagagc tcggtgtacc    10200
tgagacgcga gtaagccctc gagtcaaata cgtagtcgtt gcaagtccgc accaggtact    10260
ggtatcccac caaaaagtgc ggcggcggct ggcggtagag gggccagcgt agggtggccg    10320
gggctccggg ggcgagatct tccaacataa ggcgatgata tccgtagatg tacctggaca    10380
tccaggtgat gccggcggcg gtggtggagg cgcgcggaaa gtcgcggacg cggttccaga    10440
tgttgcgcag cggcaaaaag tgctccatgg tcgggacgct ctggccggtc aggcgcgcgc    10500
aatcgttgac gctctagacc gtgcaaaagg agagcctgta agcgggcact cttccgtggt    10560
ctggtggata aattcgcaag ggtatcatgg cggacgaccg gggttcgagc cccgtatccg    10620
gccgtccgcc gtgatccatg cggttaccgc ccgcgtgtcg aacccaggtg tgcgacgtca    10680
gacaacgggg gagtgctcct tttggcttcc ttccaggcgc ggcggctgct gcgctagctt    10740
ttttggccac tggccgcgcg cagcgtaagc ggttaggctg gaaagcgaaa gcattaagtg    10800
gctcgctccc tgtagccgga gggttatttt ccaagggttg agtcgcggga ccccggttc    10860
gagtctcgga ccggccggac tgcggcgaac ggggtttgc ctccccgtca tgcaagaccc    10920
cgcttgcaaa ttcctccgga aacagggacg agcccttttt ttgcttttcc cagatgcatc    10980
cggtgctgcg gcagatgcgc cccctcctc agcagcggca gagcaagag cagcggcaga    11040
catgcagggc accctcccct cctcctaccg cgtcaggagg ggcgacatcc gcggttgacg    11100
cggcagcaga tggtgattac gaaccccgc ggcgccgggc ccggcactac ctggacttgg    11160
aggagggcga gggcctggcg cggctaggag cgccctctcc tgagcggcac ccaagggtgc    11220
agctgaagcg tgatacgcgt gaggcgtacg tgccgcggca gaacctgttt cgcgaccgcg    11280
agggagagga gcccgaggag atgcgggatc gaaagttcca cgcagggcgc gagctgcggc    11340
atggcctgaa tcgcgagcgg ttgctgcgcg aggaggactt tgagcccgac gcgcgaaccg    11400
ggattagtcc cgcgcgcgca cacgtggcgg ccgccgacct ggtaaccgca tacgagcaga    11460
cggtgaacca ggagattaac tttcaaaaaa gctttaacaa ccacgtgcgt acgcttgtgg    11520
cgcgcgagga ggtggctata ggactgatgc atctgtggga cttttgtaagc gcgctggagc    11580
aaaacccaaa tagcaagccg ctcatggcgc agctgttcct tatagtgcag cacagcaggg    11640
acaacgaggc attcagggat gcgctgctaa acatagtaga gcccgagggc cgctggctgc    11700
tcgatttgat aaacatcctg cagagcatag tggtgcagga cgcagcttg agcctggctg    11760
acaaggtggc cgccatcaac tattccatgc ttagcctggg caagttttac gcccgcaaga    11820
tataccatac ccccttacgtt cccatagaca aggaggtaaa gatcgagggg ttctacatgc    11880
gcatggcgct gaaggtgctt accttgagcg acgacctggg cgtttatcgc aacgagcgca    11940
tccacaaggc cgtgagcgtg agccggcggc gcgagctcag cgaccgcgag ctgatgcaca    12000
gcctgcaaag ggccctggct ggcacgggca gcggcgatag agaggccgag tcctactttg    12060
acgcgggcgc tgacctgcgc tgggcccaa gccgacgcgc cctggaggca gctgggccg    12120
gacctgggct ggcggtggca cccgcgcgcg ctggcaacgt cggcggcgtg gaggaatatg    12180
acgaggacga tgagtacgag ccagaggacg gcgagtacta agcggtgatg tttctgatca    12240
gatgatgcaa gacgcaacgg acccggcggt gcggcggcg ctgcagagcc agccgtccgg    12300
ccttaactcc acggacgact ggcgccaggt catggaccgc atcatgtcgc tgactgcgcg    12360
caatcctgac gcgttccggc agcagccgca ggccaaccgg ctctccgcaa ttctggaagc    12420
ggtggtcccg cgcgcgcgcaa accccacgca cgagaaggtg ctggcgatcg taaacgcgct    12480
ggccgaaaac agggccatcc ggcccgacga ggccggcctg gtctacgacg cgctgcttca    12540
```

```
gcgcgtggct cgttacaaca gcggcaacgt gcagaccaac ctggaccggc tggtggggga   12600
tgtgcgcgag gccgtggcgc agcgtgagcg cgcgcagcag cagggcaacc tgggctccat   12660
ggttgcacta aacgccttcc tgagtacaca gcccgccaac gtgccgcggg gacaggagga   12720
ctacaccaac tttgtgagcg cactgcggct aatggtgact gagacaccgc aaagtgaggt   12780
gtaccagtct gggccagact attttttcca gaccagtaga caaggcctgc agaccgtaaa   12840
cctgagccag gctttcaaaa acttgcaggg gctgtggggg gtgcgggctc ccacaggcga   12900
ccgcgcgacc gtgtctagct tgctgacgcc caactcgcgc tgttgctgc tgctaatagc    12960
gcccttcacg gacagtggca gcgtgtcccg ggacacatac ctaggtcact tgctgacact   13020
gtaccgcgag gccataggtc aggcgcatgt ggacgagcat actttccagg agattacaag   13080
tgtcagccgc gcgctgggc aggaggacac gggcagcctg gaggcaaccc taaactacct    13140
gctgaccaac cggcggcaga agatcccctc gttgcacagt ttaaacagcg aggaggagcg   13200
cattttgcgc tacgtgcagc agagcgtgag ccttaacctg atgcgcgacg ggtaacgcc    13260
cagcgtggcg ctggacatga ccgcgcgcaa catggaaccg ggcatgtatg cctcaaaccg   13320
gccgtttatc aaccgcctaa tggactactt gcatcgcgcg gccgccgtga accccgagta   13380
tttcaccaat gccatcttga acccgcactg gctaccgccc cctggtttct acaccggggg   13440
attcgaggtg cccgagggta acgatggatt cctctgggac gacatagacg acagcgtgtt   13500
ttccccgcaa ccgcagaccc tgctagagtt gcaacagcgc gagcaggcag aggcggcgct   13560
gcgaaaggaa agcttccgca ggccaagcag cttgtccgat ctaggcgctg cggccccgcg   13620
gtcagatgct agtagcccat ttccaagctt gatagggtct cttaccagca ctcgcaccac   13680
ccgcccgcgc ctgctgggcg aggaggagta cctaaacaac tcgctgctgc agccgcagcg   13740
cgaaaaaaac ctgcctccgg catttcccaa caacgggata gagagcctag tggacaagat   13800
gagtagatgg aagacgtacg cgcaggagca cagggacgtg ccaggcccgc gcccgcccac   13860
ccgtcgtcaa aggcacgacc gtcagcgggg tctggtgtgg gaggacgatg actcggcaga   13920
cgacagcagc gtcctggatt tgggagggag tggcaacccg tttgcgcacc ttcgccccag   13980
gctggggaga atgttttaaa aaaaaaaaa gcatgatgca aataaaaaa ctcaccaagg     14040
ccatggcacc gagcgttggt tttcttgtat tccccttagt atgcggcgcg cggcgatgta   14100
tgaggaaggt cctcctccct cctacgagag tgtggtgagc gcggcgccag tggcggcggc   14160
gctgggttct cccttcgatg ctcccctgga cccgccgttt gtgcctccgc ggtacctgcg   14220
gcctaccggg gggagaaaca gcatccgtta ctctgagttg gcaccccat tcgacaccac    14280
ccgtgtgtac ctggtggaca acaagtcaac ggatgtggca tccctgaact accagaacga   14340
ccacagcaac tttctgacca cggtcattca aaacaatgac tacagcccgg gggaggcaag   14400
cacacagacc atcaatcttg acgaccggtc gcactggggc ggcgacctga aaaccatcct   14460
gcataccaac atgccaaatg tgaacgagtt catgtttacc aataagttta aggcgcgggt   14520
gatggtgtcg cgcttgccta ctaaggacaa tcaggtggag ctgaaatacg agtgggtgga   14580
gttcacgctg cccgagggca actactccga gaccatgacc atagacctta tgaacaacgc   14640
gatcgtggag cactacttga agtgggcag acagaacggg gttctggaaa gcgacatcgg   14700
ggtaaagttt gacacccgca acttcagact gggggtttgac cccgtcactg gtcttgtcat   14760
gcctgggggta tatacaaacg aagccttcca tccagacatc attttgctgc caggatgcgg   14820
ggtggacttc acccacagcc gcctgagcaa cttgttgggc atccgcaagc ggcaacccct   14880
```

```
ccaggagggc tttaggatca cctacgatga tctggagggt ggtaacattc ccgcactgtt  14940
ggatgtggac gcctaccagg cgagcttgaa agatgacacc gaacagggcg ggggtggcgc  15000
aggcggcagc aacagcagtg gcagcggcgc ggaagagaac tccaacgcgg cagccgcggc  15060
aatgcagccg gtggaggaca tgaacgatca tgccattcgc ggcgacacct ttgccacacg  15120
ggctgaggag aagcgcgctg aggccgaagc agcggccgaa gctgccgccc ccgctgcgca  15180
acccgaggtc gagaagcctc agaagaaacc ggtgatcaaa cccctgacag aggacagcaa  15240
gaaacgcagt tacaacctaa taagcaatga cagcaccttc acccagtacc gcagctggta  15300
ccttgcatac aactacggcg accctcagac cggaatccgc tcatggaccc tgctttgcac  15360
tcctgacgta acctgcggct cggagcaggt ctactggtcg ttgccagaca tgatgcaaga  15420
ccccgtgacc ttccgctcca cgcgccagat cagcaacttt ccggtggtgg cgccgagct   15480
gttgcccgtg cactccaaga gcttctacaa cgaccaggcc gtctactccc aactcatccg  15540
ccagtttacc tctctgaccc acgtgttcaa tcgctttccc gagaaccaga ttttggcgcg  15600
cccgccagcc cccaccatca ccaccgtcag tgaaaacgtt cctgctctca cagatcacgg  15660
gacgctaccg ctgcgcaaca gcatcggagg agtccagcga gtgaccatta ctgacgccag  15720
acgccgcacc tgcccctacg tttacaaggc cctgggcata gtctcgccgc gcgtcctatc  15780
gagccgcact ttttgagcaa gcatgtccat ccttatatcg cccagcaata acacaggctg  15840
gggcctgcgc ttcccaagca agatgtttgg cggggccaag aagcgctccg accaacaccc  15900
agtgcgcgtg cgcgggcact accgcgcgcc ctggggcgcg cacaaacgcg gccgcactgg  15960
gcgcaccacc gtcgatgacg ccatcgacgc ggtggtggag gaggcgcgca actacacgcc  16020
cacgccgcca ccagtgtcca cagtggacgc ggccattcag accgtggtgc gcggagcccg  16080
gcgctatgct aaaatgaaga acggcgcgag gcgcgtagca cgtcgccacc gccgccgacc  16140
cggcactgcc gcccaacgcg cggcggcggc cctgcttaac cgcgcacgtc gcaccggccg  16200
acgggcggcc atgcgggccg ctcgaaggct ggccgcgggt attgtcactg tgcccccccag  16260
gtccaggcga cgagcggccg ccgcagcagc cgcggccatt agtgctatga ctcagggtcg  16320
cagggggcaac gtgtattggg tgcgcgactc ggttagcggc ctgcgcgtgc ccgtgcgcac  16380
ccgccccccg cgcaactaga ttgcaagaaa aaactactta gactcgtact gttgtatgta  16440
tccagcggcg gcgcgcgcca acgaagctat gtccaagcgc aaaatcaaag aagagatgct  16500
ccaggtcatc gcgccggaga tctatggccc cccgaagaag gaagagcagg attacaagcc  16560
ccgaaagcta aagcgggtca aaagaaaaa gaaagatgat gatgatgaac ttgacgacga  16620
ggtggaactg ctgcacgcta ccgcgcccag gcgacgggta cagtggaaag gtcgacgcgt  16680
aaaacgtgtt ttgcgacccg gcaccaccgt agtctttacg cccggtgagc gctccacccg  16740
cacctacaag cgcgtgtatg atgaggtgta cggcgacgag gacctgcttg agcaggccaa  16800
cgagcgcctc ggggagtttg cctacggaaa gcggcataag gacatgctgg cgttgccgct  16860
ggacgagggc aacccaacac ctagcctaaa gcccgtaaca ctgcagcagg tgctgccgc   16920
gcttgcaccg tccgaagaaa agcgcggcct aaagcgcgag tctggtgact ggcacccac   16980
cgtgcagctg atggtaccca agcgccacg actggaagat gtcttggaaa aaatgaccgt  17040
ggaacctggg ctggagcccg aggtccgcgt gcggccaatc aagcaggtgg cgccgggact  17100
gggcgtgcag accgtggacg ttcagatacc cactaccagt agcaccagta ttgccaccgc  17160
cacagagggc atgagacac aaacgtcccc ggttgcctca gcggtggcgg atgccgcggt  17220
gcaggcggtc gctgcggccg cgtccaagac ctctacggag gtgcaaacgg acccgtggat  17280
```

```
gtttcgcgtt tcagcccccc ggcgcccgcg ccgttcgagg aagtacggcg ccgccagcgc   17340
gctactgccc gaatatgccc tacatccttc cattgcgcct accccggct atcgtggcta    17400 cacctaccgc cccagaagac gagcaactac ccgacgccga accaccactg gaacccgccg   17460
ccgccgtcgc cgtcgccagc ccgtgctggc cccgatttcc gtgcgcaggg tggctcgcga   17520
aggaggcagg accctggtgc tgccaacagc gcgctaccac cccagcatcg tttaaaagcc   17580
ggtctttgtg gttcttgcag atatggccct cacctgccgc ctccgtttcc cggtgccggg   17640
attccgagga agaatgcacc gtaggagggg catggccggc cacggcctga cgggcggcat   17700
gcgtcgtgcg caccaccggc ggcggcgcgc gtcgcaccgt cgcatgcgcg gcggtatcct   17760 gccccctcctt attccactga tcgccgcggc gattggcgcc gtgcccggaa ttgcatccgt   17820
ggccttgcag gcgcagagac actgattaaa aacaagttgc atgtggaaaa atcaaaataa   17880
aaagtctgga ctctcacgct cgcttggtcc tgtaactatt ttgtagaatg aagacatca    17940 actttgcgtc tctggccccg cgacacggct cgcgcccgtt catgggaaac tgcaagata    18000 tcggcaccag caatatgagc ggtggcgcct tcagctgggg ctcgctgtgg agcggcatta   18060
aaaatttcgg ttccaccgtt aagaactatg gcagcaaggc ctggaacagc agcacaggcc   18120
agatgctgag ggataagttg aaagagcaaa atttccaaca aaaggtggta gatggcctgg   18180
cctctggcat tagcggggtg gtggacctgg ccaaccaggc agtgcaaaat aagattaaca   18240
gtaagcttga tccccgccct cccgtagagg agcctccacc ggccgtggag acagtgtctc   18300
cagaggggcg tggcgaaaag cgtccgcgcc ccgacaggga agaaactctg gtgacgcaaa   18360
tagacgagcc tccctcgtac gaggaggcac taaagcaagg cctgcccacc accgtccca    18420 tcgcgcccat ggctaccgga gtgctgggcc agcacacacc cgtaacgctg acctgcctc    18480 cccccgccga cacccagcag aaacctgtgc tgccaggccc gaccgccgtt gttgtaaccc   18540
gtcctagccg cgcgtccctg cgccgcgccg ccagcgtcc gcgatcgttg cggcccgtag   18600
ccagtggcaa ctggcaaagc acactgaaca gcatcgtggg tctgggggtg caatccctga   18660
agcgccgacg atgcttctga tagctaacgt gtcgtatgtg tgtcatgtat gcgtccatgt   18720
cgccgccaga ggagctgctg agccgccgcg cgcccgcttt ccaagatggc taccccttcg   18780
atgatgccgc agtggtctta catgcacatc tcgggccagg acgcctcgga gtacctgagc   18840
cccgggctgg tgcagtttgc ccgcgccacc gagacgtact tcagcctgaa taacaagttt   18900
agaaacccca cggtggcgcc tacgcacgac gtgaccacag accggtccca gcgtttgacg   18960
ctgcggttca tccctgtgga ccgtgaggat actgcgtact cgtacaaggc gcggttcacc   19020
ctagctgtgg gtgataaccg tgtgctggac atggcttcca cgtactttga catccgcggc   19080
gtgctggaca ggggccctac ttttaagccc tactctggca ctgcctacaa cgccctggct   19140
cccaagggtg ccccaaatcc ttgcgaatgg gatgaagctg ctactgctct tgaaataaac   19200
ctagaagaag aggacgatga caacgaagac gaagtagacg agcaagctga gcagcaaaaa   19260
actcacgtat ttgggcaggc gccttattct ggtataaata ttacaaagga gggtattcaa   19320
ataggtgtcg aaggtcaaac acctaaatat gccgataaaa catttcaacc tgaacctcaa   19380
ataggagaat ctcagtggta cgaaacagaa attaatcatg cagctgggag agtcctaaaa   19440
aagactaccc caatgaaacc atgttacggt tcatatgcaa aacccacaaa tgaaatgga    19500 gggcaaggca ttcttgtaaa gcaacaaaat ggaaagctag aaagtcaagt ggaaatgcaa   19560
tttttctcaa ctactgaggc agccgcaggc aatggtgata acttgactcc taagtggta    19620
```

```
ttgtacagtg aagatgtaga tatagaaacc ccagacactc atatttctta catgcccact   19680
attaaggaag gtaactcacg agaactaatg ggccaacaat ctatgcccaa caggcctaat   19740
tacattgctt ttagggacaa ttttattggt ctaatgtatt acaacagcac gggtaatatg   19800
ggtgttctgg cgggccaagc atcgcagttg aatgctgttg tagatttgca agacagaaac   19860
acagagcttt cataccagct tttgcttgat tccattggtg atagaaccag gtactttttct  19920
atgtggaatc aggctgttga cagctatgat ccagatgtta gaattattga aaatcatgga   19980
actgaagatg aacttccaaa ttactgcttt ccactgggag gtgtgattaa tacagagact   20040
cttaccaagg taaaacctaa aacaggtcag gaaaatggat gggaaaaaga tgctacagaa   20100
ttttcagata aaaatgaaat aagagttgga aataattttg ccatggaaat caatctaaat   20160
gccaacctgt ggagaaattt cctgtactcc aacatagcgc tgtatttgcc cgacaagcta   20220
aagtacagtc cttccaacgt aaaaatttct gataacccaa acacctacga ctacatgaac   20280
aagcgagtgg tggctcccgg gctagtggac tgctacatta accttggagc acgctggtcc   20340
cttgactata tggacaacgt caacccattt aaccaccacc gcaatgctgg cctgcgctac   20400
cgctcaatgt tgctgggcaa tggtcgctat gtgcccttcc acatccaggt gcctcagaag   20460
ttctttgcca ttaaaaacct ccttctcctg ccgggctcat acacctacga gtggaacttc   20520
aggaaggatg ttaacatggt tctgcagagc tccctaggaa atgacctaag ggttgacgga   20580
gccagcatta agtttgatag catttgcctt tacgccacct tcttccccat ggcccacaac   20640
accgcctcca cgcttgaggc catgcttaga aacgacacca cgaccagtc ctttaacgac   20700
tatctctccg ccgccaacat gctctaccct ataccggcca acgctaccaa cgtgcccata   20760
tccatcccct cccgcaactg ggcggctttc cgcggctggg ccttcacgcg ccttaagact   20820
aaggaaaccc catcactggg ctcgggctac gacccttatt acacctactc tggctctata   20880
ccctacctag atggaaccctt ttacctcaac cacaccttta gaaggtggc cattacccttt 20940
gactcttctg tcagctggcc tggcaatgac cgcctgctta cccccaacga gtttgaaatt   21000
aagcgctcag ttgacgggga gggttacaac gttgcccagt gtaacatgac caaagactgg   21060
ttcctggtac aaatgctagc taactataac attggctacc agggcttcta tatcccagag   21120
agctacaagg accgcatgta ctccttcttt agaaacttcc agcccatgag ccgtcaggtg   21180
gtggatgata ctaaatacaa ggactaccaa caggtgggca tcctacacca acacaacaac   21240
tctggatttg ttggctacct tgcccccacc atgcgcgaag gacaggccta ccctgctaac   21300
ttcccctatc cgcttatagg caagaccgca gttgacagca ttacccagaa aaagtttctt   21360
tgcgatcgca ccctttggcg catcccattc tccagtaact ttatgtccat gggcgcactc   21420
acagacctgg gccaaaaacct tctctacgcc aactccgccc acgcgctaga catgactttt   21480
gaggtggatc ccatggacga gcccacccctt ctttatgttt tgtttgaagt ctttgacgtg   21540
gtccgtgtgc accagccgca ccgcggcgtc atcgaaaccg tgtacctgcg cacgcccttc   21600
tcggccggca acgccacaac ataaagaagc aagcaacatc aacaacagct gccgccaaat   21660
aatgtactag agacactttc aataaaggca aatgctttta tttgtacact ctcgggtgat   21720
tatttacccc cacccttgcc gtctgcgccg tttaaaaatc aaaggggttc tgccgcgcat   21780
cgctatgcgc cactggcagg gacacgttgc gatactggtg tttagtgctc cacttaaact   21840
caggcacaac catccgcggc agctcggtga agttttcact ccacaggctg cgcaccatca   21900
ccaacgcgtt tagcaggtcg ggcgccgata tcttgaagtc gcagtggggg cctccgcctt   21960
gcgcgcgcga gttgcgatac acagggttgc agcactggaa cactatcagc gccgggtggt   22020
```

```
gcacgctggc cagcacgctc ttgtcggaga tcagatccgc gtccaggtcc tccgcgttgc   22080
tcagggcgaa cggagtcaac tttggtagct gccttcccaa aaagggcgcg tgcccaggct   22140
ttgagttgca ctcgcaccgt agtggcatca aaaggtgacc gtgcccggtc tgggcgttag   22200
gatacagcgc ctgcataaaa gccttgatct gcttaaaagc cacctgagcc tttgcgcctt   22260
cagagaagaa catgccgcaa gacttgccgg aaaactgatt ggccggacag gccgcgtcgt   22320
gcacgcagca ccttgcgtcg gtgttggaga tctgcaccac atttcggccc caccggttct   22380
tcacgatctt ggccttgcta gactgctcct tcagcgcgcg ctgcccgttt cgctcgtca    22440
catccatttc aatcacgtgc tccttattta tcataatgct tccgtgtaga cacttaagct   22500
cgccttcgat ctcagcgcag cggtgcagcc acaacgcgca gcccgtgggc tcgtgatgct   22560
tgtaggtcac ctctgcaaac gactgcaggt acgcctgcag gaatcgcccc atcatcgtca   22620
caaaggtctt gttgctggtg aaggtcagct gcaacccgcg gtgctcctcg ttcagccagg   22680
tcttgcatac ggccgccaga gcttccactt ggtcaggcag tagtttgaag ttcgccttta   22740
gatcgttatc cacgtggtac ttgtccatca gcgcgcgcgc agcctccatg cccttctccc   22800
acgcagacac gatcggcaca ctcagcgggt tcatcaccgt aatttcactt tccgcttcgc   22860
tgggctcttc ctcttcctct tgcgtccgca taccacgcgc cactgggtcg tcttcattca   22920
gccgccgcac tgtgcgctta cctcctttgc catgcttgat tagcaccggt gggttgctga   22980
aacccaccat ttgtagcgcc acatcttctc tttcttcctc gctgtccacg attacctctg   23040
gtgatgcgg gcgctcgggc ttgggagaag ggcgcttctt tttcttcttg ggcgcaatgg    23100
ccaaatccgc cgccgaggtc gatggccgcg ggctgggtgt gcgcggcacc agcgcgtctt   23160
gtgatgagtc ttcctcgtcc tcggactcga tacgccgcct catccgcttt tttgggggcg   23220
cccggggagg cggcggcgac ggggacgggg acgacacgtc ctccatggtt ggggggacgtc  23280
gcgccgcacc gcgtccgcgc tcggggtgg tttcgcgctg ctcctcttcc cgactggcca    23340
tttccttctc ctataggcag aaaaagatca tggagtcagt cgagaagaag gacagcctaa   23400
ccgcccctc tgagttcgcc accaccgcct ccaccgatgc cgccaacgcg cctaccacct    23460
tccccgtcga ggcacccccg cttgaggagg aggaagtgat tatcgagcag gacccaggtt   23520
ttgtaagcga agacgacgag gaccgctcag taccaacaga ggataaaaag caagaccagg   23580
acaacgcaga ggcaaacgag gaacaagtcg ggcgggggga cgaaaggcat ggcgactacc   23640
tagatgtggg agacgacgtg ctgttgaagc atctgcagcg ccagtgcgcc attatctgcg   23700
acgcgttgca agagcgcagc gatgtgcccc tcgccatagc ggatgtcagc cttgcctacg   23760
aacgccacct attctcaccg cgcgtacccc ccaaacgcca agaaaacggc acatgcgagc   23820
ccaacccgcg cctcaacttc taccccgtat ttgccgtgcc agaggtgctt gccacctatc   23880
acatcttttt ccaaaactgc aagatacccc tatcctgccg tgccaaccgc agccgagcgg   23940
acaagcagct ggccttgcgg cagggcgctg tcatacctga tatcgcctcg ctcaacgaag   24000
tgccaaaaat ctttgagggt cttggacgcg acgagaagcg cgcggcaaac gctctgcaac   24060
aggaaaacag cgaaaatgaa agtcactctg gagtgttggt ggaactcgag ggtgacaacg   24120
cgcgcctagc cgtactaaaa cgcagcatcg aggtcaccca ctttgcctac ccggcactta   24180
acctaccccc caaggtcatg agcacagtca tgagtgagct gatcgtgcgc cgtgcgcagc   24240
ccctggagag ggatgcaaat ttgcaagaac aaacagagga gggcctaccc gcagttggcg   24300
acgagcagct agcgcgctgg cttcaaacgc gcgagcctgc cgacttggag gagcgacgca   24360
```

```
aactaatgat ggccgcagtg ctcgttaccg tggagcttga gtgcatgcag cggttctttg   24420
ctgacccgga gatgcagcgc aagctagagg aaacattgca ctacacccttt cgacagggct   24480 acgtacgcca ggcctgcaag atctccaacg tggagctctg caacctggtc tcctaccttg   24540
gaattttgca cgaaaaccgc cttgggcaaa acgtgcttca ttccacgctc aagggcgagg   24600
cgcgccgcga ctacgtccgc gactgcgttt acttatttct atgctacacc tggcagacgg   24660
ccatgggcgt ttggcagcag tgcttggagg agtgcaacct caaggagctg cagaaactgc   24720
taaagcaaaa cttgaaggac ctatggacgg ccttcaacga gcgctccgtg gccgcgcacc   24780
tggcggacat cattttcccc gaacgcctgc ttaaaaccct gcaacagggt ctgccagact   24840
tcaccagtca aagcatgttg cagaacttta ggaactttat cctagagcgc tcaggaatct   24900
tgcccgccac ctgctgtgca cttcctagcg actttgtgcc cattaagtac gcgaatgcc    24960 ctccgccgct ttggggccac tgctaccttc tgcagctagc caactacctt gcctaccact   25020
ctgacataat ggaagacgtg agcggtgacg gtctactgga gtgtcactgt cgctgcaacc   25080
tatgcacccc gcaccgctcc ctggtttgca attcgcagct gcttaacgaa agtcaaatta   25140
tcggtacctt tgagctgcag ggtccctcgc ctgacgaaaa gtccgcggct ccggggttga   25200
aactcactcc ggggctgtgg acgtcggctt accttcgcaa atttgtacct gaggactacc   25260
acgcccacga gattaggttc tacgaagacc aatcccgccc gcctaatgcg agcttaccg    25320 cctgcgtcat tacccagggc cacattcttg gccaattgca agccatcaac aaagcccgcc   25380
aagagtttct gctacgaaag ggacgggggg tttacttgga cccccagtcc ggcgaggagc   25440
tcaacccaat ccccccgccg ccgcagccct atcagcagca gccgcgggcc cttgcttccc   25500
aggatggcac ccaaaaagaa gctgcagctg ccgccgccac ccacggacga ggaggaatac   25560
tgggacagtc aggcagagga ggttttggac gaggaggagg aggacatgat ggaagactgg   25620
gagagcctag acgaggaagc ttccgaggtc gaagaggtgt cagacgaaac accgtcaccc   25680
tcggtcgcat tcccctcgcc ggcgcccag aaatcggcaa ccggttccag catggctaca    25740
acctccgctc ctcaggcgcc gccggcactg cccgttcgcc gacccaaccg tagatgggac   25800
accactggaa ccagggccgg taagtccaag cagccgccgc cgttagccca agagcaacaa   25860
cagcgccaag gctaccgctc atggcgcggg cacaagaacg ccatagttgc ttgcttgcaa   25920
gactgtgggg gcaacatctc cttcgcccgc cgctttcttc tctaccatca cggcgtggcc   25980
ttcccccgta acatcctgca ttactaccgt catctctaca gcccatactg caccggcggc   26040
agcggcagca acagcagcgg ccacacagaa gcaaaggcga ccggatagca agactctgac   26100
aaagcccaag aaatccacag cggcggcagc agcaggagga ggagcgctgc gtctggcgcc   26160
caacgaaccc gtatcgaccc gcgagcttag aaacaggatt tttcccactc tgtatgctat   26220
atttcaacag agcaggggcc aagaacaaga gctgaaaata aaaaacaggt ctctgcgatc   26280
cctcacccgc agctgcctgt atcacaaaag cgaagatcag cttcggcgca cgctggaaga   26340
cgcggaggct ctcttcagta atactgcgcg gctgactctt aaggactagt ttcgcgccct   26400
ttctcaaatt taagcgcgaa aactacgtca tctccagcgg ccacacccgg cgccagcacc   26460
tgttgtcagc gccattatga gcaaggaaat tcccacgccc tacatgtgga gttaccagcc   26520
acaaatggga cttgcggctg gagctgccca agactactca acccgaataa actacatgag   26580
cgcgggaccc cacatgatat cccgggtcaa cggaatacgc gcccaccgaa accgaattct   26640
cctgaaacag gcggctatta ccaccacacc tcgtaataac cttaatcccc gtagttggcc   26700
cgctgccctg gtgtaccagg aaagtcccgc tcccaccact gtggtacttc ccagagacgc   26760
```

```
ccaggccgaa gttcagatga ctaactcagg ggcgcagctt gcgggcggct ttcgtcacag   26820
ggtgcggtcg cccgggcagg gtataactca cctgacaatc agagggcgag gtattcagct   26880
caacgacgag tcggtgagct cctcgcttgg tctccgtccg gacgggacat ttcagatcgg   26940
cggcgccggc cgctcttcat tcacgcctcg tcaggcaatc ctaactctgc agacctcgtc   27000
ctctgagccg cgctctggag gcattggaac tctgcaattt attgaggagt ttgtgccatc   27060
ggtctacttt aaccccttct cgggacctcc cggccactat ccggatcaat ttattcctaa   27120 cttttgacgcg gtaaaggact cggcggacgg ctacgactga atgttaagtg gagaggcaga   27180
gcaactgcgc ctgaaacacc tggtccactg tcgccgccac aagtgctttg cccgcgactc   27240
cggtgagttt tgctactttg aattgcccga ggatcatatc gagggcccgg cgcacggcgt   27300
ccggcttacc gcccagggag agcttgcccg tagcctgatt cgggagttta cccagcgccc   27360
cctgctagtt gagcgggaca ggggaccctg tgttctcact gtgatttgca actgtcctaa   27420
ccctggatta catcaagatc tttgttgcca tctctgtgct gagtataata aatacagaaa   27480
ttaaaatata ctggggctcc tatcgccatc ctgtaaacgc caccgtcttc acccgcccaa   27540
gcaaaccaag gcgaacctta cctggtactt ttaacatctc tccctctgtg atttacaaca   27600
gtttcaaccc agacggagtg agtctacgag agaacctctc cgagctcagc tactccatca   27660
gaaaaaacac caccctcctt acctgccggg aacgtacgag tgcgtcaccg gccgctgcac   27720
cacacctacc gcctgaccgt aaaccagact ttttccggac agacctcaat aactctgttt   27780
accagaacag gaggtgagct tagaaaaccc ttagggtatt aggccaaagg cgcagctact   27840
gtggggttta tgaacaattc aagcaactct acgggctatt ctaattcagg tttctctaga   27900
aatggacgga attattacag agcagcgcct gctagaaaga cgcagggcag cggccgagca   27960
acagcgcatg aatcaagagc tccaagacat ggttaacttg caccagtgca aaggggtat   28020 cttttgtctg gtaaagcagg ccaaagtcac ctacgacagt aataccaccg gacaccgcct   28080
tagctacaag ttgccaacca agcgtcagaa attggtggtc atggtgggag aaaagcccat   28140
taccataact cagcactcgg tagaaaccga aggctgcatt cactcacctt gtcaaggacc   28200
tgaggatctc tgcaccctta ttaagaccct gtgcggtctc aaagatctta ttcccttta   28260 ctaataaaaa aaaataataa agcatcactt acttaaaatc agttagcaaa tttctgtcca   28320
gtttattcag cagcacctcc ttgccctcct cccagctctg gtattgcagc ttcctcctgg   28380
ctgcaaactt tctccacaat ctaaatggaa tgtcagtttc ctcctgttcc tgtccatccg   28440
cacccactat cttcatgttg ttgcagatga agcgcgcaag accgtctgaa gataccttca   28500
accccgtgta tccatatgac acggaaaccg gtcctccaac tgtgccttt cttactcctc   28560 cctttgtatc ccccaatggg tttcaagaga gtcccctgg ggtactctct ttgcgcctat   28620
ccgaacctct agttacctcc aatggcatgc ttgcgctcaa aatgggcaac ggcctctctc   28680
tggacgaggc cggcaacctt acctcccaaa atgtaaccac tgtgagccca cctctcaaaa   28740
aaaccaagtc aaacataaac ctggaaatat ctgcaccct cacagttacc tcagaagccc   28800
taactgtggc tgccgccgca cctctaatgg tcgcgggcaa cacactcacc atgcaatcac   28860
aggccccgct aaccgtgcac gactccaaac ttagcattgc cacccaagga cccctcacag   28920
tgtcagaagg aaagctagcc ctgcaaacat caggcccct caccaccacc gatagcagta   28980
cccttactat cactgcctca ccccctctaa ctactgccac tggtagcttg ggcattgact   29040
tgaaagagcc catttataca caaaatggaa aactaggact aaagtacggg gctcctttgc   29100
```

```
atgtaacaga cgacctaaac actttgaccg tagcaactgg tccaggtgtg actattaata    29160
atacttcctt gcaaactaaa gttactggag ccttgggttt tgattcacaa ggcaatatgc    29220
aacttaatgt agcaggagga ctaaggattg attctcaaaa cagacgcctt atacttgatg    29280
ttagttatcc gtttgatgct caaaaccaac taaatctaag actaggacag ggccctcttt    29340
ttataaactc agcccacaac ttggatatta actacaacaa aggcctttac ttgtttacag    29400
cttcaaacaa ttccaaaaag cttgaggtta acctaagcac tgccaagggg ttgatgtttg    29460
acgctacagc catagccatt aatgcaggag atgggcttga atttggttca cctaatgcac    29520
caaacacaaa tcccctcaaa acaaaaattg gccatggcct agaatttgat tcaaacaagg    29580
ctatggttcc taaactagga actggcctta gttttgacag cacaggtgcc attacagtag    29640
gaaacaaaaa taatgataag ctaactttgt ggaccacacc agctccatct cctaactgta    29700
gactaaatgc agagaaagat gctaaactca ctttggtctt aacaaaatgt ggcagtcaaa    29760
tacttgctac agtttcagtt ttggctgtta aaggcagttt ggctccaata tctggaacag    29820
ttcaaagtgc tcatcttatt ataagatttg acgaaaatgg agtgctacta acaattcct     29880
tcctggaccc agaatattgg aactttagaa atggagatct tactgaaggc acagcctata    29940
caaacgctgt tggatttatg cctaacctat cagcttatcc aaaatctcac ggtaaaactg    30000
ccaaaagtaa cattgtcagt caagtttact aaacggaga caaaactaaa cctgtaacac    30060
taaccattac actaaacggt acacaggaaa caggagacac aactccaagt gcatactcta    30120
tgtcattttc atgggactgg tctggccaca actacattaa tgaaatattt gccacatcct    30180
cttacacttt ttcatacatt gcccaagaat aaagaatcgt tgtgttatg tttcaacgtg     30240
tttattttc aattgcagaa aatttcgaat cattttcat tcagtagtat agccccacca     30300
ccacatagct tatacagatc accgtacctt aatcaaactc acagaaccct agtattcaac    30360
ctgccacctc cctcccaaca cacagagtac acagtccttt ctccccggct ggccttaaaa    30420
agcatcatat catgggtaac agacatattc ttaggtgtta tattccacac ggtttcctgt    30480
cgagccaaac gctcatcagt gatattaata aactccccgg gcagctcact taagttcatg    30540
tcgctgtcca gctgctgagc cacaggctgc tgtccaactt gcggttgctt aacgggcggc    30600
gaaggagaag tccacgccta catggggggta gagtcataat cgtgcatcag gatagggcgg    30660
tggtgctgca gcagcgcgcg aataaactgc tgccgccgcc gctccgtcct gcaggaatac    30720
aacatggcag tggtctcctc agcgatgatt cgcaccgccc gcagcataag gcgccttgtc    30780
ctccgggcac agcagcgcac cctgatctca cttaaatcag cacagtaact gcagcacagc    30840
accacaatat tgttcaaaat cccacagtgc aaggcgctgt atccaaagct catggcgggg    30900
accacagaac ccacgtggcc atcataccac aagcgcaggt agattaagtg gcgacccctc    30960
ataaacacgc tggacataaa cattacctct tttggcatgt tgtaattcac cacctcccgg    31020
taccatataa acctctgatt aaacatggcg ccatccacca ccatcctaaa ccagctggcc    31080
aaaacctgcc cgccggctat acactgcagg gaaccgggac tggaacaatg acagtggaga    31140
gcccaggact cgtaaccatg gatcatcatg ctcgtcatga tatcaatgtt ggcacaacac    31200
aggcacacgt gcatacactt cctcaggatt acaagctcct cccgcgttag aaccatatcc    31260
cagggaacaa cccattcctg aatcagcgta atcccacac tgcagggaag acctcgcacg     31320
taactcacgt tgtgcattgt caaagtgtta cattcgggca gcagcggatg atcctccagt    31380
atggtagcgc gggtttctgt ctcaaaagga ggtagacgat ccctactgta cggagtgcgc    31440
cgagacaacc gagatcgtgt tggtcgtagt gtcatgccaa atggaacgcc ggacgtagtc    31500
```

-continued

```
atatttcctg aagcaaaacc aggtgcgggc gtgacaaaca gatctgcgtc tccggtctcg    31560
ccgcttagat cgctctgtgt agtagttgta gtatatccac tctctcaaag catccaggcg    31620
cccccctggct tcgggttcta tgtaaactcc ttcatgcgcc gctgccctga taacatccac   31680
caccgcagaa taagccacac ccagccaacc tacacattcg ttctgcgagt cacacacggg    31740
aggagcggga agagctggaa gaaccatgtt ttttttttta ttccaaaaga ttatccaaaa    31800
cctcaaaatg aagatctatt aagtgaacgc gctcccctcc ggtggcgtgg tcaaactcta   31860
cagccaaaga acagataatg gcatttgtaa gatgttgcac aatggcttcc aaaaggcaaa    31920
cggccctcac gtccaagtgg acgtaaaggc taaacccttc agggtgaatc tcctctataa    31980
acattccagc accttcaacc atgcccaaat aattctcatc tcgccacctt ctcaatatat    32040
ctctaagcaa atcccgaata ttaagtccgg ccattgtaaa aatctgctcc agagcgccct    32100
ccaccttcag cctcaagcag cgaatcatga ttgcaaaaat tcaggttcct cacagacctg    32160
tataagattc aaaagcggaa cattaacaaa aataccgcga tcccgtaggt cccttcgcag    32220
ggccagctga acataatcgt gcaggtctgc acggaccagc gcggccactt ccccgccagg    32280
aaccatgaca aaagaaccca cactgattat gacacgcata ctcggagcta tgctaaccag    32340
cgtagccccg atgtaagctt gttgcatggg cggcgatata aaatgcaagg tgctgctcaa    32400
aaaatcaggc aaagcctcgc gcaaaaaaga aagcacatcg tagtcatgct catgcagata    32460
aaggcaggta agctccggaa ccaccacaga aaaagacacc atttttctct caaacatgtc    32520
tgcgggtttc tgcataaaca caaaataaaa taacaaaaaa acatttaaac attagaagcc    32580
tgtcttacaa caggaaaaac aacccttata agcataagac ggactacggc catgccggcg    32640
tgaccgtaaa aaaactggtc accgtgatta aaaagcacca ccgacagctc ctcggtcatg    32700
tccggagtca taatgtaaga ctcggtaaac acatcaggtt gattcacatc ggtcagtgct    32760
aaaaagcgac cgaaatagcc cgggggaata catacccgca ggcgtagaga caacattaca    32820
gcccccatag gaggtataac aaaattaata ggagagaaaa acacataaac acctgaaaaa    32880
ccctcctgcc taggcaaaat agcaccctcc cgctccagaa caacatacag cgcttccaca    32940
gcggcagcca taacagtcag ccttaccagt aaaaaagaaa acctattaaa aaaacaccac    33000
tcgacacggc accagctcaa tcagtcacag tgtaaaaaag ggccaagtgc agagcgagta    33060
tataggac taaaaaatga cgtaacggtt aaagtccaca aaaaacaccc agaaaaccgc     33120
acgcgaacct acgcccagaa acgaaagcca aaaaacccac aacttcctca aatcgtcact    33180
tccgttttcc cacgttactt ctgtggaatg tgtgtcagtt agggtgtgga aagtccccag    33240
gctcccagc aggcagaagt atgcaaagca tgcatctcaa ttagtcagca accaggtgtg    33300
gaaagtcccc aggctcccca gcaggcagaa gtatgcaaag catgcatctc aattagtcag    33360
caaccatagt cccgccccta actccgccca tcccgcccct aactccgccc agttccgccc   33420
attctccgcc ccatggctga ctaattttt ttatttatgc agaggccgag gccgcctctg    33480
cctctgagct attccagaag tagtgaggag gcttttttgg aggcctaggc ttttgcaaac    33540
ctccgcgggg atccgcacca tggtgagcaa gggcgaggag gataacatgg ccatcatcaa   33600
ggagttcatg cgcttcaagg tgcacatgga gggctccgtg aacggccacg agttcgagat    33660
cgagggcgag ggcgagggcc gcccctacga gggcacccag accgccaagc tgaaggtgac    33720
caagggtggc cccctgccct tcgcctggga catcctgtcc cctcagttca tgtacggctc    33780
caaggcctac gtgaagcacc ccgccgacat ccccgactac ttgaagctgt ccttccccga    33840
```

```
gggcttcaag tgggagcgcg tgatgaactt cgaggacggc ggcgtggtga ccgtgaccca   33900
ggactcctcc ctgcaggacg gcgagttcat ctacaaggtg aagctgcgcg caccaacttt   33960
cccctccgac ggccccgtaa tgcagaagaa gaccatgggc tgggaggcct cctccgagcg   34020
gatgtacccc gaggacggcg ccctgaaggg cgagatcaag cagaggctga agctgaagga   34080
cggcggccac tacgacgctg aggtcaagac cacctacaag gccaagaagc ccgtgcagct   34140
gcccggcgcc tacaacgtca acatcaagtt ggacatcacc tcccacaacg aggactacac   34200
catcgtggaa cagtacgaac gcgccgaggg ccgccactcc accggcggca tggacgagct   34260
gtacaagtag ttcgaaatga ccgaccaagc gacgcccaac ctgccatcac gagatttcga   34320
ttccaccgcc gccttctatg aaaggttggg cttcggaatc gttttccggg acgccggctg   34380
gatgatcctc cagcgcgggg atctcatgct ggagttcttc gcccacccca acttgtttat   34440
tgcagcttat aatggttaca aataaagcaa tagcatcaca aatttcacaa ataaagcatt   34500
tttttcactg cattctagtt gtggtttgtc caaactcatc aatgtatctt atcatgtctg   34560
tataccgtcg acctctagct agaggtcact tcccatttta agaaaactac aattcccaac   34620
acatacaagt tactccgccc taaaacctac gtcacccgcc ccgttcccac gccccgcgcc   34680
acgtcacaaa ctccaccccc tcattatcat attggcttca atccaaaata aggtatatta   34740
ttgatgatgt taattaattt aaatccgcat gcgatatcga gctctcccgg gaattcggat   34800
ctgcgacgcg aggctggatg gccttcccca ttatgattct tctcgcgttt aagggcacca   34860
ataactgcct taaaaaaatt acgccccgcc ctgccactca tcgcagtact gttgtaattc   34920
attaagcatt ctgccgacat ggaagccatc acaaacggca tgatgaacct gaatcgccag   34980
cggcatcagc accttgtcgc cttgcgtata atatttgccc atggtgaaaa cggggggcgaa   35040 gaagttgtcc atattggcca cgtttaaatc aaaactggtg aaactcaccc agggattggc   35100
tgagacgaaa aacatattct caataaaccc tttagggaaa taggccaggt tttcaccgta   35160
acacgccaca tcttgcgaat atatgtgtag aaactgccgg aaatcgtcgt ggtattcact   35220
ccagagcgat gaaaacgttt cagtttgctc atggaaaacg gtgtaacaag ggtgaacact   35280
atcccatatc accagctcac cgtctttcat tgccatacgg aattccggat gagcattcat   35340
caggcgggca agaatgtgaa taaaggccgg ataaaacttg tgcttatttt tctttacggt   35400
ctttaaaaag gccgtaatat ccagctgaac ggtctggtta taggtacatt gagcaactga   35460
ctgaaatgcc tcaaaatgtt ctttacgatg ccattgggat atatcaacgg tggtatatcc   35520
agtgattttt ttctccattt tagcttcctt agctcctgaa atctcgata actcaaaaaa   35580 tacgcccggt agtgatctta tttcattatg gtgaaagttg gaacctctta cgtgccgatc   35640
aacgtctcat tttcgccaaa agttggccca gggcttcccg gtatcaacag ggacaccagg   35700
atttatttat tctgcgaagt gatcttccgt cacaggtatt tattcgcgat aagctcatgg   35760
agcggcgtaa ccgtcgcaca ggaaggacag agaaagcgcg gatctgggaa gtgacggaca   35820
gaacggtcag gacctggatt ggggaggcgg ttgccgccgc tgctgctgac ggtgtgacgt   35880
tctctgttcc ggtcacacca catacgttcc gccattccta tgcgatgcac atgctgtatg   35940
ccggtatacc gctgaaagtt ctgcaaagcc tgatgggaca taagtccatc agttcaacgg   36000
aagtctacac gaaggttttt gcgctggatg tggctgcccg gcaccgggtg cagtttgcga   36060
tgccggagtc tgatgcggtt gcgatgctga acaattatc ctgagaataa atgccttggc   36120
ctttatatgg aaatgtggaa ctgagtggat atgctgtttt tgtctgttaa acagagaagc   36180
tggctgttat ccactgagaa gcgaacgaaa cagtcgggaa aatctcccat tatcgtagag   36240
```

-continued

```
atccgcatta ttaatctcag gagcctgtgt agcgtttata ggaagtagtg ttctgtcatg   36300
atgcctgcaa gcggtaacga aaacgatttg aatatgcctt caggaacaat agaaatcttc   36360
gtgcggtgtt acgttgaagt ggagcggatt atgtcagcaa tggacagaac aacctaatga   36420
acacagaacc atgatgtggt ctgtcctttt acagccagta gtgctcgccg cagtcgagcg   36480
acagggcgaa gccctcgagt gagcgaggaa gcaccaggga acagcactta tatattctgc   36540
ttacacacga tgcctgaaaa aacttccctt ggggttatcc acttatccac ggggatattt   36600
ttataattat ttttttttata gttttttagat cttcttttttt agagcgcctt gtaggccttt   36660
atccatgctg gttctagaga aggtgttgtg acaaattgcc ctttcagtgt gacaaatcac   36720
cctcaaatga cagtcctgtc tgtgacaaat tgcccttaac cctgtgacaa attgccctca   36780
gaagaagctg ttttttcaca aagttatccc tgcttattga ctcttttttta tttagtgtga   36840 caatctaaaa acttgtcaca cttcacatgg atctgtcatg gcggaaacag cggttatcaa   36900
tcacaagaaa cgtaaaaata gcccgcgaat cgtccagtca aacgacctca ctgaggcggc   36960
atatagtctc tcccgggatc aaaaacgtat gctgtatctg ttcgttgacc agatcagaaa   37020
atctgatggc accctacagg aacatgacgg tatctgcgag atccatgttg ctaaatatgc   37080
tgaaatattc ggattgacct ctgcggaagc cagtaaggat atacggcagg cattgaagag   37140
tttcgcgggg aaggaagtgg ttttttatcg ccctgaagag gatgccggcg atgaaaaagg   37200
ctatgaatct tttccttggt ttatcaaacg tgcgcacagt ccatccagag ggctttacag   37260
tgtacatatc aacccatatc tcattcccttt ctttatcggg ttacagaacc ggtttacgca   37320
gtttcggctt agtgaaacaa aagaaatcac caatccgtat gccatgcgtt tatacgaatc   37380
cctgtgtcag tatcgtaagc cggatggctc aggcatcgtc tctctgaaaa tcgactggat   37440
catagagcgt taccagctgc ctcaaagtta ccagcgtatg cctgacttcc gccgccgctt   37500
cctgcaggtc tgtgttaatg agatcaacag cagaactcca atgcgcctct catacattga   37560 gaaaagaaa ggccgccaga cgactcatat cgtatttttcc ttccgcgata tcacttccat   37620
gacgacagga tagtctgagg gttatctgtc acagatttga gggtggttcg tcacatttgt   37680
tctgacctac tgagggtaat ttgtcacagt tttgctgttt ccttcagcct gcatggattt   37740
tctcatactt tttgaactgt aatttttaag gaagccaaat tgagggcag tttgtcacag   37800 ttgatttcct tctctttccc ttcgtcatgt gacctgatat cggggttag ttcgtcatca   37860 ttgatgaggg ttgattatca cagtttatta ctctgaattg gctatccgcg tgtgtacctc   37920
tacctggagt ttttcccacg gtggatattt cttcttgcgc tgagcgtaag agctatctga   37980
cagaacagtt cttctttgct tcctcgccag ttcgctcgct atgctcggtt acacggctgc   38040
ggcgagcgct agtgataata agtgactgag gtatgtgctc ttcttatctc cttttgtagt   38100
gttgctctta tttttaaacaa ctttgcggtt ttttgatgac tttgcgattt tgttgttgct   38160
ttgcagtaaa ttgcaagatt taataaaaaa acgcaaagca atgattaaag gatgttcaga   38220
atgaaactca tggaaacact taaccagtgc ataaacgctg gtcatgaaat gacgaaggct   38280
atcgccattg cacagtttaa tgatgacagc ccggaagcga ggaaaataac ccggcgctgg   38340
agaataggtg aagcagcgga tttagttggg gtttcttctc aggctatcag agatgccgag   38400
aaagcagggc gactaccgca cccggatatg gaaattcgag gacgggttga gcaacgtgtt   38460
ggttatacaa ttgaacaaat taatcatatg cgtgatgtgt ttggtacgcg attgcgacgt   38520
gctgaagacg tatttccacc ggtgatcggg gttgctgccc ataaaggtgg cgtttacaaa   38580
```

```
acctcagttt ctgttcatct tgctcaggat ctggctctga aggggctacg tgttttgctc    38640
gtggaaggta acgaccccca gggaacagcc tcaatgtatc acggatgggt accagatctt    38700
catattcatg cagaagacac tctcctgcct ttctatcttg gggaaaagga cgatgtcact    38760
tatgcaataa agcccacttg ctggccgggg cttgacatta ttccttcctg tctggctctg    38820
caccgtattg aaactgagtt aatgggcaaa tttgatgaag gtaaactgcc caccgatcca    38880
cacctgatgc tccgactggc cattgaaact gttgctcatg actatgatgt catagttatt    38940
gacagcgcgc ctaacctggg tatcggcacg attaatgtcg tatgtgctgc tgatgtgctg    39000
attgttccca cgcctgctga gttgtttgac tacacctccg cactgcagtt tttcgatatg    39060
cttcgtgatc tgctcaagaa cgttgatctt aaagggttcg agcctgatgt acgtattttg    39120
cttaccaaat acagcaatag taatggctct cagtccccgt ggatggagga gcaaattcgg    39180
gatgcctggg gaagcatggt tctaaaaaat gttgtacgtg aaacggatga agttggtaaa    39240
ggtcagatcc ggatgagaac tgtttttgaa caggccattg atcaacgctc ttcaactggt    39300
gcctggagaa atgctctttc tatttgggaa cctgtctgca atgaaatttt cgatcgtctg    39360
attaaaccac gctgggagat tagataatga agcgtgcgcc tgttattcca aaacatacgc    39420
tcaatactca accggttgaa gatacttcgt tatcgacacc agctgccccg atggtggatt    39480
cgttaattgc gcgcgtagga gtaatggctc gcggtaatgc cattactttg cctgtatgtg    39540
gtcgggatgt gaagtttact cttgaagtgc tccggggtga tagtgttgag aagacctctc    39600
gggtatggtc aggtaatgaa cgtgaccagg agctgcttac tgaggacgca ctggatgatc    39660
tcatcccttc ttttctactg actggtcaac agacaccggc gttcggtcga agagtatctg    39720
gtgtcataga aattgccgat gggagtcgcc gtcgtaaagc tgctgcactt accgaaagtg    39780
attatcgtgt tctggttggc gagctggatg atgagcagat ggctgcatta ccagattgg    39840 gtaacgatta tcgcccaaca agtgcttatg aacgtggtca gcgttatgca agccgattgc    39900
agaatgaatt tgctggaaat atttctgcgc tggctgatgc ggaaaatatt tcacgtaaga    39960
ttattacccg ctgtatcaac accgccaaat tgcctaaatc agttgttgct ctttttttctc    40020 accccggtga actatctgcc cggtcaggtg atgcacttca aaaagccttt acagataaag    40080
aggaattact taagcagcag gcatctaacc ttcatgagca gaaaaaagct ggggtgatat    40140
ttgaagctga agaagttatc actcttttaa cttctgtgct taaaacgtca tctgcatcaa    40200
gaactagttt aagctcacga catcagtttg ctcctggagc gacagtattg tataagggcg    40260
ataaaatggt gcttaacctg gacaggtctc gtgttccaac tgagtgtata gagaaaattg    40320
aggccattct taaggaactt gaaaagccag caccctgatg cgaccacgtt ttagtctacg    40380
tttatctgtc tttacttaat gtcctttgtt acaggccaga aagcataact ggcctgaata    40440
ttctctctgg gcccactgtt ccacttgtat cgtcggtctg ataatcagac tgggaccacg    40500
gtcccactcg tatcgtcggt ctgattatta gtctgggacc acggtcccac tcgtatcgtc    40560
ggtctgatta ttagtctggg accacggtcc cactcgtatc gtcggtctga taatcagact    40620
gggaccacgg tcccactcgt atcgtcggtc tgattattag tctgggacca tggtcccact    40680
cgtatcgtcg gtctgattat tagtctggga ccacggtccc actcgtatcg tcggtctgat    40740
tattagtctg gaaccacggt cccactcgta tcgtcggtct gattattagt ctgggaccac    40800
ggtcccactc gtatcgtcgg tctgattatt agtctgggac cacgatccca ctcgtgttgt    40860
cggtctgatt atcggtctgg gaccacggtc ccacttgtat tgtcgatcag actatcagcg    40920
tgagactacg attccatcaa tgcctgtcaa gggcaagtat tgacatgtcg tcgtaacctg    40980
```

```
tagaacggag taacctcggt gtgcggttgt atgcctgctg tggattgctg ctgtgtcctg    41040
cttatccaca acattttgcg cacggttatg tggacaaaat acctggttac ccaggccgtg    41100
ccggcacgtt aaccgggcac atttccccga aaagtgccac ctgacgtcta agaaaccatt    41160
attatcatga cattaaccta taaaatagg cgtatcacga ggccctttcg tcttcaagaa    41220
ttggatccga attcccggga gagctcgata tcgcatgcgg atttaaatta attaa         41275
```

<210> SEQ ID NO 101
<211> LENGTH: 38585
<212> TYPE: DNA
<213> ORGANISM: Artificial Sequence
<220> FEATURE:
<223> OTHER INFORMATION: Vector

<400> SEQUENCE: 101

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg     180 gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagtcgaag cttggatccg gtacctctag    480
aattctcgag cggccgctag cgacatcgga tctcccgatc ccctatggtg cactctcagt    540
acaatctgct ctgatgccgc atagttaagc cagtatctgc tccctgcttg tgtgttggag    600
gtcgctgagt agtgcgcgag caaaatttaa gctacaacaa ggcaaggctt gaccgacaat    660
tgcatgaaga atctgcttag ggttaggcgt tttgcgctgc ttcgcgatgt acgggccaga    720
tatacgcgtt gacattgatt attgactagt tattaatagt aatcaattac ggggtcatta    780
gttcatagcc catatatgga gttccgcgtt acataactta cggtaaatgg cccgcctggc    840
tgaccgccca acgacccccg cccattgacg tcaataatga cgtatgttcc catagtaacg    900 ccaatagga ctttccattg acgtcaatgg gtggactatt tacggtaaac tgcccacttg    960
gcagtacatc aagtgtatca tatgccaagt acgccccta ttgacgtcaa tgacggtaaa   1020
tggcccgcct ggcattatgc ccagtacatg accttatggg actttcctac ttggcagtac   1080
atctacgtat tagtcatcgc tattaccatg gtgatgcggt tttggcagta catcaatggg   1140
cgtggatagc ggtttgactc acggggattt ccaagtctcc accccattga cgtcaatggg   1200
agtttgtttt ggcaccaaaa tcaacgggac tttccaaaat gtcgtaacaa ctccgcccca   1260
ttgacgcaaa tgggcggtag gcgtgtacgg tgggaggtct atataagcag agctctctgg   1320
ctaactagag aacccactgc ttactggctt atcgaaatta atacgactca ctataggag    1380 acccaagctg gctagttaag ctatcaacaa gtttgtacaa aaaagcaggc tttaaggaa    1440 ccaattcagt cgactggatc cggtaccacc atgttcctga actgctgccc aggttgctgt   1500
atggagccta aattcaccat ggtgagcaag ggcgaggagc tgttcaccgg ggtggtgccc   1560
atcctggtcg agctggacgg cgacgtaaac ggccacaagt tcagcgtgtc cggcgagggc   1620
gagggcgatg ccacctacgg caagctgacc ctgaagttca tctgcaccac cggcaagctg   1680
cccgtgccct ggcccaccct cgtgaccacc ctgacctggg gcgtgcagtg cttcgcccgc   1740
```

-continued

```
taccccgacc acatgaagca gcacgacttc ttcaagtccg ccatgcccga aggctacgtc    1800
caggagcgca ccatcttctt caaggacgac ggcaactaca agacccgcgc cgaggtgaag    1860
ttcgagggcg acaccctggt gaaccgcatc gagctgaagg gcatcgactt caaggaggac    1920
ggcaacatcc tggggcacaa gctggagtac aacgccatca gcgacaacgt ctatatcacc    1980
gccgacaagc agaagaacgg catcaaggcc aacttcaaga tccgccacaa catcgaggac    2040
ggcagcgtgc agctcgccga ccactaccag cagaacaccc ccatcggcga cggccccgtg    2100
ctgctgcccg acaaccacta cctgagcacc cagtccaagc tgagcaaaga ccccaacgag    2160
aagcgcgatc acatggtcct gctggagttc gtgaccgccg ccgggatcac tctcggcatg    2220
gacgagctgt acaaggtcga ctatccgtac gacgtaccag actacgcata accgcggccg    2280
cactcgagat atctagaccc agctttcttg tacaaagtgg ttgatctaga ggcccgcgg    2340
ttcgaaggta agcctatccc taaccctctc ctcggtctcg attctacgcg taccggttag    2400
taatgagttt aaacggggga ggctaactga aacacgaaag agacaatac cggaaggaac    2460
ccgcgctatg acggcaataa aaagacagaa taaaacgcac gggtgttggg tcgtttgttc    2520
ataaacgcgg ggttcggtcc cagggctggc actctgtcga taccccaccg agaccccatt    2580
ggggccaata cgcccgcgtt tcttcctttt ccccaccca cccccaagt tcgggtgaag    2640
gcccagggct cgcagccaac gtcggggcgg caggccctgc catagcagat ccgattcgac    2700
agatcactga aatgtgtggg cgtggcttaa gggtgggaaa gaatatataa ggtgggggtc    2760
ttatgtagtt ttgtatctgt tttgcagcag ccgccgccgc catgagcacc aactcgtttg    2820
atggaagcat tgtgagctca tatttgacaa cgcgcatgcc cccatgggcc ggggtgcgtc    2880
agaatgtgat gggctccagc attgatggtc gccccgtcct gcccgcaaac tctactacct    2940
tgacctacga gaccgtgtct ggaacgccgt tggagactgc agcctccgcc gccgcttcag    3000
ccgctgcagc caccgcccgc gggattgtga ctgactttgc tttcctgagc ccgcttgcaa    3060
gcagtgcagc ttcccgttca tccgcccgcg atgacaagtt gacggctctt ttggcacaat    3120
tggattcttt gacccgggaa cttaatgtcg tttctcagca gctgttggat ctgcgccagc    3180
aggtttctgc cctgaaggct tcctcccctc ccaatgcggt ttaaaacata aataaaaaac    3240
cagactctgt ttggatttgg atcaagcaag tgtcttgctg tctttattta ggggttttgc    3300
gcgcgcggta ggcccgggac cagcggtctc ggtcgttgag ggtcctgtgt attttttcca    3360
ggacgtggta aaggtgactc tggatgttca gatacatggg cataagcccg tctctggggt    3420
ggaggtagca ccactgcaga gcttcatgct gcggggtggt gttgtagatg atccagtcgt    3480
agcaggagcg ctgggcgtgg tgcctaaaaa tgtctttcag tagcaagctg attgccaggg    3540
gcaggccctt ggtgtaagtg tttacaaagc ggttaagctg ggatgggtgc atacgtgggg    3600
atatgagatg catcttggac tgtattttta ggttggctat gttcccagcc atatccctcc    3660
ggggattcat gttgtgcaga accaccagca cagtgtatcc ggtgcacttg gaaatttgt    3720
catgtagctt agaaggaaat gcgtggaaga acttggagac gcccttgtga cctccaagat    3780
tttccatgca ttcgtccata atgatggcaa tgggcccacg ggcggcggcc tgggcgaaga    3840
tatttctggg atcactaacg tcatagttgt gttccaggat gagatcgtca taggccattt    3900
ttacaaagcg cggcggagg gtgccagact gcggtataat ggttccatcc ggcccagggg    3960
cgtagttacc ctcacagatt tgcatttccc acgctttgag ttcagatggg gggatcatgt    4020
ctacctgcgg ggcgatgaag aaaacggttt ccggggtagg ggagatcagc tgggaagaaa    4080
gcaggttcct gagcagctgc gacttaccgc agccggtggg cccgtaaatc acacctatta    4140
```

-continued

| | | | | |
|---|---|---|---|---|
| ccggctgcaa | ctggtagtta | agagagctgc | agctgccgtc | atccctgagc | agggggggcca | 4200 |
| cttcgttaag | catgtccctg | actcgcatgt | tttccctgac | caaatccgcc | agaaggcgct | 4260 |
| cgccgcccag | cgatagcagt | tcttgcaagg | aagcaaagtt | tttcaacggt | ttgagaccgt | 4320 |
| ccgccgtagg | catgcttttg | agcgtttgac | caagcagttc | caggcggtcc | cacagctcgg | 4380 |
| tcacctgctc | tacggcatct | cgatccagca | tatctcctcg | tttcgcgggt | tggggcggct | 4440 |
| ttcgctgtac | ggcagtagtc | ggtgctcgtc | cagacgggcc | agggtcatgt | ctttccacgg | 4500 |
| gcgcagggtc | ctcgtcagcg | tagtctgggt | cacggtgaag | gggtgcgctc | cgggctgcgc | 4560 |
| gctggccagg | gtgcgcttga | ggctggtcct | gctggtgctg | aagcgctgcc | ggtcttcgcc | 4620 |
| ctgcgcgtcg | gccaggtagc | atttgaccat | ggtgtcatag | tccagcccct | ccgcggcgtg | 4680 |
| gcccttggcg | cgcagcttgc | ccttggagga | ggcgccgcac | gaggggcagt | gcagactttt | 4740 |
| gagggcgtag | agcttgggcg | cgagaaatac | cgattccggg | gagtaggcat | ccgcgccgca | 4800 |
| ggccccgcag | acggtctcgc | attccacgag | ccaggtgagc | tctggccgtt | cggggtcaaa | 4860 |
| aaccaggttt | cccccatgct | ttttgatgcg | tttcttacct | ctggtttcca | tgagccggtg | 4920 |
| tccacgctcg | gtgacgaaaa | ggctgtccgt | gtccccgtat | acagacttga | gaggcctgtc | 4980 |
| ctcgagcggt | gttccgcggt | cctcctcgta | tagaaactcg | gaccactctg | agacaaaggc | 5040 |
| tcgcgtccag | gccagcacga | aggaggctaa | gtgggagggg | tagcggtcgt | tgtccactag | 5100 |
| ggggtccact | cgctccaggg | tgtgaagaca | catgtcgccc | tcttcggcat | caaggaaggt | 5160 |
| gattggtttg | taggtgtagg | ccacgtgacc | gggtgttcct | gaagggggggc | tataaagggg | 5220 |
| ggtgggggcg | cgttcgtcct | cactctcttc | cgcatcgctg | tctgcgaggg | ccagctgttg | 5280 |
| gggtgagtac | tccctctgaa | aagcgggcat | gacttctgcg | ctaagattgt | cagtttccaa | 5340 |
| aaacgaggag | gatttgatat | tcacctggcc | cgcggtgatg | cctttgaggg | tggccgcatc | 5400 |
| catctggtca | gaaaagacaa | tcttttttgtt | gtcaagcttg | gtggcaaacg | acccgtagag | 5460 |
| ggcgttggac | agcaacttgg | cgatggagcg | cagggttttgg | ttttttgtcgc | gatcggcgcg | 5520 |
| ctccttggcc | gcgatgttta | gctgcacgta | ttcgcgcgca | acgcaccgcc | attcgggaaa | 5580 |
| gacggtggtg | cgctcgtcgg | gcaccaggtg | cacgcgccaa | ccgcggttgt | gcagggtgac | 5640 |
| aaggtcaacg | ctggtggcta | cctctccgcg | taggcgctcg | ttggtccagc | agaggcggcc | 5700 |
| gcccttgcgc | gagcagaatg | gcggtagggg | gtctagctgc | gtctcgtccg | ggggggtctgc | 5760 |
| gtccacggta | aagaccccgg | gcagcaggcg | cgcgtcgaag | tagtctatct | tgcatccttg | 5820 |
| caagtctagc | gcctgctgcc | atgcgcgggc | ggcaagcgcg | cgctcgtatg | ggttgagtgg | 5880 |
| gggaccccat | ggcatggggt | gggtgagcgc | ggaggcgtac | atgccgcaaa | tgtcgtaaac | 5940 |
| gtagagggggc | tctctgagta | ttccaagata | tgtaggtgtag | catcttccac | cgcggatgct | 6000 |
| ggcgcgcacg | taatcgtata | gttcgtgcga | gggagcgagg | aggtcgggac | cgaggttgct | 6060 |
| acgggcgggc | tgctctgctc | ggaagactat | ctgcctgaag | atggcatgtg | agttggatga | 6120 |
| tatggttgga | cgctggaaga | cgttgaagct | ggcgtctgtg | agacctaccg | cgtcacgcac | 6180 |
| gaaggaggcg | taggagtcgc | gcagcttgtt | gaccagctcg | gcggtgacct | gcacgtctag | 6240 |
| ggcgcagtag | tccagggttt | ccttgatgat | gtcatactta | tcctgtccct | ttttttttcca | 6300 |
| cagctcgcgg | ttgaggacaa | actcttcgcg | gtctttccag | tactcttgga | tcggaaaccc | 6360 |
| gtcggcctcc | gaacgtaagc | agcctagcat | gtagaactgg | ttgacggcct | ggtaggcgca | 6420 |
| gcatcccttt | tctacgggta | gcgcgtatgc | ctgcgcggcc | ttccggagcg | aggtgtgggt | 6480 |

```
gagcgcaaag gtgtccctga ccatgaccag catgaagggc acgagctgct tcccaaaggc    6540
ccccatccaa gtataggtct ctacatcgta ggtgacaaag agacgctcgg tgcgaggatg    6600
cgagccgatc gggaagaact ggatctcccg ccaccaattg gaggagtggc tattgatgtg    6660
gtgaaagtag aagtccctgc gacgggccga acactcgtgc tggcttttgt aaaaacgtgc    6720
gcagtactgg cagcggtgca cgggctgtac atcctgcacg aggttgacct gacgaccgcg    6780
cacaaggaag cagagtggga atttgagccc ctcgcctggc gggtttggct ggtggtcttc    6840
tacttcggct gcttgtcctt gaccgtctgg ctgctcgagg ggagttacgg tggatcggac    6900
caccacgccg cgcgagccca aagtccagat gtccgcgcgc ggcggtcgga gcttgatgac    6960
aacatcgcgc agatgggagc tgtccatggt ctggagctcc cgcggcgtca ggtcaggcgg    7020
gagctcctgc aggtttacct cgcatagacg ggtcagggcg cgggctagat ccaggtgata    7080
cctaatttcc aggggctggt tggtggcggc gtcgatggct tgcaagaggc cgcatccccg    7140
cggcgcgact acggtaccgc gcggcggggc gtgggccgcg ggggtgtcct tggatgatgc    7200
atctaaaagc ggtgacgcgg cgagccccc ggaggtaggg ggggctccgg acccgccggg    7260
agagggggca ggggcacgtc ggcgccgcgc gcgggcagga gctggtgctg cgcgcgtagg    7320
ttgctggcga acgcgacgac gcggcggttg atctcctgaa tctggcgcct ctgcgtgaag    7380
acgacgggcc cggtgagctt gaacctgaaa gagagttcga cagaatcaat ttcggtgtcg    7440
ttgacgcggg cctggcgcaa aatctcctgc acgtctcctg agttgtcttg ataggcgatc    7500
tcggccatga actgctcgat ctcttcctcc tggagatctc cgcgtccggc tcgctccacg    7560
gtggcggcga ggtcgttgga aatgcgggcc atgagctgcg agaaggcgtt gaggcctccc    7620
tcgttccaga cgcggctgta gaccacgccc ccttcggcat cgcgggcgcg catgaccacc    7680
tgcgcgagat tgagctccac gtgccgggcg aagacgcgcg agtttcgcag cgcctgaaag    7740
aggtagttga gggtggtggc ggtgtgttct gccacgaaga agtacataac ccagcgtcgc    7800
aacgtggatt cgttgatatc ccccaaggcc tcaaggcgct ccatggcctc gtagaagtcc    7860
acggcgaagt tgaaaaactg ggagttgcgc gccgacacgg ttaactcctc ctccagaaga    7920
cggatgagct cggcgacagt gtcgcgcacc tcgcgctcaa aggctacagg gcctcttct    7980 tcttcttcaa tctcctcttc cataagggcc tccccttctt cttcttctgg cggcggtggg    8040 ggaggggggca cacggcggcg acgacggcgc accgggaggc ggtcgacaaa gcgctcgatc    8100
atctccccgc ggcgacggcg catggtctcg gtgacggcgc ggccgttctc gcggggcgc    8160 agttggaaga cgccgcccgt catgtcccgg ttatgggttg gcgggggggct gccatgcggc    8220 agggatacgg cgctaacgat gcatctcaac aattgttgtg taggtactcc gccgccgagg    8280
gacctgagcg agtccgcatc gaccggatcg gaaaacctct cgagaaaggc gtctaaccag    8340
tcacagtcgc aaggtaggct gagcaccgtg gcgggcggca gcgggcggcg gtcggggttg    8400
tttctggcgg aggtgctgct gatgatgtaa ttaaagtagg cggtcttgag acggcggatg    8460
gtcgacagaa gcaccatgtc cttgggtccg gcctgctgaa tgcgcaggcg gtcggccatg    8520
ccccaggctt cgttttgaca tcggcgcagg tctttgtagt agtcttgcat gagcctttct    8580
accggcactt cttcttctcc ttcctcttgt cctgcatctc ttgcatctat cgctgcggcg    8640
gcggcggagt ttggccgtag gtggcgccct cttcctccca tgcgtgtgac cccgaagccc    8700
ctcatcggct gaagcagggc taggtcggcg acaacgcgct cggctaatat ggcctgctgc    8760
acctgcgtga gggtagactg gaagtcatcc atgtccacaa agcggtggta tgcgcccgtg    8820
ttgatggtgt aagtgcagtt ggccataacg gaccagttaa cggtctggtg acccggctgc    8880
```

```
gagagctcgg tgtacctgag acgcgagtaa gccctcgagt caaatacgta gtcgttgcaa   8940
gtccgcacca ggtactggta tcccaccaaa aagtgcggcg gcggctggcg gtagaggggc   9000
cagcgtaggg tggccggggc tccggggcg  agatcttcca acataaggcg atgatatccg   9060
tagatgtacc tggacatcca ggtgatgccg gcggcggtgg tggaggcgcg cggaaagtcg   9120
cggacgcggt tccagatgtt gcgcagcggc aaaaagtgct ccatggtcgg gacgctctgg   9180
ccggtcaggc gcgcgcaatc gttgacgctc tagaccgtgc aaaaggagag cctgtaagcg   9240
ggcactcttc cgtggtctgg tggataaatt cgcaagggta tcatggcgga cgaccggggt   9300
tcgagccccg tatccggccg tccgccgtga tccatgcgt  taccgcccgc gtgtcgaacc   9360
caggtgtgcg acgtcagaca acgggggagt gctccttttg gcttccttcc aggcgcggcg   9420
gctgctgcgc tagcttttt  ggccactggc cgcgcgcagc gtaagcggtt aggctggaaa   9480
gcgaaagcat taagtggctc gctccctgta gccggagggt tattttccaa gggttgagtc   9540
gcgggacccc cggttcgagt ctcggaccgg ccggactgcg gcgaacgggg gtttgcctcc   9600
ccgtcatgca agacccgct  tgcaaattcc tccggaaaca gggacgagcc ccttttttgc   9660
ttttcccaga tgcatccggt gctgcggcag atgcgcccc  ctcctcagca gcggcaagag   9720
caagagcagc ggcagacatg cagggcaccc tcccctcctc ctaccgcgtc aggaggggcg   9780
acatccgcgg ttgacgcggc agcagatggt gattacgaac cccgcggcg  ccgggcccgg   9840
cactacctgg acttggagga gggcgagggc ctggcgcggc taggagcgcc ctctcctgag   9900
cggcacccaa gggtgcagct gaagcgtgat acgcgtgagg cgtacgtgcc gcggcagaac   9960
ctgtttcgcg accgcgaggg agaggagccc gaggagatgc gggatcgaaa gttccacgca  10020
gggcgcgagc tgcggcatgg cctgaatcgc gagcggttgc tgcgcgagga ggactttgag  10080
cccgacgcgc gaaccgggat tagtcccgcg cgcgcacacg tggcggccgc cgacctggta  10140
accgcatacg agcagacggt gaaccaggag attaactttc aaaaaagctt taacaaccac  10200
gtgcgtacgc ttgtggcgcg cgaggaggtg gctataggac tgatgcatct gtgggacttt  10260
gtaagcgcgc tggagcaaaa cccaaatagc aagccgctca tggcgcagct gttccttata  10320
gtgcagcaca gcagggacaa cgaggcattc agggatgcgc tgctaaacat agtagagccc  10380
gagggccgct ggctgctcga tttgataaac atcctgcaga gcatagtggt gcaggagcgc  10440
agcttgagcc tggctgacaa ggtggccgcc atcaactatt ccatgcttag cctgggcaag  10500
ttttacgccc gcaagatata ccataccct  tacgttccca tagacaagga ggtaaagatc  10560
gaggggttct acatgcgcat ggcgctgaag gtgcttacct tgagcgacga cctgggcgtt  10620
tatcgcaacg agcgcatcca caaggccgtg agcgtgagcc ggcggcgcga gctcagcgac  10680
cgcgagctga tgcacagcct gcaaagggcc ctggctggca cggcagcgg  cgatagagag  10740
gccgagtcct actttgacgc gggcgctgac ctgcgctggg ccccaagccg acgcgccctg  10800
gaggcagctg gggccggacc tgggctggcg gtggcacccg cgcgcgctgg caacgtcggc  10860
ggcgtggagg aatatgacga ggacgatgag tacgagccag aggacggcga gtactaagcg  10920
gtgatgtttc tgatcagatg atgcaagacg caacggaccc ggcggtgcgg gcggcgctgc  10980
agagccagcc gtccggcctt aactccacgg acgactggcg ccaggtcatg gaccgcatca  11040
tgtcgctgac tgcgcgcaat cctgacgcgt tccggcagca gccgcaggcc aacgggctct  11100
ccgcaattct ggaagcggtg gtcccggcgc gcgcaaaccc cacgcacgag aaggtgctgg  11160
cgatcgtaaa cgcgctggcc gaaaacaggg ccatccggcc cgacgaggcc ggcctggtct  11220
```

```
acgacgcgct gcttcagcgc gtggctcgtt acaacagcgg caacgtgcag accaacctgg    11280
accggctggt gggggatgtg cgcgaggccg tggcgcagcg tgagcgcgcg cagcagcagg    11340
gcaacctggg ctccatggtt gcactaaacg ccttcctgag tacacagccc gccaacgtgc    11400
cgcggggaca ggaggactac accaactttg tgagcgcact gcggctaatg gtgactgaga    11460
caccgcaaag tgaggtgtac cagtctgggc cagactattt tttccagacc agtagacaag    11520
gcctgcagac cgtaaacctg agccaggctt tcaaaaactt gcaggggctg tgggggtgc     11580 gggctcccac aggcgaccgc gcgaccgtgt ctagcttgct gacgcccaac tcgcgcctgt    11640
tgctgctgct aatagcgccc ttcacggaca gtggcagcgt gtcccgggac acatacctag    11700
gtcacttgct gacactgtac cgcgaggcca taggtcaggc gcatgtggac gagcatactt    11760
tccaggagat tacaagtgtc agccgcgcgc tggggcagga ggacacgggc agcctggagg    11820
caaccctaaa ctacctgctg accaaccggc ggcagaagat cccctcgttg cacagtttaa    11880
acagcgagga ggagcgcatt ttgcgctacg tgcagcagag cgtgagccct aacctgatgc    11940
gcgacggggt aacgcccagc gtggcgctgg acatgaccgc gcgcaacatg gaaccgggca    12000
tgtatgcctc aaaccggccg tttatcaacc gcctaatgga ctacttgcat cgcgcggccg    12060
ccgtgaaccc cgagtatttc accaatgcca tcttgaaccc gcactggcta ccgccccctg    12120
gtttctacac cggggattc gaggtgcccg agggtaacga tggattcctc tgggacgaca    12180
tagacgacag cgtgttttcc ccgcaaccgc agacctgct agagttgcaa cagcgcgagc     12240
aggcagaggc ggcgctgcga aaggaaagct ccgcaggcc aagcagcttg tccgatctag     12300
gcgctgcggc cccgcggtca gatgctagta gcccatttcc aagcttgata gggtctctta    12360
ccagcactcg caccacccgc ccgcgcctgc tgggcgagga ggagtaccta aacaactcgc    12420
tgctgcagcc gcagcgcgaa aaaaacctgc ctccggcatt tcccaacaac gggatagaga    12480
gcctagtgga caagatgagt agatggaaga cgtacgcgca ggagcacagg gacgtgccag    12540
gcccgcgccc gcccacccgt cgtcaaaggc acgaccgtca gcggggtctg tgtgggagg    12600 acgatgactc ggcagacgac agcagcgtcc tggatttggg agggagtggc aacccgtttg    12660
cgcaccttcg ccccaggctg gggagaatgt tttaaaaaaa aaaaagcat gatgcaaaat     12720 aaaaaactca ccaaggccat ggcaccgagc gttggttttc ttgtattccc cttagtatgc    12780
ggcgcgcggc gatgtatgag gaaggtcctc ctccctccta cgagagtgtg gtgagcgcgg    12840
cgccagtggc ggcggcgctg ggttctccct tcgatgctcc cctggacccg ccgtttgtgc    12900
ctccgcggta cctgcggcct accgggggga gaaacagcat ccgttactct gagttggcac    12960
ccctattcga caccacccgt gtgtacctgg tggacaacaa gtcaacggat gtggcatccc    13020
tgaactacca gaacgaccac agcaactttc tgaccacggt cattcaaaac aatgactaca    13080 gcccgggggga ggcaagcaca cagaccatca atcttgacga ccggtcgcac tggggcggcg    13140
acctgaaaac catcctgcat accaacatgc caaatgtgaa cgagttcatg tttaccaata    13200
agtttaaggc gcgggtgatg gtgtcgcgct tgcctactaa ggacaatcag gtggagctga    13260
aatacgagtg ggtggagttc acgctgcccg agggcaacta ctccgagacc atgaccatag    13320
accttatgaa caacgcgatc gtggagcact acttgaaagt gggcagacag aacgggttc     13380 tggaaagcga catcggggta aagtttgaca cccgcaactt cagactgggg tttgaccccg    13440
tcactggtct tgtcatgcct ggggtatata caaacgaagc cttccatcca gacatcattt    13500
tgctgccagg atgcggggtg gacttcaccc acagccgcct gagcaacttg ttgggcatcc    13560
gcaagcggca acccttccag gagggctta ggatcaccta cgatgatctg gagggtggta    13620
```

```
acattcccgc actgttggat gtggacgcct accaggcgag cttgaaagat gacaccgaac   13680
agggcggggg tggcgcaggc ggcagcaaca gcagtggcag cggcgcgaaa gagaactcca   13740
acgcggcagc cgcggcaatg cagccggtgg aggacatgaa cgatcatgcc attcgcggcg   13800
acacctttgc cacacgggct gaggagaagc gcgctgaggc cgaagcagcg gccgaagctg   13860
ccgcccccgc tgcgcaaccc gaggtcgaga agcctcagaa gaaaccggtg atcaaacccc   13920
tgacagagga cagcaagaaa cgcagttaca acctaataag caatgacagc accttcaccc   13980
agtaccgcag ctggtacctt gcatacaact acggcgaccc tcagaccgga atccgctcat   14040
ggaccctgct ttgcactcct gacgtaacct gcggctcgga gcaggtctac tggtcgttgc   14100
cagacatgat gcaagacccc gtgaccttcc gctccacgcg ccagatcagc aactttccgg   14160
tggtgggcgc cgagctgttg cccgtgcact ccaagagctt ctacaacgac caggccgtct   14220
actcccaact catccgccag tttacctctc tgacccacgt gttcaatcgc tttcccgaga   14280
accagatttt ggcgcgcccg ccagccccca ccatcaccac cgtcagtgaa aacgttcctg   14340
ctctcacaga tcacgggacg ctaccgctgc gcaacagcat cggaggagtc cagcgagtga   14400
ccattactga cgccagacgc cgcacctgcc cctacgttta caaggccctg gcatagtct   14460 cgccgcgcgt cctatcgagc cgcactttt t gagcaagcat gtccatcctt atatcgccca   14520
gcaataacac aggctggggc ctgcgcttcc caagcaagat gtttggcggg gccaagaagc   14580
gctccgacca acacccagtg cgcgtgcgcg ggcactaccg cgcgccctgg ggcgcgcaca   14640
aacgcggccg cactgggcgc accaccgtcg atgacgccat cgacgcggtg gtggaggagg   14700
cgcgcaacta cacgcccacg ccgccaccag tgtccacagt ggacgcggcc attcagaccg   14760
tggtgcgcgg agcccggcgc tatgctaaaa tgaagagacg gcggaggcgc gtagcacgtc   14820
gccaccgccg ccgacccggc actgccgccc aacgcgcggc ggcggccctg cttaaccgcg   14880
cacgtcgcac cggccgacgg gcggccatgc gggccgctcg aaggctggcc gcgggtattg   14940
tcactgtgcc ccccaggtcc aggcgacgag cggccgccgc agcagccgcg gccattagtg   15000
ctatgactca gggtcgcagg ggcaacgtgt attgggtgcg cgactcggtt agcggcctgc   15060
gcgtgcccgt gcgcacccgc ccccgcgca actagattgc aagaaaaac tacttagact    15120 cgtactgttg tatgtatcca gcggcggcgg cgcgcaacga agctatgtcc aagcgcaaaa   15180
tcaaagaaga gatgctccag gtcatcgcgc cggagatcta tggccccccg aagaaggaag   15240
agcaggatta caagccccga aagctaaagc gggtcaaaaa gaaaaagaaa gatgatgatg   15300
atgaacttga cgacgaggtg gaactgctgc acgctaccgc gcccaggcga cgggtacagt   15360
ggaaaggtcg acgcgtaaaa cgtgttttgc gacccggcac caccgtagtc tttacgcccg   15420
gtgagcgctc caccgcacc tacaagcgcg tgtatgatga ggtgtacggc gacgaggacc    15480
tgcttgagca ggccaacgag cgcctcgggg agtttgccta cggaaagcgg cataaggaca   15540
tgctggcgtt gccgctggac gagggcaacc caacacctag cctaaagccc gtaacactgc   15600
agcaggtgct gcccgcgctt gcaccgtccg aagaaaagcg cggcctaaag cgcgagtctg   15660
gtgacttggc acccaccgtg cagctgatgg tacccaagcg ccagcgactg gaagatgtct   15720
tggaaaaaat gaccgtggaa cctgggctgg agccgaggt ccgcgtgcgg ccaatcaagc     15780
aggtggcgcc gggactgggc gtgcagaccg tggacgttca gatacccact accagtagca   15840
ccagtattgc caccgccaca gagggcatgg agacacaaac gtccccggtt gcctcagcgg   15900
tggcggatgc cgcggtgcag gcggtcgctg cggccgcgtc caagacctct acggaggtgc   15960
```

```
aaacggaccc gtggatgttt cgcgtttcag ccccccggcg cccgcgccgt tcgaggaagt   16020
acggcgccgc cagcgcgcta ctgcccgaat atgccctaca tccttccatt gcgcctaccc   16080
ccggctatcg tggctacacc taccgcccca gaagacgagc aactacccga cgccgaacca   16140
ccactggaac ccgccgccgc cgtcgccgtc gccagcccgt gctggcccg atttccgtgc   16200 gcagggtggc tcgcgaagga ggcaggaccc tggtgctgcc aacagcgcgc taccacccca   16260
gcatcgttta aaagccggtc tttgtggttc ttgcagatat ggccctcacc tgccgcctcc   16320
gtttcccggt gccgggattc cgaggaagaa tgcaccgtag gaggggcatg gccggccacg   16380
gcctgacggg cggcatgcgt cgtgcgcacc accggcggcg gcgcgcgtcg caccgtcgca   16440
tgcgcggcgg tatcctgccc ctccttattc cactgatcgc cgcggcgatt ggcgccgtgc   16500
ccggaattgc atccgtggcc ttgcaggcgc agagacactg attaaaaaca agttgcatgt   16560
ggaaaaatca aaataaaaag tctggactct cacgctcgct tggtcctgta actattttgt   16620
agaatggaag acatcaactt tgcgtctctg gccccgcgac acggctcgcg cccgttcatg   16680
ggaaactggc aagatatcgg caccagcaat atgagcggtg gcgccttcag ctggggctcg   16740
ctgtggagcg gcattaaaaa tttcggttcc accgttaaga actatggcag caaggcctgg   16800
aacagcagca caggccagat gctgagggat aagttgaaag agcaaaattt ccaacaaaag   16860
gtggtagatg gcctggcctc tggcattagc ggggtggtgg acctggccaa ccaggcagtg   16920
caaaataaga ttaacagtaa gcttgatccc cgccctcccg tagaggagcc tccaccggcc   16980
gtggagacag tgtctccaga ggggcgtggc gaaaagcgtc cgcgccccga cagggaagaa   17040
actctggtga cgcaaataga cgagcctccc tcgtacgagg aggcactaaa gcaaggcctg   17100
cccaccaccc gtcccatcgc gcccatggct accggagtgc tgggccagca cacacccgta   17160
acgctggacc tgcctccccc cgccgacacc cagcagaaac ctgtgctgcc aggcccgacc   17220
gccgttgttg taacccgtcc tagccgcgcg tccctgcgcc gcgccgccag cggtccgcga   17280
tcgttgcggc ccgtagccag tggcaactgg caaagcacac tgaacagcat cgtgggtctg   17340
ggggtgcaat ccctgaagcg ccgacgatgc ttctgatagc taacgtgtcg tatgtgtgtc   17400
atgtatgcgt ccatgtcgcc gccagaggag ctgctgagcc gccgcgcgcc cgcttttccaa   17460 gatggctacc ccttcgatga tgccgcagtg gtcttacatg cacatctcgg gccaggacgc   17520
ctcggagtac ctgagcccgg ggctggtgca gtttgcccgc gccaccgaga cgtacttcag   17580
cctgaataac aagtttagaa accccacggt ggcgcctacg cacgacgtga ccacagaccg   17640
gtcccagcgt ttgacgctgc ggttcatccc tgtggaccgt gaggatactg cgtactcgta   17700
caaggcgcgg ttcaccctag ctgtgggtga taaccgtgtg ctggacatgg cttccacgta   17760
ctttgacatc cgcggcgtgc tggacagggg ccctactttt aagccctact ctggcactgc   17820
ctacaacgcc ctggctccca agggtgcccc aaatccttgc gaatgggatg aagctgctac   17880
tgctcttgaa ataaacctag aagaagagga cgatgacaac gaagacgaag tagacgagca   17940
agctgagcag caaaaaactc acgtatttgg gcaggcgcct tattctggta taaatattac   18000
aaaggagggt attcaaatag gtgtcgaagg tcaaacacct aaatatgccg ataaaacatt   18060
tcaacctgaa cctcaaatag gagaatctca gtggtacgaa acagaaatta atcatgcagc   18120
tgggagagtc ctaaaaaaga ctaccccaat gaaaccatgt tacggttcat atgcaaaacc   18180
cacaaatgaa aatggagggc aaggcattct tgtaaagcaa caaaatgaaa gctagaaag   18240 tcaagtggaa atgcaatttt tctcaactac tgaggcagcc gcaggcaatg gtgataactt   18300
gactcctaaa gtggtattgt acagtgaaga tgtagatata gaaaccccag acactcatat   18360
```

```
ttcttacatg cccactatta aggaaggtaa ctcacgagaa ctaatgggcc aacaatctat   18420
gcccaacagg cctaattaca ttgcttttag ggacaatttt attggtctaa tgtattacaa   18480
cagcacgggt aatatgggtg ttctggcggg ccaagcatcg cagttgaatg ctgttgtaga   18540
tttgcaagac agaaacacag agctttcata ccagcttttg cttgattcca ttggtgatag   18600
aaccaggtac ttttctatgt ggaatcaggc tgttgacagc tatgatccag atgttagaat   18660
tattgaaaat catggaactg aagatgaact tccaaattac tgctttccac tgggaggtgt   18720
gattaataca gagactctta ccaaggtaaa acctaaaaca ggtcaggaaa atggatggga   18780
aaaagatgct acagaatttt cagataaaaa tgaaataaga gttggaaata attttgccat   18840
ggaaatcaat ctaaatgcca acctgtggag aaatttcctg tactccaaca tagcgctgta   18900
tttgcccgac aagctaaagt acagtccttc caacgtaaaa atttctgata cccaaacac    18960 ctacgactac atgaacaagc gagtggtggc tcccgggcta gtggactgct acattaacct   19020
tggagcacgc tggtcccttg actatatgga caacgtcaac ccatttaacc accaccgcaa   19080
tgctggcctg cgctaccgct caatgttgct gggcaatggt cgctatgtgc ccttccacat   19140
ccaggtgcct cagaagttct ttgccattaa aaacctcctt ctcctgccgg gctcatacac   19200
ctacgagtgg aacttcagga aggatgttaa catggttctg cagagctccc taggaaatga   19260
cctaagggtt gacggagcca gcattaagtt tgatagcatt tgcctttacg ccaccttctt   19320
ccccatggcc cacaacaccg cctccacgct tgaggccatg cttagaaacg acaccaacga   19380
ccagtccttt aacgactatc tctccgccgc caacatgctc taccctatac ccgccaacgc   19440
taccaacgtg cccatatcca tcccctcccg caactgggcg gctttccgcg gctgggcctt   19500
cacgcgcctt aagactaagg aaaccccatc actgggctcg ggctacgacc cttattacac   19560
ctactctggc tctataccct acctagatgg aacctttttac ctcaaccaca cctttaagaa   19620
ggtggccatt accttttgact cttctgtcag ctggcctggc aatgaccgcc tgcttacccc   19680
caacgagttt gaaattaagc gctcagttga cggggagggt tacaacgttg cccagtgtaa   19740
catgaccaaa gactggttcc tggtacaaat gctagctaac tataacattg gctaccaggg   19800
cttctatatc ccagagagct acaaggaccg catgtactcc ttctttagaa acttccagcc   19860
catgagccgt caggtggtgg atgatactaa atacaaggac taccaacagg tgggcatcct   19920
acaccaacac aacaactctg gatttgttgg ctaccttgcc cccaccatgc gcgaaggaca   19980
ggcctaccct gctaacttcc cctatccgct tataggcaag accgcagttg acagcattac   20040
ccagaaaaag tttctttgcg atcgcaccct ttggcgcatc ccattctcca gtaactttat   20100
gtccatgggc gcactcacag acctgggcca aaaccttctc tacgccaact ccgcccacgc   20160
gctagacatg acttttgagg tggatccat ggacgagccc acccttcttt atgttttgtt   20220
tgaagtcttt gacgtggtcc gtgtgcacca gccgcaccgc ggcgtcatcg aaaccgtgta   20280
cctgcgcacg cccttctcgg ccggcaacgc cacaacataa gaagcaagc aacatcaaca   20340 acagctgccg ccaaataatg tactagagac actttcaata aaggcaaatg cttttatttg   20400
tacactctcg ggtgattatt taccccccacc cttgccgtct cgccgtttta aaatcaaag    20460 gggttctgcc gcgcatcgct atgcgccact ggcagggaca cgttgcgata ctggtgttta   20520
gtgctccact taaactcagg cacaaccatc cgcggcagct cggtgaagtt ttcactccac   20580
aggctgcgca ccatcaccaa cgcgtttagc aggtcgggcg ccgatatctt gaagtcgcag   20640 ttgggggcctc cgccctgcgc gcgcgagttg cgatacacag ggttgcagca ctggaacact   20700
```

```
atcagcgccg ggtggtgcac gctggccagc acgctcttgt cggagatcag atccgcgtcc   20760
aggtcctccg cgttgctcag ggcgaacgga gtcaactttg gtagctgcct tcccaaaaag   20820
ggcgcgtgcc caggctttga gttgcactcg caccgtagtg gcatcaaaag gtgaccgtgc   20880
ccggtctggg cgttaggata cagcgcctgc ataaaagcct tgatctgctt aaaagccacc   20940
tgagcctttg cgccttcaga aagaacatg ccgcaagact tgccggaaaa ctgattggcc    21000
ggacaggccg cgtcgtgcac gcagcacctt cgtcggtgt tggagatctg caccacattt    21060
cggccccacc ggttcttcac gatcttggcc ttgctagact gctccttcag cgcgcgctgc   21120
ccgttttcgc tcgtcacatc catttcaatc acgtgctcct tatttatcat aatgcttccg   21180
tgtagacact taagctcgcc ttcgatctca gcgcagcggt gcagccacaa cgcgcagccc   21240
gtgggctcgt gatgcttgta ggtcacctct gcaaacgact gcaggtacgc ctgcaggaat   21300
cgccccatca tcgtcacaaa ggtcttgttg ctggtgaagg tcagctgcaa cccgcggtgc   21360
tcctcgttca gccaggtctt gcatacggcc gccagagctt ccacttggtc aggcagtagt   21420
ttgaagttcg cctttagatc gttatccacg tggtacttgt ccatcagcgc gcgcgcagcc   21480
tccatgccct tctcccacgc agacacgatc ggcacactca gcgggttcat caccgtaatt   21540
tcactttccg cttcgctggg ctcttcctct tcctcttgcg tccgcatacc acgcgccact   21600
gggtcgtctt cattcagccg ccgcactgtg cgcttacctc ctttgccatg cttgattagc   21660
accggtgggt tgctgaaacc caccatttgt agcgccacat cttctctttc ttcctcgctg   21720
tccacgatta cctctggtga tggcgggcgc tcgggcttgg gagaagggcg cttctttttc   21780
ttcttgggcg caatggccaa atccgccgcc gaggtcgatg gccgcgggct gggtgtgcgc   21840
ggcaccagcg cgtcttgtga tgagtcttcc tcgtcctcgg actcgatacg ccgcctcatc   21900 cgctttttg ggggcgcccg gggaggcggc ggcgacgggg acgggacga cacgtcctcc    21960 atggttgggg gacgtcgcgc cgcaccgcgt ccgcgctcgg gggtggtttc gcgctgctcc   22020
tcttcccgac tggccatttc cttctcctat aggcagaaaa agatcatgga gtcagtcgag   22080
aagaaggaca gcctaaccgc cccctctgag ttcgccacca ccgcctccac cgatgccgcc   22140
aacgcgccta ccaccttccc cgtcgaggca ccccgcttg aggaggagga agtgattatc    22200
gagcaggacc caggttttgt aagcgaagac gacgaggacc gctcagtacc aacagaggat   22260
aaaaagcaag accaggacaa cgcagaggca aacgaggaac aagtcgggcg ggggacgaa    22320 aggcatggcg actacctaga tgtgggagac gacgtgctgt tgaagcatct gcagcgccag   22380
tgcgccatta tctgcgacgc gttgcaagag cgcagcgatg tgccctcgc catagcggat     22440 gtcagccttg cctacgaacg ccacctattc tcaccgcgcg taccccccaa acgccaagaa   22500
aacggcacat gcgagcccaa cccgcgcctc aacttctacc ccgtatttgc cgtgccagag   22560
gtgcttgcca cctatcacat cttttttccaa aactgcaaga tacccctatc ctgccgtgcc   22620
aaccgcagcc gagcggacaa gcagctggcc ttgcggcagg gcgctgtcat acctgatatc   22680
gcctcgctca acgaagtgcc aaaaatcttt gagggtcttg gacgcgacga gaagcgcgcg   22740
gcaaacgctc tgcaacagga aaacagcgaa aatgaaagtc actctggagt gttggtggaa   22800
ctcgagggtg acaacgcgcg cctagccgta ctaaaacgca gcatcgaggt cacccacttt   22860
gcctacccgg cacttaacct accccccaag gtcatgagca cagtcatgag tgagctgatc   22920
gtgcgccgtg cgcagcccct ggagagggat gcaaatttgc aagaacaaac agaggagggc   22980
ctacccgcag ttgcgacga gcagctagcg cgctggcttc aaacgcgcga gcctgccgac   23040
ttggaggagc gacgcaaact aatgatggcc gcagtgctcg ttaccgtgga gcttgagtgc   23100
```

| | | | | |
|---|---|---|---|---|
| atgcagcggt | tctttgctga | cccggagatg | cagcgcaagc | tagaggaaac | attgcactac | 23160 |
| accttt cgac | agggctacgt | acgccaggcc | tgcaagatct | ccaacgtgga | gctctgcaac | 23220 |
| ctggtctcct | accttggaat | tttgcacgaa | aaccgccttg | ggcaaaacgt | gcttcattcc | 23280 |
| acgctcaagg | gcgaggcgcg | ccgcgactac | gtccgcgact | gcgtttactt | atttctatgc | 23340 |
| tacacctggc | agacggccat | gggcgtttgg | cagcagtgct | tggaggagtg | caacctcaag | 23400 |
| gagctgcaga | aactgctaaa | gcaaaacttg | aaggacctat | ggacggcctt | caacgagcgc | 23460 |
| tccgtggccg | cgcacctggc | ggacatcatt | ttccccgaac | gcctgcttaa | aaccctgcaa | 23520 |
| cagggtctgc | cagacttcac | cagtcaaagc | atgttgcaga | actttaggaa | ctttatccta | 23580 |
| gagcgctcag | gaatcttgcc | cgccacctgc | tgtgcacttc | ctagcgactt | tgtgcccatt | 23640 |
| aagtaccgcg | aatgccctcc | gccgctttgg | ggccactgct | accttctgca | gctagccaac | 23700 |
| taccttgcct | accactctga | cataatggaa | gacgtgagcg | gtgacggtct | actggagtgt | 23760 |
| cactgtcgct | gcaacctatg | cacccccgcac | cgctccctgg | tttgcaattc | gcagctgctt | 23820 |
| aacgaaagtc | aaattatcgg | tacctttgag | ctgcagggtc | cctcgcctga | cgaaaagtcc | 23880 |
| gcggctccgg | ggttgaaact | cactccgggg | ctgtggacgt | cggcttacct | tcgcaaattt | 23940 |
| gtacctgagg | actaccacgc | ccacgagatt | aggttctacg | aagaccaatc | ccgcccgcct | 24000 |
| aatgcggagc | ttaccgcctg | cgtcattacc | cagggccaca | ttcttggcca | attgcaagcc | 24060 |
| atcaacaaag | cccgccaaga | gtttctgcta | cgaaagggac | gggggggttta | cttggacccc | 24120 |
| cagtccggcg | aggagctcaa | cccaatcccc | ccgccgccgc | agccctatca | gcagcagccg | 24180 |
| cgggcccttg | cttcccagga | tggcacccaa | aaagaagctg | cagctgccgc | cgccacccac | 24240 |
| ggacgaggag | gaatactggg | acagtcaggc | agaggaggtt | ttggacgagg | aggaggagga | 24300 |
| catgatggaa | gactgggaga | gcctagacga | ggaagcttcc | gaggtcgaag | aggtgtcaga | 24360 |
| cgaaacaccg | tcaccctcgg | tcgcattccc | ctcgccggcg | ccccagaaat | cggcaaccgg | 24420 |
| ttccagcatg | gctacaacct | ccgctcctca | ggcgccgccg | gcactgcccg | ttcgccgacc | 24480 |
| caaccgtaga | tgggacacca | ctggaaccag | ggccggtaag | tccaagcagc | cgccgccgtt | 24540 |
| agcccaagag | caacaacagc | gccaaggcta | ccgctcatgg | cgcgggcaca | gaacgccat | 24600 |
| agttgcttgc | ttgcaagact | gtgggggcaa | catctccttc | gcccgccgct | tcttctcta | 24660 |
| ccatcacggc | gtggccttcc | cccgtaacat | cctgcattac | taccgtcatc | tctacagccc | 24720 |
| atactgcacc | ggcggcagcg | gcagcaacag | cagcggccac | acagaagcaa | aggcgaccgg | 24780 |
| atagcaagac | tctgacaaag | cccaagaaat | ccacagcggc | ggcagcagca | ggaggaggag | 24840 |
| cgctgcgtct | ggcgcccaac | gaacccgtat | cgacccgcga | gcttagaaac | aggatttttc | 24900 |
| ccactctgta | tgctatattt | caacagagca | ggggccaaga | acaagagctg | aaaataaaaa | 24960 |
| acaggtctct | gcgatccctc | acccgcagct | gcctgtatca | caaaagcgaa | gatcagcttc | 25020 |
| ggcgcacgct | ggaagacgcg | gaggctctct | tcagtaaata | ctgcgcgctg | actcttaagg | 25080 |
| actagtttcg | cgcccttttct | caaatttaag | cgcgaaaact | acgtcatctc | cagcggccac | 25140 |
| acccggcgcc | agcacctgtt | gtcagcgcca | ttatgagcaa | ggaaattccc | acgccctaca | 25200 |
| tgtggagtta | ccagccacaa | atgggacttg | cggctggagc | tgcccaagac | tactcaaccc | 25260 |
| gaataaacta | catgagcgcg | ggaccccaca | tgatatcccg | ggtcaacgga | atacgcgccc | 25320 |
| accgaaaccg | aattctcctg | gaacaggcgg | ctattaccac | cacacctcgt | aataacctta | 25380 |
| atccccgtag | ttggcccgct | gccctggtgt | accaggaaag | tcccgctccc | accactgtgg | 25440 |

```
tacttcccag agacgcccag gccgaagttc agatgactaa ctcaggggcg cagcttgcgg    25500
gcggctttcg tcacagggtg cggtcgcccg ggcagggtat aactcacctg acaatcagag    25560
ggcgaggtat tcagctcaac gacgagtcgg tgagctcctc gcttggtctc cgtccggacg    25620
ggacatttca gatcggcggc gccggccgct cttcattcac gcctcgtcag gcaatcctaa    25680
ctctgcagac ctcgtcctct gagccgcgct ctggaggcat tggaactctg caatttattg    25740
aggagtttgt gccatcggtc tactttaacc ccttctcggg acctcccggc cactatccgg    25800
atcaatttat tcctaacttt gacgcggtaa aggactcggc ggacggctac gactgaatgt    25860
taagtggaga ggcagagcaa ctgcgcctga aacacctggt ccactgtcgc cgccacaagt    25920
gctttgcccg cgactccggt gagttttgct actttgaatt gcccgaggat catatcgagg    25980
gcccggcgca cggcgtccgg cttaccgccc agggagagct tgcccgtagc ctgattcggg    26040
agtttaccca gcgcccctg ctagttgagc gggacagggg accctgtgtt ctcactgtga    26100
tttgcaactg tcctaaccct ggattacatc aagatctttg ttgccatctc tgtgctgagt    26160
ataataaata cagaaattaa aatatactgg ggctcctatc gccatcctgt aaacgccacc    26220
gtcttcaccc gcccaagcaa accaaggcga accttacctg gtacttttaa catctctccc    26280
tctgtgattt acaacagttt caacccagac ggagtgagtc tacgagagaa cctctccgag    26340
ctcagctact ccatcagaaa aaacaccacc ctccttacct gccgggaacg tacgagtgcg    26400
tcaccggccg ctgcaccaca cctaccgcct gaccgtaaac cagacttttt ccggacagac    26460
ctcaataact ctgtttacca gaacaggagg tgagcttaga aaacccttag ggtattaggc    26520
caaaggcgca gctactgtgg ggtttatgaa caattcaagc aactctacgg gctattctaa    26580
ttcaggtttc tctagaaatg gacggaatta ttacagagca gcgcctgcta gaaagacgca    26640
gggcagcggc cgagcaacag cgcatgaatc aagagctcca agacatggtt aacttgcacc    26700
agtgcaaaag gggtatcttt tgtctggtaa agcaggccaa agtcacctac gacagtaata    26760
ccaccggaca ccgccttagc tacaagttgc caaccaagcg tcagaaattg gtggtcatgg    26820
tgggagaaaa gcccattacc ataactcagc actcggtaga aaccgaaggc tgcattcact    26880
caccttgtca aggacctgag gatctctgca cccttattaa gaccctgtgc ggtctcaaag    26940
atcttattcc ctttaactaa taaaaaaaaa taataaagca tcacttactt aaaatcagtt    27000
agcaaatttc tgtccagttt attcagcagc acctccttgc cctcctccca gctctggtat    27060
tgcagcttcc tcctggctgc aaactttctc cacaatctaa atggaatgtc agtttcctcc    27120
tgttcctgtc catccgcacc cactatcttc atgttgttgc agatgaagcg cgcaagaccg    27180
tctgaagata ccttcaaccc cgtgtatcca tatgacacgg aaaccggtcc tccaactgtg    27240
ccttttctta ctcctccctt tgtatccccc aatgggtttc aagagagtcc ccctgggta    27300 ctctctttgc gcctatccga acctctagtt acctccaatg gcatgcttgc gctcaaaatg    27360
ggcaacggcc tctctctgga cgaggccggc aaccttacct cccaaaatgt aaccactgtg    27420
agcccacctc tcaaaaaaac caagtcaaac ataaacctgg aaatatctgc accccctcaca    27480 gttacctcag aagccctaac tgtggctgcc gccgcacctc taatggtcgc gggcaacaca    27540
ctcaccatga atcacaggc cccgctaacc gtgcacgact ccaaacttag cattgccacc    27600
caaggacccc tcacagtgtc agaaggaaag ctagccctgc aaacatcagg cccctcacc    27660 accaccgata gcagtaccct tactatcact gcctcacccc ctctaactac tgccactggt    27720
agcttgggca ttgacttgaa agagcccatt tatacacaaa atggaaaact aggactaaag    27780
tacgggcctc ctttgcatgt aacagacgac ctaaacactt tgaccgtagc aactggtcca    27840
```

```
ggtgtgacta ttaataatac ttccttgcaa actaaagtta ctggagcctt gggttttgat   27900
tcacaaggca atatgcaact taatgtagca ggaggactaa ggattgattc tcaaaacaga   27960
cgccttatac ttgatgttag ttatccgttt gatgctcaaa accaactaaa tctaagacta   28020
ggacagggcc ctcttttat aaactcagcc cacaacttgg atattaacta caacaaaggc    28080
ctttacttgt ttacagcttc aaacaattcc aaaaagcttg aggttaacct aagcactgcc   28140
aagggggttga tgtttgacgc tacagccata gccattaatg caggagatgg gcttgaattt   28200
ggttcaccta atgcaccaaa cacaaatccc ctcaaaacaa aaattggcca tggcctagaa   28260
tttgattcaa acaaggctat ggttcctaaa ctaggaactg gccttagttt tgacagcaca   28320
ggtgccatta cagtaggaaa caaaaataat gataagctaa ctttgtggac cacaccagct   28380
ccatctccta actgtagact aaatgcagag aaagatgcta aactcacttt ggtcttaaca   28440
aaatgtggca gtcaaatact tgctacagtt tcagttttgg ctgttaaagg cagtttggct   28500
ccaatatctg gaacagttca aagtgctcat cttattataa gatttgacga aaatggagtg   28560
ctactaaaca attccttcct ggacccagaa tattggaact ttagaaatgg agatcttact   28620
gaaggcacag cctatacaaa cgctgttgga tttatgccta acctatcagc ttatccaaaa   28680
tctcacggta aaactgccaa agtaacatt gtcagtcaag tttacttaaa cggagacaaa    28740
actaaacctg taacactaac cattacacta aacggtacac aggaaacagg agacacaact   28800
ccaagtgcat actctatgtc attttcatgg gactggtctg ccacaactta cattaatgaa   28860
atatttgcca catcctctta cacttttca tacattgccc aagaataaag aatcgtttgt    28920
gttatgtttc aacgtgttta ttttcaatt gcagaaaatt cgaatcatt tttcattcag     28980
tagtatagcc ccaccaccac atagcttata cagatcaccg taccttaatc aaactcacag   29040
aaccctagta ttcaacctgc cacctccctc caacacaca gagtacacag tcctttctcc    29100
ccggctggcc ttaaaaagca tcatatcatg ggtaacagac atattcttag gtgttatatt   29160
ccacacggtt tcctgtcgag ccaaacgctc atcagtgata ttaataaact ccccgggcag   29220
ctcacttaag ttcatgtcgc tgtccagctg ctgagccaca ggctgctgtc aacttgcgg    29280
ttgcttaacg ggcggcgaag gagaagtcca cgcctacatg ggggtagagt cataatcgtg   29340
catcaggata gggcggtggt gctgcagcag cgcgcgaata aactgctgcc gccgccgctc   29400
cgtcctgcag gaatacaaca tggcagtggt ctcctcagcg atgattcgca ccgcccgcag   29460
cataaggcgc cttgtcctcc gggcacagca gcgcaccctg atctcactta aatcagcaca   29520
gtaactgcag cacagcacca caatattgtt caaaatccca cagtgcaagg cgctgtatcc   29580
aaagctcatg gcggggacca cagaacccac gtggccatca taccacaagc gcaggtagat   29640
taagtggcga cccctcataa acacgctgga cataaacatt acctcttttg gcatgttgta   29700
attcaccacc tcccggtacc atataaacct ctgattaaac atggcgccat ccaccaccat   29760
cctaaaccag ctggccaaaa cctgcccgcc ggctatacac tgcagggaac cgggactgga   29820
acaatgacag tggagagccc aggactcgta accatggatc atcatgctcg tcatgatatc   29880
aatgttggca caacaggc acacgtgcat acacttcctc aggattacaa gctcctcccg     29940
cgttagaacc atatcccagg gaacaaccca ttcctgaatc agcgtaaatc ccacactgca   30000
gggaagacct cgcacgtaac tcacgttgtg cattgtcaaa gtgttacatt cgggcagcag   30060
cggatgatcc tccagtatgg tagcgcgggt ttctgtctca aaaggaggta gacgatccct   30120
actgtacgga gtgcgccgag acaaccgaga tcgtgttggt cgtagtgtca tgccaaatgg   30180
```

```
aacgccggac gtagtcatat ttcctgaagc aaaaccaggt gcgggcgtga caaacagatc  30240
tgcgtctccg gtctcgccgc ttagatcgct ctgtgtagta gttgtagtat atccactctc  30300
tcaaagcatc caggcgcccc ctggcttcgg gttctatgta aactccttca tgcgccgctg  30360
ccctgataac atccaccacc gcagaataag ccacacccag ccaacctaca cattcgttct  30420
gcgagtcaca cacgggagga gcgggaagag ctggaagaac catgtttttt tttttattcc  30480
aaaagattat ccaaaacctc aaaatgaaga tctattaagt gaacgcgctc ccctccggtg  30540
gcgtggtcaa actctacagc caaagaacag ataatggcat ttgtaagatg ttgcacaatg  30600
gcttccaaaa ggcaaacggc cctcacgtcc aagtggacgt aaaggctaaa cccttcaggg  30660
tgaatctcct ctataaacat tccagcacct tcaaccatgc ccaaataatt ctcatctcgc  30720
caccttctca atatatctct aagcaaatcc cgaatattaa gtccggccat tgtaaaaatc  30780
tgctccagag cgccctccac cttcagcctc aagcagcgaa tcatgattgc aaaaattcag  30840
gttcctcaca gacctgtata agattcaaaa gcggaacatt aacaaaaata ccgcgatccc  30900
gtaggtccct tcgcagggcc agctgaacat aatcgtgcag gtctgcacgg accagcgcgg  30960
ccacttcccc gccaggaacc atgacaaaag aacccacact gattatgaca cgcatactcg  31020
gagctatgct aaccagcgta gccccgatgt aagcttgttg catgggcggc gatataaaat  31080
gcaaggtgct gctcaaaaaa tcaggcaaag cctcgcgcaa aaagaaagc acatcgtagt  31140 catgctcatg cagataaagg caggtaagct ccggaaccac cacagaaaaa gacaccattt  31200
ttctctcaaa catgtctgcg ggtttctgca taaacacaaa ataaaataac aaaaaaacat  31260
ttaaacatta gaagcctgtc ttacaacagg aaaaacaacc cttataagca taagacggac  31320
tacggccatg ccggcgtgac cgtaaaaaaa ctggtcaccg tgattaaaaa gcaccaccga  31380
cagctcctcg gtcatgtccg gagtcataat gtaagactcg gtaaacacat caggttgatt  31440
cacatcggtc agtgctaaaa agcgaccgaa atagcccggg ggaatacata cccgcaggcg  31500
tagagacaac attacagccc ccataggagg tataacaaaa ttaataggag agaaaaacac  31560
ataaacacct gaaaaaccct cctgcctagg caaaatagca ccctcccgct ccagaacaac  31620
atacagcgct tccacagcgg cagccataac agtcagcctt accagtaaaa aagaaaacct  31680
attaaaaaaa caccactcga cacggcacca gctcaatcag tcacagtgta aaaaagggcc  31740
aagtgcagag cgagtatata taggactaaa aaatgacgta acggttaaag tccacaaaaa  31800
acacccagaa aaccgcacgc gaacctacgc ccagaaacga aagccaaaaa acccacaact  31860
tcctcaaatc gtcacttccg tttttcccacg ttacgtcact tcccatttta agaaaactac  31920
aattcccaac acatacaagt tactccgccc taaaacctac gtcacccgcc ccgttcccac  31980
gccccgcgcc acgtcacaaa ctccaccccc tcattatcat attggcttca atccaaaata  32040
aggtatatta ttgatgatgt taattaattt aaatccgcat gcgatatcga gctctcccgg  32100
gaattcggat ctgcgacgcg aggctggatg gccttcccca ttatgattct tctcgcgttt  32160
aagggcacca ataactgcct taaaaaaatt acgccccgcc ctgccactca tcgcagtact  32220
gttgtaattc attaagcatt ctgccgacat ggaagccatc acaaacggca tgatgaacct  32280
gaatcgccag cggcatcagc accttgtcgc cttgcgtata atatttgccc atggtgaaaa  32340
cgggggcgaa gaagttgtcc atattggcca cgtttaaatc aaaactggtg aaactcaccc  32400
agggattggc tgagacgaaa aacatattct caataaaccc tttagggaaa taggccaggt  32460
tttcaccgta acacgccaca tcttgcgaat atatgtgtag aaactgccgg aaatcgtcgt  32520
ggtattcact ccagagcgat gaaaacgttt cagtttgctc atggaaaacg gtgtaacaag  32580
```

```
ggtgaacact atcccatatc accagctcac cgtctttcat tgccatacgg aattccggat   32640
gagcattcat caggcgggca agaatgtgaa taaaggccgg ataaaacttg tgcttatttt   32700
tctttacggt cttaaaaag gccgtaatat ccagctgaac ggtctggtta taggtacatt    32760
gagcaactga ctgaaatgcc tcaaaatgtt ctttacgatg ccattgggat atatcaacgg   32820
tggtatatcc agtgattttt ttctccattt tagcttcctt agctcctgaa atctcgata    32880
actcaaaaaa tacgcccggt agtgatctta tttcattatg gtgaaagttg gaacctctta  32940
cgtgccgatc aacgtctcat tttcgccaaa agttggccca gggcttcccg gtatcaacag  33000
ggacaccagg atttatttat tctgcgaagt gatcttccgt cacaggtatt tattcgcgat  33060
aagctcatgg agcggcgtaa ccgtcgcaca ggaaggacag agaaagcgcg gatctgggaa  33120
gtgacggaca gaacggtcag gacctggatt ggggaggcgg ttgccgccgc tgctgctgac  33180
ggtgtgacgt tctctgttcc ggtcacacca catacgttcc gccattccta tgcgatgcac  33240
atgctgtatg ccggtatacc gctgaaagtt ctgcaaagcc tgatgggaca taagtccatc  33300
agttcaacgg aagtctacac gaaggttttt gcgctggatg tggctgcccg gcaccgggtg  33360
cagtttgcga tgccggagtc tgatgcggtt gcgatgctga acaattatc ctgagaataa   33420
atgccttggc ctttatatgg aaatgtggaa ctgagtggat atgctgtttt tgtctgttaa  33480
acagagaagc tggctgttat ccactgagaa gcgaacgaaa cagtcgggaa atctcccat   33540
tatcgtagag atccgcatta ttaatctcag gagcctgtgt agcgtttata ggaagtagtg  33600
ttctgtcatg atgcctgcaa gcggtaacga aaacgatttg aatatgcctt caggaacaat  33660
agaaatcttc gtgcggtgtt acgttgaagt ggagcggatt atgtcagcaa tggacagaac  33720
aacctaatga acacagaacc atgatgtggt ctgtccttt acagccagta gtgctcgccg   33780
cagtcgagcg acagggcgaa gccctcgagt gagcgaggaa gcaccaggga acagcactta  33840
tatattctgc ttacacacga tgcctgaaaa aacttccctt ggggttatcc acttatccac  33900
ggggatattt ttataattat ttttttttata gtttttagat cttctttttt agagcgcctt  33960
gtaggccttt atccatgctg gttctagaga aggtgttgtg acaaattgcc ctttcagtgt  34020
gacaaatcac cctcaaatga cagtcctgtc tgtgacaaat tgcccttaac cctgtgacaa  34080
attgccctca gaagaagctg ttttttcaca agttatccc tgcttattga ctcttttta    34140
tttagtgtga caatctaaaa acttgtcaca cttcacatgg atctgtcatg gcggaaacag  34200
cggttatcaa tcacaagaaa cgtaaaaata gcccgcgaat cgtccagtca acgacctca   34260
ctgaggcggc atatagtctc tcccgggatc aaaaacgtat gctgtatctg ttcgttgacc  34320
agatcagaaa atctgatggc accctacagg aacatgacgg tatctgcgag atccatgttg  34380
ctaaatatgc tgaaatattc ggattgacct ctgcggaagc cagtaaggat atacggcagg  34440
cattgaagag tttcgcgggg aaggaagtgg ttttttatcg ccctgaagag gatgccggcg  34500
atgaaaaagg ctatgaatct tttccttggt ttatcaaacg tgcgcacagt ccatccagag  34560
ggctttacag tgtacatatc aacccatatc tcattccctt ctttatcggg ttacagaacc  34620
ggttacgca gtttcggctt agtgaaacaa aagaaatcac caatccgtat gccatgcgtt   34680
tatacgaatc cctgtgtcag tatcgtaagc cggatggctc aggcatcgtc tctctgaaaa  34740
tcgactggat catagagcgt taccagctgc ctcaaagtta ccagcgtatg cctgacttcc  34800
gccgccgctt cctgcaggtc tgtgttaatg agatcaacag cagaactcca atgcgcctct  34860
catacattga gaaaagaaa ggccgccaga cgactcatat cgtatttcc ttccgcgata    34920
```

```
tcacttccat gacgacagga tagtctgagg gttatctgtc acagatttga gggtggttcg   34980
tcacatttgt tctgacctac tgagggtaat ttgtcacagt tttgctgttt ccttcagcct   35040
gcatggattt tctcatactt tttgaactgt aattttaag gaagccaaat ttgagggcag    35100
tttgtcacag ttgatttcct tctctttccc ttcgtcatgt gacctgatat cggggggttag  35160 ttcgtcatca ttgatgaggg ttgattatca cagtttatta ctctgaattg ctatccgcg    35220 tgtgtacctc tacctggagt ttttcccacg gtggatattt cttcttgcgc tgagcgtaag   35280
agctatctga cagaacagtt cttctttgct tcctcgccag ttcgctcgct atgctcggtt   35340
acacggctgc ggcgagcgct agtgataata agtgactgag gtatgtgctc ttcttatctc   35400
cttttgtagt gttgctctta ttttaaacaa ctttgcggtt ttttgatgac tttgcgattt   35460
tgttgttgct ttgcagtaaa ttgcaagatt taataaaaaa acgcaaagca atgattaaag   35520
gatgttcaga atgaaactca tggaaacact taaccagtgc ataaacgctg gtcatgaaat   35580
gacgaaggct atcgccattg cacagtttaa tgatgacagc ccggaagcga ggaaaataac   35640
ccggcgctgg agaataggtg aagcagcgga tttagttggg gtttcttctc aggctatcag   35700
agatgccgag aaagcagggc gactaccgca cccggatatg gaaattcgag gacgggttga   35760
gcaacgtgtt ggttatacaa ttgaacaaat taatcatatg cgtgatgtgt ttggtacgcg   35820
attgcgacgt gctgaagacg tatttccacc ggtgatcggg gttgctgccc ataaaggtgg   35880
cgtttacaaa acctcagttt ctgttcatct tgctcaggat ctggctctga aggggctacg   35940
tgttttgctc gtggaaggta acgaccccca gggaacagcc tcaatgtatc acggatgggt   36000
accagatctt catattcatg cagaagacac tctcctgcct ttctatcttg gggaaaagga   36060
cgatgtcact tatgcaataa agcccacttg ctggccgggg cttgacatta ttccttcctg   36120
tctggctctg caccgtattg aaactgagtt aatgggcaaa tttgatgaag gtaaactgcc   36180
caccgatcca cacctgatgc tccgactggc cattgaaact gttgctcatg actatgatgt   36240
catagttatt gacagcgcgc ctaacctggg tatcggcacg attaatgtcg tatgtgctgc   36300
tgatgtgctg attgttccca cgcctgctga gttgtttgac tacacctccg cactgcagtt   36360
tttcgatatg cttcgtgatc tgctcaagaa cgttgatctt aaagggttcg agcctgatgt   36420
acgtattttg cttaccaaat acagcaatag taatggctct cagtccccgt ggatggagga   36480
gcaaattcgg gatgcctggg gaagcatggt tctaaaaaat gttgtacgtg aaacggatga   36540
agttggtaaa ggtcagatcc ggatgagaac tgtttttgaa caggccattg atcaacgctc   36600
ttcaactggt gcctggagaa atgctctttc tatttgggaa cctgtctgca atgaaatttt   36660
cgatcgtctg attaaaccac gctgggagat tagataatga agcgtgcgcc tgttattcca   36720
aaacatacgc tcaatactca accggttgaa gatacttcgt tatcgacacc agctgccccg   36780
atggtggatt cgttaattgc gcgcgtagga gtaatggctc gcggtaatgc cattactttg   36840
cctgtatgtg gtcgggatgt gaagtttact cttgaagtgc tccggggtga tagtgttgag   36900
aagacctctc gggtatggtc aggtaatgaa cgtgaccagg agctgcttac tgaggacgca   36960
ctggatgatc tcatcccttc ttttctactg actggtcaac agacaccggc gttcggtcga   37020
agagtatctg tgtcataga aattgccgat gggagtcgcc gtcgtaaagc tgctgcactt    37080
accgaaagtg attatcgtgt tctggttggc gagctggatg atgagcagat ggctgcatta   37140
tccagattgg gtaacgatta tcgcccaaca agtgcttatg aacgtggtca gcgttatgca   37200
agccgattgc agaatgaatt tgctggaaat atttctgcgc tggctgatgc ggaaaatatt   37260
tcacgtaaga ttattacccg ctgtatcaac accgccaaat tgcctaaatc agttgttgct   37320
```

| | | |
|---|---|---|
| cttttttctc accccggtga actatctgcc cggtcaggtg atgcacttca aaaagccttt | 37380 | |
| acagataaag aggaattact taagcagcag gcatctaacc ttcatgagca gaaaaaagct | 37440 | |
| ggggtgatat ttgaagctga agaagttatc actcttttaa cttctgtgct taaaacgtca | 37500 | |
| tctgcatcaa gaactagttt aagctcacga catcagtttg ctcctggagc gacagtattg | 37560 | |
| tataagggcg ataaaatggt gcttaacctg gacaggtctc gtgttccaac tgagtgtata | 37620 | |
| gagaaaattg aggccattct taaggaactt gaaaagccag caccctgatg cgaccacgtt | 37680 | |
| ttagtctacg tttatctgtc tttacttaat gtcctttgtt acaggccaga aagcataact | 37740 | |
| ggcctgaata ttctctctgg gcccactgtt ccacttgtat cgtcggtctg ataatcagac | 37800 | |
| tgggaccacg gtcccactcg tatcgtcggt ctgattatta gtctgggacc acggtcccac | 37860 | |
| tcgtatcgtc ggtctgatta ttagtctggg accacggtcc cactcgtatc gtcggtctga | 37920 | |
| taatcagact gggaccacgg tcccactcgt atcgtcggtc tgattattag tctgggacca | 37980 | |
| tggtcccact cgtatcgtcg gtctgattat tagtctggga ccacggtccc actcgtatcg | 38040 | |
| tcggtctgat tattagtctg gaaccacggt cccactcgta tcgtcggtct gattattagt | 38100 | |
| ctgggaccac ggtcccactc gtatcgtcgg tctgattatt agtctgggac cacgatccca | 38160 | |
| ctcgtgttgt cggtctgatt atcggtctgg gaccacggtc ccacttgtat tgtcgatcag | 38220 | |
| actatcagcg tgagactacg attccatcaa tgcctgtcaa gggcaagtat tgacatgtcg | 38280 | |
| tcgtaacctg tagaacggag taacctcggt gtgcggttgt atgcctgctg tggattgctg | 38340 | |
| ctgtgtcctg cttatccaca acattttgcg cacggttatg tggacaaaat acctggttac | 38400 | |
| ccaggccgtg ccggcacgtt aaccgggcac atttccccga aaagtgccac ctgacgtcta | 38460 | |
| agaaaccatt attatcatga cattaaccta taaaaatagg cgtatcacga ggccctttcg | 38520 | |
| tcttcaagaa ttggatccga attcccggga gagctcgata tcgcatgcgg atttaaatta | 38580 | |
| attaa | 38585 | |

<210> SEQ ID NO 102
<211> LENGTH: 75
<212> TYPE: DNA
<213> ORGANISM: Artificial Sequence
<220> FEATURE:
<223> OTHER INFORMATION: Primer

<400> SEQUENCE: 102

| | | |
|---|---|---|
| tcccgcgctt cttggaactt tacattgtgg gccacaacat caacggccct ccctcatcag | 60 | |
| tgccaacata gtaag | 75 | |

<210> SEQ ID NO 103
<211> LENGTH: 67
<212> TYPE: DNA
<213> ORGANISM: Artificial Sequence
<220> FEATURE:
<223> OTHER INFORMATION: Primer

<400> SEQUENCE: 103

| | | |
|---|---|---|
| ggcacctcgg aacggttgtt aattacctgg gcggcgagca cgatctcgtc ccgctcatta | 60 | |
| ggcgggc | 67 | |

<210> SEQ ID NO 104
<211> LENGTH: 99
<212> TYPE: DNA
<213> ORGANISM: Artificial Sequence
<220> FEATURE:

<223> OTHER INFORMATION: Primer

<400> SEQUENCE: 104
gcgcggcctt ccggagcgag gtgtgggtga gcgcaaaggt gtccctgacc atgaccagca    60
tgaagggcac gagctgcttc ccaaaggccc ccatccaag                            99

<210> SEQ ID NO 105
<211> LENGTH: 99
<212> TYPE: DNA
<213> ORGANISM: Artificial Sequence
<220> FEATURE:
<223> OTHER INFORMATION: Primer

<400> SEQUENCE: 105
cttggatggg ggcctttggg aagcagctcg tgcccttcat gctggtcatg gtcagggaca    60
cctttgcgct cacccacacc tcgctccgga aggccgcgc                            99

<210> SEQ ID NO 106
<211> LENGTH: 75
<212> TYPE: DNA
<213> ORGANISM: Artificial Sequence
<220> FEATURE:
<223> OTHER INFORMATION: Primer

<400> SEQUENCE: 106
accatttgta gcgccacatc ttctctttct tcctcgctgt ccacgattac ccctcatcag    60
tgccaacata gtaag                                                      75

<210> SEQ ID NO 107
<211> LENGTH: 67
<212> TYPE: DNA
<213> ORGANISM: Artificial Sequence
<220> FEATURE:
<223> OTHER INFORMATION: Primer

<400> SEQUENCE: 107
agaggagcag cgcgaaacca ccccgagcg cggacgcggt gcggcgcgac ccgctcatta    60
ggcgggc                                                               67

<210> SEQ ID NO 108
<211> LENGTH: 100
<212> TYPE: DNA
<213> ORGANISM: Artificial Sequence
<220> FEATURE:
<223> OTHER INFORMATION: Primer

<400> SEQUENCE: 108
accatttgta gcgccacatc ttctctttct tcctcgctgt ccacgattac gtcgcgccgc    60
accgcgtccg cgctcggggg tggtttcgcg ctgctcctct                          100

<210> SEQ ID NO 109
<211> LENGTH: 100
<212> TYPE: DNA
<213> ORGANISM: Artificial Sequence
<220> FEATURE:
<223> OTHER INFORMATION: Primer

<400> SEQUENCE: 109
agaggagcag cgcgaaacca ccccgagcg cggacgcggt gcggcgcgac gtaatcgtgg    60
acagcgagga agaaagagaa gatgtggcgc tacaaatggt                          100

-continued

```
<210> SEQ ID NO 110
<211> LENGTH: 75
<212> TYPE: DNA
<213> ORGANISM: Artificial Sequence
<220> FEATURE:
<223> OTHER INFORMATION: Primer

<400> SEQUENCE: 110
ctccacaggc tgcgcaccat caccaacgcg tttagcaggt cgggcgccga ccctcatcag      60
tgccaacata gtaag                                                      75

<210> SEQ ID NO 111
<211> LENGTH: 67
<212> TYPE: DNA
<213> ORGANISM: Artificial Sequence
<220> FEATURE:
<223> OTHER INFORMATION: Primer

<400> SEQUENCE: 111
ccccaaccat ggaggacgtg tcgtccccgt ccccgtcgcc gccgcctccc ccgctcatta      60
ggcgggc                                                               67

<210> SEQ ID NO 112
<211> LENGTH: 100
<212> TYPE: DNA
<213> ORGANISM: Artificial Sequence
<220> FEATURE:
<223> OTHER INFORMATION: Primer

<400> SEQUENCE: 112
ctccacaggc tgcgcaccat caccaacgcg tttagcaggt cgggcgccga gggaggcggc      60
ggcgacgggg acggggacga cacgtcctcc atggttgggg                          100

<210> SEQ ID NO 113
<211> LENGTH: 100
<212> TYPE: DNA
<213> ORGANISM: Artificial Sequence
<220> FEATURE:
<223> OTHER INFORMATION: Primer

<400> SEQUENCE: 113
ccccaaccat ggaggacgtg tcgtccccgt ccccgtcgcc gccgcctccc tcggcgcccg      60
acctgctaaa cgcgttggtg atggtgcgca gcctgtggag                          100

<210> SEQ ID NO 114
<211> LENGTH: 75
<212> TYPE: DNA
<213> ORGANISM: Artificial Sequence
<220> FEATURE:
<223> OTHER INFORMATION: Primer

<400> SEQUENCE: 114
taaaaagtct ggactctcac gctcgcttgg tcctgtaact attttgtaga ccctcatcag      60
tgccaacata gtaag                                                      75

<210> SEQ ID NO 115
<211> LENGTH: 67
<212> TYPE: DNA
<213> ORGANISM: Artificial Sequence
<220> FEATURE:
<223> OTHER INFORMATION: Primer

<400> SEQUENCE: 115
```
tctggcggcg acatggacgc atacatgaca cacatacgac acgttagcta ccgctcatta    60
ggcgggc    67

<210> SEQ ID NO 116
<211> LENGTH: 100
<212> TYPE: DNA
<213> ORGANISM: Artificial Sequence
<220> FEATURE:
<223> OTHER INFORMATION: Primer

<400> SEQUENCE: 116
ataaaaagtc tggactctca cgctcgcttg gtcctgtaac tattttgtag atagctaacg    60
tgtcgtatgt gtgtcatgta tgcgtccatg tcgccgccag    100

<210> SEQ ID NO 117
<211> LENGTH: 100
<212> TYPE: DNA
<213> ORGANISM: Artificial Sequence
<220> FEATURE:
<223> OTHER INFORMATION: Primer

<400> SEQUENCE: 117
tctggcggcg acatggacgc atacatgaca cacatacgac acgttagcta tctacaaaat    60
agttacagga ccaagcgagc gtgagagtcc agacttttta    100

<210> SEQ ID NO 118
<211> LENGTH: 75
<212> TYPE: DNA
<213> ORGANISM: Artificial Sequence
<220> FEATURE:
<223> OTHER INFORMATION: Primer

<400> SEQUENCE: 118
tttcctcctg ttcctgtcca tccgcaccca ctatcttcat gttgttgcag ccctcatcag    60
tgccaacata gtaag    75

<210> SEQ ID NO 119
<211> LENGTH: 67
<212> TYPE: DNA
<213> ORGANISM: Artificial Sequence
<220> FEATURE:
<223> OTHER INFORMATION: Primer

<400> SEQUENCE: 119
tggcaaatat ttcattaatg tagttgtggc cagaccagtc ccatgaaaat ccgctcatta    60
ggcgggc    67

<210> SEQ ID NO 120
<211> LENGTH: 100
<212> TYPE: DNA
<213> ORGANISM: Artificial Sequence
<220> FEATURE:
<223> OTHER INFORMATION: Primer

<400> SEQUENCE: 120
tttcctcctg ttcctgtcca tccgcaccca ctatcttcat gttgttgcag attttcatgg    60
gactggtctg gccacaacta cattaatgaa atatttgcca    100

<210> SEQ ID NO 121
<211> LENGTH: 100
<212> TYPE: DNA
<213> ORGANISM: Artificial Sequence

```
<220> FEATURE:
<223> OTHER INFORMATION: Primer

<400> SEQUENCE: 121
tggcaaatat ttcattaatg tagttgtggc cagaccagtc ccatgaaaat ctgcaacaac      60
atgaagatag tgggtgcgga tggacaggaa caggaggaaa                           100

<210> SEQ ID NO 122
<211> LENGTH: 75
<212> TYPE: DNA
<213> ORGANISM: Artificial Sequence
<220> FEATURE:
<223> OTHER INFORMATION: Primer

<400> SEQUENCE: 122
ggcaacgcca caacataaag aagcaagcaa catcaacaac agctgccgcc ccctcatcag      60
tgccaacata gtaag                                                      75

<210> SEQ ID NO 123
<211> LENGTH: 67
<212> TYPE: DNA
<213> ORGANISM: Artificial Sequence
<220> FEATURE:
<223> OTHER INFORMATION: Primer

<400> SEQUENCE: 123
tacaaataaa agcatttgcc tttattgaaa gtgtctctag tacattattt ccgctcatta     60
ggcgggc                                                               67

<210> SEQ ID NO 124
<211> LENGTH: 100
<212> TYPE: DNA
<213> ORGANISM: Artificial Sequence
<220> FEATURE:
<223> OTHER INFORMATION: Primer

<400> SEQUENCE: 124
ggcaacgcca caacataaag aagcaagcaa catcaacaac agctgccgcc aaataatgta     60
ctagagacac tttcaataaa ggcaaatgct tttatttgta                           100

<210> SEQ ID NO 125
<211> LENGTH: 100
<212> TYPE: DNA
<213> ORGANISM: Artificial Sequence
<220> FEATURE:
<223> OTHER INFORMATION: Primer

<400> SEQUENCE: 125
tacaaataaa agcatttgcc tttattgaaa gtgtctctag tacattattt ggcggcagct     60
gttgttgatg ttgcttgctt ctttatgttg tggcgttgcc                           100

<210> SEQ ID NO 126
<211> LENGTH: 75
<212> TYPE: DNA
<213> ORGANISM: Artificial Sequence
<220> FEATURE:
<223> OTHER INFORMATION: Primer

<400> SEQUENCE: 126
caaaaaaccc acaacttcct caaatcgtca cttccgtttt cccacgttac ccctcatcag     60
tgccaacata gtaag                                                      75
```

<210> SEQ ID NO 127
<211> LENGTH: 67
<212> TYPE: DNA
<213> ORGANISM: Artificial Sequence
<220> FEATURE:
<223> OTHER INFORMATION: Primer

<400> SEQUENCE: 127
agtaacttgt atgtgttggg aattgtagtt ttcttaaaat gggaagtgac ccgctcatta    60
ggcgggc    67

<210> SEQ ID NO 128
<211> LENGTH: 76
<212> TYPE: DNA
<213> ORGANISM: Artificial Sequence
<220> FEATURE:
<223> OTHER INFORMATION: Primer

<400> SEQUENCE: 128
caaaaaaccc acaacttcct caaatcgtca cttccgtttt cccacgttac ttctgtggaa    60
tgtgtgtcag ttaggg    76

<210> SEQ ID NO 129
<211> LENGTH: 75
<212> TYPE: DNA
<213> ORGANISM: Artificial Sequence
<220> FEATURE:
<223> OTHER INFORMATION: Primer

<400> SEQUENCE: 129
agtaacttgt atgtgttggg aattgtagtt ttcttaaaat gggaagtgac ctctagctag    60
aggtcgacgg tatac    75

<210> SEQ ID NO 130
<211> LENGTH: 19
<212> TYPE: DNA
<213> ORGANISM: Artificial Sequence
<220> FEATURE:
<223> OTHER INFORMATION: Primer

<400> SEQUENCE: 130
cccgggaatt cggatctgc    19

<210> SEQ ID NO 131
<211> LENGTH: 24
<212> TYPE: DNA
<213> ORGANISM: Artificial Sequence
<220> FEATURE:
<223> OTHER INFORMATION: Primer

<400> SEQUENCE: 131
ccgggaattc ggatccttga agac    24

<210> SEQ ID NO 132
<211> LENGTH: 38
<212> TYPE: DNA
<213> ORGANISM: Artificial Sequence
<220> FEATURE:
<223> OTHER INFORMATION: Primer

<400> SEQUENCE: 132
aaaaaaggat ccaccatgga agacatcaac tttgcgtc    38

```
<210> SEQ ID NO 133
<211> LENGTH: 29
<212> TYPE: DNA
<213> ORGANISM: Artificial Sequence
<220> FEATURE:
<223> OTHER INFORMATION: Primer

<400> SEQUENCE: 133
aaaaaagtcg actcagaagc atcgtcggc                                    29

<210> SEQ ID NO 134
<211> LENGTH: 34
<212> TYPE: DNA
<213> ORGANISM: Artificial Sequence
<220> FEATURE:
<223> OTHER INFORMATION: Primer

<400> SEQUENCE: 134
atcgcctgga gaattcactc tcttccgcat cgct                              34

<210> SEQ ID NO 135
<211> LENGTH: 37
<212> TYPE: DNA
<213> ORGANISM: Artificial Sequence
<220> FEATURE:
<223> OTHER INFORMATION: Primer

<400> SEQUENCE: 135
aaagttgatg tcttccattg cgactgtgac tggttag                           37

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
atggaagaca tcaactttgc                                              20

<210> SEQ ID NO 137
<211> LENGTH: 19
<212> TYPE: DNA
<213> ORGANISM: Artificial Sequence
<220> FEATURE:
<223> OTHER INFORMATION: Primer

<400> SEQUENCE: 137
gaattctcca ggcgatctg                                               19

<210> SEQ ID NO 138
<211> LENGTH: 26
<212> TYPE: DNA
<213> ORGANISM: Artificial Sequence
<220> FEATURE:
<223> OTHER INFORMATION: Primer

<400> SEQUENCE: 138
aaaaaaggat ccaccatgaa gcgcgc                                       26

<210> SEQ ID NO 139
<211> LENGTH: 40
<212> TYPE: DNA
<213> ORGANISM: Artificial Sequence
<220> FEATURE:
<223> OTHER INFORMATION: Primer
```

```
<400> SEQUENCE: 139
aaaaaagtcg acttattctt gggcaatgta tgaaaaagtg                              40

<210> SEQ ID NO 140
<211> LENGTH: 34
<212> TYPE: DNA
<213> ORGANISM: Artificial Sequence
<220> FEATURE:
<223> OTHER INFORMATION: Primer

<400> SEQUENCE: 140
atcgcctgga gaattcactc tcttccgcat cgct                                    34

<210> SEQ ID NO 141
<211> LENGTH: 35
<212> TYPE: DNA
<213> ORGANISM: Artificial Sequence
<220> FEATURE:
<223> OTHER INFORMATION: Primer

<400> SEQUENCE: 141
gtcttgcgcg cttcattgcg actgtgactg gttag                                   35

<210> SEQ ID NO 142
<211> LENGTH: 18
<212> TYPE: DNA
<213> ORGANISM: Artificial Sequence
<220> FEATURE:
<223> OTHER INFORMATION: Primer

<400> SEQUENCE: 142
atgaagcgcg caagaccg                                                      18

<210> SEQ ID NO 143
<211> LENGTH: 21
<212> TYPE: DNA
<213> ORGANISM: Artificial Sequence
<220> FEATURE:
<223> OTHER INFORMATION: Primer

<400> SEQUENCE: 143
gaattctcca ggcgatctga c                                                  21

<210> SEQ ID NO 144
<211> LENGTH: 30
<212> TYPE: DNA
<213> ORGANISM: Artificial Sequence
<220> FEATURE:
<223> OTHER INFORMATION: Primer

<400> SEQUENCE: 144
aaaaaagcgg ccgcactctc ttccgcatcg                                         30

<210> SEQ ID NO 145
<211> LENGTH: 40
<212> TYPE: DNA
<213> ORGANISM: Artificial Sequence
<220> FEATURE:
<223> OTHER INFORMATION: Primer

<400> SEQUENCE: 145
aaaaaatcta gattattctt gggcaatgta tgaaaaagtg                              40

<210> SEQ ID NO 146
<211> LENGTH: 30
```

```
<212> TYPE: DNA
<213> ORGANISM: Artificial Sequence
<220> FEATURE:
<223> OTHER INFORMATION: Primer

<400> SEQUENCE: 146
aaaaaaggat ccaccatggg ctccagtgag                                    30

<210> SEQ ID NO 147
<211> LENGTH: 40
<212> TYPE: DNA
<213> ORGANISM: Artificial Sequence
<220> FEATURE:
<223> OTHER INFORMATION: Primer

<400> SEQUENCE: 147
aaaaagtcga cttacatgtt tttcaagtga caaaaagaag                         40

<210> SEQ ID NO 148
<211> LENGTH: 44
<212> TYPE: DNA
<213> ORGANISM: Artificial Sequence
<220> FEATURE:
<223> OTHER INFORMATION: Primer

<400> SEQUENCE: 148
atctagagcc ggcgcttaca tgttttttcaa gtgacaaaaa gaag                   44

<210> SEQ ID NO 149
<211> LENGTH: 18
<212> TYPE: DNA
<213> ORGANISM: Artificial Sequence
<220> FEATURE:
<223> OTHER INFORMATION: Primer

<400> SEQUENCE: 149
atgggctcca gtgagcag                                                 18

<210> SEQ ID NO 150
<211> LENGTH: 19
<212> TYPE: DNA
<213> ORGANISM: Artificial Sequence
<220> FEATURE:
<223> OTHER INFORMATION: Primer

<400> SEQUENCE: 150
gaattctcca ggcgatctg                                                19

<210> SEQ ID NO 151
<211> LENGTH: 41
<212> TYPE: DNA
<213> ORGANISM: Artificial Sequence
<220> FEATURE:
<223> OTHER INFORMATION: Primer

<400> SEQUENCE: 151
aaaaaatcta gattacatgt ttttcaagtg acaaaaagaa g                       41

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
```
agacctggct gaacgaggag                                              20

<210> SEQ ID NO 153
<211> LENGTH: 20
<212> TYPE: DNA
<213> ORGANISM: Artificial Sequence
<220> FEATURE:
<223> OTHER INFORMATION: Primer

<400> SEQUENCE: 153
tgggctcgtg atgcttgtag                                              20

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
gggtacccaa ctccatgctc                                              20

<210> SEQ ID NO 155
<211> LENGTH: 20
<212> TYPE: DNA
<213> ORGANISM: Artificial Sequence
<220> FEATURE:
<223> OTHER INFORMATION: Primer

<400> SEQUENCE: 155
aagtggcgct cctaatctgc                                              20

<210> SEQ ID NO 156
<211> LENGTH: 24
<212> TYPE: DNA
<213> ORGANISM: Artificial Sequence
<220> FEATURE:
<223> OTHER INFORMATION: Primer

<400> SEQUENCE: 156
ccattcagct cactgataac cttg                                         24

<210> SEQ ID NO 157
<211> LENGTH: 18
<212> TYPE: DNA
<213> ORGANISM: Artificial Sequence
<220> FEATURE:
<223> OTHER INFORMATION: Primer

<400> SEQUENCE: 157
cgtcgcctcc tacctgct                                                18

<210> SEQ ID NO 158
<211> LENGTH: 67
<212> TYPE: DNA
<213> ORGANISM: Artificial Sequence
<220> FEATURE:
<223> OTHER INFORMATION: Primer

<400> SEQUENCE: 158
ggcacctcgg aacggttgtt aattacctgg gcggcgagca cgatctcgtc ccgctcatta  60
ggcgggc                                                            67

<210> SEQ ID NO 159
<211> LENGTH: 99

<212> TYPE: DNA
<213> ORGANISM: Artificial Sequence
<220> FEATURE:
<223> OTHER INFORMATION: Primer

<400> SEQUENCE: 159
gcgcggcctt ccggagcgag gtgtgggtga gcgcaaaggt gtccctgacc atgaccagca    60
tgaagggcac gagctgcttc ccaaaggccc ccatccaag                           99

<210> SEQ ID NO 160
<211> LENGTH: 99
<212> TYPE: DNA
<213> ORGANISM: Artificial Sequence
<220> FEATURE:
<223> OTHER INFORMATION: Primer

<400> SEQUENCE: 160
cttggatggg ggcctttggg aagcagctcg tgcccttcat gctggtcatg gtcagggaca    60
cctttgcgct cacccacacc tcgctccgga aggccgcgc                           99

<210> SEQ ID NO 161
<211> LENGTH: 75
<212> TYPE: DNA
<213> ORGANISM: Artificial Sequence
<220> FEATURE:
<223> OTHER INFORMATION: Primer

<400> SEQUENCE: 161
atacaaaact acataagacc cccaccttat atattctttc ccacccttaa ccctcatcag    60
tgccaacata gtaag                                                    75

<210> SEQ ID NO 162
<211> LENGTH: 67
<212> TYPE: DNA
<213> ORGANISM: Artificial Sequence
<220> FEATURE:
<223> OTHER INFORMATION: Primer

<400> SEQUENCE: 162
aataagagga agtgaaatct gaataatttt gtgttactca tagcgcgtaa ccgctcatta    60
ggcgggc                                                             67

<210> SEQ ID NO 163
<211> LENGTH: 81
<212> TYPE: DNA
<213> ORGANISM: Artificial Sequence
<220> FEATURE:
<223> OTHER INFORMATION: Primer

<400> SEQUENCE: 163
atacaaaact acataagacc cccaccttat atattctttc ccacccttaa gccacgccca    60
cagatatacg cgttgacatt g                                             81

<210> SEQ ID NO 164
<211> LENGTH: 69
<212> TYPE: DNA
<213> ORGANISM: Artificial Sequence
<220> FEATURE:
<223> OTHER INFORMATION: Primer

<400> SEQUENCE: 164
aataagagga agtgaaatct gaataatttt gtgttactca tagcgcgtaa tagaagccat    60
agagcccac 69

<210> SEQ ID NO 165
<211> LENGTH: 75
<212> TYPE: DNA
<213> ORGANISM: Artificial Sequence
<220> FEATURE:
<223> OTHER INFORMATION: Primer

<400> SEQUENCE: 165
caaaaaaccc acaacttcct caaatcgtca cttccgtttt cccacgttac ccctcatcag 60
tgccaacata gtaag 75

<210> SEQ ID NO 166
<211> LENGTH: 67
<212> TYPE: DNA
<213> ORGANISM: Artificial Sequence
<220> FEATURE:
<223> OTHER INFORMATION: Primer

<400> SEQUENCE: 166
agtaacttgt atgtgttggg aattgtagtt ttcttaaaat gggaagtgac ccgctcatta 60
ggcgggc 67

<210> SEQ ID NO 167
<211> LENGTH: 76
<212> TYPE: DNA
<213> ORGANISM: Artificial Sequence
<220> FEATURE:
<223> OTHER INFORMATION: Primer

<400> SEQUENCE: 167
caaaaaaccc acaacttcct caaatcgtca cttccgtttt cccacgttac ttctgtggaa 60
tgtgtgtcag ttaggg 76

<210> SEQ ID NO 168
<211> LENGTH: 75
<212> TYPE: DNA
<213> ORGANISM: Artificial Sequence
<220> FEATURE:
<223> OTHER INFORMATION: Primer

<400> SEQUENCE: 168
agtaacttgt atgtgttggg aattgtagtt ttcttaaaat gggaagtgac ctctagctag 60
aggtcgacgg tatac 75

<210> SEQ ID NO 169
<211> LENGTH: 67
<212> TYPE: DNA
<213> ORGANISM: Artificial Sequence
<220> FEATURE:
<223> OTHER INFORMATION: Primer

<400> SEQUENCE: 169
tggaactaat catatgtggc ctggagaaac agctaaagtg cgaaagcggc ccgctcatta 60
ggcgggc 67

<210> SEQ ID NO 170
<211> LENGTH: 75
<212> TYPE: DNA
<213> ORGANISM: Artificial Sequence
<220> FEATURE:
<223> OTHER INFORMATION: Primer

<400> SEQUENCE: 170
cgcgaacaaa tgtggtatgg ctgattatga tcctctagag ataattctag ccctcatcag    60
tgccaacata gtaag                                                     75

<210> SEQ ID NO 171
<211> LENGTH: 77
<212> TYPE: DNA
<213> ORGANISM: Artificial Sequence
<220> FEATURE:
<223> OTHER INFORMATION: Primer

<400> SEQUENCE: 171
tggctagcgt ttaaacttaa gcttggtacc cctccgcggg gatcctctag gccaccatgc    60
ccaagaagaa gaggaag                                                   77

<210> SEQ ID NO 172
<211> LENGTH: 72
<212> TYPE: DNA
<213> ORGANISM: Artificial Sequence
<220> FEATURE:
<223> OTHER INFORMATION: Primer

<400> SEQUENCE: 172
cgcgaacaaa tgtggtatgg ctgattatga tcctctagag ataattctag ctaatcgcca    60
tcttccagca gg                                                        72

<210> SEQ ID NO 173
<211> LENGTH: 33
<212> TYPE: DNA
<213> ORGANISM: Artificial Sequence
<220> FEATURE:
<223> OTHER INFORMATION: Primer

<400> SEQUENCE: 173
tggagaagga tccgcactct cttccgcatc gct                                 33

<210> SEQ ID NO 174
<211> LENGTH: 30
<212> TYPE: DNA
<213> ORGANISM: Artificial Sequence
<220> FEATURE:
<223> OTHER INFORMATION: Primer

<400> SEQUENCE: 174
aaaaaaagcg gccgccgcca ccatggtgag                                     30

<210> SEQ ID NO 175
<211> LENGTH: 30
<212> TYPE: DNA
<213> ORGANISM: Artificial Sequence
<220> FEATURE:
<223> OTHER INFORMATION: Primer

<400> SEQUENCE: 175
aaaaaagaat tccggccgct ttacttgtac                                     30

<210> SEQ ID NO 176
<211> LENGTH: 31
<212> TYPE: DNA
<213> ORGANISM: Artificial Sequence
<220> FEATURE:
<223> OTHER INFORMATION: Primer

<400> SEQUENCE: 176
aaaaaagcgg ccgcgcacca tggtgagcaa g                            31

<210> SEQ ID NO 177
<211> LENGTH: 35
<212> TYPE: DNA
<213> ORGANISM: Artificial Sequence
<220> FEATURE:
<223> OTHER INFORMATION: Primer

<400> SEQUENCE: 177
aaaaaactcg agactacttg tacagctcgt ccatg                        35

<210> SEQ ID NO 178
<211> LENGTH: 37
<212> TYPE: DNA
<213> ORGANISM: Artificial Sequence
<220> FEATURE:
<223> OTHER INFORMATION: Primer

<400> SEQUENCE: 178
aaaaaagtcg acatgtctag actggacaag agcaaag                      37

<210> SEQ ID NO 179
<211> LENGTH: 34
<212> TYPE: DNA
<213> ORGANISM: Artificial Sequence
<220> FEATURE:
<223> OTHER INFORMATION: Primer

<400> SEQUENCE: 179
aaaaaaggat ccttacccgg ggagcatgtc aagg                         34

<210> SEQ ID NO 180
<211> LENGTH: 41
<212> TYPE: DNA
<213> ORGANISM: Artificial Sequence
<220> FEATURE:
<223> OTHER INFORMATION: Primer

<400> SEQUENCE: 180
aaaaaatcta gattacatgt ttttcaagtg acaaaagaa g                  41

<210> SEQ ID NO 181
<211> LENGTH: 42
<212> TYPE: DNA
<213> ORGANISM: Artificial Sequence
<220> FEATURE:
<223> OTHER INFORMATION: Primer

<400> SEQUENCE: 181
taatctagac ccagctttct tgtacaaagt tggcattata ag                42

<210> SEQ ID NO 182
<211> LENGTH: 75
<212> TYPE: DNA
<213> ORGANISM: Artificial Sequence
<220> FEATURE:
<223> OTHER INFORMATION: Primer

<400> SEQUENCE: 182
agaaagctgg gtctagatta cttatcgtcg tcatccttgt aatccatgtt tttcaagtga    60
caaaagaaag tggcg                                                    75

```
<210> SEQ ID NO 183
<211> LENGTH: 37
<212> TYPE: DNA
<213> ORGANISM: Artificial Sequence
<220> FEATURE:
<223> OTHER INFORMATION: Primer

<400> SEQUENCE: 183
agtcgactgg atccggtacc gccgcatcaa cgagctc                              37

<210> SEQ ID NO 184
<211> LENGTH: 37
<212> TYPE: DNA
<213> ORGANISM: Artificial Sequence
<220> FEATURE:
<223> OTHER INFORMATION: Primer

<400> SEQUENCE: 184
gagagtgcgg ccgcgaattc gaggcccaga gggtacc                              37

<210> SEQ ID NO 185
<211> LENGTH: 16
<212> TYPE: DNA
<213> ORGANISM: Artificial Sequence
<220> FEATURE:
<223> OTHER INFORMATION: Primer

<400> SEQUENCE: 185
gaattcgcgg ccgcac                                                     16

<210> SEQ ID NO 186
<211> LENGTH: 19
<212> TYPE: DNA
<213> ORGANISM: Artificial Sequence
<220> FEATURE:
<223> OTHER INFORMATION: Primer

<400> SEQUENCE: 186
ggtaccggat ccagtcgac                                                  19

<210> SEQ ID NO 187
<211> LENGTH: 45
<212> TYPE: DNA
<213> ORGANISM: Artificial Sequence
<220> FEATURE:
<223> OTHER INFORMATION: Primer

<400> SEQUENCE: 187
cagtgagcag gaatagaaag ccattgtcaa agatcttggt tgtgg                     45

<210> SEQ ID NO 188
<211> LENGTH: 42
<212> TYPE: DNA
<213> ORGANISM: Artificial Sequence
<220> FEATURE:
<223> OTHER INFORMATION: Primer

<400> SEQUENCE: 188
ctttgacaat ggctttctat tcctgctcac tggagcccat tg                        42

<210> SEQ ID NO 189
<211> LENGTH: 32
<212> TYPE: DNA
<213> ORGANISM: Artificial Sequence
<220> FEATURE:
<223> OTHER INFORMATION: Primer
```

```
<400> SEQUENCE: 189
aaaaaaaagc ttatgcaaga gcaataccgc cc                               32

<210> SEQ ID NO 190
<211> LENGTH: 36
<212> TYPE: DNA
<213> ORGANISM: Artificial Sequence
<220> FEATURE:
<223> OTHER INFORMATION: Primer

<400> SEQUENCE: 190
aaaaaactcg agttagccaa cgaccagatt gaggag                           36

<210> SEQ ID NO 191
<211> LENGTH: 26
<212> TYPE: DNA
<213> ORGANISM: Artificial Sequence
<220> FEATURE:
<223> OTHER INFORMATION: Primer

<400> SEQUENCE: 191
agggcgatgc cacctagggc aagctg                                      26

<210> SEQ ID NO 192
<211> LENGTH: 26
<212> TYPE: DNA
<213> ORGANISM: Artificial Sequence
<220> FEATURE:
<223> OTHER INFORMATION: Primer

<400> SEQUENCE: 192
cagcttgccc taggtggcat cgccct                                      26

<210> SEQ ID NO 193
<211> LENGTH: 31
<212> TYPE: DNA
<213> ORGANISM: Artificial Sequence
<220> FEATURE:
<223> OTHER INFORMATION: Primer

<400> SEQUENCE: 193
aaaaaaaagc ttgccaccat ggtgagcaag g                                31

<210> SEQ ID NO 194
<211> LENGTH: 36
<212> TYPE: DNA
<213> ORGANISM: Artificial Sequence
<220> FEATURE:
<223> OTHER INFORMATION: Primer

<400> SEQUENCE: 194
aaaaaactcg agttacttgt acagctcgtc catgcc                           36

<210> SEQ ID NO 195
<211> LENGTH: 20
<212> TYPE: DNA
<213> ORGANISM: Artificial Sequence
<220> FEATURE:
<223> OTHER INFORMATION: Primer

<400> SEQUENCE: 195
ctggagaacg cactgtacgc                                             20

<210> SEQ ID NO 196
<211> LENGTH: 20
```

```
<212> TYPE: DNA
<213> ORGANISM: Artificial Sequence
<220> FEATURE:
<223> OTHER INFORMATION: Primer

<400> SEQUENCE: 196 gaagtgggggg catagaatcg                                              20

<210> SEQ ID NO 197
<211> LENGTH: 20
<212> TYPE: DNA
<213> ORGANISM: Artificial Sequence
<220> FEATURE:
<223> OTHER INFORMATION: Primer

<400> SEQUENCE: 197
tcaagcagag gctgaagctg                                               20

<210> SEQ ID NO 198
<211> LENGTH: 20
<212> TYPE: DNA
<213> ORGANISM: Artificial Sequence
<220> FEATURE:
<223> OTHER INFORMATION: Primer

<400> SEQUENCE: 198
tcgttgtggg aggtgatgtc                                               20

<210> SEQ ID NO 199
<211> LENGTH: 33
<212> TYPE: DNA
<213> ORGANISM: Artificial Sequence
<220> FEATURE:
<223> OTHER INFORMATION: Primer

<400> SEQUENCE: 199
ctacataaga cccccaccttt atatattctt tcc                               33

<210> SEQ ID NO 200
<211> LENGTH: 32
<212> TYPE: DNA
<213> ORGANISM: Artificial Sequence
<220> FEATURE:
<223> OTHER INFORMATION: Primer

<400> SEQUENCE: 200
agcgggaaaa ctgaataaga ggaagtgaaa tc                                 32

<210> SEQ ID NO 201
<211> LENGTH: 17
<212> TYPE: DNA
<213> ORGANISM: Artificial Sequence
<220> FEATURE:
<223> OTHER INFORMATION: Primer

<400> SEQUENCE: 201
cggggcgcgt ctggaac                                                  17

<210> SEQ ID NO 202
<211> LENGTH: 19
<212> TYPE: DNA
<213> ORGANISM: Artificial Sequence
<220> FEATURE:
<223> OTHER INFORMATION: Primer

<400> SEQUENCE: 202
```

```
ggtaagcttg ggctgcagg                                               19
```

<210> SEQ ID NO 203
<211> LENGTH: 35
<212> TYPE: DNA
<213> ORGANISM: Artificial Sequence
<220> FEATURE:
<223> OTHER INFORMATION: Primer

<400> SEQUENCE: 203

```
acctgcagcc caagcttacc atggccaagc ctttg                             35
```

<210> SEQ ID NO 204
<211> LENGTH: 45
<212> TYPE: DNA
<213> ORGANISM: Artificial Sequence
<220> FEATURE:
<223> OTHER INFORMATION: Primer

<400> SEQUENCE: 204

```
attgttccag acgcgccccg ttagccctcc cacacataac cagag                  45
```

<210> SEQ ID NO 205
<211> LENGTH: 38
<212> TYPE: DNA
<213> ORGANISM: Artificial Sequence
<220> FEATURE:
<223> OTHER INFORMATION: Primer

<400> SEQUENCE: 205

```
aaaaaagcgg ccgcaccatg accgagtaca agcccacg                          38
```

<210> SEQ ID NO 206
<211> LENGTH: 29
<212> TYPE: DNA
<213> ORGANISM: Artificial Sequence
<220> FEATURE:
<223> OTHER INFORMATION: Primer

<400> SEQUENCE: 206

```
aaaaaagaat tctcaggcac cgggcttgc                                    29
```

<210> SEQ ID NO 207
<211> LENGTH: 32
<212> TYPE: DNA
<213> ORGANISM: Artificial Sequence
<220> FEATURE:
<223> OTHER INFORMATION: Primer

<400> SEQUENCE: 207

```
aaaaaagcgg ccgcaccatg gccaagcctt tg                                32
```

<210> SEQ ID NO 208
<211> LENGTH: 35
<212> TYPE: DNA
<213> ORGANISM: Artificial Sequence
<220> FEATURE:
<223> OTHER INFORMATION: Primer

<400> SEQUENCE: 208

```
aaaaaagaat tcttagccct cccacacata accag                             35
```

<210> SEQ ID NO 209
<211> LENGTH: 15
<212> TYPE: DNA
<213> ORGANISM: Artificial Sequence

```
<220> FEATURE:
<223> OTHER INFORMATION: Consensus Sequence

<400> SEQUENCE: 209
cctatcagtg ataga                                                    15

<210> SEQ ID NO 210
<211> LENGTH: 15
<212> TYPE: DNA
<213> ORGANISM: Artificial Sequence
<220> FEATURE:
<223> OTHER INFORMATION: Operator

<400> SEQUENCE: 210
cccgtcagtg acgga                                                    15
```